US012692515B2

(12) United States Patent
Daigle et al.

(10) Patent No.: US 12,692,515 B2
(45) Date of Patent: Jul. 28, 2026

(54) ARTIFICIAL EXPRESSION CONSTRUCTS FOR SELECTIVELY MODULATING GENE EXPRESSION IN INHIBITORY NEOCORTICAL NEURONS

(71) Applicant: Allen Institute, Seattle, WA (US)

(72) Inventors: Tanya Daigle, Lake Forest Park, WA (US); Lucas T. Graybuck, Seattle, WA (US); Edward Sebastian Lein, Mercer Island, WA (US); Boaz P. Levi, Seattle, WA (US); John K. Mich, Seattle, WA (US); Adriana Estela Sedeño Cortés, Seattle, WA (US); Bosiljka Tasic, Seattle, WA (US); Jonathan Ting, Lake Forest Park, WA (US); Miranda Walker, Ann Arbor, MI (US); Hongkui Zeng, Seattle, WA (US)

(73) Assignee: Allen Institute, Seattle, WA (US)

( * ) Notice: Subject to any disclaimer, the term of this patent is extended or adjusted under 35 U.S.C. 154(b) by 852 days.

(21) Appl. No.: 18/000,574

(22) PCT Filed: Jun. 4, 2021

(86) PCT No.: PCT/US2021/036028
§ 371 (c)(1),
(2) Date: Dec. 2, 2022

(87) PCT Pub. No.: WO2021/248085
PCT Pub. Date: Dec. 9, 2021

(65) Prior Publication Data
US 2023/0212608 A1    Jul. 6, 2023

Related U.S. Application Data

(60) Provisional application No. 63/034,794, filed on Jun. 4, 2020.

(51) Int. Cl.
C12N 15/86    (2006.01)
A61K 9/00     (2006.01)
C12N 15/11    (2006.01)

(52) U.S. Cl.
CPC ............ *C12N 15/86* (2013.01); *A61K 9/0019* (2013.01); *A61K 9/0085* (2013.01); *C12N 15/11* (2013.01);
(Continued)

(58) Field of Classification Search
None
See application file for complete search history.

(56) References Cited

U.S. PATENT DOCUMENTS 5,753,506 A    5/1998  Johe
5,766,948 A    6/1998  Gage
(Continued)

FOREIGN PATENT DOCUMENTS

WO    WO2001036623 A2    5/2001
WO    WO2017184768 A1    10/2017
(Continued)

OTHER PUBLICATIONS

Search Report and Written Opinion for European Application No. 21818145.1, Dated Jun. 24, 2024, 17 pages.
(Continued)

*Primary Examiner* — Tracy Vivlemore
*Assistant Examiner* — Hanna Marie Thueson
(74) *Attorney, Agent, or Firm* — C. Rachal Winger; Shan Liao; Lee & Hayes PC

(57) ABSTRACT

Artificial expression constructs for selectively modulating gene expression in selected central nervous system cell types are described. The artificial expression constructs can be used to selectively express synthetic genes or modify gene expression in inhibitory neocortical GABAergic neurons
(Continued)

including somatostatin GABAergic neurons, parvalbumin GABAergic neurons, vasointestinal peptide GABAergic neurons, Lamp5 GABAergic neurons, and in some instances astrocytes.

20 Claims, 120 Drawing Sheets

Specification includes a Sequence Listing.

(52) U.S. Cl.
CPC .................... *C12N 2510/02* (2013.01); *C12N 2750/14141* (2013.01)

(56) References Cited

U.S. PATENT DOCUMENTS

| | | | |
|---|---|---|---|
| 5,851,832 | A | 12/1998 | Weiss |
| 5,948,428 | A | 9/1999 | Lee |
| 6,001,654 | A | 12/1999 | Anderson |
| 6,395,546 | B1 | 5/2002 | Zobe |
| 6,812,339 | B1 * | 11/2004 | Venter .................. C12Q 1/6883 536/23.1 |
| 10,113,201 | B2 * | 10/2018 | Davuluri .............. C12Q 1/6886 |
| 11,001,841 | B2 * | 5/2021 | Lee ...................... C12N 15/113 |
| 2004/0087028 | A1 | 5/2004 | Cunningham |
| 2012/0308530 | A1 | 12/2012 | Hu |
| 2012/0329714 | A1 | 12/2012 | Shingo |
| 2016/0208243 | A1 | 7/2016 | Zhang |
| 2018/0030425 | A1 | 2/2018 | Joung |

FOREIGN PATENT DOCUMENTS

| | | | |
|---|---|---|---|
| WO | WO2019199867 | A1 | 10/2019 |
| WO | WO2020076614 | A1 | 4/2020 |
| WO | WO2020097121 | A1 | 5/2020 |

OTHER PUBLICATIONS

Graybuck, et al., "Prospective, brain-wide labeling of neuronal subclasses with enhancer-driven AAVs", retreived on Feb. 2, 2022 at URL:https://www.biorxiv.org/content/10.1101/525014v2.full, bioRixiv, Jan. 31, 2019.

Mich, et al., "Functional enhancer elements drive subcalss-seletive expression from ouse to pimate neocortex", Cell Rep, vol. 34, No. 13, 2021, 108754, 54 pages.

Search Report and Written Opinion for European Application No. 21818145.1, Dated Sep. 16, 2024, 15 pages.

Choi, et al., "Optimization of AAV expression cassettes to improve packaging capacity and transgene expression on heurons", Molecular Brain, vol. 7, No. 17, 2014, 10 pages.

Search Report and Written Opinion for International Application No. PCT/US2021/036028, mailed Dec. 2, 2021, 14 pages.

Abhyankar, et al., "A novel CpG-free vertebrate insulator silences the testis-specific SP-10 gene in somatic tissues: role for TDP-43 in insulator function," J. Biol. Chem., vol. 282, No. 50, 2007, pp. 36143-36154.

Albright, et al., "Mapping the Structural Determinants Required for AAVrh.10 Transport across the Blood-Brain Barrier," Mol. Ther., vol. 26, No. 2, 2018, pp. 510-523.

Bell, et al., "The protein CTCF is required for the enhancer blocking activity of vertebrate insulators," Cell, vol. 98, No. 3, 1999, pp. 387-396.

Bibel, et al., "Generation of a defined and uniform population of CNS progenitors and neurons from mouse embryonic stem cells," Nat. Protoc., vol. 2, No. 5, 2007, pp. 1034-1043.

Caldwell, et al., "Growth factors regulate the survival and fate of cells derived from human neurospheres," Nat. Biotechnol., vol. 19, No. 5, 2001, pp. 475-479.

Chan, et al., "Engineered AAVs for efficient noninvasive gene delivery to the central and peripheral nervous systems," Nat. Neurosci., vol. 20, No. 8, 2017, pp. 1172-1179.

Chatzi, et al., "Derivation of homogeneous GABAergic neurons from mouse embryonic stem cells," Exp. Neurol., vol. 217, No. 2, 2009, pp. 407-416.

Chen, et al., "Molecular signatures of disease brain endothelia provide new sites for CNS-directed enzyme therapy," Nat. Med., vol. 15, No. 10, 2009, pp. 1215-1218.

Chung, et al., "A 5' element of the chicken beta-globin domain serves as an insulator in human erythroid cells and protects against position effect in Drosophila," Cell., vol. 74, No. 3, 1993, pp. 505-514.

Chung, et al., "Characterization of the chicken beta-globin insulator," PNAS USA., vol. 94, No. 2, 1997, pp. 575-580.

Deverman, et al., "Cre-dependent selection yields AAV variants for widespread gene transfer to the adult brain," Nat Biotechnol., vol. 34, No. 2, 2016, pp. 204-209.

Gombash, et al., "Intravenous AAV9 efficiently transduces myenteric neurons in neonate and juvenile mice," Front. Mol. Neurosci., vol. 7, No. 81, 2014, 11 pages.

Hu, et al., "Differentiation of human oligodendrocytes from pluripotent stem cells," Nat. Protoc., vol. 4, No. 11, 2009, pp. 1614-1622.

Jinek, et al., "A programmable dual-RNA-guided DNA endonuclease in adaptive bacterial immunity," Science, vol. 337, No. 6096, 2012, pp. 816-821.

Jinek, et al., "RNA-programmed genome editing in human cells," Elife, vol. 2, 2013, 9 pages.

Liu, et al., "Genomic discovery of potent chromatin insulators for human gene therapy," Nat. Biotechnol., vol. 33, No. 2, 2015, pp. 198-203.

Marchio, et al., "Brain endothelial cell-targeted gene therapy of neurovascular disorders," EMBO Mol. Med., vol. 8, No. 6, 2016, pp. 592-594.

Naso, et al., "Adeno-Associated Virus (AAV) as a Vector for Gene Therapy," BioDrugs., vol. 31, No. 4, 2017, pp. 317-334.

GenBank Accession No. NCT03612869 "Open-label, Single-arm, Multi-center Study of Intracerebral Administration of Adeno-associated Viral (AAV) Serotype rh.10 Carrying Human N-sulfoglucosamine Sulfohydrolase (SGSH) cDNA for Treatment of Mucopolysaccharidosis Type IIIA," Dec. 12, 2018, Accessed onlin Jan. 10, 2023 at https://clinicaltrials.gov/ct2/show/NCT03612869?term=NCT03612869&draw=2&rank=1.

Segal, David J., "Bacteria herald a new era of gene editing," Elife, vol. 2, 2013, 3 pages.

Selot, et al., "Optimized AAV rh.10 Vectors That Partially Evade Neutralizing Antibodies during Hepatic Gene Transfer," Front Pharmacol., vol. 8, 2017, 10 pages.

Shetty and Turner, "In vitro survival and differentiation of neurons derived from epidermal growth factor-responsive postnatal hippocampal stem cells: inducing effects of brain-derived neurotrophic factor," J. Neurobiol., vol. 35, No. 4, 1998, pp. 395-425.

Yang, et al., "Global CNS transduction of adult mice by intravenously delivered rAAVrh.8 and rAAVrh.10 and nonhuman primates by rAAVrh.10," Mol. Ther., vol. 22, No. 7, 2014, pp. 1299-1309.

Zetsche, et al., "Cpf1 is a single RNA-guided endonuclease of a class 2 CRISPR-Cas system," Cell., vol. 163, No. 3, 2015, pp. 759-771.

* cited by examiner

CN2039 single cells mapping to mouse cell type taxonomy

FIG. 2K                    FIG. 2L                    FIG. 2M
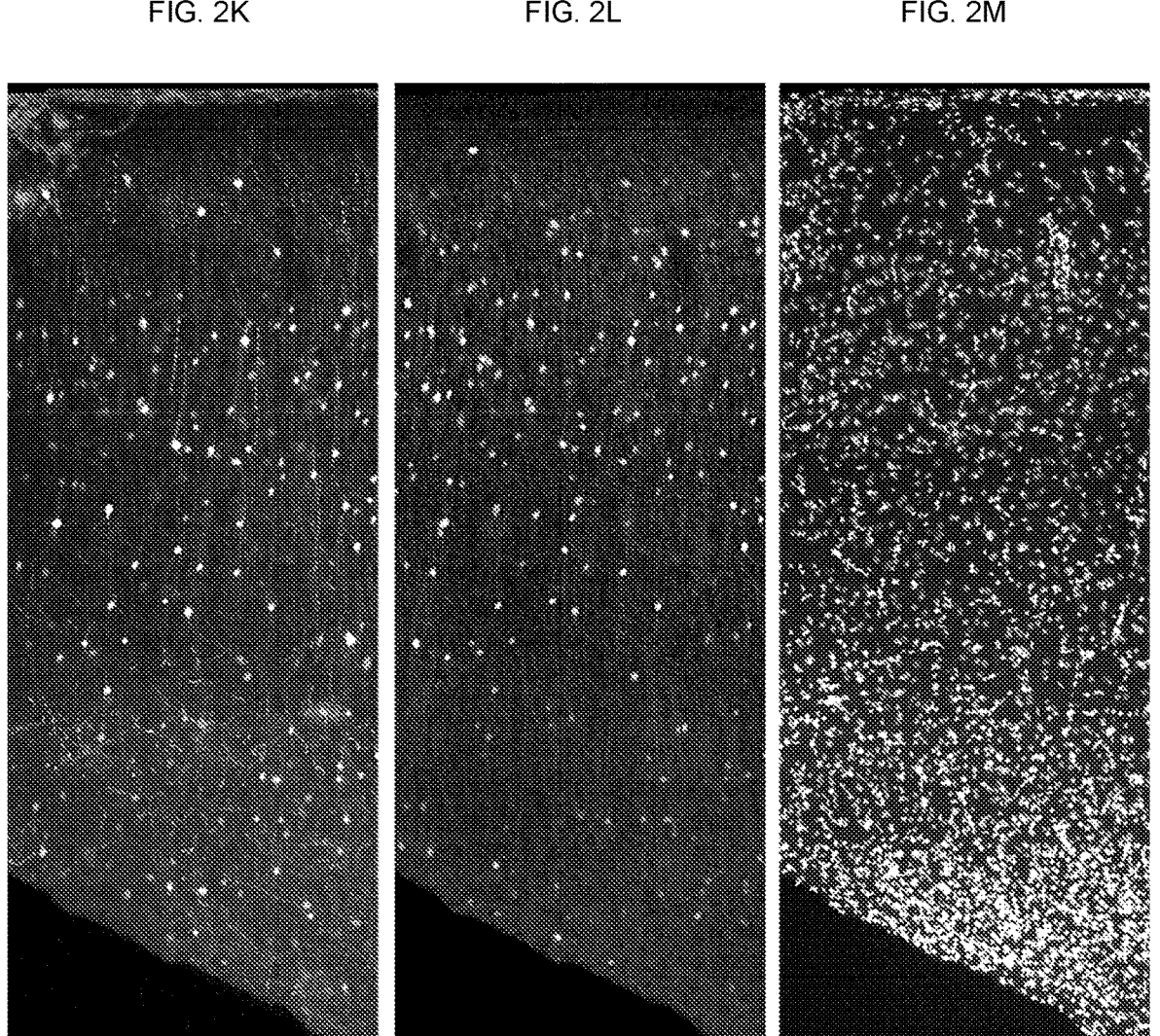

FIG. 5C
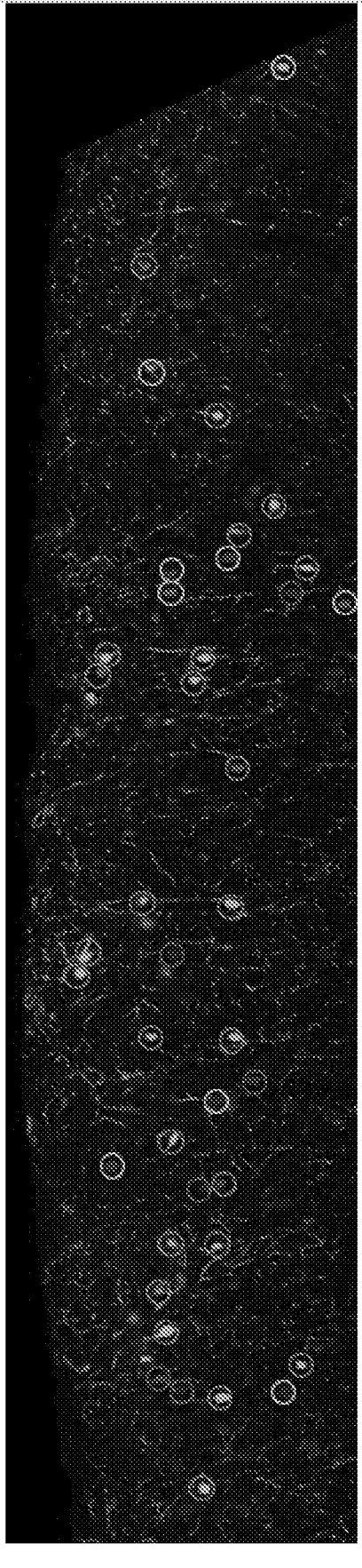
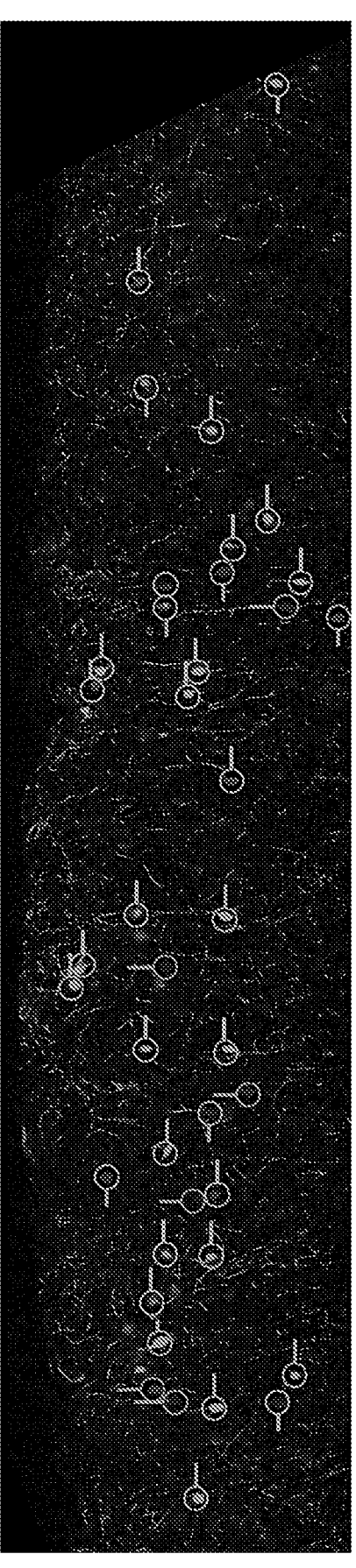

FIG. 5D
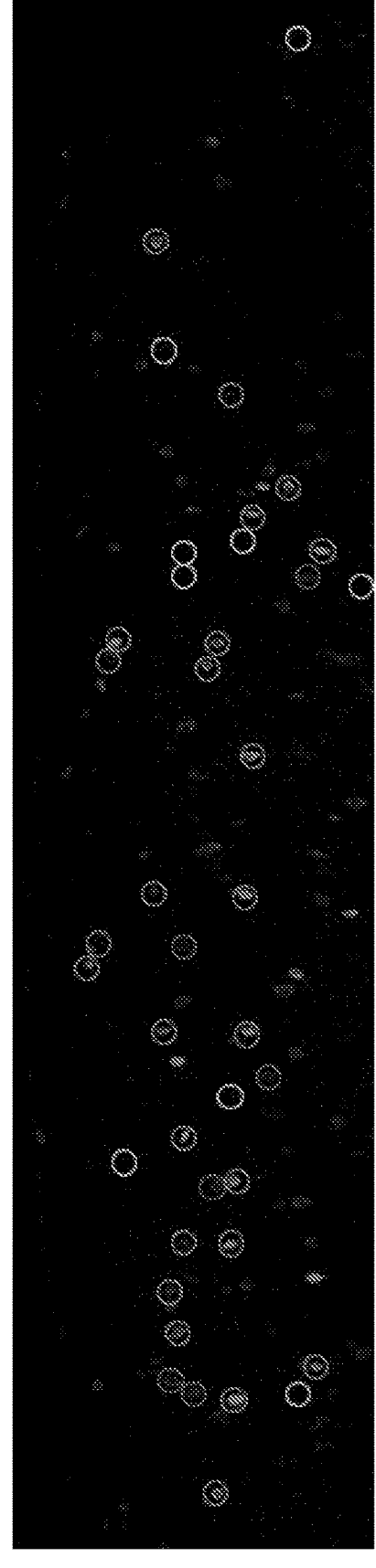
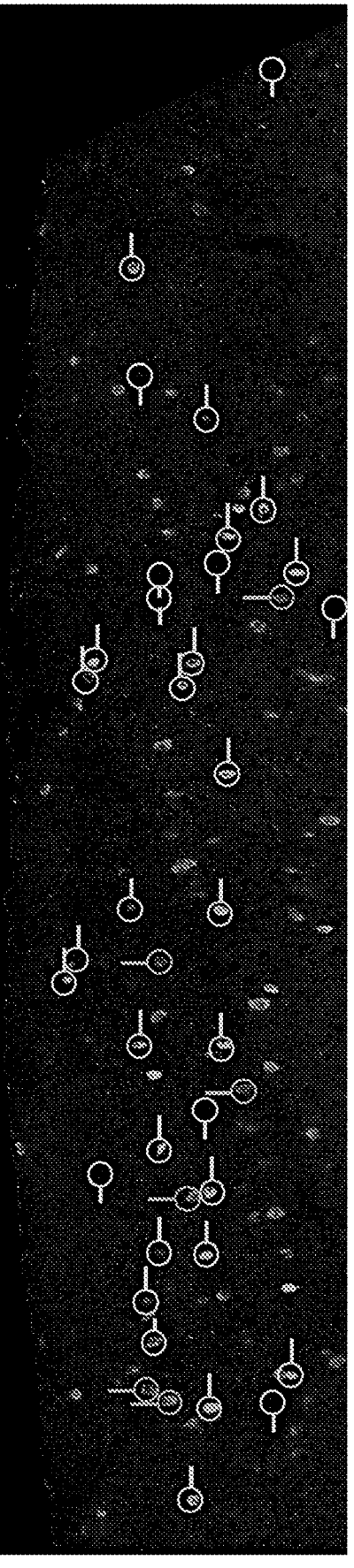

FIG. 5E
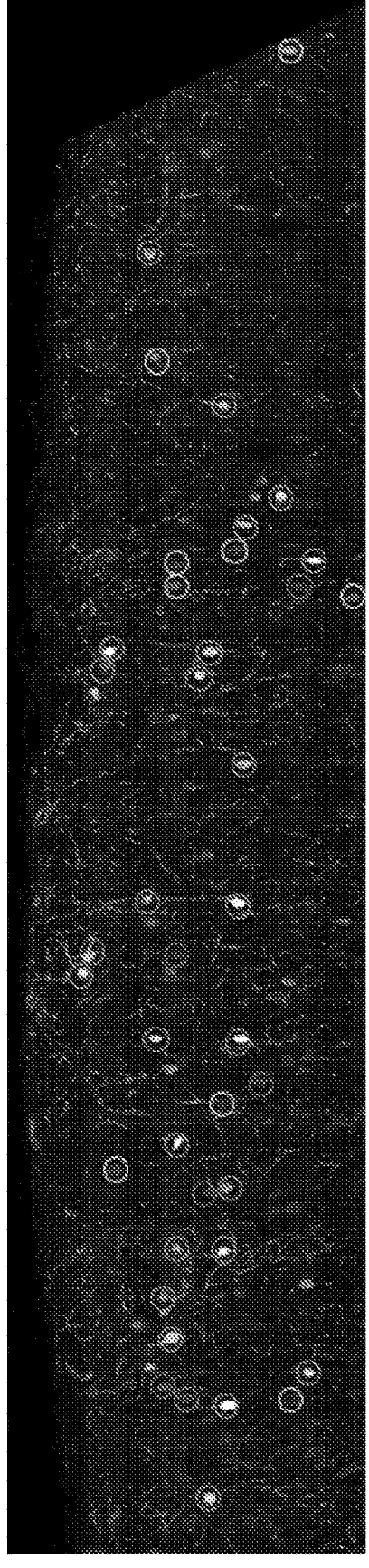
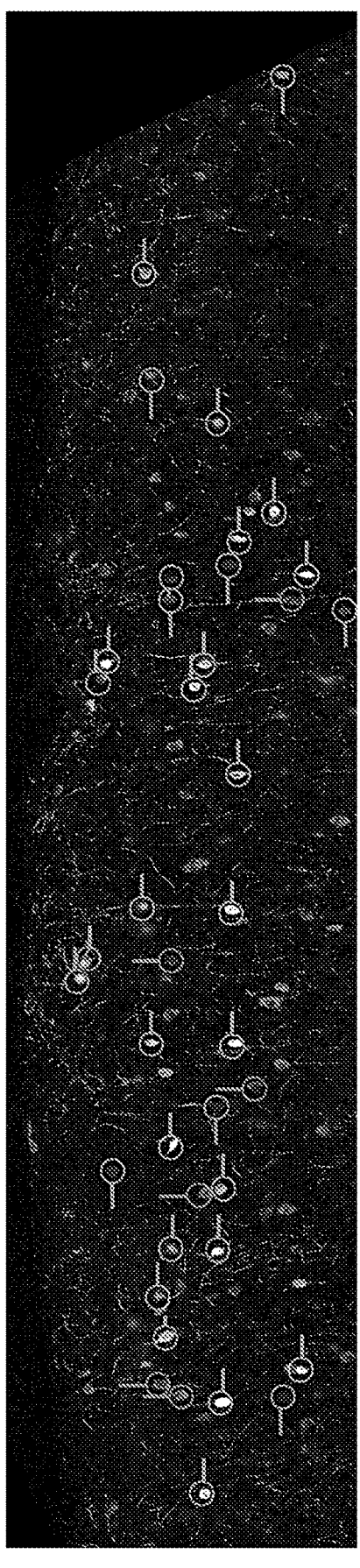

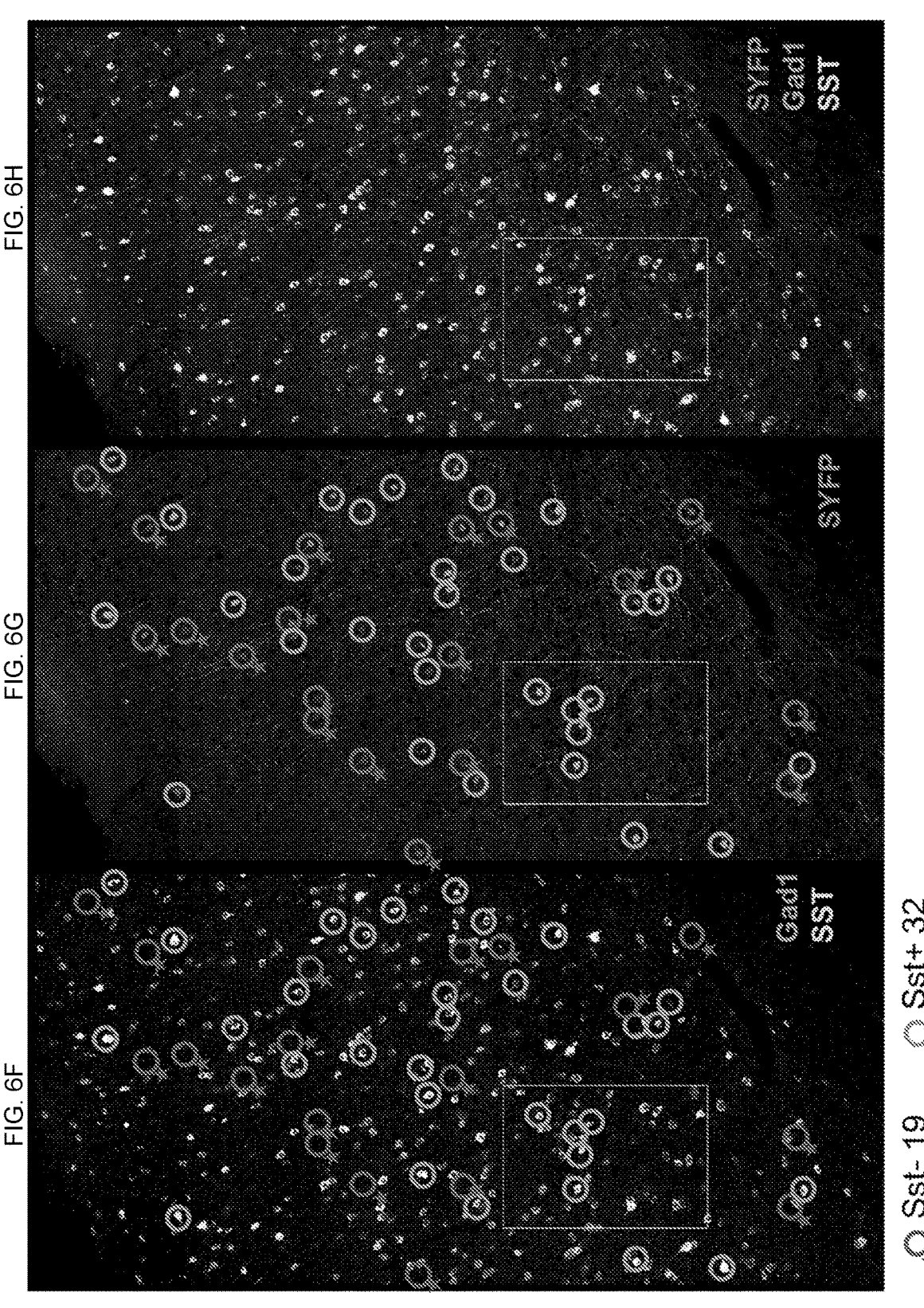

FIG. 7A                                FIG. 7B
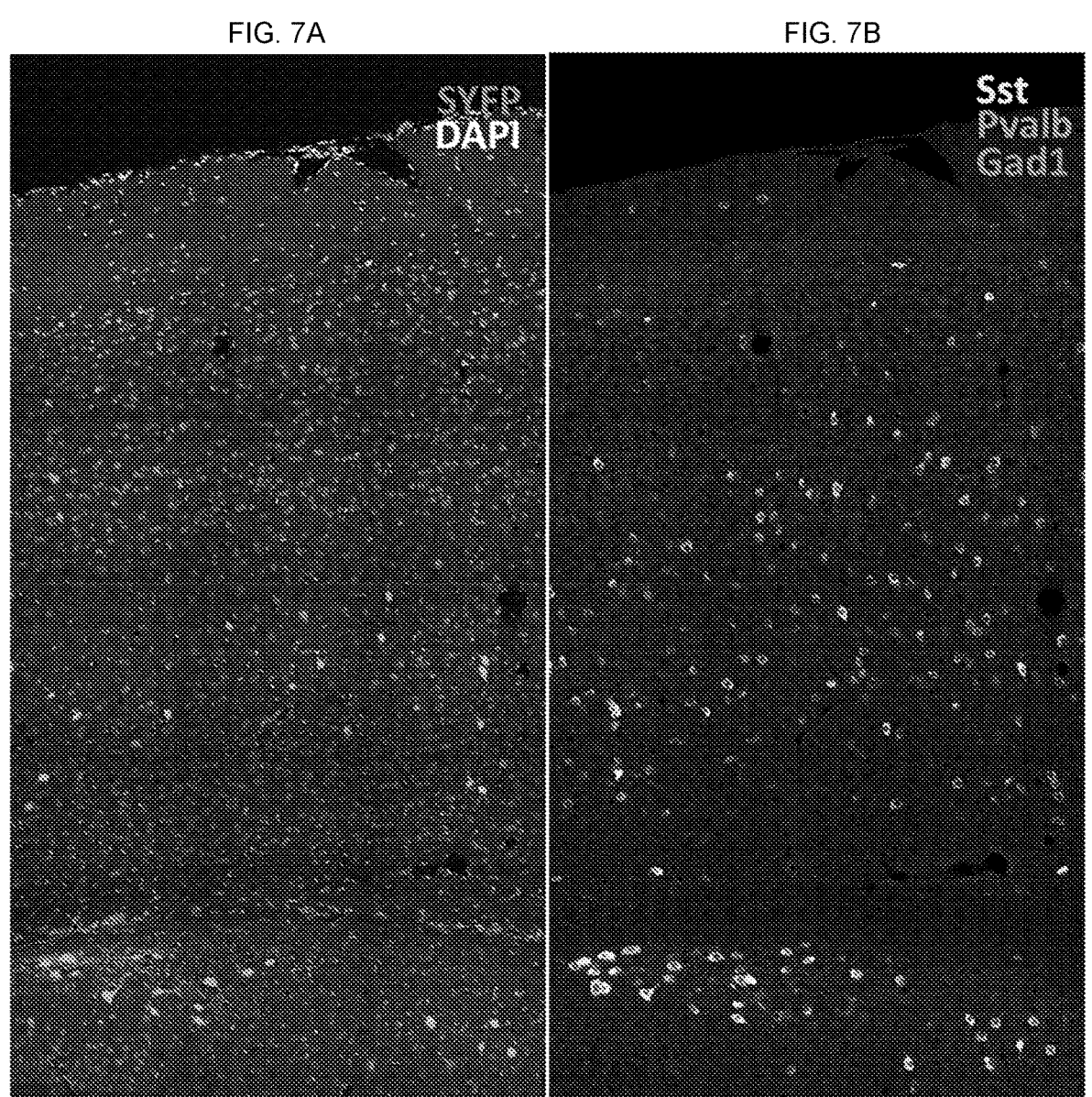

FIG. 7C                    FIG. 7D
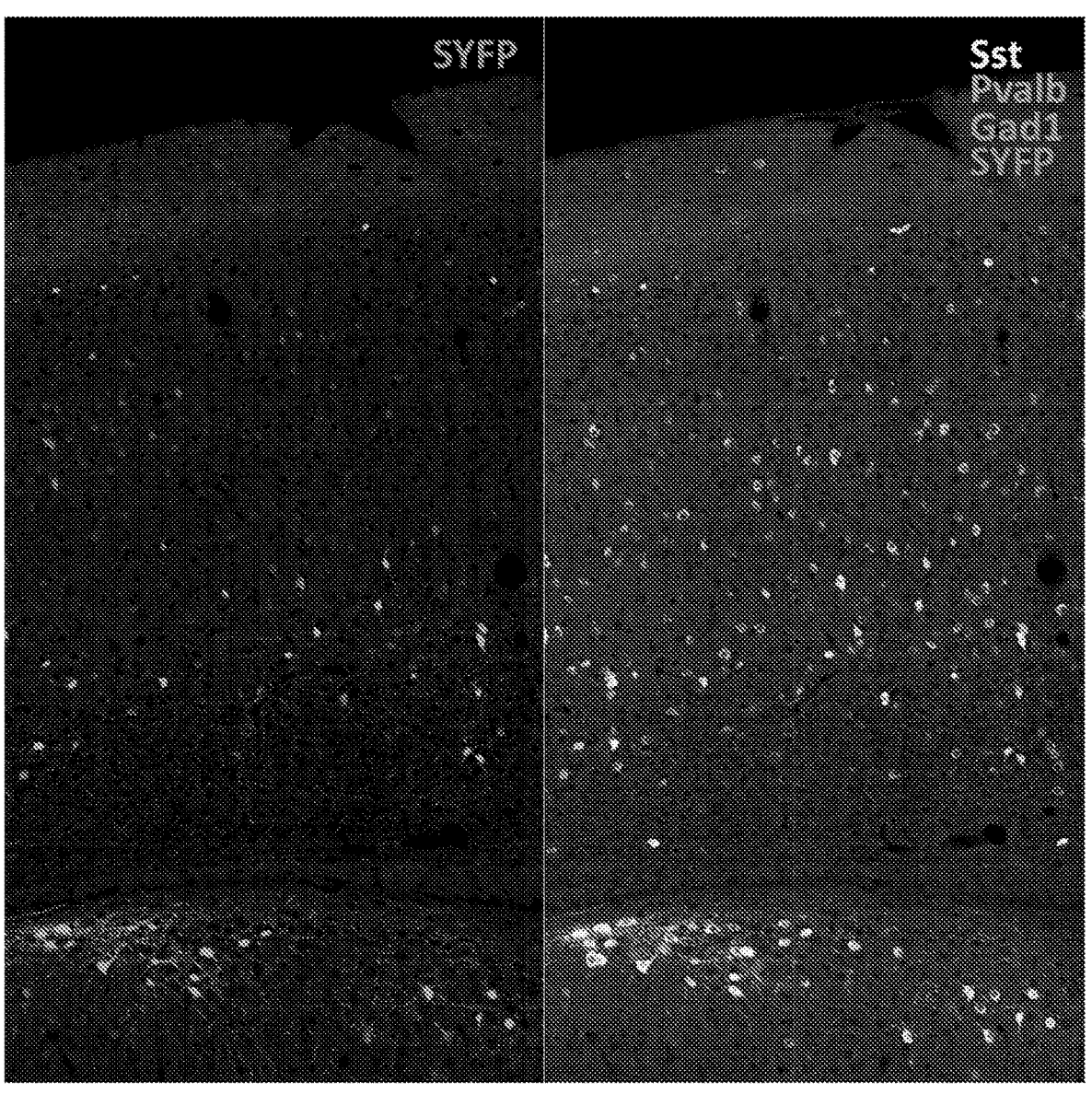

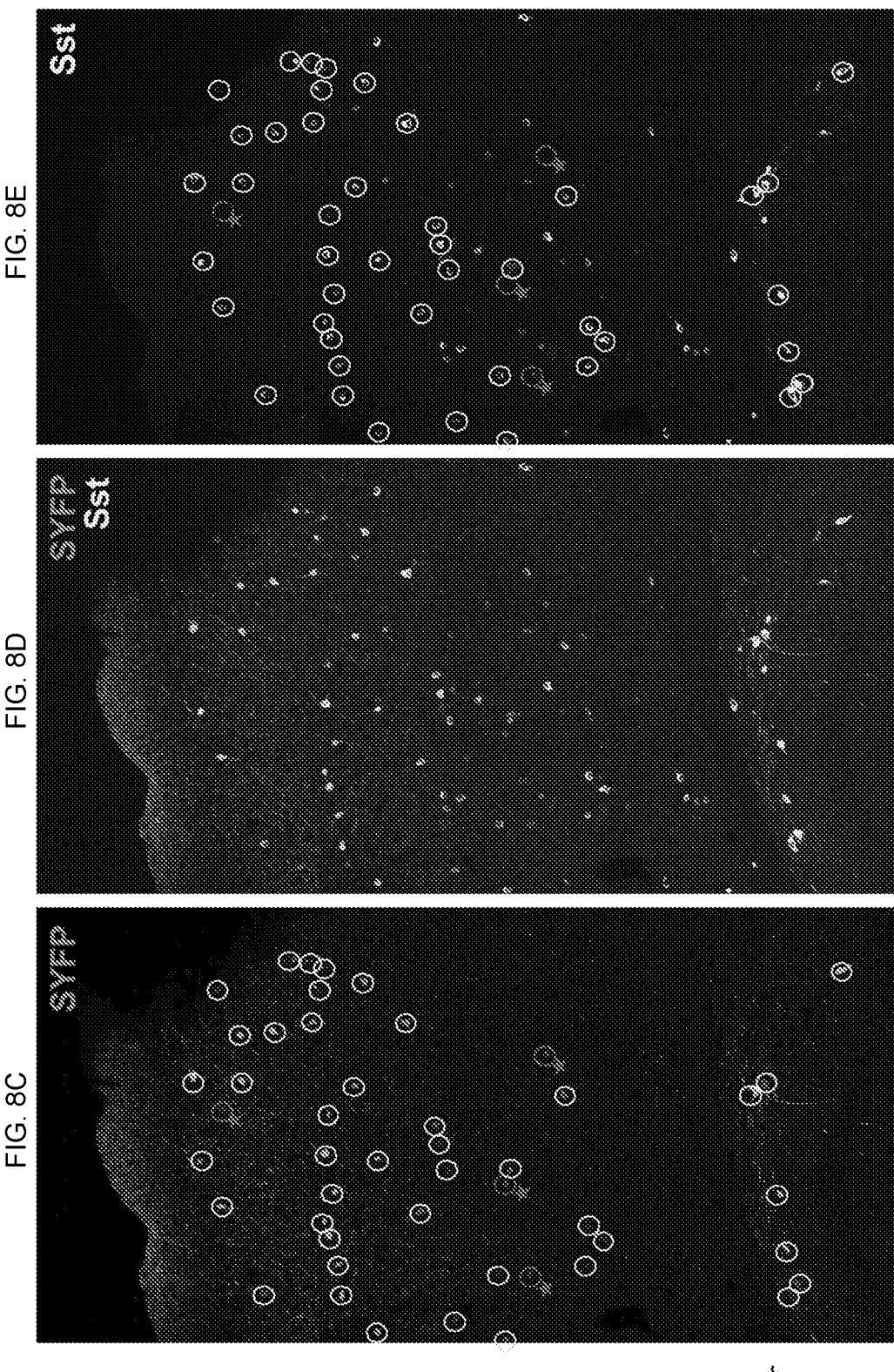

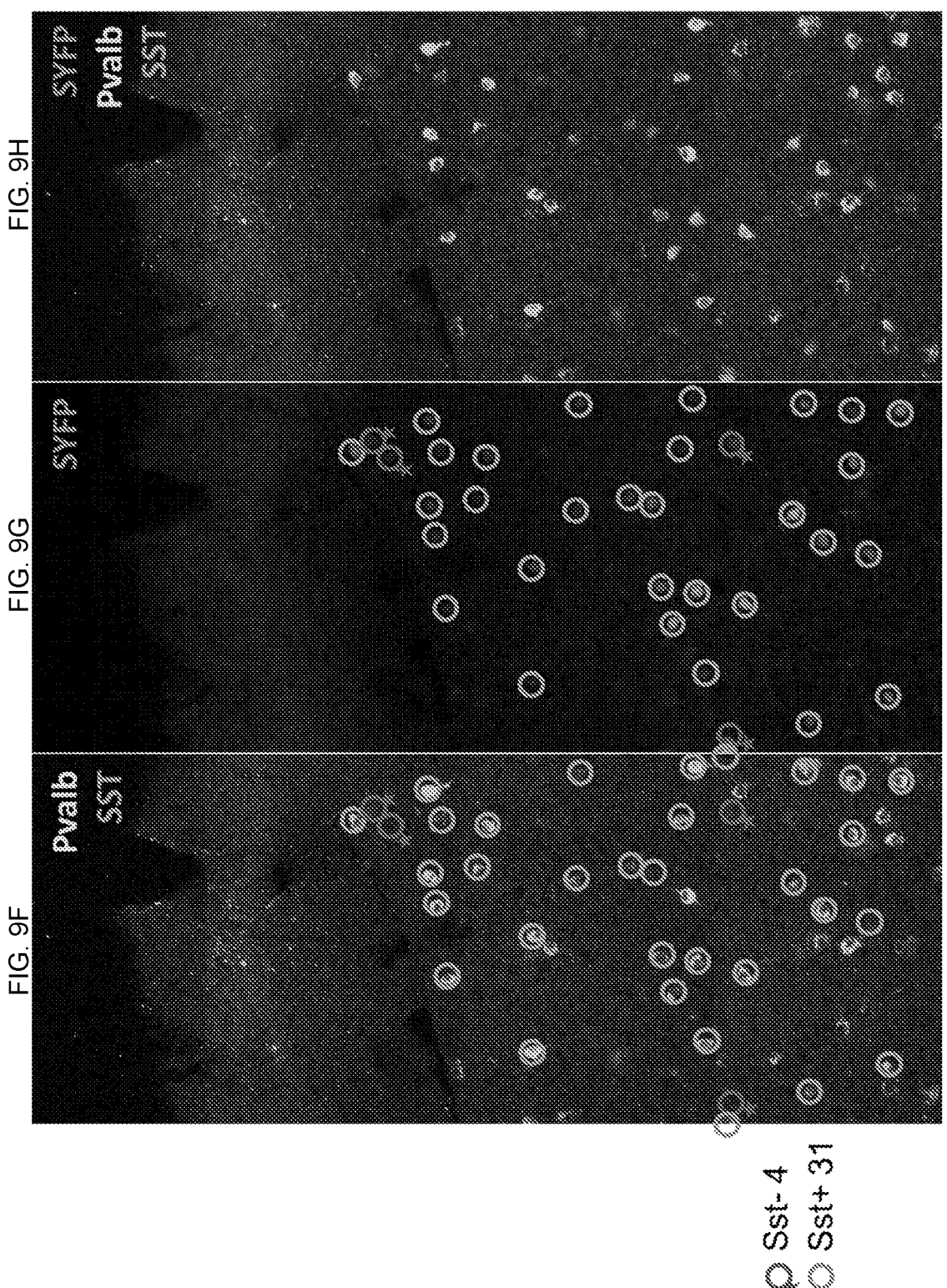

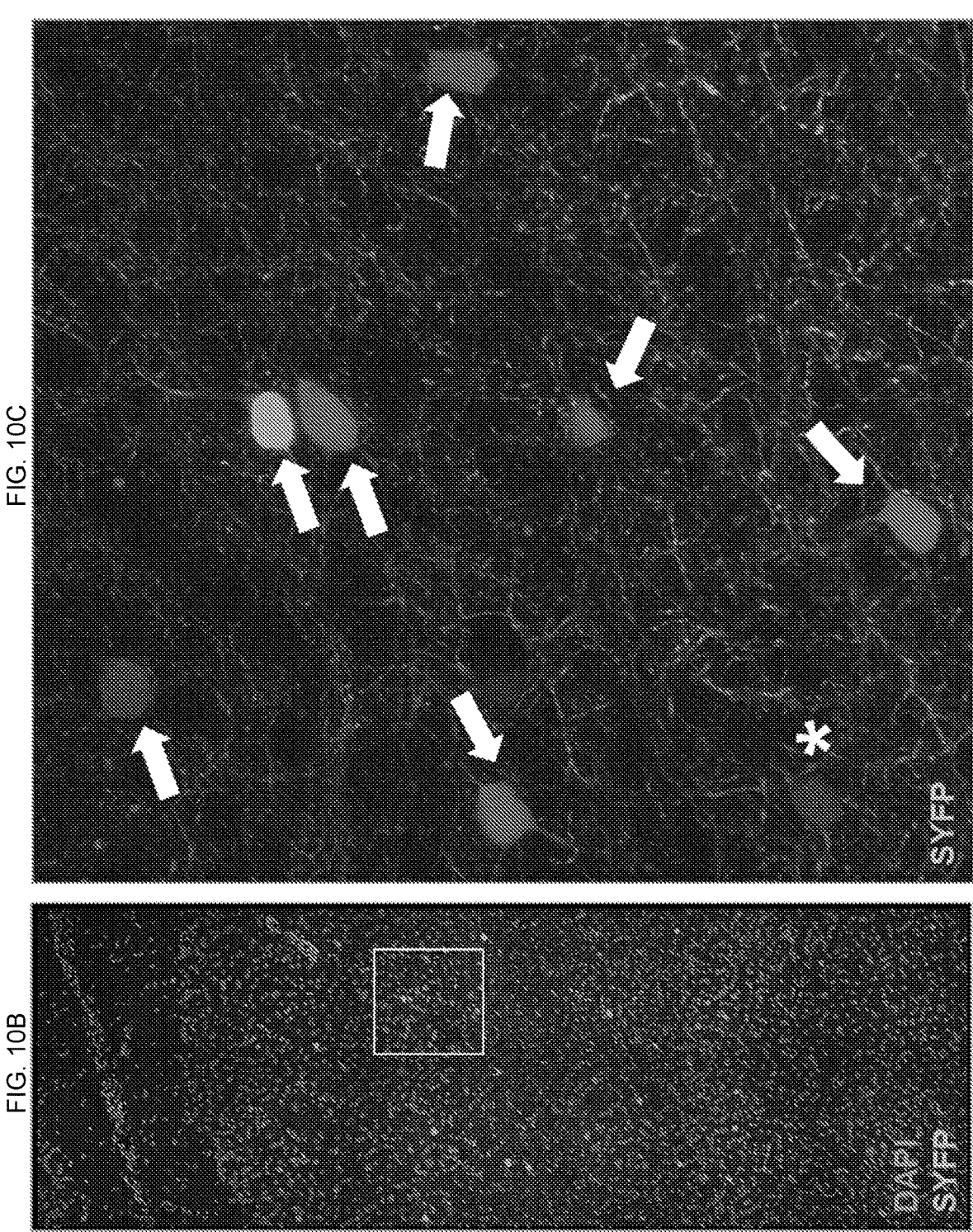

CN2367+ single cells mapping to mouse cell type taxonomy

FIG. 13

| Sequence Components | Sequence Name | Sequence Length between ITRs (bp) | Enhancer ID & Promoter | Product Class | Primary Product | Other Components |
|---|---|---|---|---|---|---|
| rAAV-hsA2-eHGT_089h-minRho-SYFP2-WPRE3-BGHpA | CN1535 | 2303 | eHGT_089h<br><br>minRho | Fluoro-phore | SYFP2 | hsA2<br>WPRE3<br>BGHpA |
| rAAV-hsA2-eHGT_087h-minRho-SYFP2-WPRE3-BGHpA | CN1533 | 2212 | eHGT_087h<br><br>minRho | Fluoro-phore | SYFP2 | hsA2<br>WPRE3<br>BGHpA |
| rAAV-hsA2-eHGT_154h-minRho-SYFP2-WPRE3-BGHpA | CN1647 | 2085 | eHGT_154h<br><br>minRho | Fluoro-phore | SYFP2 | hsA2<br>WPRE3<br>BGHpA |
| rAAV-hsA2-eHGT_226h-minRho-SYFP2-WPRE3-BGHpA | CN1719 | 2461 | eHGT_226h<br><br>minRho | Fluoro-phore | SYFP2 | hsA2<br>WPRE3<br>BGHpA |
| rAAV-eHGT_526h-minBglobin-SYFP2-WPRE3-BGHpA | CN2365 | 2204 | eHGT_526h<br><br>minBglobin | Fluoro-phore | SYFP2 | WPRE3<br>BGHpA |
| rAAV-eHGT_512h-minBglobin-SYFP2-WPRE3-BGHpA | CN2355 | 1882 | eHGT_512h<br><br>minBglobin | Fluoro-phore | SYFP2 | WPRE3<br>BGHpA |
| rAAV-hsA2-eHGT_283h-minRho-SYFP2-WPRE3-BGHpA | CN1797 | 2370 | eHGT_283h<br><br>minRho | Fluoro-phore | SYFP2 | hsA2<br>WPRE3<br>BGHpA |
| rAAV-hsA2-eHGT_090m-minRho-SYFP2-WPRE3-BGHpA | CN1584 | 2006 | eHGT_090m<br><br>minRho | Fluoro-phore | SYFP2 | hsA2<br>WPRE3<br>BGHpA |
| rAAV-eHGT_076h-minBglobin-SYFP2-WPRE3-BGHpA | CN1455 | 1763 | eHGT_076h<br><br>minBglobin | Fluoro-phore | SYFP2 | WPRE3<br>BGHpA |
| rAAV-eHGT_072h-minBglobin-SYFP2-WPRE3-BGHpA | CN1451 | 2050 | eHGT_072h<br><br>minBglobin | Fluoro-phore | SYFP2 | WPRE3<br>BGHpA |
| rAAV-3xSP10ins-eHGT_354h-minRho*-SYFP2-WPRE3-BGHpA | CN2039 | 2209 | eHGT_354h<br><br>minRho* | Fluoro-phore | SYFP2 | 3xSP10ins<br>WPRE3<br>BGHpA |
| rAAV-3xSP10ins-eHGT_354m-minRho*-SYFP2-WPRE3-BGHpA | CN2040 | 2140 | eHGT_354m<br><br>minRho* | Fluoro-phore | SYFP2 | 3xSP10ins<br>WPRE3<br>BGHpA |

FIG. 13 cont'd

| rAAV-hsA2-eHGT_121h-minRho-SYFP2-WPRE3-BGHpA | CN1567 | 2051 | eHGT_121h<br><br>minRho | Fluoro-phore | SYFP2 | hsA2<br>WPRE3<br>BGHpA |
|---|---|---|---|---|---|---|
| rAAV-hsA2-eHGT_133h-minRho-SYFP2-WPRE3-BGHpA | CN1626 | 2058 | eHGT_133h<br><br>minRho | Fluoro-phore | SYFP2 | hsA2<br>WPRE3<br>BGHpA |
| rAAV-hsA2-eHGT_219h-minRho-SYFP2-WPRE3-BGHpA | CN1712 | 1923 | eHGT_219h<br><br>minRho | Fluoro-phore | SYFP2 | hsA2<br>WPRE3<br>BGHpA |
| rAAV-hsA2-eHGT_207h-minRho-SYFP2-WPRE3-BGHpA | CN1700 | 1969 | eHGT_207h<br><br>minRho | Fluoro-phore | SYFP2 | hsA2<br>WPRE3<br>BGHpA |
| rAAV-hsA2-eHGT_113m-minRho-SYFP2-WPRE3-BGHpA | CN1607 | 2032 | eHGT_113m<br><br>minRho | Fluoro-phore | SYFP2 | hsA2<br>WPRE3<br>BGHpA |
| rAAV-hsA2-eHGT_111m-minRho-SYFP2-WPRE3-BGHpA | CN1605 | 2570 | eHGT_111m<br><br>minRho | Fluoro-phore | SYFP2 | hsA2<br>WPRE3<br>BGHpA |
| rAAV-hsA2-eHGT_110h-minRho-SYFP2-WPRE3-BGHpA | CN1556 | 2443 | eHGT_110h<br><br>minRho | Fluoro-phore | SYFP2 | hsA2<br>WPRE3<br>BGHpA |
| rAAV-hsA2-eHGT_080h-minRho-SYFP2-WPRE3-BGHpA | CN1526 | 2262 | eHGT_080h<br><br>minRho | Fluoro-phore | SYFP2 | hsA2<br>WPRE3<br>BGHpA |
| rAAV-eHGT_060m-minBglobin-SYFP2-WPRE3-BGHpA | CN1418 | 1852 | eHGT_060m<br><br>minBglobin | Fluoro-phore | SYFP2 | WPRE3<br>BGHpA |
| rAAV-eHGT_060h-minBglobin-SYFP2-WPRE3-BGHpA | CN1404 | 1984 | eHGT_060h<br><br>minBglobin | Fluoro-phore | SYFP2 | WPRE3<br>BGHpA |
| rAAV-MGT_E36-minBglobin-FlpO-WPRE-hGHpA | AiV1173 | 3009 | MGT_E36<br><br>minBglobin | Recom-binase | FlpO | WPRE<br>hGHpA |
| rAAV-MGT_E37-minBglobin-FlpO-WPRE-hGHpA | AiV1174 | 3152 | MGT_E37<br><br>minBglobin | Recom-binase | FlpO | WPRE<br>hGHpA |
| rAAV-MGT_E41-minBglobin-FlpO-WPRE-hGHpA | AiV1177 | 3208 | MGT_E41<br><br>minBglobin | Recom-binase | FlpO | WPRE<br>hGHpA |

FIG. 14

| Enh. ID | Origin Species | GABAergic | Lamp5 \| LAMP5 | Vip \| VIP | Sst \| SST | Pvalb \| PVALB | Astrocytes |
|---|---|---|---|---|---|---|---|
| eHGT_089h | human | x | | | S | | |
| eHGT_087h | human | x | | | S | | |
| eHGT_154h | human | x | | | S | | |
| eHGT_226h | human | x | | | S | | |
| eHGT_526h | human | x | | | S | | |
| eHGT_512h | human | x | | | S | | |
| eHGT_283h | human | x | | | S | | |
| eHGT_090m | mouse | x | | | S | | |
| eHGT_076h | human | x | | | S | S | |
| eHGT_072h | human | x | | | | S | |
| eHGT_354h | human | x | | A | | S | |
| eHGT_354m | mouse | x | | A | | | S |
| eHGT_121h | human | x | | A | | | |
| eHGT_133h | human | x | | S | | | |
| eHGT_219h | human | x | | S | | | |
| eHGT_207h | human | x | | S | | | |
| eHGT_113m | mouse | x | | S | | | |
| eHGT_111m | mouse | x | | S | | | |
| eHGT_110h | human | x | | S | | | |
| eHGT_080h | human | x | | S | | | |
| eHGT_060m | mouse | x | | S | | S | |
| eHGT_060h | human | x | | S | | S | |
| MGT_E36 | mouse | x | S | | | | |
| MGT_E37 | mouse | x | S | | | | |
| MGT_E41 | mouse | x | S | | | | |
| eHGT_089h | human | x | | | S | | |
| eHGT_087h | human | x | | | S | | |
| eHGT_025h | human | x | A | | | | |
| eHGT_096h | human | x | A | | | | |
| eHGT_098h | human | x | A | | | | |
| eHGT_104m | mouse | x | A | | | | |
| eHGT_107h | human | x | | S | | | |
| eHGT_340m | mouse | x | | | S | | |

A = all subtypes in group; S = subset of types in group.

FIG. 15 eHGT_089h (643 bp):
TTCCAGCTTCTTCCCTAACAATTCCTAAGAAATGTTATTGCTAGTTAGAAATGCTTTATCTTT
TCTTCTATCATATCCAATGAAGGCCTGATCTTACAGAGTCTAAACAATTGCAGTAAATACATT
CCAGATTTCAGCAGCACTTTACCAACACTTGTGAATCGCTGTCATTCTTCCAGGATTCAGTT
TAAGAGTGGCAATTACAAGTCACTTTAATGTCTGAGGAAAGGATGGAAAGCAAGCCCTGCA
AATAGAAGGCCACATTTACTCTTTTCAAACCACAGCTCAAACTATCAGAGGAAAATACAGTT
TTTATGTAAGCGCTCAAACAGTTTTCCCCAAATCTTGCAGAATCCATTACTTTTAAGAAATTT
CCACATGAATAGACCAAACGAATCAGGCATACTAATACTTTGTACATGCACACACACAAGT
GCCAGTTCCATATCATACTGTCACAAACTCTAGAGCTAAACACATTCACACGCTTCGGATTA
AATGATCAGGGTAGAAATATGCATTGTGAATAAAATAACTTACCTATCTTACCTATAAAATTC
CCCATTTCAGTTGTTTCTGCCACTGCCACTTTTGAAGTTATCCTCAACTGAACTCTTTGTAC
ACATTCCTGCAAACCAGCTC (SEQ ID NO: 1)

eHGT_087h (530 bp):
AATGGGGCCTCAGTTTCTCCCTTGGGATTAAGTGGGTACCAGGCAGGACAAAATAAGCCA
CCTGTGCCATTCTACCCTTTCCATCCTGCTGTTTTTCCACCCTGCAGCTGCTTTCTCAAAGA
ATCCCTGAATCTCCTCTCTAAATAGTGCAAGCTTGCTGTTGGGAACACCCACAGATGCACT
CTACAAATACACAACTCACTTTGAGTAATCATATTGATTCGGAATTATCGGCCATTCAAATAC
CTCATTGAAGATGCCATCTGGGATGTTATTGCTCTTCAGAGGTAGATCATATTCTGAGAAAA
TCTGTCAAAATGTAGAAATAACTCATCAAAATGGCCATTGCAGAATCTAGCTGCACTTCTTA
AGGAAGCAGACTCTGATGCTGCGGGTTTCATTGCCCCTAAGTGAGATGCTGAAGGAAGAA
GGGCTGTTTCTTTTCTGTTTTCAAGTGTCATGAGAAATTTAAAGTTCAGGAATGTGCAAGTT
CAGAGTGCTCCTGGACTCCTTTGCTCATTCAGAGACAT (SEQ ID NO: 2)

eHGT_154h (433 bp):
TTCTTTCCAGTTCCACGTAGCCTTGAAAACCATAACTTTGCAAATACAGGAGTTGTGAAAAC
GAGCATCCTAGAAGTCACTGTAAGGGCAGAATGTGTTTGGAGAAAGTCCCATTCCCAGAAA
ATTGTCACTATTTAGCCCATCTGAAAGTCGCATAAAAAGCTCTACTGTCGACATTTGTCTTT
ATTTGAGCTGATTCAGAGCTTGCTTTGTGCAACTAGCACAACCCATCAGAGGCAATTGCTT
AATATTGCAGCTGCCTTCAGTGGAGATTCCAGTTGTGACTAACAAGAAGCTGTTTAGAAAA
ATAAAATACCCTTAAAAATAAAAACTAATACACTCATGGAAACCTAAAAAAATTATGCATATG
ATTAGGGTTGTGAATACACTTAGGAAAGACCTAAGAGGGCCCTAATCTCTCACAGCTGGCT
G (SEQ ID NO: 3)

eHGT_226h (733 bp):
CACATTTCTCATGAAGCTGAGGTAGCCCAGCATTCTCTACTTTAGAAATCTGGATGTATTTT
TTCCTCATGGGTCTGTAATTGAGTCCGTAATTGACATTTGTACACTTTTAAGATAAATCTAGC
CTGTCTTCAAGTATATTTTAGATCTAGTGAAATACAGAGTACTATAGATTAGATATTCTGAAT
ATCATCTGTTTGTTATTTAGTAATGTGATATGCCTTGTGTACCCACTTTTGTATTTACCATTAT
TGCAAAATCAATCAAATGTGAGCAAAGCAAAGGCAATTTGAATGACTCAAAATTGAAATTT
GAGCTGCCAAATCAAGCAGTAAACAATTTTACCAGCTCTATTGATTGTTAGAAAGATAAG
TTATAAACTTTATTTCAAGTAAATTTCTAAAGATCTGGGAATGTGATTATTCCAAGGCAGAT
GGCGAAGACCTTTATTTCCACTGATTATTCACAGATGCAAATTATTATGCAACTGGAAGCAT
ACTAAGATATTGCAAAGATGTTCTGACATTAGTCATCTGCTGCCTTTGTTACTTTGGTGTCA
ATTTTCTTATTCTTTCCAAAGGAAGATCCTTACAGTTTGTATTCTTTCACAGCTGGGAAATGA
TCAGTTGAGAATTATTCAAACACACCAATCTGTTAACCGTACTTCTTCCCAGATAATGCAAT
ATTTTGCAGGGTGACAGGCAAAAGTGGTCATTTTTTACTTCATA (SEQ ID NO: 4)

FIG. 15 cont'd eHGT_526h (846 bp):
ACCACCTGTGTACATTCATTGGCAAGTCACCATCCTATCCTCTTGCTGCATCTTGCCTTTCC
ACTGCGATTATTTTTAGGGGTGTGTGTGCACCGCGCTGGGAATATGGCAAACGTCCCCACT
CCCCATCAGACGTCATGATTCCTGCACACACTGGGCTCTCACTAACCCCAGCTTCCTTTCC
CCTGGTGGTTTTGAGAGCATAAATTTTATTTCCAGCTGTGGGTTTGGGTCCTATGCAGAAC
ACCTCCCTGGAGAATTGCAACTAAGATGTTTATGGCAATCGCCCTGCAAGTGTCTATTTAAT
TCCTGAAAATGTCATTTACTGGTGTGTTTCTGTAAAAATCATTTCTGAAAAGTTTTGTCAGCT
TGGCTTAGCAGCTGGGGGAAAAAAGCAGCAAAATGAGTCCCCTCAATCAAGCCTGTGATTT
TTTATTTTTTCAGACTCATGAATCCTCCTGAGAATTAGGCTTATGACAAGCACCCACCCCCT
CCACCTACTCCCTGGTTTAAACCAGGTGCCTGCTGACACGAAGGAAGATTCCGGGGCATT
TTGATCCTAGTCACACAGTGTTTCTAAGTGGGCATTACTCCTGTCAATCCACAGTCTTAAAG
ATGTTCCTCAGACAAAAGATAATTAGTGACAAGAAGGCCCACTAGATTCCATGTCATATCTT
AGTTGGCGGGCCAGAGAAGGACAGGGTCTCTGGTTGGGGCCGTGTCTCCCATCGCATTCT
CCCTTTGCAGGTGCTGAAGTGAGGAAGGCCCACAGCTCAGCCAAGCACATGGGGTGCCT
CCCTCCTGGGCCACTAGCCCACTGGCCAGTAAGAGAACCAGGGAGCCTTT (SEQ ID NO: 5)

eHGT_512h (524 bp):
TGTTTGATACTTAGGGGAATAGTGGGAAAAAATAGGTGACCCTTTATGTGGAAAATACATCA
CCTTCTTTAATCAAGATATCATGAAAGAAACACAGTGGTTTCCATTCAGATTAATTTATTCTC
CAGATGTCCTGATAGAGTGATTCAGCTGTGATAAAACGGTGGAGTCAGGTTTAGTTCTCCT
CTTCGCGAGCTAGTTCTCACACAATGAGTTGAATACAGTTCTCAGAAATCATTCTTACTTTC
TTCCTCTTCTCCATCAACTTCCTCAGTCTGGGGATGAGAGATAGTATAATTCTGAGTAATCA
GGCTCCTCTTGAAATCCCATTTCAGCAGAAAACTGGCTGGGTTCCTAGCCAAAAAGAACA
CCTGCCAGACTGACTTTTCCCTAGGTAATGTAAGAAGCACAGATGTCATCAGTCACTGTTTA
CTTAACAATATATTTCCACTGGCCACAGTCTGGCCTTGTTTCTTCCATTTCTGCTTCCACCT
CTCATACAACTACAAAAACAGCCCTTGAC (SEQ ID NO: 6)

eHGT_283h (623 bp):
TAAATCAAAGATATCAGCTTGTGATAAAATAATAAATAGATTGATCTAGTATGATTGGTTTTC
TTGTCAAGTAATCCTTACTTACATAGTCTGAACACATTAAATAGCCCCAGTCACTCACAAAA
TAATATCATTATTCTGGATAAAATGTAATGAGATTGTGAATGAAAACAGTGTTGATAGTGGTA
GAGAGAAGTGCCACAGTCCCTAATACACACCAGATGTTCAAAGAATGATTGTGGAATGAAT
AAATGTTCATATTTAATGAACATTCATGTAATTGAATGGTAGGGCATTATGAGAAGTGGGAT
GAGGAAAAAGGATGAATCAAAGATGATTTTCATGTTTCTATCTTGGTAATCACTGAGATGTG
AAATTCAGGAATATGAAAAGATTCTAGGAAAGAGCTGATAAGTTTACTTTTTAAATTAATCT
ATTTGAAAGGTACCTGCATACACAGATGTTGCAGATAAATGAAAGATGAATGGAGCTGGAG
CGTAAGAAAGCTCTCTGGGCTGTATATTTATGCTCTAATATCATCTGTTTACATACAAATGG
TAAAAGCCAAAGGGATGAATAAAAGTCATTTATTCATTCATAAAATATGTATTAAGACCTAGG
C (SEQ ID NO: 7)

eHGT_090m (240 bp):
ACTTCAGCCATACCCTCCCCTTCCACTCCATCCCAAATAAAAATGAGTTACACAGAACCCAC
CAGCAGTACTTTACGAGTACCAGCAATTGCAACCGTGCATCCTTAATAGTGGCGTAATCAA
AAGTTATGATGCATTTTTCTGTAATCACAAGAAATGATACCACTTAGTGCTAAGTAAAGCCA
ATTCCCTACCACACAGAAAGGCAAAGCGCTTCCATTTTCACTTTGAAATGAGTG (SEQ ID
NO: 8)

FIG. 15 cont'd eHGT_076h (369 bp):
TGAATGAAAAATTAGACTGCCCAGATAGTCAACAATTAAAAAATGGTTAAGTGAATGATAGC
AAACGCTGTCAATGACAGCTTCAGCCGCTTAGGAAAATGTTGATGATGTAACATTAAGGGA
ACTGGTGCAAGCATTGCAATTACAATGCTTAAAAAGTGCTCTGCGTAAACAGGGCCTGGAA
GAATATAGAGACAAATGAGAACAGCTGTGGTGCCGGAGACACGAGATCTTGCTTAAAATTT
TCCACTCAGTTTTGGCAAACCGTAACAACCTTGTGGCTCTTCATATCCTTGAACCTTGAAAT
CAATCTCATTTCTAGAGACTGCTGATAAGAGTCGGAAAGACAAAGCTTTAGGTAGTAATCTG
(SEQ ID NO: 9)

eHGT_072h (677 bp):
CCTGTAGACACGGTGCCAGAACAGTGACCTCAGACCACAGCTTGGACGCTGATTACAAGT
AATCCAGCTCCAGAGGTGATAGAGTGTCCTTTCTTTAAAAAGGAGATAAAAATAGCGAAGA
AACAACACTTTCCTTAGTTCTCTGAAAGGTTGGCATTCTTCCAGAGTAGACTTATGTACTTTT
TGTACTTGGAGGAAAAAAAGAGATGGGATCTGGTCCAAGAATAGTCCTGCAAACAAGAGAA
ATATGGAGCAGGCAGCTGGAGCTGAGCATCCAAGTGGTACCACCAGCTGCAGGCCCATTA
ATTAACGATCCCTGGTATGTAGCGGTTCCCGTGACCTTGATTCTTGTTGAATTCACAGAGAT
AATTTTTACAGAGTCTCTACTTTTCTCACTGCGGTATATTTATCCAAGGAGTACCTTGCATAT
TTCCCCCCATCTCTCCAAGCAGTAAATTTATTCTAATTGCAAAGAGATACAGTAAAAGCCTG
ATTGAATACTTGGCAGTTTATAGAGATTTATTTCGGGAGCTTAAGGGGGTTTTTAGACTGTA
TGACTAGAGCAGGGTTGAGGGGAGCTGGGGAAAGGAGCCCAAGAGAAAATGTAGATTTAA
TGGATCTATAAAATGACCCTGCTGTAGATAAACGTTTGTTCCAAGAAGTTTAAACAGCCTG
A (SEQ ID NO: 10)

eHGT_354h (621 bp):
AGGTACCTCTACATTGATGGACCTTTCTCCAGAATGAGGAGCCAAAATCATCTGAATTAAGT
AGAGATCTCATTTGTCCCTGACTCATGATAATGTCTGTGCTACAGTCCTGCATTAATTACTT
TGCCCAAGTAGAAATACACTACCCATATAAGAATTTCACTTCTGAACAAAACAAAATAAAAAT
CCACGAGTGGTGACCTCAAAATGAACTGGTTAAATTTAAGGACTCATTTTTAAAGGTCAATG
TCCTTTTGCTGCAAATACAGTTCCTATGCAGATGAGAAGTTGAACCTGACCTATGGAGCCG
AGCATAATTAGCCAGCTGCACCCTCATAATAAGGTGCAGATGGTTAATTGCACCAGCAAAT
AACTGCTTACTTGTGGGCACAAAGCCTGTACCTAAATCATTGAAAGTATACTTGGGACTA
TTTATGCTCATGGCAAACAAAACACATTTCCAAGGTTTCATCTGCGAACAGATCACAGCCAG
CTCCAAATCCCTGCTTTGCGGGAGAGCCATTCACGCTGCTGAGGTCTGGTCCAAGAGAGG
GACCACTGGCCACAAAGCCACATATTAACTGGTGAAATATTTCTTGGGGTGCTGAATCGTT
GTTGA (SEQ ID NO: 11)

eHGT_354m (552 bp):
AGATTCCTCACCCCCAAGAAGTATTTAAGCAGTTGAGATGTGGCCCCCAGTCCCTCCCTTG
AACTCGACCTCGGCAATGTGAACCACAAAGCCCTGCAGTTGGAGGCTGCCGAGGTCTATT
CACAGATGAAATTTTGGAAATGTGTTTTGTTTGCCTGTGCATAAATACGCCCAAGCATACTA
TCGATACTTTTAGGTACAGGCTTTTGTGCCTACTGGTAAGCAGTCATTTGCCGGGGCAATT
AACCATCTGCACTTTATTATCAGGGTGCAGCTGGCTAATGATGCTCAGTGCCACGGGGCA
GGATCAGCTTCTCATCTGCACAGGAACTGTATTCACAGCAAAGGACATTGACCTTTAACAAT
GAATCTTTAAATTTAACCGGGTCCCCCAGAGATCACCGCACACAAGGTTTCATTGTGTTTC
GATCTGAGGTGAGATTCAAATGTGGGCCGTGGGATTCCTGTTTTGGGTAGAGCGGTTAAC
ACAGAACAGTAGGATAGGTCAGCAATTATCAGCCAAGAACAAAGGAGAACCCTGATGCTCA
GTCT (SEQ ID NO: 12)

FIG. 15 cont'd eHGT_121h (359 bp):
GAAAATGACTCTATCTGGTTTATAATTAGAAGTGAAATGATTTTAAATGGCTTCCACATGGC
TTAGTTTTCCAAGCAGTTCCAGTTACATAGAACTTCATATAAACAGATAATGAGAGGCTAGA
GTTGGAGAGCACAGTTCCTGCTTCCAAATTGGCTTGAAGTGGGGACATCTGCTCTGCATGA
AGCCTGGGTCAGGCTGCCCCTCTCATCTGTGACCTCCTGTGGTCGGGAGGGACTTGCTCT
GGATTATATAAAGGCTTCACAAGAGTACTGGAAGCGGGGACGGAATCAACTTGAGCAAAAA
ACCTAATTGGCTTGAATCTTTCCTTGACCATCAGTAATTATTTTGAGATTGAT (SEQ ID NO:
13)

eHGT_133h (283 bp):
AAATTTAGTTCTTATATTCTCAAATTAATAACTCAATGAATTGCTTTAAGTTTTGAAAATTTAC
TTTCATAAGAGTCAGATCTGAACTGGCTTCTCTATTTCGGCAGAAGCACCATCATGAATCTC
AGAACCTTTAAAAAGACACCCAAGAGTAGCAATTTTCTTTCTGAGAGTACGGATTCTATTTC
TGACATGTAATTTTCCTTATACCCAACACCAAAAATGGGGACTTGAATCATAAACATATTTAA
CACTCAGAGGAGACATTAGTAGGATCCTTTTA (SEQ ID NO: 14)

eHGT_219h (227 bp):
TGGTCTTGATCAATTGTCCCAGCAGAGTTGGTGCATGGGAAAGCCTTTCTTGGCCTTATCA
GCAGCTCAGCCTGGGAGGTTGGCCCGGGGGCTGACCAAGCACAAAATAGAAAGCCACT
AATAAGATCCAGCTGGAACAAATAGCCTCTATTTATTTTAGGAAACTAATGATATGTCATCAT
GACACATATCTAACCTTAGTATTTCTGATTGGACAGGCCAGTTA (SEQ ID NO: 15)

eHGT_207h (229 bp):
AGATGTATTTCTTTCATGGGTACCACAGCTGCTAAACCAAGCAGGTCTTCTCAGGACATAA
CCCACAGTGAGCATGTTAGGATGCAGGAACATGTGCAGGGCTCTGGCAAGAGGTACTGAA
ACATTGAAAACGGCCTTGATAGAGTATCTCTCTTTGAAAGAGGTTTAAAAAAGATACACTAA
AAGTTATTTTGCTTAACACTGTCCATATAAACCAAAGAGGGCATTG (SEQ ID NO: 16)

eHGT_113m (297 bp):
TGCGCATCCCACAATTCACCGAGGTTTGTTTTCCCCTCCAACTCCAGATGGCCTATCTGGG
GACAGCAGAGGCCCCTAGGTGCGGGCCGTTGCAGTTTTTTGATGAGCTGCACACATATGG
ATACCCGAACATCTGGAGCGGCCATGTGCTGCTTGGGGCAGGCCAGCCCTGGTGAGCCA
ATCCAGGGGCCCCGGGGTGCCGGGAGGCAGCAGGGCCCAGCCAGTGAGCGCGGATAAA
TTATTCATGAACGAGTTATTTGTGGTGCAAGGGGTTCATCAGCTACTTTGATTAAAAGT
(SEQ ID NO: 17)

eHGT_111m (844 bp):
ATAGTTGAGAGAGATCCCTACTCTCCCTGGCCCTGGCCTCCAAACCCTACCACACCATCAG
CTCTGGGGTCAGGGGATGCCCTGTGGTGGATTCTGAATTTCTGTGTATGTGCAACTGCATG
GGGAACAGGCAGATTATTGGGCACATGAGACTAGGCTGTCTGAATCTTCCTTGAGAGACTC
CCTTACCTCCAGACACCGACACTTGTCTCCCTACCCTACAGTCAGAGGCCTGTAGGACCTC
AGCACTCGAGAAAGATAAGGCTGCCAAACATTGCTGTGTCCACCTCCCAGACGGGACATC
CTGTGTGGTTGCTGTCAAGTCCGGGTTCTCCATCAAAGAGATTCTGTCTGGATTGTGTGAA
CGGCATGGCATCAATGGGGCTGCTGTGGACCTCTTCCTGGTGGGCGGAGACAAGGTACT
GTGCCATGCAGGAGTGAGTGAGCCACCAGTATCCTAGCTCTGTCTGCTCCCTTCCTCCTG
CCTTGTTAGTGCTCCACTCCTGACACCACCACTACCACCCGTGAGGCAGAGCAGCTGCAG
GTGGAGGCTCCCAGGGGGTCGGTGGGTGCACGGCAGCACACCCAGTGTCTAGAGGGT
GTCAGGCTAATTTTGCCCTGGTCTTTTGTTCTCGCAGCTGTGTGCTGTTACATGTCAAGCC
CACGTGCTCCCACATTAACTCTGGTGTCTTTGTTCCTCAGCCTCTTGTGCTGCATCAGGAC

FIG. 15 cont'd

AGCAGCATCCTGGCCACCAGGGACCTACGCTTGGAAAAGCGGACTTTGTTTCGGTAAGAA
AACCGCACACAGGTTTCTGGAGATTTCCAAAGTCTCCACAGTGTGAGCCTCAGGACTTGT
(SEQ ID NO: 18)

eHGT_110h (761 bp):
TTAGTTCCTTCCTCTCAAATAATCTGGTTGGGATGAGCCAGTCTGGGGTCCCAGGGAACAT
TGAGAGCCTACCCTCCCCACCTTCACTCGGGCCCAGTGTCCTTTGCCCCGAGGAGGGCCT
GGCTGTCAGCCAAGCCACCCCCATCCCCAGGGTCACGGTGTGGGCAGTGCAGCCACAGG
AACCAGCATGGACCCTTCATAGACCTGGATGCTCCCAACTTGTCACTCGGAGCAGAGCAC
ACTGCCATCTGCAGGGTCACCGCTGGGCCTCGTCACTTATCATGATTGCTAATTAAAGACA
AAATTAACCGACCCTGGCCTGGTGGCACCTCTCCCAATGCCTGGCTCTGGCTGGCTGGGC
CTCAGTGGGGAAGGTCTGCCCCTGATACTTGGGATGGTGGCCAGAGCGAGGGGAGTGGA
ATCCCACCCAGAACGGAGAAGGTGCCAAGCCATCTGGAAAGCTGGGGCCAGCCCGACAC
CTCACCAGCCAGCTGGGAGAAATGAGATCTTGGGCCAATCTGGGGGTGACAGGAAAGGG
AGGGTGAGATGTGGACGTCTTATTCCCAACTGTATCCCCAGCCCCTTAGAGCAGTTGTTGT
TGTCAGAGAGAACAGATGTGATGTACTGAGCATGCCAGGCACGAAGGGGGCATTTGATAA
ATAATAAATTGCTGCGTGGCTTGATGGATGGGGCTGCAAGTGCATAGTCAGTGCTCAGCGT
TTTCCGCATACACTTTCAGAATAACAAACCCCTCTATGGTG (SEQ ID NO: 19)

eHGT_080h (507 bp):
ATGCTGAATCACAGAAAAAAATCCAAAGCTTGCTCTGTGTATTAAAACATCCATTTAAAAATA
TTTAGAAAGAGCCACCAAGCACTTGTGAGCATATGTGCATATGCCCGCAGTTCCCTTTGCT
CTGGAAAATATTCAAGTGGAAAGCTACTGCTCTGTTTCATAAGTAACAGCAATTTGTGACAA
GCATGGAATATGCTGGGCATCATCAACTGCATTGTTATCAGCTGCAGTACAATTTAATTAGC
GAGCCTGAGTTTGATTATCTGCCAGTGCATGCTACCTTAACTGCTCTGTTCCAGTTTGAGG
ACTAAATTTTGTCTGATCATGTTAACATATTTGAGAGCATACCTCAACATTCTCAAGTGTTTT
GTTCGTCATATTATGCTCCCGCATCAACAAAATTGTATTAAAAGCCTTGACGTCAGCTCAAA
ATATTCTGAAGTGAATCAAAAGCTTATTATTTCTAGACGTAAGAATAACTTGACTTCATGTTA
GATATGATTT (SEQ ID NO: 20)

eHGT_060m (490 bp):
CCAGCTCCTCGTTGTAGCCCCCCACACACAAGATCAAGGGTACAGACAGCCCCTAGAAGG
GCAGGAGGCCAAGGCTCCATGGGCACCTTACTCTCTCCATTCCCCCTTGGCTCCCAGGCT
TCCCTCCCCCTCCCAGTCCTCCTTCCCCGCACGCTGGTGACTGCCGTGACTATTAATCACT
AGCCCTGTTCTCTTCCTCTCTACTAATCAGGCACAATTAGACAAGGCCTCTTCCAGCTGGG
CAGTCCCCCCCTGCCCTCCCCCTCCCTTCACAGCCCTCCCTATCCGATACCCAGGACAGC
TCTGAGGCAATGAGGACTTGATGTAAGCCCTGAGCTACTCTGGTTGCCCTGGTGCCCAGT
TTGGGGCTTTTCAGCAATCTCCTCTTTCCATTTGTCTCCTCCTTGGTCCCTGGTCTTGTCTA
GCGCTGTAGATCAGCCAATATTAGCAGGCTCAATCTCTAACCCACTGCCACTGTCAATCAA
AGGGG (SEQ ID NO: 21)

eHGT_060h (632 bp):
GAGGCATGGGTAGGAGCCAGCCCCACTCCTCAGGGTCCTCAAGGGTCCAGGCAGCCCCG
GGGGGCCAGGAGCCTGGGGCCCTGTGGGCGCCTCACTATCTCCATCCCCTATGGGCTCT
CCGGTCTCCCTCCCCCTCCCGACCCTCCTTCTCCACATGCTGGTGACTGCCATGACTATTA
ATCACTCGCCCTGTTCTCTTCCTCTCTACTAATCAGGCACAATTAGACAAGGCCTCTTCCAG
CTGGGCAGTCCCTCCCCTGCCCTCCTCTCTCCTCTCCCTGCCCCACCCAGCCGCCAGCCA

FIG. 15 cont'd

GGACAGCTCTGAGGCACAGAAAGCATGCAAGCCCTCTCTCTCTCTGGCTGTCCCAGGACC
CAGTTTCGGGCTCCTTAGCACCCACTCCTTCTGTCCCAGCGACCTCCTTAGCTCCTTCTCT
TCCCAGTGTGTGGTCAGGCCACTACTGACAGTCTCTGCCCTCCACCCCCTACACTTGGCC
CTGGGAGGAGCTACTCCACACTCCATCGAGCTCTAAGAAGGCGGCACTGTCCCTGGCTCC
TCTGTCCTCCTGCTCAGCCATCCTCAGCATGTGCCTCTCATCACCACTCTTGTCACCACAG
ATCGCCGAGCAGCTACTCCACACTCCATC (SEQ ID NO: 22)

MGT_E36 (460 bp):
GAGTAATAGGCAGATCTCTATACCAGCCTAACTTCTCCCTACCACCCCCCTCCATCTTCCTT
CTTCTTGCAGTGCAAACGCCAAGTCATATGGACTTGGATTCCGACTCTCTTTTCTTTGCCAA
GACTCATATTATTGAGCAAGTGAGGAGAGTTGAGCCAAACTGAACTAAGTGACGCCACAGC
ACACTGTGTAGTGCAGAGCTAGCACTTTGGATATTGTGTAATTAAGGCTTTAATGAACATCA
CATAGAGAATTAGACTGCAGATTGTGACACAAATAAATCTACTTGGCTTTTAGAAACATTCC
TTAAAAAGAAATATTTTGGTACCAGAATGTGTTCAGGAGGGAAAGAGCCTGTGCCCTTGAC
ACAGGAAGTAGATAACACCTGTCAGAAGAATCGAAACCACCTGCTTGGGTGCATCTGGTAA
TAAGTTTGCAGCTGGTGCTACACTCTACC (SEQ ID NO: 23)

MGT_E37 (604 bp):
GACAATCATGAGAGTACGAAAGCATGAGAGATATTATTTCAACAACTTATTCTTTATTTTAGA
GGAAGAACATCTGAGAACAAAAATATCTATAAAGGCATGATTAGCATAGAAAACAAGGGTAT
TGATCATTAATGGCACCTAATGTCATAGATAAAAAGAGACACTCAAACTTTATACATCTCCA
AATAGAACACTTCACAATCTATGAAGCAAAAATAAAGGAAAAAAAAAACAACACAAATCTAA
TCTTACAGAACTAAGTACCAATTTACAGCAAGTGTAGACAAAGTAGCACATCAAATGACAAT
AGGAGATGCCATCAAGCGAAATCAATTCTGGGAAGGTCTTAGAGAACAAGCAATAGTACTT
CTTGAACACATCCATTATAAGTGAAAATAAAATGCTCTAGATAAAAAGAGCCTTAGAGATGA
ATGAAGGATAATGAATCTGCTGCTTAATCACAAACATTTTGGTGATGAGATGATCAAGAAAA
CAAAAAGCTATTACTGAAATAGCTGGAAGTGTAATTAGTTACTGTGGAGAAGGACAGAGTT
GAGAAGAAGTAAAAGGATTGTGGTTGTGATAGATGTATGCCAATGTC (SEQ ID NO: 24)

MGT_E41 (659 bp):
CCTCATGGTATTAGTAGTAACCATTTTGGAGAGAACTATACCACTAATCCTTACTACCCCCC
CCCCAATTAATGACACCCCATTCGAGCATCTCCAATGAAAGGCGCATTATTAATATTCAAGG
AAAAAAACCCTTGTAACCATTTTAGCAGATACAGCTAACAATGAACTAAATTTGCTTTGTGC
AAGACAGAGAGTGAGCATCCCAAATTAGTTTATGTAAAAGCTGAAATCCTCCCCTGAAAGG
TCTCAGTACCATCCTCAAAGAATATCCCGATCATCAGCAGTGCCGTCAAGATTCCCGCCAA
CATTATCCCCTTTGTTGTCTGAAATGTAGAATCAAGCACATCTGGCAAATGTCCTGGAGCTC
ACAAATCTCTCAAACGGCGTCTAATTCCCAGTGGTGAAAGAGAGCGCCACTGCCTAATCGT
GCTTCTCTTCAAAACAGCACTGACTTTCCTTCAATCAGAAACAATGGCTTTGCTTTCTTAAAA
ATATCACACGCCAGTGATTATTTGCAGAGAGGCCCATTTTATGCTTGAACCTGCGGGTCCC
AGACAGAATTCACAATTAAGACCGTGAACCTCATTTGAATGTACGCTTAGTTCAGTGGACA
GTGGGAAGAAAGATTGTGACCTGTCTTCTGTGGTTTGGAGGCT (SEQ ID NO: 25)

eHGT_025h (475 bp):
CCCAAACTCTCATCTGCTCCAAGCTGTATAGAAGTTTCTTTCAGAGTTATTTCAGTTCATTTC
AATGAAAAAATTATCAAATATAATAAAACATTTTTGGAAAGACAGGAGGGATTTGGGACATT
ACAATTGGTATTAAAAGAACTAATGAGCTTTGCTACTGATAAAGTATTTCTTGCATTCTTTTT
TGGTTCAAAGAGTGATACCCAATTATTAATTCTTAAGCACATAAATCTTTTCCATTTTTGTTTT
TCCTGCTCGGTGCCTGAATTTTCTTGGCTACTACTGAAATGTGTTGAATAGGCTGATTCTAC
TTTTTATCTGCATATTCTATGGATCTAGTGGCTCTGAATCCAAGCCACTATAATAATGATGG

FIG. 15 cont'd

AAACAAAATATTTCTGATGAACATATAACCAGATATTGCTGACAAATAGAAAAAAGAACAGG
CTGATGGGGGCCAGACTGTGCATATGATCTGTATTCC (SEQ ID NO: 132)

eHGT_096h (371 bp):
CAGAGACCCAGTGACTGATGTTGTCCCAGAAAGTAGAATTCTTGTGATGCATAAATGATAG
CTGATCCAGCCAACACAACTGTTGGAGGAATTATAGCTTATAGAGTTGCTTGGCAGATGAA
ATCACTTGACTAATTAGAAAATAATGCATTATGCTGTGCTAGAAAAATCACAGAGCAGCAGA
AGCGGAACTGTGTTCTGGGTTGCTGTGGGCTGCCAGTCACAATTTTGAGCCTGTGCCTTG
CATTCTTTACCTTTTTTTTTCCCACTATCCCTACAGCCCAGAAATTGAAACAGACCCTGGAG
CCTTGTGATACTGAATATCCAGCATTCGTCTCTGAGCGCACCATCAAGGAGACTACAGGGA
ATAT (SEQ ID NO: 133)

eHGT_098h (869 bp):
TCCCTGAAAACTAGCATCGGGGAATGACATACAGTTTGATAACATAAGATGCTTAGGTTTTT
TGGCTCAAGTGAGATGTTCAGAGCTAATAGCCCTGCGAGCTGAGTTTTAGCTGTGATCTGC
ACCTTGAGATATCCGTTATGTCTGGATCAGGAAAAAGGGAAAAGAATGAGAGCTTATTTCTA
GAAAGGTTTCCGATGAGCAGCATTTGTCATTGAAGGGGAAGATGGGTATAATTAGCTTGTC
AGTCTAGTTTGGGCTGAGCAGGCTGTCTCTGCTAAGAAAGATGGACTAACTGCCAGGGCC
ACTGACAGGCAGTCGATAGCGCAGCAATTAATGTCATAAATAATTCCAGAACCAATTACATC
AAAATGGACTCAGAGCTTTAAAAAGGTACAGAATTCTCTTATTCTTCCTGCTAACAGCAAGA
AACAGCTTTCATTTTTCTCTGTAATTACTTTTCATTGTATATAGCAATACAGCTGAGCTTTTCT
GTCCATATTTAAGCCTTGTCTTTCTCCAAGCCTCTTCCCCCACCACCAGCCTCCCTCCTTCA
CCCCACAGGATAAGGCTGTTAAAGTTGTTCTTCCCTGCCAGAGCAGTGGGGTGAATGTATA
ATCTTTTAACTTGGCTGTTGCAGGAGAACTCCAGCTACACCTAAATGATTAAGAGCCAAGTT
TTTGAAAATGTCATGGACAATGACAGCACAGTGCCCCAAACAATGGCATTTGGAAATGAAG
ACATTTGTGAAATAAATGGATTTGTCTTATTATTTTAAAGGTTGCTGTGACTTTGCTTACACT
GAATTTATTGATTTTTCCCCCTTCTCCTTCTCCTTCCTCTTCTTGTTCTCCTCCTCCTTCTGT
ACA (SEQ ID NO: 134)

eHGT_104m (269 bp):
AGTGGCCTGGTATTGGGTGGACCCGTCACCTGAGACAAGGACTCCTGACAACCCAAGTCC
CCAGAGGCCTCCCTGCCCTTCCCTCATTCCGTTGTTCCACTTTTAGAGAACCCCGGGACTC
CTCAGCAGGCAGCAGCCTATTTTGCCAGGATCCACATAGAGCAGTGCCTGGCACAGTAGC
GGTGAAGCGGGAAGTGGGTCTCTGTTGGCGGGCACCGTGGTGCCCGGAACTCGCTATTC
CTCCCCAGTGTTAATTATCAAAATTAACC (SEQ ID NO: 135)

eHGT_107h (1084 bp):
ACAAGTTTTCCTGTGGCAGAAAGATGTTTCCATTGTTTTGTTTTGTTTGTTTTGTTTCGTTTT
GTTTTAAATGCATCTCTGCCTTACCTTACTTGCGGGCCAGTGAGCTAGCCTAAAATCGAAG
CTCTGTGAAGCCCGCTCTTGCCATTTTATTTTTGAAGGCTGTCCCTTGGCCACATCTGACC
CACCAGCTCCTGTCATTAGCATCTGAGTGTTAAGCCAGAGGAACTCAATCTGGGAACACCA
CCAACGTGGCCAGTAAGCTGCAATTTAGTTAATGTGCACTCCTTGTAGGCCCTGGTTTTGG
CCCGAGTGTATTTGGGTAGAGTGTGTGGTGGTGATGGTAGGGAGCTAGAGAGGAAGGGG
AGGGTGATGGACTCATTTGCAAGAACTGCCCAGCTGAGATAACATTTAAAATGAACAGGAG
AAGGTCCAATGCTTTGTAATCCTCCAGCAGCTGCTCATTTTGGGTTGGGATCAGGAAGGAG
CACTTTGCCATTAGTCCCCGAGCCAAAAGTGGCCGGTGGTGGTTTCTGGTCTCCCTAAGC
CACCTCCAAAGGGGTCACTCAGCTGTGTCCTAGGGAAGCGAAACAAGAGAAAAAGAACAA
GATGGCTTGTACGCTCCATCCATGTGTGTGGCCCCAGGGATGCCCCTGCAGATGGGCCTG
GTTGGAGATGGTGATATCTTGGATGGGTTCACTGCAGCTCCGTGCCCGAAAAGGGCAGCT

FIG. 15 cont'd

GGTGGGCTTGTTCCGCTGTTCTTCAGCCTGTCACTGCACCACTCTTAACAAGTTATCCACA
TCCCAGAGATGCAGATTATGCCTCAGCTTAGAGGGCCAAGCTTCCCTCCAAGAGACTGAG
CCTGCAAAAAGCTGCCAGAGTCCCTGTAGCCTGCCCAGATCCTGCCTGAACCCAGCCCAA
AGAGATGGTTGTCATTCCAGGCAAGGGCTCACCCGGGCCAGATGCCTTCCTTCCCCAGGC
CTGTGGTTTCTCCCACTTGAGGAAGAATTGCTATTTCTTTTGCTGTATCATTACAAATAAAAC
AAAACTGACTTTGAACATATTAATGATAACAGATGGCTTCATAAAATGTAAA (SEQ ID NO:
136)

eHGT_340m (807 bp):
TACCTGCCATTCCAACTCTGGCCTCTGTGAGCATATACACACACATGCGCACATTAACATC
CCCCCCCCCCCACACACACCTCAGGCATAGACATACACTTTTAAAAAGGCAGCCACAATAT
CAATTTAATTCAGATAAAATCACAACACAACCTTCTTTAGTACTGAGTCTTACAAAGTTGTAT
GCTTGAGGTGTCCTGAGAACCCCACTAAGGTAATGGCTGTAACATTCCTCAGAGGTGAACT
CATTTCCATGACTCATTCTGAAAAGCACAGGCTCCTTGTCCTTTCACACGCATCACAATGCA
ACCTAAAATAGATCCTCATCAGCGCCTCTTTCAGGGTTATGAATAGCACTACCTTGAAAAGG
GCCAAGAGGGATGCATGCATGGGATTCAGAAGGAGGCATTCAAGAAAACCAAGCAGGAG
GCAGGCTGCCTAAGTACTTTGAGCATGGAGCATGACGGGACCCCCTCTGGCTCCCACGCA
GGCAACCAGGTGCCACACTCAATGGAGATGGAGTGGGTGGGAGCTCTGAGAAGGAGCTG
CATCTACTGGGCAAAGTGGTTGAAAAACCCGAAGAGGACCTAAGTAAGCATCGGCTTAGA
CTGCTGACCCCGTTCTCCACCTCTTTATCCACCCCCCTTTCTGGGTGGCTGGAAAAATCAA
ATGGTATTTCTCTACCTTCCTGATTGTCACATTCAATGTACCCAACGGAAGGAATTCACAGT
GGGCCACCTCCTGCTCAAGAAGCCAAGGCACTTTGCATTCTGCCTCTTGTCTTTGCTGGGA
GAATGGCATGACAA (SEQ ID NO: 137)

eHGT_528h (680 bp):
ACAAGCATGACTATAAAACCCAAGCAATGTTTTTGCACCAGATCCCAGAAGTAAAGTTTATT
AGTCAGTGGAATTCTTGTATTAGATTTCAGAAAGCACCCAACTACCAAACGAGAATGAGGTT
CCTCCACCATTCCAGCAGAGGGCACACTTTTAGCAGCTTTTGTAGCTGGTTGCTTCCTGGA
TGTTTGAATACCAATTGATTTGTCAGCAATGAGCCATTGCAGCAATGCTGTCAAAGTCTGGA
TCCCTGACTGGTGGCTGCAAACTGTTTATTAACAGCTTGATGCTCATTAAGGACATTGAGC
CAGAATATAAGTCAACTGTGTCACTAAGTGTGCTATTTAGCATAGCTGGCATTATGTGTGTT
GTGGGAGAGGCAAGACTCTCAATGAAAGAGGCAATACATTGATTTTCATTCTGATGTAAGC
CATTTCACTTTTGATTGGGACTTCACAGAATTCTTTTCATAGCTGGCCTCTCTCCTCATTCTG
ATGGAAATCTGCAAGCTAAAGGCAGTCCTGATGATAGGAAGCAAAACAGCAACCTCAGAAG
GATTTCAAAATGATTCATTTTCTTTACAAAAATATATATCATTAGCCTAACATAAGTAAGTGTT
GAATATTATGATCTTGAGAATGAAAAGATATACCTTTAGTGTTGCTGTGACTGAAGATGA
(SEQ ID NO: 138)

eHGT_515h (596 bp):
TCCACCATTCCAGCAGAGGGCACACTTTTAGCAGCTTTTGTAGCTGGTTGCTTCCTGGATG
TTTGAATACCAATTGATTTGTCAGCAATGAGCCATTGCAGCAATGCTGTCAAAGTCTGGATC
CCTGACTGGTGGCTGCAAACTGTTTATTAACAGCTTGATGCTCATTAAGGACATTGAGCCA
GAATATAAGTCAACTGTGTCACTAAGTGTGCTATTTAGCATAGCTGGCATTATGTGTGTTGT
GGGAGAGGCAAGACTCTCAATGAAAGAGGCAATACATTGATTTTCATTCTGATGTAAGCCA
TTTCACTTTTGATTGGGACTTCACAGAATTCTTTTCATAGCTGGCCTCTCTCCTCATTCTGAT
GGAAATCTGCAAGCTAAAGGCAGTCCTGATGATAGGAAGCAAAACAGCAACCTCAGAAGG
ATTTCAAAATGATTCATTTTCTTTACAAAAATATATATCATTAGCCTAACATAAGTAAGCGTTG
AATATTATGATCTTGAGAATGAAAAGATATACCTTTAGTGTTGCTGTGACTGAAGATGATAT
TTGACCCTTTAAAATGCATTAAGTTTCTTTCTATTGGCC (SEQ ID NO: 139)

FIG. 15 cont'd eHGT_682h (749 bp):
AAGACGGTCTGATTGCAACCCTCCAGGAGGAAAACAAATTCACAAAGCAGTCCCAGGTTG
CCAGTTCTCAAAGTCAGCAAACCAAATCCTAACGTGCAATCTTCCCAGGTTTTTCAAAAGCC
ATGGGATTGATAGTCAGTGGGGAAAGGAAGAGGTGTCGAATCCAGGCCTGATGGATGGGT
GCAGAGGCAATCAGACGTGTTTTCAGAGCCACTGTGCTCTGACACCTGCCCCCATTTTCCA
CAGAGTTTGGCTCTGAATGCGTCCCTGGACCACGCCCTCCGTCTCCTTTACCTGGCGTTC
CTATTCTTGTAGAAAGGAACACAGCCTAATGATGGATTTGTTCAATGTGATCATTCTCGCTT
ATGTACAAAACAAAGGCAGGATTGATGAACTCCTAAAGAAGCACATTCACAGGCCTGATCT
ATGCCTCTTACCTTGGAGCAGGCAGCAAGTACAGCCTCCAAGGGAATGTCAACATCTTTGC
ACTTTGTCAATAGGACCTTGATTCTCTAAAGGCTGAAAGGTGTTTTCATGGGTGAATGCTTA
GAGCCAGCTCATGGTTTTCCAAACCCCACTCAAAGCTTCCAGATGACTCTTTTTGCATCTGT
GAGCTTCTTTCATCCCTAGATATCACCCTGGGGAGAGGGCAGGCAAAAGATGTTCTCTGTA
CTTGCAAGGAAGAAATGGTAAAGGCATGGGGGTCGAGTGGGGGCTGGGGACTCCTATGTT
CCGGAAAGAGCGAGGTT (SEQ ID NO: 140)

eHGT_600m (893 bp):
AACAGGACTTCAGGGAAGGCCACGGAGCTTAAGCAAGAACTTGCCCAAAGTTTAGAAAGA
AAGCTCCAAGTTACAGAACCAAGTGCCCGACCCCAGAGTCTTTCTTTGTCTGACCTGAGGG
CTTTCTGTTAAAATCCTTATACAGCAGATAAGTAAGTCAGCAGTCTTAGAGGTGGGAAGAG
GTCTGTCTGCCAGTCATCTGGCTCCCTGCAAACACAGGCATCCCCACCCCTGAACAATTTT
CTTCATAGGAAAGTTGTGAGGGAAGTCACAGGTGCAGACACCGCCCCGGGGGGGGAGGG
GGGGCTCAGAGTTGTTCCTTCATTCAGTCACCAATTCAGTCTTCCAGAATCAAGGCCCTAT
TGACAGAGGGCTAAGCCACCGGGGCGCTGCCTTCAAGGTAAGAGGCATAGATCAGTCTCC
TGAATGTAGAGGGATGAATTCCCTCCTTCACATAAGTGAAAGCGATCATAGGGAACGGAGG
CATCATTAGGGCGCCCTCCTTCTGACAGGGATGCAGACAGGCAGGTGAGGGTGGAGGGG
TGTGGCCCAGGGCACATTCAGAGCCAAACTCTGTTGAGAACAAGGCAGGTGTTTCTGAAA
ACCTCTCTGATTGCACCCGTACCCTCCCATCAGGCCCGAATCGCACACCTCTCTGCCTCTC
CTCAGACGCCGGCCCACATGGCTTTTGAAAACCTGGGGAGATTATACCTTCCAGCTTGCTT
TGCTGAGTCTGAGGAACCTGGCTGCCTTTTCTCTTCTGTTAACTGCAATCAAACTGGTTTTG
AGCACCAGCCCCAAGATGTCTTTGCCAGTCCACATCCATCTTCCATGATGAGCTAAGGTTC
CCTATTTGTACCCTTACTTTCTGGGCTGAGTCATGACATCTGGGA (SEQ ID NO: 141)

eHGT_759m (770 bp):
TTCTGCCATAGAAAAGCATCAGTGTCTATAGAGAGAAATGATAACAAATGAAGGAAATTGTC
TAATTTTCTAACTCACTTACATAATGGACAGATGCGGTAAGTAAACAGCACACTAGTGCA
TCTTAGATGGGCACTGTACTAAGATGTGATAATGATGTTTCAGCCAGACTTACTTATTTTAT
CCCGTAATCACAGGAAGCTCTAATCAGAGGAAGCATGAGGAAGAGACAGAATGTGCTAAG
GATGTGTCACACTCTGATGGGTCACTGGAAGTGAGGAAACAAGGGTGTGCAGCTGTGTAT
CAGGTCCAGGCAGAGAGCAGATGTTCTATTCACGAGTATGCTTACTTACATCTGTCGCCCT
CCAACACACCATTCCAAACTGAAAACTGAGTGTGCTTCATCAAGCCAGAAACTTAGGAAAA
TGTTGTAAGGGACAATGTTTGCATGTCACAGTGAAGTAAACGCAGGAGAGTGATGGCATCT
AGCTGCTGTGAGAAGTGGCTGGAAAAATGCAGCTAACACGACTAACTCAAAACGCTGGGA
CACAAGAGAAGGAAGACAGGCACCTCACGCTTGCTGGGATCTACAAGTTTAGCCAGACCA
GTTCTTAAGATAAACTGCAATGGGTATGCCTGAAAGGCCATTCTTGTTTGTTTCTTTATCTG
TTTCAGTGTTGGTTATAACTTACCCTATCTTGCCACAGGAAGGGCACTTCCTTAGACAGGAA
GATAGCTGATTTTAAAAAGCCCTGTTTCAACCTACAG (SEQ ID NO: 142)

FIG. 15 cont'd eHGT_468m (791 bp):
AGAATGCTCAGGGCCTCAGCATCAGCTAAGAGGCTTTCTGGTTGCTTGATTCTCCCCAATA
AACACCCTGAAGTCTCATCAAACTGCTCATTTATTTTCCTGTAAANGCTTCTATTGCTAACCA
GGCCTTGGCCATTTTTCCCATGGGAAATGGAGTTGTTGGCTTCCCCTGGTTCCTGTTCACC
ATCCAGGAAGTCGAATAAATAATGACCGTAGCCCATACTGGTGGGATGGATACAGGAGGA
GGACTGAAAGCAGGAGAATATCAAACCCATCAAAAATCACCGAGATCAGTGCAAAGACTGA
AGCAGAAAGACACAGCCTCTAAATAGGAGCGGCCTTAATGAAAGTGCATCACCTCAGAGC
CAACATGAAGTCTGCAGATGGGATGCACCTGCCTCCTGAGAACCTCACAGAGGGAAATCA
AGCATCAGAACCCAGAATGGAAGCAGAAAACCCCCAATCAGACTCCTCGGAGACACTTCA
GAAAAGGAACTCTCAGCTTGCAAAACAACAGGTGCATCTCTAAAGAGATGTGGCTCCTGCC
CCCACCCCATACCACCGCACCCTGAGATTGCAGCACTGCTCTGAACTCTCCAATCAAGCCT
CTTTCTTTGGTCACTCTTAAAGTGGTTGGTTTCCAGCACTAACCCTCACTCCTCCACCGAAA
TGAAATCTGCTAGCTTTGGCTGATGTTTAAACAGCTTCAATCTCTGGGGTCTTTTGTGAGAG
AGGATAATTTTAACACTGGTGATAAACCCACCAGAATTTCCAGGTGAGAGGAGAAGCCT
(SEQ ID NO: 143)

eHGT_170h (641 bp):
CCACTGAACATACTCCCCCTTATTTATTCCATATACACATAAATAGCACCACCATGCACCTG
TGGCCAAAAGCCAGAAAATGGAGTGCCATCCTCCACAACACCTTACTCACACTACCTTGAT
GCCTAGATGGTCTTAAAGTCTTAAAGATTCTGCTTCCTTATTACTTCTAAAATCTGTTCCCAC
CACCCTACTTCTACTGTCTTTTAGCTAATCTCACAATATTCAATATTTCTTGCCAGGATTATT
GCAATTCCCTCCTGTTAAGTCTCCCCACTTAAACTCCAGCTGCACCAATCTACACTTTACAA
TTCTGCAGAGATGTCTTTTTAACATGCAAATATGCTTATATTATTTCTTTGCTTACACATTCC
AATAACTCCTCTAAATAAAACTCTTAAGTTGCTTAGACTGACACAAGGCTCTCATGAATGTG
TCCCTGCCTGCCCTTCTGCTTCTACCTTCTAGCATTCCCCTTTGTAAATCCTATGCACTTCT
CTGAGCACATCATTTTCTGTCTTTTCTTTTTTTCTTTTTCTTTGAGATGAAGTCTTTCAACATT
GCCCAGGCTGGTCTCAAACTCCTGGGCTCAAGCGATCCTCTCGCCTCAACCTCCTGAGTA
GCTGGGACTACAGCCACGC (SEQ ID NO: 144)

eHGT_131hv1 (526 bp):
TATTTTGGGATGTATAAATCAGACGAAAAGTCACAAAATCGTGTGCCATTCAAAGGTGGTG
GAAGTTGAAGAGGAAGCGTATCTAAATGACAGATAATGAGTCTTTATGAAGTTACGAAAAA
GAGGTCAGCACCTGAGAAACAGACTAAACTAGAATAGTCATATGACATCTGATGTTCACTG
TAAAATGAGATGAGTGCTGTTGGTGTAATGAGGTTCCTTAGTATGCTACTAAGTTTAACTGC
ATAAATTATACCAATTAGCTCCAAAATGAATGTAAATCCTCAACTATAAAATGTTTCAATGTG
TACTTAGTGCTAATAGGAAATGTTTGTGGCTGTGAGCCATCCTGAAACTTCTGACTTAAAGC
TCTGAAAGAAATGCCACTATATATATTTTTCTAGCCCATAGAAGGATAAACTTTTTGCCCTCT
GATTGCAGTGGGGATGAGGAGTCCAAGTAACATGATATTCATATTGTTAAAACTGATCCCT
CGCATTGCCTCTTAGGGTCAGTGACTGCTAG (SEQ ID NO: 145)

eHGT_519h (385 bp):
AGCTCCTTGTTTGCACGTGTGTTCTCACAGTTCTCTTTGTCCAGACCAGGTACACTGCAGC
CAAAGACAGCGTGGTTCAGTTCTTCTTTTACCAGCCCATCAGTCATCAGTGGAGACAAACT
GACTTCTTTCCCTGCACTGTGACGTGTGGAGGAGGTGAGGCCCAGGCTTTGTTCATGAATA
TTTAGAGCTCAGAGTTAGATAAATTACACATTTACATTTTTGAAGCTGATTTTAAAATTGGTG
TGGTGATTAGAGATGTCTCATCACACAGCACCTTACTCAGCAGCCTGAATGCAATCGTGTT
AATGAAGAAGATGCATTTGCCTTTATTCTTGAAGACAGGTGCAAAACTGGATTTGGAAAATA
CCTTTTACTTTTAGCC (SEQ ID NO: 146)

FIG. 15 cont'd eHGT_131hv2 (601 bp):
AGCAGCCTCTCCAGTGGAGTATGATTCCTTTTAATTTTGGAGTTAAAGTTTTGGATGTTATTT
TGGGATGTATAAATCAGACGAAAAGTCACAAAATCGTGTGCCATTCAAAGGTGGTGGAAGT
TGAAGAGGAAGCGTATCTAAATGACAGATAATGAGTCTTTATGAAGTTACGAAAAAGAGGT
CAGCACCTGAGAAACAGACTAAACTAGAATAGTCATATGACATCTGATGTTCACTGTAAAAT
GAGATGAGTGCTGTTGGTGTAATGAGGTTCCTTAGTATGCTACTAAGTTTAACTGCATAAAT
TATACCAATTAGCTCCAAAATGAATGTAAATCCTCAACTATAAAATGTTTCAATGTGTACTTA
GTGCTAATAGGAAATGTTTGTGGCTGTGAGCCATCCTGAAACTTCTGACTTAAAGCTCTGA
AAGAAATGCCACTATATATATTTTTCTAGCCCATAGAAGGATAAACTTTTTGCCCTCTGATTG
CAGTGGGGATGAGGAGTCCAAGTAACATGATATTCATATTGTTAAAACTGATCCCTCGCATT
GCCTCTTTAGGGTCAGTGACTGCTAGCATGGCTGCTCAGTGAT (SEQ ID NO: 147)

eHGT_130h (512 bp):
GGGAAGGGCAGCTACAGCTAGAGGTCAGAAGGCTGGTGGGGTGAGGGCTGCAGAGCGTT
GCCTTCAAGGGTTCACTGGAGATCTGACCAGTGCATGCACATGAGAAAGCTTCCCCAAAGT
ATTAGAGGAACAATTCTCAGATACCACACAGGGCTGAGGATGCTGCTTCTTCCTGTCATCC
GGAATGCAAAGCCTTACGCTATATAGGACATTGAGCAGAGCAATCAGAAGGGTTTAACTTT
AGCAATGGGCCAATTTTAGCCATAGTCTAACAGCTGCTCTGGTTTCAGCAAACAAAGTTTA
GAAGCAAGACTCTAAAAGAACAAGCCATTTCTAAGTAACTTAAACACATCCTGGAATGAAAT
TCAAAAACAGTTATAAAAATAAAAAAGAATCCCATACCCAGAACACTGAAATTCACAACATC
TGGCAGCCAATCAACAACTAACAGGCAAGGAAAGAAGCAGAAAATGGGAGCTGCCAAAAT
ATTTGAATAAATAATGGCTGAAGCA (SEQ ID NO: 148)

eHGT_527h (324 bp):
TTCGGCCTCTGTCTTCTGCCATCTTCATAAATTATTCACACTACCCAGCGCTTATGCCTTCC
CGCTTCAGACCCTCTCCATAACTGTTCTCTGCTCTTTCATTTACAGCTGTGGAACAACTATT
TTCATCTGGCAGTGGCTTTTATCACCCAGGATTCTCTGCAGCTGGAGCAGTTCTCACACGC
CAAATACAACAAAATCCTGAATAAGTAGGTTGCATTTTTGGATTTCCTGAAGAGGGGGAGG
TCCATGAGATCCTCTGAGATGGTGCCTGAAGCAGAGGTTTTTGTTCCTCCTAGGTATGGGG
ACATGAGACGGCTAATT (SEQ ID NO: 149)

eHGT_470m (611 bp):
GGAGGGGCATAGTGTCCACACTTCAGTCTTCATTCTTCTTGAGTTTCATGTGTTTAGCAAAT
GAAAACTTTTATATTTCTGTCTTTGATAGGCTTACCAAATCCAAAGTGCTCCCCCTCCCCCA
ACTATTTCAGGTTGAATATCTGTTCTCTGAAATGTTTGGTCTGAAAAGCATATCCAAATTTGG
AAGATCTGCATATATGTAATGAGACCTCTTGGGATGCATCTCAAGTCCAAACACAAAGTCA
TTTATGTTTCATGCACACTTGACACACCTAGCCTGAAGCTAATTTGATACCATGTCTTTAGT
GCACCTGTGTTCTGACTGCAAACCACTATAAGGAGTCAGGTGTGGAATTTTCCATTTACAG
CATCGAGTCACTGTTCCAAAATGTTCAGCTTTTAGAGTGCTCTGTGATTTGTATTTTTGGAT
CAGGAATGCTCAACCTGTATTTTAATGCTTTGGCCTGAAACCTTCCCCTCAGAAGGAAATGT
TTGATTGCAGACTGGCATTTTTGCCTCCTGGGATAGTGAGTTGTGTTTTGACTTTTTTCATTT
ATTTATTTATTTTTATATTCATGCCTGATTGAGGGAGGCTTTTAGACCATGGT (SEQ ID NO:
150)

eHGT_174h (1035 bp):
TGCTACCCTAAATATTCCCTGTGCTCCATCTATTCATTTCTCCTCCCTTCCATCTTGAAACCA
CTGATCTTTCTGCTTCCTCTATAATTTTGCCTTTTCCTTTTCCAGAATGTTATAAGGGTGGAA
TCATATAGTGTGCAGCCTTGAAAGAGTGGCTTCTTCCACCAAATAATGTGCATTTAAGGTTC
CTTCATGTCTTTACATGGCTTGATAGCTCACTTTTTATCCCTGAATAATAACTCATTATACAG

FIG. 15 cont'd

ATGTATCACCATTTGTTTACCCATTCATCTGTTGAAGGGCATGTTGATTGCTTCCAGCTTTT
GTCAATTATGGATAGGCTGCTATAAACATTCATGTGTAGGCTTTTACCAACACATTTGGACA
AACTCCAAGGAGCACAATTGCTGGATTATGTAAGTAGACTATGTTTCATTACGTAAGAAGCT
TTCAACCTGTCTTGTAAAGTGGTTCTATCATTTTGCATTCCCACTAGCAATAAAGGAGAGTT
GTTCTACATTTTTGGAACATTTGGTGTTGTCATATTGGGCAAGGGGTATTTTAGCTATTCTA
AAAGGGATCTCATAAGTTTAATTTGCAATATCCTAATAAAATATGATGTTGAACATCTTTTCA
TACGATTATTTGCTATTTGTATATTGTCTTTGATGACGTGCCTACTCAGACATTTTCCCCACT
GTTTAAATGGATTTTTTGTTTTCCAATTTGTTTCATGTGGACAAAATTATAATTTATGTTATAT
TGCCTTGTAGAATGCTGTGTAGATAATGTAACAGGCTAAGGAATAGAAATAATTTGATGGAA
AAACAAATCTACTTTTTGTTTTACAAAGAAATGTTATGAAAGCCCTTTCTGAGGAGAAAGCC
TTTTACTTGAAAATTTTTTAATAGAGGCAGGGTCTTGTTCTGTTCCCCAGGTTGGAGTGCAG
TGACACAACCATAGCTCATTGCAGCCTTGAACTCCTGAGCTCAAGCGATCCTCCAGAGTAG
CTAGCACTTTAGGCCAGAGCCACTATAACCCAGCCAG (SEQ ID NO: 151)

eHGT_087m (584 bp):
GGCCAAGAAAAGGAAGCAGTGAATGAATGGATGATGATTCTGACTTCTGCTTTGGGGATGA
AGTGGGTACCACGCACTGAGAGAGAACTCACGTTCATCCTTCTAAGCTTTCCCCATTCTGT
TCCCTGTTCTTCCCCCCCTGCAGCTGTTTTCCTAAAGAATCTCTGAATCTCTCCCTTTTTTTT
GAATCACAAGCACTGGCTGTTGGGAACACCCACAGATGCACTCTACAAACACACAACTTAC
TCTGAGTAATCACATTGATTTGGAATTAACGGCCATTCAGATACCTCATTGAAGATACCATC
TGGGATGTTGCCGCTCTTCTGAGGTATATCATATTCTGAGAAAATCCGTCCGATTGTACAAA
TAACTCATCAGAATGGCTCTGGCTGCATCTTGATGTGCTGGCTAGGCGCACGAGAGTCGG
AGGCTTCAGCTTCCCCTTCCCCCTCTCGAGACACTGAAGGAAGTAGAGCCATTTCTTCTTC
TCAAGAGAAAAGCAACAGAGAGTTTGGCAACATCCAAAAAGTTGGTCCTGGTGCCACCAG
GCATCCAAAAACATCTCCTTGAAAATTGCCTT (SEQ ID NO: 152)

eHGT_156h (429 bp):
GAGCACCTGTTCCTCCCAATAGGACCTGCCCAATTTCAGTTCCTTGAGCTTTCCTGGTTGG
GCTGATCTGCATTTCCACAAAGTGTTTTCTGAGACATGGGCCTCAGCTCATGCGAAGGGT
TTTCAGCATAAAGAATACTGGTCGGGTCCATCTGGTAGCATTGCATATTCAAGGTTCTGCAT
GATTTGAATGAAACATGAAACAATAAATTCATCCACTGCCTAGAAACATCTGGTCTCTTTTAA
TAAACTCCTACCACTTGGCTGTCTGAAACAAGACTATTTGTATCCAACATGTATGCTGAGAG
TTCTTTTATTTTTTTCCCTCTCTCCAGCTGCAAAGCCACATGAGAAGTAAACATGCTCTTTCA
TGTTATTCTCCATTGAATATGATCTGAAAGTACTTCCCAACTTCCTGAATAGACTCA (SEQ ID
NO: 153)

eHGT_338m (972 bp):
TTCCCTTTAGCTCCTTGGTTACTTTCTCTAGCTCCTCCCTTGGGAGCCCTGCGATTTATCCA
TGTAATGTTTTGGAATTTTTACCAAGTCTGATACATATAAAGATAAAACAAAACAAAATATTTT
CTTATGACTAGTCCAAGCATGAAGAAGGACAAGGCTAAGCAGAAGTTTATCAAAGCAGCAT
TCAAATTAGAAGGTAGTCAAAACAAAAATACAATGAATCAGAACAGAAAAAGAACCTGAATC
TCAAAGGTTTAGGGAATTCTGCTGAGATGGTAAAAGTGTAATGGGTTGTTAGGAACATATG
GTTCAAAGTCTCTTGCTCTCTCTTTTCATTTCTGTTAGTTTTACTTAAGAGATAGGTCCAACA
AAATCAAGTTATAAGTATAATTGTCTCAGTAAGAAGATGACTAAATTGATAAGGATCCGAAG
AGTGAATAAAGATGCTGACGACATGGCCAAAGTAAAATGGATTAGGCTGTCTTCATGCTAG
GACTTTAAATTGATGTGTACAAAATTAAGAAGTGCTGTTGCAACAGTGTTTCAAACATCCTA
GCCAGGTGATGTTTATTCTGGGGTTAAACACAAGAAGGGTAAATGTAGGCAGATGGATTCT
GAAGAAATCAAAAGCTTGTTTAAATGCAAATTTTTCTACAGAGAAGAAGCATTCAGAGAAGA
AATGATATCTAAATAAATTTTCTTTCAGCAGAATGCTTTCTTTTTCAGGTTTGAAAGAGGCAA

FIG. 15 cont'd

ACTCAGGTGTCTAATGGAGATTTACTAAAGAACTAAAACTGGGTACCTTTGCAAACGGAATT
TCAGTGCCTCTAAAAGCCTACTCTCTGAAGCACTTTACTTAGCTGTGGAGCTGAACCTGCA
ATCAAATTACAATCTTCTTTGAATTTTGCATACCAATCTTGACTTCAAGATGAGTTGATACTT
CAAGACATAAATGTACAATTTGGTCTCTCTCTTATGATCCAC (SEQ ID NO: 154)

eHGT_341m (422 bp):
CCTGTAGTGACAGGGACAGATAGGGGCACGTTTAGAATCCAAACTCTCAGAGCACCCCTA
CACTTCATGTTAAGGGAATCTGCATATTCACTGTTTAAGCAGCCCAGCCCACACACCAGTG
CTTAGCCTTTCTGAGTTAAGCTTTGAGATGCTAAAAGGCCACCTGGAAGGATGTGGGGCTC
AGCCACCTCGGTGCATTGAGTAACTCCCACTATGTGGAGCTAGGAGAAGATGCAAGGAGA
AAAACACCCACATCTTCAGTGTTACAGACAAGGTTGAGCACCTGGCTGGAGGGGCGAGAT
TAAGCTTTGGAGGGAGGGCAGCCTCTGAGTCCACTCCCTTGTGTCTGGCTGAGACGGAGT
GGAAGACAGCTATCTAGGATTTCCATCCAATGCCTTTTCAGGTTACCTGTTCTCTGGGTA
(SEQ ID NO: 155)

eHGT_339m (386 bp):
ACACAAGGACAAGCTGGTGAGCGCTGTTAAATCTCTACTACAAGCTGACACTGTCACACCC
ACAGATACACCGGAGTGTCAGATGGCCCCATCTCATGGTACATGAAATGCAGTAATCCTGC
GGTGCAATTTTCTGAGCTATTTTCCAGAGCTTTCTCTTGAAAAGCAGGTGACTTCTTGGGTA
GCAGCAATTTACCTTTCACACCGGGTAATCATCAAGGTGCCTGATTGCCCTGAATACCTTT
CCCGGCTGTCAGAATACTTCAAGGCTGAGAATTAGCATTTCAAAACCTTTTCAAATGAGGG
TAGGGGGGCTCATTCCCTTGGTTGAAGGTTCCCCAGGCTGCAAAGAAGCAAGTGTTAAGT
GCACACCTGGGGAAGCCATA (SEQ ID NO: 156)

MGT_E81 (621 bp):
ATACTGTAAAAAGCAAGAAGAACCAATCACTTAATCTAAAATTTAGAACTCTGAAGTGATTC
ATTCCACTGACCATTCTCTTTTCCCAGTTCTCTTATCTTGTCAGATACACAGGAAGCTCAGG
ACAGTTTTGCTCATCCCTTTGTTTCTAGCAGTTCTGAGTAATGAATTCAAATAGCAGTTATTA
TCTCAATGCCATGACAATTGGCTAAGCTAACTACCCAGTTCACTTATCGAGGGAGCAAAAC
ACTAGATGGCCAATAAGAATGACAGACAGAATGTATGATTGATGTGAAACACCCAGAGAAT
CAAGTGCTTTCAAAGAGTTAAATGTGTTCTCCATTATGGCTGACAGCTGGAGAAACTATCAT
TGGAAACTGAGATGAATTGTTTGCTCTGTGCAGGTGGGAGAAGAGAATTAAATGACAGACA
CATGAAACTGTGCTTTGCATCTTCTTGTCAGCACTACTCTGTTGGCCAAGAGTGAAATGCAA
TTTCAGTTGGCTTGAACGCCACAGGATTTTACATCTGAATCAACTAAGTTCTAATTATGGGC
AGATTTATCTACTAATACCATCACCATAACAACCAAACCATGCCCCATGCCTTTCATGTCT
TCA (SEQ ID NO: 157)

MGT_E85 (818 bp):
AGCTGTAAAGTCTGGAGGTGTGCTTTTCAGGAGCTGGGGAGGTTAGAGGGAAGACCTCGA
ACAGGACACACTATCACTGTCTTTCTTGTGCCAATGCAATTGGAAGAAACAAACACAGCCA
TCATTTAGCCCACATGAATTAGGTCCTGTAAAGAGTGAAGGGGAAAAGGTTGTTGGAAATC
TAATTAGTAGGCTTTGCAAGTGTGGAGTTTATGGCTACATATTCAGTTAAATTCAGTTCTGTT
TTGTAGCTATCAGCCAGGGAAGAGTCAAGTGCCATGTGGATTGGGAACATAAATAGCCCAT
TCTTCATGTCCATTGCTCTATCATTAACCTTCCCACTCAGTCCTGGAAATGAAAAACCCAGC
GTCCTTCCATCTGCTCCACGTTATTTATGATGATGCCTCTAATTATGTTCAATTGAGTTGCT
GTCGATGATTAAAGGTAATAGGTAATAATAACTTGGCCTCATCATTACCACCATTATTATTAG
CTCATTGATTGCAATAATTTCTAAAATTACCCCTTGGAATAAAATATGTTAAGCACCTGGTTT
ATCCTTTTTTTTTTTTTTTTAAAAAAGGAACATCTGCTCTAAATGTGTGATAGCAGAGGACCAA
ACGTGTCTTGATCTGAAGGGGAAGCAAAAACGATGCTGACACTGGGGAGCCTTGTCTGGG

FIG. 15 cont'd

CTGGAATGGATGTATTGTGGGATGCTGAGAGGAAGAGTAGTCACGATCAAGTTCAATGCTA
GGATTACAGGGCTGCTGAGAGACGGAGACACGTGGGAAGCTGAGCTATTCCATGGCTACT
GCAGGCTTTACTTCTTCT (SEQ ID NO: 158)

MGT_E88 (757 bp):
ATTTTAGTAGGAAAGTGGGATACTATCTTCTAAAGAGACTGTGCATCTTATACTCCTATCTA
CCACATCATATTTACTGTCTATTCTTAGTTGGGTCTAAATTTCTAAGTAATTTTAAGTATTCAT
ATTCTAGGCTACTGGGTCCTATAGATTAATATAAATATTTGATTGTAAGTTATGCAATAAAAA
TGAAGAGATTTGTTTATATGCATCTAAATAAGAACATGCAGAATGTGTTCGGAACTTGAATA
TCCTTATCTCCATGAAAATGGGAAAAATAAAAATAATTTAAACAAAGTGTTGAGTGGAACAT
GTGTAGCTGAAACACTTGATTTTCCCTAAAATATCTGAGTAATTACTTGAATTTCCTACTTTA
TCATTTGTCCATGGACAGCTGGTATCAGGCTATAAAAACAACAATAATTAGAGGCCCAAATA
GTTCTTTTAATTACCCTAAAAGTCTGAAATTCACGTTTTTGTTGTCTAGAAGTATTCTAATCA
TGTTAACAGCTGATTAGCAATTGGTCCATTTTTATGTTGTAGAAAAGTGAAATGTGAATGG
AAAATTGAAGAATAATTCCAAACCAAGGTAAATTATTACTGCTTTTCCCTGCAATTGTTAGTT
GAAAGGTGTGATTTGAGATAAGATCATTTACACTTAAAAGTGAATAGAAGAAATATAATAAG
AGGGAATAGGCCTGTGAAGTTGTCAAGAATAAATTTTAAAATAAATGCAGCATTTTTTGCAT
TTATGTC (SEQ ID NO: 159)

MGT_E83 (1044 bp):
CTGGCTGTCCTGGAACTCACTCTGTAGACCAGGCTGGCCTCAAACTCAGAAATCTGCCTG
CCTCTGCCTCCCAAGTGCTGGGATTAAAGGCATGTGCCACCACACCTGGCCTAGAAATAAT
GACTTTTAAAATTATCTAAAGGTTACCAGATGAAATTATCAACCTCAGCTCTGTGGTATAATT
TAAATCTAGTTCTGATTCAGTAAGAGTGTTATTTTCAGTACCCTCAGTAGCAGAATCCTATT
GCCTCTTATATCTAAGCAGGAGAGGCAATTCAGAAACAAAGACCCAAGGACAGGAGCCCT
ATTGCATCTACTCTCAATAATTAAGGCCTTTGATGACTAAAATAATTTAGATAATAAGATTGG
TTTGGGTAAATAAATATCAAATTAGGGTTTATGGCAGTCACAGGTGTTTGGCAGGTCTGGC
CTATAATCACAGAGAAAATGAATGCATTTTATTTAGCATAATTGGGAAAAGGAATGAAGCTT
ATATGCAAATTGTGTACCACTTTTGTTAAAGATAGCTGGTCAGACTCATGATGATAATCCAA
ACCTTTATCCCAGTGAAAATTTTCAACATATCTATTTTCTGTGGAATTTTACCACATCTGACT
GCATTCTCCCAGTCTTCTGAGATGGATTTCAGTGTCCTTGGTCACCATCTAGCCTTTCTATT
TTGTTGACAGGATGCCTGAGTTTAGCTGTTTCTGTTTATTTGTTTGTTTTTAAGCTTGATTTC
TCCTACTCGTGTCTATAGCTGGAATCGGAGGTTACATGAGATTTCTCAGCATCAGCATCCA
GCACTGCCACAAAGGGGATGTGGGAGATGAGAAGGGAAAACAAGACAGTGAAGAGAATAA
AAATGAAATCCTGGAGGCAAGATAATTAAGAGACCAGAAAATAGAGTTGAATTTCCATTAGG
AACATTTACAAGAATGTGTTCACAGGCACACACACAGGAATCCCCAACTGCTAGCTTTGGA
ATGCCCATAGATGCCACTGCTACTGGACTCTGTGATCAGCGCTCTTGACTAGGACTAC
(SEQ ID NO: 160)

Core of 3xCore2_eHGT_226h (279 bp):
CCACTTTTGTATTTACCATTATTGCAAAATCAATCAAATGTGAGCAAAAGCAAAGGCAATTT
GAATGACTCAAAATTGAAATTTGAGCTGCCAAATCAAGCAGTAAAACAATTTTTACCAGCTC
TATTGATTGTTAGAAAGATAAGTTATAAACTTTATTTCAAGTAAATTTCTAAAAGATCTGGGA
ATGTGATTATTCCAAGGCAGATGGCGAAGACCTTTATTTCCACTGATTATTCACAGATGCAA
ATTATTATGCAACTGGAAGCATACTAAGAT (SEQ ID NO: 161)

3xCore2_eHGT_226h (837 bp):
CCACTTTTGTATTTACCATTATTGCAAAATCAATCAAATGTGAGCAAAAGCAAAGGCAATTT
GAATGACTCAAAATTGAAATTTGAGCTGCCAAATCAAGCAGTAAAACAATTTTTACCAGCTC

FIG. 15 cont'd

TATTGATTGTTAGAAAGATAAGTTATAAACTTTATTTCAAGTAAATTTCTAAAAGATCTGGGA
ATGTGATTATTCCAAGGCAGATGGCGAAGACCTTTATTTCCACTGATTATTCACAGATGCAA
ATTATTATGCAACTGGAAGCATACTAAGATCCACTTTTGTATTTACCATTATTGCAAAATCAA
TCAAATGTGAGCAAAAGCAAAGGCAATTTGAATGACTCAAAATTGAAATTTGAGCTGCCAAA
TCAAGCAGTAAAACAATTTTTACCAGCTCTATTGATTGTTAGAAAGATAAGTTATAAACTTTA
TTTCAAGTAAATTTCTAAAAGATCTGGGAATGTGATTATTCCAAGGCAGATGGCGAAGACCT
TTATTTCCACTGATTATTCACAGATGCAAATTATTATGCAACTGGAAGCATACTAAGATCCAC
TTTTGTATTTACCATTATTGCAAAATCAATCAAATGTGAGCAAAAGCAAAGGCAATTTGAATG
ACTCAAAATTGAAATTTGAGCTGCCAAATCAAGCAGTAAAACAATTTTTACCAGCTCTATTG
ATTGTTAGAAAGATAAGTTATAAACTTTATTTCAAGTAAATTTCTAAAAGATCTGGGAATGTG
ATTATTCCAAGGCAGATGGCGAAGACCTTTATTTCCACTGATTATTCACAGATGCAAATTAT
TATGCAACTGGAAGCATACTAAGAT (SEQ ID NO: 162)

Core of 3xCore3_eHGT_226h (280 bp):
TTTCCACTGATTATTCACAGATGCAAATTATTATGCAACTGGAAGCATACTAAGATATTGCAA
AGATGTTCTGACATTAGTCATCTGCTGCCTTTGTTACTTTGGTGTCAATTTTCTTATTCTTTC
CAAAGGAAGATCCTTACAGTTTGTATTCTTTCACAGCTGGGAAATGATCAGTTGAGAATTAT
TCAAACACACCAATCTGTTAACCGTACTTCTTCCCAGATAATGCAATATTTTGCAGGGTGAC
AGGCAAAAGTGGTCATTTTTTACTTCATA (SEQ ID NO: 163)

3xCore3_eHGT_226h (840 bp):
TTTCCACTGATTATTCACAGATGCAAATTATTATGCAACTGGAAGCATACTAAGATATTGCAA
AGATGTTCTGACATTAGTCATCTGCTGCCTTTGTTACTTTGGTGTCAATTTTCTTATTCTTTC
CAAAGGAAGATCCTTACAGTTTGTATTCTTTCACAGCTGGGAAATGATCAGTTGAGAATTAT
TCAAACACACCAATCTGTTAACCGTACTTCTTCCCAGATAATGCAATATTTTGCAGGGTGAC
AGGCAAAAGTGGTCATTTTTTACTTCATATTTCCACTGATTATTCACAGATGCAAATTATTA
TGCAACTGGAAGCATACTAAGATATTGCAAAGATGTTCTGACATTAGTCATCTGCTGCCTTT
GTTACTTTGGTGTCAATTTTCTTATTCTTTCCAAAGGAAGATCCTTACAGTTTGTATTCTTTC
ACAGCTGGGAAATGATCAGTTGAGAATTATTCAAACACACCAATCTGTTAACCGTACTTCTT
CCCAGATAATGCAATATTTTGCAGGGTGACAGGCAAAAGTGGTCATTTTTTACTTCATATT
TCCACTGATTATTCACAGATGCAAATTATTATGCAACTGGAAGCATACTAAGATATTGCAAA
GATGTTCTGACATTAGTCATCTGCTGCCTTTGTTACTTTGGTGTCAATTTTCTTATTCTTTCC
AAAGGAAGATCCTTACAGTTTGTATTCTTTCACAGCTGGGAAATGATCAGTTGAGAATTATT
CAAACACACCAATCTGTTAACCGTACTTCTTCCCAGATAATGCAATATTTTGCAGGGTGACA
GGCAAAAGTGGTCATTTTTTACTTCATA (SEQ ID NO: 164)

Core of eHGT_064h (242 bp):
TTCAATTGGTAAAGTTGTGGTATATAATTACAATTGAACTCTCTTGTACTTGCCTCTTTTACA
AAAATTCTCTCCTAGCAGAACGTAGTGTGAGTCATCTACACAGCTGTTTTTCTGATTATTGG
AATTTTCTTTTGACATGAAGGAAGTATCTCATTGACAGAACTGCGTTGTGAAGGAGTGCTAA
CTGTAGCATAAAATACAAAATTGGATTTTTAGATTGCAAAATACAGTAAAGCTTT (SEQ ID
NO: 165)

3xCore_eHGT_064h (726 bp):
TTCAATTGGTAAAGTTGTGGTATATAATTACAATTGAACTCTCTTGTACTTGCCTCTTTTACA
AAAATTCTCTCCTAGCAGAACGTAGTGTGAGTCATCTACACAGCTGTTTTTCTGATTATTGG
AATTTTCTTTTGACATGAAGGAAGTATCTCATTGACAGAACTGCGTTGTGAAGGAGTGCTAA
CTGTAGCATAAAATACAAAATTGGATTTTTAGATTGCAAAATACAGTAAAGCTTTTTCAATTG
GTAAAGTTGTGGTATATAATTACAATTGAACTCTCTTGTACTTGCCTCTTTTACAAAAATTCT

FIG. 15 cont'd

CTCCTAGCAGAACGTAGTGTGAGTCATCTACACAGCTGTTTTTCTGATTATTGGAATTTTCT
TTTGACATGAAGGAAGTATCTCATTGACAGAACTGCGTTGTGAAGGAGTGCTAACTGTAGC
ATAAAATACAAAATTGGATTTTTAGATTGCAAAATACAGTAAAGCTTTTTCAATTGGTAAAGT
TGTGGTATATAATTACAATTGAACTCTCTTGTACTTGCCTCTTTTACAAAAATTCTCTCCTAG
CAGAACGTAGTGTGAGTCATCTACACAGCTGTTTTTCTGATTATTGGAATTTTCTTTTGACAT
GAAGGAAGTATCTCATTGACAGAACTGCGTTGTGAAGGAGTGCTAACTGTAGCATAAAATA
CAAAATTGGATTTTTAGATTGCAAAATACAGTAAAGCTTT (SEQ ID NO: 166)

Beta-Globin Minimal Promoter (pBGmin/minBGlobin/minBGprom):
GGGCTGGGCATAAAAGTCAGGGCAGAGCCATCTATTGCTTACATTTGCTTCTG (SEQ ID
NO: 26)

minCMV Promoter:
GAGGTAGGCGTGTACGGTGGGAGGCCTATATAAGCAGAGCTCGTTTAGTGAACCGTCAGA
TCGCCTGG (SEQ ID NO: 27)

Mutated minCMV Promoter (SacI RE site removed):
GAGGTAGGCGTGTACGGTGGGAGGCCTATATAAGCAGAGCTGGTTTAGTGAACCGTCAGA
TCGCCTGG (SEQ ID NO: 28)

minRho Promoter:
GATTCAGCCGGGAGCTTAGGGAGGGGAGGTCACTTCATAAGGGCCTGGGGGGGGAGTTG
GAGCCACGAGTCGTCCAGCCGGAGCCCCGTGTGGCTGAGCTCCGGCCTCAGAAGCATCC
CC (SEQ ID NO: 29)

**minRho* Promoter:**
GATTCAGCCGGGAGCTTAGGGAGGGGAGGTCACTTCATAAGGGCTTGGGGGGGGAGTTG
GAGCCACGAGTCGTCCAGCCGGAGCCCCGTGTGGCTGTGCTCCGGCCTCAGAAGCATCC
CC (SEQ ID NO: 30)

Hsp68 minimal Promoter (proHsp68):
CAGGAACATCCAAACTGAGCAGCCGGGGTCCCCCCCACCCCCCACCCCGCCCCACGCGG
CAACTTTGAGCCTGTGCTGGGACAGAGCCTCTAGTTCCTAAATTAGTCCATGAGGTCAGAG
GCAGCACTGCCATTGTAACGCGATTGGAGAGGATCACGTCACCGGACACGCCCCCAGGC
ATCTCCCTGGGTCTCCTAAACTTGGCGGGGAGAAGTTTTAGCCCTTAAGTTTTAGCCTTTAA
CCCCCATATTCAGAACTGTGCGAGTTGGCGAAACCCCACAAATCACAACAAACTGTACACA
ACACCGAGCTAGAGGTGATCTTTCTTGTCCATTCCACACAGGCCTTAGTAATGCGTCGCCA
TAGCAACAGTGTCACTAGTAGCACCAGCACTTCCCCACACCCTCCCCCTCAGGAATCCGTA
CTCTCCAGTGAACCCCAGAAACCTCTGGAGAGTTCTGGACAAGGGCGGAACCCACAACTC
CGATTACTCAAGGGAGGCGGGGAAGCTCCACCAGACGCGAAACTGCTGGAAGATTCCTG
GCCCCAAGGCCTCCTCCGGCTCGCTGATTGGCCCAGCGGAGAGTGGGCGGGGCCGGTG
AAGACTCCTTAAAGGCGCAGGGCGGCGAGCAGGTCACCAGACGCTGACAGCTACTCAGA
ACCAAATCTGGTTCCATCCAGAGACAAGCGAAGACAAGAGAAGCAGAGCGAGCGGCGCGT
TCCCGATCCTCGGCCAGGACCAGCCTTCCCCAGAGCATCCCTGCCGCGGAGCGCAACCT
TCCCAGGAGCATCCCTGCCGCGGAGCGCAACTTTCCCCGGAGCATCCACGCCGCGGAGC
GCAGCCTTCCAGAAGCAGAGCGCGGCGCC (SEQ ID NO: 31)

FIG. 15 cont'd

SYFP2:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAA (SEQ ID NO: 32)

EGFP:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAA
GAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGTAA (SEQ ID NO: 33)

Optimized Flp recombinase (FlpO):
ATGGCTCCTAAGAAGAAGAGGAAGGTGATGAGCCAGTTCGACATCCTGTGCAAGACCCCC
CCCAAGGTGCTGGTGCGGCAGTTCGTGGAGAGATTCGAGAGGCCCAGCGGCGAGAAGAT
CGCCAGCTGTGCCGCCGAGCTGACCTACCTGTGCTGGATGATCACCCACAACGGCACCG
CCATCAAGAGGGCCACCTTCATGAGCTACAACACCATCATCAGCAACAGCCTGAGCTTCGA
CATCGTGAACAAGAGCCTGCAGTTCAAGTACAAGACCCAGAAGGCCACCATCCTGGAGGC
CAGCCTGAAGAAGCTGATCCCCGCCTGGGAGTTCACCATCATCCCTTACAACGGCCAGAA
GCACCAGAGCGACATCACCGACATCGTGTCCAGCCTGCAGCTGCAGTTCGAGAGCAGCG
AGGAGGCCGACAAGGGCAACAGCCACAGCAAGAAGATGCTGAAGGCCCTGCTGTCCGAG
GGCGAGAGCATCTGGGAGATCACCGAGAAGATCCTGAACAGCTTCGAGTACACCAGCAGG
TTCACCAAGACCAAGACCCTGTACCAGTTCCTGTTCCTGGCCACATTCATCAACTGCGGCA
GGTTCAGCGACATCAAGAACGTGGACCCCAAGAGCTTCAAGCTGGTGCAGAACAAGTACC
TGGGCGTGATCATTCAGTGCCTGGTGACCGAGACCAAGACAAGCGTGTCCAGGCACATCT
ACTTTTTCAGCGCCAGAGGCAGGATCGACCCCCTGGTGTACCTGGACGAGTTCCTGAGGA
ACAGCGAGCCCGTGCTGAAGAGAGTGAACAGGACCGGCAACAGCAGCAGCAACAAGCAG
GAGTACCAGCTGCTGAAGGACAACCTGGTGCGCAGCTACAACAAGGCCCTGAAGAAGAAC
GCCCCCTACCCCATCTTCGCTATCAAGAACGGCCCTAAGAGCCACATCGGCAGGCACCTG
ATGACCAGCTTTCTGAGCATGAAGGGCCTGACCGAGCTGACAAACGTGGTGGGCAACTGG
AGCGACAAGAGGGCCTCCGCCGTGGCCAGGACCACCTACACCCACCAGATCACCGCCAT

FIG. 15 cont'd

CCCCGACCACTACTTCGCCCTGGTGTCCAGGTACTACGCCTACGACCCCATCAGCAAGGA
GATGATCGCCCTGAAGGACGAGACCAACCCCATCGAGGAGTGGCAGCACATCGAGCAGC
TGAAGGGCAGCGCCGAGGGCAGCATCAGATACCCCGCCTGGAACGGCATCATCAGCCAG
GAGGTGCTGGACTACCTGAGCAGCTACATCAACAGGCGGATCTGA (SEQ ID NO: 34)

Improved Cre recombinase (iCre):
ATGGTGCCCAAGAAGAAGAGGAAAGTCTCCAACCTGCTGACTGTGCACCAAAACCTGCCT
GCCCTCCCTGTGGATGCCACCTCTGATGAAGTCAGGAAGAACCTGATGGACATGTTCAGG
GACAGGCAGGCCTTCTCTGAACACACCTGGAAGATGCTCCTGTCTGTGTGCAGATCCTGG
GCTGCCTGGTGCAAGCTGAACAACAGGAAATGGTTCCCTGCTGAACCTGAGGATGTGAGG
GACTACCTCCTGTACCTGCAAGCCAGAGGCCTGGCTGTGAAGACCATCCAACAGCACCTG
GGCCAGCTCAACATGCTGCACAGGAGATCTGGCCTGCCTCGCCCTTCTGACTCCAATGCT
GTGTCCCTGGTGATGAGGAGAATCAGAAAGGAGAATGTGGATGCTGGGGAGAGAGCCAA
GCAGGCCCTGGCCTTTGAACGCACTGACTTTGACCAAGTCAGATCCCTGATGGAGAACTC
TGACAGATGCCAGGACATCAGGAACCTGGCCTTCCTGGGCATTGCCTACAACACCCTGCT
GCGCATTGCCGAAATTGCCAGAATCAGAGTGAAGGACATCTCCCGCACCGATGGTGGGAG
AATGCTGATCCACATTGGCAGGACCAAGACCCTGGTGTCCACAGCTGGTGTGGAGAAGGC
CCTGTCCCTGGGGGGTTACCAAGCTGGTGGAGAGATGGATCTCTGTGTCTGGTGTGGCTGA
TGACCCCAACAACTACCTGTTCTGCCGGGTCAGAAAGAATGGTGTGGCTGCCCCTTCTGC
CACCTCCCAACTGTCCACCCGGGCCCTGGAAGGGATCTTTGAGGCCACCCACCGCCTGAT
CTATGGTGCCAAGGATGACTCTGGGCAGAGATACCTGGCCTGGTCTGGCCACTCTGCCAG
AGTGGGTGCTGCCAGGGACATGGCCAGGGCTGGTGTGTCCATCCCTGAAATCATGCAGG
CTGGTGGCTGGACCAATGTGAACATTGTGATGAACTACATCAGAAACCTGGACTCTGAGAC
TGGGGCCATGGTGAGGCTGCTCGAGGATGGGGACTAA (SEQ ID NO: 35)

SP10 insulator (SP10ins):
GAAGCTACCCCTAACACACTATTCTACACACAGAAAATGCTCTTCACTAG (SEQ ID NO: 36)

3xSP10ins:
GAAGCTACCCCTAACACACTATTCTACACACAGAAAATGCTCTTCACTAGGAAGCTACCCC
TAACACACTATTCTACACACAGAAAATGCTCTTCACTAGGAAGCTACCCCTAACACACTATT
CTACACACAGAAAATGCTCTTCACTAG (SEQ ID NO: 37)

WPRE3:
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTAGTTCTTGCCACGGCGGAACTCATCGC
CGCCTGCCTTGCCCGCTGCTGGACAGGGGCTCGGCTGTTGGGCACTGACAATTCCGTGG
(SEQ ID NO: 38)

WPRE:
GCTTATCGATAATCAACCTCTGGATTACAAAATTTGTGAAAGATTGACTGGTATTCTTAACTA
TGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGCAACCCCC
ACTGGTTGGGGCATTGCCACCACCTGTCAGCTCCTTTCCGGGACTTTCGCTTTCCCCCTCC
CTATTGCCACGGCGGAACTCATCGCCGCCTGCCTTGCCCGCTGCTGGACAGGGGCTCGG
CTGTTGGGCACTGACAATTCCGTGGTGTTGTCGGGGAAATCATCGTCCTTTCCTTGGCTGC
TCGCCTATGTTGCCACCTGGATTCTGCGCGGGACGTCCTTCTGCTACGTCCCTTCGGCCC

FIG. 15 cont'd

TCAATCCAGCGGACCTTCCTTCCCGCGGCCTGCTGCCGGCTCTGCGGCCTCTTCCGCGTC
TTCGCCTTCGCCCTCAGACGAGTCGGATCTCCCTTTGGGCCGCCTCCCCGCATCGATACC
G (SEQ ID NO: 39)

BGHpA:
CGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGA
TTGGGAAGACAATAGCAGGCATG (SEQ ID NO: 40)

HGHpA:
ACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTCC
TTCTATAATATTATGGGGTGGAGGGGGGTGGTATGGAGCAAGGGGCAAGTTGGGAAGACA
ACCTGTAGGGCCTGCGGGGTCTATTGGGAACCAAGCTGGAGTGCAGTGGCACAATCTTGG
CTCACTGCAATCTCCGCCTCCTGGGTTCAAGCGATTCTCCTGCCTCAGCCTCCCGAGTTGT
TGGGATTCCAGGCATGCATGACCAGGCTCAGCTAATTTTTGTTTTTTTGGTAGAGACGGGG
TTTCACCATATTGGCCAGGCTGGTCTCCAACTCCTAATCTCAGGTGATCTACCCACCTTGG
CCTCCCAAATTGCTGGGATTACAGGCGTGAACCACTGCTCCCTTCCCTGTCCTT (SEQ ID
NO: 41)

P2A:
GGCAGCGGCGCCACCAACTTCAGCCTGCTGAAGCAGGCCGGCGACGTGGAGGAGAACCC
CGGCCCCGGAGCTAGCGGA (SEQ ID NO: 42)

T2A:
(GSG)EGRGSLLTCGDVEENPGP (SEQ ID NO: 43)

E2A:
(GSG)QCTNYALLKLAGDVESNPGPP (SEQ ID NO: 44)

F2A:
(GSG)VKQTLNFDLLKLAGDVESNPGP (SEQ ID NO: 45)

Exemplary Plasmid Backbone 1 – Left ITR:
CCTGCAGGCAGCTGCGCGCTCGCTCGCTCACTGAGGCCGCCCGGGCGTCGGGCGACCTT
TGGTCGCCCGGCCTCAGTGAGCGAGCGAGCGCGCAGAGAGGGAGTGGCCAACTCCATCA
CTAGGGGTTCCT (SEQ ID NO: 46)

Exemplary Plasmid Backbone 1 – Right ITR:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCT (SEQ ID NO:47)

Exemplary Plasmid Backbone 2 – Left ITR:
CATGTCCTGCAGGCAGCTGCGCGCTCGCTCGCTCACTGAGGCCGCCCGGGCAAAGCCCG
GGCGTCGGGCGACCTTTGGTCGCCCGGCCTCAGTGAGCGAGCGAGCGCGCAGAGAGGG
AGTGGCCAACTCCATCACTAGGGGTTCCT (SEQ ID NO:48)

FIG. 15 cont'd

Exemplary Plasmid Backbone 2 – Right ITR:
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGCTGCCTGCAGGGGCGCCTG (SEQ ID NO: 49)

PHP.eB capsid:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQS<u>DGTLAVPFK</u>AQAQTGWVQNQGILPGMVWQDRDV
YLQGPIWAKIPHTDGNFHPSPLMGGFGMKHPPPQILIKNTPVPADPPTAFNKDKLNSFITQYST
GQVSVEIEWELQKENSKRWNPEIQYTSNYYKSNNVEFAVNTEGVYSEPRPIGTRYLTRNL
(SEQ ID NO: 50)

AAV9 VP1 capsid protein:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSAQAQAQTGWVQNQGILPGMVWQDRDVYLQGPIW
AKIPHTDGNFHPSPLMGGFGMKHPPPQILIKNTPVPADPPTAFNKDKLNSFITQYSTGQVSVEIE
WELQKENSKRWNPEIQYTSNYYKSNNVEFAVNTEGVYSEPRPIGTRYLTRNL (SEQ ID NO:
51)

tet-Transactivator version 2 (tTA2):
ATGTCTAGACTGGACAAGAGCAAAGTCATAAACTCTGCTCTGGAATTACTCAATGAAGTCG
GTATCGAAGGCCTGACGACAAGGAAACTCGCTCAAAAGCTGGGAGTTGAGCAGCCTACCC
TGTACTGGCACGTGAAGAACAAGCGGGCCCTGCTCGATGCCCTGGCAATCGAGATGCTGG
ACAGGCATCATACCCACTTCTGCCCCCTGGAAGGCGAGTCATGGCAAGACTTTCTGCGGA
ACAACGCCAAGTCATTCCGCTGTGCTCTCCTCTCACATCGCGACGGGGCTAAAGTGCATCT
CGGCACCCGCCCAACAGAGAAACAGTACGAAACCCTGGAAAATCAGCTCGCGTTCCTGTG
TCAGCAAGGCTTCTCCCTGGAGAACGCACTGTACGCTCTGTCCGCCGTGGGCCACTTTAC
ACTGGGCTGCGTATTGGAGGATCAGGAGCATCAAGTAGCAAAGAGGAAAGAGAGACACC
TACCACCGATTCTATGCCCCCACTTCTGAGACAAGCAATTGAGCTGTTCGACCATCAGGGA
GCCGAACCTGCCTTCCTTTTCGGCCTGGAACTAATCATATGTGGCCTGGAGAAACAGCTAA
AGTGCGAAAGCGGCGGGCCGGCCGACGCCCTTGACGATTTTGACTTAGACATGCTCCCAG
CCGATGCCCTTGACGACTTTGACCTTGATATGCTGCCTGCTGACGCTCTTGACGATTTTGA
CCTTGACATGCTCCCCGGGTAA (SEQ ID NO: 52)

FIG. 15 cont'd

GTPase HRas [Homo sapiens]:
MTEYKLVVVGAGGVGKSALTIQLIQNHFVDEYDPTIEDSYRKQVVIDGETCLLDILDTAGQEEYS
AMRDQYMRTGEGFLCVFAINNTKSFEDIHQYREQIKRVKDSDDVPMVLVGNKCDLAARTVESR
QAQDLARSYGIPYIETSAKTRQGVEDAFYTLVREIRQHKLRKLNPPDESGPGCMSCKCVLS
(SEQ ID NO: 80)

GCaMP6m
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAGGGA
GCTACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 92)

GCaMP6s
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCCACATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC

FIG. 15 cont'd

CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 93)

GCaMP6f
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGAATTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 94)

FIG. 15 cont'd

CN1535 (2303 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCCACTTCCAGCTTCTTC
CCTAACAATTCCTAAGAAATGTTATTGCTAGTTAGAAATGCTTTATCTTTTCTTCTATCATATC
CAATGAAGGCCTGATCTTACAGAGTCTAAACAATTGCAGTAAATACATTCCAGATTTCAGCA
GCACTTTACCAACACTTGTGAATCGCTGTCATTCTTCCAGGATTCAGTTAAGAGTGGCAAT
TACAAGTCACTTTAATGTCTGAGGAAAGGATGGAAAGCAAGCCCTGCAAATAGAAGGCCAC
ATTTACTCTTTTCAAACCACAGCTCAAACTATCAGAGGAAAATACAGTTTTTATGTAAGCGCT
CAAACAGTTTTCCCCAAATCTTGCAGAATCCATTACTTTTAAGAAATTTCCACATGAATAGAC
CAAACGAATCAGGCATACTAATACTTTGTACATGCACACACACAAGTGCCAGTTCCATATCA
TACTGTCACAAACTCTAGAGCTAAACACATTCACACGCTTCGGATTAAATGATCAGGGTAGA
AATATGCATTGTGAATAAAATAACTTACCTATCTTACCTATAAAATTCCCCATTTCAGTTGTTT
TCTGCCACTGCCACTTTTGAAGTTATCCTCAACTGAACTCTTTGTACACATTCCTGCAAACC
AGCTCACTGTTGGAATGTCTCTGAATTCGATATCATAATCAACCATAGGTACCGAGCTCGG
GATTCAGCCGGGAGCTTAGGGAGGGGAGGTCACTTCATAAGGGCCTGGGGGGGGAGTTG
GAGCCACGAGTCGTCCAGCCGGAGCCCCGTGTGGCTGAGCTCCGGCCTCAGAAGCATCC
CCGGGTTGGATCCTTCGAAGCTAGCGCTACCGGTCGCCACCATGGTGAGCAAGGGCGAG
GAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGA
AGCTGATCTGCACCACCGGCAAGCTGCCCGTGCCCTGGCCCACCCTCGTGACCACCCTG
GGCTACGGCGTGCAGTGCTTCGCCCGCTACCCCGACCACATGAAGCAGCACGACTTCTTC
AAGTCCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCATCGA
GCTGAAGGGCATCGACTTCAAGGAGGACGGCAACATCCTGGGGCACAAGCTGGAGTACA
ACTACAACAGCCACAACGTCTATATCACCGCCGACAAGCAGAAGAACGGCATCAAGGCCA
ACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACATCAT
AATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGC
TTTCATTTTCTCCTCCTTGTATAAATCCTGGTTAGTTCTTGCCACGGCGGAACTCATCGCCG
CCTGCCTTGCCCGCTGCTGGACAGGGGCTCGGCTGTTGGGCACTGACAATTCCGTGGCT
CGAGAGATCTTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCA
AGGGGGAGGATTGGGAAGACAATAGCAGGCATGCACGTGCGGACCGAGCGGCCGC (SEQ
ID NO: 107)

CN1533 (2212 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTAATGGGGCCTCAGTTT
CTCCCTTGGGATTAAGTGGGTACCAGGCAGGACAAAATAAGCCACCTGTGCCATTCTACCC
TTTCCATCCTGCTGTTTTTCCACCCTGCAGCTGCTTTCTCAAAGAATCCCTGAATCTCCTCT
CTAAATAGTGCAAGCTTGCTGTTGGGAACACCCACAGATGCACTCTACAAATACACAACTC

FIG. 15 cont'd

ACTTTGAGTAATCATATTGATTCGGAATTATCGGCCATTCAAATACCTCATTGAAGATGCCA
TCTGGGATGTTATTGCTCTTCAGAGGTAGATCATATTCTGAGAAAATCTGTCAAAATGTAGA
AATAACTCATCAAAATGGCCATTGCAGAATCTAGCTGCACTTCTTAAGGAAGCAGACTCTGA
TGCTGCGGGTTTCATTGCCCCTAAGTGAGATGCTGAAGGAAGAAGGGCTGTTTCTTTTCTG
TTTTCAAGTGTCATGAGAAATTTAAAGTTCAGGAATGTGCAAGTTCAGAGTGCTCCTGGACT
CCTTTGCTCATTCAGAGACATCTCACTGAAAACAAACATTCCTCAAGGTTATCTCTGGTCCT
GGGAATTCGATATCATAATCAACCATAGGTACCGAGCTCGGGATTCAGCCGGGAGCTTAG
GGAGGGGAGGTCACTTCATAAGGGCCTGGGGGGGGAGTTGGAGCCACGAGTCGTCCAGC
CGGAGCCCCGTGTGGCTGAGCTCCGGCCTCAGAAGCATCCCCGGGTTGGATCCTTCGAA
GCTAGCGCTACCGGTCGCCACCATGGTGAGCAAGGGCGAGGAGCTGTTCACCGGGGTGG
TGCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGCTGATCTGCACCACCGG
CAAGCTGCCCGTGCCCTGGCCCACCCTCGTGACCACCCTGGGCTACGGCGTGCAGTGCT
TCGCCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCG
AGGTGAAGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCACAACGTCT
ATATCACCGCCGACAAGCAGAAGAACGGCATCAAGGCCAACTTCAAGATCCGCCACAACA
TCGAGGACGGCGGCGTGCAGCTCGCCGACCACTACCAGCAGAACACCCCCATCGGCGAC
GGCCCCGTGCTGCTGCCCGACAACCACTACCTGAGCTACCAGTCCAAGCTGAGCAAAGAC
CCCAACGAGAAGCGCGATCACATGGTCCTGCTGGAGTTCGTGACCGCCGCCGGGATCAC
TCTCGGCATGGACGAGCTGTACAAGTAAGTCGACATCATAATCAACCTCTGGATTACAAAA
TTTGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTGTAT
AAATCCTGGTTAGTTCTTGCCACGGCGGAACTCATCGCCGCCTGCCTTGCCCGCTGCTGG
ACAGGGGCTCGGCTGTTGGGCACTGACAATTCCGTGGCTCGAGAGATCTTCGACTGTGCC
TTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGT
GTCATTCTATTCTGGGGGGTGGGGTGGGGCAGGACAGCAAGGGGGAGGATTGGGAAGAC
AATAGCAGGCATGCACGTGCGGACCGAGCGGCCGC (SEQ ID NO: 108)

CN1647 (2085 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCCCTTCTTTCCAGTTCC
ACGTAGCCTTGAAAACCATAACTTTGCAAATACAGGAGTTGTGAAAACGAGCATCCTAGAA
GTCACTGTAAGGGCAGAATGTGTTTGGAGAAAGTCCCATTCCCAGAAAATTGTCACTATTTA
GCCCATCTGAAAGTCGCATAAAAAGCTCTACTGTCGACATTTGTCTTTATTTGAGCTGATTC
AGAGCTTGCTTTGTGCAACTAGCACAACCCATCAGAGGCAATTGCTTAATATTGCAGCTGC
CTTCAGTGGAGATTCCAGTTGTGACTAACAAGAAGCTGTTTTAGAAAAATAAAATACCCTTA
AAAATAAAAACTAATACACTCATGGAAACCTAAAAAAATTATGCATATGATTAGGGTTGTGAA
TACACTTAGGAAAGACCTAAGAGGGCCCTAATCTCTCACAGCTGGCTGAGGATAAGGCGA
ATTCGATATCATAATCAACCATAGGTACCGAGCTCGGGATTCAGCCGGGAGCTTAGGGAG
GGGAGGTCACTTCATAAGGGCCTGGGGGGGGAGTTGGAGCCACGAGTCGTCCAGCCGGA
GCCCCGTGTGGCTGAGCTCCGGCCTCAGAAGCATCCCCGGGTTGGATCCTTCGAAGCTA
GCGCTACCGGTCGCCACCATGGTGAGCAAGGGCGAGGAGCTGTTCACCGGGGTGGTGCC

FIG. 15 cont'd

CATCCTGGTCGAGCTGGACGGCGACGTAAACGGCCACAAGTTCAGCGTGTCCGGCGAGG
GCGAGGGCGATGCCACCTACGGCAAGCTGACCCTGAAGCTGATCTGCACCACCGGCAAG
CTGCCCGTGCCCTGGCCCACCCTCGTGACCACCCTGGGCTACGGCGTGCAGTGCTTCGC
CCGCTACCCCGACCACATGAAGCAGCACGACTTCTTCAAGTCCGCCATGCCCGAAGGCTA
CGTCCAGGAGCGCACCATCTTCTTCAAGGACGACGGCAACTACAAGACCCGCGCCGAGGT
GAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATA
TCACCGCCGACAAGCAGAAGAACGGCATCAAGGCCAACTTCAAGATCCGCCACAACATCG
AGGACGGCGGCGTGCAGCTCGCCGACCACTACCAGCAGAACACCCCCATCGGCGACGGC
CCCGTGCTGCTGCCCGACAACCACTACCTGAGCTACCAGTCCAAGCTGAGCAAAGACCCC
AACGAGAAGCGCGATCACATGGTCCTGCTGGAGTTCGTGACCGCCGCCGGGATCACTCTC
GGCATGGACGAGCTGTACAAGTAAGTCGACATCATAATCAACCTCTGGATTACAAAATTTG
TGAAAGATTGACTGGTATTCTTAACTATGTTGCTCCTTTTACGCTATGTGGATACGCTGCTT
TAATGCCTTTGTATCATGCTATTGCTTCCCGTATGGCTTTCATTTTCTCCTCCTTGTATAAAT
CCTGGTTAGTTCTTGCCACGGCGGAACTCATCGCCGCCTGCCTTGCCCGCTGCTGGACAG
GGGCTCGGCTGTTGGGCACTGACAATTCCGTGGCTCGAGAGATCTTCGACTGTGCCTTCT
AGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATA
GCAGGCATGCACGTGCGGACCGAGCGGCCGC (SEQ ID NO: 109)

CN1719 (2461 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTACTGCACGTACCACTCT
ATGTTAGGAAATAAACGACTCATAGTCGTGAAATGCTTCACATTTCTCATGAAGCTGAGGTA
GCCCAGCATTCTCTACTTTAGAAATCTGGATGTATTTTTTCCTCATGGGTCTGTAATTGAGT
CCGTAATTGACATTTGTACACTTTTAAGATAAATCTAGCCTGTCTTCAAGTATATTTTAGATC
TAGTGAAATACAGAGTACTATAGATTAGATATTCTGAATATCATCTGTTTGTTATTTAGTAAT
GTGATATGCCTTGTGTACCCACTTTTGTATTTACCATTATTGCAAAATCAATCAAATGTGAGC
AAAAGCAAAGGCAATTTGAATGACTCAAAATTGAAATTTGAGCTGCCAAATCAAGCAGTAAA
ACAATTTTTACCAGCTCTATTGATTGTTAGAAAGATAAGTTATAAACTTTATTTCAAGTAAATT
TCTAAAAGATCTGGGAATGTGATTATTCCAAGGCAGATGGCGAAGACCTTTATTTCCACTGA
TTATTCACAGATGCAAATTATTATGCAACTGGAAGCATACTAAGATATTGCAAAGATGTTCT
GACATTAGTCATCTGCTGCCTTTGTTACTTTGGTGTCAATTTTCTTATTCTTTCCAAAGGAAG
ATCCTTACAGTTTGTATTCTTTCACAGCTGGGAAATGATCAGTTGAGAATTATTCAAACACA
CCAATCTGTTAACCGTACTTCTTCCCAGATAATGCAATATTTTGCAGGGTGACAGGCAAAAA
GTGGTCATTTTTTACTTCATATATTTTAGGGTTATTTGGTTTTGATTAAATGAGTGAATTCGA
TATCATAATCAACCATAGGTACCGAGCTCGGGATTCAGCCGGGAGCTTAGGGAGGGGAGG
TCACTTCATAAGGGCCTGGGGGGGGAGTTGGAGCCACGAGTCGTCCAGCCGGAGCCCCG
TGTGGCTGAGCTCCGGCCTCAGAAGCATCCCCGGGTTGGATCCTTCGAAGCTAGCGCTAC
CGGTCGCCACCATGGTGAGCAAGGGCGAGGAGCTGTTCACCGGGGTGGTGCCCATCCTG
GTCGAGCTGGACGGCGACGTAAACGGCCACAAGTTCAGCGTGTCCGGCGAGGGCGAGG
GCGATGCCACCTACGGCAAGCTGACCCTGAAGCTGATCTGCACCACCGGCAAGCTGCCC
GTGCCCTGGCCCACCCTCGTGACCACCCTGGGCTACGGCGTGCAGTGCTTCGCCCGCTA
CCCCGACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACG

FIG. 15 cont'd

GCAACATCCTGGGGCACAAGCTGGAGTACAACTACAACAGCCACAACGTCTATATCACCG
CCGACAAGCAGAAGAACGGCATCAAGGCCAACTTCAAGATCCGCCACAACATCGAGGACG
GCGGCGTGCAGCTCGCCGACCACTACCAGCAGAACACCCCCATCGGCGACGGCCCCGTG
CTGCTGCCCGACAACCACTACCTGAGCTACCAGTCCAAGCTGAGCAAAGACCCCAACGAG
AAGCGCGATCACATGGTCCTGCTGGAGTTCGTGACCGCCGCCGGGATCACTCTCGGCATG
GACGAGCTGTACAAGTAAGTCGACATCATAATCAACCTCTGGATTACAAAATTTGTGAAAGA
TTGACTGGTATTCTTAACTATGTTGCTCCTTTTACGCTATGTGGATACGCTGCTTTAATGCC
TTTGTATCATGCTATTGCTTCCCGTATGGCTTTCATTTTCTCCTCCTTGTATAAATCCTGGTT
AGTTCTTGCCACGGCGGAACTCATCGCCGCCTGCCTTGCCCGCTGCTGGACAGGGGCTC
GGCTGTTGGGCACTGACAATTCCGTGGCTCGAGAGATCTTCGACTGTGCCTTCTAGTTGC
CAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGG
CATGCACGTGCGGACCGAGCGGCCGC (SEQ ID NO: 110)

CN2365 (2204 bp between ITRs):
GCGGCCGCACGCGTACCACCTGTGTACATTCATTGGCAAGTCACCATCCTATCCTCTTGCT
GCATCTTGCCTTTCCACTGCGATTATTTTTAGGGGTGTGTGTGCACCGCGCTGGGAATATG
GCAAACGTCCCCACTCCCCATCAGACGTCATGATTCCTGCACACACTGGGCTCTCACTAAC
CCCAGCTTCCTTTCCCCTGGTGGTTTTGAGAGCATAAATTTTATTTCCAGCTGTGGGTTTGG
GTCCTATGCAGAACACCTCCCTGGAGAATTGCAACTAAGATGTTTATGGCAATCGCCCTGC
AAGTGTCTATTTAATTCCTGAAAATGTCATTTACTGGTGTGTTTCTGTAAAAATCATTTCTGA
AAAGTTTTGTCAGCTTGGCTTAGCAGCTGGGGGAAAAAAGCAGCAAAATGAGTCCCCTCAA
TCAAGCCTGTGATTTTTTATTTTTTCAGACTCATGAATCCTCCTGAGAATTAGGCTTATGACA
AGCACCCACCCCCTCCACCTACTCCCTGGTTTAAACCAGGTGCCTGCTGACACGAAGGAA
GATTCCGGGGCATTTTGATCCTAGTCACACAGTGTTTCTAAGTGGGCATTACTCCTGTCAAT
CCACAGTCTTAAAGATGTTCCTCAGACAAAAGATAATTAGTGACAAGAAGGCCCACTAGATT
CCATGTCATATCTTAGTTGGCGGGCCAGAGAAGGACAGGGTCTCTGGTTGGGGCCGTGTC
TCCCATCGCATTCTCCCTTTGCAGGTGCTGAAGTGAGGAAGGCCCACAGCTCAGCCAAGC
ACATGGGGTGCCTCCCTCCTGGGCCACTAGCCCACTGGCCAGTAAGAGAACCAGGGAGC
CTTTGAGCTCGGGCTGGGCATAAAAGTCAGGGCAGAGCCATCTATTGCTTACATTTGCTTC
TGGGATCCAGATCTTTCGAAGCTAGCGCTACCGGTCGCCACCATGGTGAGCAAGGGCGAG
GAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGA
AGCTGATCTGCACCACCGGCAAGCTGCCCGTGCCCTGGCCCACCCTCGTGACCACCCTG
GGCTACGGCGTGCAGTGCTTCGCCCGCTACCCCGACCACATGAAGCAGCACGACTTCTTC
AAGTCCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCATCGA
GCTGAAGGGCATCGACTTCAAGGAGGACGGCAACATCCTGGGGCACAAGCTGGAGTACA
ACTACAACAGCCACAACGTCTATATCACCGCCGACAAGCAGAAGAACGGCATCAAGGCCA
ACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG

FIG. 15 cont'd

CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATAGCAGGCATG
AGATCTCACGTGCGGACCGAGCGGCCGC (SEQ ID NO: 111)

CN2355 (1882 bp between ITRs):
GCGGCCGCACGCGTTGTTTGATACTTAGGGGAATAGTGGGAAAAAATAGGTGACCCTTTAT
GTGGAAAATACATCACCTTCTTTAATCAAGATATCATGAAAGAAACACAGTGGTTTCCATTC
AGATTAATTTATTCTCCAGATGTCCTGATAGAGTGATTCAGCTGTGATAAAACGGTGGAGTC
AGGTTTAGTTCTCCTCTTCGCGAGCTAGTTCTCACACAATGAGTTGAATACAGTTCTCAGAA
ATCATTCTTACTTTCTTCCTCTTCTCCATCAACTTCCTCAGTCTGGGGATGAGAGATAGTAT
AATTCTGAGTAATCAGGCTCCTCTTGAAATCCCATTTCAGCAGAAAACTGGCTGGGTTCCTA
GCCAAAAAGAACACCTGCCAGACTGACTTTTCCCTAGGTAATGTAAGAAGCACAGATGTC
ATCAGTCACTGTTTACTTAACAATATATTTCCACTGGCCACAGTCTGGCCTTGTTTCTTCCAT
TTCTGCTTCCACCTCTCATACAACTACAAAAACAGCCCTTGACGAGCTCGGGCTGGGCATA
AAAGTCAGGGCAGAGCCATCTATTGCTTACATTTGCTTCTGGGATCCAGATCTTTCGAAGC
TAGCGCTACCGGTCGCCACCATGGTGAGCAAGGGCGAGGAGCTGTTCACCGGGGTGGTG
CCCATCCTGGTCGAGCTGGACGGCGACGTAAACGGCCACAAGTTCAGCGTGTCCGGCGA
GGGCGAGGGCGATGCCACCTACGGCAAGCTGACCCTGAAGCTGATCTGCACCACCGGCA
AGCTGCCCGTGCCCTGGCCCACCCTCGTGACCACCCTGGGCTACGGCGTGCAGTGCTTC
GCCCGCTACCCCGACCACATGAAGCAGCACGACTTCTTCAAGTCCGCCATGCCCGAAGGC
TACGTCCAGGAGCGCACCATCTTCTTCAAGGACGACGGCAACTACAAGACCCGCGCCGAG
GTGAAGTTCGAGGGCGACACCCTGGTGAACCGCATCGAGCTGAAGGGCATCGACTTCAAG
GAGGACGGCAACATCCTGGGGCACAAGCTGGAGTACAACTACAACAGCCACAACGTCTAT
ATCACCGCCGACAAGCAGAAGAACGGCATCAAGGCCAACTTCAAGATCCGCCACAACATC
GAGGACGGCGGCGTGCAGCTCGCCGACCACTACCAGCAGAACACCCCCATCGGCGACGG
CCCCGTGCTGCTGCCCGACAACCACTACCTGAGCTACCAGTCCAAGCTGAGCAAAGACCC
CAACGAGAAGCGCGATCACATGGTCCTGCTGGAGTTCGTGACCGCCGCCGGGATCACTCT
CGGCATGGACGAGCTGTACAAGTAAGTCGACGGCGCGCCGCGGCCGCGAATTCGATATC
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTAGTTCTTGCCACGGCGGAACTCATCGC
CGCCTGCCTTGCCCGCTGCTGGACAGGGGCTCGGCTGTTGGGCACTGACAATTCCGTGG
CTCGAGAGATCTTCGACTGTGCCTTCTAGTTGCCAGCCATCTGTTGTTTGCCCCTCCCCCG
TGCCTTCCTTGACCCTGGAAGGTGCCACTCCCACTGTCCTTTCCTAATAAAATGAGGAAAT
TGCATCGCATTGTCTGAGTAGGTGTCATTCTATTCTGGGGGGTGGGGTGGGGCAGGACAG
CAAGGGGGAGGATTGGGAAGACAATAGCAGGCATGAGATCTCACGTGCGGACCGAGCGG
CCGC (SEQ ID NO: 112)

CN1797 (2370 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTGTGTGATATTTTTTCC
CACCACTTATTCTATATGAATGGACTAAAGTTAAATATGGTTCTAATTATAAATCAAAGATAT
CAGCTTGTGATAAAATAATAAATAGATTGATCTAGTATGATTGGTTTTCTTGTCAAGTAATCC
TTACTTACATAGTCTGAACACATTAAATAGCCCCAGTCACTCACAAAATAATATCATTATTCT
GGATAAAATGTAATGAGATTGTGAATGAAAACAGTGTTGATAGTGGTAGAGAGAAGTGCCA
CAGTCCCTAATACACACCAGATGTTCAAAGAATGATTGTGGAATGAATAAATGTTCATATTT

FIG. 15 cont'd

AATGAACATTCATGTAATTGAATGGTAGGGCATTATGAGAAGTGGGATGAGGAAAAAGGAT
GAATCAAAGATGATTTTCATGTTTCTATCTTGGTAATCACTGAGATGTGAAATTCAGGAATAT
GAAAAAGATTCTAGGAAAGAGCTGATAAGTTTACTTTTTAAATTAATCTATTTGAAAGGTACC
TGCATACACAGATGTTGCAGATAAATGAAAGATGAATGGAGCTGGAGCGTAAGAAAGCTCT
CTGGGCTGTATATTTATGCTCTAATATCATCTGTTTACATACAAATGGTAAAAGCCAAAGGG
ATGAATAAAAGTCATTTATTCATTCATAAAATATGTATTAAGACCTAGGCCAATTTCTGGAAT
AAGAGAACCAGATGTCAAAATTCTTCGGGGAATTCGATATCATAATCAACCATAGGTACCG
AGCTCGGGATTCAGCCGGGAGCTTAGGGAGGGGAGGTCACTTCATAAGGGCCTGGGGGGG
GGAGTTGGAGCCACGAGTCGTCCAGCCGGAGCCCCGTGTGGCTGAGCTCCGGCCTCAGA
AGCATCCCCGGGTTGGATCCTTCGAAGCTAGCGCTACCGGTCGCCACCATGGTGAGCAAG
GGCGAGGAGCTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAGGA
CGACGGCAACTACAAGACCCGCGCCGAGGTGAAGTTCGAGGGCGACACCCTGGTGAACC
GCATCGAGCTGAAGGGCATCGACTTCAAGGAGGACGGCAACATCCTGGGGCACAAGCTG
GAGTACAACTACAACAGCCACAACGTCTATATCACCGCCGACAAGCAGAAGAACGGCATC
AAGGCCAACTTCAAGATCCGCCACAACATCGAGGACGGCGGCGTGCAGCTCGCCGACCA
CTACCAGCAGAACACCCCCATCGGCGACGGCCCCGTGCTGCTGCCCGACAACCACTACCT
GAGCTACCAGTCCAAGCTGAGCAAAGACCCCAACGAGAAGCGCGATCACATGGTCCTGCT
GGAGTTCGTGACCGCCGCCGGGATCACTCTCGGCATGGACGAGCTGTACAAGTAAGTCGA
CATCATAATCAACCTCTGGATTACAAAATTTGTGAAAGATTGACTGGTATTCTTAACTATGTT
GCTCCTTTTACGCTATGTGGATACGCTGCTTTAATGCCTTTGTATCATGCTATTGCTTCCCG
TATGGCTTTCATTTTCTCCTCCTTGTATAAATCCTGGTTAGTTCTTGCCACGGCGGAACTCA
TCGCCGCCTGCCTTGCCCGCTGCTGGACAGGGGCTCGGCTGTTGGGCACTGACAATTCC
GTGGCTCGAGAGATCTTCGACTGTGCCTTCTAGTTGCCAGCCATCTGTTGTTTGCCCCTCC
CCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCACGTGCGGACCGAGCGGCC
GC (SEQ ID NO: 113)

CN1584 (2006 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCAGGCAAGGCTTCCTC
CCTTGAGTCCCTTTCTGTCTCAGGTGGATGATCTCATTATACAAGTCAAGCTTTGAATTACT
TCAGCCATACCCTCCCCTTCCACTCCATCCCAAATAAAAATGAGTTACACAGAACCCACCA
GCAGTACTTTACGAGTACCAGCAATTGCAACCGTGCATCCTTAATAGTGGCGTAATCAAAA
GTTATGATGCATTTTTCTGTAATCACAAGAAATGATACCACTTAGTGCTAAGTAAAGCCAATT
CCCTACCACACAGAAAGGCAAAAGCGCTTCCATTTTCACTTTGAAATGAGTGAGTCAGAAT
CAATTTGGTAAAGCAGTTAACAGCAACTGTGTGCCCCTTTCGAGAATTCGATATCATAATCA
ACCATAGGTACCGAGCTCGGGATTCAGCCGGGAGCTTAGGGAGGGGAGGTCACTTCATAA
GGGCCTGGGGGGGGAGTTGGAGCCACGAGTCGTCCAGCCGGAGCCCCGTGTGGCTGAG
CTCCGGCCTCAGAAGCATCCCCGGGTTGGATCCTTCGAAGCTAGCGCTACCGGTCGCCAC
CATGGTGAGCAAGGGCGAGGAGCTGTTCACCGGGGTGGTGCCCATCCTGGTCGAGCTGG
ACGGCGACGTAAACGGCCACAAGTTCAGCGTGTCCGGCGAGGGCGAGGGCGATGCCACC
TACGGCAAGCTGACCCTGAAGCTGATCTGCACCACCGGCAAGCTGCCCGTGCCCTGGCC

FIG. 15 cont'd

CACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAAGTCGACATCATAATCAACCTCTGGATTACAAAATTTGTGAAAGATTGACTGGTA
TTCTTAACTATGTTGCTCCTTTTACGCTATGTGGATACGCTGCTTTAATGCCTTTGTATCATG
CTATTGCTTCCCGTATGGCTTTCATTTTCTCCTCCTTGTATAAATCCTGGTTAGTTCTTGCCA
CGGCGGAACTCATCGCCGCCTGCCTTGCCCGCTGCTGGACAGGGGCTCGGCTGTTGGGC
ACTGACAATTCCGTGGCTCGAGAGATCTTCGACTGTGCCTTCTAGTTGCCAGCCATCTGTT
GTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCACGTGCG
GACCGAGCGGCCGC (SEQ ID NO: 114)

CN1455 (1763 bp between ITRs):
GCGGCCGCACGCGTCTGGAACTGTTGAATGAATGAATGAATGAATGAATGAATGAATGAAT
GAAAAATTAGACTGCCCAGATAGTCAACAATTAAAAAATGGTTAAGTGAATGATAGCAAACG
CTGTCAATGACAGCTTCAGCCGCTTAGGAAATGTTGATGATGTAACATTAAGGGAACTGG
TGCAAGCATTGCAATTACAATGCTTAAAAAGTGCTCTGCGTAAACAGGGCCTGGAAGAATA
TAGAGACAAATGAGAACAGCTGTGGTGCCGGAGACACGAGATCTTGCTTAAAATTTTCCAC
TCAGTTTTGGCAAACCGTAACAACCTTGTGGCTCTTCATATCCTTGAACCTTGAAATCAATC
TCATTTCTAGAGACTGCTGATAAGAGTCGGAAAGACAAAGCTTTAGGTAGTAATCTGGAGC
TCGGGCTGGGCATAAAGTCAGGGCAGAGCCATCTATTGCTTACATTTGCTTCTGGGATCC
AGATCTTTCGAAGCTAGCGCTACCGGTCGCCACCATGGTGAGCAAGGGCGAGGAGCTGTT
CACCGGGGTGGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTGAAGCTGATC
TGCACCACCGGCAAGCTGCCCGTGCCCTGGCCCACCCTCGTGACCACCCTGGGCTACGG
CGTGCAGTGCTTCGCCCGCTACCCCGACCACATGAAGCAGCACGACTTCTTCAAGTCCGC
CATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGG
GCATCGACTTCAAGGAGGACGGCAACATCCTGGGGCACAAGCTGGAGTACAACTACAACA
GCCACAACGTCTATATCACCGCCGACAAGCAGAAGAACGGCATCAAGGCCAACTTCAAGA
TCCGCCACAACATCGAGGACGGCGGCGTGCAGCTCGCCGACCACTACCAGCAGAACACC
CCCATCGGCGACGGCCCCGTGCTGCTGCCCGACAACCACTACCTGAGCTACCAGTCCAA
GCTGAGCAAAGACCCCAACGAGAAGCGCGATCACATGGTCCTGCTGGAGTTCGTGACCGC
CGCCGGGATCACTCTCGGCATGGACGAGCTGTACAAGTAAGTCGACGGCGCGCCGCGGC
CGCGAATTCGATATCATAATCAACCTCTGGATTACAAAATTTGTGAAAGATTGACTGGTATT
CTTAACTATGTTGCTCCTTTTACGCTATGTGGATACGCTGCTTTAATGCCTTTGTATCATGCT
ATTGCTTCCCGTATGGCTTTCATTTTCTCCTCCTTGTATAAATCCTGGTTAGTTCTTGCCAC
GGCGGAACTCATCGCCGCCTGCCTTGCCCGCTGCTGGACAGGGGCTCGGCTGTTGGGCA
CTGACAATTCCGTGGCTCGAGAGATCTTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGG

FIG. 15 cont'd

GTGGGGCAGGACAGCAAGGGGGAGGATTGGGAAGACAATAGCAGGCATGCACGTGCGGA
CCGAGCGGCCGC (SEQ ID NO: 115)

CN1451 (2050 bp between ITRs):
GCGGCCGCACGCGTCAAGACATCTCCCTGTAGACACGGTGCCAGAACAGTGACCTCAGAC
CACAGCTTGGACGCTGATTACAAGTAATCCAGCTCCAGAGGTGATAGAGTGTCCTTTCTTT
AAAAAGGAGATAAAAATAGCGAAGAAACAACACTTTCCTTAGTTCTCTGAAAGGTTGGCATT
CTTCCAGAGTAGACTTATGTACTTTTTGTACTTGGAGGAAAAAAAGAGATGGGATCTGGTC
CAAGAATAGTCCTGCAAACAAGAGAAATATGGAGCAGGCAGCTGGAGCTGAGCATCCAAG
TGGTACCACCAGCTGCAGGCCCATTAATTAACGATCCCTGGTATGTAGCGGTTCCCGTGAC
CTTGATTCTTGTTGAATTCACAGAGATAATTTTTACAGAGTCTCTACTTTTCTCACTGCGGTA
TATTTATCCAAGGAGTACCTTGCATATTTCCCCCCATCTCTCCAAGCAGTAAATTTATTCTAA
TTGCAAAGAGATACAGTAAAAGCCTGATTGAATACTTGGCAGTTTATAGAGATTTATTTCGG
GAGCTTAAGGGGGTTTTTAGACTGTATGACTAGAGCAGGGTTGAGGGGAGCTGGGGAAAG
GAGCCCAAGAGAAATGTAGATTTAATGGATCTATAAAATGACCCTGCTGTAGATAAACGTT
TGTTCCAAGAAGTTTAAACAGCCTGACCCAAACCAGGAGCTCGGGCTGGGCATAAAAGT
CAGGGCAGAGCCATCTATTGCTTACATTTGCTTCTGGGATCCAGATCTTTCGAAGCTAGCG
CTACCGGTCGCCACCATGGTGAGCAAGGGCGAGGAGCTGTTCACCGGGGTGGTGCCCAT
CCTGGTCGAGCTGGACGGCGACGTAAACGGCCACAAGTTCAGCGTGTCCGGCGAGGGCG
AGGGCGATGCCACCTACGGCAAGCTGACCCTGAAGCTGATCTGCACCACCGGCAAGCTG
CCCGTGCCCTGGCCCACCCTCGTGACCACCCTGGGCTACGGCGTGCAGTGCTTCGCCCG
CTACCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGGTGAA
GTTCGAGGGCGACACCCTGGTGAACCGCATCGAGCTGAAGGGCATCGACTTCAAGGAGG
ACGGCAACATCCTGGGGCACAAGCTGGAGTACAACTACAACAGCCACAACGTCTATATCA
CCGCCGACAAGCAGAAGAACGGCATCAAGGCCAACTTCAAGATCCGCCACAACATCGAGG
ACGGCGGCGTGCAGCTCGCCGACCACTACCAGCAGAACACCCCCATCGGCGACGGCCCC
GTGCTGCTGCCCGACAACCACTACCTGAGCTACCAGTCCAAGCTGAGCAAAGACCCCAAC
GAGAAGCGCGATCACATGGTCCTGCTGGAGTTCGTGACCGCCGCCGGGATCACTCTCGG
CATGGACGAGCTGTACAAGTAAGTCGACGGCGCGCCGCGGCCGCGAATTCGATATCATAA
TCAACCTCTGGATTACAAAATTTGTGAAAGATTGACTGGTATTCTTAACTATGTTGCTCCTTT
TACGCTATGTGGATACGCTGCTTTAATGCCTTTGTATCATGCTATTGCTTCCCGTATGGCTT
TCATTTTCTCCTCCTTGTATAAATCCTGGTTAGTTCTTGCCACGGCGGAACTCATCGCCGCC
TGCCTTGCCCGCTGCTGGACAGGGGCTCGGCTGTTGGGCACTGACAATTCCGTGGCTCG
AGAGATCTTCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCAT
CGCATTGTCTGAGTAGGTGTCATTCTATTCTGGGGGGTGGGGTGGGGCAGGACAGCAAG
GGGGAGGATTGGGAAGACAATAGCAGGCATGCACGTGCGGACCGAGCGGCCGC (SEQ ID
NO: 116)

CN2039 (2209 bp between ITRs):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTAGGTAC
CTCTACATTGATGGACCTTTCTCCAGAATGAGGAGCCAAAATCATCTGAATTAAGTAGAGAT
CTCATTTGTCCCTGACTCATGATAATGTCTGTGCTACAGTCCTGCATTAATTACTTTGCCCA
AGTAGAAATACACTACCCATATAAGAATTTCACTTCTGAACAAAACAAAATAAAAATCCACG
AGTGGTGACCTCAAAATGAACTGGTTAAATTTAAGGACTCATTTTTAAAGGTCAATGTCCTT
TTGCTGCAAATACAGTTCCTATGCAGATGAGAAGTTGAACCTGACCTATGGAGCCGAGCAT

FIG. 15 cont'd

AATTAGCCAGCTGCACCCTCATAATAAGGTGCAGATGGTTAATTGCACCAGCAAATAACTG
CTTACTTGTGGGCACAAAAGCCTGTACCTAAAATCATTGAAAGTATACTTGGGACTATTTAT
GCTCATGGCAAACAAAACACATTTCCAAGGTTTCATCTGCGAACAGATCACAGCCAGCTCC
AAATCCCTGCTTTGCGGGAGAGCCATTCACGCTGCTGAGGTCTGGTCCAAGAGAGGGACC
ACTGGCCACAAAGCCACATATTAACTGGTGAAATATTTCTTGGGGTGCTGAATCGTTGTTG
AGAGCTCGATTCAGCCGGGAGCTTAGGGAGGGGAGGTCACTTCATAAGGGCTTGGGGGG
GGAGTTGGAGCCACGAGTCGTCCAGCCGGAGCCCCGTGTGGCTGTGCTCCGGCCTCAGA
AGCATCCCCGGATCCAGATCTTTCGAAGCTAGCGCTACCGGTCGCCACCATGGTGAGCAA
GGGCGAGGAGCTGTTCACCGGGGTGGTGCCCATCCTGGTCGAGCTGGACGGCGACGTAA
ACGGCCACAAGTTCAGCGTGTCCGGCGAGGGCGAGGGCGATGCCACCTACGGCAAGCTG
ACCCTGAAGCTGATCTGCACCACCGGCAAGCTGCCCGTGCCCTGGCCCACCCTCGTGAC
CACCCTGGGCTACGGCGTGCAGTGCTTCGCCCGCTACCCCGACCACATGAAGCAGCACG
ACTTCTTCAAGTCCGCCATGCCCGAAGGCTACGTCCAGGAGCGCACCATCTTCTTCAAGG
ACGACGGCAACTACAAGACCCGCGCCGAGGTGAAGTTCGAGGGCGACACCCTGGTGAAC
CGCATCGAGCTGAAGGGCATCGACTTCAAGGAGGACGGCAACATCCTGGGGCACAAGCT
GGAGTACAACTACAACAGCCACAACGTCTATATCACCGCCGACAAGCAGAAGAACGGCAT
CAAGGCCAACTTCAAGATCCGCCACAACATCGAGGACGGCGGCGTGCAGCTCGCCGACC
ACTACCAGCAGAACACCCCCATCGGCGACGGCCCCGTGCTGCTGCCCGACAACCACTAC
CTGAGCTACCAGTCCAAGCTGAGCAAAGACCCCAACGAGAAGCGCGATCACATGGTCCTG
CTGGAGTTCGTGACCGCCGCCGGGATCACTCTCGGCATGGACGAGCTGTACAAGTAAGTC
GACGGCGCGCCGCGGCCGCGAATTCGATATCATAATCAACCTCTGGATTACAAAATTTGTG
AAAGATTGACTGGTATTCTTAACTATGTTGCTCCTTTTACGCTATGTGGATACGCTGCTTTA
ATGCCTTTGTATCATGCTATTGCTTCCCGTATGGCTTTCATTTTCTCCTCCTTGTATAAATCC
TGGTTAGTTCTTGCCACGGCGGAACTCATCGCCGCCTGCCTTGCCCGCTGCTGGACAGGG
GCTCGGCTGTTGGGCACTGACAATTCCGTGGCTCGAGAGATCTTCGACTGTGCCTTCTAG
TTGCCAGCCATCTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAGTAGGTGTCATTC
TATTCTGGGGGGTGGGGTGGGGCAGGACAGCAAGGGGGAGGATTGGGAAGACAATAGCA
GGCATGAGATCTCACGTGCGGACCGAGCGGCCGC (SEQ ID NO: 117)

CN2040 (2140 bp between ITRs):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTAGATTCC
TCACCCCCAAGAAGTATTTAAGCAGTTGAGATGTGGCCCCCAGTCCCTCCCTTGAACTCGA
CCTCGGCAATGTGAACCACAAAGCCCTGCAGTTGGAGGCTGCCGAGGTCTATTCACAGAT
GAAATTTTGGAAATGTGTTTTGTTTGCCTGTGCATAAATACGCCCAAGCATACTATCGATAC
TTTTAGGTACAGGCTTTTGTGCCTACTGGTAAGCAGTCATTTGCCGGGGCAATTAACCATC
TGCACTTTATTATCAGGGTGCAGCTGGCTAATGATGCTCAGTGCCACGGGGCAGGATCAG
CTTCTCATCTGCACAGGAACTGTATTCACAGCAAAGGACATTGACCTTTAACAATGAATCTT
TAAATTTAACCGGGTCCCCCAGAGATCACCGCACACAAGGTTTCATTGTGTTTCGATCTGA
GGTGAGATTCAAATGTGGGCCGTGGGATTCCTGTTTTGGGTAGAGCGGTTAACACAGAAC
AGTAGGATAGGTCAGCAATTATCAGCCAAGAACAAAGGAGAACCCTGATGCTCAGTCTGAG
CTCGATTCAGCCGGGAGCTTAGGGAGGGGAGGTCACTTCATAAGGGCTTGGGGGGGGAG
TTGGAGCCACGAGTCGTCCAGCCGGAGCCCCGTGTGGCTGTGCTCCGGCCTCAGAAGCA
TCCCCGGATCCAGATCTTTCGAAGCTAGCGCTACCGGTCGCCACCATGGTGAGCAAGGGC
GAGGAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGACCC
TGAAGCTGATCTGCACCACCGGCAAGCTGCCCGTGCCCTGGCCCACCCTCGTGACCACC

FIG. 15 cont'd

CTGGGCTACGGCGTGCAGTGCTTCGCCCGCTACCCCGACCACATGAAGCAGCACGACTTC
TTCAAGTCCGCCATGCCCGAAGGCTACGTCCAGGAGCGCACCATCTTCTTCAAGGACGAC
GGCAACTACAAGACCCGCGCCGAGGTGAAGTTCGAGGGCGACACCCTGGTGAACCGCAT
CGAGCTGAAGGGCATCGACTTCAAGGAGGACGGCAACATCCTGGGGCACAAGCTGGAGT
ACAACTACAACAGCCACAACGTCTATATCACCGCCGACAAGCAGAAGAACGGCATCAAGG
CCAACTTCAAGATCCGCCACAACATCGAGGACGGCGGCGTGCAGCTCGCCGACCACTACC
AGCAGAACACCCCCATCGGCGACGGCCCCGTGCTGCTGCCCGACAACCACTACCTGAGC
TACCAGTCCAAGCTGAGCAAAGACCCCAACGAGAAGCGCGATCACATGGTCCTGCTGGAG
TTCGTGACCGCCGCCGGGATCACTCTCGGCATGGACGAGCTGTACAAGTAAGTCGACGGC
GCGCCGCGGCCGCGAATTCGATATCATAATCAACCTCTGGATTACAAAATTTGTGAAAGAT
TGACTGGTATTCTTAACTATGTTGCTCCTTTTACGCTATGTGGATACGCTGCTTTAATGCCT
TTGTATCATGCTATTGCTTCCCGTATGGCTTTCATTTTCTCCTCCTTGTATAAATCCTGGTTA
GTTCTTGCCACGGCGGAACTCATCGCCGCCTGCCTTGCCCGCTGCTGGACAGGGGCTCG
GCTGTTGGGCACTGACAATTCCGTGGCTCGAGAGATCTTCGACTGTGCCTTCTAGTTGCCA
GCCATCTGTTGTTTGCCCCTCCCCCGTGCCTTCCTTGACCCTGGAAGGTGCCACTCCCACT
GTCCTTTCCTAATAAAATGAGGAAATTGCATCGCATTGTCTGAGTAGGTGTCATTCTATTCT
GGGGGGTGGGGTGGGGCAGGACAGCAAGGGGGAGGATTGGGAAGACAATAGCAGGCAT
GAGATCTCACGTGCGGACCGAGCGGCCGC (SEQ ID NO: 118)

CN1567 (2051 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTGAAGTGTTCCTGCCCT
TGCATGAAAATGACTCTATCTGGTTTATAATTAGAAGTGAAATGATTTTAAATGGCTTCCACA
TGGCTTAGTTTTCCAAGCAGTTCCAGTTACATAGAACTTCATATAAACAGATAATGAGAGGC
TAGAGTTGGAGAGCACAGTTCCTGCTTCCAAATTGGCTTGAAGTGGGGACATCTGCTCTGC
ATGAAGCCTGGGTCAGGCTGCCCCTCTCATCTGTGACCTCCTGTGGTCGGGAGGGACTTG
CTCTGGATTATATAAAGGCTTCACAAGAGTACTGGAAGCGGGGACGGAATCAACTTGAGCA
AAAAACCTAATTGGCTTGAATCTTTCCTTGACCATCAGTAATTATTTTGAGATTGATAGCCTA
TCTTATAATAAAATAACTGTTTCCTGAATTCGATATCATAATCAACCATAGGTACCGAGCTCG
GGATTCAGCCGGGAGCTTAGGGAGGGGAGGTCACTTCATAAGGGCCTGGGGGGGGAGTT
GGAGCCACGAGTCGTCCAGCCGGAGCCCCGTGTGGCTGAGCTCCGGCCTCAGAAGCATC
CCCGGGTTGGATCCTTCGAAGCTAGCGCTACCGGTCGCCACCATGGTGAGCAAGGGCGA
GGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTG
AAGCTGATCTGCACCACCGGCAAGCTGCCCGTGCCCTGGCCCACCCTCGTGACCACCCT
GGGCTACGGCGTGCAGTGCTTCGCCCGCTACCCCGACCACATGAAGCAGCACGACTTCTT
CAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTAC
AACTACAACAGCCACAACGTCTATATCACCGCCGACAAGCAGAAGAACGGCATCAAGGCC
AACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACATCAT
AATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGC
TTTCATTTTCTCCTCCTTGTATAAATCCTGGTTAGTTCTTGCCACGGCGGAACTCATCGCCG

FIG. 15 cont'd

CCTGCCTTGCCCGCTGCTGGACAGGGGCTCGGCTGTTGGGCACTGACAATTCCGTGGCT
CGAGAGATCTTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCA
AGGGGGAGGATTGGGAAGACAATAGCAGGCATGCACGTGCGGACCGAGCGGCCGC (SEQ
ID NO: 119)

CN1626 (2058 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTGCTTAGAACGTCCACC
AGGATTTTTGTGGCAGATCGTAATATAGGTCAAGAAGGATTTAAATTTAGTTCTTATATTCTC
AAATTAATAACTCAATGAATTGCTTTAAGTTTTGAAAATTTACTTTCATAAGAGTCAGATCTG
AACTGGCTTCTCTATTTCGGCAGAAGCACCATCATGAATCTCAGAACCTTTAAAAAGACACC
CAAGAGTAGCAATTTTCTTTCTGAGAGTACGGATTCTATTTCTGACATGTAATTTTCCTTATA
CCCAACACCAAAAATGGGGACTTGAATCATAAACATATTTAACACTCAGAGGAGACATTAGT
AGGATCCTTTTAAATATTGAAAACATAATGAAATCAGGATCCCAGTCCAAATAATGTGCCTT
TTCTTAAAAGGCAAAAACAGTGTGGGAGGAATTCGATATCATAATCAACCATAGGTACCGA
GCTCGGGATTCAGCCGGGAGCTTAGGGAGGGGAGGTCACTTCATAAGGGCCTGGGGGGGG
GAGTTGGAGCCACGAGTCGTCCAGCCGGAGCCCCGTGTGGCTGAGCTCCGGCCTCAGAA
GCATCCCCGGGTTGGATCCTTCGAAGCTAGCGCTACCGGTCGCCACCATGGTGAGCAAG
GGCGAGGAGCTGTTCACCGGGGTGGTGCCCATCCTGGTCGAGCTGGACGGCGACGTAAA
CGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAGGA
CGACGGCAACTACAAGACCCGCGCCGAGGTGAAGTTCGAGGGCGACACCCTGGTGAACC
GCATCGAGCTGAAGGGCATCGACTTCAAGGAGGACGGCAACATCCTGGGGCACAAGCTG
GAGTACAACTACAACAGCCACAACGTCTATATCACCGCCGACAAGCAGAAGAACGGCATC
AAGGCCAACTTCAAGATCCGCCACAACATCGAGGACGGCGGCGTGCAGCTCGCCGACCA
CTACCAGCAGAACACCCCCATCGGCGACGGCCCCGTGCTGCTGCCCGACAACCACTACCT
GAGCTACCAGTCCAAGCTGAGCAAAGACCCCAACGAGAAGCGCGATCACATGGTCCTGCT
GGAGTTCGTGACCGCCGCCGGGATCACTCTCGGCATGGACGAGCTGTACAAGTAAGTCGA
CATCATAATCAACCTCTGGATTACAAAATTTGTGAAAGATTGACTGGTATTCTTAACTATGTT
GCTCCTTTTACGCTATGTGGATACGCTGCTTTAATGCCTTTGTATCATGCTATTGCTTCCCG
TATGGCTTTCATTTTCTCCTCCTTGTATAAATCCTGGTTAGTTCTTGCCACGGCGGAACTCA
TCGCCGCCTGCCTTGCCCGCTGCTGGACAGGGGCTCGGCTGTTGGGCACTGACAATTCC
GTGGCTCGAGAGATCTTCGACTGTGCCTTCTAGTTGCCAGCCATCTGTTGTTTGCCCCTCC
CCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCACGTGCGGACCGAGCGGCC
GC (SEQ ID NO: 120)

CN1712 (1923 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTACCAGGCTGACTAGTG

FIG. 15 cont'd

CTCTGTGGTCTTGATCAATTGTCCCAGCAGAGTTGGTGCATGGGAAAGCCTTTCTTGGCCT
TATCAGCAGCTCAGCCTGGGAGGTTGGCCCGGGGGCTGACCAAGCACAAAATAGAAAAGC
CACTAATAAGATCCAGCTGGAACAAATAGCCTCTATTTATTTTAGGAAACTAATGATATGTC
ATCATGACACATATCTAACCTTAGTATTTCTGATTGGACAGGCCAGTTATGTGGGCTATGAT
TCAAGCCATGGTTACGGCTCTGCGAATTCGATATCATAATCAACCATAGGTACCGAGCTCG
GGATTCAGCCGGGAGCTTAGGGAGGGGAGGTCACTTCATAAGGGCCTGGGGGGGGAGTT
GGAGCCACGAGTCGTCCAGCCGGAGCCCCGTGTGGCTGAGCTCCGGCCTCAGAAGCATC
CCCGGGTTGGATCCTTCGAAGCTAGCGCTACCGGTCGCCACCATGGTGAGCAAGGGCGA
GGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTG
AAGCTGATCTGCACCACCGGCAAGCTGCCCGTGCCCTGGCCCACCCTCGTGACCACCCT
GGGCTACGGCGTGCAGTGCTTCGCCCGCTACCCCGACCACATGAAGCAGCACGACTTCTT
CAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTAC
AACTACAACAGCCACAACGTCTATATCACCGCCGACAAGCAGAAGAACGGCATCAAGGCC
AACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACATCAT
AATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGC
TTTCATTTTCTCCTCCTTGTATAAATCCTGGTTAGTTCTTGCCACGGCGGAACTCATCGCCG
CCTGCCTTGCCCGCTGCTGGACAGGGGCTCGGCTGTTGGGCACTGACAATTCCGTGGCT
CGAGAGATCTTCGACTGTGCCTTCTAGTTGCCAGCCATCTGTTGTTTGCCCCTCCCCCGTG
CCTTCCTTGACCCTGGAAGGTGCCACTCCCACTGTCCTTTCCTAATAAAATGAGGAAATTG
CATCGCATTGTCTGAGTAGGTGTCATTCTATTCTGGGGGGTGGGGTGGGGCAGGACAGCA
AGGGGGAGGATTGGGAAGACAATAGCAGGCATGCACGTGCGGACCGAGCGGCCGC (SEQ
ID NO: 121)

CN1700 (1969 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTGGTATAGGGGGTCTT
ACGGAAATGCAGGGAAATTTGATTTCACTTACCACAGGATCAGAGATGTATTTCTTTCATGG
GTACCACAGCTGCTAAACCAAGCAGGTCTTCTCAGGACATAACCCACAGTGAGCATGTTAG
GATGCAGGAACATGTGCAGGGCTCTGGCAAGAGGTACTGAAACATTGAAAACGGCCTTGA
TAGAGTATCTCTCTTTGAAAGAGGTTTAAAAAAGATACACTAAAAGTTATTTTGCTTAACACT
GTCCATATAAACCAAAGAGGGCATTGAAATTACCAATGGCCCTGTATCTCTTGGGCAACAG
ATAAGGCGAATTCGATATCATAATCAACCATAGGTACCGAGCTCGGGATTCAGCCGGGAG
CTTAGGGAGGGGAGGTCACTTCATAAGGGCCTGGGGGGGGAGTTGGAGCCACGAGTCGT
CCAGCCGGAGCCCCGTGTGGCTGAGCTCCGGCCTCAGAAGCATCCCCGGGTTGGATCCT
TCGAAGCTAGCGCTACCGGTCGCCACCATGGTGAGCAAGGGCGAGGAGCTGTTCACCGG
GGTGGTGCCCATCCTGGTCGAGCTGGACGGCGACGTAAACGGCCACAAGTTCAGCGTGT
CCGGCGAGGGCGAGGGCGATGCCACCTACGGCAAGCTGACCCTGAAGCTGATCTGCACC
ACCGGCAAGCTGCCCGTGCCCTGGCCCACCCTCGTGACCACCCTGGGCTACGGCGTGCA
GTGCTTCGCCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCCG

FIG. 15 cont'd

CGCCGAGGTGAAGTTCGAGGGCGACACCCTGGTGAACCGCATCGAGCTGAAGGGCATCG
ACTTCAAGGAGGACGGCAACATCCTGGGGCACAAGCTGGAGTACAACTACAACAGCCACA
ACGTCTATATCACCGCCGACAAGCAGAAGAACGGCATCAAGGCCAACTTCAAGATCCGCC
ACAACATCGAGGACGGCGGCGTGCAGCTCGCCGACCACTACCAGCAGAACACCCCCATC
GGCGACGGCCCCGTGCTGCTGCCCGACAACCACTACCTGAGCTACCAGTCCAAGCTGAG
CAAAGACCCCAACGAGAAGCGCGATCACATGGTCCTGCTGGAGTTCGTGACCGCCGCCG
GGATCACTCTCGGCATGGACGAGCTGTACAAGTAAGTCGACATCATAATCAACCTCTGGAT
TACAAAATTTGTGAAAGATTGACTGGTATTCTTAACTATGTTGCTCCTTTTACGCTATGTGGA
TACGCTGCTTTAATGCCTTTGTATCATGCTATTGCTTCCCGTATGGCTTTCATTTTCTCCTCC
TTGTATAAATCCTGGTTAGTTCTTGCCACGGCGGAACTCATCGCCGCCTGCCTTGCCCGCT
GCTGGACAGGGGCTCGGCTGTTGGGCACTGACAATTCCGTGGCTCGAGAGATCTTCGACT
GTGCCTTCTAGTTGCCAGCCATCTGTTGTTTGCCCCTCCCCCGTGCCTTCCTTGACCCTGG
AAGGTGCCACTCCCACTGTCCTTTCCTAATAAAATGAGGAAATTGCATCGCATTGTCTGAGT
AGGTGTCATTCTATTCTGGGGGGTGGGGTGGGGCAGGACAGCAAGGGGGAGGATTGGGA
AGACAATAGCAGGCATGCACGTGCGGACCGAGCGGCCGC (SEQ ID NO: 122)

CN1607 (2032 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCCGGATGCCATCGAAG
GAAACTGCGCATCCCACAATTCACCGAGGTTTGTTTTCCCCTCCAACTCCAGATGGCCTAT
CTGGGGACAGCAGAGGCCCCTAGGTGCGGGCCGTTGCAGTTTTTTGATGAGCTGCACACA
TATGGATACCCGAACATCTGGAGCGGCCATGTGCTGCTTGGGGCAGGCCAGCCCTGGTG
AGCCAATCCAGGGGCCCCGGGGTGCCGGGAGGCAGCAGGGCCCAGCCAGTGAGCGCGG
ATAAATTATTCATGAACGAGTTATTTGTGGTGCAAGGGGTTCATCAGCTACTTTGATTAAAA
GTCCAACGAGTAATGAATATGCAAACGCCAGCGACTGCTCCAAGCAACAGATTTGTCAAAT
TGTCTGTACTTCACCGGAATTCGATATCATAATCAACCATAGGTACCGAGCTCGGGATTCA
GCCGGGAGCTTAGGGAGGGGAGGTCACTTCATAAGGGCCTGGGGGGGGAGTTGGAGCC
ACGAGTCGTCCAGCCGGAGCCCCGTGTGGCTGAGCTCCGGCCTCAGAAGCATCCCCGGG
TTGGATCCTTCGAAGCTAGCGCTACCGGTCGCCACCATGGTGAGCAAGGGCGAGGAGCT
GTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGCTG
ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA
ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGTCGACATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGA
GATCTTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCG

FIG. 15 cont'd

CATTGTCTGAGTAGGTGTCATTCTATTCTGGGGGGTGGGGTGGGGCAGGACAGCAAGGG
GGAGGATTGGGAAGACAATAGCAGGCATGCACGTGCGGACCGAGCGGCCGC (SEQ ID
NO: 123)

CN1605 (2570 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTGCAGGACAGCAGCCAT
GCTCCAGTTGTAAGCCATATAGTTACCATAGTTGAGAGAGATCCCTACTCTCCCTGGCCCT
GGCCTCCAAACCCTACCACACCATCAGCTCTGGGGTCAGGGGATGCCCTGTGGTGGATTC
TGAATTTCTGTGTATGTGCAACTGCATGGGGAACAGGCAGATTATTGGGCACATGAGACTA
GGCTGTCTGAATCTTCCTTGAGAGACTCCCTTACCTCCAGACACCGACACTTGTCTCCCTA
CCCTACAGTCAGAGGCCTGTAGGACCTCAGCACTCGAGAAAGATAAGGCTGCCAAACATT
GCTGTGTCCACCTCCCAGACGGGACATCCTGTGTGGTTGCTGTCAAGTCCGGGTTCTCCA
TCAAAGAGATTCTGTCTGGATTGTGTGAACGGCATGGCATCAATGGGGCTGCTGTGGACC
TCTTCCTGGTGGGCGGAGACAAGGTACTGTGCCATGCAGGAGTGAGTGAGCCACCAGTAT
CCTAGCTCTGTCTGCTCCCTTCCTCCTGCCTTGTTAGTGCTCCACTCCTGACACCACCACT
ACCACCCGTGAGGCAGAGCAGCTGCAGGTGGAGGCTCCCAGGGGGTCGGTGGGTGCAC
GGCAGCACACCCCAGTGTCTAGAGGGTGTCAGGCTAATTTTGCCCTGGTCTTTTGTTCTCG
CAGCTGTGTGCTGTTACATGTCAAGCCCACGTGCTCCCACATTAACTCTGGTGTCTTTGTT
CCTCAGCCTCTTGTGCTGCATCAGGACAGCAGCATCCTGGCCACCAGGGACCTACGCTTG
GAAAAGCGGACTTTGTTTCGGTAAGAAAACCGCACACAGGTTTCTGGAGATTTCCAAAGTC
TCCACAGTGTGAGCCTCAGGACTTGTATTCCTTTCTAATGTGAGCATGTACTTGTCCCATGT
CAGGCCATGAATTCGATATCATAATCAACCATAGGTACCGAGCTCGGGATTCAGCCGGGA
GCTTAGGGAGGGGAGGTCACTTCATAAGGGCCTGGGGGGGGAGTTGGAGCCACGAGTCG
TCCAGCCGGAGCCCCGTGTGGCTGAGCTCCGGCCTCAGAAGCATCCCCGGGTTGGATCC
TTCGAAGCTAGCGCTACCGGTCGCCACCATGGTGAGCAAGGGCGAGGAGCTGTTCACCG
GGGTGGTGCCCATCCTGGTCGAGCTGGACGGCGACGTAAACGGCCACAAGTTCAGCGTG
TCCGGCGAGGGCGAGGGCGATGCCACCTACGGCAAGCTGACCCTGAAGCTGATCTGCAC
CACCGGCAAGCTGCCCGTGCCCTGGCCCACCCTCGTGACCACCCTGGGCTACGGCGTGC
AGTGCTTCGCCCGCTACCCCGACCACATGAAGCAGCACGACTTCTTCAAGTCCGCCATGC
CCGAAGGCTACGTCCAGGAGCGCACCATCTTCTTCAAGGACGACGGCAACTACAAGACCC
GCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCAC
AACGTCTATATCACCGCCGACAAGCAGAAGAACGGCATCAAGGCCAACTTCAAGATCCGC
CACAACATCGAGGACGGCGGCGTGCAGCTCGCCGACCACTACCAGCAGAACACCCCCAT
CGGCGACGGCCCCGTGCTGCTGCCCGACAACCACTACCTGAGCTACCAGTCCAAGCTGA
GCAAAGACCCCAACGAGAAGCGCGATCACATGGTCCTGCTGGAGTTCGTGACCGCCGCC
GGGATCACTCTCGGCATGGACGAGCTGTACAAGTAAGTCGACATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGAGATCTTCGAC
TGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGCACGTGCGGACCGAGCGGCCGC (SEQ ID NO: 124)

FIG. 15 cont'd

CN1556 (2443 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTGTGCTTATGGTAGGGG
CTCAAAAATATTTAGTTCCTTCCTCTCAAATAATCTGGTTGGGATGAGCCAGTCTGGGGTCC
CAGGGAACATTGAGAGCCTACCCTCCCCACCTTCACTCGGGCCCAGTGTCCTTTGCCCCG
AGGAGGGCCTGGCTGTCAGCCAAGCCACCCCCATCCCCAGGGTCACGGTGTGGGCAGTG
CAGCCACAGGAACCAGCATGGACCCTTCATAGACCTGGATGCTCCCAACTTGTCACTCGG
AGCAGAGCACACTGCCATCTGCAGGGTCACCGCTGGGCCTCGTCACTTATCATGATTGCT
AATTAAAGACAAAATTAACCGACCCTGGCCTGGTGGCACCTCTCCCAATGCCTGGCTCTGG
CTGGCTGGGCCTCAGTGGGGAAGGTCTGCCCCTGATACTTGGGATGGTGGCCAGAGCGA
GGGGAGTGGAATCCCACCCAGAACGGAGAAGGTGCCAAGCCATCTGGAAAGCTGGGGCC
AGCCCGACACCTCACCAGCCAGCTGGGAGAAATGAGATCTTGGGCCAATCTGGGGGTGA
CAGGAAAGGGAGGGTGAGATGTGGACGTCTTATTCCCAACTGTATCCCCAGCCCCTTAGA
GCAGTTGTTGTTGTCAGAGAGAACAGATGTGATGTACTGAGCATGCCAGGCACGAAGGGG
GCATTTGATAAATAATAAATTGCTGCGTGGCTTGATGGATGGGGCTGCAAGTGCATAGTCA
GTGCTCAGCGTTTTCCGCATACACTTTCAGAATAACAAACCCCTCTATGGTGCTTTTAGTGA
GGTGTTGAATTCGATATCATAATCAACCATAGGTACCGAGCTCGGGATTCAGCCGGGAGCT
TAGGGAGGGGAGGTCACTTCATAAGGGCCTGGGGGGGGAGTTGGAGCCACGAGTCGTCC
AGCCGGAGCCCCGTGTGGCTGAGCTCCGGCCTCAGAAGCATCCCCGGGTTGGATCCTTC
GAAGCTAGCGCTACCGGTCGCCACCATGGTGAGCAAGGGCGAGGAGCTGTTCACCGGGG
TGGTGCCCATCCTGGTCGAGCTGGACGGCGACGTAAACGGCCACAAGTTCAGCGTGTCC
GGCGAGGGCGAGGGCGATGCCACCTACGGCAAGCTGACCCTGAAGCTGATCTGCACCAC
CGGCAAGCTGCCCGTGCCCTGGCCCACCCTCGTGACCACCCTGGGCTACGGCGTGCAGT
GCTTCGCCCGCTACCCCGACCACATGAAGCAGCACGACTTCTTCAAGTCCGCCATGCCCG
AAGGCTACGTCCAGGAGCGCACCATCTTCTTCAAGGACGACGGCAACTACAAGACCCGCG
CCGAGGTGAAGTTCGAGGGCGACACCCTGGTGAACCGCATCGAGCTGAAGGGCATCGAC
TTCAAGGAGGACGGCAACATCCTGGGGCACAAGCTGGAGTACAACTACAACAGCCACAAC
GTCTATATCACCGCCGACAAGCAGAAGAACGGCATCAAGGCCAACTTCAAGATCCGCCAC
AACATCGAGGACGGCGGCGTGCAGCTCGCCGACCACTACCAGCAGAACACCCCCATCGG
CGACGGCCCCGTGCTGCTGCCCGACAACCACTACCTGAGCTACCAGTCCAAGCTGAGCAA
AGACCCCAACGAGAAGCGCGATCACATGGTCCTGCTGGAGTTCGTGACCGCCGCCGGGA
TCACTCTCGGCATGGACGAGCTGTACAAGTAAGTCGACATCATAATCAACCTCTGGATTAC
AAAATTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTCCTTG
TATAAATCCTGGTTAGTTCTTGCCACGGCGGAACTCATCGCCGCCTGCCTTGCCCGCTGCT
GGACAGGGGCTCGGCTGTTGGGCACTGACAATTCCGTGGCTCGAGAGATCTTCGACTGTG
CCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAG
ACAATAGCAGGCATGCACGTGCGGACCGAGCGGCCGC (SEQ ID NO: 125)

CN1526 (2262 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTGATGGAGTACTTGACAA
TGCTGAATCACAGAAAAAAATCCAAAGCTTGCTCTGTGTATTAAAACATCCATTTAAAAATAT

FIG. 15 cont'd

TTAGAAAGAGCCACCAAGCACTTGTGAGCATATGTGCATATGCCCGCAGTTCCCTTTGCTC
TGGAAAATATTCAAGTGGAAAGCTACTGCTCTGTTTCATAAGTAACAGCAATTTGTGACAAG
CATGGAATATGCTGGGCATCATCAACTGCATTGTTATCAGCTGCAGTACAATTTAATTAGCG
AGCCTGAGTTTGATTATCTGCCAGTGCATGCTACCTTAACTGCTCTGTTCCAGTTTGAGGA
CTAAATTTTGTCTGATCATGTTAACATATTTGAGAGCATACCTCAACATTCTCAAGTGTTTTG
TTCGTCATATTATGCTCCCGCATCAACAAAATTGTATTAAAAGCCTTGACGTCAGCTCAAAA
TATTCTGAAGTGAATCAAAAGCTTATTATTTCTAGACGTAAGAATAACTTGACTTCATGTTAG
ATATGATTTCCTCATTTATAGTGCTGCTTAAATCAGATGAATGTAAAAGGATATACTGGTCAC
TATAATTTCAAGATTTTTTTAGATTTAGGTGTGTTTGTGTTCATGTGAATTCGATATCATAATC
AACCATAGGTACCGAGCTCGGGATTCAGCCGGGAGCTTAGGGAGGGGAGGTCACTTCATA
AGGGCCTGGGGGGGGAGTTGGAGCCACGAGTCGTCCAGCCGGAGCCCCGTGTGGCTGA
GCTCCGGCCTCAGAAGCATCCCCGGGTTGGATCCTTCGAAGCTAGCGCTACCGGTCGCCA
CCATGGTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGATGCCAC
CTACGGCAAGCTGACCCTGAAGCTGATCTGCACCACCGGCAAGCTGCCCGTGCCCTGGC
CCACCCTCGTGACCACCCTGGGCTACGGCGTGCAGTGCTTCGCCCGCTACCCCGACCAC
ATGAAGCAGCACGACTTCTTCAAGTCCGCCATGCCCGAAGGCTACGTCCAGGAGCGCACC
ATCTTCTTCAAGGACGACGGCAACTACAAGACCCGCGCCGAGGTGAAGTTCGAGGGCGAC
ACCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAAGTCGACATCATAATCAACCTCTGGATTACAAAATTTGTGAAAGATTGACTGGTA
TTCTTAACTATGTTGCTCCTTTTACGCTATGTGGATACGCTGCTTTAATGCCTTTGTATCATG
CTATTGCTTCCCGTATGGCTTTCATTTTCTCCTCCTTGTATAAATCCTGGTTAGTTCTTGCCA
CGGCGGAACTCATCGCCGCCTGCCTTGCCCGCTGCTGGACAGGGGCTCGGCTGTTGGGC
ACTGACAATTCCGTGGCTCGAGAGATCTTCGACTGTGCCTTCTAGTTGCCAGCCATCTGTT
GTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCACGTGCG
GACCGAGCGGCCGC (SEQ ID NO: 126)

FIG. 15 cont'd

CN1418 (1852 bp between ITRs):
GCGGCCGCACGCGTGGTCCCAGCTCCTCGTTGTAGCCCCCCACACACAAGATCAAGGGT
ACAGACAGCCCCTAGAAGGGCAGGAGGCCAAGGCTCCATGGGCACCTTACTCTCTCCATT
CCCCCTTGGCTCCCAGGCTTCCCTCCCCCTCCCAGTCCTCCTTCCCCGCACGCTGGTGAC
TGCCGTGACTATTAATCACTAGCCCTGTTCTCTTCCTCTCTACTAATCAGGCACAATTAGAC
AAGGCCTCTTCCAGCTGGGCAGTCCCCCCCTGCCCTCCCCCTCCCTTCACAGCCCTCCCT
ATCCGATACCCAGGACAGCTCTGAGGCAATGAGGACTTGATGTAAGCCCTGAGCTACTCT
GGTTGCCCTGGTGCCCAGTTTGGGGCTTTTCAGCAATCTCCTCTTTCCATTTGTCTCCTCC
TTGGTCCCTGGTCTTGTCTAGCGCTGTAGATCAGCCAATATTAGCAGGCTCAATCTCTAAC
CCACTGCCACTGTCAATCAAAGGGGCGACTCGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAGGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGTAAGTCGACGGCGCGCCGCGGCCGCGAATTCGATATCATAATCAACC
TCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTT
CTCCTCCTTGTATAAATCCTGGTTAGTTCTTGCCACGGCGGAACTCATCGCCGCCTGCCTT
GCCCGCTGCTGGACAGGGGCTCGGCTGTTGGGCACTGACAATTCCGTGGCTCGAGAGAT
CTTCGACTGTGCCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGA
GGATTGGGAAGACAATAGCAGGCATGCACGTGCGGACCGAGCGGCCGC (SEQ ID NO:
127)

CN1404 (1984 bp between ITRs):
GCGGCCGCACGCGTGAGGCATGGGTAGGAGCCAGCCCCACTCCTCAGGGTCCTCAAGGG
TCCAGGCAGCCCCGGGGGGCCAGGAGCCTGGGGCCCTGTGGGCGCCTCACTATCTCCAT
CCCCTATGGGCTCTCCGGTCTCCCTCCCCCTCCCGACCCTCCTTCTCCACATGCTGGTGA
CTGCCATGACTATTAATCACTCGCCCTGTTCTCTTCCTCTCTACTAATCAGGCACAATTAGA
CAAGGCCTCTTCCAGCTGGGCAGTCCCTCCCCTGCCCTCCTCTCTCCTCTCCCTGCCCCA
CCCAGCCGCCAGCCAGGACAGCTCTGAGGCACAGAAAGCATGCAAGCCCTCTCTCTCTCT
GGCTGTCCCAGGACCCAGTTTCGGGCTCCTTAGCACCCACTCCTTCTGTCCCAGCGACCT
CCTTAGCTCCTTCTCTTCCCAGTGTGTGGTCAGGCCACTACTGACAGTCTCTGCCCTCCAC
CCCCTACACTTGGCCCTGGGAGGAGCTACTCCACACTCCATCGAGCTCTAAGAAGGCGGC
ACTGTCCCTGGCTCCTCTGTCCTCCTGCTCAGCCATCCTCAGCATGTGCCTCTCATCACCA
CTCTTGTCACCACAGATCGCCGAGCAGCTACTCCACACTCCATCGAGCTCGGGCTGGGCA
TAAAAGTCAGGGCAGAGCCATCTATTGCTTACATTTGCTTCTGGGATCCAGATCTTTCGAA
GCTAGCGCTACCGGTCGCCACCATGGTGAGCAAGGGCGAGGAGCTGTTCACCGGGGTGG
TGCCCATCCTGGTCGAGCTGGACGGCGACGTAAACGGCCACAAGTTCAGCGTGTCCGGC

FIG. 15 cont'd

GAGGGCGAGGGCGATGCCACCTACGGCAAGCTGACCCTGAAGCTGATCTGCACCACCGG
CAAGCTGCCCGTGCCCTGGCCCACCCTCGTGACCACCCTGGGCTACGGCGTGCAGTGCT
TCGCCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCG
AGGTGAAGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCACAACGTCT
ATATCACCGCCGACAAGCAGAAGAACGGCATCAAGGCCAACTTCAAGATCCGCCACAACA
TCGAGGACGGCGGCGTGCAGCTCGCCGACCACTACCAGCAGAACACCCCCATCGGCGAC
GGCCCCGTGCTGCTGCCCGACAACCACTACCTGAGCTACCAGTCCAAGCTGAGCAAAGAC
CCCAACGAGAAGCGCGATCACATGGTCCTGCTGGAGTTCGTGACCGCCGCCGGGATCAC
TCTCGGCATGGACGAGCTGTACAAGTAAGTCGACGGCGCGCCGCGGCCGCGAATTCGAT
ATCATAATCAACCTCTGGATTACAAAATTTGTGAAAGATTGACTGGTATTCTTAACTATGTTG
CTCCTTTTACGCTATGTGGATACGCTGCTTTAATGCCTTTGTATCATGCTATTGCTTCCCGT
ATGGCTTTCATTTTCTCCTCCTTGTATAAATCCTGGTTAGTTCTTGCCACGGCGGAACTCAT
CGCCGCCTGCCTTGCCCGCTGCTGGACAGGGGCTCGGCTGTTGGGCACTGACAATTCCG
TGGCTCGAGAGATCTTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGGA
CAGCAAGGGGGAGGATTGGGAAGACAATAGCAGGCATGCACGTGCGGACCGAGCGGCC
GC (SEQ ID NO: 128)

AiV1173 (3009 bp between ITRs):
GCGGCCGCACGCGTGAGTAATAGGCAGATCTCTATACCAGCCTAACTTCTCCCTACCACC
CCCCTCCATCTTCCTTCTTCTTGCAGTGCAAACGCCAAGTCATATGGACTTGGATTCCGAC
TCTCTTTTCTTTGCCAAGACTCATATTATTGAGCAAGTGAGGAGAGTTGAGCCAAACTGAAC
TAAGTGACGCCACAGCACACTGTGTAGTGCAGAGCTAGCACTTTGGATATTGTGTAATTAA
GGCTTTAATGAACATCACATAGAGAATTAGACTGCAGATTGTGACACAAATAAATCTACTTG
GCTTTTAGAAACATTCCTTAAAAAGAAATATTTTGGTACCAGAATGTGTTCAGGAGGGAAAG
AGCCTGTGCCCTTGACACAGGAAGTAGATAACACCTGTCAGAAGAATCGAAACCACCTGCT
TGGGTGCATCTGGTAATAAGTTTGCAGCTGGTGCTACACTCTACCCTTAAGGAGCTCGGGC
TGGGCATAAAAGTCAGGGCAGAGCCATCTATTGCTTACATTTGCTTCTGGCGTGGCCACCA
TGGCTCCTAAGAAGAAGAGGAAGGTGATGAGCCAGTTCGACATCCTGTGCAAGACCCCCC
CCAAGGTGCTGGTGCGGCAGTTCGTGGAGAGATTCGAGAGGCCCAGCGGCGAGAAGATC
GCCAGCTGTGCCGCCGAGCTGACCTACCTGTGCTGGATGATCACCCACAACGGCACCGC
CATCAAGAGGGCCACCTTCATGAGCTACAACACCATCATCAGCAACAGCCTGAGCTTCGAC
ATCGTGAACAAGAGCCTGCAGTTCAAGTACAAGACCCAGAAGGCCACCATCCTGGAGGCC
AGCCTGAAGAAGCTGATCCCCGCCTGGGAGTTCACCATCATCCCTTACAACGGCCAGAAG
CACCAGAGCGACATCACCGACATCGTGTCCAGCCTGCAGCTGCAGTTCGAGAGCAGCGA
GGAGGCCGACAAGGGCAACAGCCACAGCAAGAAGATGCTGAAGGCCCTGCTGTCCGAGG
GCGAGAGCATCTGGGAGATCACCGAGAAGATCCTGAACAGCTTCGAGTACACCAGCAGGT
TCACCAAGACCAAGACCCTGTACCAGTTCCTGTTCCTGGCCACATTCATCAACTGCGGCAG
GTTCAGCGACATCAAGAACGTGGACCCCAAGAGCTTCAAGCTGGTGCAGAACAAGTACCT
GGGCGTGATCATTCAGTGCCTGGTGACCGAGACCAAGACAAGCGTGTCCAGGCACATCTA
CTTTTTCAGCGCCAGAGGCAGGATCGACCCCCTGGTGTACCTGGACGAGTTCCTGAGGAA
CAGCGAGCCCGTGCTGAAGAGAGTGAACAGGACCGGCAACAGCAGCAGCAACAAGCAGG
AGTACCAGCTGCTGAAGGACAACCTGGTGCGCAGCTACAACAAGGCCCTGAAGAAGAACG
CCCCCTACCCCATCTTCGCTATCAAGAACGGCCCTAAGAGCCACATCGGCAGGCACCTGA
TGACCAGCTTTCTGAGCATGAAGGGCCTGACCGAGCTGACAAACGTGGTGGGCAACTGGA
GCGACAAGAGGGCCTCCGCCGTGGCCAGGACCACCTACACCCACCAGATCACCGCCATC

FIG. 15 cont'd

CCCGACCACTACTTCGCCCTGGTGTCCAGGTACTACGCCTACGACCCCATCAGCAAGGAG
ATGATCGCCCTGAAGGACGAGACCAACCCCATCGAGGAGTGGCAGCACATCGAGCAGCT
GAAGGGCAGCGCCGAGGGCAGCATCAGATACCCCGCCTGGAACGGCATCATCAGCCAGG
AGGTGCTGGACTACCTGAGCAGCTACATCAACAGGCGGATCTGAGAATTCGATATCAAGCT
TATCGATAATCAACCTCTGGATTACAAAATTTGTGAAAGATTGACTGGTATTCTTAACTATGT
TGCTCCTTTTACGCTATGTGGATACGCTGCTTTAATGCCTTTGTATCATGCTATTGCTTCCC
GTATGGCTTTCATTTTCTCCTCCTTGTATAAATCCTGGTTGCTGTCTCTTTATGAGGAGTTGT
GGCCCGTTGTCAGGCAACGTGGCGTGGTGTGCACTGTGTTTGCTGACGCAACCCCCACTG
GTTGGGGCATTGCCACCACCTGTCAGCTCCTTTCCGGGACTTTCGCTTTCCCCCTCCCTAT
TGCCACGGCGGAACTCATCGCCGCCTGCCTTGCCCGCTGCTGGACAGGGGCTCGGCTGT
TGGGCACTGACAATTCCGTGGTGTTGTCGGGGAAATCATCGTCCTTTCCTTGGCTGCTCGC
CTATGTTGCCACCTGGATTCTGCGCGGGACGTCCTTCTGCTACGTCCCTTCGGCCCTCAAT
CCAGCGGACCTTCCTTCCCGCGGCCTGCTGCCGGCTCTGCGGCCTCTTCCGCGTCTTCG
CCTTCGCCCTCAGACGAGTCGGATCTCCCTTTGGGCCGCCTCCCCGCATCGATACCGAGC
GCTGCTCGAGAGATCTACGGGTGGCATCCCTGTGACCCCTCCCCAGTGCCTCTCCTGGCC
CTGGAAGTTGCCACTCCAGTGCCCACCAGCCTTGTCCTAATAAAATTAAGTTGCATCATTTT
GTCTGACTAGGTGTCCTTCTATAATATTATGGGGTGGAGGGGGGTGGTATGGAGCAAGGG
GCAAGTTGGGAAGACAACCTGTAGGGCCTGCGGGGTCTATTGGGAACCAAGCTGGAGTG
CAGTGGCACAATCTTGGCTCACTGCAATCTCCGCCTCCTGGGTTCAAGCGATTCTCCTGCC
TCAGCCTCCCGAGTTGTTGGGATTCCAGGCATGCATGACCAGGCTCAGCTAATTTTTGTTT
TTTTGGTAGAGACGGGGTTTCACCATATTGGCCAGGCTGGTCTCCAACTCCTAATCTCAGG
TGATCTACCCACCTTGGCCTCCCAAATTGCTGGGATTACAGGCGTGAACCACTGCTCCCTT
CCCTGTCCTTCTGATTTTGTAGGTAACCACGTGCGGACCGAGCGGCCGC (SEQ ID NO:
129)

AiV1174 (3152 bp between ITRs):
GCGGCCGCACGCGTGACAATCATGAGAGTACGAAAGCATGAGAGATATTATTTCAACAACT
TATTCTTTATTTTAGAGGAAGAACATCTGAGAACAAAAATATCTATAAAGGCATGATTAGCAT
AGAAAACAAGGGTATTGATCATTAATGGCACCTAATGTCATAGATAAAAAGAGACACTCAAA
CTTTATACATCTCCAAATAGAACACTTCACAATCTATGAAGCAAAATAAAGGAAAAAAAAAA
CAACACAAATCTAATCTTACAGAACTAAGTACCAATTTACAGCAAGTGTAGACAAAGTAGCA
CATCAAATGACAATAGGAGATGCCATCAAGCGAAATCAATTCTGGGAAGGTCTTAGAGAAC
AAGCAATAGTACTTCTTGAACACATCCATTATAAGTGAAAATAAAATGCTCTAGATAAAAAGA
GCCTTAGAGATGAATGAAGGATAATGAATCTGCTGCTTAATCACAAACATTTTGGTGATGAG
ATGATCAAGAAAACAAAAAGCTATTACTGAAATAGCTGGAAGTGTAATTAGTTACTGTGGAG
AAGGACAGAGTTGAGAAGAAGTAAAAGGATTGTGGTTGTGATAGATGTATGCCAATGTCCT
TAAGGAGCTCGGGCTGGGCATAAAAGTCAGGGCAGAGCCATCTATTGCTTACATTTGCTTC
TGGCGTGGCCACCATGGCTCCTAAGAAGAAGAGGAAGGTGATGAGCCAGTTCGACATCCT
GTGCAAGACCCCCCCAAGGTGCTGGTGCGGCAGTTCGTGGAGAGATTCGAGAGGCCCA
GCGGCGAGAAGATCGCCAGCTGTGCCGCCGAGCTGACCTACCTGTGCTGGATGATCACC
CACAACGGCACCGCCATCAAGAGGGCCACCTTCATGAGCTACAACACCATCATCAGCAAC
AGCCTGAGCTTCGACATCGTGAACAAGAGCCTGCAGTTCAAGTACAAGACCCAGAAGGCC
ACCATCCTGGAGGCCAGCCTGAAGAAGCTGATCCCCGCCTGGGAGTTCACCATCATCCCT
TACAACGGCCAGAAGCACCAGAGCGACATCACCGACATCGTGTCCAGCCTGCAGCTGCAG
TTCGAGAGCAGCGAGGAGGCCGACAAGGGCAACAGCCACAGCAAGAAGATGCTGAAGGC
CCTGCTGTCCGAGGGCGAGAGCATCTGGGAGATCACCGAGAAGATCCTGAACAGCTTCGA
GTACACCAGCAGGTTCACCAAGACCAAGACCCTGTACCAGTTCCTGTTCCTGGCCACATTC
ATCAACTGCGGCAGGTTCAGCGACATCAAGAACGTGGACCCCAAGAGCTTCAAGCTGGTG
CAGAACAAGTACCTGGGCGTGATCATTCAGTGCCTGGTGACCGAGACCAAGACAAGCGTG

FIG. 15 cont'd

TCCAGGCACATCTACTTTTTCAGCGCCAGAGGCAGGATCGACCCCCTGGTGTACCTGGAC
GAGTTCCTGAGGAACAGCGAGCCCGTGCTGAAGAGAGTGAACAGGACCGGCAACAGCAG
CAGCAACAAGCAGGAGTACCAGCTGCTGAAGGACAACCTGGTGCGCAGCTACAACAAGGC
CCTGAAGAAGAACGCCCCCTACCCCATCTTCGCTATCAAGAACGGCCCTAAGAGCCACAT
CGGCAGGCACCTGATGACCAGCTTTCTGAGCATGAAGGGCCTGACCGAGCTGACAAACGT
GGTGGGCAACTGGAGCGACAAGAGGGCCTCCGCCGTGGCCAGGACCACCTACACCCACC
AGATCACCGCCATCCCCGACCACTACTTCGCCCTGGTGTCCAGGTACTACGCCTACGACC
CCATCAGCAAGGAGATGATCGCCCTGAAGGACGAGACCAACCCCATCGAGGAGTGGCAG
CACATCGAGCAGCTGAAGGGCAGCGCCGAGGGCAGCATCAGATACCCCGCCTGGAACGG
CATCATCAGCCAGGAGGTGCTGGACTACCTGAGCAGCTACATCAACAGGCGGATCTGAGA
ATTCGATATCAAGCTTATCGATAATCAACCTCTGGATTACAAAATTTGTGAAAGATTGACTG
GTATTCTTAACTATGTTGCTCCTTTTACGCTATGTGGATACGCTGCTTTAATGCCTTTGTATC
ATGCTATTGCTTCCCGTATGGCTTTCATTTTCTCCTCCTTGTATAAATCCTGGTTGCTGTCTC
TTTATGAGGAGTTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTCCGGGACTTTCG
CTTTCCCCCTCCCTATTGCCACGGCGGAACTCATCGCCGCCTGCCTTGCCCGCTGCTGGA
CAGGGGCTCGGCTGTTGGGCACTGACAATTCCGTGGTGTTGTCGGGGAAATCATCGTCCT
TTCCTTGGCTGCTCGCCTATGTTGCCACCTGGATTCTGCGCGGGACGTCCTTCTGCTACGT
CCCTTCGGCCCTCAATCCAGCGGACCTTCCTTCCCGCGGCCTGCTGCCGGCTCTGCGGC
CTCTTCCGCGTCTTCGCCTTCGCCCTCAGACGAGTCGGATCTCCCTTTGGGCCGCCTCCC
CGCATCGATACCGAGCGCTGCTCGAGAGATCTACGGGTGGCATCCCTGTGACCCCTCCCC
AGTGCCTCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAGGGGGGT
GGTATGGAGCAAGGGGCAAGTTGGGAAGACAACCTGTAGGGCCTGCGGGGTCTATTGGG
AACCAAGCTGGAGTGCAGTGGCACAATCTTGGCTCACTGCAATCTCCGCCTCCTGGGTTC
AAGCGATTCTCCTGCCTCAGCCTCCCGAGTTGTTGGGATTCCAGGCATGCATGACCAGGC
TCAGCTAATTTTTGTTTTTTGGTAGAGACGGGGTTTCACCATATTGGCCAGGCTGGTCTCC
AACTCCTAATCTCAGGTGATCTACCCACCTTGGCCTCCCAAATTGCTGGGATTACAGGCGT
GAACCACTGCTCCCTTCCCTGTCCTTCTGATTTTGTAGGTAACCACGTGCGGACCGAGCG
GCCGC (SEQ ID NO: 130)

AiV1177 (3208 bp between ITRs):
GCGGCCGCACGCGTCCTCATGGTATTAGTAGTAACCATTTTGGAGAGAACTATACCACTAA
TCCTTACTACCCCCCCCCCAATTAATGACACCCCATTCGAGCATCTCCAATGAAAGGCGCA
TTATTAATATTCAAGGAAAAAAACCCTTGTAACCATTTTAGCAGATACAGCTAACAATGAACT
AAATTTGCTTTGTGCAAGACAGAGAGTGAGCATCCCAAATTAGTTTATGTAAAAGCTGAAAT
CCTCCCCTGAAAGGTCTCAGTACCATCCTCAAAGAATATCCCGATCATCAGCAGTGCCGTC
AAGATTCCCGCCAACATTATCCCCTTTGTTGTCTGAAATGTAGAATCAAGCACATCTGGCAA
ATGTCCTGGAGCTCACAAATCTCTCAAACGGCGTCTAATTCCCAGTGGTGAAAGAGAGCGC
CACTGCCTAATCGTGCTTCTCTTCAAAACAGCACTGACTTTCCTTCAATCAGAAACAATGGC
TTTGCTTTCTTAAAAATATCACACGCCAGTGATTATTTGCAGAGAGGCCCATTTTATGCTTG
AACCTGCGGGTCCCAGACAGAATTCACAATTAAGACCGTGAACCTCATTTGAATGTACGCT
TAGTTCAGTGGACAGTGGGAAGAAAGATTGTGACCTGTCTTCTGTGGTTTGGAGGCTCTTA
AGGAGCTCGGGCTGGGCATAAAAGTCAGGGCAGAGCCATCTATTGCTTACATTTGCTTCTG
GCGTGGCCACCATGGCTCCTAAGAAGAAGAGGAAGGTGATGAGCCAGTTCGACATCCTGT
GCAAGACCCCCCCCAAGGTGCTGGTGCGGCAGTTCGTGGAGAGATTCGAGAGGCCCAGC
GGCGAGAAGATCGCCAGCTGTGCCGCCGAGCTGACCTACCTGTGCTGGATGATCACCCA
CAACGGCACCGCCATCAAGAGGGCCACCTTCATGAGCTACAACACCATCATCAGCAACAG
CCTGAGCTTCGACATCGTGAACAAGAGCCTGCAGTTCAAGTACAAGACCCAGAAGGCCAC

FIG. 15 cont'd

CATCCTGGAGGCCAGCCTGAAGAAGCTGATCCCCGCCTGGGAGTTCACCATCATCCCTTA
CAACGGCCAGAAGCACCAGAGCGACATCACCGACATCGTGTCCAGCCTGCAGCTGCAGTT
CGAGAGCAGCGAGGAGGCCGACAAGGGCAACAGCCACAGCAAGAAGATGCTGAAGGCCC
TGCTGTCCGAGGGCGAGAGCATCTGGGAGATCACCGAGAAGATCCTGAACAGCTTCGAGT
ACACCAGCAGGTTCACCAAGACCAAGACCCTGTACCAGTTCCTGTTCCTGGCCACATTCAT
CAACTGCGGCAGGTTCAGCGACATCAAGAACGTGGACCCCAAGAGCTTCAAGCTGGTGCA
GAACAAGTACCTGGGCGTGATCATTCAGTGCCTGGTGACCGAGACCAAGACAAGCGTGTC
CAGGCACATCTACTTTTTCAGCGCCAGAGGCAGGATCGACCCCCTGGTGTACCTGGACGA
GTTCCTGAGGAACAGCGAGCCCGTGCTGAAGAGAGTGAACAGGACCGGCAACAGCAGCA
GCAACAAGCAGGAGTACCAGCTGCTGAAGGACAACCTGGTGCGCAGCTACAACAAGGCC
CTGAAGAAGAACGCCCCCTACCCCATCTTCGCTATCAAGAACGGCCCTAAGAGCCACATC
GGCAGGCACCTGATGACCAGCTTTCTGAGCATGAAGGGCCTGACCGAGCTGACAAACGTG
GTGGGCAACTGGAGCGACAAGAGGGCCTCCGCCGTGGCCAGGACCACCTACACCCACCA
GATCACCGCCATCCCCGACCACTACTTCGCCCTGGTGTCCAGGTACTACGCCTACGACCC
CATCAGCAAGGAGATGATCGCCCTGAAGGACGAGACCAACCCCATCGAGGAGTGGCAGC
ACATCGAGCAGCTGAAGGGCAGCGCCGAGGGCAGCATCAGATACCCCGCCTGGAACGGC
ATCATCAGCCAGGAGGTGCTGGACTACCTGAGCAGCTACATCAACAGGCGGATCTGAGAA
TTCGATATCAAGCTTATCGATAATCAACCTCTGGATTACAAAATTTGTGAAAGATTGACTGG
TATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGA
CGCAACCCCCACTGGTTGGGGCATTGCCACCACCTGTCAGCTCCTTTCCGGGACTTTCGC
TTTCCCCCTCCCTATTGCCACGGCGGAACTCATCGCCGCCTGCCTTGCCCGCTGCTGGAC
AGGGGCTCGGCTGTTGGGCACTGACAATTCCGTGGTGTTGTCGGGGAAATCATCGTCCTT
TCCTTGGCTGCTCGCCTATGTTGCCACCTGGATTCTGCGCGGGACGTCCTTCTGCTACGT
CCCTTCGGCCCTCAATCCAGCGGACCTTCCTTCCCGCGGCCTGCTGCCGGCTCTGCGGC
CTCTTCCGCGTCTTCGCCTTCGCCCTCAGACGAGTCGGATCTCCCTTTGGGCCGCCTCCC
CGCATCGATACCGAGCGCTGCTCGAGAGATCTACGGGTGGCATCCCTGTGACCCCTCCCC
AGTGCCTCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAGGGGGGT
GGTATGGAGCAAGGGGCAAGTTGGGAAGACAACCTGTAGGGCCTGCGGGGTCTATTGGG
AACCAAGCTGGAGTGCAGTGGCACAATCTTGGCTCACTGCAATCTCCGCCTCCTGGGTTC
AAGCGATTCTCCTGCCTCAGCCTCCCGAGTTGTTGGGATTCCAGGCATGCATGACCAGGC
TCAGCTAATTTTTGTTTTTTTGGTAGAGACGGGGTTTCACCATATTGGCCAGGCTGGTCTCC
AACTCCTAATCTCAGGTGATCTACCCACCTTGGCCTCCCAAATTGCTGGGATTACAGGCGT
GAACCACTGCTCCCTTCCCTGTCCTTCTGATTTTGTAGGTAACCACGTGCGGACCGAGCG
GCCGC (SEQ ID NO: 131)

CN1261 (1802 bp between ITRs):
CCTAGGACGCGTCCCAAACTCTCATCTGCTCCAAGCTGTATAGAAGTTTCTTTCAGAGTTAT
TTCAGTTCATTTCAATGAAAAAATTATCAAATATAATAAAACATTTTTGGAAAGACAGGAGGG
ATTTGGGACATTACAATTGGTATTAAAAGAACTAATGAGCTTTGCTACTGATAAAGTATTTCT
TGCATTCTTTTTTGGTTCAAAGAGTGATACCCAATTATTAATTCTTAAGCACATAAATCTTTT
CCATTTTTGTTTTTCCTGCTCGGTGCCTGAATTTTCTTGGCTACTACTGAAATGTGTTGAATA
GGCTGATTCTACTTTTTATCTGCATATTCTATGGATCTAGTGGCTCTGAATCCAAGCCACTA
TAATAATGATGGAAACAAAATATTTCTGATGAACATATAACCAGATATTGCTGACAAATAGAA
AAAAGAACAGGCTGATGGGGGCCAGACTGTGCATATGATCTGTATTCCGAGCTCGGGCTG
GGCATAAAAGTCAGGGCAGAGCCATCTATTGCTTACATTTGCTTCTGGGATCCAGATCTTT
CGAAGCTAGCGCTACCGGTCGCCACCATGGTGAGCAAGGGCGAGGAGCTGTTCACCGGG

FIG. 15 cont'd

GTGGTGCCCATCCTGGTCGAGCTGGACGGCGACGTAAACGGCCACAAGTTCAGCGTGTC
CGGCGAGGGCGAGGGCGATGCCACCTACGGCAAGCTGACCCTGAAGCTGATCTGCACCA
CCGGCAAGCTGCCCGTGCCCTGGCCCACCCTCGTGACCACCCTGGGCTACGGCGTGCAG
TGCTTCGCCCGCTACCCCGACCACATGAAGCAGCACGACTTCTTCAAGTCCGCCATGCCC
GAAGGCTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCATCGA
CTTCAAGGAGGACGGCAACATCCTGGGGCACAAGCTGGAGTACAACTACAACAGCCACAA
CGTCTATATCACCGCCGACAAGCAGAAGAACGGCATCAAGGCCAACTTCAAGATCCGCCA
CAACATCGAGGACGGCGGCGTGCAGCTCGCCGACCACTACCAGCAGAACACCCCCATCG
GCGACGGCCCCGTGCTGCTGCCCGACAACCACTACCTGAGCTACCAGTCCAAGCTGAGC
AAAGACCCCAACGAGAAGCGCGATCACATGGTCCTGCTGGAGTTCGTGACCGCCGCCGG
GATCACTCTCGGCATGGACGAGCTGTACAAGTAAGTCGACGGCGCGCCGCGGCCGCGAA
TTCGATATCATAATCAACCTCTGGATTACAAAATTTGTGAAAGATTGACTGGTATTCTTAACT
ATGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTAGTTCTTGCCACGGCGGAA
CTCATCGCCGCCTGCCTTGCCCGCTGCTGGACAGGGGCTCGGCTGTTGGGCACTGACAA
TTCCGTGGCTCGAGCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAA
TTGCATCGCATTGTCTGAGTAGGTGTCATTCTATTCTGGGGGGTGGGGTGGGGCAGGACA
GCAAGGGGGAGGATTGGGAAGACAATAGCAGGCATGACTAGT (SEQ ID NO: 167)

CN1542 (2031 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTCAGAGACCCAGTGAC
TGATGTTGTCCCAGAAAGTAGAATTCTTGTGATGCATAAATGATAGCTGATCCAGCCAACAC
AACTGTTGGAGGAATTATAGCTTATAGAGTTGCTTGGCAGATGAAATCACTTGACTAATTAG
AAAATAATGCATTATGCTGTGCTAGAAAAATCACAGAGCAGCAGAAGCGGAACTGTGTTCT
GGGTTGCTGTGGGCTGCCAGTCACAATTTTGAGCCTGTGCCTTGCATTCTTTACCTTTTTTT
TTCCCACTATCCCTACAGCCCAGAAATTGAAACAGACCCTGGAGCCTTGTGATACTGAATA
TCCAGCATTCGTCTCTGAGCGCACCATCAAGGAGACTACAGGGAATATTGCTTGTGAAGAC
TGCTCCAGAATTCGATATCATAATCAACCATAGGTACCGAGCTCGGGATTCAGCCGGGAGC
TTAGGGAGGGGAGGTCACTTCATAAGGGCCTGGGGGGGGAGTTGGAGCCACGAGTCGTC
CAGCCGGAGCCCCGTGTGGCTGAGCTCCGGCCTCAGAAGCATCCCCGGGTTGGATCCTT
CGAAGCTAGCGCTACCGGTCGCCACCATGGTGAGCAAGGGCGAGGAGCTGTTCACCGGG
GTGGTGCCCATCCTGGTCGAGCTGGACGGCGACGTAAACGGCCACAAGTTCAGCGTGTC
CGGCGAGGGCGAGGGCGATGCCACCTACGGCAAGCTGACCCTGAAGCTGATCTGCACCA
CCGGCAAGCTGCCCGTGCCCTGGCCCACCCTCGTGACCACCCTGGGCTACGGCGTGCAG
TGCTTCGCCCGCTACCCCGACCACATGAAGCAGCACGACTTCTTCAAGTCCGCCATGCCC
GAAGGCTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCATCGA
CTTCAAGGAGGACGGCAACATCCTGGGGCACAAGCTGGAGTACAACTACAACAGCCACAA
CGTCTATATCACCGCCGACAAGCAGAAGAACGGCATCAAGGCCAACTTCAAGATCCGCCA
CAACATCGAGGACGGCGGCGTGCAGCTCGCCGACCACTACCAGCAGAACACCCCCATCG
GCGACGGCCCCGTGCTGCTGCCCGACAACCACTACCTGAGCTACCAGTCCAAGCTGAGC
AAAGACCCCAACGAGAAGCGCGATCACATGGTCCTGCTGGAGTTCGTGACCGCCGCCGG
GATCACTCTCGGCATGGACGAGCTGTACAAGTAAGTCGACATCATAATCAACCTCTGGATT
ACAAAATTTGTGAAAGATTGACTGGTATTCTTAACTATGTTGCTCCTTTTACGCTATGTGGAT

FIG. 15 cont'd

ACGCTGCTTTAATGCCTTTGTATCATGCTATTGCTTCCCGTATGGCTTTCATTTTCTCCTCCT
TGTATAAATCCTGGTTAGTTCTTGCCACGGCGGAACTCATCGCCGCCTGCCTTGCCCGCTG
CTGGACAGGGGCTCGGCTGTTGGGCACTGACAATTCCGTGGCTCGAGAGATCTTCGACTG
TGCCTTCTAGTTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGGGAA
GACAATAGCAGGCATGCACGTGCGGACCGAGCGGCCGC (SEQ ID NO: 168)

CN1544 (2557 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTGACTGACAGGCCGGG
CCCCTGCTCATCCCTGAAAACTAGCATCGGGGAATGACATACAGTTTGATAACATAAGATG
CTTAGGTTTTTTGGCTCAAGTGAGATGTTCAGAGCTAATAGCCCTGCGAGCTGAGTTTTAG
CTGTGATCTGCACCTTGAGATATCCGTTATGTCTGGATCAGGAAAAAGGGAAAGAATGAG
AGCTTATTTCTAGAAAGGTTTCCGATGAGCAGCATTTGTCATTGAAGGGGAAGATGGGTAT
AATTAGCTTGTCAGTCTAGTTTGGGCTGAGCAGGCTGTCTCTGCTAAGAAAGATGGACTAA
CTGCCAGGGCCACTGACAGGCAGTCGATAGCGCAGCAATTAATGTCATAAATAATTCCAGA
ACCAATTACATCAAAATGGACTCAGAGCTTTAAAAAGGTACAGAATTCTCTTATTCTTCCTG
CTAACAGCAAGAAACAGCTTTCATTTTTCTCTGTAATTACTTTTCATTGTATATAGCAATACA
GCTGAGCTTTTCTGTCCATATTTAAGCCTTGTCTTTCTCCAAGCCTCTTCCCCCACCACCAG
CCTCCCTCCTTCACCCCACAGGATAAGGCTGTTAAAGTTGTTCTTCCCTGCCAGAGCAGTG
GGGTGAATGTATAATCTTTTAACTTGGCTGTTGCAGGAGAACTCCAGCTACACCTAAATGAT
TAAGAGCCAAGTTTTTGAAAATGTCATGGACAATGACAGCACAGTGCCCCAAACAATGGCA
TTTGGAAATGAAGACATTTGTGAAATAAATGGATTTGTCTTATTATTTTAAAGGTTGCTGTGA
CTTTGCTTACACTGAATTTATTGATTTTTCCCCCTTCTCCTTCTCCTTCCTCTTCTTGTTCTC
CTCCTCCTTCTGTACAGTTGCAGGCATAGAAGCTGGGCCGAATTCGATATCATAATCAACC
ATAGGTACCGAGCTCGGGATTCAGCCGGGAGCTTAGGGAGGGGAGGTCACTTCATAAGG
GCCTGGGGGGGGAGTTGGAGCCACGAGTCGTCCAGCCGGAGCCCCGTGTGGCTGAGCT
CCGGCCTCAGAAGCATCCCCGGGTTGGATCCTTCGAAGCTAGCGCTACCGGTCGCCACCA
TGGTGAGCAAGGGCGAGGAGCTGTTCACCGGGGTGGTGCCCATCCTGGTCGAGCTGGAC
GGCGACGTAAACGGCCACAAGTTCAGCGTGTCCGGCGAGGGCGAGGGCGATGCCACCTA
CGGCAAGCTGACCCTGAAGCTGATCTGCACCACCGGCAAGCTGCCCGTGCCCTGGCCCA
CCCTCGTGACCACCCTGGGCTACGGCGTGCAGTGCTTCGCCCGCTACCCCGACCACATG
AAGCAGCACGACTTCTTCAAGTCCGCCATGCCCGAAGGCTACGTCCAGGAGCGCACCATC
TTCTTCAAGGACGACGGCAACTACAAGACCCGCGCCGAGGTGAAGTTCGAGGGCGACAC
CCTGGTGAACCGCATCGAGCTGAAGGGCATCGACTTCAAGGAGGACGGCAACATCCTGG
GGCACAAGCTGGAGTACAACTACAACAGCCACAACGTCTATATCACCGCCGACAAGCAGA
AGAACGGCATCAAGGCCAACTTCAAGATCCGCCACAACATCGAGGACGGCGGCGTGCAG
CTCGCCGACCACTACCAGCAGAACACCCCCATCGGCGACGGCCCCGTGCTGCTGCCCGA
CAACCACTACCTGAGCTACCAGTCCAAGCTGAGCAAAGACCCCAACGAGAAGCGCGATCA
CATGGTCCTGCTGGAGTTCGTGACCGCCGCCGGGATCACTCTCGGCATGGACGAGCTGTA
CAAGTAAGTCGACATCATAATCAACCTCTGGATTACAAAATTTGTGAAAGATTGACTGGTAT
TCTTAACTATGTTGCTCCTTTTACGCTATGTGGATACGCTGCTTTAATGCCTTTGTATCATGC
TATTGCTTCCCGTATGGCTTTCATTTTCTCCTCCTTGTATAAATCCTGGTTAGTTCTTGCCAC
GGCGGAACTCATCGCCGCCTGCCTTGCCCGCTGCTGGACAGGGGCTCGGCTGTTGGGCA
CTGACAATTCCGTGGCTCGAGAGATCTTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTA

FIG. 15 cont'd

ATAAAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGCACGTGCGGA
CCGAGCGGCCGC (SEQ ID NO: 169)

CN1598 (1988 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTGTTTGGATCTGGGGC
GAAGCTTCCCTAGCCCTGTCCCTGCAGTGGCCTGGTATTGGGTGGACCCGTCACCTGAGA
CAAGGACTCCTGACAACCCAAGTCCCCAGAGGCCTCCCTGCCCTTCCCTCATTCCGTTGTT
CCACTTTTAGAGAACCCCGGGACTCCTCAGCAGGCAGCAGCCTATTTTGCCAGGATCCAC
ATAGAGCAGTGCCTGGCACAGTAGCGGTGAAGCGGGAAGTGGGTCTCTGTTGGCGGGCA
CCGTGGTGCCCGGAACTCGCTATTCCTCCCCAGTGTTAATTATCAAAATTAACCGAACACT
ATAAATAACCCAACTCAGAGACTCGAAGTGCCGAATTCGATATCATAATCAACCATAGGTAC
CGAGCTCGGGATTCAGCCGGGAGCTTAGGGAGGGGAGGTCACTTCATAAGGGCCTGGGG
GGGGAGTTGGAGCCACGAGTCGTCCAGCCGGAGCCCCGTGTGGCTGAGCTCCGGCCTCA
GAAGCATCCCCGGGTTGGATCCTTCGAAGCTAGCGCTACCGGTCGCCACCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTACGGCAAGCT
GACCCTGAAGCTGATCTGCACCACCGGCAAGCTGCCCGTGCCCTGGCCCACCCTCGTGA
CCACCCTGGGCTACGGCGTGCAGTGCTTCGCCCGCTACCCCGACCACATGAAGCAGCAC
GACTTCTTCAAGTCCGCCATGCCCGAAGGCTACGTCCAGGAGCGCACCATCTTCTTCAAG
GACGACGGCAACTACAAGACCCGCGCCGAGGTGAAGTTCGAGGGCGACACCCTGGTGAA
CCGCATCGAGCTGAAGGGCATCGACTTCAAGGAGGACGGCAACATCCTGGGGCACAAGC
TGGAGTACAACTACAACAGCCACAACGTCTATATCACCGCCGACAAGCAGAAGAACGGCA
TCAAGGCCAACTTCAAGATCCGCCACAACATCGAGGACGGCGGCGTGCAGCTCGCCGAC
CACTACCAGCAGAACACCCCCATCGGCGACGGCCCCGTGCTGCTGCCCGACAACCACTA
CCTGAGCTACCAGTCCAAGCTGAGCAAAGACCCCAACGAGAAGCGCGATCACATGGTCCT
GCTGGAGTTCGTGACCGCCGCCGGGATCACTCTCGGCATGGACGAGCTGTACAAGTAAGT
CGACATCATAATCAACCTCTGGATTACAAAATTTGTGAAAGATTGACTGGTATTCTTAACTAT
GTTGCTCCTTTTACGCTATGTGGATACGCTGCTTTAATGCCTTTGTATCATGCTATTGCTTC
CCGTATGGCTTTCATTTTCTCCTCCTTGTATAAATCCTGGTTAGTTCTTGCCACGGCGGAAC
TCATCGCCGCCTGCCTTGCCCGCTGCTGGACAGGGGCTCGGCTGTTGGGCACTGACAATT
CCGTGGCTCGAGAGATCTTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCA
GGACAGCAAGGGGGAGGATTGGGAAGACAATAGCAGGCATGCACGTGCGGACCGAGCG
GCCGC (SEQ ID NO: 170)

CN1553 (2768 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCAGTTATGAAGTACAAG
TTTTCCTGTGGCAGAAAGATGTTTCCATTGTTTTGTTTTGTTTGTTTTGTTTCGTTTTGTTTTA
AATGCATCTCTGCCTTACCTTACTTGCGGGCCAGTGAGCTAGCCTAAAATCGAAGCTCTGT
GAAGCCCGCTCTTGCCATTTTATTTTTGAAGGCTGTCCCTTGGCCACATCTGACCCACCAG
CTCCTGTCATTAGCATCTGAGTGTTAAGCCAGAGGAACTCAATCTGGGAACACCACCAACG

FIG. 15 cont'd

TGGCCAGTAAGCTGCAATTTAGTTAATGTGCACTCCTTGTAGGCCCTGGTTTTGGCCCGAG
TGTATTTGGGTAGAGTGTGTGGTGGTGATGGTAGGGAGCTAGAGAGGAAGGGGAGGGTG
ATGGACTCATTTGCAAGAACTGCCCAGCTGAGATAACATTTAAAATGAACAGGAGAAGGTC
CAATGCTTTGTAATCCTCCAGCAGCTGCTCATTTTGGGTTGGGATCAGGAAGGAGCACTTT
GCCATTAGTCCCCGAGCCAAAAGTGGCCGGTGGTGGTTTCTGGTCTCCCTAAGCCACCTC
CAAAGGGGTCACTCAGCTGTGTCCTAGGGAAGCGAAACAAGAGAAAAAGAACAAGATGGC
TTGTACGCTCCATCCATGTGTGTGGCCCCAGGGATGCCCCTGCAGATGGGCCTGGTTGGA
GATGGTGATATCTTGGATGGGTTCACTGCAGCTCCGTGCCCGAAAAGGGCAGCTGGTGGG
CTTGTTCCGCTGTTCTTCAGCCTGTCACTGCACCACTCTTAACAAGTTATCCACATCCCAGA
GATGCAGATTATGCCTCAGCTTAGAGGGCCAAGCTTCCCTCCAAGAGACTGAGCCTGCAA
AAAGCTGCCAGAGTCCCTGTAGCCTGCCCAGATCCTGCCTGAACCCAGCCCAAAGAGATG
GTTGTCATTCCAGGCAAGGGCTCACCCGGGCCAGATGCCTTCCTTCCCCAGGCCTGTGGT
TTCTCCCACTTGAGGAAGAATTGCTATTTCTTTTGCTGTATCATTACAAATAAAACAAAACTG
ACTTTGAACATATTAATGATAACAGATGGCTTCATAAAATGTAAACAGAGCAATGAAAGTAC
AAATGGGGGTCCTACCGAATTCGATATCATAATCAACCATAGGTACCGAGCTCGGGATTCA
GCCGGGAGCTTAGGGAGGGGAGGTCACTTCATAAGGGCCTGGGGGGGGAGTTGGAGCC
ACGAGTCGTCCAGCCGGAGCCCCGTGTGGCTGAGCTCCGGCCTCAGAAGCATCCCCGGG
TTGGATCCTTCGAAGCTAGCGCTACCGGTCGCCACCATGGTGAGCAAGGGCGAGGAGCT
GTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGCTG
ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA
ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGTCGACATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGA
GATCTTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGG
GGAGGATTGGGAAGACAATAGCAGGCATGCACGTGCGGACCGAGCGGCCGC (SEQ ID
NO: 171)

CN1992 (2401 bp between ITRs):
GCGGCCGCACGCGCCGGTACCGAAGCTACCCCTAACACACTATTCTACACACAGAAAATG
CTCTTCACTAGGAAGCTACCCCTAACACACTATTCTACACACAGAAAATGCTCTTCACTAGG
AAGCTACCCCTAACACACTATTCTACACACAGAAAATGCTCTTCACTAGACGCGTTACCTGC
CATTCCAACTCTGGCCTCTGTGAGCATATACACACACATGCGCACATTAACATCCCCCCCC
CCCCACACACACCTCAGGCATAGACATACACTTTTAAAAAGGCAGCCACAATATCAATTTAA
TTCAGATAAAATCACAACACAACCTTCTTTAGTACTGAGTCTTACAAAGTTGTATGCTTGAG
GTGTCCTGAGAACCCCACTAAGGTAATGGCTGTAACATTCCTCAGAGGTGAACTCATTTCC
ATGACTCATTCTGAAAGCACAGGCTCCTTGTCCTTTCACACGCATCACAATGCAACCTAAA

FIG. 15 cont'd

ATAGATCCTCATCAGCGCCTCTTTCAGGGTTATGAATAGCACTACCTTGAAAAGGGCCAAG
AGGGATGCATGCATGGGATTCAGAAAGGAGGCATTCAAGAAAACCAAGCAGGAGGCAGGC
TGCCTAAGTACTTTGAGCATGGAGCATGACGGGACCCCCTCTGGCTCCCACGCAGGCAAC
CAGGTGCCACACTCAATGGAGATGGAGTGGGTGGGAGCTCTGAGAAGGAGCTGCATCTAC
TGGGCAAAGTGGTTGAAAAACCCGAAGAGGACCTAAGTAAGCATCGGCTTAGACTGCTGA
CCCCGTTCTCCACCTCTTTATCCACCCCCCTTTCTGGGTGGCTGGAAAAATCAAATGGTAT
TTCTCTACCTTCCTGATTGTCACATTCAATGTACCCAACGGAAGGAATTCACAGTGGGCCA
CCTCCTGCTCAAGAAGCCAAGGCACTTTGCATTCTGCCTCTTGTCTTTGCTGGGAGAATGG
CATGACAACTTAAGGAGCTCGATTCAGCCGGGAGCTTAGGGAGGGGAGGTCACTTCATAA
GGGCTTGGGGGGGGAGTTGGAGCCACGAGTCGTCCAGCCGGAGCCCCGTGTGGCTGTG
CTCCGGCCTCAGAAGCATCCCCGGATCCAGATCTTTCGAAGCTAGCGCTACCGGTCGCCA
CCATGGTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGATGCCAC
CTACGGCAAGCTGACCCTGAAGCTGATCTGCACCACCGGCAAGCTGCCCGTGCCCTGGC
CCACCCTCGTGACCACCCTGGGCTACGGCGTGCAGTGCTTCGCCCGCTACCCCGACCAC
ATGAAGCAGCACGACTTCTTCAAGTCCGCCATGCCCGAAGGCTACGTCCAGGAGCGCACC
ATCTTCTTCAAGGACGACGGCAACTACAAGACCCGCGCCGAGGTGAAGTTCGAGGGCGAC
ACCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAAGTCGACGGCGCGCCGCGGCCGCGAATTCGATATCATAATCAACCTCTGGATT
ACAAAATTTGTGAAAGATTGACTGGTATTCTTAACTATGTTGCTCCTTTTACGCTATGTGGAT
ACGCTGCTTTAATGCCTTTGTATCATGCTATTGCTTCCCGTATGGCTTTCATTTTCTCCTCCT
TGTATAAATCCTGGTTAGTTCTTGCCACGGCGGAACTCATCGCCGCCTGCCTTGCCCGCTG
CTGGACAGGGGCTCGGCTGTTGGGCACTGACAATTCCGTGGCTCGAGAGATCTTCGACTG
TGCCTTCTAGTTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGGGAA
GACAATAGCAGGCATGAGATCTCACGTGCGGACCGAGCGGCCGC (SEQ ID NO: 172)

CN2367 (2038 bp between ITRs):
GCGGCCGCACGCGTACAAGCATGACTATAAAACCCAAGCAATGTTTTTGCACCAGATCCCA
GAAGTAAAGTTTATTAGTCAGTGGAATTCTTGTATTAGATTTCAGAAAGCACCCAACTACCA
AACGAGAATGAGGTTCCTCCACCATTCCAGCAGAGGGCACACTTTTAGCAGCTTTTGTAGC
TGGTTGCTTCCTGGATGTTTGAATACCAATTGATTTGTCAGCAATGAGCCATTGCAGCAATG
CTGTCAAAGTCTGGATCCCTGACTGGTGGCTGCAAACTGTTTATTAACAGCTTGATGCTCA
TTAAGGACATTGAGCCAGAATATAAGTCAACTGTGTCACTAAGTGTGCTATTTAGCATAGCT
GGCATTATGTGTGTTGTGGGAGAGGCAAGACTCTCAATGAAAGAGGCAATACATTGATTTT
CATTCTGATGTAAGCCATTTCACTTTTGATTGGGACTTCACAGAATTCTTTTCATAGCTGGC
CTCTCTCCTCATTCTGATGGAAATCTGCAAGCTAAAGGCAGTCCTGATGATAGGAAGCAAA
ACAGCAACCTCAGAAGGATTTCAAAATGATTCATTTTCTTTACAAAAATATATATCATTAGCC
TAACATAAGTAAGTGTTGAATATTATGATCTTGAGAATGAAAAGATATACCTTTAGTGTTGC
TGTGACTGAAGATGAGAGCTCGGGCTGGGCATAAAAGTCAGGGCAGAGCCATCTATTGCT
TACATTTGCTTCTGGGATCCAGATCTTTCGAAGCTAGCGCTACCGGTCGCCACCATGGTGA
GCAAGGGCGAGGAGCTGTTCACCGGGGTGGTGCCCATCCTGGTCGAGCTGGACGGCGAC
GTAAACGGCCACAAGTTCAGCGTGTCCGGCGAGGGCGAGGGCGATGCCACCTACGGCAA

FIG. 15 cont'd

GCTGACCCTGAAGCTGATCTGCACCACCGGCAAGCTGCCCGTGCCCTGGCCCACCCTCG
TGACCACCCTGGGCTACGGCGTGCAGTGCTTCGCCCGCTACCCCGACCACATGAAGCAG
CACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGT
GAACCGCATCGAGCTGAAGGGCATCGACTTCAAGGAGGACGGCAACATCCTGGGGCACA
AGCTGGAGTACAACTACAACAGCCACAACGTCTATATCACCGCCGACAAGCAGAAGAACG
GCATCAAGGCCAACTTCAAGATCCGCCACAACATCGAGGACGGCGGCGTGCAGCTCGCC
GACCACTACCAGCAGAACACCCCCATCGGCGACGGCCCCGTGCTGCTGCCCGACAACCA
CTACCTGAGCTACCAGTCCAAGCTGAGCAAAGACCCCAACGAGAAGCGCGATCACATGGT
CCTGCTGGAGTTCGTGACCGCCGCCGGGATCACTCTCGGCATGGACGAGCTGTACAAGTA
AGTCGACGGCGCGCCGCGGCCGCGAATTCGATATCATAATCAACCTCTGGATTACAAAATT
TGTGAAAGATTGACTGGTATTCTTAACTATGTTGCTCCTTTTACGCTATGTGGATACGCTGC
TTTAATGCCTTTGTATCATGCTATTGCTTCCCGTATGGCTTTCATTTTCTCCTCCTTGTATAA
ATCCTGGTTAGTTCTTGCCACGGCGGAACTCATCGCCGCCTGCCTTGCCCGCTGCTGGAC
AGGGGCTCGGCTGTTGGGCACTGACAATTCCGTGGCTCGAGAGATCTTCGACTGTGCCTT
CTAGTTGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAAT
AGCAGGCATGAGATCTCACGTGCGGACCGAGCGGCCGC (SEQ ID NO: 173)

CN2357 (1954 bp between ITRs):
GCGGCCGCACGCGTTCCACCATTCCAGCAGAGGGCACACTTTTAGCAGCTTTTGTAGCTG
GTTGCTTCCTGGATGTTTGAATACCAATTGATTTGTCAGCAATGAGCCATTGCAGCAATGCT
GTCAAAGTCTGGATCCCTGACTGGTGGCTGCAAACTGTTTATTAACAGCTTGATGCTCATTA
AGGACATTGAGCCAGAATATAAGTCAACTGTGTCACTAAGTGTGCTATTTAGCATAGCTGG
CATTATGTGTGTTGTGGGAGAGGCAAGACTCTCAATGAAAGAGGCAATACATTGATTTTCAT
TCTGATGTAAGCCATTTCACTTTTGATTGGGACTTCACAGAATTCTTTTCATAGCTGGCCTC
TCTCCTCATTCTGATGGAAATCTGCAAGCTAAAGGCAGTCCTGATGATAGGAAGCAAAACA
GCAACCTCAGAAGGATTTCAAAATGATTCATTTTCTTTACAAAAATATATATCATTAGCCTAA
CATAAGTAAGCGTTGAATATTATGATCTTGAGAATGAAAAGATATACCTTTAGTGTTGCTG
TGACTGAAGATGATATTTGACCCTTTAAAATGCATTAAGTTTCTTTCTATTGGCCGAGCTCG
GGCTGGGCATAAAAGTCAGGGCAGAGCCATCTATTGCTTACATTTGCTTCTGGGATCCAGA
TCTTTCGAAGCTAGCGCTACCGGTCGCCACCATGGTGAGCAAGGGCGAGGAGCTGTTCAC
CGGGGTGGTGCCCATCCTGGTCGAGCTGGACGGCGACGTAAACGGCCACAAGTTCAGCG
TGTCCGGCGAGGGCGAGGGCGATGCCACCTACGGCAAGCTGACCCTGAAGCTGATCTGC
ACCACCGGCAAGCTGCCCGTGCCCTGGCCCACCCTCGTGACCACCCTGGGCTACGGCGT
GCAGTGCTTCGCCCGCTACCCCGACCACATGAAGCAGCACGACTTCTTCAAGTCCGCCAT
GCCCGAAGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAAGGGCA
TCGACTTCAAGGAGGACGGCAACATCCTGGGGCACAAGCTGGAGTACAACTACAACAGCC
ACAACGTCTATATCACCGCCGACAAGCAGAAGAACGGCATCAAGGCCAACTTCAAGATCC
GCCACAACATCGAGGACGGCGGCGTGCAGCTCGCCGACCACTACCAGCAGAACACCCCC
ATCGGCGACGGCCCCGTGCTGCTGCCCGACAACCACTACCTGAGCTACCAGTCCAAGCTG
AGCAAAGACCCCAACGAGAAGCGCGATCACATGGTCCTGCTGGAGTTCGTGACCGCCGC
CGGGATCACTCTCGGCATGGACGAGCTGTACAAGTAAGTCGACGGCGCGCCGCGGCCGC
GAATTCGATATCATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTAGTTCTTGCCACGGC
GGAACTCATCGCCGCCTGCCTTGCCCGCTGCTGGACAGGGGCTCGGCTGTTGGGCACTG FIG. 15 cont'd
ACAATTCCGTGGCTCGAGAGATCTTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGC (SEQ ID NO: 174)

CN2568 (2189 bp between ITRs):
GCGGCCGCACGCGTCCACTTTTGTATTTACCATTATTGCAAAATCAATCAAATGTGAGCAAA
AGCAAAGGCAATTTGAATGACTCAAAATTGAAATTTGAGCTGCCAAATCAAGCAGTAAAACA
ATTTTTACCAGCTCTATTGATTGTTAGAAAGATAAGTTATAAACTTTATTTCAAGTAAATTTCT
AAAAGATCTGGGAATGTGATTATTCCAAGGCAGATGGCGAAGACCTTTATTTCCACTGATTA
TTCACAGATGCAAATTATTATGCAACTGGAAGCATACTAAGATCCACTTTTGTATTTACCATT
ATTGCAAAATCAATCAAATGTGAGCAAAAGCAAAGGCAATTTGAATGACTCAAAATTGAAAT
TTGAGCTGCCAAATCAAGCAGTAAAACAATTTTTACCAGCTCTATTGATTGTTAGAAAGATA
AGTTATAAACTTTATTTCAAGTAAATTTCTAAAAGATCTGGGAATGTGATTATTCCAAGGCAG
ATGGCGAAGACCTTTATTTCCACTGATTATTCACAGATGCAAATTATTATGCAACTGGAAGC
ATACTAAGATCCACTTTTGTATTTACCATTATTGCAAAATCAATCAAATGTGAGCAAAAGCAA
AGGCAATTTGAATGACTCAAAATTGAAATTTGAGCTGCCAAATCAAGCAGTAAAACAATTTT
TACCAGCTCTATTGATTGTTAGAAAGATAAGTTATAAACTTTATTTCAAGTAAATTTCTAAAA
GATCTGGGAATGTGATTATTCCAAGGCAGATGGCGAAGACCTTTATTTCCACTGATTATTCA
CAGATGCAAATTATTATGCAACTGGAAGCATACTAAGATGAGCTCGGGCTGGGCATAAAAG
TCAGGGCAGAGCCATCTATTGCTTACATTTGCTTCTGGGATCCAGATCTTTCGAAGCTAGC
GCTACCGGTCGCCACCATGGTGAGCAAGGGCGAGGAGCTGTTCACCGGGGTGGTGCCCA
TCCTGGTCGAGCTGGACGGCGACGTAAACGGCCACAAGTTCAGCGTGTCCGGCGAGGGC
GAGGGCGATGCCACCTACGGCAAGCTGACCCTGAAGCTGATCTGCACCACCGGCAAGCT
GCCCGTGCCCTGGCCCACCCTCGTGACCACCCTGGGCTACGGCGTGCAGTGCTTCGCCC
GCTACCCCGACCACATGAAGCAGCACGACTTCTTCAAGTCCGCCATGCCCGAAGGCTACG
TCCAGGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAGGAG
GACGGCAACATCCTGGGGCACAAGCTGGAGTACAACTACAACAGCCACAACGTCTATATC
ACCGCCGACAAGCAGAAGAACGGCATCAAGGCCAACTTCAAGATCCGCCACAACATCGAG
GACGGCGGCGTGCAGCTCGCCGACCACTACCAGCAGAACACCCCCATCGGCGACGGCCC
CGTGCTGCTGCCCGACAACCACTACCTGAGCTACCAGTCCAAGCTGAGCAAAGACCCCAA
CGAGAAGCGCGATCACATGGTCCTGCTGGAGTTCGTGACCGCCGCCGGGATCACTCTCG
GCATGGACGAGCTGTACAAGTAAGTCGACGGCGCGCCGCGGCCGCGAATTCGATATCATA
ATCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTAGTTCTTGCCACGGCGGAACTCATCGCCGC
CTGCCTTGCCCGCTGCTGGACAGGGGCTCGGCTGTTGGGCACTGACAATTCCGTGGCTC
GAGAGATCTTCGACTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAA
GGGGGAGGATTGGGAAGACAATAGCAGGCATGCACGTGCGGACCGAGCGGCCGC (SEQ
ID NO: 175)

CN2569 (2192 bp between ITRs):
GCGGCCGCACGCGTTTTCCACTGATTATTCACAGATGCAAATTATTATGCAACTGGAAGCA
TACTAAGATATTGCAAAGATGTTCTGACATTAGTCATCTGCTGCCTTTGTTACTTTGGTGTC
AATTTTCTTATTCTTTCCAAAGGAAGATCCTTACAGTTTGTATTCTTTCACAGCTGGGAAATG

FIG. 15 cont'd

ATCAGTTGAGAATTATTCAAACACACCAATCTGTTAACCGTACTTCTTCCCAGATAATGCAA
TATTTTGCAGGGTGACAGGCAAAAAGTGGTCATTTTTTACTTCATATTTCCACTGATTATTCA
CAGATGCAAATTATTATGCAACTGGAAGCATACTAAGATATTGCAAAGATGTTCTGACATTA
GTCATCTGCTGCCTTTGTTACTTTGGTGTCAATTTTCTTATTCTTTCCAAAGGAAGATCCTTA
CAGTTTGTATTCTTTCACAGCTGGGAAATGATCAGTTGAGAATTATTCAAACACACCAATCT
GTTAACCGTACTTCTTCCCAGATAATGCAATATTTTGCAGGGTGACAGGCAAAAAGTGGTC
ATTTTTTACTTCATATTTCCACTGATTATTCACAGATGCAAATTATTATGCAACTGGAAGCAT
ACTAAGATATTGCAAAGATGTTCTGACATTAGTCATCTGCTGCCTTTGTTACTTTGGTGTCA
ATTTTCTTATTCTTTCCAAAGGAAGATCCTTACAGTTTGTATTCTTTCACAGCTGGGAAATGA
TCAGTTGAGAATTATTCAAACACACCAATCTGTTAACCGTACTTCTTCCCAGATAATGCAAT
ATTTTGCAGGGTGACAGGCAAAAAGTGGTCATTTTTTACTTCATAGAGCTCGGGCTGGGCA
TAAAAGTCAGGGCAGAGCCATCTATTGCTTACATTTGCTTCTGGGATCCAGATCTTTCGAA
GCTAGCGCTACCGGTCGCCACCATGGTGAGCAAGGGCGAGGAGCTGTTCACCGGGGTGG
TGCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGCTGATCTGCACCACCGG
CAAGCTGCCCGTGCCCTGGCCCACCCTCGTGACCACCCTGGGCTACGGCGTGCAGTGCT
TCGCCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCG
AGGTGAAGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCACAACGTCT
ATATCACCGCCGACAAGCAGAAGAACGGCATCAAGGCCAACTTCAAGATCCGCCACAACA
TCGAGGACGGCGGCGTGCAGCTCGCCGACCACTACCAGCAGAACACCCCCATCGGCGAC
GGCCCCGTGCTGCTGCCCGACAACCACTACCTGAGCTACCAGTCCAAGCTGAGCAAAGAC
CCCAACGAGAAGCGCGATCACATGGTCCTGCTGGAGTTCGTGACCGCCGCCGGGATCAC
TCTCGGCATGGACGAGCTGTACAAGTAAGTCGACGGCGCGCCGCGGCCGCGAATTCGAT
ATCATAATCAACCTCTGGATTACAAAATTTGTGAAAGATTGACTGGTATTCTTAACTATGTTG
CTCCTTTTACGCTATGTGGATACGCTGCTTTAATGCCTTTGTATCATGCTATTGCTTCCCGT
ATGGCTTTCATTTTCTCCTCCTTGTATAAATCCTGGTTAGTTCTTGCCACGGCGGAACTCAT
CGCCGCCTGCCTTGCCCGCTGCTGGACAGGGGCTCGGCTGTTGGGCACTGACAATTCCG
TGGCTCGAGAGATCTTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGGA
CAGCAAGGGGGAGGATTGGGAAGACAATAGCAGGCATGCACGTGCGGACCGAGCGGCC
GC (SEQ ID NO: 176)

CN2689 (2107 bp between ITRs):
GCGGCCGCACGCGTAAGACGGTCTGATTGCAACCCTCCAGGAGGAAAACAAATTCACAAA
GCAGTCCCAGGTTGCCAGTTCTCAAAGTCAGCAAACCAAATCCTAACGTGCAATCTTCCCA
GGTTTTTCAAAAGCCATGGGATTGATAGTCAGTGGGGAAAGGAAGAGGTGTCGAATCCAG
GCCTGATGGATGGGTGCAGAGGCAATCAGACGTGTTTTCAGAGCCACTGTGCTCTGACAC
CTGCCCCCATTTTCCACAGAGTTTGGCTCTGAATGCGTCCCTGGACCACGCCCTCCGTCTC
CTTTACCTGGCGTTCCTATTCTTGTAGAAAGGAACACAGCCTAATGATGGATTTGTTCAATG
TGATCATTCTCGCTTATGTACAAAACAAAGGCAGGATTGATGAACTCCTAAAGAAGCACATT
CACAGGCCTGATCTATGCCTCTTACCTTGGAGCAGGCAGCAAGTACAGCCTCCAAGGGAA
TGTCAACATCTTTGCACTTTGTCAATAGGACCTTGATTCTCTAAAGGCTGAAAGGTGTTTTC
ATGGGTGAATGCTTAGAGCCAGCTCATGGTTTTCCAAACCCCACTCAAAGCTTCCAGATGA
CTCTTTTTGCATCTGTGAGCTTCTTTCATCCCTAGATATCACCCTGGGGAGAGGGCAGGCA
AAAGATGTTCTCTGTACTTGCAAGGAAGAAATGGTAAAGGCATGGGGGGTCGAGTGGGGGC
TGGGGACTCCTATGTTCCGGAAAGAGCGAGGTTGAGCTCGGGCTGGGCATAAAAGTCAGG

FIG. 15 cont'd

GCAGAGCCATCTATTGCTTACATTTGCTTCTGGGATCCAGATCTTTCGAAGCTAGCGCTAC
CGGTCGCCACCATGGTGAGCAAGGGCGAGGAGCTGTTCACCGGGGTGGTGCCCATCCTG
GTCGAGCTGGACGGCGACGTAAACGGCCACAAGTTCAGCGTGTCCGGCGAGGGCGAGG
GCGATGCCACCTACGGCAAGCTGACCCTGAAGCTGATCTGCACCACCGGCAAGCTGCCC
GTGCCCTGGCCCACCCTCGTGACCACCCTGGGCTACGGCGTGCAGTGCTTCGCCCGCTA
CCCCGACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATCACCG
CCGACAAGCAGAAGAACGGCATCAAGGCCAACTTCAAGATCCGCCACAACATCGAGGACG
GCGGCGTGCAGCTCGCCGACCACTACCAGCAGAACACCCCCATCGGCGACGGCCCCGTG
CTGCTGCCCGACAACCACTACCTGAGCTACCAGTCCAAGCTGAGCAAAGACCCCAACGAG
AAGCGCGATCACATGGTCCTGCTGGAGTTCGTGACCGCCGCCGGGATCACTCTCGGCATG
GACGAGCTGTACAAGTAAGTCGACGGCGCGCCGCGGCCGCGAATTCGATATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGA
GATCTTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGG
GGAGGATTGGGAAGACAATAGCAGGCATGAGATCTCACGTGCGGACCGAGCGGCCGC
(SEQ ID NO: 177)

CN2408 (2251 bp between ITRs):
GCGGCCGCACGCGTAACAGGACTTCAGGGAAGGCCACGGAGCTTAAGCAAGAACTTGCC
CAAAGTTTAGAAAGAAAGCTCCAAGTTACAGAACCAAGTGCCCGACCCCAGAGTCTTTCTT
TGTCTGACCTGAGGGCTTTCTGTTAAAATCCTTATACAGCAGATAAGTAAGTCAGCAGTCTT
AGAGGTGGGAAGAGGTCTGTCTGCCAGTCATCTGGCTCCCTGCAAACACAGGCATCCCCA
CCCCTGAACAATTTTCTTCATAGGAAAGTTGTGAGGGAAGTCACAGGTGCAGACACCGCCC
CGGGGGGGGGAGGGGGGGCTCAGAGTTGTTCCTTCATTCAGTCACCAATTCAGTCTTCCAG
AATCAAGGCCCTATTGACAGAGGGCTAAGCCACCGGGGCGCTGCCTTCAAGGTAAGAGGC
ATAGATCAGTCTCCTGAATGTAGAGGGATGAATTCCCTCCTTCACATAAGTGAAAGCGATC
ATAGGGAACGGAGGCATCATTAGGGCGCCCTCCTTCTGACAGGGATGCAGACAGGCAGG
TGAGGGTGGAGGGGTGTGGCCCAGGGCACATTCAGAGCCAAACTCTGTTGAGAACAAGG
CAGGTGTTTCTGAAAACCTCTCTGATTGCACCCGTACCCTCCCATCAGGCCCGAATCGCAC
ACCTCTCTGCCTCTCCTCAGACGCCGGCCCACATGGCTTTTGAAAACCTGGGGAGATTATA
CCTTCCAGCTTGCTTTGCTGAGTCTGAGGAACCTGGCTGCCTTTTCTCTTCTGTTAACTGCA
ATCAAACTGGTTTTGAGCACCAGCCCCAAGATGTCTTTGCCAGTCCACATCCATCTTCCAT
GATGAGCTAAGGTTCCCTATTTGTACCCTTACTTTCTGGGCTGAGTCATGACATCTGGGAG
AGCTCGGGCTGGGCATAAAAGTCAGGGCAGAGCCATCTATTGCTTACATTTGCTTCTGGGA
TCCAGATCTTTCGAAGCTAGCGCTACCGGTCGCCACCATGGTGAGCAAGGGCGAGGAGCT
GTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGCTG
ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA

FIG. 15 cont'd

ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGTCGACGGCGCGCCGC
GGCCGCGAATTCGATATCATAATCAACCTCTGGATTACAAAATTTGTGAAAGATTGACTGGT
ATTCTTAACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTAGTTCTTGCC
ACGGCGGAACTCATCGCCGCCTGCCTTGCCCGCTGCTGGACAGGGGCTCGGCTGTTGGG
CACTGACAATTCCGTGGCTCGAGAGATCTTCGACTGTGCCTTCTAGTTGCCAGCCATCTGT
TGTTTGCCCCTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGAGATCTCA
CGTGCGGACCGAGCGGCCGC (SEQ ID NO: 178)

CN2596 (2128 bp between ITRs):
GCGGCCGCACGCGTTTCTGCCATAGAAAAGCATCAGTGTCTATAGAGAGAAATGATAACAA
ATGAAGGAAATTGTCTAATTTTCTAACTCACTTACATAATGGACAGATGCGGTAAGTAAACA
GCACACACTAGTGCATCTTAGATGGGCACTGTACTAAGATGTGATAATGATGTTTCAGCCA
GACTTACTTATTTTATCCCGTAATCACAGGAAGCTCTAATCAGAGGAAGCATGAGGAAGAG
ACAGAATGTGCTAAGGATGTGTCACACTCTGATGGGTCACTGGAAGTGAGGAAACAAGGG
TGTGCAGCTGTGTATCAGGTCCAGGCAGAGAGCAGATGTTCTATTCACGAGTATGCTTACT
TACATCTGTCGCCCTCCAACACACCATTCCAAACTGAAAACTGAGTGTGCTTCATCAAGCC
AGAAACTTAGGAAAATGTTGTAAGGGACAATGTTTGCATGTCACAGTGAAGTAAACGCAGG
AGAGTGATGGCATCTAGCTGCTGTGAGAAGTGGCTGGAAAAATGCAGCTAACACGACTAA
CTCAAAACGCTGGGACACAAGAGAAGGAAGACAGGCACCTCACGCTTGCTGGGATCTACA
AGTTTAGCCAGACCAGTTCTTAAGATAAACTGCAATGGGTATGCCTGAAAGGCCATTCTTG
TTTGTTTCTTTATCTGTTTCAGTGTTGGTTATAACTTACCCTATCTTGCCACAGGAAGGGCA
CTTCCTTAGACAGGAAGATAGCTGATTTTAAAAAGCCCTGTTTCAACCTACAGGAGCTCGG
GCTGGGCATAAAAGTCAGGGCAGAGCCATCTATTGCTTACATTTGCTTCTGGGATCCAGAT
CTTTCGAAGCTAGCGCTACCGGTCGCCACCATGGTGAGCAAGGGCGAGGAGCTGTTCACC
GGGGTGGTGCCCATCCTGGTCGAGCTGGACGGCGACGTAAACGGCCACAAGTTCAGCGT
GTCCGGCGAGGGCGAGGGCGATGCCACCTACGGCAAGCTGACCCTGAAGCTGATCTGCA
CCACCGGCAAGCTGCCCGTGCCCTGGCCCACCCTCGTGACCACCCTGGGCTACGGCGTG
CAGTGCTTCGCCCGCTACCCCGACCACATGAAGCAGCACGACTTCTTCAAGTCCGCCATG
CCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCAT
CGACTTCAAGGAGGACGGCAACATCCTGGGGCACAAGCTGGAGTACAACTACAACAGCCA
CAACGTCTATATCACCGCCGACAAGCAGAAGAACGGCATCAAGGCCAACTTCAAGATCCG
CCACAACATCGAGGACGGCGGCGTGCAGCTCGCCGACCACTACCAGCAGAACACCCCCA
TCGGCGACGGCCCCGTGCTGCTGCCCGACAACCACTACCTGAGCTACCAGTCCAAGCTGA
GCAAAGACCCCAACGAGAAGCGCGATCACATGGTCCTGCTGGAGTTCGTGACCGCCGCC
GGGATCACTCTCGGCATGGACGAGCTGTACAAGTAAGTCGACGGCGCGCCGCGGCCGCG
AATTCGATATCATAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGCTATTG
CTTCCCGTATGGCTTTCATTTTCTCCTCCTTGTATAAATCCTGGTTAGTTCTTGCCACGGCG
GAACTCATCGCCGCCTGCCTTGCCCGCTGCTGGACAGGGGCTCGGCTGTTGGGCACTGA
CAATTCCGTGGCTCGAGAGATCTTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAATAA

FIG. 15 cont'd

AATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGC (SEQ ID NO: 179)

CN2317 (2149 bp between ITRs):
GCGGCCGCACGCGTAGAATGCTCAGGGCCTCAGCATCAGCTAAGAGGCTTTCTGGTTGCT
TGATTCTCCCCAATAAACACCCTGAAGTCTCATCAAACTGCTCATTTATTTTCCTGTAAANG
CTTCTATTGCTAACCAGGCCTTGGCCATTTTTCCCATGGGAAATGGAGTTGTTGGCTTCCC
CTGGTTCCTGTTCACCATCCAGGAAGTCGAATAAATAATGACCGTAGCCCATACTGGTGGG
ATGGATACAGGAGGAGGACTGAAAGCAGGAGAATATCAAACCCATCAAAAATCACCGAGAT
CAGTGCAAAGACTGAAGCAGAAAGACACAGCCTCTAAATAGGAGCGGCCTTAATGAAAGT
GCATCACCTCAGAGCCAACATGAAGTCTGCAGATGGGATGCACCTGCCTCCTGAGAACCT
CACAGAGGGAAATCAAGCATCAGAACCCAGAATGGAAGCAGAAAACCCCCAATCAGACTC
CTCGGAGACACTTCAGAAAAGGAACTCTCAGCTTGCAAAACAACAGGTGCATCTCTAAAGA
GATGTGGCTCCTGCCCCCACCCCATACCACCGCACCCTGAGATTGCAGCACTGCTCTGAA
CTCTCCAATCAAGCCTCTTTCTTTGGTCACTCTTAAAGTGGTTGGTTTCCAGCACTAACCCT
CACTCCTCCACCGAAATGAAATCTGCTAGCTTTGGCTGATGTTTAAACAGCTTCAATCTCTG
GGGTCTTTTGTGAGAGAGGATAATTTTAACACTGGTGATAAACCCACCAGAATTTCCAGGT
GAGAGGAGAAGCCTGAGCTCGGGCTGGGCATAAAAGTCAGGGCAGAGCCATCTATTGCTT
ACATTTGCTTCTGGGATCCAGATCTTTCGAAGCTAGCGCTACCGGTCGCCACCATGGTGAG
CAAGGGCGAGGAGCTGTTCACCGGGGTGGTGCCCATCCTGGTCGAGCTGGACGGCGACG
TAAACGGCCACAAGTTCAGCGTGTCCGGCGAGGGCGAGGGCGATGCCACCTACGGCAAG
CTGACCCTGAAGCTGATCTGCACCACCGGCAAGCTGCCCGTGCCCTGGCCCACCCTCGT
GACCACCCTGGGCTACGGCGTGCAGTGCTTCGCCCGCTACCCCGACCACATGAAGCAGC
ACGACTTCTTCAAGTCCGCCATGCCCGAAGGCTACGTCCAGGAGCGCACCATCTTCTTCAA
GGACGACGGCAACTACAAGACCCGCGCCGAGGTGAAGTTCGAGGGCGACACCCTGGTGA
ACCGCATCGAGCTGAAGGGCATCGACTTCAAGGAGGACGGCAACATCCTGGGGCACAAG
CTGGAGTACAACTACAACAGCCACAACGTCTATATCACCGCCGACAAGCAGAAGAACGGC
ATCAAGGCCAACTTCAAGATCCGCCACAACATCGAGGACGGCGGCGTGCAGCTCGCCGA
CCACTACCAGCAGAACACCCCCATCGGCGACGGCCCCGTGCTGCTGCCCGACAACCACT
ACCTGAGCTACCAGTCCAAGCTGAGCAAAGACCCCAACGAGAAGCGCGATCACATGGTCC
TGCTGGAGTTCGTGACCGCCGCCGGGATCACTCTCGGCATGGACGAGCTGTACAAGTAAG
TCGACGGCGCGCCGCGGCCGCGAATTCGATATCATAATCAACCTCTGGATTACAAAATTTG
TGAAAGATTGACTGGTATTCTTAACTATGTTGCTCCTTTTACGCTATGTGGATACGCTGCTT
TAATGCCTTTGTATCATGCTATTGCTTCCCGTATGGCTTTCATTTTCTCCTCCTTGTATAAAT
CCTGGTTAGTTCTTGCCACGGCGGAACTCATCGCCGCCTGCCTTGCCCGCTGCTGGACAG
GGGCTCGGCTGTTGGGCACTGACAATTCCGTGGCTCGAGAGATCTTCGACTGTGCCTTCT
AGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATA
GCAGGCATGAGATCTCACGTGCGGACCGAGCGGCCGC (SEQ ID NO: 180)

CN2571 (2078 bp between ITRs):
GCGGCCGCACGCGTTTCAATTGGTAAAGTTGTGGTATATAATTACAATTGAACTCTCTTGTA
CTTGCCTCTTTTACAAAAATTCTCTCCTAGCAGAACGTAGTGTGAGTCATCTACACAGCTGT
TTTTCTGATTATTGGAATTTTCTTTTGACATGAAGGAAGTATCTCATTGACAGAACTGCGTTG
TGAAGGAGTGCTAACTGTAGCATAAAATACAAAATTGGATTTTTAGATTGCAAAATACAGTA
AAGCTTTTTCAATTGGTAAAGTTGTGGTATATAATTACAATTGAACTCTCTTGTACTTGCCTC
TTTTACAAAAATTCTCTCCTAGCAGAACGTAGTGTGAGTCATCTACACAGCTGTTTTTCTGA

FIG. 15 cont'd

TTATTGGAATTTTCTTTTGACATGAAGGAAGTATCTCATTGACAGAACTGCGTTGTGAAGGA
GTGCTAACTGTAGCATAAAATACAAAATTGGATTTTTAGATTGCAAAATACAGTAAAGCTTTT
TCAATTGGTAAAGTTGTGGTATATAATTACAATTGAACTCTCTTGTACTTGCCTCTTTTACAA
AAATTCTCTCCTAGCAGAACGTAGTGTGAGTCATCTACACAGCTGTTTTTCTGATTATTGGA
ATTTTCTTTTGACATGAAGGAAGTATCTCATTGACAGAACTGCGTTGTGAAGGAGTGCTAAC
TGTAGCATAAAATACAAAATTGGATTTTTAGATTGCAAAATACAGTAAAGCTTTGAGCTCGG
GCTGGGCATAAAGTCAGGGCAGAGCCATCTATTGCTTACATTTGCTTCTGGGATCCAGAT
CTTTCGAAGCTAGCGCTACCGGTCGCCACCATGGTGAGCAAGGGCGAGGAGCTGTTCACC
GGGGTGGTGCCCATCCTGGTCGAGCTGGACGGCGACGTAAACGGCCACAAGTTCAGCGT
GTCCGGCGAGGGCGAGGGCGATGCCACCTACGGCAAGCTGACCCTGAAGCTGATCTGCA
CCACCGGCAAGCTGCCCGTGCCCTGGCCCACCCTCGTGACCACCCTGGGCTACGGCGTG
CAGTGCTTCGCCCGCTACCCCGACCACATGAAGCAGCACGACTTCTTCAAGTCCGCCATG
CCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCAT
CGACTTCAAGGAGGACGGCAACATCCTGGGGCACAAGCTGGAGTACAACTACAACAGCCA
CAACGTCTATATCACCGCCGACAAGCAGAAGAACGGCATCAAGGCCAACTTCAAGATCCG
CCACAACATCGAGGACGGCGGCGTGCAGCTCGCCGACCACTACCAGCAGAACACCCCCA
TCGGCGACGGCCCCGTGCTGCTGCCCGACAACCACTACCTGAGCTACCAGTCCAAGCTGA
GCAAAGACCCCAACGAGAAGCGCGATCACATGGTCCTGCTGGAGTTCGTGACCGCCGCC
GGGATCACTCTCGGCATGGACGAGCTGTACAAGTAAGTCGACGGCGCGCCGCGGCCGCG
AATTCGATATCATAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGCTATTG
CTTCCCGTATGGCTTTCATTTTCTCCTCCTTGTATAAATCCTGGTTAGTTCTTGCCACGGCG
GAACTCATCGCCGCCTGCCTTGCCCGCTGCTGGACAGGGGCTCGGCTGTTGGGCACTGA
CAATTCCGTGGCTCGAGAGATCTTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGCACGTGCGGACC
GAGCGGCCGC (SEQ ID NO: 181)

CN1663 (2280 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCCACTGAACATACTCCC
CCTTATTTATTCCATATACACATAAATAGCACCACCATGCACCTGTGGCCAAAAGCCAGAAA
ATGGAGTGCCATCCTCCACAACACCTTACTCACACTACCTTGATGCCTAGATGGTCTTAAA
GTCTTAAAGATTCTGCTTCCTTATTACTTCTAAAATCTGTTCCCACCACCCTACTTCTACTGT
CTTTTAGCTAATCTCACAATATTCAATATTTCTTGCCAGGATTATTGCAATTCCCTCCTGTTA
AGTCTCCCCACTTAAACTCCAGCTGCACCAATCTACACTTTACAATTCTGCAGAGATGTCTT
TTTAACATGCAAATATGCTTATATTATTTCTTTGCTTACACATTCCAATAACTCCTCTAAATAA
AACTCTTAAGTTGCTTAGACTGACACAAGGCTCTCATGAATGTGTCCCTGCCTGCCCTTCT
GCTTCTACCTTCTAGCATTCCCCTTTGTAAATCCTATGCACTTCTCTGAGCACATCATTTTCT
GTCTTTTCTTTTTTTCTTTTTCTTTGAGATGAAGTCTTTCAACATTGCCCAGGCTGGTCTCAA
ACTCCTGGGCTCAAGCGATCCTCTCGCCTCAACCTCCTGAGTAGCTGGGACTACAGCCAC
GCGAATTCGATATCATAATCAACCATAGGTACCGAGCTCGGGATTCAGCCGGGAGCTTAG
GGAGGGGAGGTCACTTCATAAGGGCCTGGGGGGGGAGTTGGAGCCACGAGTCGTCCAGC
CGGAGCCCCGTGTGGCTGAGCTCCGGCCTCAGAAGCATCCCCGGGTTGGATCCTTCGAA
GCTAGCGCTACCGGTCGCCACCATGGTGAGCAAGGGCGAGGAGCTGTTCACCGGGGTGG

FIG. 15 cont'd

TGCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGCTGATCTGCACCACCGG
CAAGCTGCCCGTGCCCTGGCCCACCCTCGTGACCACCCTGGGCTACGGCGTGCAGTGCT
TCGCCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCG
AGGTGAAGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCACAACGTCT
ATATCACCGCCGACAAGCAGAAGAACGGCATCAAGGCCAACTTCAAGATCCGCCACAACA
TCGAGGACGGCGGCGTGCAGCTCGCCGACCACTACCAGCAGAACACCCCCATCGGCGAC
GGCCCCGTGCTGCTGCCCGACAACCACTACCTGAGCTACCAGTCCAAGCTGAGCAAAGAC
CCCAACGAGAAGCGCGATCACATGGTCCTGCTGGAGTTCGTGACCGCCGCCGGGATCAC
TCTCGGCATGGACGAGCTGTACAAGTAAGTCGACATCATAATCAACCTCTGGATTACAAAA
TTTGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTGTAT
AAATCCTGGTTAGTTCTTGCCACGGCGGAACTCATCGCCGCCTGCCTTGCCCGCTGCTGG
ACAGGGGCTCGGCTGTTGGGCACTGACAATTCCGTGGCTCGAGAGATCTTCGACTGTGCC
TTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGT
GTCATTCTATTCTGGGGGGTGGGGTGGGGCAGGACAGCAAGGGGGAGGATTGGGAAGAC
AATAGCAGGCATGCACGTGCGGACCGAGCGGCCGC (SEQ ID NO: 182)

CN2310 (1884 bp between ITRs):
GCGGCCGCACGCGTTATTTTGGGATGTATAAATCAGACGAAAAGTCACAAAATCGTGTGCC
ATTCAAAGGTGGTGGAAGTTGAAGAGGAAGCGTATCTAAATGACAGATAATGAGTCTTTAT
GAAGTTACGAAAAAGAGGTCAGCACCTGAGAAACAGACTAAACTAGAATAGTCATATGACA
TCTGATGTTCACTGTAAAATGAGATGAGTGCTGTTGGTGTAATGAGGTTCCTTAGTATGCTA
CTAAGTTTAACTGCATAAATTATACCAATTAGCTCCAAAATGAATGTAAATCCTCAACTATAA
AATGTTTCAATGTGTACTTAGTGCTAATAGGAAATGTTTGTGGCTGTGAGCCATCCTGAAAC
TTCTGACTTAAAGCTCTGAAAGAAATGCCACTATATATATTTTTCTAGCCCATAGAAGGATAA
ACTTTTTGCCCTCTGATTGCAGTGGGGATGAGGAGTCCAAGTAACATGATATTCATATTGTT
AAAACTGATCCCTCGCATTGCCTCTTTAGGGTCAGTGACTGCTAGGAGCTCGGGCTGGGC
ATAAAAGTCAGGGCAGAGCCATCTATTGCTTACATTTGCTTCTGGGATCCAGATCTTTCGAA
GCTAGCGCTACCGGTCGCCACCATGGTGAGCAAGGGCGAGGAGCTGTTCACCGGGGTGG
TGCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGCTGATCTGCACCACCGG
CAAGCTGCCCGTGCCCTGGCCCACCCTCGTGACCACCCTGGGCTACGGCGTGCAGTGCT
TCGCCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCG
AGGTGAAGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCACAACGTCT
ATATCACCGCCGACAAGCAGAAGAACGGCATCAAGGCCAACTTCAAGATCCGCCACAACA
TCGAGGACGGCGGCGTGCAGCTCGCCGACCACTACCAGCAGAACACCCCCATCGGCGAC
GGCCCCGTGCTGCTGCCCGACAACCACTACCTGAGCTACCAGTCCAAGCTGAGCAAAGAC
CCCAACGAGAAGCGCGATCACATGGTCCTGCTGGAGTTCGTGACCGCCGCCGGGATCAC
TCTCGGCATGGACGAGCTGTACAAGTAAGTCGACGGCGCGCCGCGGCCGCGAATTCGAT
ATCATAATCAACCTCTGGATTACAAAATTTGTGAAAGATTGACTGGTATTCTTAACTATGTTG
CTCCTTTTACGCTATGTGGATACGCTGCTTTAATGCCTTTGTATCATGCTATTGCTTCCCGT
ATGGCTTTCATTTTCTCCTCCTTGTATAAATCCTGGTTAGTTCTTGCCACGGCGGAACTCAT
CGCCGCCTGCCTTGCCCGCTGCTGGACAGGGGCTCGGCTGTTGGGCACTGACAATTCCG

FIG. 15 cont'd

TGGCTCGAGAGATCTTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGTGGGGCAGGA
CAGCAAGGGGGAGGATTGGGAAGACAATAGCAGGCATGAGATCTCACGTGCGGACCGAG
CGGCCGC (SEQ ID NO: 183)

CN2360 (1743 bp between ITRs):
GCGGCCGCACGCGTAGCTCCTTGTTTGCACGTGTGTTCTCACAGTTCTCTTTGTCCAGACC
AGGTACACTGCAGCCAAAGACAGCGTGGTTCAGTTCTTCTTTTACCAGCCCATCAGTCATC
AGTGGAGACAAACTGACTTCTTTCCCTGCACTGTGACGTGTGGAGGAGGTGAGGCCCAGG
CTTTGTTCATGAATATTTAGAGCTCAGAGTTAGATAAATTACACATTTACATTTTTGAAGCTG
ATTTTAAAATTGGTGTGGTGATTAGAGATGTCTCATCACACAGCACCTTACTCAGCAGCCTG
AATGCAATCGTGTTAATGAAGAAGATGCATTTGCCTTTATTCTTGAAGACAGGTGCAAAACT
GGATTTGGAAAATACCTTTTACTTTTAGCCGAGCTCGGGCTGGGCATAAAAGTCAGGGCAG
AGCCATCTATTGCTTACATTTGCTTCTGGGATCCAGATCTTTCGAAGCTAGCGCTACCGGT
CGCCACCATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGAGGGCGAT
GCCACCTACGGCAAGCTGACCCTGAAGCTGATCTGCACCACCGGCAAGCTGCCCGTGCC
CTGGCCCACCCTCGTGACCACCCTGGGCTACGGCGTGCAGTGCTTCGCCCGCTACCCCG
ACCACATGAAGCAGCACGACTTCTTCAAGTCCGCCATGCCCGAAGGCTACGTCCAGGAGC
GCACCATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGCAAC
ATCCTGGGGCACAAGCTGGAGTACAACTACAACAGCCACAACGTCTATATCACCGCCGAC
AAGCAGAAGAACGGCATCAAGGCCAACTTCAAGATCCGCCACAACATCGAGGACGGCGGC
GTGCAGCTCGCCGACCACTACCAGCAGAACACCCCCATCGGCGACGGCCCCGTGCTGCT
GCCCGACAACCACTACCTGAGCTACCAGTCCAAGCTGAGCAAAGACCCCAACGAGAAGCG
CGATCACATGGTCCTGCTGGAGTTCGTGACCGCCGCCGGGATCACTCTCGGCATGGACGA
GCTGTACAAGTAAGTCGACGGCGCGCCGCGGCCGCGAATTCGATATCATAATCAACCTCT
GGATTACAAAATTTGTGAAAGATTGACTGGTATTCTTAACTATGTTGCTCCTTTTACGCTATG
TGGATACGCTGCTTTAATGCCTTTGTATCATGCTATTGCTTCCCGTATGGCTTTCATTTTCTC
CTCCTTGTATAAATCCTGGTTAGTTCTTGCCACGGCGGAACTCATCGCCGCCTGCCTTGCC
CGCTGCTGGACAGGGGCTCGGCTGTTGGGCACTGACAATTCCGTGGCTCGAGAGATCTTC
GACTGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGAT
TGGGAAGACAATAGCAGGCATGAGATCTCACGTGCGGACCGAGCGGCCGC (SEQ ID NO:
184)

CN1624 (2240 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTAGCAGCCTCTCCAGTG
GAGTATGATTCCTTTTAATTTTGGAGTTAAAGTTTTGGATGTTATTTTGGGATGTATAAATCA
GACGAAAAGTCACAAAATCGTGTGCCATTCAAAGGTGGTGGAAGTTGAAGAGGAAGCGTA
TCTAAATGACAGATAATGAGTCTTTATGAAGTTACGAAAAGAGGTCAGCACCTGAGAAACA
GACTAAACTAGAATAGTCATATGACATCTGATGTTCACTGTAAAATGAGATGAGTGCTGTTG
GTGTAATGAGGTTCCTTAGTATGCTACTAAGTTTAACTGCATAAATTATACCAATTAGCTCCA
AAATGAATGTAAATCCTCAACTATAAAATGTTTCAATGTGTACTTAGTGCTAATAGGAAATGT

FIG. 15 cont'd

TTGTGGCTGTGAGCCATCCTGAAACTTCTGACTTAAAGCTCTGAAAGAAATGCCACTATATA
TATTTTTCTAGCCCATAGAAGGATAAACTTTTTGCCCTCTGATTGCAGTGGGGATGAGGAGT
CCAAGTAACATGATATTCATATTGTTAAAACTGATCCCTCGCATTGCCTCTTTAGGGTCAGT
GACTGCTAGCATGGCTGCTCAGTGATGAATTCGATATCATAATCAACCATAGGTACCGAGC
TCGGGATTCAGCCGGGAGCTTAGGGAGGGGAGGTCACTTCATAAGGGCCTGGGGGGGGA
GTTGGAGCCACGAGTCGTCCAGCCGGAGCCCCGTGTGGCTGAGCTCCGGCCTCAGAAGC
ATCCCCGGGTTGGATCCTTCGAAGCTAGCGCTACCGGTCGCCACCATGGTGAGCAAGGG
CGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACC
CTGAAGCTGATCTGCACCACCGGCAAGCTGCCCGTGCCCTGGCCCACCCTCGTGACCAC
CCTGGGCTACGGCGTGCAGTGCTTCGCCCGCTACCCCGACCACATGAAGCAGCACGACTT
CTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAG
TACAACTACAACAGCCACAACGTCTATATCACCGCCGACAAGCAGAAGAACGGCATCAAG
GCCAACTTCAAGATCCGCCACAACATCGAGGACGGCGGCGTGCAGCTCGCCGACCACTA
CCAGCAGAACACCCCCATCGGCGACGGCCCCGTGCTGCTGCCCGACAACCACTACCTGA
GCTACCAGTCCAAGCTGAGCAAAGACCCCAACGAGAAGCGCGATCACATGGTCCTGCTGG
AGTTCGTGACCGCCGCCGGGATCACTCTCGGCATGGACGAGCTGTACAAGTAAGTCGACA
TCATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTA
TGGCTTTCATTTTCTCCTCCTTGTATAAATCCTGGTTAGTTCTTGCCACGGCGGAACTCATC
GCCGCCTGCCTTGCCCGCTGCTGGACAGGGGCTCGGCTGTTGGGCACTGACAATTCCGT
GGCTCGAGAGATCTTCGACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGAC
AGCAAGGGGGAGGATTGGGAAGACAATAGCAGGCATGCACGTGCGGACCGAGCGGCCG
C (SEQ ID NO: 185)

CN2309 (1870 bp between ITRs):
GCGGCCGCACGCGTGGGAAGGGCAGCTACAGCTAGAGGTCAGAAGGCTGGTGGGGTGA
GGGCTGCAGAGCGTTGCCTTCAAGGGTTCACTGGAGATCTGACCAGTGCATGCACATGAG
AAAGCTTCCCCAAAGTATTAGAGGAACAATTCTCAGATACCACACAGGGCTGAGGATGCTG
CTTCTTCCTGTCATCCGGAATGCAAAGCCTTACGCTATATAGGACATTGAGCAGAGCAATC
AGAAGGGTTTAACTTTAGCAATGGGCCAATTTTAGCCATAGTCTAACAGCTGCTCTGGTTTC
AGCAAACAAAGTTTAGAAGCAAGACTCTAAAAGAACAAGCCATTTCTAAGTAACTTAAACAC
ATCCTGGAATGAAATTCAAAAACAGTTATAAAAATAAAAAAGAATCCCATACCCAGAACACT
GAAATTCACAACATCTGGCAGCCAATCAACAACTAACAGGCAAGGAAAGAAGCAGAAAATG
GGAGCTGCCAAAATATTTGAATAAATAATGGCTGAAGCAGAGCTCGGGCTGGGCATAAAAG
TCAGGGCAGAGCCATCTATTGCTTACATTTGCTTCTGGGATCCAGATCTTTCGAAGCTAGC
GCTACCGGTCGCCACCATGGTGAGCAAGGGCGAGGAGCTGTTCACCGGGGTGGTGCCCA
TCCTGGTCGAGCTGGACGGCGACGTAAACGGCCACAAGTTCAGCGTGTCCGGCGAGGGC
GAGGGCGATGCCACCTACGGCAAGCTGACCCTGAAGCTGATCTGCACCACCGGCAAGCT
GCCCGTGCCCTGGCCCACCCTCGTGACCACCCTGGGCTACGGCGTGCAGTGCTTCGCCC
GCTACCCCGACCACATGAAGCAGCACGACTTCTTCAAGTCCGCCATGCCCGAAGGCTACG
TCCAGGAGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCAAGGAG
GACGGCAACATCCTGGGGCACAAGCTGGAGTACAACTACAACAGCCACAACGTCTATATC
ACCGCCGACAAGCAGAAGAACGGCATCAAGGCCAACTTCAAGATCCGCCACAACATCGAG

FIG. 15 cont'd

GACGGCGGCGTGCAGCTCGCCGACCACTACCAGCAGAACACCCCCATCGGCGACGGCCC
CGTGCTGCTGCCCGACAACCACTACCTGAGCTACCAGTCCAAGCTGAGCAAAGACCCCAA
CGAGAAGCGCGATCACATGGTCCTGCTGGAGTTCGTGACCGCCGCCGGGATCACTCTCG
GCATGGACGAGCTGTACAAGTAAGTCGACGGCGCGCCGCGGCCGCGAATTCGATATCATA
ATCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTAGTTCTTGCCACGGCGGAACTCATCGCCGC
CTGCCTTGCCCGCTGCTGGACAGGGGCTCGGCTGTTGGGCACTGACAATTCCGTGGCTC
GAGAGATCTTCGACTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGGCAGGACAGCAA
GGGGGAGGATTGGGAAGACAATAGCAGGCATGAGATCTCACGTGCGGACCGAGCGGCCG
C (SEQ ID NO: 186)

CN2366 (1682 bp between ITRs):
GCGGCCGCACGCGTTTCGGCCTCTGTCTTCTGCCATCTTCATAAATTATTCACACTACCCA
GCGCTTATGCCTTCCCGCTTCAGACCCTCTCCATAACTGTTCTCTGCTCTTTCATTTACAGC
TGTGGAACAACTATTTTCATCTGGCAGTGGCTTTTATCACCCAGGATTCTCTGCAGCTGGA
GCAGTTCTCACACGCCAAATACAACAAAATCCTGAATAAGTAGGTTGCATTTTTGGATTTCC
TGAAGAGGGGGAGGTCCATGAGATCCTCTGAGATGGTGCCTGAAGCAGAGGTTTTTGTTC
CTCCTAGGTATGGGGACATGAGACGGCTAATTGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAGGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGTAAGTCGACGGCGCGCCGCGGCCGCGAATTCGATATCATAATCAACC
TCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTT
CTCCTCCTTGTATAAATCCTGGTTAGTTCTTGCCACGGCGGAACTCATCGCCGCCTGCCTT
GCCCGCTGCTGGACAGGGGCTCGGCTGTTGGGCACTGACAATTCCGTGGCTCGAGAGAT
CTTCGACTGTGCCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGA
GGATTGGGAAGACAATAGCAGGCATGAGATCTCACGTGCGGACCGAGCGGCCGC (SEQ
ID NO: 187)

CN2257 (1969 bp between ITRs):
GCGGCCGCACGCGTGGAGGGGCATAGTGTCCACACTTCAGTCTTCATTCTTCTTGAGTTTC
ATGTGTTTAGCAAATGAAAACTTTTATATTTCTGTCTTTGATAGGCTTACCAAATCCAAAGTG
CTCCCCCTCCCCCAACTATTTCAGGTTGAATATCTGTTCTCTGAAATGTTTGGTCTGAAAAG

FIG. 15 cont'd

CATATCCAAATTTGGAAGATCTGCATATATGTAATGAGACCTCTTGGGATGCATCTCAAGTC
CAAACACAAAAGTCATTTATGTTTCATGCACACTTGACACACCTAGCCTGAAGCTAATTTGA
TACCATGTCTTTAGTGCACCTGTGTTCTGACTGCAAACCACTATAAGGAGTCAGGTGTGGA
ATTTTCCATTTACAGCATCGAGTCACTGTTCCAAAATGTTCAGCTTTTAGAGTGCTCTGTGA
TTTGTATTTTTGGATCAGGAATGCTCAACCTGTATTTTAATGCTTTGGCCTGAAACCTTCCC
CTCAGAAGGAAATGTTTGATTGCAGACTGGCATTTTTGCCTCCTGGGATAGTGAGTTGTGT
TTTGACTTTTTTCATTTATTTATTTATTTTATATTCATGCCTGATTGAGGGAGGCTTTTAGACC
ATGGTGAGCTCGGGCTGGGCATAAAAGTCAGGGCAGAGCCATCTATTGCTTACATTTGCTT
CTGGGATCCAGATCTTTCGAAGCTAGCGCTACCGGTCGCCACCATGGTGAGCAAGGGCGA
GGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTG
AAGCTGATCTGCACCACCGGCAAGCTGCCCGTGCCCTGGCCCACCCTCGTGACCACCCT
GGGCTACGGCGTGCAGTGCTTCGCCCGCTACCCCGACCACATGAAGCAGCACGACTTCTT
CAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTAC
AACTACAACAGCCACAACGTCTATATCACCGCCGACAAGCAGAAGAACGGCATCAAGGCC
AACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG
CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATAGCAGGCATG
AGATCTCACGTGCGGACCGAGCGGCCGC (SEQ ID NO: 188)

CN1667 (2674 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTTGCTACCCTAAATATTC
CCTGTGCTCCATCTATTCATTTCTCCTCCCTTCCATCTTGAAACCACTGATCTTTCTGCTTCC
TCTATAATTTTGCCTTTTCCTTTTCCAGAATGTTATAAGGGTGGAATCATATAGTGTGCAGC
CTTGAAAGAGTGGCTTCTTCCACCAAATAATGTGCATTTAAGGTTCCTTCATGTCTTTACAT
GGCTTGATAGCTCACTTTTTATCCCTGAATAATAACTCATTATACAGATGTATCACCATTTGT
TTACCCATTCATCTGTTGAAGGGCATGTTGATTGCTTCCAGCTTTTGTCAATTATGGATAGG
CTGCTATAAACATTCATGTGTAGGCTTTTACCAACACATTTGGACAAACTCCAAGGAGCACA
ATTGCTGGATTATGTAAGTAGACTATGTTTCATTACGTAAGAAGCTTTCAACCTGTCTTGTAA
AGTGGTTCTATCATTTTGCATTCCCACTAGCAATAAAGGAGAGTTGTTCTACATTTTTGGAA
CATTTGGTGTTGTCATATTGGGCAAGGGGTATTTTAGCTATTCTAAAAGGGATCTCATAAGT
TTAATTTGCAATATCCTAATAAAATATGATGTTGAACATCTTTTCATACGATTATTTGCTATTT
GTATATTGTCTTTGATGACGTGCCTACTCAGACATTTTCCCCACTGTTTAAATGGATTTTTTG
TTTTCCAATTTGTTTCATGTGGACAAAATTATAATTTATGTTATATTGCCTTGTAGAATGCTGT
GTAGATAATGTAACAGGCTAAGGAATAGAAATAATTTGATGGAAAAACAAATCTACTTTTTG

FIG. 15 cont'd

TTTTACAAAGAAATGTTATGAAAGCCCTTTCTGAGGAGAAAGCCTTTTACTTGAAAATTTTTT
AATAGAGGCAGGGTCTTGTTCTGTTCCCCAGGTTGGAGTGCAGTGACACAACCATAGCTCA
TTGCAGCCTTGAACTCCTGAGCTCAAGCGATCCTCCAGAGTAGCTAGCACTTTAGGCCAGA
GCCACTATAACCCAGCCAGGAATTCGATATCATAATCAACCATAGGTACCGAGCTCGGGAT
TCAGCCGGGAGCTTAGGGAGGGGAGGTCACTTCATAAGGGCCTGGGGGGGGAGTTGGAG
CCACGAGTCGTCCAGCCGGAGCCCCGTGTGGCTGAGCTCCGGCCTCAGAAGCATCCCCG
GGTTGGATCCTTCGAAGCTAGCGCTACCGGTCGCCACCATGGTGAGCAAGGGCGAGGAG
CTGTTCACCGGGGTGGTGCCCATCCTGGTCGAGCTGGACGGCGACGTAAACGGCCACAA
GTTCAGCGTGTCCGGCGAGGGCGAGGGCGATGCCACCTACGGCAAGCTGACCCTGAAGC
TGATCTGCACCACCGGCAAGCTGCCCGTGCCCTGGCCCACCCTCGTGACCACCCTGGGC
TACGGCGTGCAGTGCTTCGCCCGCTACCCCGACCACATGAAGCAGCACGACTTCTTCAAG
TCCGCCATGCCCGAAGGCTACGTCCAGGAGCGCACCATCTTCTTCAAGGACGACGGCAAC
TACAAGACCCGCGCCGAGGTGAAGTTCGAGGGCGACACCCTGGTGAACCGCATCGAGCT
GAAGGGCATCGACTTCAAGGAGGACGGCAACATCCTGGGGCACAAGCTGGAGTACAACTA
CAACAGCCACAACGTCTATATCACCGCCGACAAGCAGAAGAACGGCATCAAGGCCAACTT
CAAGATCCGCCACAACATCGAGGACGGCGGCGTGCAGCTCGCCGACCACTACCAGCAGA
ACACCCCCATCGGCGACGGCCCCGTGCTGCTGCCCGACAACCACTACCTGAGCTACCAGT
CCAAGCTGAGCAAAGACCCCAACGAGAAGCGCGATCACATGGTCCTGCTGGAGTTCGTGA
CCGCCGCCGGGATCACTCTCGGCATGGACGAGCTGTACAAGTAAGTCGACATCATAATCA
ACCTCTGGATTACAAAATTTGTGAAAGATTGACTGGTATTCTTAACTATGTTGCTCCTTTTAC
GCTATGTGGATACGCTGCTTTAATGCCTTTGTATCATGCTATTGCTTCCCGTATGGCTTTCA
TTTTCTCCTCCTTGTATAAATCCTGGTTAGTTCTTGCCACGGCGGAACTCATCGCCGCCTG
CCTTGCCCGCTGCTGGACAGGGGCTCGGCTGTTGGGCACTGACAATTCCGTGGCTCGAG
AGATCTTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGG
GGGAGGATTGGGAAGACAATAGCAGGCATGCACGTGCGGACCGAGCGGCCGC (SEQ ID
NO: 189)

CN1581 (2223 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTGGCCAAGAAAAGGAAG
CAGTGAATGAATGGATGATGATTCTGACTTCTGCTTTGGGGATGAAGTGGGTACCACGCAC
TGAGAGAGAACTCACGTTCATCCTTCTAAGCTTTCCCCATTCTGTTCCCTGTTCTTCCCCCC
CTGCAGCTGTTTTCCTAAAGAATCTCTGAATCTCTCCCTTTTTTTTGAATCACAAGCACTGG
CTGTTGGGAACACCCACAGATGCACTCTACAAACACACAACTTACTCTGAGTAATCACATT
GATTTGGAATTAACGGCCATTCAGATACCTCATTGAAGATACCATCTGGGATGTTGCCGCT
CTTCTGAGGTATATCATATTCTGAGAAATCCGTCCGATTGTACAAATAACTCATCAGAATG
GCTCTGGCTGCATCTTGATGTGCTGGCTAGGCGCACGAGAGTCGGAGGCTTCAGCTTCCC
CTTCCCCCTCTCGAGACACTGAAGGAAGTAGAGCCATTTCTTCTTCTCAAGAGAAAAAGCA
ACAGAGAGTTTGGCAACATCCAAAAAGTTGGTCCTGGTGCCACCAGGCATCCAAAAACATC
TCCTTGAAAATTGCCTTGAATTCGATATCATAATCAACCATAGGTACCGAGCTCGGGATTCA
GCCGGGAGCTTAGGGAGGGGAGGTCACTTCATAAGGGCCTGGGGGGGGAGTTGGAGCC
ACGAGTCGTCCAGCCGGAGCCCCGTGTGGCTGAGCTCCGGCCTCAGAAGCATCCCCGGG
TTGGATCCTTCGAAGCTAGCGCTACCGGTCGCCACCATGGTGAGCAAGGGCGAGGAGCT
GTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGCTG

FIG. 15 cont'd

ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA
ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGTCGACATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGA
GATCTTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGG
GGAGGATTGGGAAGACAATAGCAGGCATGCACGTGCGGACCGAGCGGCCGC (SEQ ID
NO: 190)

CN1649 (2068 bp between ITRs):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTGAGCACCTGTTCCTCC
CAATAGGACCTGCCCAATTTCAGTTCCTTGAGCTTTCCTGGTTGGGCTGATCTGCATTTCC
ACAAAGTGTTTTTCTGAGACATGGGCCTCAGCTCATGCGAAGGGTTTTCAGCATAAAGAAT
ACTGGTCGGGTCCATCTGGTAGCATTGCATATTCAAGGTTCTGCATGATTTGAATGAAACAT
GAAACAATAAATTCATCCACTGCCTAGAAACATCTGGTCTCTTTTAATAAACTCCTACCACTT
GGCTGTCTGAAACAAGACTATTTGTATCCAACATGTATGCTGAGAGTTCTTTTATTTTTTTCC
CTCTCTCCAGCTGCAAAGCCACATGAGAAGTAAACATGCTCTTTCATGTTATTCTCCATTGA
ATATGATCTGAAAGTACTTCCCAACTTCCTGAATAGACTCAGAATTCGATATCATAATCAAC
CATAGGTACCGAGCTCGGGATTCAGCCGGGAGCTTAGGGAGGGGAGGTCACTTCATAAG
GGCCTGGGGGGGGAGTTGGAGCCACGAGTCGTCCAGCCGGAGCCCCGTGTGGCTGAGC
TCCGGCCTCAGAAGCATCCCCGGGTTGGATCCTTCGAAGCTAGCGCTACCGGTCGCCACC
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAAGTCGACATCATAATCAACCTCTGGATTACAAAATTTGTGAAAGATTGACTGGTA
TTCTTAACTATGTTGCTCCTTTTACGCTATGTGGATACGCTGCTTTAATGCCTTTGTATCATG

FIG. 15 cont'd

CTATTGCTTCCCGTATGGCTTTCATTTTCTCCTCCTTGTATAAATCCTGGTTAGTTCTTGCCA
CGGCGGAACTCATCGCCGCCTGCCTTGCCCGCTGCTGGACAGGGGCTCGGCTGTTGGGC
ACTGACAATTCCGTGGCTCGAGAGATCTTCGACTGTGCCTTCTAGTTGCCAGCCATCTGTT
GTTTGCCCCTCCCCCGTGCCTTCCTTGACCCTGGAAGGTGCCACTCCCACTGTCCTTTCCT
AATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCACGTGCG
GACCGAGCGGCCGC (SEQ ID NO: 191)

AiP1099 (3515 bp between ITRs):
GCGGCCGCACGCGTTTCCCTTTAGCTCCTTGGTTACTTTCTCTAGCTCCTCCCTTGGGAGC
CCTGCGATTTATCCATGTAATGTTTTGGAATTTTTACCAAGTCTGATACATATAAAGATAAAA
CAAAACAAAATATTTTCTTATGACTAGTCCAAGCATGAAGAAGGACAAGGCTAAGCAGAAGT
TTATCAAAGCAGCATTCAAATTAGAAGGTAGTCAAAACAAAAATACAATGAATCAGAACAGA
AAAAGAACCTGAATCTCAAAGGTTTAGGGAATTCTGCTGAGATGGTAAAAGTGTAATGGGT
TGTTAGGAACATATGGTTCAAAGTCTCTTGCTCTCTCTTTTCATTTCTGTTAGTTTTACTTAA
GAGATAGGTCCAACAAAATCAAGTTATAAGTATAATTGTCTCAGTAAGAAGATGACTAAATT
GATAAGGATCCGAAGAGTGAATAAAGATGCTGACGACATGGCCAAAGTAAAATGGATTAGG
CTGTCTTCATGCTAGGACTTTAAATTGATGTGTACAAAATTAAGAAGTGCTGTTGCAACAGT
GTTTCAAACATCCTAGCCAGGTGATGTTTATTCTGGGGTTAAACACAAGAAGGGTAAATGTA
GGCAGATGGATTCTGAAGAAATCAAAAGCTTGTTTAAATGCAAATTTTTCTACAGAGAAGAA
GCATTCAGAGAAGAAATGATATCTAAATAAATTTTCTTTCAGCAGAATGCTTTCTTTTTCAGG
TTTGAAAGAGGCAAACTCAGGTGTCTAATGGAGATTTACTAAAGAACTAAAACTGGGTACCT
TTGCAAACGGAATTTCAGTGCCTCTAAAAGCCTACTCTCTGAAGCACTTTACTTAGCTGTGG
AGCTGAACCTGCAATCAAATTACAATCTTCTTTGAATTTTGCATACCAATCTTGACTTCAAGA
TGAGTTGATACTTCAAGACATAAATGTACAATTTGGTCTCTCTCTTATGATCCACGAGCTCG
GGCTGGGCATAAAAGTCAGGGCAGAGCCATCTATTGCTTACATTTGCTTCTGGCGTGGCC
ACCATGGCTCCTAAGAAGAAGAGGAAGGTGATGAGCCAGTTCGACATCCTGTGCAAGACC
CCCCCCAAGGTGCTGGTGCGGCAGTTCGTGGAGAGATTCGAGAGGCCCAGCGGCGAGAA
GATCGCCAGCTGTGCCGCCGAGCTGACCTACCTGTGCTGGATGATCACCCACAACGGCAC
CGCCATCAAGAGGGCCACCTTCATGAGCTACAACACCATCATCAGCAACAGCCTGAGCTT
CGACATCGTGAACAAGAGCCTGCAGTTCAAGTACAAGACCCAGAAGGCCACCATCCTGGA
GGCCAGCCTGAAGAAGCTGATCCCCGCCTGGGAGTTCACCATCATCCCTTACAACGGCCA
GAAGCACCAGAGCGACATCACCGACATCGTGTCCAGCCTGCAGCTGCAGTTCGAGAGCAG
CGAGGAGGCCGACAAGGGCAACAGCCACAGCAAGAAGATGCTGAAGGCCCTGCTGTCCG
AGGGCGAGAGCATCTGGGAGATCACCGAGAAGATCCTGAACAGCTTCGAGTACACCAGCA
GGTTCACCAAGACCAAGACCCTGTACCAGTTCCTGTTCCTGGCCACATTCATCAACTGCGG
CAGGTTCAGCGACATCAAGAACGTGGACCCCAAGAGCTTCAAGCTGGTGCAGAACAAGTA
CCTGGGCGTGATCATTCAGTGCCTGGTGACCGAGACCAAGACAAGCGTGTCCAGGCACAT
CTACTTTTTCAGCGCCAGAGGCAGGATCGACCCCCTGGTGTACCTGGACGAGTTCCTGAG
GAACAGCGAGCCCGTGCTGAAGAGAGTGAACAGGACCGGCAACAGCAGCAGCAACAAGC
AGGAGTACCAGCTGCTGAAGGACAACCTGGTGCGCAGCTACAACAAGGCCCTGAAGAAGA
ACGCCCCCTACCCCATCTTCGCTATCAAGAACGGCCCTAAGAGCCACATCGGCAGGCACC
TGATGACCAGCTTTCTGAGCATGAAGGGCCTGACCGAGCTGACAAACGTGGTGGGCAACT
GGAGCGACAAGAGGGCCTCCGCCGTGGCCAGGACCACCTACACCCACCAGATCACCGCC
ATCCCCGACCACTACTTCGCCCTGGTGTCCAGGTACTACGCCTACGACCCCATCAGCAAG
GAGATGATCGCCCTGAAGGACGAGACCAACCCCATCGAGGAGTGGCAGCACATCGAGCA
GCTGAAGGGCAGCGCCGAGGGCAGCATCAGATACCCCGCCTGGAACGGCATCATCAGCC
AGGAGGTGCTGGACTACCTGAGCAGCTACATCAACAGGCGGATCTGAGAATTCGATATCA
AGCTTATCGATAATCAACCTCTGGATTACAAAATTTGTGAAAGATTGACTGGTATTCTTAACT

FIG. 15 cont'd

ATGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGCAACCCCC
ACTGGTTGGGGCATTGCCACCACCTGTCAGCTCCTTTCCGGGACTTTCGCTTTCCCCCTCC
CTATTGCCACGGCGGAACTCATCGCCGCCTGCCTTGCCCGCTGCTGGACAGGGGCTCGG
CTGTTGGGCACTGACAATTCCGTGGTGTTGTCGGGGAAATCATCGTCCTTTCCTTGGCTGC
TCGCCTATGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTC
TTCGCCTTCGCCCTCAGACGAGTCGGATCTCCCTTTGGGCCGCCTCCCCGCATCGATACC
GAGCGCTGCTCGAGAGATCTACGGGTGGCATCCCTGTGACCCCTCCCCAGTGCCTCTCCT
GGCCCTGGAAGTTGCCACTCCAGTGCCCACCAGCCTTGTCCTAATAAAATTAAGTTGCATC
ATTTTGTCTGACTAGGTGTCCTTCTATAATATTATGGGGTGGAGGGGGGTGGTATGGAGCA
AGGGGCAAGTTGGGAAGACAACCTGTAGGGCCTGCGGGGTCTATTGGGAACCAAGCTGG
AGTGCAGTGGCACAATCTTGGCTCACTGCAATCTCCGCCTCCTGGGTTCAAGCGATTCTCC
TGCCTCAGCCTCCCGAGTTGTTGGGATTCCAGGCATGCATGACCAGGCTCAGCTAATTTTT
GTTTTTTTGGTAGAGACGGGGTTTCACCATATTGGCCAGGCTGGTCTCCAACTCCTAATCT
CAGGTGATCTACCCACCTTGGCCTCCCAAATTGCTGGGATTACAGGCGTGAACCACTGCT
CCCTTCCCTGTCCTTCTGATTTTGTAGGTAACCACGTGCGGACCGAGCGGCCGC (SEQ ID
NO: 192)

AiP1102 (2965 bp between ITRs):
GCGGCCGCACGCGTCCTGTAGTGACAGGGACAGATAGGGGCACGTTTAGAATCCAAACTC
TCAGAGCACCCCTACACTTCATGTTAAGGGAATCTGCATATTCACTGTTTAAGCAGCCCAG
CCCACACACCAGTGCTTAGCCTTTCTGAGTTAAGCTTTGAGATGCTAAAAGGCCACCTGGA
AGGATGTGGGGCTCAGCCACCTCGGTGCATTGAGTAACTCCCACTATGTGGAGCTAGGAG
AAGATGCAAGGAGAAAAACACCCACATCTTCAGTGTTACAGACAAGGTTGAGCACCTGGCT
GGAGGGGCGAGATTAAGCTTTGGAGGGAGGGCAGCCTCTGAGTCCACTCCCTTGTGTCTG
GCTGAGACGGAGTGGAAGACAGCTATCTAGGATTTCCATCCAATGCCTTTTCAGGTTACCT
GTTCTCTGGGTAGAGCTCGGGCTGGGCATAAAAGTCAGGGCAGAGCCATCTATTGCTTAC
ATTTGCTTCTGGCGTGGCCACCATGGCTCCTAAGAAGAAGAGGAAGGTGATGAGCCAGTT
CGACATCCTGTGCAAGACCCCCCCCAAGGTGCTGGTGCGGCAGTTCGTGGAGAGATTCGA
GAGGCCCAGCGGCGAGAAGATCGCCAGCTGTGCCGCCGAGCTGACCTACCTGTGCTGGA
TGATCACCCACAACGGCACCGCCATCAAGAGGGCCACCTTCATGAGCTACAACACCATCA
TCAGCAACAGCCTGAGCTTCGACATCGTGAACAAGAGCCTGCAGTTCAAGTACAAGACCC
AGAAGGCCACCATCCTGGAGGCCAGCCTGAAGAAGCTGATCCCCGCCTGGGAGTTCACC
ATCATCCCTTACAACGGCCAGAAGCACCAGAGCGACATCACCGACATCGTGTCCAGCCTG
CAGCTGCAGTTCGAGAGCAGCGAGGAGGCCGACAAGGGCAACAGCCACAGCAAGAAGAT
GCTGAAGGCCCTGCTGTCCGAGGGCGAGAGCATCTGGGAGATCACCGAGAAGATCCTGA
ACAGCTTCGAGTACACCAGCAGGTTCACCAAGACCAAGACCCTGTACCAGTTCCTGTTCCT
GGCCACATTCATCAACTGCGGCAGGTTCAGCGACATCAAGAACGTGGACCCCAAGAGCTT
CAAGCTGGTGCAGAACAAGTACCTGGGCGTGATCATTCAGTGCCTGGTGACCGAGACCAA
GACAAGCGTGTCCAGGCACATCTACTTTTTCAGCGCCAGAGGCAGGATCGACCCCCTGGT
GTACCTGGACGAGTTCCTGAGGAACAGCGAGCCCGTGCTGAAGAGAGTGAACAGGACCG
GCAACAGCAGCAGCAACAAGCAGGAGTACCAGCTGCTGAAGGACAACCTGGTGCGCAGC
TACAACAAGGCCCTGAAGAAGAACGCCCCCTACCCCATCTTCGCTATCAAGAACGGCCCT
AAGAGCCACATCGGCAGGCACCTGATGACCAGCTTTCTGAGCATGAAGGGCCTGACCGAG
CTGACAAACGTGGTGGGCAACTGGAGCGACAAGAGGGCCTCCGCCGTGGCCAGGACCAC
CTACACCCACCAGATCACCGCCATCCCCGACCACTACTTCGCCCTGGTGTCCAGGTACTA
CGCCTACGACCCCATCAGCAAGGAGATGATCGCCCTGAAGGACGAGACCAACCCCATCGA FIG. 15 cont'd
GGAGTGGCAGCACATCGAGCAGCTGAAGGGCAGCGCCGAGGGCAGCATCAGATACCCCG
CCTGGAACGGCATCATCAGCCAGGAGGTGCTGGACTACCTGAGCAGCTACATCAACAGGC
GGATCTGAGAATTCGATATCAAGCTTATCGATAATCAACCTCTGGATTACAAAATTTGTGAA
AGATTGACTGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCAC
TGTGTTTGCTGACGCAACCCCCACTGGTTGGGGCATTGCCACCACCTGTCAGCTCCTTTCC
GGGACTTTCGCTTTCCCCCTCCCTATTGCCACGGCGGAACTCATCGCCGCCTGCCTTGCC
CGCTGCTGGACAGGGGCTCGGCTGTTGGGCACTGACAATTCCGTGGTGTTGTCGGGGAA
ATCATCGTCCTTTCCTTGGCTGCTCGCCTATGTTGCCACCTGGATTCTGCGCGGGACGTCC
TTCTGCTACGTCCCTTCGGCCCTCAATCCAGCGGACCTTCCTTCCCGCGGCCTGCTGCCG
GCTCTGCGGCCTCTTCCGCGTCTTCGCCTTCGCCCTCAGACGAGTCGGATCTCCCTTTGG
GCCGCCTCCCCGCATCGATACCGAGCGCTGCTCGAGAGATCTACGGGTGGCATCCCTGT
GACCCCTCCCCAGTGCCTCTCCTGGCCCTGGAAGTTGCCACTCCAGTGCCCACCAGCCTT
GTCCTAATAAAATTAAGTTGCATCATTTTGTCTGACTAGGTGTCCTTCTATAATATTATGGGG
TGGAGGGGGGTGGTATGGAGCAAGGGGCAAGTTGGGAAGACAACCTGTAGGGCCTGCGG
GGTCTATTGGGAACCAAGCTGGAGTGCAGTGGCACAATCTTGGCTCACTGCAATCTCCGC
CTCCTGGGTTCAAGCGATTCTCCTGCCTCAGCCTCCCGAGTTGTTGGGATTCCAGGCATG
CATGACCAGGCTCAGCTAATTTTTGTTTTTTTGGTAGAGACGGGGTTTCACCATATTGGCCA
GGCTGGTCTCCAACTCCTAATCTCAGGTGATCTACCCACCTTGGCCTCCCAAATTGCTGGG
ATTACAGGCGTGAACCACTGCTCCCTTCCCTGTCCTTCTGATTTTGTAGGTAACCACGTGC
GGACCGAGCGGCCGC (SEQ ID NO: 193)

AiP1100 (2929 bp between ITRs):
GCGGCCGCACGCGTACACAAGGACAAGCTGGTGAGCGCTGTTAAATCTCTACTACAAGCT
GACACTGTCACACCCACAGATACACCGGAGTGTCAGATGGCCCCATCTCATGGTACATGA
AATGCAGTAATCCTGCGGTGCAATTTTCTGAGCTATTTTCCAGAGCTTTCTCTTGAAAAGCA
GGTGACTTCTTGGGTAGCAGCAATTTACCTTTCACACCGGGTAATCATCAAGGTGCCTGAT
TGCCCTGAATACCTTTCCCGGCTGTCAGAATACTTCAAGGCTGAGAATTAGCATTTCAAAAC
CTTTTCAAATGAGGGTAGGGGGGCTCATTCCCTTGGTTGAAGGTTCCCCAGGCTGCAAAG
AAGCAAGTGTTAAGTGCACACCTGGGGAAGCCATAGAGCTCGGGCTGGGCATAAAAGTCA
GGGCAGAGCCATCTATTGCTTACATTTGCTTCTGGCGTGGCCACCATGGCTCCTAAGAAGA
AGAGGAAGGTGATGAGCCAGTTCGACATCCTGTGCAAGACCCCCCCCAAGGTGCTGGTGC
GGCAGTTCGTGGAGAGATTCGAGAGGCCCAGCGGCGAGAAGATCGCCAGCTGTGCCGCC
GAGCTGACCTACCTGTGCTGGATGATCACCCACAACGGCACCGCCATCAAGAGGGCCACC
TTCATGAGCTACAACACCATCATCAGCAACAGCCTGAGCTTCGACATCGTGAACAAGAGCC
TGCAGTTCAAGTACAAGACCCAGAAGGCCACCATCCTGGAGGCCAGCCTGAAGAAGCTGA
TCCCCGCCTGGGAGTTCACCATCATCCCTTACAACGGCCAGAAGCACCAGAGCGACATCA
CCGACATCGTGTCCAGCCTGCAGCTGCAGTTCGAGAGCAGCGAGGAGGCCGACAAGGGC
AACAGCCACAGCAAGAAGATGCTGAAGGCCCTGCTGTCCGAGGGCGAGAGCATCTGGGA
GATCACCGAGAAGATCCTGAACAGCTTCGAGTACACCAGCAGGTTCACCAAGACCAAGAC
CCTGTACCAGTTCCTGTTCCTGGCCACATTCATCAACTGCGGCAGGTTCAGCGACATCAAG
AACGTGGACCCCAAGAGCTTCAAGCTGGTGCAGAACAAGTACCTGGGCGTGATCATTCAG
TGCCTGGTGACCGAGACCAAGACAAGCGTGTCCAGGCACATCTACTTTTTCAGCGCCAGA
GGCAGGATCGACCCCCTGGTGTACCTGGACGAGTTCCTGAGGAACAGCGAGCCCGTGCT
GAAGAGAGTGAACAGGACCGGCAACAGCAGCAGCAACAAGCAGGAGTACCAGCTGCTGA
AGGACAACCTGGTGCGCAGCTACAACAAGGCCCTGAAGAAGAACGCCCCCTACCCCATCT
TCGCTATCAAGAACGGCCCTAAGAGCCACATCGGCAGGCACCTGATGACCAGCTTTCTGA
GCATGAAGGGCCTGACCGAGCTGACAAACGTGGTGGGCAACTGGAGCGACAAGAGGGCC

FIG. 15 cont'd

TCCGCCGTGGCCAGGACCACCTACACCCACCAGATCACCGCCATCCCCGACCACTACTTC
GCCCTGGTGTCCAGGTACTACGCCTACGACCCCATCAGCAAGGAGATGATCGCCCTGAAG
GACGAGACCAACCCCATCGAGGAGTGGCAGCACATCGAGCAGCTGAAGGGCAGCGCCGA
GGGCAGCATCAGATACCCCGCCTGGAACGGCATCATCAGCCAGGAGGTGCTGGACTACC
TGAGCAGCTACATCAACAGGCGGATCTGAGAATTCGATATCAAGCTTATCGATAATCAACC
TCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTT
CTCCTCCTTGTATAAATCCTGGTTGCTGTCTCTTTATGAGGAGTTGTGGCCCGTTGTCAGG
CAACGTGGCGTGGTGTGCACTGTGTTTGCTGACGCAACCCCCACTGGTTGGGGCATTGCC
ACCACCTGTCAGCTCCTTTCCGGGACTTTCGCTTTCCCCCTCCCTATTGCCACGGCGGAAC
TCATCGCCGCCTGCCTTGCCCGCTGCTGGACAGGGGCTCGGCTGTTGGGCACTGACAATT
CCGTGGTGTTGTCGGGGAAATCATCGTCCTTTCCTTGGCTGCTCGCCTATGTTGCCACCTG
GATTCTGCGCGGGACGTCCTTCTGCTACGTCCTTCGGCCCTCAATCCAGCGGACCTTCC
TTCCCGCGGCCTGCTGCCGGCTCTGCGGCCTCTTCCGCGTCTTCGCCTTCGCCCTCAGAC
GAGTCGGATCTCCCTTTGGGCCGCCTCCCCGCATCGATACCGAGCGCTGCTCGAGAGATC
TACGGGTGGCATCCCTGTGACCCCTCCCCAGTGCCTCTCCTGGCCCTGGAAGTTGCCACT
CCAGTGCCCACCAGCCTTGTCCTAATAAAATTAAGTTGCATCATTTTGTCTGACTAGGTGTC
CTTCTATAATATTATGGGGTGGAGGGGGGTGGTATGGAGCAAGGGGCAAGTTGGGAAGAC
AACCTGTAGGGCCTGCGGGGTCTATTGGGAACCAAGCTGGAGTGCAGTGGCACAATCTTG
GCTCACTGCAATCTCCGCCTCCTGGGTTCAAGCGATTCTCCTGCCTCAGCCTCCCGAGTT
GTTGGGATTCCAGGCATGCATGACCAGGCTCAGCTAATTTTTGTTTTTTTGGTAGAGACGG
GGTTTCACCATATTGGCCAGGCTGGTCTCCAACTCCTAATCTCAGGTGATCTACCCACCTT
GGCCTCCCAAATTGCTGGGATTACAGGCGTGAACCACTGCTCCCTTCCCTGTCCTTCTGAT
TTTGTAGGTAACCACGTGCGGACCGAGCGGCCGC (SEQ ID NO: 194)

AiP1270 (1995 bp between ITRs):
GCGGCCGCACGCGTATACTGTAAAAAGCAAGAAGAACCAATCACTTAATCTAAAATTTAGA
ACTCTGAAGTGATTCATTCCACTGACCATTCTCTTTTCCCAGTTCTCTTATCTTGTCAGATAC
ACAGGAAGCTCAGGACAGTTTTGCTCATCCCTTTGTTTCTAGCAGTTCTGAGTAATGAATTC
AAATAGCAGTTATTATCTCAATGCCATGACAATTGGCTAAGCTAACTACCCAGTTCACTTAT
CGAGGGAGCAAAACACTAGATGGCCAATAAGAATGACAGACAGAATGTATGATTGATGTGA
AACACCCAGAGAATCAAGTGCTTTCAAAGAGTTAAATGTGTTCTCCATTATGGCTGACAGCT
GGAGAAACTATCATTGGAAACTGAGATGAATTGTTTGCTCTGTGCAGGTGGGAGAAGAGAA
TTAAATGACAGACACATGAAACTGTGCTTTGCATCTTCTTGTCAGCACTACTCTGTTGGCCA
AGAGTGAAATGCAATTTCAGTTGGCTTGAACGCCACAGGATTTTACATCTGAATCAACTAAG
TTCTAATTATGGGCAGATTTATCTACTAATACCATCACCATAACAACCAAAACCATGCCCCA
TGCCTTTCATGTCTTCACTATTTCACTGAGTTTGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAGGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG

FIG. 15 cont'd

CGCGATCACATGGTCCTGCTGGAGTTCGTGACCGCCGCCGGGATCACTCTCGGCATGGA
CGAGCTGTACAAGTAAGTCGACGGCGCGCCGCGGCCGCGAATTCGATATCATAATCAACC
TCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTT
CTCCTCCTTGTATAAATCCTGGTTAGTTCTTGCCACGGCGGAACTCATCGCCGCCTGCCTT
GCCCGCTGCTGGACAGGGGCTCGGCTGTTGGGCACTGACAATTCCGTGGCTCGAGAGAT
CTTCGACTGTGCCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGGGGA
GGATTGGGAAGACAATAGCAGGCATGAGATCTCACGTGCGGACCGAGCGGCCGC (SEQ
ID NO: 195)

AiP1271 (2209 bp between ITRs):
GCGGCCGCACGCGTTGACTCACTAAAGTATTTGCATGTTTTCAAAGCTGTAAAGTCTGGAG
GTGTGCTTTTCAGGAGCTGGGGAGGTTAGAGGGAAGACCTCGAACAGGACACACTATCAC
TGTCTTTCTTGTGCCAATGCAATTGGAAGAAACAAACACAGCCATCATTTAGCCCACATGAA
TTAGGTCCTGTAAAGAGTGAAGGGGAAAAGGTTGTTGGAAATCTAATTAGTAGGCTTTGCA
AGTGTGGAGTTTATGGCTACATATTCAGTTAAATTCAGTTCTGTTTTGTAGCTATCAGCCAG
GGAAGAGTCAAGTGCCATGTGGATTGGGAACATAAATAGCCCATTCTTCATGTCCATTGCT
CTATCATTAACCTTCCCACTCAGTCCTGGAAATGAAAAACCCAGCGTCCTTCCATCTGCTCC
ACGTTATTTATGATGATGCCTCTAATTATGTTCAATTGAGTTGCTGTCGATGATTAAAGGTAA
TAGGTAATAATAACTTGGCCTCATCATTACCACCATTATTATTAGCTCATTGATTGCAATAAT
TTCTAAAATTACCCCTTGGAATAAAATATGTTAAGCACCTGGTTTATCCTTTTTTTTTTTTTTT
AAAAAAGGAACATCTGCTCTAAATGTGTGATAGCAGAGGACCAAACGTGTCTTGATCTGAA
GGGGAAGCAAAACGATGCTGACACTGGGGAGCCTTGTCTGGGCTGGAATGGATGTATTG
TGGGATGCTGAGAGGAAGAGTAGTCACGATCAAGTTCAATGCTAGGATTACAGGGCTGCT
GAGAGACGGAGACACGTGGGAAGCTGAGCTATTCCATGGCTACTGCAGGCTTTACTTCTT
CTTCTGAGCTCGGGCTGGGCATAAAAGTCAGGGCAGAGCCATCTATTGCTTACATTTGCTT
CTGGGATCCAGATCTTTCGAAGCTAGCGCTACCGGTCGCCACCATGGTGAGCAAGGGCGA
GGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTG
AAGCTGATCTGCACCACCGGCAAGCTGCCCGTGCCCTGGCCCACCCTCGTGACCACCCT
GGGCTACGGCGTGCAGTGCTTCGCCCGCTACCCCGACCACATGAAGCAGCACGACTTCTT
CAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCG
AGCTGAAGGGCATCGACTTCAAGGAGGACGGCAACATCCTGGGGCACAAGCTGGAGTAC
AACTACAACAGCCACAACGTCTATATCACCGCCGACAAGCAGAAGAACGGCATCAAGGCC
AACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG
CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG

FIG. 15 cont'd

GGGGGTGGGGTGGGGCAGGACAGCAAGGGGGAGGATTGGGAAGACAATAGCAGGCATG
AGATCTCACGTGCGGACCGAGCGGCCGC (SEQ ID NO: 196)

AiP1272 (2133 bp between ITRs):
GCGGCCGCACGCGTTCATTTTAGTAGGAAAGTGGGATACTATCTTCTAAAGAGACTGTGCA
TCTTATACTCCTATCTACCACATCATATTTACTGTCTATTCTTAGTTGGGTCTAAATTTCTAA
GTAATTTTAAGTATTCATATTCTAGGCTACTGGGTCCTATAGATTAATATAAATATTTGATTG
TAAGTTATGCAATAAAAATGAAGAGATTTGTTTATATGCATCTAAATAAGAACATGCAGAATG
TGTTCGGAACTTGAATATCCTTATCTCCATGAAAATGGGAAAAATAAAAATAATTTAAACAAA
GTGTTGAGTGGAACATGTGTAGCTGAAACACTTGATTTTCCCTAAAATATCTGAGTAATTAC
TTGAATTTCCTACTTTATCATTTGTCCATGGACAGCTGGTATCAGGCTATAAAAACAACAATA
ATTAGAGGCCCAAATAGTTCTTTTAATTACCCTAAAAGTCTGAAATTCACGTTTTTGTTGTCT
AGAAGTATTCTAATCATGTTTAACAGCTGATTAGCAATTGGTCCATTTTTATGTTGTAGAAAA
GTGAAATGTGAATGGAAAATTGAAGAATAATTCCAAACCAAGGTAAATTATTACTGCTTTTC
CCTGCAATTGTTAGTTGAAAGGTGTGATTTGAGATAAGATCATTTACACTTAAAAGTGAATA
GAAGAAATATAATAAGAGGGAATAGGCCTGTGAAGTTGTCAAGAATAAATTTTAAAATAAAT
GCAGCATTTTTTGCATTTATGTCATAGTCTGTTTAAGCAGAGCTCGGGCTGGGCATAAAAGT
CAGGGCAGAGCCATCTATTGCTTACATTTGCTTCTGGGATCCAGATCTTTCGAAGCTAGCG
CTACCGGTCGCCACCATGGTGAGCAAGGGCGAGGAGCTGTTCACCGGGGTGGTGCCCAT
CCTGGTCGAGCTGGACGGCGACGTAAACGGCCACAAGTTCAGCGTGTCCGGCGAGGGCG
AGGGCGATGCCACCTACGGCAAGCTGACCCTGAAGCTGATCTGCACCACCGGCAAGCTG
CCCGTGCCCTGGCCCACCCTCGTGACCACCCTGGGCTACGGCGTGCAGTGCTTCGCCCG
CTACCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGGTGAA
GTTCGAGGGCGACACCCTGGTGAACCGCATCGAGCTGAAGGGCATCGACTTCAAGGAGG
ACGGCAACATCCTGGGGCACAAGCTGGAGTACAACTACAACAGCCACAACGTCTATATCA
CCGCCGACAAGCAGAAGAACGGCATCAAGGCCAACTTCAAGATCCGCCACAACATCGAGG
ACGGCGGCGTGCAGCTCGCCGACCACTACCAGCAGAACACCCCCATCGGCGACGGCCCC
GTGCTGCTGCCCGACAACCACTACCTGAGCTACCAGTCCAAGCTGAGCAAAGACCCCAAC
GAGAAGCGCGATCACATGGTCCTGCTGGAGTTCGTGACCGCCGCCGGGATCACTCTCGG
CATGGACGAGCTGTACAAGTAAGTCGACGGCGCGCCGCGGCCGCGAATTCGATATCATAA
TCAACCTCTGGATTACAAAATTTGTGAAAGATTGACTGGTATTCTTAACTATGTTGCTCCTTT
TACGCTATGTGGATACGCTGCTTTAATGCCTTTGTATCATGCTATTGCTTCCCGTATGGCTT
TCATTTTCTCCTCCTTGTATAAATCCTGGTTAGTTCTTGCCACGGCGGAACTCATCGCCGCC
TGCCTTGCCCGCTGCTGGACAGGGGCTCGGCTGTTGGGCACTGACAATTCCGTGGCTCG
AGAGATCTTCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCAT
CGCATTGTCTGAGTAGGTGTCATTCTATTCTGGGGGGTGGGGTGGGGCAGGACAGCAAG
GGGGAGGATTGGGAAGACAATAGCAGGCATGAGATCTCACGTGCGGACCGAGCGGCCGC
(SEQ ID NO: 197)

AiP1273 (2402 bp between ITRs):
GCGGCCGCACGCGTCTGGCTGTCCTGGAACTCACTCTGTAGACCAGGCTGGCCTCAAACT
CAGAAATCTGCCTGCCTCTGCCTCCCAAGTGCTGGGATTAAAGGCATGTGCCACCACACC
TGGCCTAGAAATAATGACTTTTAAAATTATCTAAAGGTTACCAGATGAAATTATCAACCTCAG
CTCTGTGGTATAATTTAAATCTAGTTCTGATTCAGTAAGAGTGTTATTTTCAGTACCCTCAGT
AGCAGAATCCTATTGCCTCTTATATCTAAGCAGGAGAGGCAATTCAGAAACAAAGACCCAA
GGACAGGAGCCCTATTGCATCTACTCTCAATAATTAAGGCCTTTGATGACTAAAATAATTTA
GATAATAAGATTGGTTTGGGTAAATAAATATCAAATTAGGGTTTATGGCAGTCACAGGTGTT

FIG. 15 cont'd

TGGCAGGTCTGGCCTATAATCACAGAGAAAATGAATGCATTTTATTTAGCATAATTGGGAAA
AGGAATGAAGCTTATATGCAAATTGTGTACCACTTTTGTTAAAGATAGCTGGTCAGACTCAT
GATGATAATCCAAACCTTTATCCCAGTGAAAATTTTCAACATATCTATTTTCTGTGGAATTTT
ACCACATCTGACTGCATTCTCCCAGTCTTCTGAGATGGATTTCAGTGTCCTTGGTCACCATC
TAGCCTTTCTATTTTGTTGACAGGATGCCTGAGTTTAGCTGTTTCTGTTTATTTGTTTGTTTT
TAAGCTTGATTTCTCCTACTCGTGTCTATAGCTGGAATCGGAGGTTACATGAGATTTCTCAG
CATCAGCATCCAGCACTGCCACAAAGGGGATGTGGGAGATGAGAAGGGAAAACAAGACAG
TGAAGAGAATAAAAATGAAATCCTGGAGGCAAGATAATTAAGAGACCAGAAAATAGAGTTG
AATTTCCATTAGGAACATTTACAAGAATGTGTTCACAGGCACACACACAGGAATCCCCAACT
GCTAGCTTTGGAATGCCCATAGATGCCACTGCTACTGGACTCTGTGATCAGCGCTCTTGAC
TAGGACTACGAGCTCGGGCTGGGCATAAAAGTCAGGGCAGAGCCATCTATTGCTTACATTT
GCTTCTGGGATCCAGATCTTTCGAAGCTAGCGCTACCGGTCGCCACCATGGTGAGCAAGG
GCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGAC
CCTGAAGCTGATCTGCACCACCGGCAAGCTGCCCGTGCCCTGGCCCACCCTCGTGACCA
CCCTGGGCTACGGCGTGCAGTGCTTCGCCCGCTACCCCGACCACATGAAGCAGCACGAC
TTCTTCAAGTCCGCCATGCCCGAAGGCTACGTCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAGTAAGTCGAC
GGCGCGCCGCGGCCGCGAATTCGATATCATAATCAACCTCTGGATTACAAAATTTGTGAAA
GATTGACTGGTATTCTTAACTATGTTGCTCCTTTTACGCTATGTGGATACGCTGCTTTAATG
CCTTTGTATCATGCTATTGCTTCCCGTATGGCTTTCATTTTCTCCTCCTTGTATAAATCCTGG
TTAGTTCTTGCCACGGCGGAACTCATCGCCGCCTGCCTTGCCCGCTGCTGGACAGGGGCT
CGGCTGTTGGGCACTGACAATTCCGTGGCTCGAGAGATCTTCGACTGTGCCTTCTAGTTG
CCAGCCATCTGTTGTTTGCCCCTCCCCCGTGCCTTCCTTGACCCTGGAAGGTGCCACTCC
CACTGTCCTTTCCTAATAAAATGAGGAAATTGCATCGCATTGTCTGAGTAGGTGTCATTCTA
TTCTGGGGGGTGGGGTGGGGCAGGACAGCAAGGGGGAGGATTGGGAAGACAATAGCAG
GCATGAGATCTCACGTGCGGACCGAGCGGCCGC (SEQ ID NO: 198)

ARTIFICIAL EXPRESSION CONSTRUCTS FOR SELECTIVELY MODULATING GENE EXPRESSION IN INHIBITORY NEOCORTICAL NEURONS

CROSS-REFERENCE TO RELATED APPLICATION

This application is a U.S. National Phase application based on International Patent Application No. PCT/US2021/036028, filed Jun. 4, 2021, which claims priority to U.S. Provisional Patent Application No. 63/034,794, filed on Jun. 4, 2020, each of which is incorporated herein by reference in its entirety as if fully set forth herein.

STATEMENT REGARDING FEDERALLY SPONSORED RESEARCH OR DEVELOPMENT

This invention was made with government support under grants MH114126 and MH121274 awarded by the National Institutes of Health. The government has certain rights in the invention.

REFERENCE TO SEQUENCE LISTING

The Sequence Listing associated with this application is provided in text format in lieu of a paper copy, and is hereby incorporated by reference into the specification. The name of the text file containing the Sequence Listing is 2SS0742_ST25.txt. The text file is 15.1 MB, was created on Nov. 17, 2022, and is being submitted electronically via Patent Center.

FIELD OF THE DISCLOSURE

The current disclosure provides artificial expression constructs for selectively modulating gene expression in selected central nervous system cell types. The artificial expression constructs can be used to selectively express synthetic genes or modify gene expression in inhibitory neocortical GABAergic neurons including somatostatin GABAergic neurons, parvalbumin GABAergic neurons, vasointestinal peptide GABAergic neurons, and Lamp5 GABAergic neurons, and in some instances, astrocytes.

BACKGROUND OF THE DISCLOSURE

To fully understand the biology of the brain, different cell types need to be distinguished and defined and, to further study them, artificial expression constructs that can selectively label and perturb them need to be identified. In mouse, recombinase driver lines have been used to great effect to label cell populations that share marker gene expression. However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans.

SUMMARY OF THE DISCLOSURE

The current disclosure provides artificial expression constructs that selectively drive gene expression in targeted central nervous system cell populations. Targeted central nervous system cell populations include: inhibitory neocortical GABAergic neurons including somatostatin (Sst) GABAergic neurons, parvalbumin (Pvalb) GABAergic neurons, vasointestinal peptide (Vip) GABAergic neurons, and Lamp5 GABAergic neurons.

Particular embodiments of the artificial expression constructs utilize the following enhancers to selectively drive protein expression within targeted central nervous system cell populations as follows (enhancer(s)/targeted cell population): eHGT_089h, eHGT_087h, eHGT_154h, eHGT_226h, eHGT_526h, eHGT_512h, eHGT_283h, eHGT_090m, eHGT_340m, eHGT_528h, eHGT_515h, eHGT_226h, eHGT_170h, eHGT_519h, eHGT_527h, eHGT_470m, eHGT_174h, eHGT_087m, and eHGT_156h/Sst GABAergic neurons; eHGT_076h, eHGT_759m, and eHGT_064h/Pvalb/Sst GABAergic neurons; eHGT_072h, eHGT_131hv1, eHGT_131hv2, and eHGT_130h/Pvalb GABAergic neurons; eHGT_354h, eHGT_121h, eHGT_133h, eHGT_219h, eHGT_207h, eHGT_113m, eHGT_111m, eHGT_110h, eHGT_080h, eHGT_107h, MGT_E81, MGT_E85, MGT_E88, and MGT_E83/Vip GABAergic neurons; MGT_E36, MGT_E37, and MGT_E41/Lamp5_Lhx6 GABAergic neurons; eHGT_354m, eHGT_060m, and eHGT_060h/VIP GABAergic neurons and astrocytes; eHGT_025h, eHGT_096h, eHGT_098h, and eHGT_104m/Lamp5 GABAergic neurons; eHGT_682h, eHGT_600m, eHGT_468m, eHGT_338m, eHGT_341m, and eHGT_339m/Sst and Chod/GABAergic neurons.

In particular embodiments, the artificial enhancer elements include a concatenated core of an enhancer. Examples include a concatenated core of eHGT_226h and/or eHGT_064h. These artificial enhancer elements can provide higher levels and more rapid onset of transgene expression compared to a single full length original (native) enhancer.

In particular embodiments, the enhancer core includes the sequence as set forth in any one of SEQ ID NOs: 161, 163, and 165. In particular embodiments, these cores are concatenated and have 2, 3, 4, 5, 6, 7, 8, 9, or 10 copies of the core sequence. SEQ ID NOs: 162, 164, and 166 provide three-copy concatemers of the selected enhancer cores.

Particular embodiments of the artificial expression constructs utilize 3xcore2_eHGT_226h, and/or 3xcore3_eHGT_226h to selectively drive protein expression within Sst GABAergic neurons, and/or 3xcore_eHGT_064h to selectively drive protein expression within Pvalb/Sst GABAergic neurons.

Particular embodiments provide artificial expression constructs including the features of vectors described herein including vectors: CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, and AiP1273.

BRIEF DESCRIPTION OF THE FIGURES

Some of the drawings submitted herein are better understood in color. Applicant considers the color versions of the drawings as part of the original submission and reserves the right to present color images of the drawings in later proceedings.

FIGS. 2A-2M. Vector: CN2039 and Enhancer: eHGT_354h. (2A-2C) Animal: 554255. Native SYFP2 fluo-rescence montage of a sagittal section of a whole mouse brain (2A), caudal cortex (2B), and visual cortex (2C) showing selective expression of SYFP2 in cells with bipolar neuronal morphology. Virus was administered in neonatal pup after intracerebroventricular (ICV) injection of CN2039 virus packaged with the PHP.eB capsid. (2D-2E) Animal: 554255 and Region: VISp. Mouse visual cortex (VISp) transduced by CN2039 virus packaged with PHP.eB capsid and delivered in neonatal pups via ICV injection. SYFP fluorescence (2D), and markers for GABAergic cell sub-classes (Sst (2E), and Vip (2F)) mRNA imaged by mFISH are shown. Images are montages. (2G-2I) Animal: 554255 and Region: VISp. Mouse visual cortex (VISp) transduced by CN2039 virus packaged with PHP.eB capsid and deliv-ered in neonatal pups via ICV injection. Vip mFISH (2G), SYFP fluorescence and VIP mFISH (2H), and SYFP fluo-rescence only (2I) are shown. Images are montages. Quan-tification of SYFP+ cells that do (red circles) or do not (blue circles with small triangle in upper right corner) overlap with Vip mFISH are shown below. (2J) Animal: 554255 and Region: VISp. Mapping of single cell transcriptomic profiles of SYPF2+ cells sorted from the VISp region of the mouse cortex after retro-orbital injection of CN2039 virus pack-aged with the PHP.eB capsid. Number of cells mapped to the final leaf are shown on the bar plot below the dendrogram. Transcriptomic cell types are shown on the bottom. This data shows eHGT_354h enhancer driven reporter expression occurs selectively in Vip+ cells when VISp is evaluated. The text along the bottom from left to right reads: 169 L2/3 IT VISp Rrad, 168 L2/3 IT VISp Adamts2, 167 L2/3 IT VISp Agmat, 164 L4 IT VISp Rspo1, 163 L5 IT VISp Hsd11b1 Endou, 162 L5 IT VISp Whrn Tox2, 160 L5 IT VISp Batf3, 158 L5 IT VISp Col6a1 Fezf2, 157 L5 IT VISp Col27a1, 154 L6 IT VISp Penk Col27a1, 153 L6 IT VISp Penk Fst, L6 IT VISp Col23a1 Adamts2, 149 L6 IT VISp Col18a1, 146 L6 IT VISp Car3, 144 L5 PT VISp Chrna6, 143 L5 PT VISp Lgr5, 142 L5 PT VISp Clql2 Ptgfr, 141 L5 PT VISp Clql2 Cdh13, 140 L5 PT VISp Krt80, 134 L5 NP VISp Trhr Cpne7, 133 L5 NP VISp Trhr Met, L6 CT Nxph2 Sla, 130 L6 CT VISp Krt80 Sla, L6 CT VISp Nxph2 VIs, 127 L6 CT VISp Ctxn3 Brinp3, 126 L6 CT VISp Ctxn3 Sla, 122 L6 CT VISp Gpr139, 120 L6b Col8a1 Rprm, 119 L6b VISp Mup5, 118 L6b VISp Col8a1 Rxfp1, 115 L6b P2ry12, L6b VISp Crh, 110 Lamp5 Krt73, Lamp5 Fam19a1 Pax6, 108 Lamp5 Fam19a1 Tmem182, 106 Lamp5 Ntn1 Npy2r, 105 Lamp5 Plch2 Dock5, 101 Lamp5 Lsp1, 100 Lamp5 Lhx6, Sncg Slc17a8, 96 Sncg Vip Nptx2, 95 Sncg Gpr50, 93 Sncg Vip Itih5, 90 Serpinf1 Clrn1, 89 Serpinf1 Aqp5 Vip, 85 Vip Igfbp6 Car10, 84 Vip Igfbp6 Pltp, Vip Lmo1 Fam159b, Vip Lmo1 My11, 79 Vip Igfbp4 Mab2111, 78 Vip Arhgap36 Hmcn1, 77 Vip Gpc3 Slc18a3, 74 Vip Ptprt Pkp2, 73 Vip Rspo4 Rxfp1 Chat, 71 Vip Lect1 Oxtr, 70 Vip Rspo1 Itga4, 67 Vip Chat Htr1f, 66 Vip Pygm C1qll, 61 Vip Crispld2 Htr2c, 60 Vip Crispld2 Kcne4, 58 Vip Col15a1 Pde1a, 54 Sst Chodl, 53 Sst Mme Fam114a1, 52 Sst Tac1 Htr1d, 50 Sst Tac1 Tacr3, 49 Sst Calb2 Necab1, 48 Sst Calb2 Pdlim5, 46 Sst Nr2f2 Necab1, 45 Sst Myh8 Etv1, 44 Sst Chrna2 Glra3, 42 Sst Myh8 Fibin, 40 Sst Chrna2 Ptgdr, 39 Sst Tac2 Myh4, 37 Sst Hpse Sema3c, 36 Sst Hpse Cbln4, 34 Sst Crhr2 Efem1, 33 Sst Crh 4930553C11 Rik, 31 Sst Esm1, 29 Sst Tac2 Tacstd2, 28 Sst Rxfp1 Eya1, 27 Sst Rxfp1 Prdm8, 23 Sst Nts, Pvalb Gabrg1, 20 Pvalb Th Sst, 18 Pvalb Calb1 Sst, 17 Pvalb Akr1c18 Ntf3, 16 Pvalb Sema3e Kank4, 14 Pvalb Gpr149 Islr, 11 Pvalb Reln Itm2a, 10 Pvalb Tac1, 9 Pvalb Tpbg, 4 Pvalb Vipr2, Meis2 Adamts19, 170 Astro Aqp4, 171 OPC Pdgfr Grm5, Oligo Serpinb1a, 174 Oligo Synpr, VLMC Osr1 Cd74, VLMC Osr1 Mc5r, VLMC Spp1 Col15a1, Peri Kcnj8, SMC Acta2, Endo Ctla2a, and 181 Microglia Siglech. (2K-2M) Animal: Macaque in vivo and Region: temporal cortex. Fluorescence image of macaque temporal cortex brain slice at 51 days following in vivo injection of CN2039 virus. (2K, 2L), anti-GFP and anti-calretinin antibody co-immunostaining. (2M) Overlay showing high on-target specificity in Calretinin+ cortical neurons, especially in upper layers. Virus was administered by stereotaxic intraparenchymal injection of CN2039 virus packaged with the PHP.eB capsid.

FIGS. 5A-5J. Vector: CN1567, Animal: 554248, and Enhancer: eHGT_121h. (5A) CN1567 packaged with PHP.eB injected stereotaxically into an adult mouse visual cortex (broken box). (5B) Box in (5A) imaged at higher resolution. Cells are indicated in (5B). (5C)-(5E) Broken rectangle in (5B) shown with higher resolution: SYFP2 intrinsic fluorescence (5C) Gad1 and Vip mRNA expression (5D), and the overlap of the three stains (5E). Scored SYFP2+ cells are surrounded by circles with hatch marks reflecting if the cell expresses Vip and GAD1 mRNA (blue in (5C) top panel; ○⁓ in (5C) bottom panel), Gad1 mRNA only (red in (5D) top panel; ⬡ in (5D) bottom panel), or neither Gad1 nor Vip (yellow in (5E) top panel; ⬡ in (5E) bottom panel). The quantification of scored cells are: Vip+ (blue/○⁓), n=25; Gad1+(red/⬡), n=9; and Gad1− (yellow/⬡), n=6. Native SYFP2 fluorescence montage of a sagittal section of a whole mouse brain (5F) and visual cortex (5G) showing selective expression of SYFP2 in cells with upper layer neuronal morphology. Virus was administered to the neonatal pup via intracerebroventricular (ICV) injection of CN1567 virus packaged with the PHP.eB capsid. (5H-5J) Region: VISp. Mouse visual cortex (VISp) transduced by CN1567 virus packaged with PHP.eB capsid and delivered in neonatal pups via ICV injection. SYFP fluorescence only (green 5H), SYFP fluorescence with Vip mFISH (5I), and Vip mFISH only (cyan 5J) are shown. Images are montages. SYFP bright cells mostly overlap with Vip mRNA, while many dim SYFP+ cells are also labeled.

FIGS. 6A-6H. Vector: CN2317, Animal: 554427, and Enhancer: eHGT_468m. Native SYFP2 fluorescence montage of a sagittal section of a whole mouse brain (6A) and visual cortex (6B) showing selective expression of SYFP2 in cells scattered neuronal morphology. In the caudal cortex, most labeled cells appear in deep layers, while in the rostral cortex, cells labeled cells are not enriched in specific layers. Virus was administered to the neonatal pup via intracerebroventricular (ICV) injection of CN2317 virus packaged with the PHP.eB capsid. (6C-6E) Region: VISp. Mouse visual cortex (VISp) transduced by CN2317 virus packaged with PHP.eB capsid and delivered in neonatal pups via ICV injection. Sst (yellow) mFISH (6C), SYFP fluorescence (green) and Sst mFISH (6D), and SYFP fluorescence only (green 6E) are shown. Images are montages. Quantification of SYFP+ cells that do (cyan circles with triangles) or do not (red circles) overlap with Sst mFISH are shown with 10 of 38 of SYFP+ cells being Sst+(26% Sst+). (6F-6H) Region: Mouse rostral cortex (ALM). ALM transduced by CN2317 virus packaged with PHP.eB capsid and delivered in neonatal pups via ICV injection. Sst (yellow) and Gad1 (cyan) mFISH (6F), SYFP fluorescence only (green 6G), and SYFP fluorescence and Sst and Gad1 mFISH (6H) are shown. Images are montages. Quantification of SYFP+ cells that do (cyan circles) or do not (red circles with stars) overlap with Sst mFISH are shown with 32 of 51 SYFP+ cells being Sst+(63% Sst+).

FIGS. 7A-7D. Enhancer: eHGT_156h, Animal: 539841, Vector: CN1649, and Region: VISp. Mouse visual cortex (VISp) transduced by CN1649 virus packaged with PHP.eB capsid and delivered in neonatal pups via ICV injection. (7A) SYFP fluorescence (Green) and DAPI (gray), (7B) Sst, Pvalb, and Gad1 mFISH, (7C) SYFP fluorescence only, and (13D) SYFP fluorescence and Sst, Pvalb, and Gad1 mFISH are shown. Colors are indicated.

FIGS. 8A-8H. Enhancer: eHGT_170h, Animal: 539842, and Vector: CN1663. Native SYFP2 fluorescence montage of a sagittal section of a whole mouse brain (8A) and visual cortex (8B) showing selective expression of SYFP2 in cells with a scattered, non-pyramidal neuron morphology. Virus was administered to the neonatal pup via intracerebroventricular (ICV) injection of CN1663 virus packaged with the PHP.eB capsid. (8C-8H) Region: VISp. Mouse visual cortex (VISp) transduced by CN1663 virus packaged with PHP.eB capsid and delivered in neonatal pups via ICV injection. SYFP fluorescence only (8C), SYFP fluorescence and Sst mFISH (8D) and Sst mFISH only (8E) are shown. Images are montages. Quantification of SYFP+ cells that do (yellow circles) or do not (red circles with a star) overlap with Sst mFISH are shown with 44 of 48 being SST+(92% SST+). 8F-8H are insets of FIGS. 8C-8E. Mouse visual cortex (VISp) transduced by CN1663 virus packaged with PHP.eB capsid and delivered in neonatal pups via ICV injection. Sst and Pvalb mFISH only (8F) SYFP fluorescence only (8G), and SYFP fluorescence with Sst and Pvalb mFISH (8H) are shown. Images are montages.

FIGS. 9A-9K. Enhancer: eHGT_526h, Animal: 554251, and Vector: CN2365. Native SYFP2 fluorescence montage of a sagittal section of a whole mouse brain (9A) and visual cortex (9B) showing selective expression of SYFP2 in cells with a scattered, non-pyramidal neuron morphology. Virus was administered to the neonatal pup via intracerebroventricular (ICV) injection of CN2365 virus packaged with the PHP.eB capsid. Strong expression is also seen in MSN neurons in the striatum and direct pathway axons. (9C-9E) Region: VISp. Mouse visual cortex (VISp) transduced by CN2365 virus packaged with PHP.eB capsid and delivered in neonatal pups via ICV injection. Sst and Pvalb mFISH only (9C) SYFP fluorescence only (9D), and SYFP fluorescence with Sst and Pvalb mFISH (9E) are shown. Images are montages. FIGS. 9F-9H are insets of FIGS. 9C-9E. Mouse visual cortex (VISp) transduced by CN2365 virus packaged with PHP.eB capsid and delivered in neonatal pups via ICV injection. Sst and Pvalb mFISH only (9F) SYFP fluorescence only (9G), and SYFP fluorescence with Sst and Pvalb mFISH (9H) are shown. Images are montages. Quantification of SYFP+ cells that do (cyan circles) or do not (red circles with a star) overlap with Sst mFISH are shown with 31 of 35 SYFP+ cells being Sst+(89% Sst+). (9I-9K) Region: Hippocampus. Mouse hippocampus transduced by CN2365 virus packaged with PHP.eB capsid and delivered in neonatal pups via ICV injection. SYFP fluorescence only (9I), Sst mFISH (9J) and Pvalb mFISH (9K) are shown. Images are montages. Quantification of SYFP+ cells that overlap (cyan circles) with Sst mFISH are shown with 24 of 24 SYFP+ cells being Sst+100% Sst+).

FIGS. 10A-10D. Vector: CN1584 and Enhancer: eHGT_090m. (10A) Region: VISp. Mapping of single cell transcriptomic profiles of SYPF2+ cells sorted from the VISp region of the mouse cortex after retro-orbital injection of CN1584 virus packaged with the PHP.eB capsid. Number of cells mapped to the final leaf are shown on the bar plot below the dendrogram. Transcriptomic cell types are shown on the bottom. This data shows eHGT_090m enhancer driven reporter expression occurs selectively in SST+ cells when VISp is evaluated. The text along the bottom is typed in the brief description of the drawing of FIG. 2J. (10B-10D) Species: Macaque and Region: Left Occipital Lateral Cortex. Macaque transduced by CN1584 virus packaged with PHP.eB capsid and delivered via intraparenchymal injection. Whole cortical column is shown with SYFP and DAPI fluorescence (10B), SYFP fluorescence only of the inset (10C) and VIP, GAD1, and SST mFISH of the inset (10D) are shown. Arrows show overlap of SYFP and SST, while asterisk shows SYFP and no SST. Images are montages. Quantification of SYFP+ cells that overlap (cyan circles) with Sst mFISH are shown with 115 of 159 SYFP+ cells being Sst+(72% Sst+). Quantification on the bottom shows specificity in two different images.

FIG. 13. provides an overview of artificial expression construct features and components.

FIG. 14. provides an overview of targeted cell type specificity of different artificial expression constructs disclosed herein.

FIG. 15. includes sequences supporting the disclosure.

DETAILED DESCRIPTION

Figure 1:
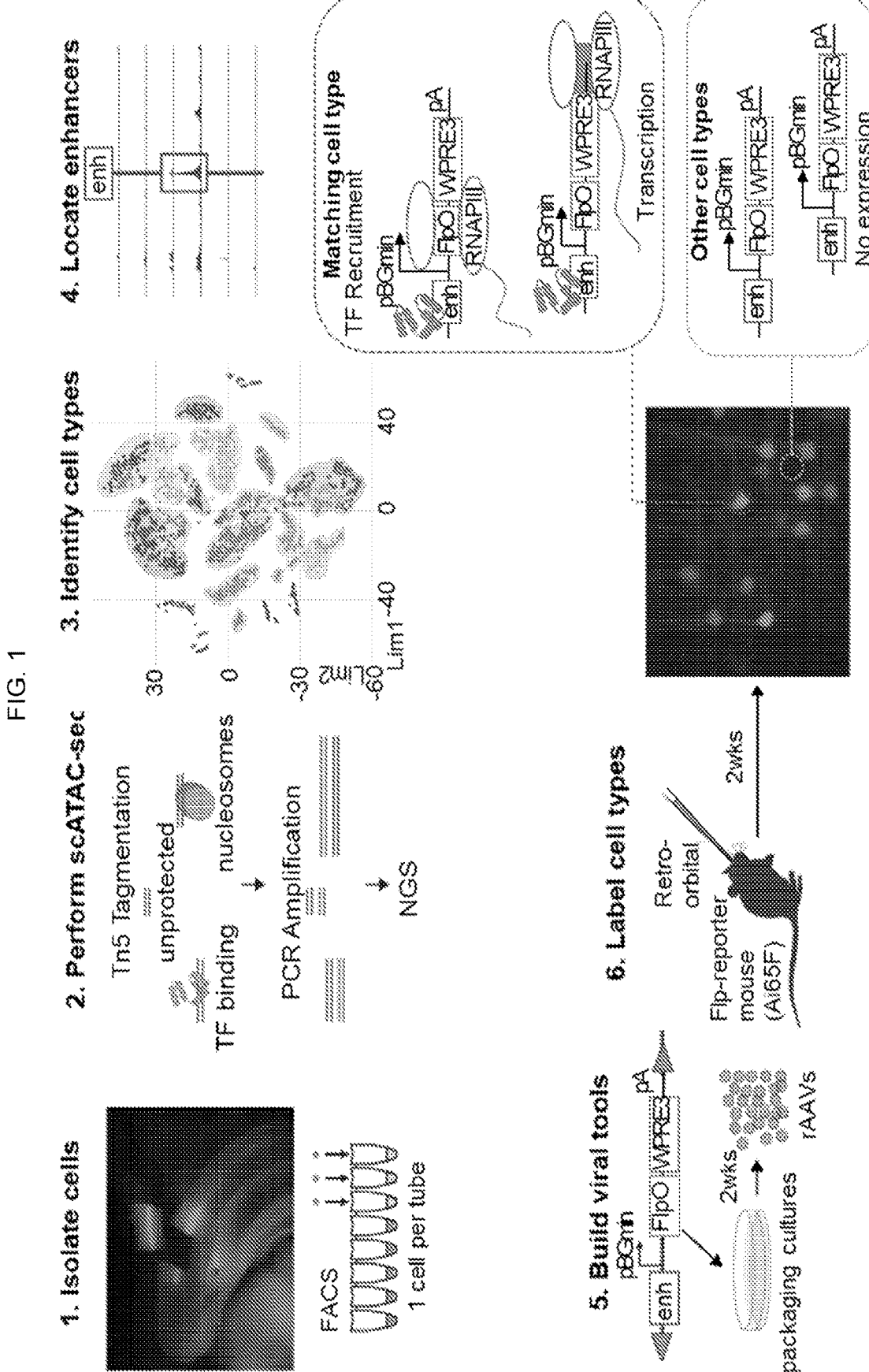
FIG. 1. Overview of enhancer discovery for viral tools. To build cell type-specific labeling tools, cells from adult mouse cortex were isolated and a single cell assay for transposase-accessible chromatin using sequencing (scATAC-seq) was performed. Single nucleus RNA-seq from human surgical tissue can be used for identifying human genomic enhancers. Samples were clustered and compared to single cell RNA sequencing (scRNA-seq) data-sets to identify the clusters. Single cells matching the same transcriptomic types were then pooled and the genome was searched for type-specific putative enhancers. These regions were cloned upstream of a minimal promoter in an AAV genomic backbone, which was used to generate self-comple-mentary adeno-associated viral vectors (scAAVs) or recom-binant adeno-associated viral vectors (rAAVs). These viral tools were delivered retro-orbitally to label specific neocor-tical glutamatergic and GABAergic neuron populations. In cells with a matching cell type, enhancers recruit their cognate transcription factors to drive cell type-specific expression. In other cells, viral genomes are present, but transcripts are not expressed.
Figure 2A:
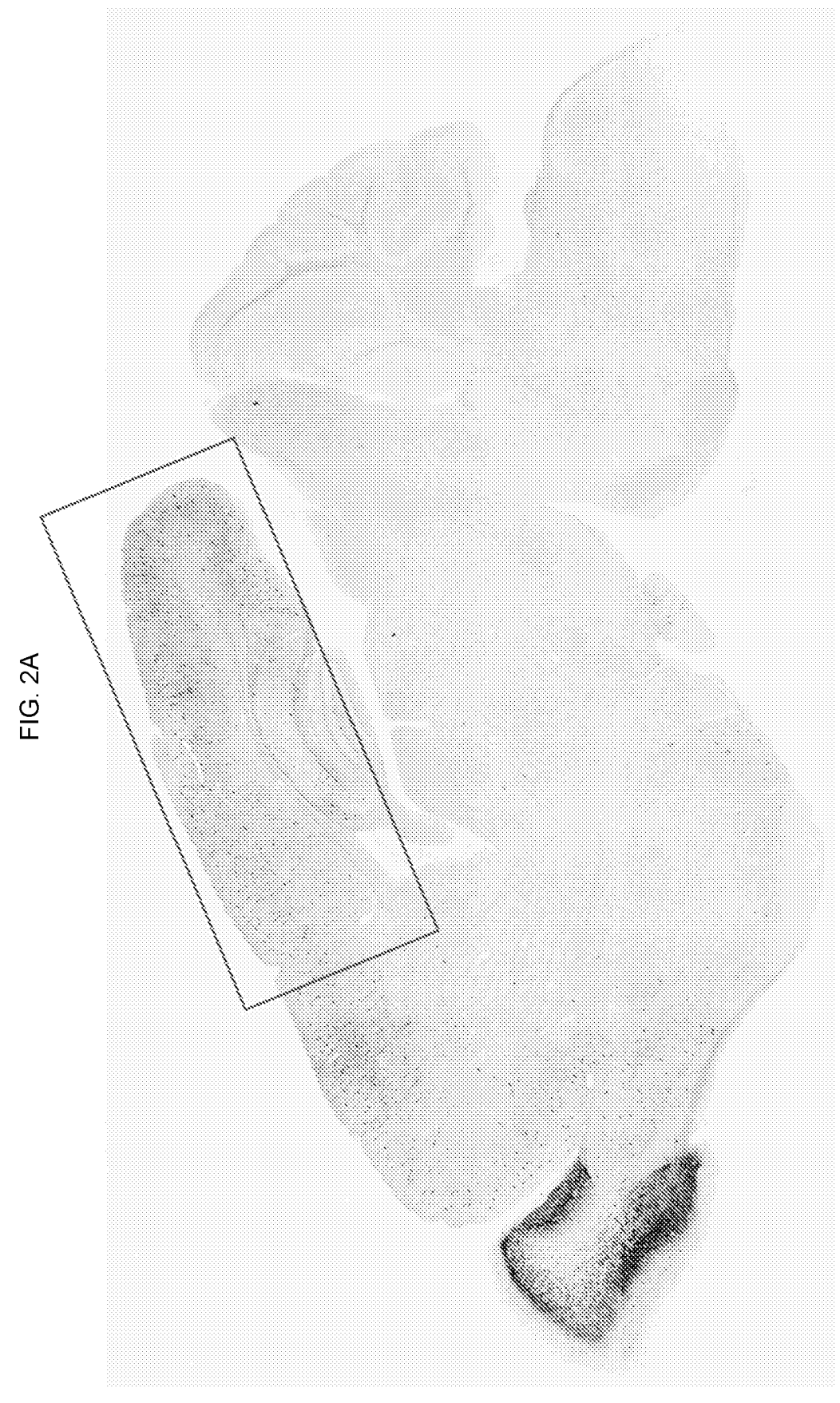
Figure 2B:
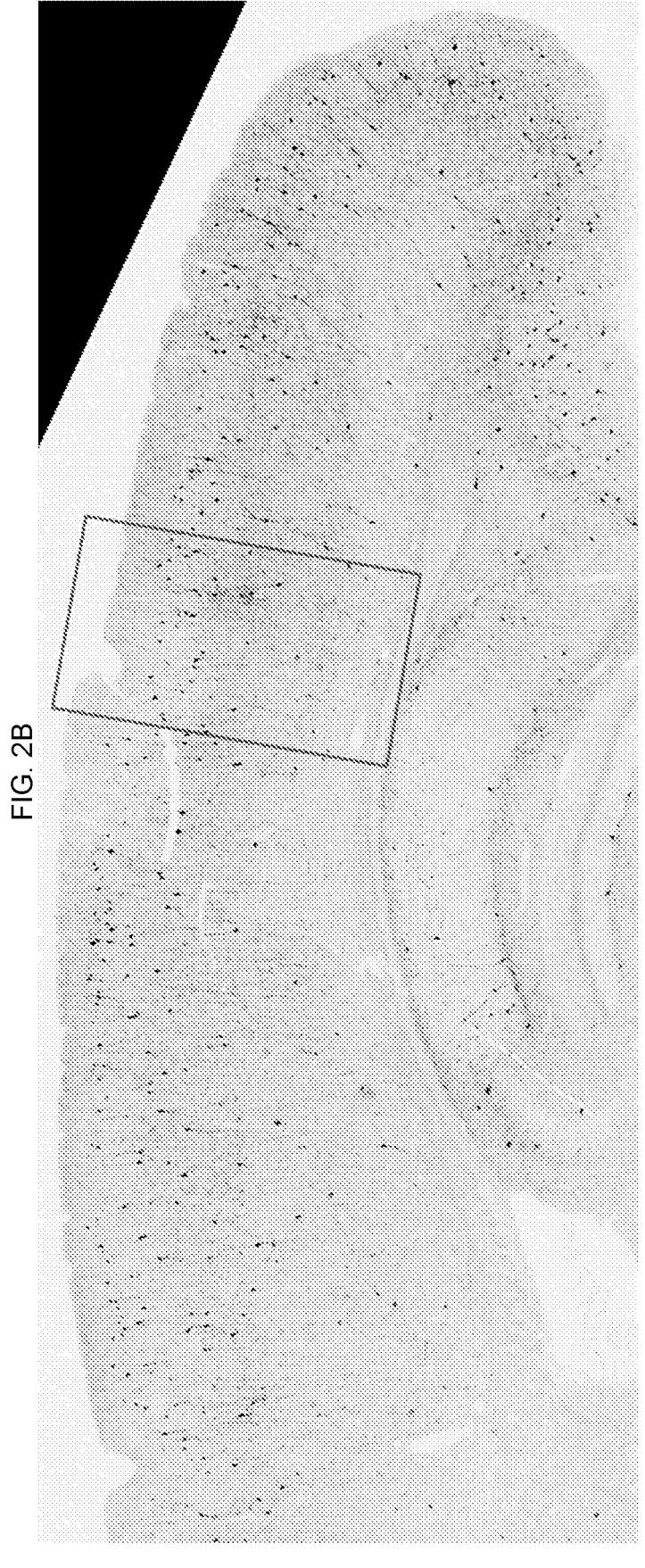
Figure 2C:
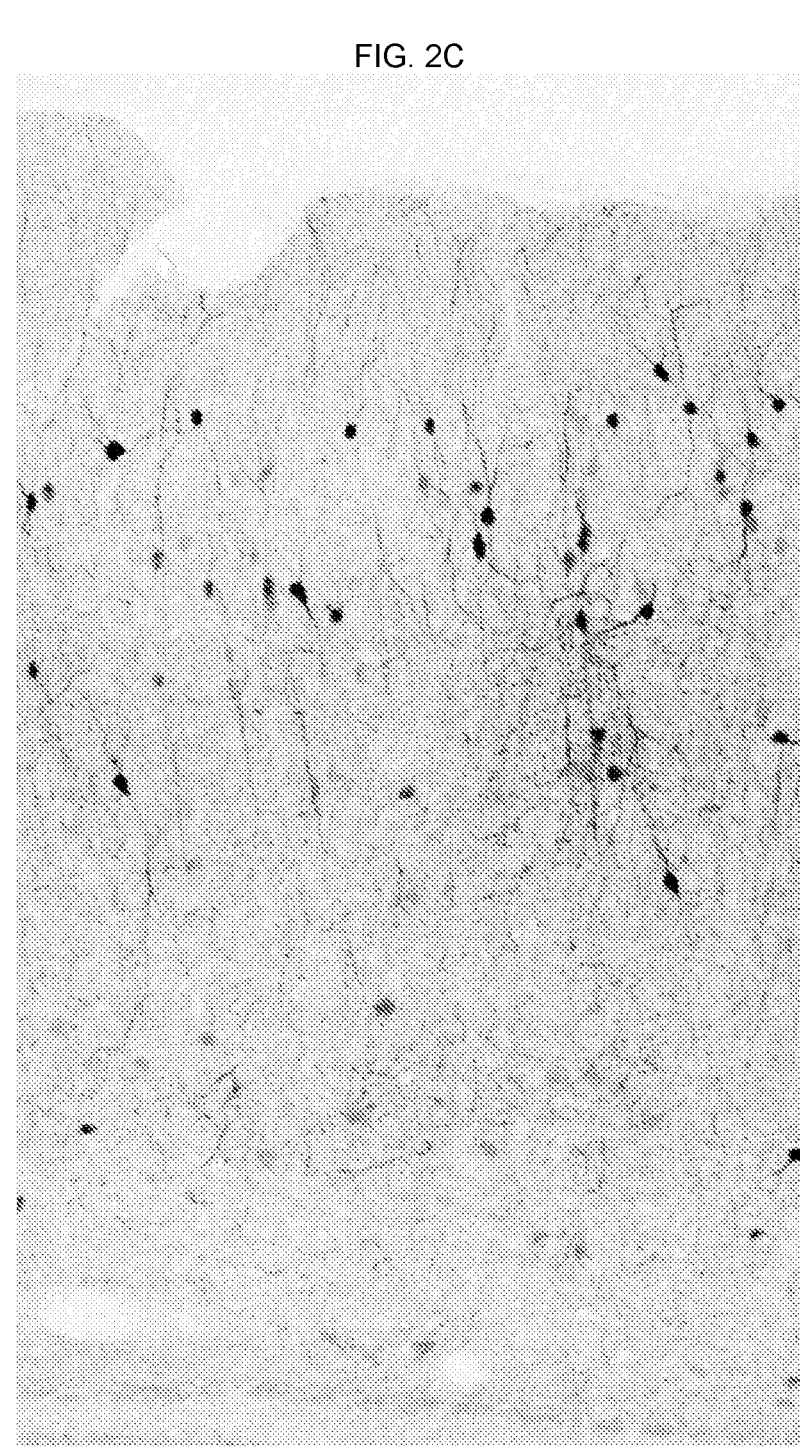
Figures 2D, 2E, 2F:
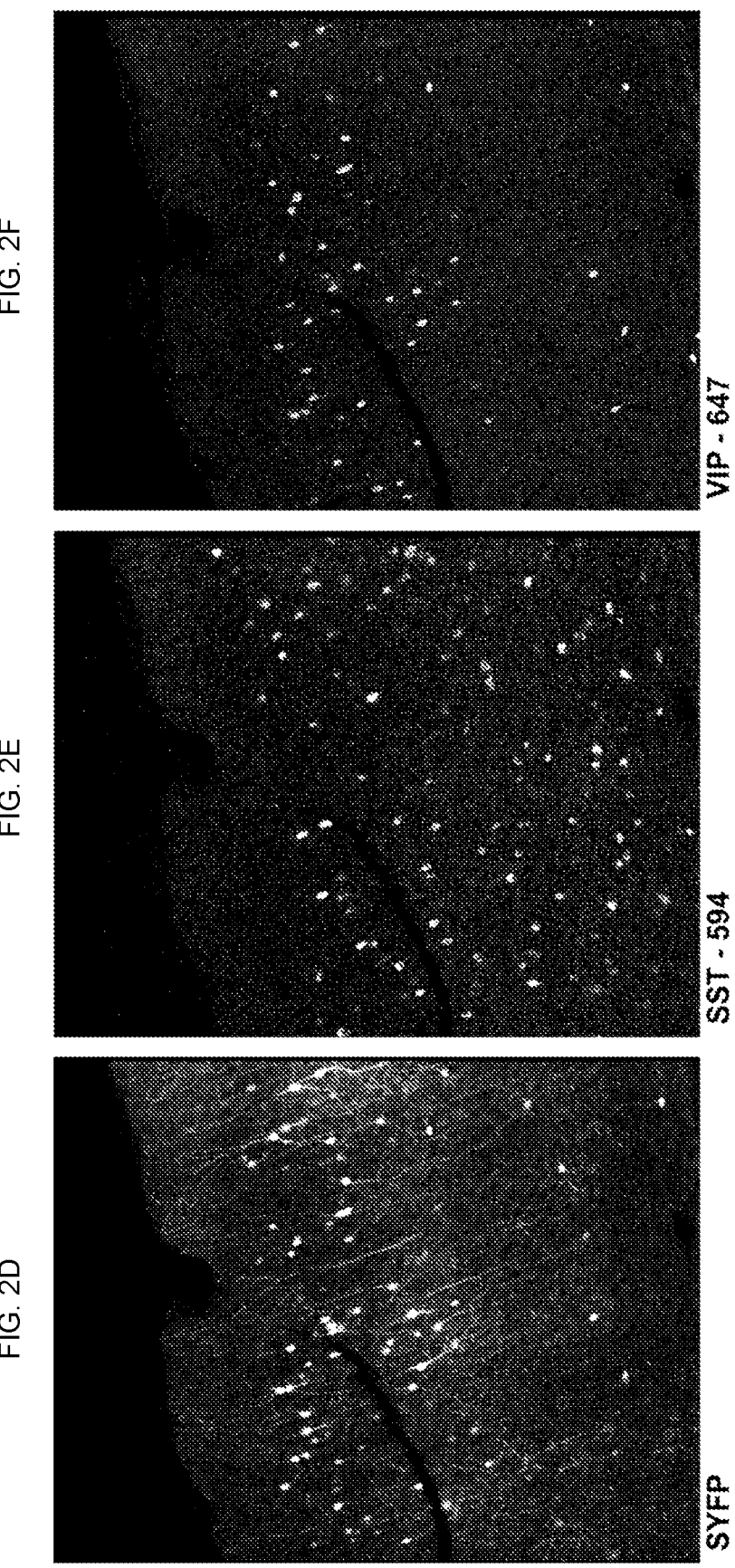
Figures 2G, 2H, 2I:
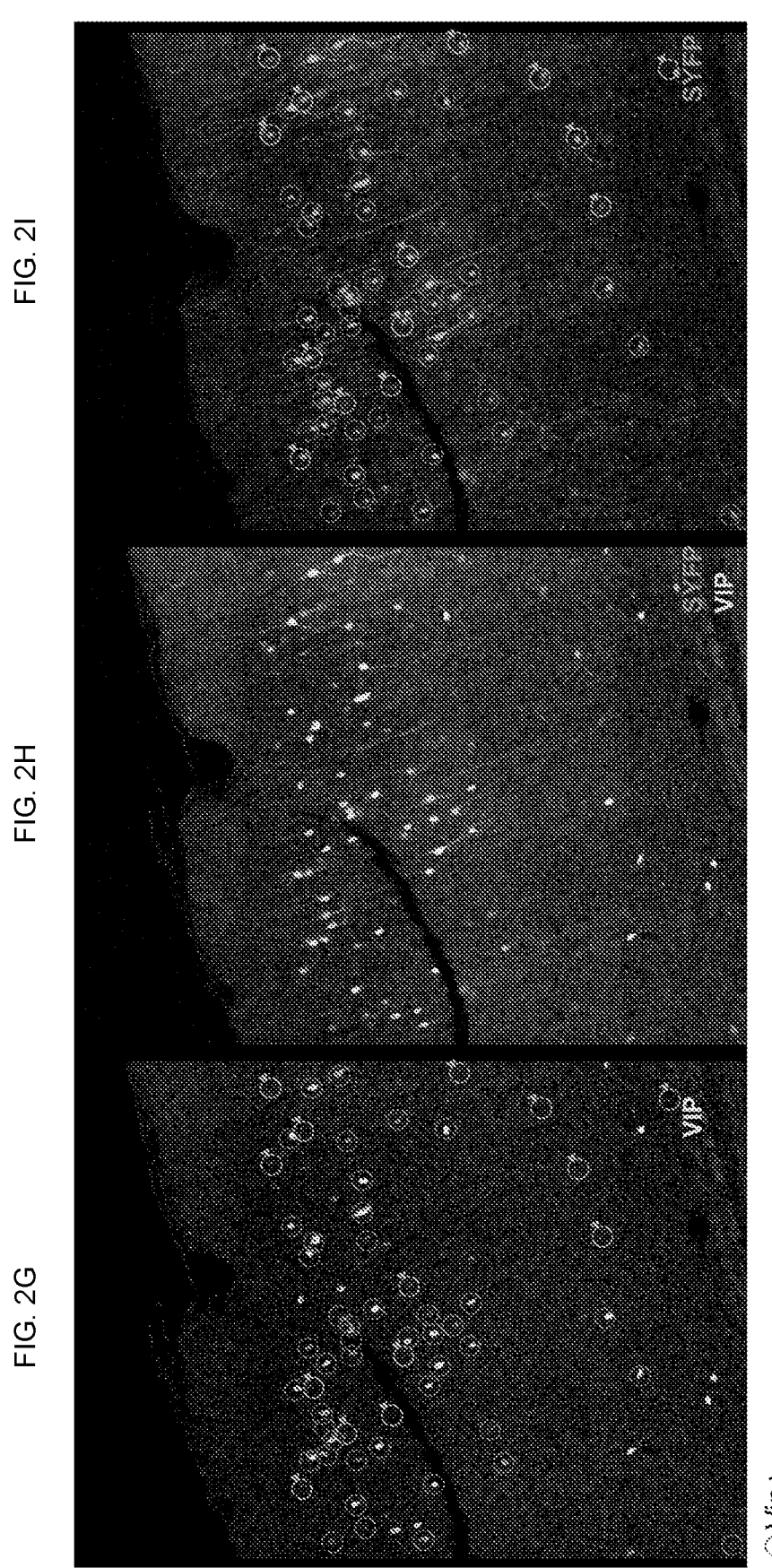
Figure 2J:
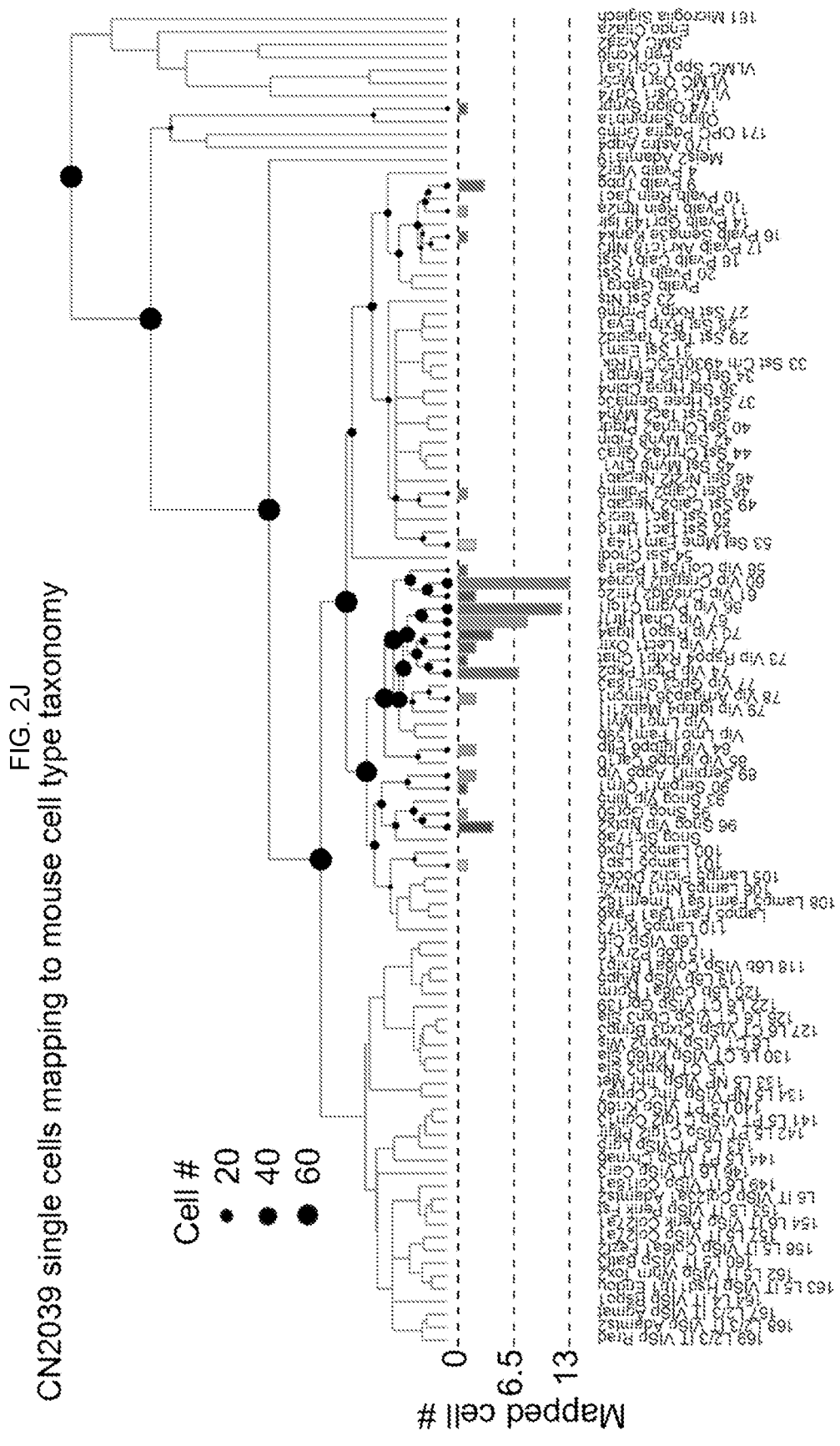
Figure 3A:
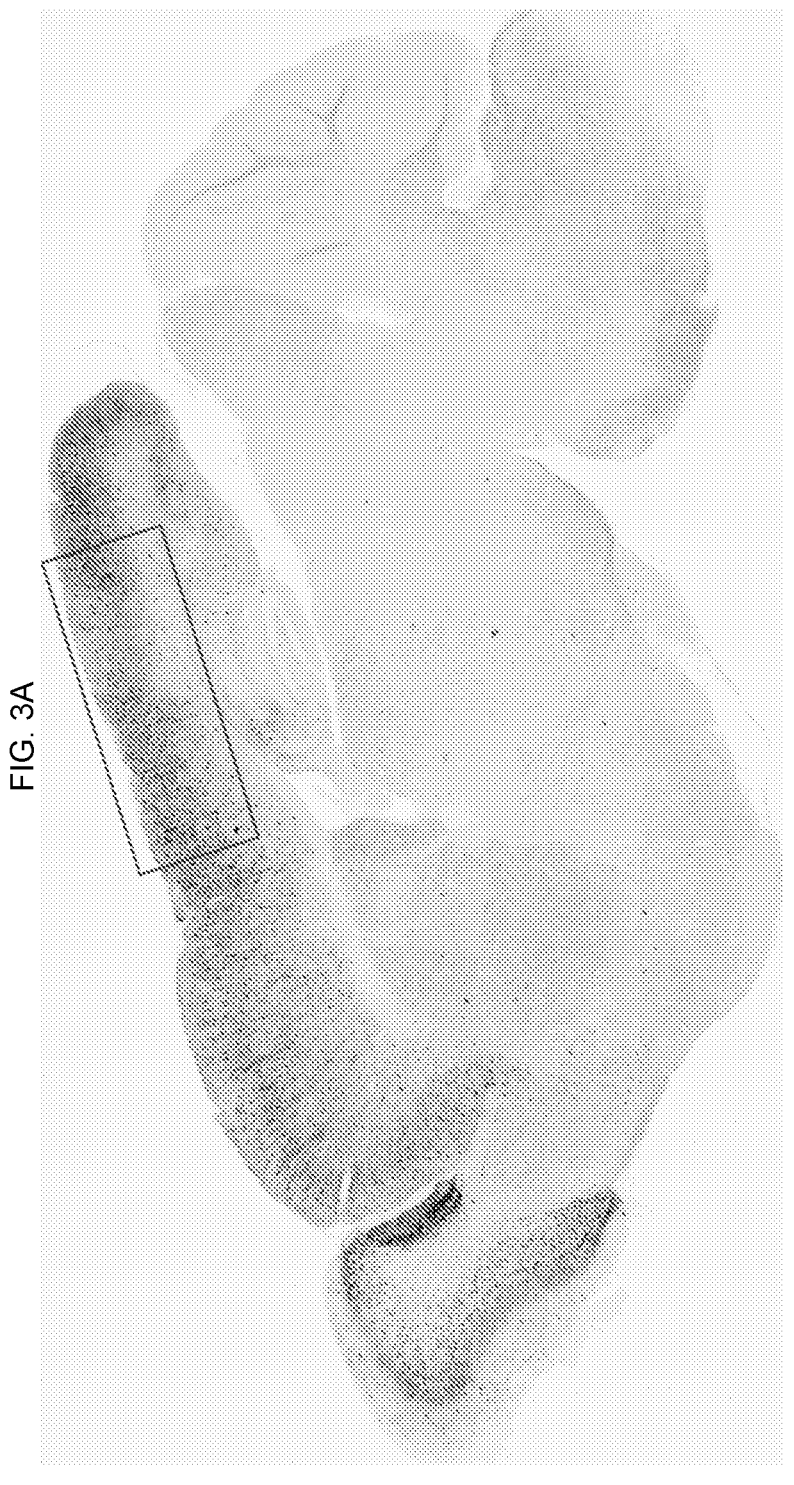
FIGS. 3A-3F. Vector: CN2040, Animal: 554252, and Enhancer: eHGT_354m. Native SYFP2 fluorescence mon-tage of a sagittal section of a whole mouse brain (3A), caudal cortex (3B), and visual cortex (3C) showing selective expression of SYFP2 in cells with bipolar neuronal mor-phology. Virus was administered in neonatal pup after intracerebroventricular (ICV) injection of CN2040 virus packaged with the PHP.eB capsid. (3D-3F) Region: VISp. Mouse visual cortex (VISp) transduced by CN2040 virus packaged with PHP.eB capsid and delivered in neonatal pups via ICV injection. Vip mFISH (3D), SYFP fluores-cence and VIP mFISH (3E), and SYFP fluorescence only (3F) are shown. Images are montages. Quantification of SYFP+ cells that do (red circles) or do not (blue circles with triangle) overlap with Vip mFISH are shown with 60 of 73 being Vip+(82% Vip+).
Figure 3B:
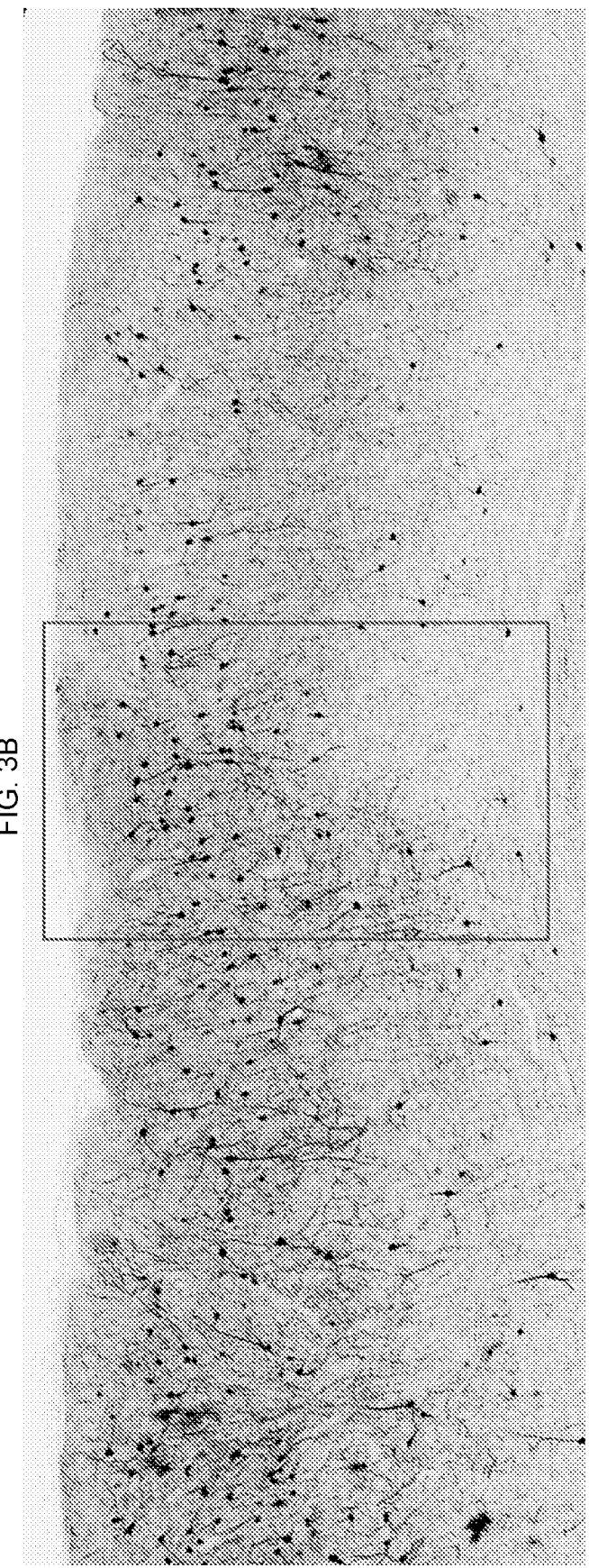
Figure 3C:
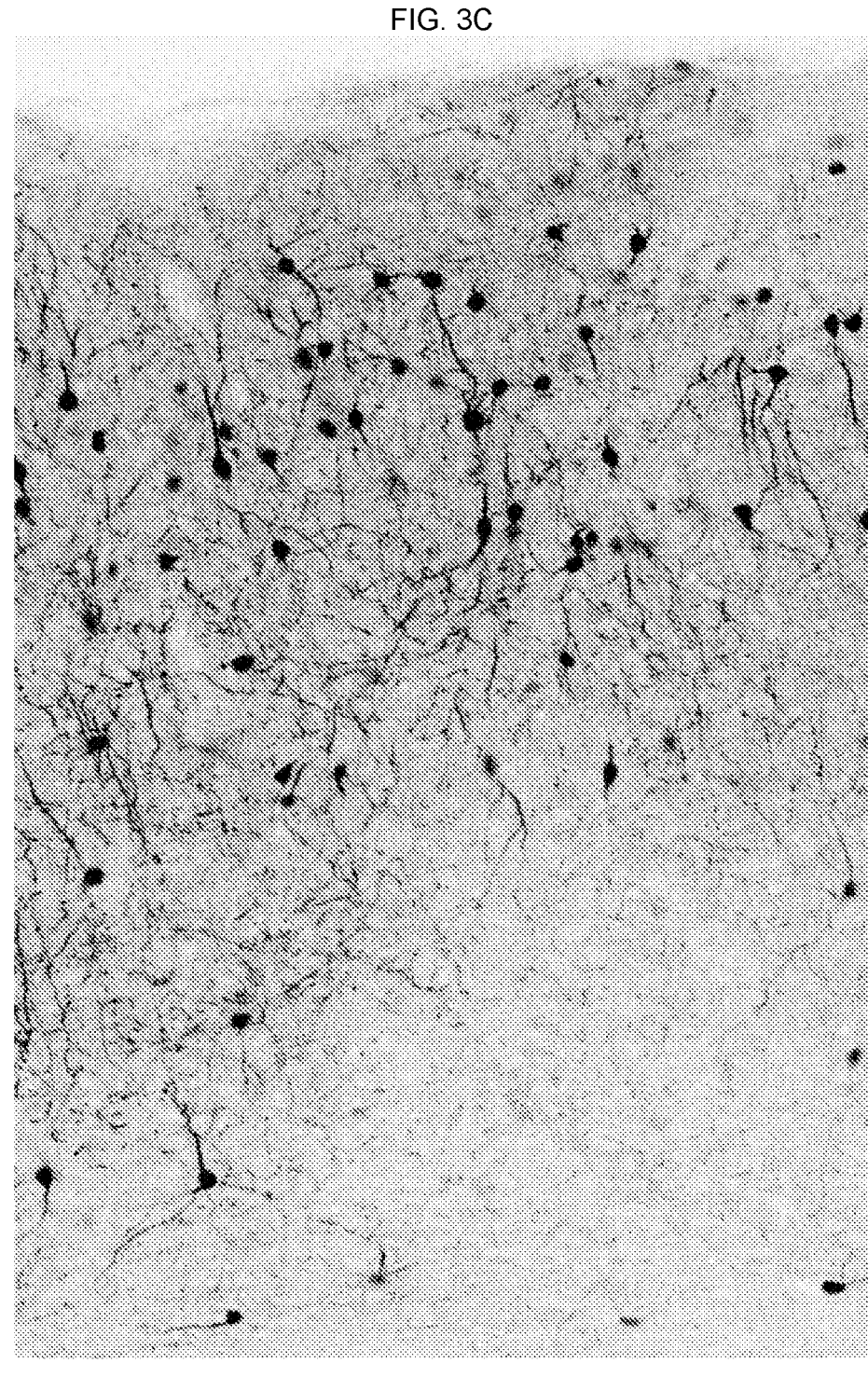
Figures 3D, 3E, 3F:
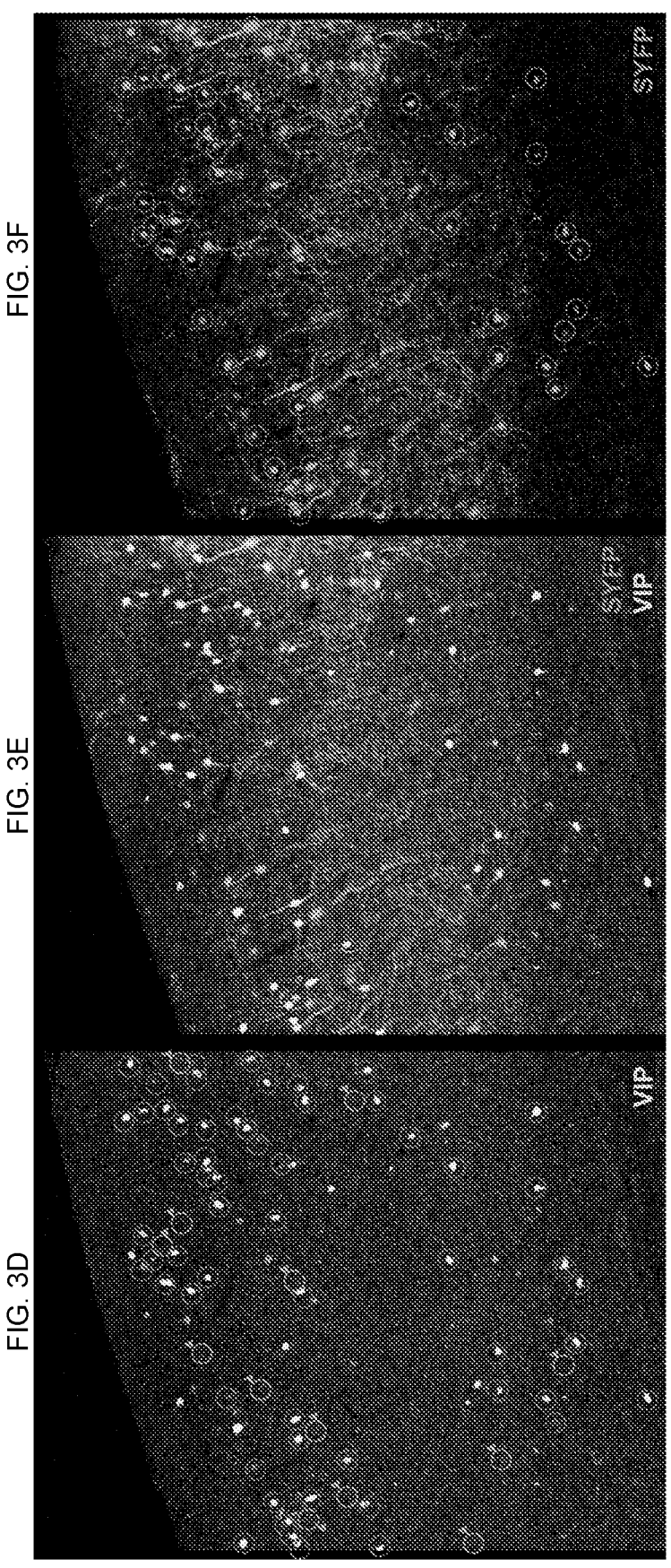
Figure 4A:
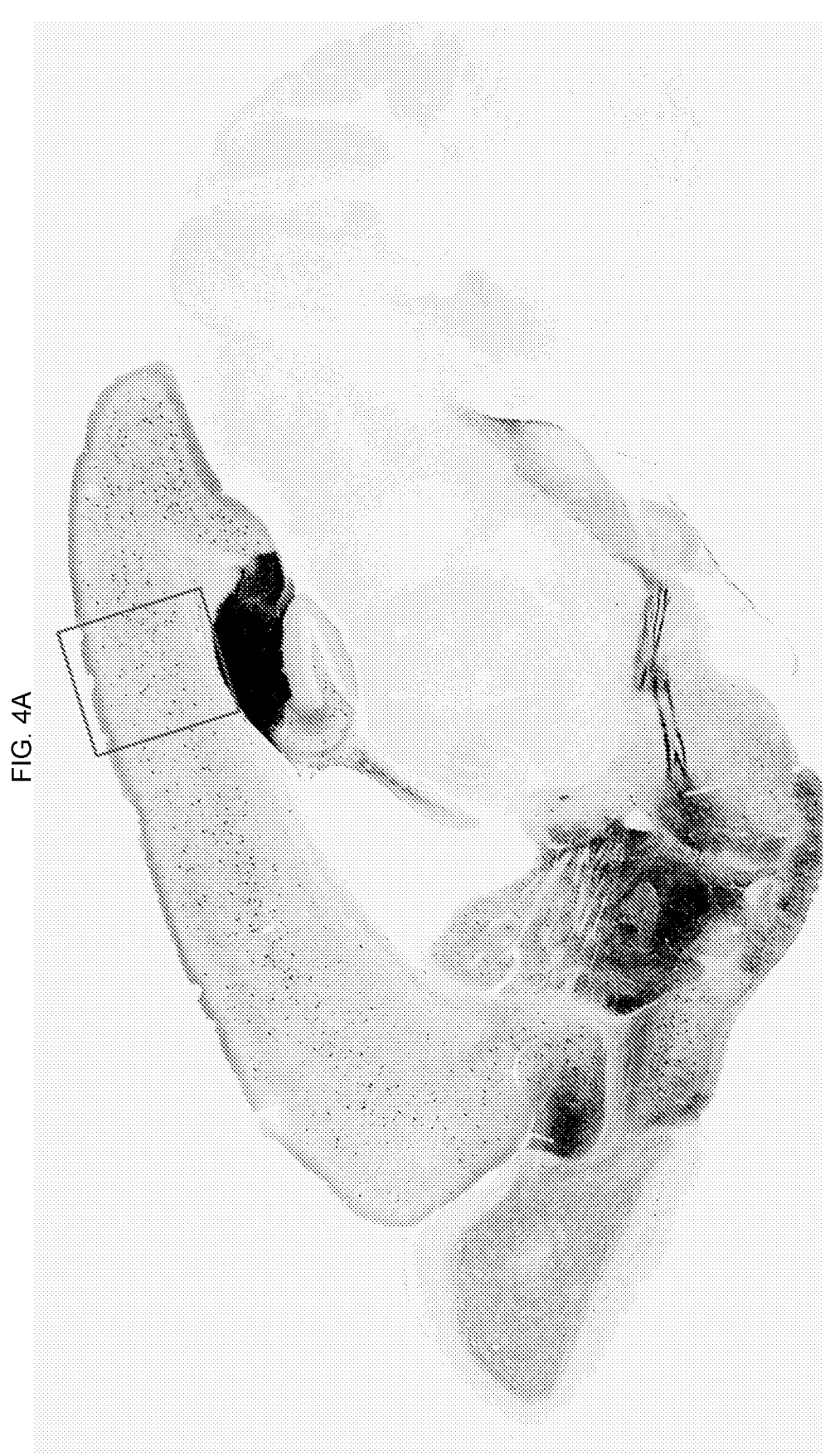
FIGS. 4A-4E. Vector: CN2569, Animal: 554257, and Enhancer: 3xCore3_eHGT_226h. Native SYFP2 fluores-cence montage of a sagittal section of a whole mouse brain (4A), and visual cortex (4B) showing selective expression of SYFP2 in scattered cells with non-pyramidal neuronal mor-phology. Virus was administered to the neonatal pup via intracerebroventricular (ICV) injection of CN2569 virus packaged with the PHP.eB capsid. (4C-4E) Region: VISp. Mouse visual cortex (VISp) transduced by CN2569 virus packaged with PHP.eB capsid and delivered in neonatal pups via ICV injection. Sst (cyan) and Pvalb (yellow) mFISH (4C), SYFP fluorescence only (green 4D), and SYFP fluorescence with Sst and Pvalb mFISH (4E) are shown. Images are montages. Quantification of SYFP+ cells that do (cyan circles) or do not (red circles with stars) overlap with Sst mFISH are shown with 43 of 47 SYFP+ cells being Sst+(91% Sst+).
Figure 4B:
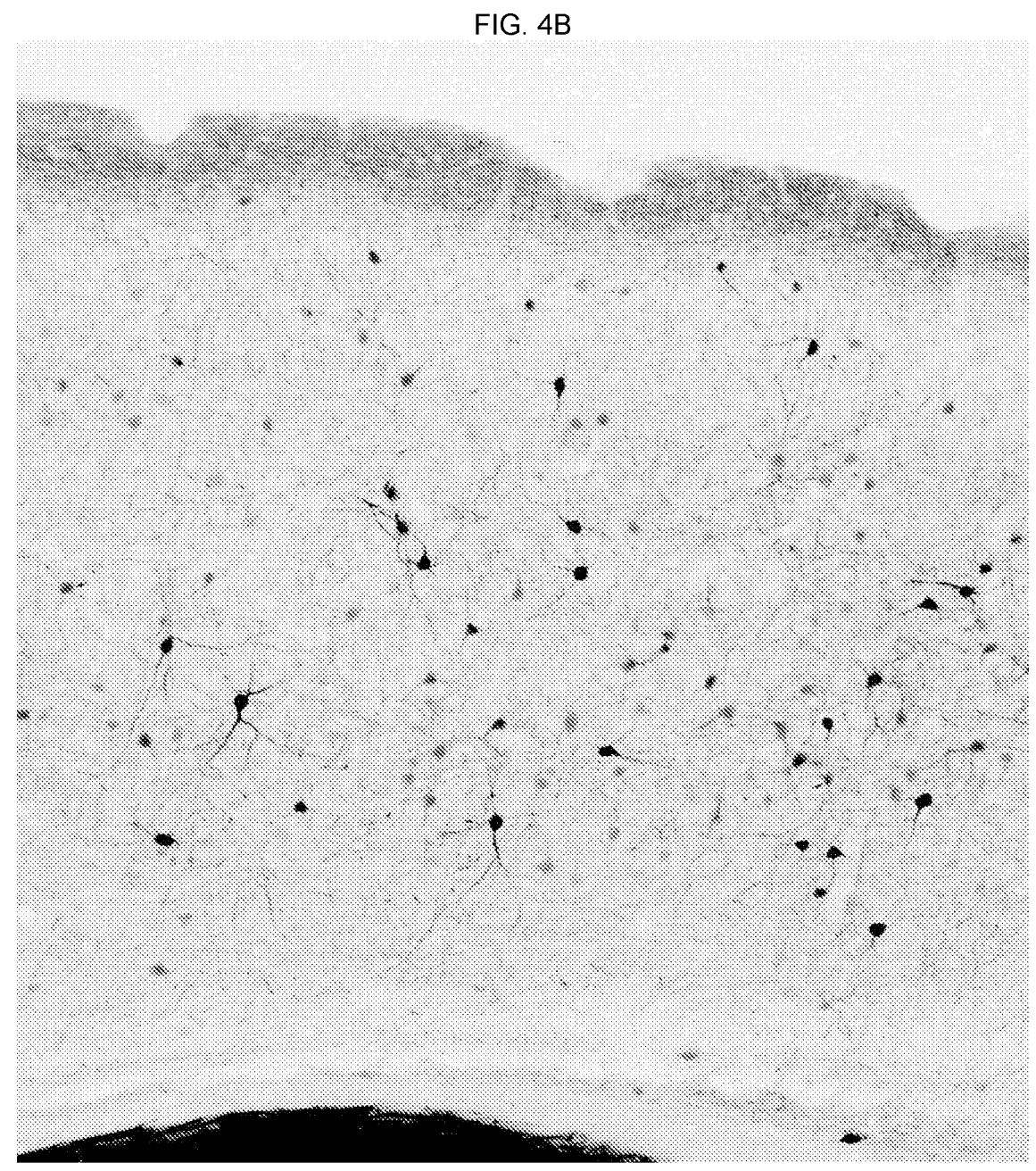
Figures 4C, 4D, 4E:
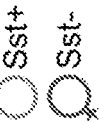
Figure 5A:
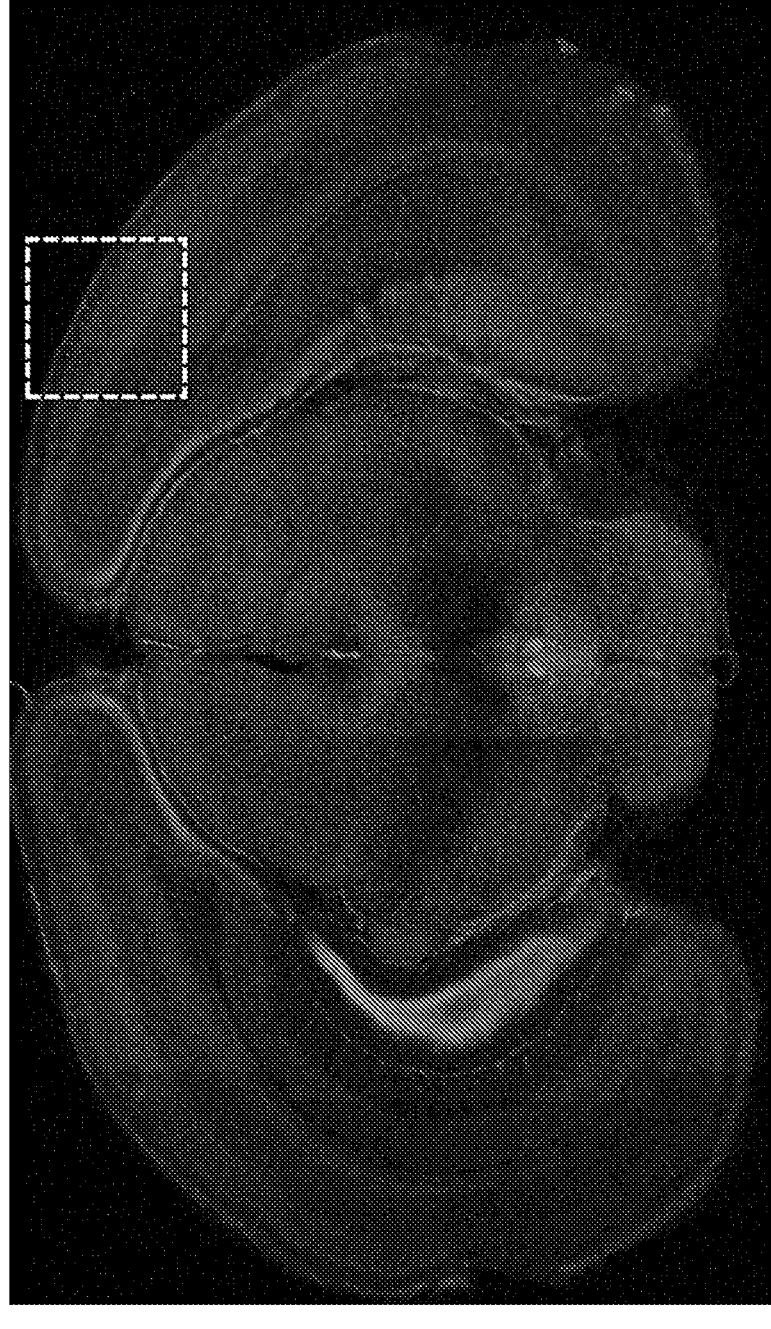
Figure 5B:
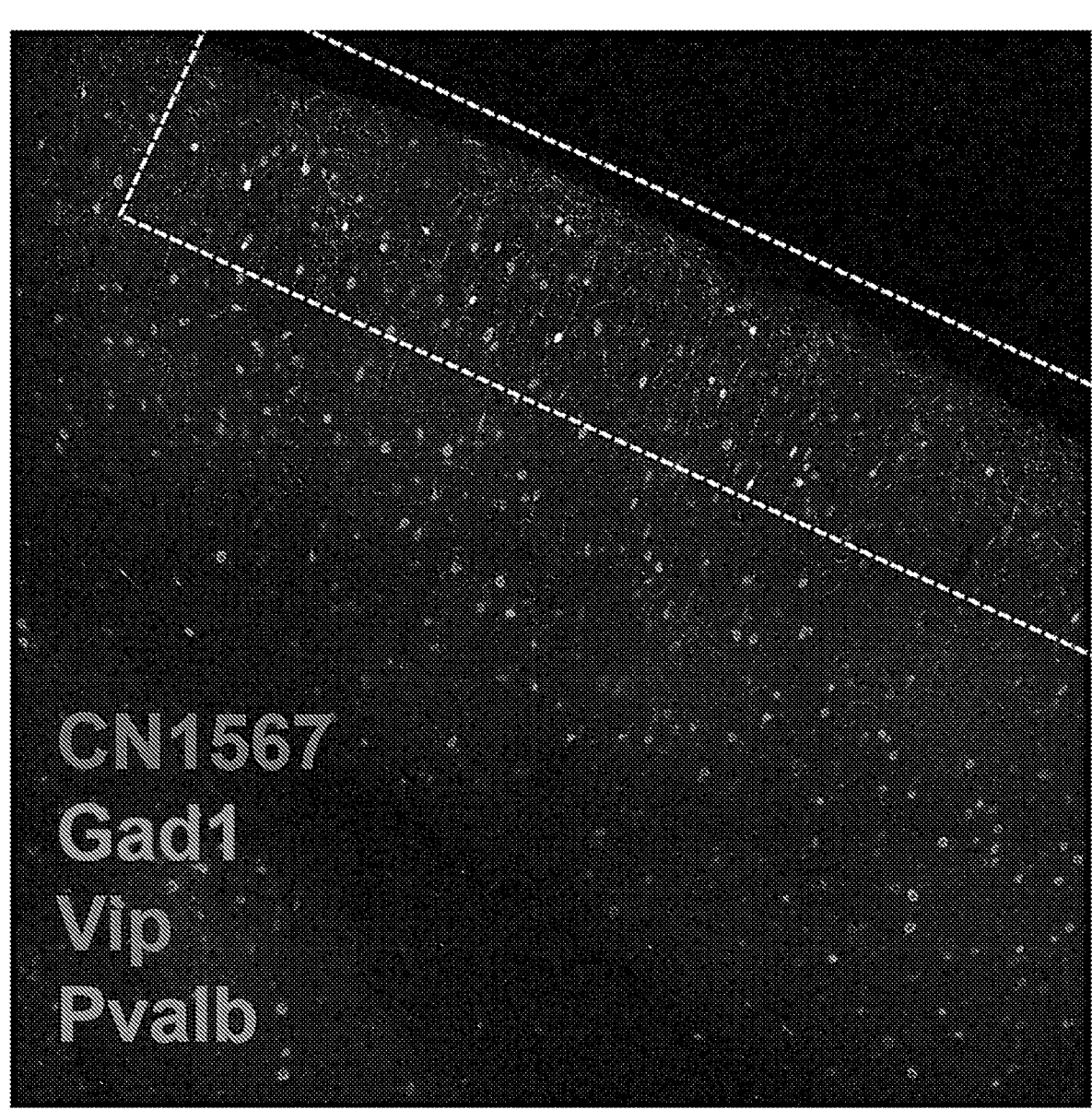
Figure 5F:
Figure 5G:
Figures 5H, 5I, 5J:
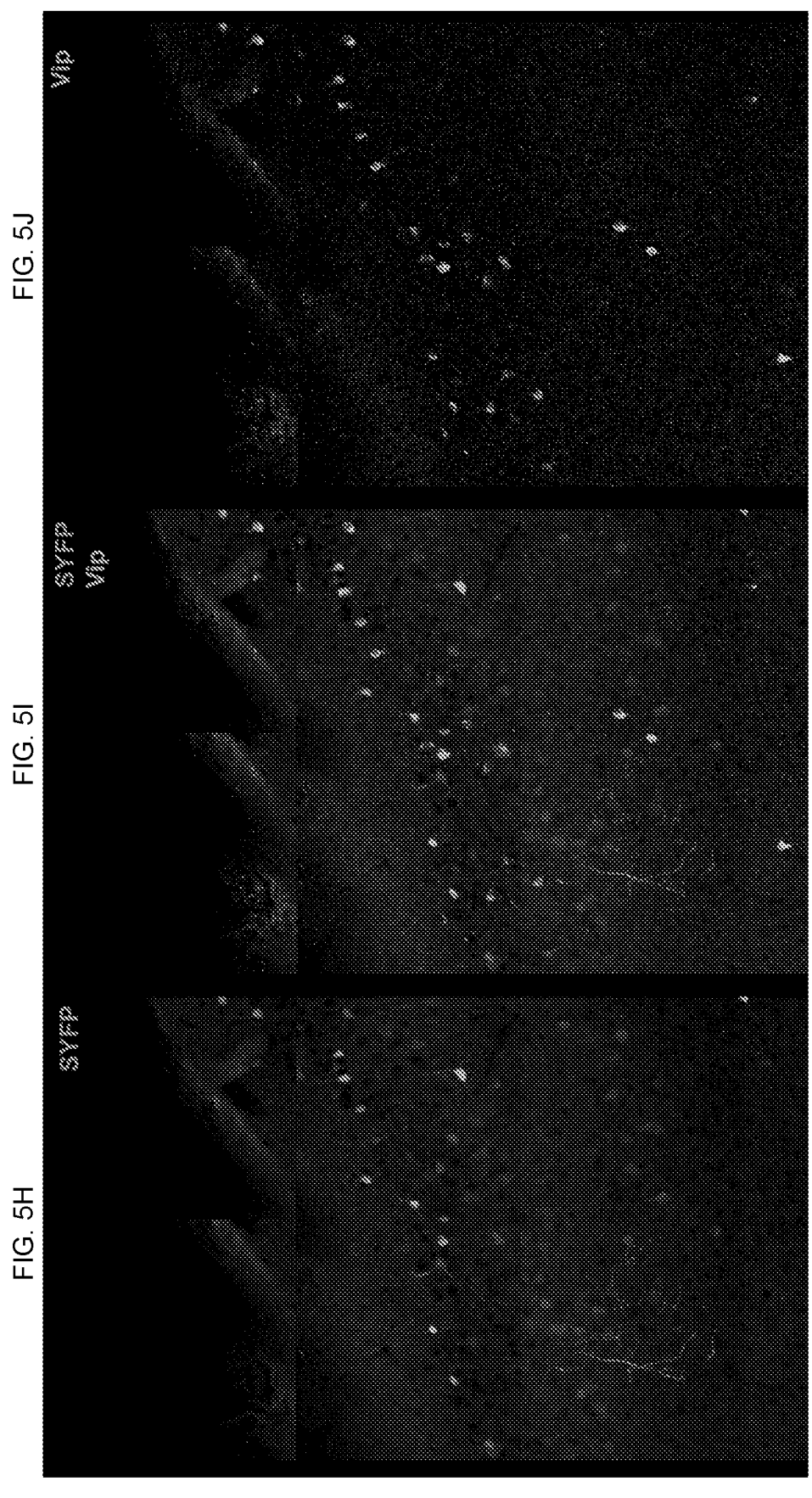
Figure 6A:
Figure 6B:
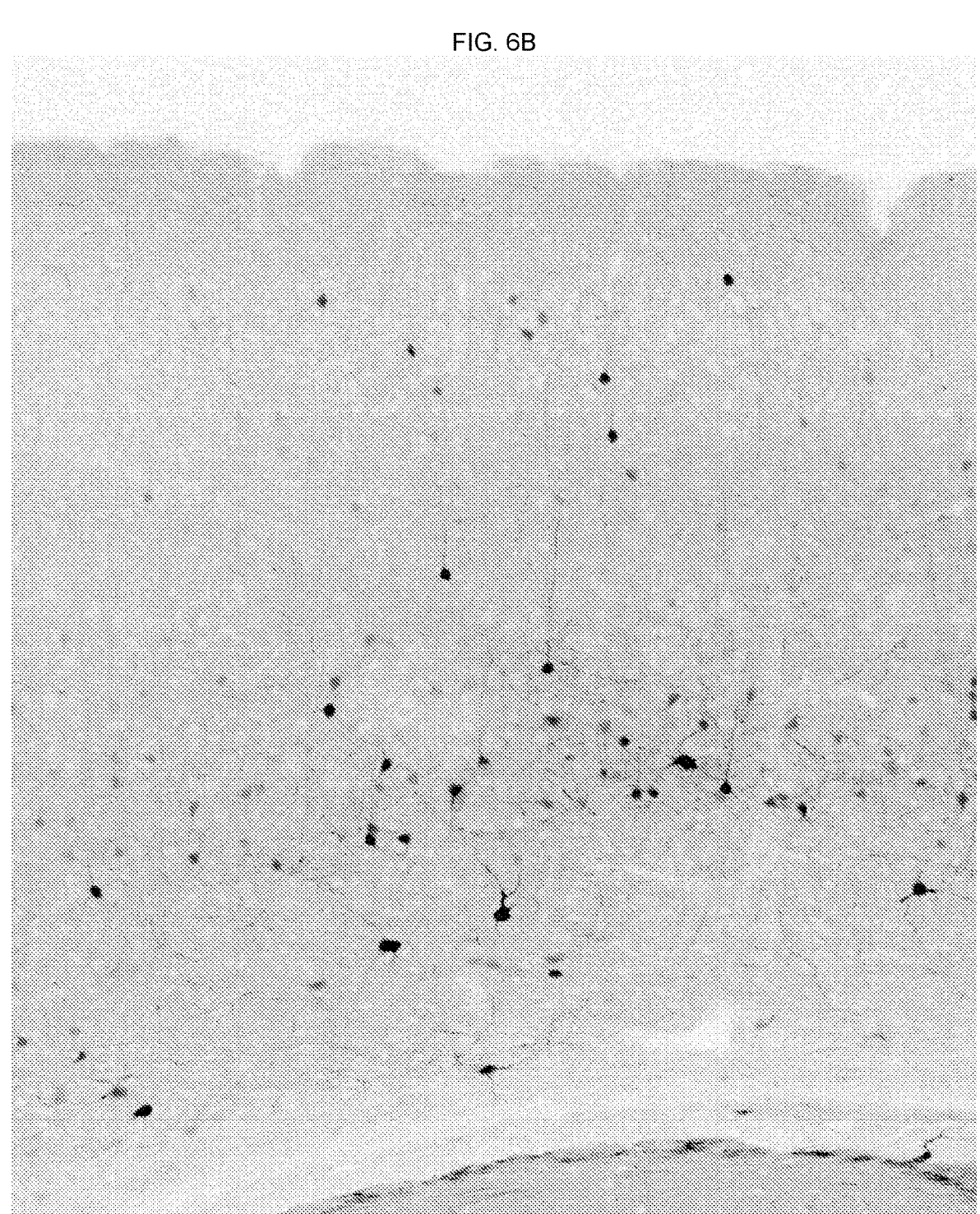
Figures 6C, 6D, 6E:
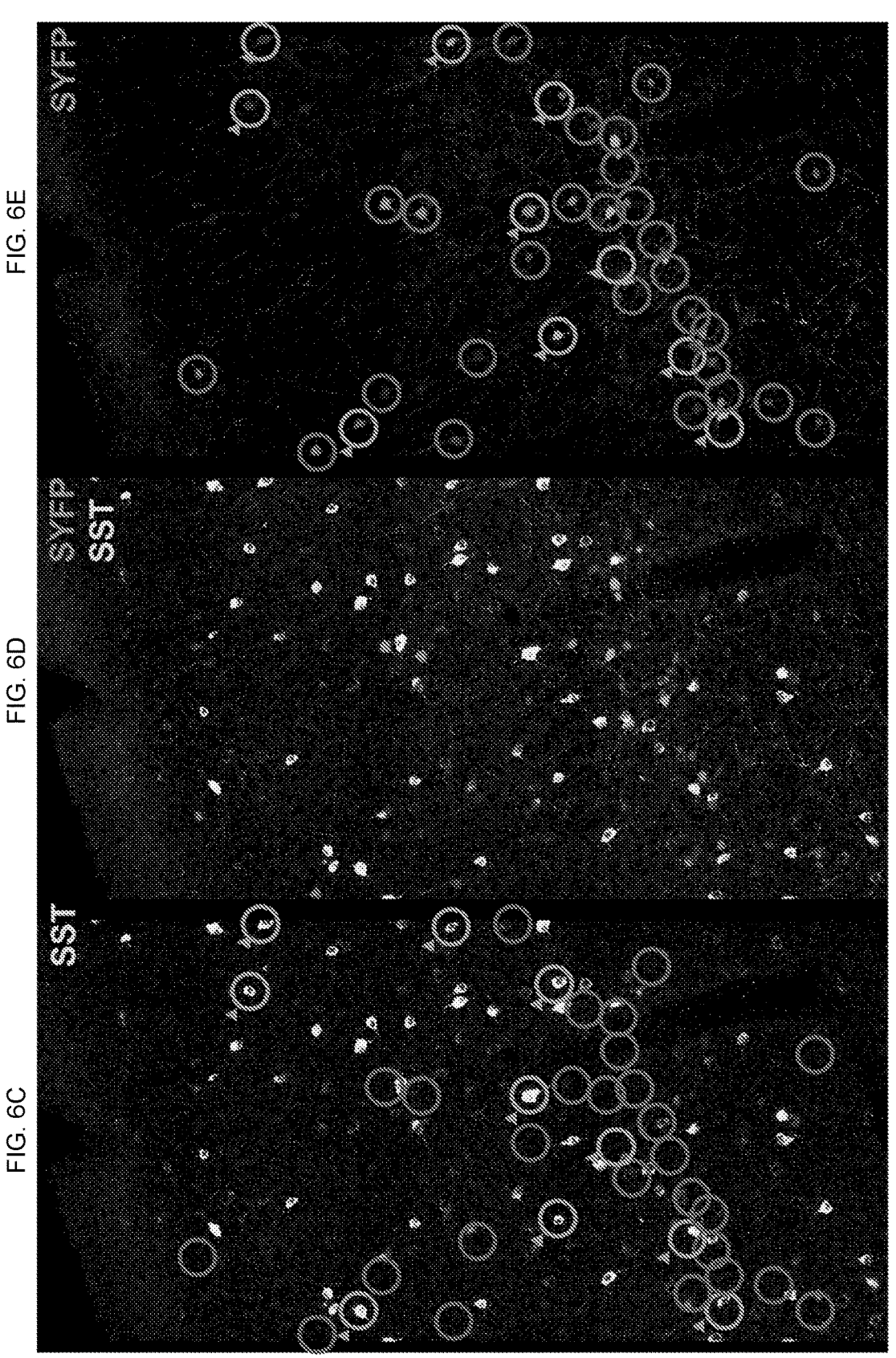
Figure 8A:
Figure 8B:
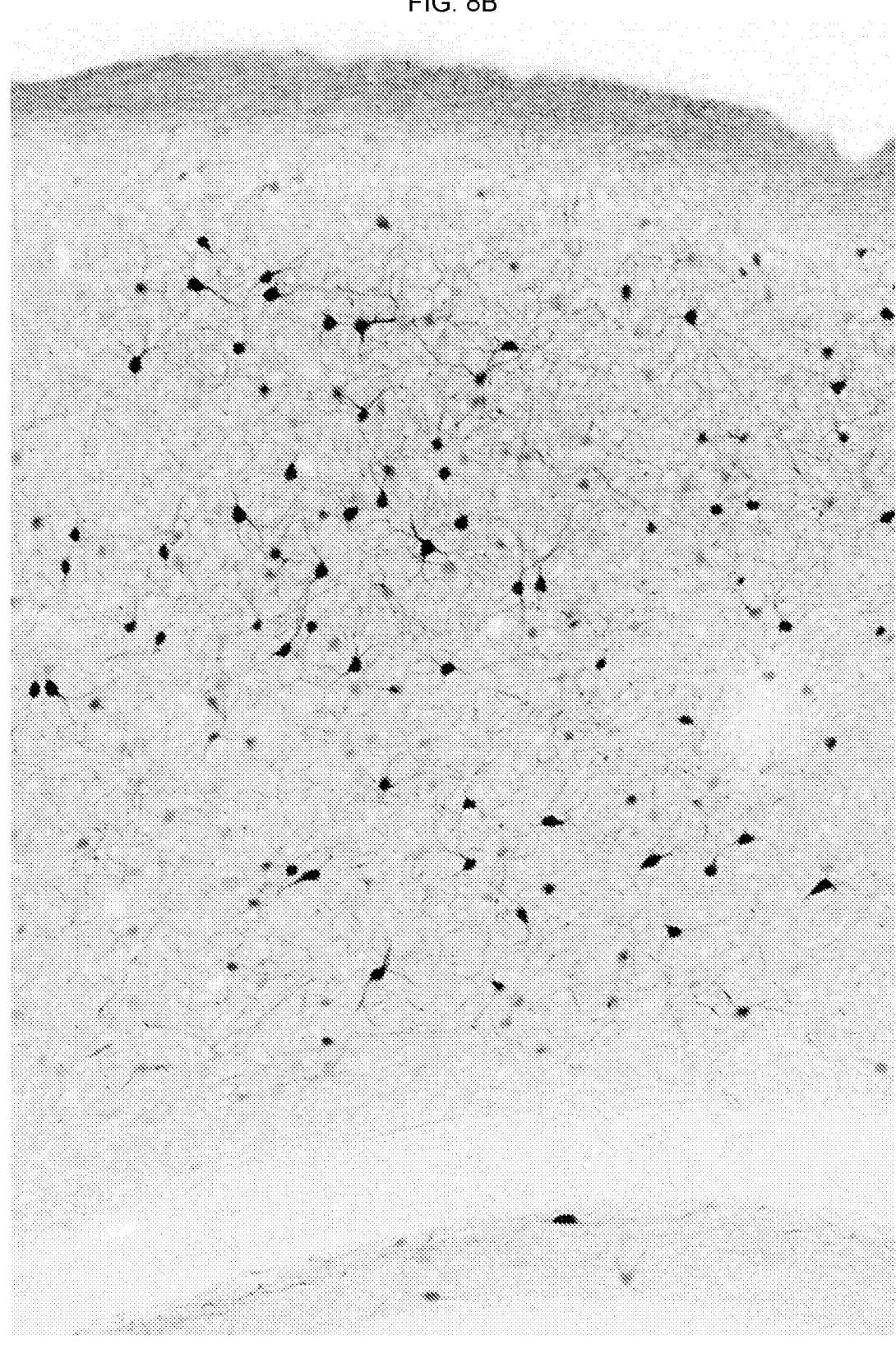
Figures 8F, 8G, 8H:
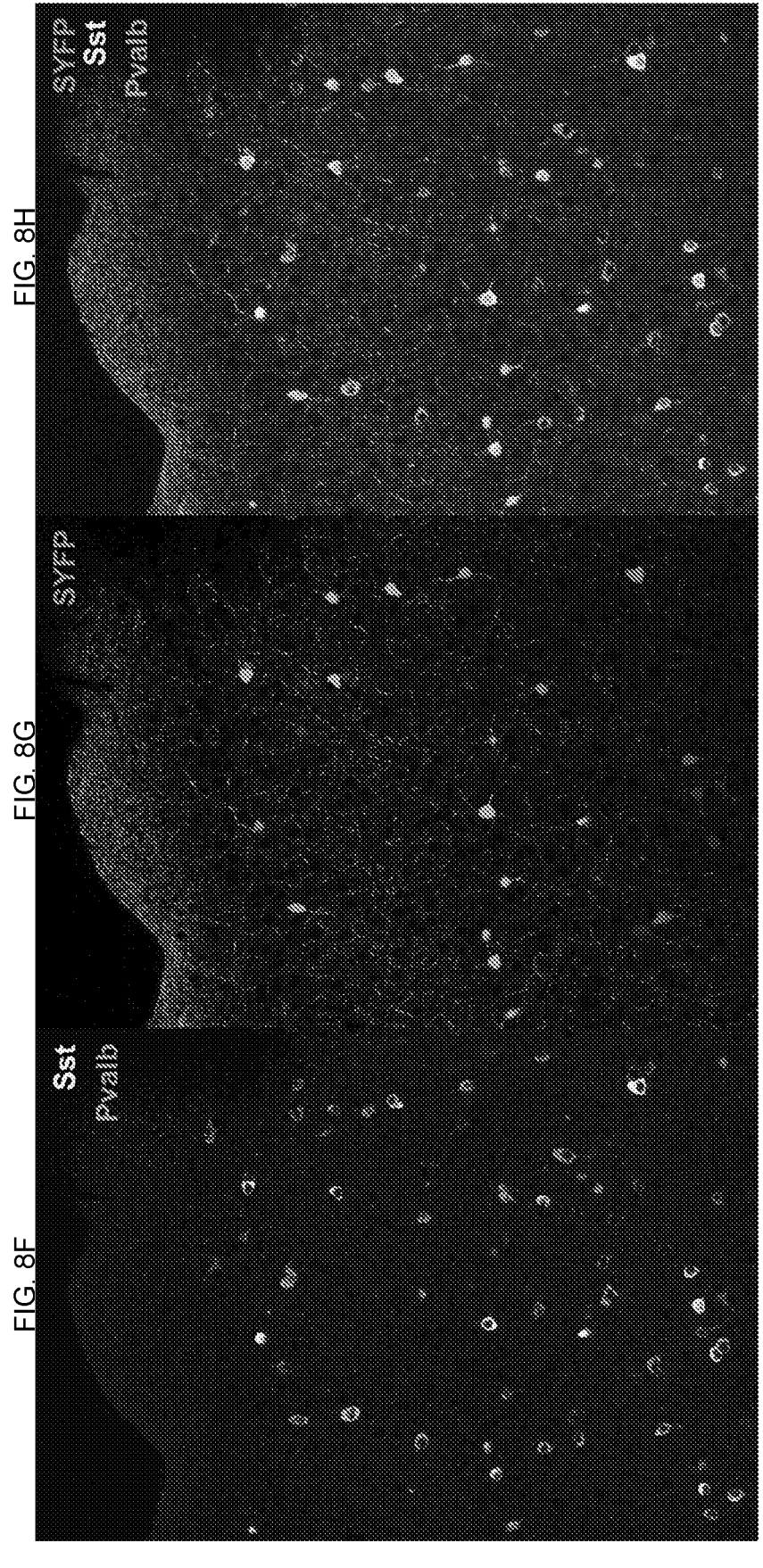
Figure 9A:
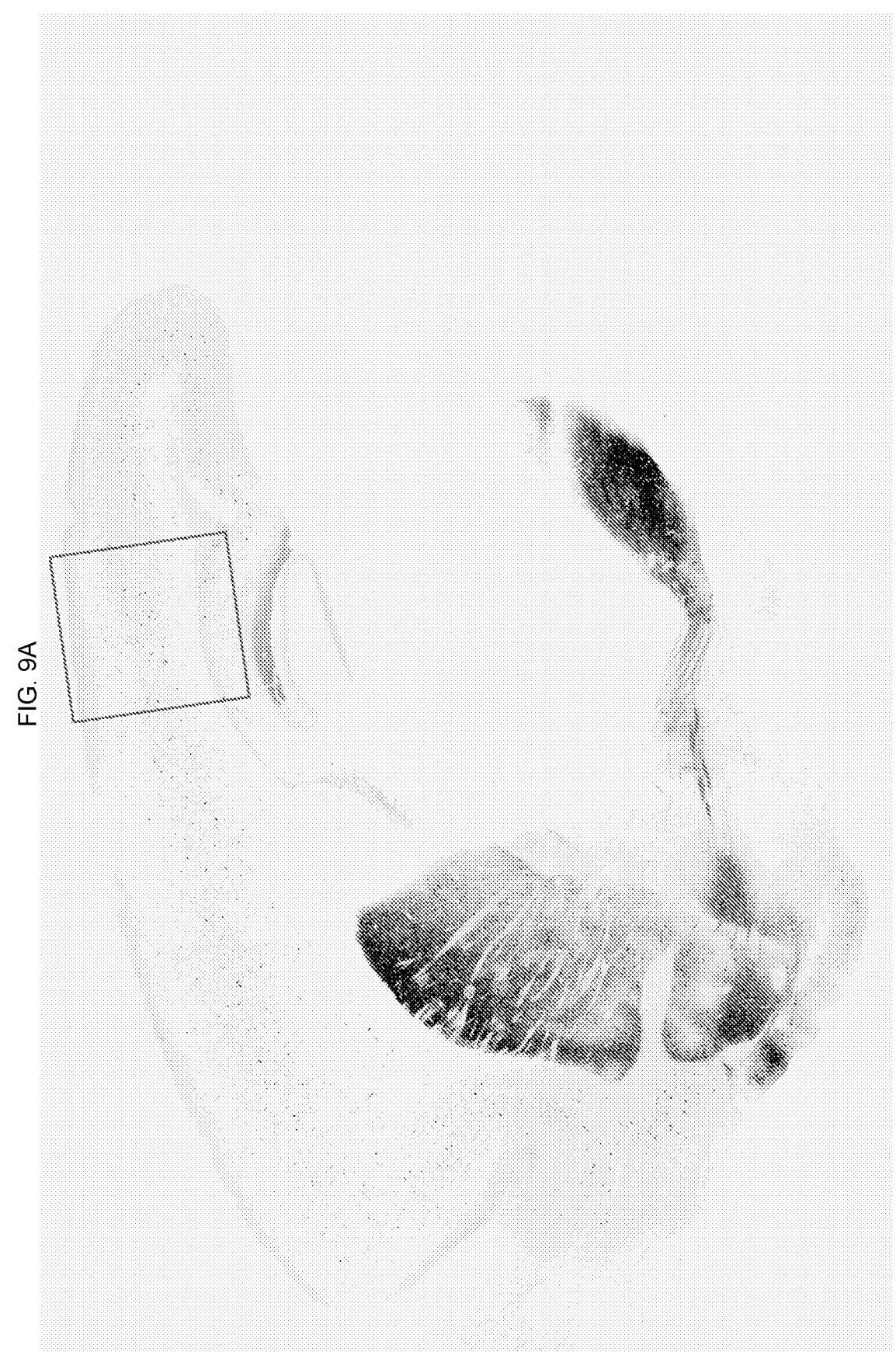
Figure 9B:
Figures 9C, 9D, 9E:
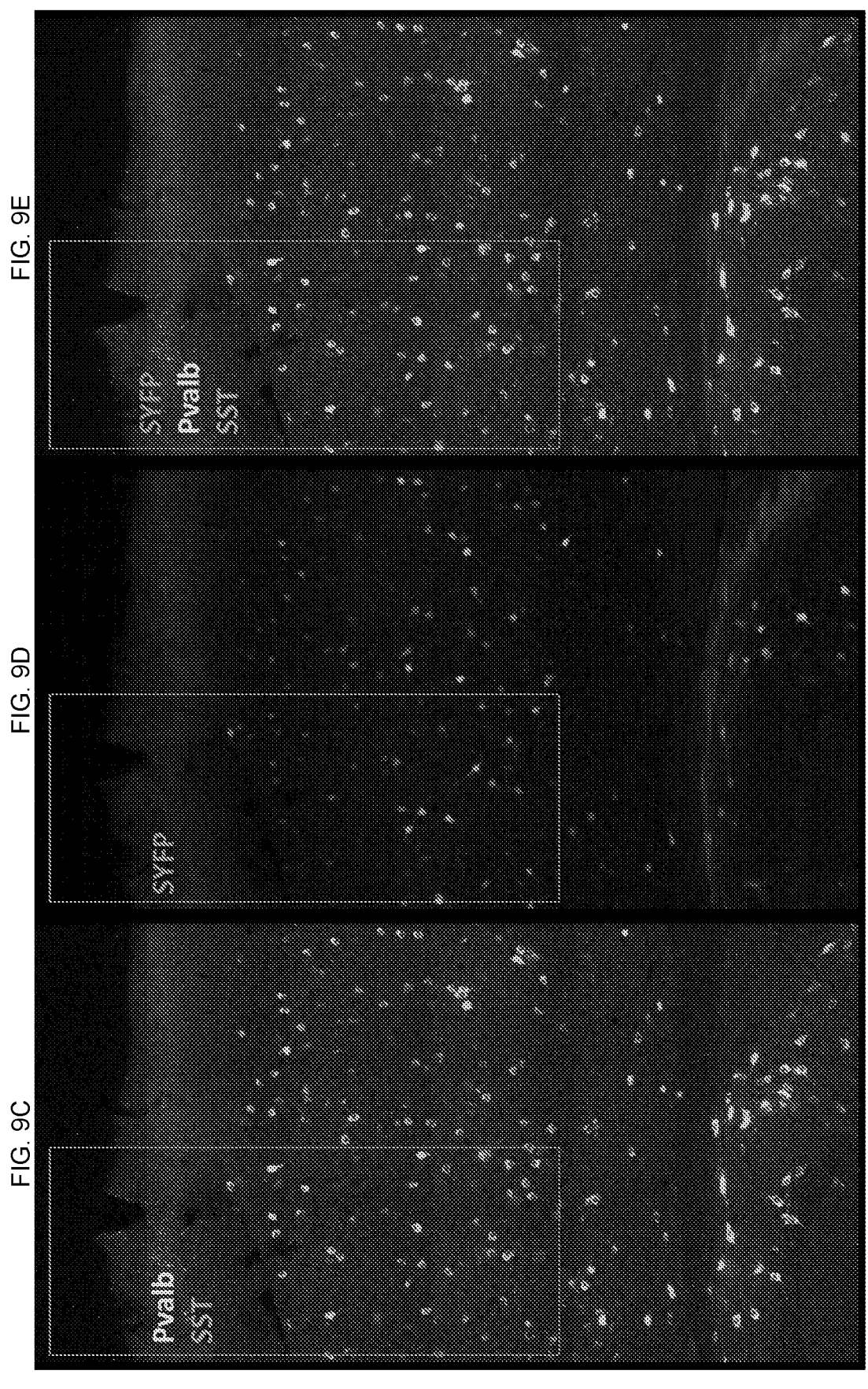
Figures 9I, 9J, 9K:
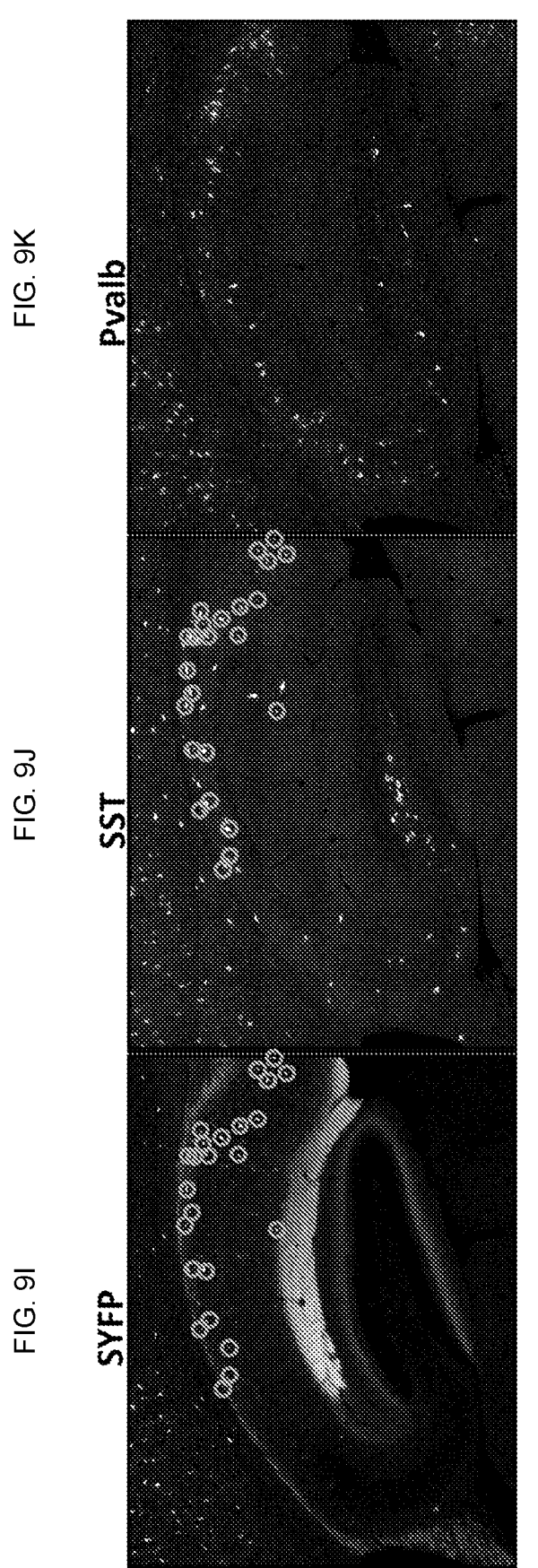
Figure 10A:
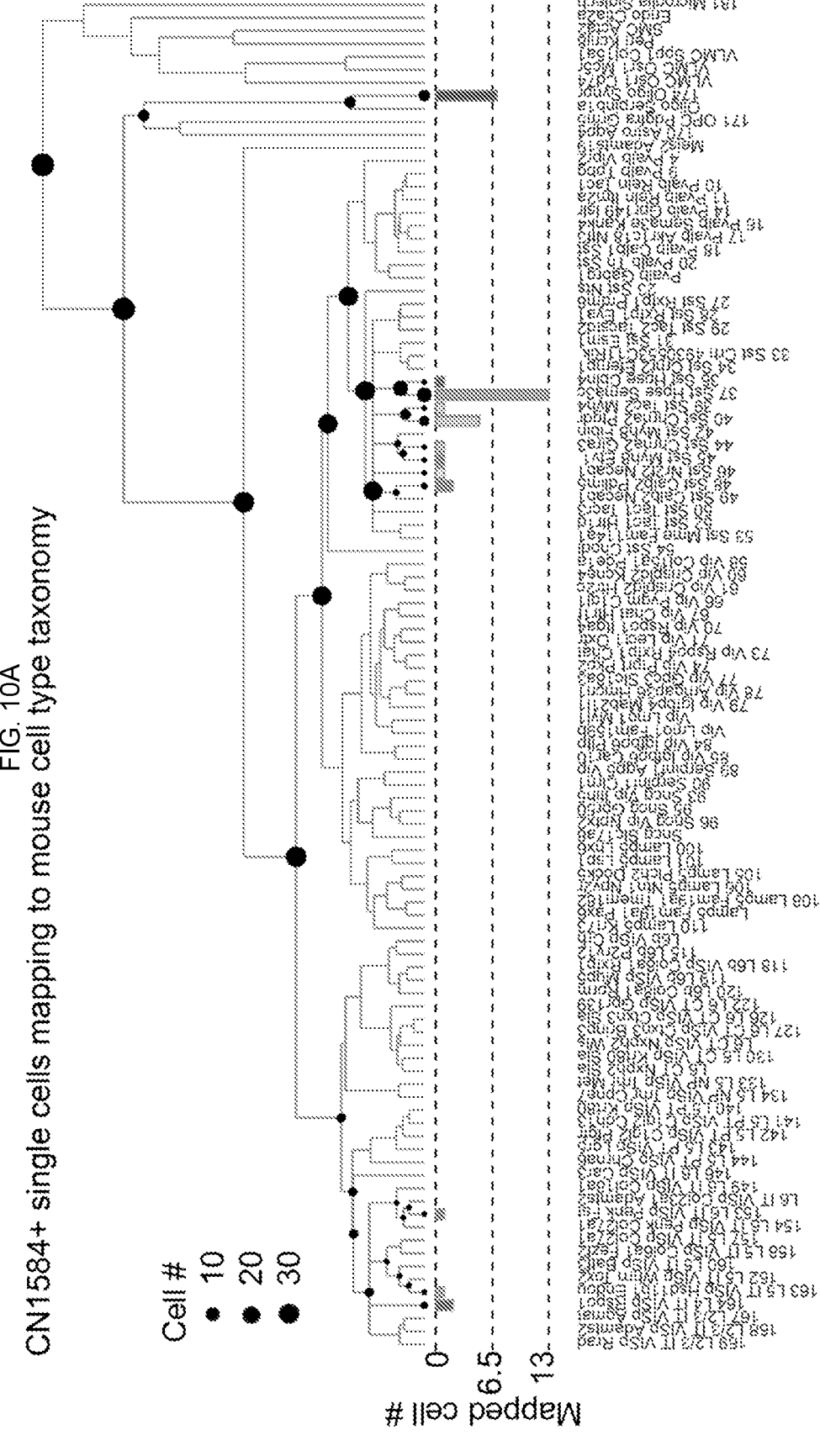
Figure 10D:
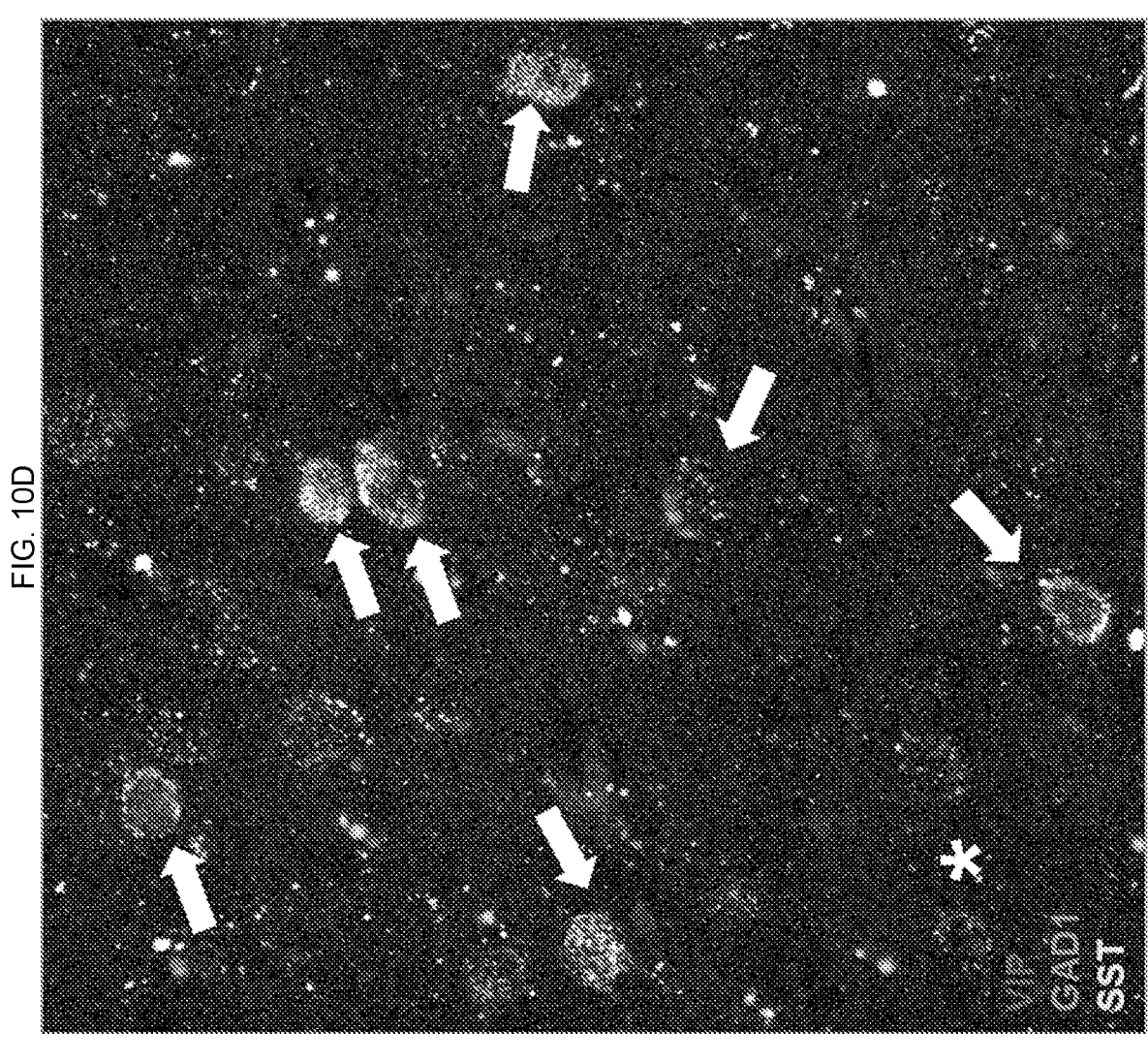
Figure 11A:
FIGS. 11A-11F. Vector: CN2367, Animal: 200826-09, and Enhancer: eHGT_528h. Native SYFP2 fluorescence montage of a sagittal section of a whole mouse brain (11A) and visual cortex (11B) showing very sparse selective expression of SYFP2. Virus was administered via retro-orbital injection of CN2367 virus packaged with the PHP.eB capsid. (11C-11F) Region: VISp. Mouse visual cortex (VISp) transduced by CN2367 virus packaged with PHP.eB capsid and delivered via retro-orbital injection. Sst and Pvalb mFISH only (11C) SYFP fluorescence only (11D), and SYFP fluorescence with Sst and Pvalb mFISH (11E) are shown. Images are montages. Quantification of SYFP+ cells is shown to the lower right. All 11 SYFP positive cells were Sst+. (11F) Mapping of single cell transcriptomic profiles of SYPF2+ cells sorted from the VISp region of the mouse cortex after retro-orbital injection of CN2367 virus packaged with the PHP.eB capsid. Number of cells mapped to the final leaf are shown on the bar plot below the dendrogram. Transcriptomic cell types are shown on the bottom. This data shows eHGT_528h enhancer driven reporter expression occurs selectively in SST+ cells when VISp is evaluated. The text along the bottom is typed in the brief description of the drawing of FIG. 2J.
Figure 11B:
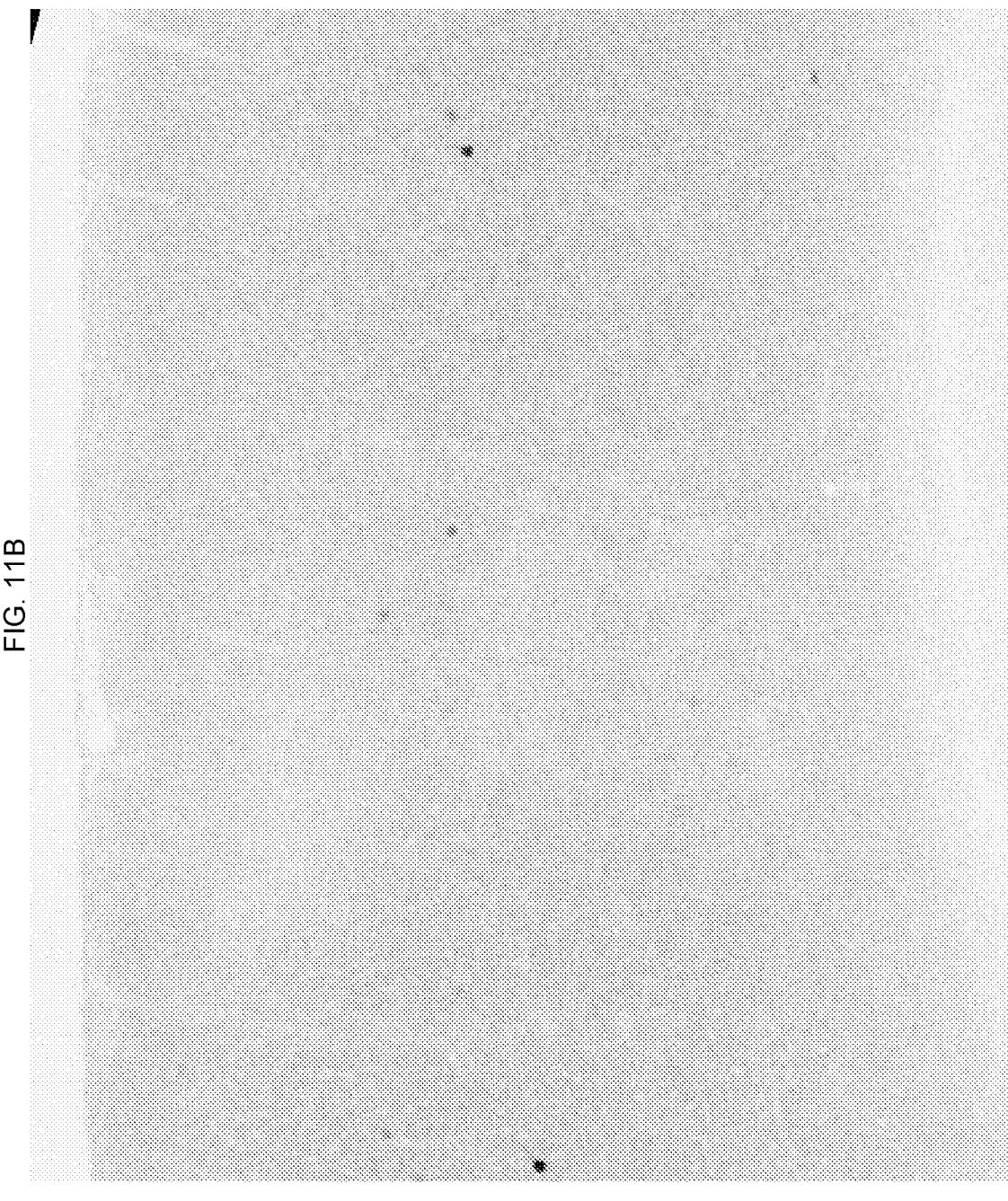
Figures 11C, 11D, 11E:
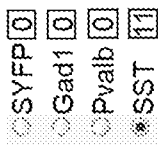
Figure 11F:
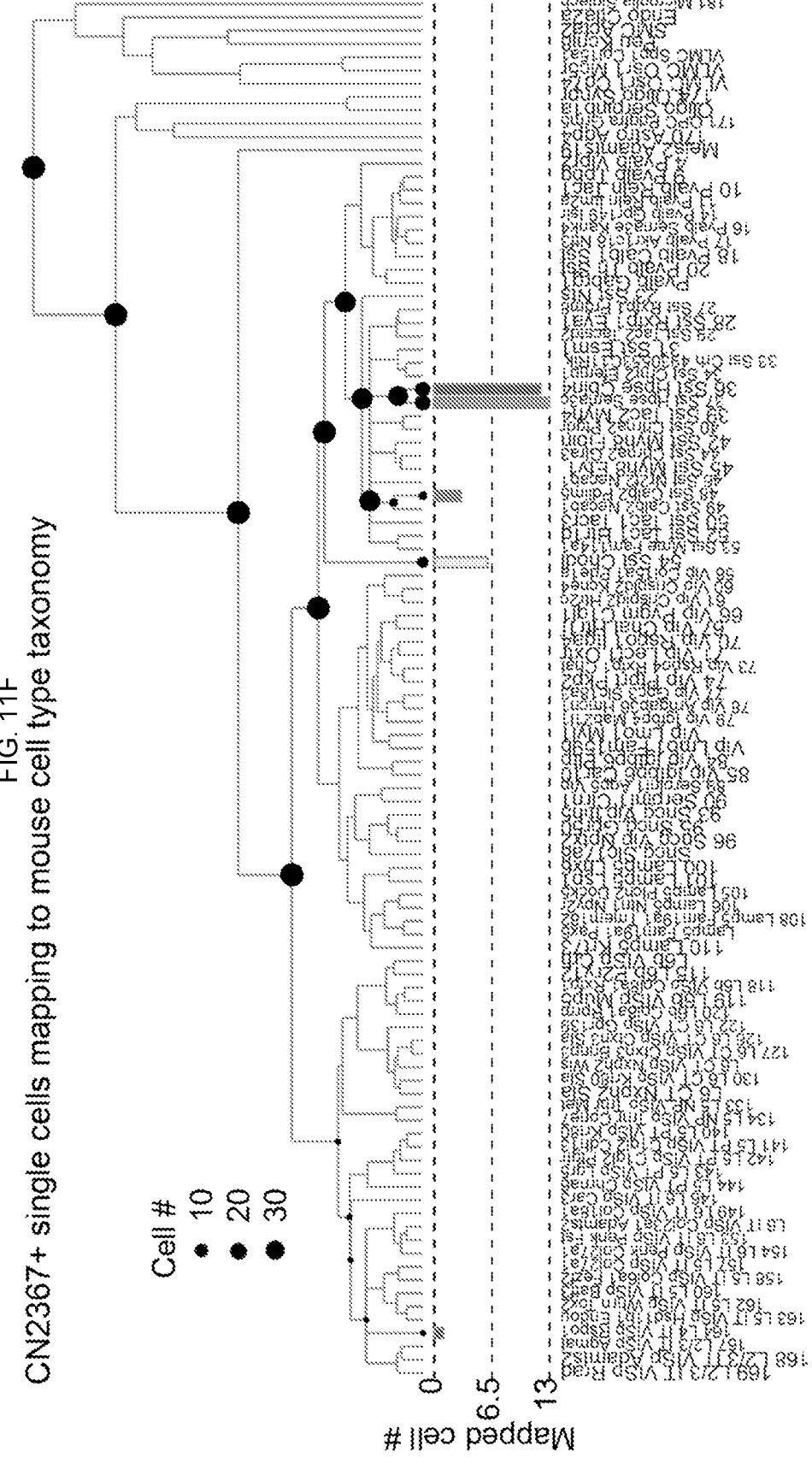
Figure 12A:
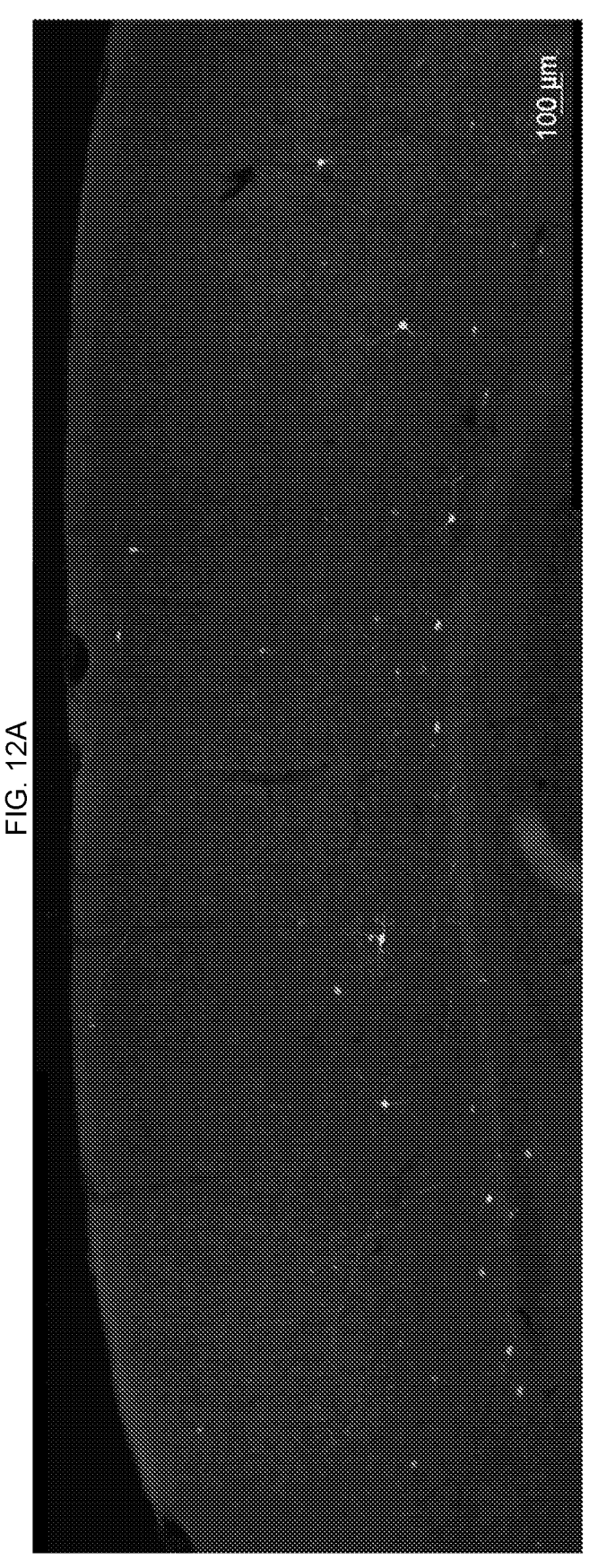
FIGS. 12A-12D. Vector: CN2689, Animal: 556452, Enhancer: eHGT_682h, and Region: neocortex. Native SYFP2 fluorescence image of a sagittal section of mouse brain (12A) showing very sparse expression of SYFP2 in the neocortex. (12B) Anti-GFP, (12C) anti-Nos1, and (12D) overlay image showing high specificity of labeling in the target Nos1+ cell population. Nos1 is a marker gene for the Sst-Chodl cell type. Virus was administered via retro-orbital injection of CN2689 virus packaged with the PHP.eB capsid.
Figure 12C:
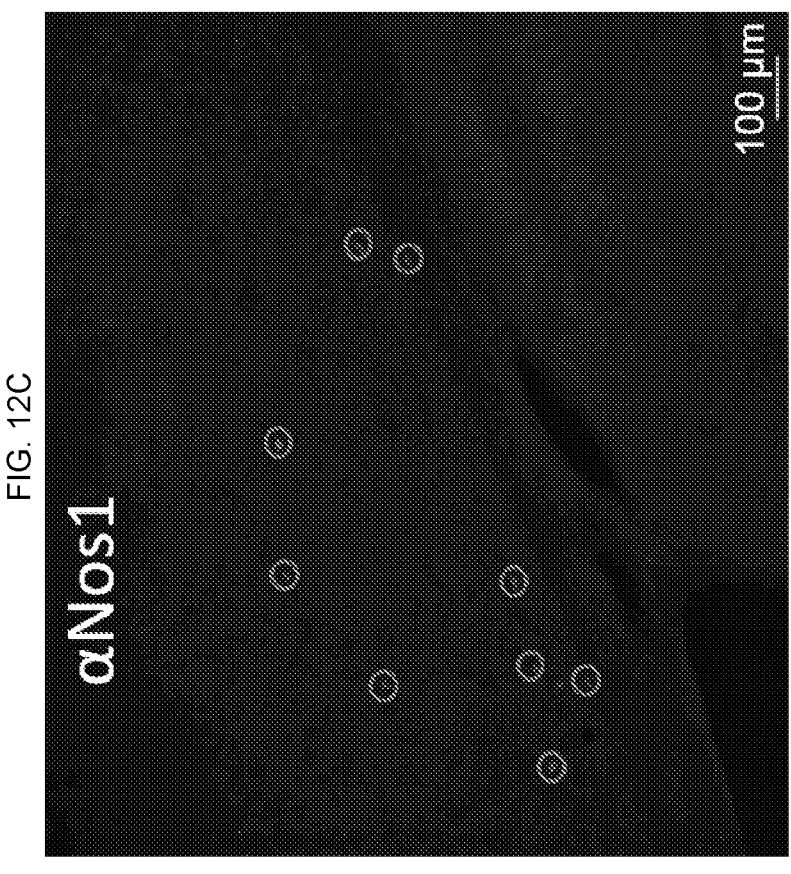
Figure 12B:
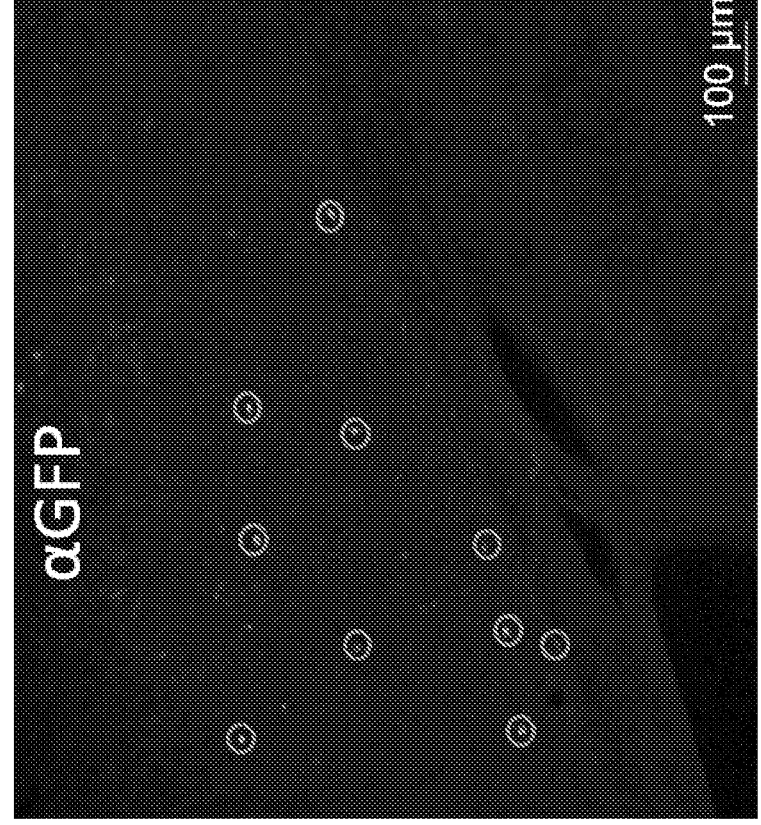
Figure 12D:
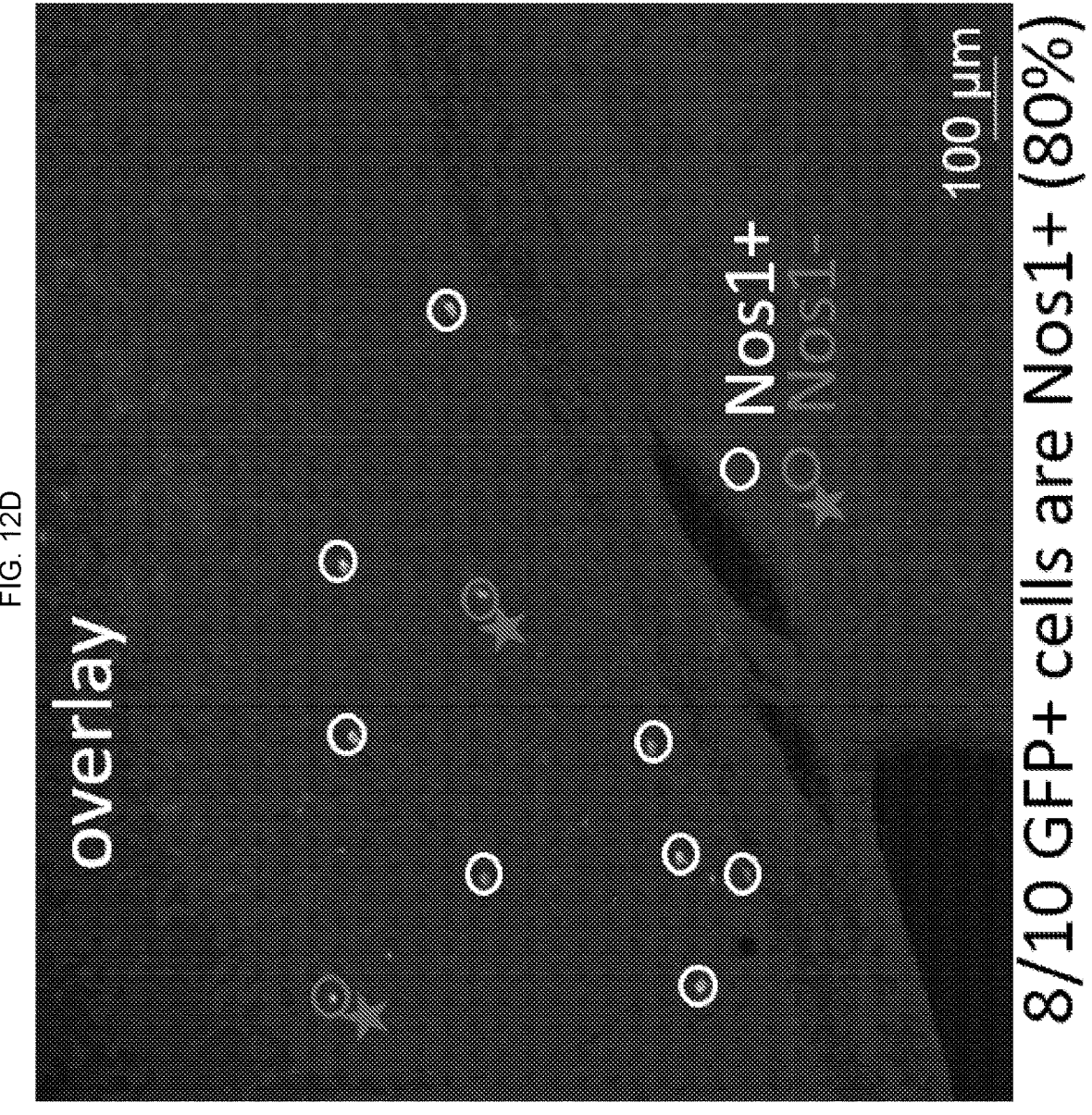

To fully understand the biology of the brain, different cell types need to be distinguished and defined and, to further study them, artificial expression constructs that can selectively label and perturb them need to be identified. Tasic, Curr. Opin. Neurobiol. 50, 242-249 (2018); Zeng & Sanes, Nat. Rev. Neurosci. 18, 530-546 (2017). In mouse, recombinase driver lines have been used to great effect to label cell populations that share marker gene expression. Daigle et al., Cell 174, 465-480.e22 (2018); Taniguchi, et al., Neuron 71, 995-1013 (2011); Gong et al., J. Neurosci. 27, 9817-9823 (2007). However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans.

The current disclosure provides artificial expression constructs that selectively drive gene expression in targeted central nervous system cell populations. Targeted central nervous system cell populations include: inhibitory neocortical GABAergic neurons including somatostatin (Sst) GABAergic neurons, parvalbumin (Pvalb) GABAergic neurons, vasointestinal peptide (Vip) GABAergic neurons, and Lamp5 GABAergic neurons, and in some instances, astrocytes.

Particular embodiments of the artificial expression constructs utilize the following enhancers to selectively drive gene expression within targeted central nervous system cell populations as follows (enhancer/targeted cell population): eHGT_089h, eHGT_087h, eHGT_154h, eHGT_226h, eHGT_526h, eHGT_512h, eHGT_283h, eHGT_090m, eHGT_340m, eHGT_528h, eHGT_515h, eHGT_226h, eHGT_170h, eHGT_519h, eHGT_527h, eHGT_470m, eHGT_174h, eHGT_087m, and eHGT_156h/Sst GABAergic neurons; eHGT_076h eHGT_759m, and eHGT_064h/Pvalb/Sst GABAergic neurons; eHGT_072h, eHGT_131hv1, eHGT_131hv2, and eHGT_130h/Pvalb GABAergic neurons; eHGT_354h, eHGT_121h, eHGT_133h, eHGT_219h, eHGT_207h, eHGT_113m, eHGT_111m, eHGT_110h, eHGT_080h, eHGT_107h, MGT_E81, MGT_E85, MGT_E88, and MGT_E83/VIP GABAergic neurons; MGT_E36, MGT_E37, and MGT_E41/Lamp5_Lhx6 GABAergic neurons; eHGT_354m, eHGT_060m, and eHGT_060h/VIP GABAergic neurons and astrocytes, eHGT_025h, eHGT_096h, eHGT_098h, and eHGT_104m/Lamp5 GABAergic neurons; eHGT_682h, eHGT_600m, eHGT_468m, eHGT_338m, eHGT_341m, and eHGT_339m/Sst and Chod/GABAergic neurons.

In particular embodiments, the artificial enhancer elements include a concatenated core of an enhancer. Examples include a concatenated core of eHGT_226h and/or eHGT_064h. These artificial enhancer elements can provide higher levels and more rapid onset of transgene expression compared to a single full length original (native) enhancer.

In particular embodiments, the enhancer core includes the sequence as set forth in any one of SEQ ID NOs: 161, 163, and 165. In particular embodiments, these cores are concatenated and have 2, 3, 4, 5, 6, 7, 8, 9, or 10 copies of the core sequence. SEQ ID NOs: 162, 164, and 166 provide three-copy concatemers of the selected enhancer cores.

Particular embodiments of the artificial expression constructs utilize 3xcore2_eHGT_226h, and/or 3xcore3_eHGT_226h to selectively drive protein expression within Sst GABAergic neurons, and/or 3xcore_eHGT_064h to selectively drive protein expression within Pvalb/Sst GABAergic neurons.

Particular embodiments provide artificial expression constructs including the features of vectors described herein including vectors: CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, and AiP1273.

Aspects of the disclosure are now described with the following additional options and detail: (i) Artificial Expression Constructs & Vectors for Selective Expression of Genes in Selected Cell Types; (ii) Compositions for Administration (iii) Cell Lines Including Artificial Expression Constructs; (iv) Transgenic Animals; (v) Methods of Use; (vi) Kits and Commercial Packages; (vii) Exemplary Embodiments; (viii) Experimental Examples; and (ix) Closing Paragraphs.

(i) Artificial Expression Constructs & Vectors for Selective Expression of Genes in Selected Cell Types Artificial expression constructs disclosed herein include (i) an enhancer sequence that leads to selective expression of a coding sequence within a targeted central nervous system cell type, (ii) a coding sequence that is expressed, and (iii) a promoter. The artificial expression construct can also include other regulatory elements if necessary or beneficial.

In particular embodiments, an "enhancer" or an "enhancer element" is a cis-acting sequence that increases the level of transcription associated with a promoter and can function in either orientation relative to the promoter and the coding sequence that is to be transcribed and can be located upstream or downstream relative to the promoter or the coding sequence to be transcribed. There are art-recognized methods and techniques for measuring function(s) of enhancer element sequences. Particular examples of enhancer sequences utilized within artificial expression constructs disclosed herein include eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, eHGT_682h, eHGT_600m, eHGT_759m, eHGT_468m, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, and MGT_E83, and concatenated cores, such as 3xCore2_eHGT_226h, 3xCore3_eHGT_226h, and 3xCore_eHGT_064h.

In particular embodiments, a targeted central nervous system cell type enhancer is an enhancer that is uniquely or predominantly utilized by the targeted central nervous system cell type. A targeted central nervous system cell type enhancer enhances expression of a gene in the targeted central nervous system cell type but does not substantially direct expression of genes in other non-targeted cell types, thus having cell type specific transcriptional activity.

When a coding sequence is selectively expressed in selected cells and is not substantially expressed in other cell types, the product of the coding sequence is preferentially expressed in the selected cell type. In particular embodiments, preferential expression is greater than 50% expression as compared to a reference cell type; greater than 60% expression as compared to a reference cell type; greater than 70% expression as compared to a reference cell type; greater than 80% expression as compared to a reference cell type; or greater than 90% expression as compared to a reference cell type. In particular embodiments, a reference cell type refers to non-targeted cells. The non-targeted cells can be within the same anatomical structure as the targeted cells and/or can project to a common anatomical area. In particular embodiments, a reference cell type is within an anatomical structure that is adjacent to an anatomical structure that includes the targeted cell type. In particular embodiments, a reference cell type is a non-targeted cell with a different gene expression profile than the targeted cells.

In particular embodiments, the product of the coding sequence may be expressed at low levels in non-selected cell types, for example at less than 1% or 1%, 2%, 3%, 5%, 10%, 15% or 20% of the levels at which the product is expressed in selected cells. In particular embodiments, the targeted central nervous system cell type is the only cell type that expresses the right combination of transcription factors that bind an enhancer disclosed herein to drive gene expression. Thus, in particular embodiments, expression occurs exclusively within the targeted cell type.

In particular embodiments, targeted cell types (e.g. neuronal, and/or non-neuronal) can be identified based on transcriptional profiles, such as those described in Tasic et al., Nature 563, 72-78 (2018) and Hodge et al., Nature 573, 61-68 (2019). For reference, the following description of cell types and distinguishing features is also provided:

Neocortical GABAergic neuron Subclasses:

All: Express GABA synthesis genes Gad1/GAD1 and Gad2/GAD2.

Lamp5, Sncg, Serpinf1, and Vip GABAergic neurons: Developmentally derived from neuronal progenitors from the caudal ganglionic eminence (CGE) or preoptic area (POA).

Sst and Pvalb GABAergic neurons: Developmentally derived from neuronal progenitors in the medial ganglionic eminence (MGE).

Lamp5 GABAergic neurons: Found in many neocortical layers, especially upper (L1-L2/3), and have mainly neurogliaform and single bouquet morphology.

Lamp5_Lhx6 GABAergic neurons: A subset of Lamp5 GABAergic neurons that co-express Lamp5 and Lhx6.

Sncg GABAergic neurons: Found in many neocortical layers, and have molecular overlaps with Lamp5 and Vip cells, but inconsistent expression of Lamp5 or Vip, with more consistent expression of Sncg.

Serpinf1 GABAergic neurons: Found in many neocortical layers, and have molecular overlaps with Sncg and Vip cells, but inconsistent expression of Sncg or Vip, with more consistent expression of Serpinf1.

Vip GABAergic neurons: Found in many neocortical layers, but especially frequent in upper layers (L1-L4), and highly express the neurotransmitter vasoactive intestinal peptide (Vip).

Sst GABAergic neurons: Found in many neocortical layers, but especially frequent in lower layers (L5-L6). They highly express the neurotransmitter somatostatin (Sst), and frequently block dendritic inputs to postsynaptic neurons. Included in this subclass are sleep-active Sst Chod/neurons (which also express Nos1 and Tacr1) that are highly distinct from other Sst neurons but express some shared marker genes including Sst. In human, SST gene expression is often detected in layer 1 LAMP5+ GABAergic neuron subtypes.

Pvalb GABAergic neurons: Found in many neocortical layers, but especially frequent in lower layers (L5-L6). They highly express the calcium-binding protein parvalbumin (Pvalb), express neuropeptide Tac1, and frequently dampen the output of postsynaptic neurons. Most fast-spiking GABAergic neurons express Pvalb strongly. Included in this subclass are chandelier cells, which have distinct, chandelier-like morphology and express the markers Cpne5 and Vipr2 in mouse, and NOG and UNC5B in human.

Meis2: A distinct subclass defined by a single type, only neocortical GABAergic neuron type that expresses Meis2 gene, and does not express some other genes that are expressed by all other neocortical GABAergic neuron types (for example, Thy1 and Scn2b). This type is found in L6b and subcortical white matter.

Neocortical glutamatergic neuron subclasses:

All: Express glutamate transmitters Slc17a6 and/or Slc17a7. They all express Snap25 and lack expression of Gad1/Gad2.

L2/3 IT glutamatergic neurons: Primarily reside in Layer 2/3 and have mainly intratelencephalic (cortico-cortical) projections.

L4 IT glutamatergic neurons: Primarily reside in Layer 4 and mainly have either local or intratelencephalic (cortico-cortical) projections.

L5 IT glutamatergic neurons: Primarily reside in Layer 5 and have mainly intratelencephalic (cortico-cortical) projections. Also called L5a.

L5 PT glutamatergic neurons: Primarily reside in Layer 5 and have mainly cortico-subcortical (pyramidal tract or corticofugal) projections. Also called L5b or L5 CF (corticofugal) or L5 ET (extratelencephalic). This subclass includes cells that are located in the primary motor cortex and neighboring areas and are corticospinal projection neurons, which are associated with motor neuron/movement disorders, such as ALS. This subclass includes thick-tufted pyramidal neurons, including distinctive subtypes found only in specialized regions, e.g. Betz cells, Meynert cells, and von Economo cells.

L5 NP glutamatergic neurons: Primarily reside in Layer 5 and have mainly nearby projections.

L6 CT glutamatergic neurons: Primarily reside in Layer 6 and have mainly cortico-thalamic projections.

L6 IT glutamatergic neurons: Primarily reside in Layer 6 and have mainly intratelencephalic (cortico-cortical) projections.

L6 IT Car3 glutamatergic neurons: Most densely present in claustrum and endopyriform nucleus, and sparsely throughout L6 in many cortical areas including the primary visual cortex. These cells have mainly intratelencephalic (cortico-cortical) projections. Additional marker genes for claustrum enriched neurons include Gnb4 and Ntng2.

L6b glutamatergic neurons: Primarily reside in the neocortical subplate (L6b), with local (near the cell body) projections and some cortico-cortical projections from VISp to anterior cingulate, and cortico-subcortical projections to the thalamus.

CR neurons: A distinct subclass defined by a single type in L1, Cajal-Retzius cells express distinct molecular markers Lhx5 and Trp73.

Cerebellar Purkinje cells: large GABAergic neurons that are the only projection neurons and the sole output from the cerebellum. Their cell bodies form a single layer, so called 'Purkinje cell layer', and they express parvalbumin.

Deep cerebellar nucleus neurons: neurons located in the deep cerebellar nuclei structures. These include glutamatergic and GABAergic cells that express the gene Pvalb.

Non-Neuronal Subclasses:

Astrocytes: Neuroectoderm-derived glial cells which express the marker Aqp4 and often GFAP, but do not express neuronal marker SNAP25. They can have a distinct star-shaped morphology and are involved in metabolic support of other cells in the brain. Multiple astrocyte morphologies are observed in mouse and human Oligodendrocytes: Neuroectoderm-derived glial cells, which express the marker Sox10. This category includes oligodendrocyte precursor cells (OPCs). Oligodendrocytes are the subclass that is primarily responsible for myelination of neurons.

VLMCs: Vascular leptomeningeal cells (VLMCs) are part of the meninges that surround the outer layer of the cortex and express the marker genes Lum and Col1a1.

Pericytes: Blood vessel-associated cells that express the marker genes Kcnj8 and Abcc9. Pericytes wrap around endothelial cells and are important for regulation of capillary blood flow and are involved in blood-brain barrier permeability.

SMCs: Specialized smooth-muscle cells which are blood vessel-associated cells that express the marker gene Acta2. SMCs cover arterioles in the brain and are involved in blood-brain barrier permeability.

Endothelial cells: Cells that line blood vessels of the brain. Endothelial cells express the markers Tek and PDGF-B.

Microglia: hematopoietic-derived immune cells, which are brain-resident macrophages, and perivascular macrophages (PVMs) that may be transitionally associated with brain tissue or included as a biproduct of brain dissection methods. Microglia are known to express Cx3cr1, Tmem119, and PTPRC (CD45).

In particular embodiments, a coding sequence is a heterologous coding sequence that encodes an effector element. An effector element is a sequence that is expressed to achieve, and that in fact achieves, an intended effect. Examples of effector elements include reporter genes/proteins and functional genes/proteins.

Exemplary reporter genes/proteins include those expressed by Addgene ID #s 83894 (pAAV-hDIx-Flex-dTomato-Fishell_7), 83895 (pAAV-hDIx-Flex-GFP-Fishell_6), 83896 (pAAV-hDIx-GiDREADD-dTomato-Fishell-5), 83898 (pAAV-mDIx-ChR2-mCherry-Fishell-3), 83899 (pAAV-mDIx-GCaMP6f-Fishell-2), 83900 (pAAV-mDIx-GFP-Fishell-1), and 89897 (pcDNA3-FLAG-mTET2 (N500)). Exemplary reporter genes particularly can include those which encode an expressible fluorescent protein, or expressible biotin; blue fluorescent proteins (e.g. eBFP, eBFP2, Azurite, mKalama1, GFPuv, Sapphire, T-sapphire); cyan fluorescent proteins (e.g. eCFP, Cerulean, CyPet, AmCyanl, Midoriishi-Cyan, mTurquoise); green fluorescent proteins (e.g. GFP, GFP-2, tagGFP, turboGFP, EGFP, Emerald, Azami Green, Monomeric Azami Green (mAzami-green), CopGFP, AceGFP, avGFP, ZsGreenl, Oregon Green™ (Thermo Fisher Scientific)); Luciferase; orange fluorescent proteins (mOrange, mKO, Kusabira-Orange, Monomeric Kusabira-Orange, mTangerine, tdTomato, dTomato); red fluorescent proteins (mKate, mKate2, mPlum, DsRed monomer, mCherry, mRuby, mRFP1, DsRed-Express, DsRed2, DsRed-Monomer, HcRed-Tandem, HcRedl, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowl); and tandem conjugates.

GFP is composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted E), also known as its optical cross section of 9.13×10-21 m²/molecule, also quoted as 55,000 L/(mol·cm). Super-folder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

Exemplary functional molecules include functioning ion transporters, cellular trafficking proteins, enzymes, transcription factors, neurotransmitters, calcium reporters, channelrhodopsins, guide RNA, nucleases, microRNA, or designer receptors exclusively activated by designer drugs (DREADDs).

Ion transporters are transmembrane proteins that mediate transport of ions across cell membranes. These transporters are pervasive throughout most cell types and important for regulating cellular excitability and homeostasis. Ion transporters participate in numerous cellular processes such as action potentials, synaptic transmission, hormone secretion, and muscle contraction. Many important biological processes in living cells involve the translocation of cations, such as calcium (Ca2+), potassium (K+), and sodium (Na+) ions, through such ion channels. In particular embodiments, ion transporters include voltage gated sodium channels (e.g., SCN1A), potassium channels (e.g., KCNQ2), and calcium channels (e.g. CACNA1C)).

Exemplary enzymes, transcription factors, receptors, membrane proteins, cellular trafficking proteins, signaling molecules, and neurotransmitters include enzymes such as lactase, lipase, helicase, alpha-glucosidase, amylase; transcription factors such as SP1, AP-1, Heat shock factor protein 1, C/EBP (CCAA-T/enhancer binding protein), and Oct-1; receptors such as transforming growth factor receptor beta 1, platelet-derived growth factor receptor, epidermal growth factor receptor, vascular endothelial growth factor receptor, and interleukin 8 receptor alpha; membrane proteins, cellular trafficking proteins such as clathrin, dynamin, caveolin, Rab-4A, and Rab-11A; signaling molecules such as nerve growth factor (NGF), platelet-derived growth factor (PDGF), transforming growth factor β (TGFβ), epidermal growth factor (EGF), GTPase and HRas; and neurotransmitters such as cocaine and amphetamine regulated transcript, substance P, oxytocin, and somatostatin.

In particular embodiments, functional molecules include reporters of cell function and states such as calcium reporters. Intracellular calcium concentration is an important predictor of numerous cellular activities, which include neuronal activation, muscle cell contraction and second messenger signaling. A sensitive and convenient technique to monitor the intracellular calcium levels is through the genetically encoded calcium indicator (GECI). Among the GECIs, green fluorescent protein (GFP) based calcium sensors named GCaMPs are efficient and widely used tools. The GCaMPs are formed by fusion of M13 and calmodulin protein to N- and C-termini of circularly permutated GFP. Some GCaMPs yield distinct fluorescence emission spectra (Zhao et al., Science, 2011, 333(6051): 1888-1891). Exemplary GECIs with green fluorescence include GCaMP3, GCaMP5G, GCaMP6s, GCaMP6m, GCaMP6f, jGCaMP7s, jGCaMP7c, jGCaMP7b, and jGCaMP7f. Furthermore, GECIs with red fluorescence include jRGECO1a and jRGECO1b. AAV products containing GECIs are commercially available. For example, Vigene Biosciences provides AAV products including AAV8-CAG-GCaMP3 (Cat. No: BS4-CX3AAV8), AAV8-Syn-FLEX-GCaMP6s-WPRE (Cat. No: BS1-NXSAAV8), AAV8-Syn-FLEX-GCaMP6s-WPRE (Cat. No: BS1-NXSAAV8), AAV9-CAG-FLEX-GCaMP6m-WPRE (Cat. No: BS2-CXMAAV9), AAV9-Syn-FLEX-jGCaMP7s-WPRE (Cat. No: BS12-NXSAAV9), AAV9-CAG-FLEX-jGCaMP7f-WPRE (Cat. No: BS12-CXFAAV9), AAV9-Syn-FLEX-jGCaMP7b-WPRE (Cat. No: BS12-NXBAAV9), AAV9-Syn-FLEX-jGCaMP7c-WPRE (Cat. No: BS12-NXCAAV9), AAV9-Syn-FLEX-NES-jRGECO1a-WPRE (Cat. No: BS8-NXAAAV9), and AAV8-Syn-FLEX-NES-jRCaMP1b-WPRE (Cat. No: BS7-NXBAAV8).

In particular embodiments calcium reporters include the genetically encoded calcium indicators GECI, NTnC; Myosin light chain kinase, GFP, Calmodulin chimera; Calcium indicator TN-XXL; BRET-based auto-luminescent calcium indicator; and/or Calcium indicator protein OeNL(Ca2+)-18u).

In particular embodiments, functional molecules include modulators of neuronal activity like channelrhodopsins (e.g., channelrhodopsin-1, channelrhodopsin-2, and variants thereof). Channelrhodopsins are a subfamily of retinylidene proteins (rhodopsins) that function as light-gated ion channels. In addition to channelrhodopsin 1 (ChR1) and channelrhodopsin 2 (ChR2), several variants of channelrhodopsins have been developed. For example, Lin et al. (Biophys J, 2009, 96(5): 1803-14) describe making chimeras of the transmembrane domains of ChR1 and ChR2, combined with site-directed mutagenesis. Zhang et al. (Nat Neurosci, 2008, 11(6): 631-3) describe VChR1, which is a red-shifted channelrhodopsin variant. VChR1 has lower light sensitivity and poor membrane trafficking and expression. Other known channelrhodopsin variants include the ChR2 variant described in Nagel, et al., Proc Natl Acad Sci USA, 2003, 100(24): 13940-5), ChR2/H134R (Nagel, G., et al., Curr Biol, 2005, 15(24): 2279-84), and ChD/ChEF/ChIEF (Lin, J. Y., et al., Biophys J, 2009, 96(5): 1803-14), which are activated by blue light (470 nm) but show no sensitivity to orange/red light. Additional variants are described in Lin, Experimental Physiology, 2010, 96.1: 19-25 and Knopfel et al., The Journal of Neuroscience, 2010, 30(45): 14998-15004).

In particular embodiments, functional molecules include DNA and RNA editing tools such CRISPR/CAS (e.g., guide RNA and a nuclease, such as Cas, Cas9 or cpf1). Functional molecules can also include engineered Cpf1s such as those described in US 2018/0030425, US 2016/0208243, WO/2017/184768 and Zetsche et al. (2015) *Cell* 163: 759-771; single gRNA (see e.g., Jinek et al. (2012) Science 337:816-821; Jinek et al. (2013) eLife 2:e00471; Segal (2013) eLife 2:e00563) or editase, guide RNA molecules, microRNA, or homologous recombination donor cassettes.

Sequences are publicly-available. As examples, lactase (e.g., GenBank: EAX11622.1), lipase (e.g., GenBank: AAA60129.1), helicase (e.g., GenBank: AMD82207.1), amylase (e.g., GenBank: AAA51724.1), alpha-glucosidase (e.g., GenBank: AB153718.1), transcription factor SP1 (e.g., UniProtKB/Swiss-Prot: P08047.3), transcription factor AP-1 (e.g., NP_002219.1), heat shock factor protein 1 (e.g., UniProtKB/Swiss-Prot: Q00613.1), CCAAT/enhancer-binding protein (C/EBP) beta isoform a (e.g., NP_005185.2), Oct-1 (e.g., UniProtKB/Swiss-Prot: P14859.2), TGFβ (e.g., GenBank: CAF02096.2), platelet-derived growth factor receptor (e.g., GenBank: AAA60049.1), epidermal growth factor receptor (e.g., GenBank: CAA25240.1), vascular endothelial growth factor receptor (e.g., GenBank: AAC16449.2), interleukin 8 receptor alpha (e.g., GenBank: AAB59436.1), caveolin (e.g., GenBank: CAA79476.1), dynamin (e.g., GenBank: AAA88025.1), clathrin heavy chain 1 isoform 1 (e.g., NP_004850.1), clathrin heavy chain 2 isoform 1 (e.g., NP_009029.3), clathrin light chain A isoform a (e.g., NP_001824.1), clathrin light chain B isoform a (e.g., NP_001825.1), ras-related protein Rab-4A isoform 1 (e.g., NP_004569.2), ras-related protein Rab-11A (e.g., UniProtKB/Swiss-Prot: P62491.3), platelet-derived growth factor (e.g., GenBank: AAA60552.1), transforming growth factor-beta3 (e.g., GenBank: AAA61161.1), nerve growth factor (e.g., GenBank: CAA37703.1), EGF (e.g., GenBank: CAA34902.2), cocaine and amphetamine regulated transcript (Chain A) (e.g., PDB: 1HY9_A), protachykinin-1 (e.g., UniProtKB—P20366), oxytocin-neurophysin 1 (e.g., UniProtKB—P01178), somatostatin (e.g., GenBank: AAH32625.1), genetically-encoded green calcium indicator NTnC (chain A) [synthetic construct] (e.g., PDB: 5MWC_A), calcium indicator TN-XXL [synthetic construct], (e.g., GenBank: ACF93133.1), BRET-based autoluminescent calcium indicator [synthetic construct] (e.g., GenBank ADF42668.1), calcium indicator protein OeNL (Ca2+)-18u [synthetic construct], ((e.g., GenBank BBB18812.1), myosin light chain kinase, Green fluorescent protein, Calmodulin chimera (Chain A) [synthetic construct] ((e.g., PDB: 3EKJ_A), channelopsin 1 (e.g., UniProtKB—F8UVI5), channelopsin 1 (e.g., GenBank: AER58217.1), channelrhodopsin-2 ((e.g., UniProtKB—B4Y105), channel rhodopsin 2 [synthetic construct] ((e.g., GenBank: AB064386.1), CRISPR-associated protein (Cas) (e.g., GenBank: AKG27598.1), Cas9 [synthetic construct] (e.g., GenBank: AST09977.1), CRISPR-associated endonuclease Cpf1 (e.g., UniProtKB/Swiss-Prot: U2UMQ6.1), ribonuclease 4 or ribonuclease L (e.g., UniProtKB/Swiss-Prot: Q05823.2), deoxyribonuclease II beta (e.g., GenBank: AAF76893.1), sodium channel protein type 1 subunit alpha (e.g., UniProtKB—P35498), potassium voltage-gated channel subfamily KQT member 2 (e.g., UniProtKB—O43526), and voltage-dependent L-type calcium channel subunit alpha-1C (e.g., UniProtKB—Q13936).

Additional effector elements include Cre, iCre, dgCre, FlpO, and tTA2. iCre refers to a codon-improved Cre. dgCre refers to an enhanced GFP/Cre recombinase fusion gene with an N terminal fusion of the first 159 amino acids of the *Escherichia coli* K-12 strain chromosomal dihydrofolate reductase gene (DHFR or folA) harboring a G67S mutation and modified to also include the R12Y/Y100I destabilizing domain mutation. FlpO refers to a codon-optimized form of FLPe that greatly increases protein expression and FRT recombination efficiency in mouse cells. Like the Cre/LoxP system, the FLP/FRT system has been widely used for gene expression (and generating conditional knockout mice, mediated by the FLP/FRT system). tTA2 refers to tetracycline transactivator.

Exemplary expressible elements are expression products that do not include effector elements, for example, a non-functioning or defective protein. In particular embodiments, expressible elements can provide methods to study the effects of their functioning counterparts. In particular embodiments, expressible elements are non-functioning or defective based on an engineered mutation that renders them non-functioning. In these aspects, non-expressible elements are as similar in structure as possible to their functioning counterparts.

Exemplary self-cleaving peptides include the 2A peptides which lead to the production of two proteins from one mRNA. The 2A sequences are short (e.g., 20 amino acids), allowing more use in size-limited constructs. Particular examples include P2A, T2A, E2A, and F2A. In particular embodiments, the artificial expression constructs include an internal ribosome entry site (IRES) sequence. IRES allow ribosomes to initiate translation at a second internal site on a mRNA molecule, leading to production of two proteins from one mRNA.

Coding sequences encoding molecules (e.g., RNA, proteins) described herein can be obtained from publicly available databases and publications. Coding sequences can further include various sequence polymorphisms, mutations, and/or sequence variants wherein such alterations do not affect the function of the encoded molecule. The term "encode" or "encoding" refers to a property of sequences of nucleic acids, such as a vector, a plasmid, a gene, cDNA, mRNA, to serve as templates for synthesis of other molecules such as proteins.

The term "gene" may include not only coding sequences but also regulatory regions such as promoters, enhancers, insulators, and/or post-regulatory elements, such as termination regions. The term further can include all introns and other DNA sequences spliced from the mRNA transcript, along with variants resulting from alternative splice sites. The sequences can also include degenerate codons of a reference sequence or sequences that may be introduced to provide codon preference in a specific organism or cell type.

Promoters can include general promoters, tissue-specific promoters, cell-specific promoters, and/or promoters specific for the cytoplasm. Promoters may include strong promoters, weak promoters, constitutive expression promoters, and/or inducible promoters. Inducible promoters direct expression in response to certain conditions, signals or cellular events. For example, the promoter may be an inducible promoter that requires a particular ligand, small molecule, transcription factor or hormone protein in order to effect transcription from the promoter. Particular examples of promoters include minBglobin, CMV, minCMV, minCMV* (minCMV* is minCMV with a SacI restriction site removed), minRho, minRho* (minRho* is minRho with a SacI restriction site removed), SV40 immediately early promoter, the Hsp68 minimal promoter (proHSP68), and the Rous Sarcoma Virus (RSV) long-terminal repeat (LTR) promoter. Minimal promoters have no activity to drive gene expression on their own but can be activated to drive gene expression when linked to a proximal enhancer element.

In particular embodiments, expression constructs are provided within vectors. The term vector refers to a nucleic acid molecule capable of transferring or transporting another nucleic acid molecule, such as an expression construct. The transferred nucleic acid is generally linked to, e.g., inserted into, the vector nucleic acid molecule. A vector may include sequences that direct autonomous replication in a cell or may include sequences that permit integration into host cell DNA. Useful vectors include, for example, plasmids (e.g., DNA plasmids or RNA plasmids), transposons, cosmids, bacterial artificial chromosomes, and viral vectors.

Viral vector is widely used to refer to a nucleic acid molecule that includes virus-derived components that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Adenovirus vectors refer to those constructs containing adenovirus sequences sufficient to (a) support packaging of an artificial expression construct and (b) to express a coding sequence that has been cloned therein in a sense or antisense orientation. A recombinant Adenovirus vector includes a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range, and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut-off. The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5-tripartite leader (TPL) sequence which makes them preferred mRNAs for translation.

Other than the requirement that an adenovirus vector be replication defective, or at least conditionally defective, the nature of the adenovirus vector is not believed to be crucial to the successful practice of particular embodiments disclosed herein. The adenovirus may be of any of the 42 different known serotypes or subgroups A-F. In particular embodiments, adenovirus type 5 of subgroup C is the preferred starting material in order to obtain a conditional replication-defective adenovirus vector for use in particular embodiments, since Adenovirus type 5 is a human adenovirus about which a great deal of biochemical and genetic information is known, and it has historically been used for most constructions employing adenovirus as a vector.

As indicated, the typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of a deleted E3 region in E3 replacement vectors or in the E4 region where a helper cell line or helper virus complements the E4 defect.

Adeno-Associated Virus (AAV) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Various serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three AAV viral promoters have been identified and named p5, p19, and p40, according to their map position. Transcription from p5 and p19 results in production of rep proteins, and transcription from p40 produces the capsid proteins.

AAVs stand out for use within the current disclosure because of their superb safety profile and because their capsids and genomes can be tailored to allow expression in selected cell populations. scAAV refers to a self-complementary AAV. pAAV refers to a plasmid adeno-associated virus. rAAV refers to a recombinant adeno-associated virus.

Other viral vectors may also be employed. For example, vectors derived from viruses such as vaccinia virus, polioviruses and herpes viruses may be employed. They offer several attractive features for various mammalian cells.

Retroviruses are a common tool for gene delivery. "Retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV), Rous Sarcoma Virus (RSV), and lentivirus.

"Lentivirus" refers to a group (or genus) of complex retroviruses. Illustrative lentiviruses include: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). In particular embodiments, HIV based vector backbones (i.e., HIV cis-acting sequence elements) can be used.

A safety enhancement for the use of some vectors can be provided by replacing the U3 region of the 5' LTR with a heterologous promoter to drive transcription of the viral genome during production of viral particles. Examples of heterologous promoters which can be used for this purpose include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In particular embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include one or more chemical compounds or the physiological conditions such as temperature or pH, in which the host cells are cultured.

In particular embodiments, viral vectors include a TAR element. The term "TAR" refers to the "trans-activation response" genetic element located in the R region of lentiviral LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly(A) tract. The R region is also defined as being flanked by the U3 and U5 regions. The R region plays a role during reverse transcription in permitting the transfer of nascent DNA from one end of the genome to the other.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid. Examples include the woodchuck hepatitis virus posttranscriptional regulatory element (WPRE; Zuffe-rey et al., 1999, J. Virol., 73:2886); the posttranscriptional regulatory element present in hepatitis B virus (HPRE) (Smith et al., Nucleic Acids Res. 26(21):4818-4827, 1998); and the like (Liu et al., 1995, Genes Dev., 9:1766). In particular embodiments, vectors include a posttranscriptional regulatory element such as a WPRE or HPRE. In particular embodiments, vectors lack or do not include a posttranscriptional regulatory element such as a WPRE or HPRE.

Elements directing the efficient termination and polyadenylation of a heterologous nucleic acid transcript can increase heterologous gene expression. Transcription termination signals are generally found downstream of the polyadenylation signal. In particular embodiments, vectors include a polyadenylation signal 3' of a polynucleotide encoding a molecule (e.g., protein) to be expressed. The term "poly(A) site" or "poly(A) sequence" denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Particular embodiments may utilize BGHpA or SV40 pA. In particular embodiments, a preferred embodiment of an expression construct includes a terminator element. These elements can serve to enhance transcript levels and to minimize read through from the construct into other plasmid sequences.

In particular embodiments, a viral vector further includes one or more insulator elements. Insulators elements may contribute to protecting viral vector-expressed sequences, e.g., effector elements or expressible elements, from integration site effects, which may be mediated by cis-acting elements present in genomic DNA and lead to deregulated expression of transferred sequences (i.e., position effect; see, e.g., Burgess-Beusse et al., PNAS., USA, 99:16433, 2002; and Zhan et al., Hum. Genet., 109:471, 2001). In particular embodiments, viral transfer vectors include one or more insulator elements at the 3' LTR and upon integration of the provirus into the host genome, the provirus includes the one or more insulators at both the 5' LTR and 3' LTR, by virtue of duplicating the 3' LTR. Suitable insulators for use in particular embodiments include the chicken β-globin insulator (see Chung et al., Cell 74:505, 1993; Chung et al., PNAS USA 94:575, 1997; and Bell et al., Cell98:387, 1999), SP10 insulator (Abhyankar et al., JBC 282:36143, 2007), or other small CTCF recognition sequences that function as enhancer blocking insulators (Liu et al., Nature Biotechnology, 33:198, 2015).

Beyond the foregoing description, a wide range of suitable expression vector types will be known to a person of ordinary skill in the art. These can include commercially available expression vectors designed for general recombinant procedures, for example plasmids that contain one or more reporter genes and regulatory elements required for expression of the reporter gene in cells. Numerous vectors are commercially available, e.g., from Invitrogen, Stratagene, Clontech, etc., and are described in numerous associated guides. In particular embodiments, suitable expression vectors include any plasmid, cosmid or phage construct that is capable of supporting expression of encoded genes in mammalian cell, such as pUC or Bluescript plasmid series.

Particular embodiments of vectors disclosed herein include:

| Expression Construct Name | Features |
|---|---|
| CN1535 | rAAV-hsA2-eHGT_089h-minRho-SYFP2-WPRE3-BGHpA |
| CN1533 | rAAV-hsA2-eHGT_087h-minRho-SYFP2-WPRE3-BGHpA |
| CN1647 | rAAV-hsA2-eHGT_154h-minRho-SYFP2-WPRE3-BGHpA |
| CN1719 | rAAV-hsA2-eHGT_226h-minRho-SYFP2-WPRE3-BGHpA |
| CN2365 | rAAV-eHGT_526h-minBglobin-SYFP2-WPRE3-BGHpA |
| CN2355 | rAAV-eHGT_512h-minBglobin-SYFP2-WPRE3-BGHpA |
| CN1797 | rAAV-hsA2-eHGT_283h-minRho-SYFP2-WPRE3-BGHpA |
| CN1584 | rAAV-hsA2-eHGT_090m-minRho-SYFP2-WPRE3-BGHpA |
| CN1455 | rAAV-eHGT_076h-minBglobin-SYFP2-WPRE3-BGHpA |

-continued

| Expression Construct Name | Features |
| --- | --- |
| CN1451 | rAAV-eHGT__072h-minBglobin-SYFP2-WPRE3-BGHpA |
| CN2039 | rAAV-3xSP10ins-eHGT__354h-minRho*-SYFP2-WPRE3-BGHpA |
| CN2040 | rAAV-3xSP10ins-eHGT__354m-minRho*-SYFP2-WPRE3-BGHpA |
| CN1567 | rAAV-hsA2-eHGT__121h-minRho-SYFP2-WPRE3-BGHpA |
| CN1626 | rAAV-hsA2-eHGT__133h-minRho-SYFP2-WPRE3-BGHpA |
| CN1712 | rAAV-hsA2-eHGT__219h-minRho-SYFP2-WPRE3-BGHpA |
| CN1700 | rAAV-hsA2-eHGT__207h-minRho-SYFP2-WPRE3-BGHpA |
| CN1607 | rAAV-hsA2-eHGT__113m-minRho-SYFP2-WPRE3-BGHpA |
| CN1605 | rAAV-hsA2-eHGT__111m-minRho-SYFP2-WPRE3-BGHpA |
| CN1556 | rAAV-hsA2-eHGT__110h-minRho-SYFP2-WPRE3-BGHpA |
| CN1526 | rAAV-hsA2-eHGT__080h-minRho-SYFP2-WPRE3-BGHpA |
| CN1418 | rAAV-eHGT__060m-minBglobin-SYFP2-WPRE3-BGHpA |
| CN1404 | rAAV-eHGT__060h-minBglobin-SYFP2-WPRE3-BGHpA |
| AiV1173 | rAAV-MGT__E36-minBglobin-FlpO-WPRE-hGHpA |
| AiV1174 | rAAV-MGT__E37-minBglobin-FlpO-WPRE-hGHpA |
| AiV1177 | rAAV-MGT__E41-minBglobin-FlpO-WPRE-hGHpA |
| CN1261 | scAAV-eHGT__025h-minBGlobin-SYFP2-WPRE3-BGHpA |
| CN1542 | rAAV-hsA2-eHGT__096h-minRho-SYFP2-WPRE3-BGHpA |
| CN1544 | rAAV-hsA2-eHGT__098h-minRho-SYFP2-WPRE3-BGHpA |
| CN1598 | rAAV-hsA2-eHGT__104m-minRho-SYFP2-WPRE3-BGHpA |
| CN1553 | rAAV-hsA2-eHGT__107h-minRho-SYFP2-WPRE3-BGHpA |
| CN1992 | rAAV-3xSP10ins-eHGT__340m-minRho*-SYFP2-WPRE3-BGHpA |
| CN2367 | rAAV-eHGT__528h-minBglobin-SYFP2-WPRE3-BGHpA |
| CN2357 | rAAV-eHGT__515h-minBglobin-SYFP2-WPRE3-BGHpA |
| CN2568 | rAAV-3xCore2__eHGT__226h-minBglobin-SYFP2-WPRE3-BGHpA |
| CN2569 | rAAV-3xCore3__eHGT__226h-minBglobin-SYFP2-WPRE3-BGHpA |
| CN2689 | rAAV-eHGT__682h-minBglobin-SYFP2-WPRE3-BGHpA |
| CN2408 | rAAV-eHGT__600m-minBG-SYFP2-WPRE3-BGHpA |
| CN2596 | rAAV-eHGT__759m-minBglobin-SYFP2-WPRE3-BGHpA |
| CN2317 | rAAV-eHGT__468m-minBglobin-SYFP2-WPRE3-BGHpA |
| CN2571 | rAAV-3xCore__eHGT__064h__minBglobin-SYFP2-WPRE3-BGHpA |
| CN1663 | rAAV-hsA2-eHGT__170h-minRho-SYFP2-WPRE3-BGHpA |
| CN2310 | rAAV-eHGT__131hv1-minBglobin-SYFP2-WPRE3-BGHpA |
| CN2360 | rAAV-eHGT__519h-minBglobin-SYFP2-WPRE3-BGHpA |
| CN1624 | rAAV-hsA2-eHGT__131hv2-minRho-SYFP2-WPRE3-BGHpA |
| CN2309 | rAAV-eHGT__130h-minBglobin-SYFP2-WPRE3-BGHpA |
| CN2366 | rAAV-eHGT__527h-minBglobin-SYFP2-WPRE3-BGHpA |
| CN2257 | rAAV-eHGT__470m-minBglobin-SYFP2-WPRE3-BGHpA |
| CN1667 | rAAV-hsA2-eHGT__174h-minRho-SYFP2-WPRE3-BGHpA |
| CN1581 | rAAV-hsA2-eHGT__087m-minRho-SYFP2-WPRE3-BGHpA |
| CN1649 | rAAV-hsA2-eHGT__156h-minRho-SYFP2-WPRE3-BGHpA |
| AiP1099 | pAAV-eHGT__338m-minBGprom-FlpO-WPRE-hGHpA |
| AiP1102 | pAAV-eHGT__341m-monBGprom-FlpO-WPRE-hGHpA |
| AiP1100 | pAAV-eHGT__339m-minBGprom-FlpO-WPRE-hGHpA |
| AiP1270 | pAAV-MGT__E81-minBGprom-SYFP2-WPRE3-bGHpA |
| AiP1271 | pAAV-MGT__E85-minBGprom-SYFP2-WPRE3-bGHpA |
| AiP1272 | pAAV-MGT__E88-minBGprom-SYFP2-WPRE3-bGHpA |
| AiP1273 | pAAV-MGT__E83-minBGprom-SYFP2-WPRE3-bGHpA |

Subcomponent sequences within the larger vector sequences can be readily identified by one of ordinary skill in the art and based on the contents of the current disclosure (see FIG. 15). Nucleotides between identifiable and enumerated subcomponents reflect restriction enzyme recognition sites used in assembly (cloning) of the constructs, and in some cases, additional nucleotides do not convey any identifiable function. These segments of complete vector sequences can be adjusted based on use of different cloning strategies and/or vectors. In general, short 6-nucleotide palindromic sequences reflect vector construction artifacts that are not important to vector function.

In particular embodiments vectors (e.g., AAV) with capsids that cross the blood-brain barrier (BBB) are selected. In particular embodiments, vectors are modified to include capsids that cross the BBB. Examples of AAV with viral capsids that cross the blood brain barrier include AAV9 (Gombash et al., Front Mol Neurosci. 2014; 7:81), AAVrh.10 (Yang, et al., Mol Ther. 2014; 22(7): 1299-1309), AAV1R6, AAV1R7 (Albright et al., Mol Ther. 2018; 26(2): 510), rAAVrh.8 (Yang, et al., supra), AAV-BR1 (Marchio et al., EMBO Mol Med. 2016; 8(6): 592), AAV-PHP.S (Chan et al., Nat Neurosci. 2017; 20(8): 1172), AAV-PHP.B (Deverman et al., Nat Biotechnol. 2016; 34(2): 204), AAV-PPS (Chen et al., Nat Med. 2009; 15: 1215), and PHP.eB. In particular embodiments, the PHP.eB capsid differs from AAV9 such that, using AAV9 as a reference, amino acids starting at residue 586: S-AQ-A (SEQ ID NO: 199) are changed to S-DGTLAVPFK-A (SEQ ID NO: 200). In particular embodiments, PHP.eb refers to SEQ ID NO: 50

AAV9 is a naturally occurring AAV serotype that, unlike many other naturally occurring serotypes, can cross the BBB following intravenous injection. It transduces large sections of the central nervous system (CNS), thus permitting minimally invasive treatments (Naso et al., BioDrugs. 2017; 31(4): 317), for example, as described in relation to clinical trials for the treatment of spinal muscular atrophy (SMA) syndrome by AveXis (AVXS-101, NCT03505099) and the treatment of CLN3 gene-Related Neuronal Ceroid-Lipofuscinosis (NCT03770572).

AAVrh.10, was originally isolated from rhesus macaques and shows low seropositivity in humans when compared with other common serotypes used for gene delivery applications (Selot et al., Front Pharmacol. 2017; 8: 441) and has been evaluated in clinical trials LYS-SAF302, LYSOGENE, and NCT03612869.

AAV1R6 and AAV1R7, two variants isolated from a library of chimeric AAV vectors (AAV1 capsid domains swapped into AAVrh.10), retain the ability to cross the BBB and transduce the CNS while showing significantly reduced hepatic and vascular endothelial transduction.

rAAVrh.8, also isolated from rhesus macaques, shows a global transduction of glial and neuronal cell types in regions of clinical importance following peripheral administration and also displays reduced peripheral tissue tropism compared to other vectors.

AAV-BR1 is an AAV2 variant displaying the NRGTEWD (SEQ ID NO: 201) epitope that was isolated during in vivo screening of a random AAV display peptide library. It shows high specificity accompanied by high transgene expression in the brain with minimal off-target affinity (including for the liver) (Körbelin et al., EMBO Mol Med. 2016; 8(6): 609).

AAV-PHP.S (Addgene, Watertown, MA) is a variant of AAV9 generated with the CREATE method that encodes the 7-mer sequence QAVRTSL (SEQ ID NO: 202), transduces neurons in the enteric nervous system, and strongly transduces peripheral sensory afferents entering the spinal cord and brain stem.

AAV-PHP.B (Addgene, Watertown, MA) is a variant of AAV9 generated with the CREATE method that encodes the 7-mer sequence TLAVPFK (SEQ ID NO: 203). It transfers genes throughout the CNS with higher efficiency than AAV9 and transduces the majority of astrocytes and neurons across multiple CNS regions.

AAV-PPS, an AAV2 variant crated by insertion of the DSPAHPS (SEQ ID NO: 204) epitope into the capsid of AAV2, shows a dramatically improved brain tropism relative to AAV2.

For additional information regarding capsids that cross the blood brain barrier, see Chan et al., Nat. Neurosci. 2017 August: 20(8): 1172-1179.

(ii) Compositions for Administration

Artificial expression constructs and vectors of the present disclosure (referred to herein as physiologically active components) can be formulated with a carrier that is suitable for administration to a cell, tissue slice, animal (e.g., mouse, non-human primate), or human. Physiologically active components within compositions described herein can be prepared in neutral forms, as freebases, or as pharmacologically acceptable salts.

Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers of physiologically active components can include solvents, dispersion media, vehicles, coatings, diluents, isotonic and absorption delaying agents, buffers, solutions, suspensions, colloids, and the like. The use of such carriers for physiologically active components is well known in the art. Except insofar as any conventional media or agent is incompatible with the physiologically active components, it can be used with compositions as described herein.

The phrase "pharmaceutically-acceptable carriers" refer to carriers that do not produce an allergic or similar untoward reaction when administered to a human, and in particular embodiments, when administered intravenously (e.g. at the retro-orbital plexus).

In particular embodiments, compositions can be formulated for intravenous, intraparenchymal, intraocular, intravitreal, parenteral, subcutaneous, intracerebro-ventricular, intramuscular, intrathecal, intraspinal, intraperitoneal, oral or nasal inhalation, or by direct injection in or application to one or more cells, tissues, or organs.

Compositions may include liposomes, lipids, lipid complexes, microspheres, microparticles, nanospheres, and/or nanoparticles.

The formation and use of liposomes is generally known to those of skill in the art. Liposomes have been developed with improved serum stability and circulation half-times (see, for instance, U.S. Pat. No. 5,741,516). Further, various methods of liposome and liposome like preparations as potential drug carriers have been described (see, for instance U.S. Pat. Nos. 5,567,434; 5,552,157; 5,565,213; 5,738,868; and 5,795,587).

The disclosure also provides for pharmaceutically acceptable nanocapsule formulations of the physiologically active components. Nanocapsules can generally entrap compounds in a stable and reproducible way (Quintanar-Guerrero et al., Drug Dev Ind Pharm 24(12):1113-1128, 1998; Quintanar-Guerrero et al., Pharm Res. 15(7):1056-1062, 1998; Quintanar-Guerrero et al., J. Microencapsul. 15(1):107-119, 1998; Douglas et al., Crit Rev Ther Drug Carrier Syst 3(3):233-261, 1987). To avoid side effects due to intracellular polymeric overloading, such ultrafine particles can be designed using polymers able to be degraded in vivo. Biodegradable polyalkyl-cyanoacrylate nanoparticles that meet these requirements are contemplated for use in the present disclosure. Such particles can be easily made, as described in Couvreur et al., J Pharm Sci 69(2):199-202, 1980; Couvreur et al., Crit Rev Ther Drug Carrier Syst. 5(1)1-20, 1988; zur Muhlen et al., Eur J Pharm Biopharm, 45(2):149-155, 1998; Zambaux et al., J Control Release 50(1-3):31-40, 1998; and U.S. Pat. No. 5,145,684.

Injectable compositions can include sterile aqueous solutions or dispersions and sterile powders for the extemporaneous preparation of sterile injectable solutions or dispersions (U.S. Pat. No. 5,466,468). For delivery via injection, the form is sterile and fluid to the extent that it can be delivered by syringe. In particular embodiments, it is stable under the conditions of manufacture and storage, and optionally contains one or more preservative compounds against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In various embodiments, the preparation will include an isotonic agent(s), for example, sugar(s) or sodium chloride. Prolonged absorption of the injectable compositions can be accomplished by including in the compositions of agents that delay absorption, for example, aluminum monostearate and gelatin. Injectable compositions can be suitably buffered, if necessary, and the liquid diluent first rendered isotonic with sufficient saline or glucose.

Dispersions may also be prepared in glycerol, liquid polyethylene glycols, and mixtures thereof and in oils. As indicated, under ordinary conditions of storage and use, these preparations can contain a preservative to prevent the growth of microorganisms.

Sterile compositions can be prepared by incorporating the physiologically active component in an appropriate amount of a solvent with other optional ingredients (e.g., as enumerated above), followed by filtered sterilization. Generally, dispersions are prepared by incorporating the various sterilized physiologically active components into a sterile vehicle that contains the basic dispersion medium and the required other ingredients (e.g., from those enumerated above). In the case of sterile powders for the preparation of sterile injectable solutions, preferred methods of preparation can be vacuum-drying and freeze-drying techniques which yield a powder of the physiologically active components plus any additional desired ingredient from a previously sterile-filtered solution thereof.

Oral compositions may be in liquid form, for example, as solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Tablets may be coated by methods well-known in the art.

Inhalable compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions can also include microchip devices (U.S. Pat. No. 5,797,898), ophthalmic formulations (Bourlais et al., *Prog Retin Eye Res,* 17(1):33-58, 1998), transdermal matrices (U.S. Pat. Nos. 5,770,219 and 5,783,208) and feedback-controlled delivery (U.S. Pat. No. 5,697,899).

Supplementary active ingredients can also be incorporated into the compositions.

Typically, compositions can include at least 0.1% of the physiologically active components or more, although the percentage of the physiologically active components may, of course, be varied and may conveniently be between 1 or 2% and 70% or 80% or more or 0.5-99% of the weight or volume of the total composition. Naturally, the amount of physiologically active components in each physiologically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of compositions and dosages may be desirable.

In particular embodiments, for administration to humans, compositions should meet sterility, pyrogenicity, and the general safety and purity standards as required by United States Food and Drug Administration (FDA) or other applicable regulatory agencies in other countries.

(iii) Cell Lines Including Artificial Expression Constructs

The present disclosure includes cells including an artificial expression construct described herein. A cell that has been transformed with an artificial expression construct can be used for many purposes, including in neuroanatomical studies, assessments of functioning and/or non-functioning proteins, and drug screens that assess the regulatory properties of enhancers.

A variety of host cell lines can be used, but in particular embodiments, the cell is a mammalian cell. In particular embodiments, the artificial express construct includes an enhancer and/or a vector sequence of eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, and/or MGT_E83 and/or CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, and/or AiP1273, and the cell line is a human, primate, or murine cell. Cell lines which can be utilized for transgenesis in the present disclosure also include primary cell lines derived from living tissue such as rat or mouse brains and organotypic cell cultures, including brain slices from animals such as rats or mice. The PC12 cell line (available from the American Type Culture Collection, ATCC, Manassas, VA) has been shown to express a number of neuronal marker proteins in response to Neuronal Growth Factor (NGF). The PC12 cell line is considered to be a neuronal cell line and is applicable for use with this disclosure. JAR cells (available from ATCC) are a platelet derived cell-line that express some neuronal genes, such as the serotonin transporter gene, and may be used with embodiments described herein.

WO 91/13150 describes a variety of cell lines, including neuronal cell lines, and methods of producing them. Similarly, WO 97/39117 describes a neuronal cell line and methods of producing such cell lines. The neuronal cell lines disclosed in these patent applications are applicable for use in the present disclosure.

In particular embodiments, "neuronal" describes something that is of, related to, or includes, neuronal cells. Neuronal cells are defined by the presence of an axon and dendrites. The term "neuronal-specific" refers to something that is found, or an activity that occurs, in neuronal cells or cells derived from neuronal cells, but is not found in or occur in, or is not found substantially in or occur substantially in, non-neuronal cells or cells not derived from neuronal cells, for example glial cells such as astrocytes or oligodendrocytes.

In particular embodiments, non-neuronal cell lines may be used, including mouse embryonic stem cells. Cultured mouse embryonic stem cells can be used to analyze expression of genetic constructs using transient transfection with plasmid constructs. Mouse embryonic stem cells are pluripotent and undifferentiated. These cells can be maintained in this undifferentiated state by Leukemia Inhibitory Factor (LIF). Withdrawal of LIF induces differentiation of the embryonic stem cells. In culture, the stem cells form a variety of differentiated cell types. Differentiation is caused by the expression of tissue specific transcription factors, allowing the function of an enhancer sequence to be evaluated. (See for example Fiskerstrand et al., *FEBS Lett* 458: 171-174, 1999).

Methods to differentiate stem cells into neuronal cells include replacing a stem cell culture media with a media including basic fibroblast growth factor (bFGF) heparin, an N2 supplement (e.g., transferrin, insulin, progesterone, putrescine, and selenite), laminin and polyornithine. A process to produce myelinating oligodendrocytes from stem cells is described in Hu, et al., 2009, *Nat. Protoc.* 4:1614-22. Bibel, et al., 2007, *Nat. Protoc.* 2:1034-43 describes a protocol to produce glutamatergic neurons from stem cells while Chatzi, et al., 2009, *Exp Neurol.* 217:407-16 describes a procedure to produce GABAergic neurons. This procedure includes exposing stem cells to all-trans-RA for three days. After subsequent culture in serum-free neuronal induction medium including Neurobasal medium supplemented with B27, bFGF and EGF, 95% GABA neurons develop U.S. Publication No. 2012/0329714 describes use of prolactin to increase neural stem cell numbers while U.S. Publication No. 2012/0308530 describes a culture surface with amino groups that promotes neuronal differentiation into neurons, astrocytes and oligodendrocytes. Thus, the fate of neural stem cells can be controlled by a variety of extracellular factors. Commonly used factors include brain derived growth factor (BDNF; Shetty and Turner, 1998, *J. Neurobiol.* 35:395-425); fibroblast growth factor (bFGF; U.S. Pat. No. 5,766,948; FGF-1, FGF-2); Neurotrophin-3 (NT-3) and Neurotrophin-4 (NT-4); Caldwell, et al., 2001, *Nat. Biotechnol.* 1; 19:475-9); ciliary neurotrophic factor (CNTF); BMP-2 (U.S. Pat. Nos. 5,948,428 and 6,001,654); isobutyl 3-methylxanthine; leukemia inhibitory growth factor (LIF; U.S. Pat. No. 6,103,530); somatostatin; amphiregulin; neurotrophins (e.g., cyclic adenosine monophosphate; epidermal growth factor (EGF); dexamethasone (glucocorticoid hormone); forskolin; GDNF family receptor ligands; potassium; retinoic acid (U.S. Pat. No. 6,395,546); tetanus toxin; and transforming growth factor-α and TGF-β (U.S. Pat. Nos. 5,851,832 and 5,753,506).

In particular embodiments, yeast one-hybrid systems may also be used to identify compounds that inhibit specific protein/DNA interactions, such as transcription factors for eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, or MGT_E83.

Transgenic animals are described below. Cell lines may also be derived from such transgenic animals. For example, primary tissue culture from transgenic mice (e.g., also as described below) can provide cell lines with the artificial expression construct already integrated into the genome. (for an example see MacKenzie & Quinn, *Proc Natl Acad Sci USA* 96: 15251-15255, 1999).

(iv) Transgenic Animals

Another aspect of the disclosure includes transgenic animals, the genome of which contains an artificial expression construct including eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, and/or MGT_E83 operatively linked to a heterologous coding sequence. 1, 2, 4, 5, 6, 7, 8, 9, or 10 copy concatemers of disclosed enhancer cores can also be used. In particular embodiments, the genome of a transgenic animal CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, and/or AiP1273. In particular embodiments, when a non-integrating vector is utilized, a transgenic animal includes an artificial expression construct including eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, and/or MGT_E83 and/or CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, and/or AiP1273 within one or more of its cells. 1, 2, 4, 5, 6, 7, 8, 9, or 10 copy concatemers of disclosed enhancer cores can also be used.

Detailed methods for producing transgenic animals are described in U.S. Pat. No. 4,736,866. Transgenic animals may be of any nonhuman species, but preferably include nonhuman primates (NHPs), sheep, horses, cattle, pigs, goats, dogs, cats, rabbits, chickens, and rodents such as guinea pigs, hamsters, gerbils, rats, mice, and ferrets.

In particular embodiments, construction of a transgenic animal results in an organism that has an engineered construct present in all cells in the same genomic integration site. Thus, cell lines derived from such transgenic animals will be consistent in as much as the engineered construct will be in the same genomic integration site in all cells and hence will suffer the same position effect variegation. In contrast, introducing genes into cell lines or primary cell cultures can give rise to heterologous expression of the construct. A disadvantage of this approach is that the expression of the introduced DNA may be affected by the specific genetic background of the host animal.

As indicated above in relation to cell lines, the artificial expression constructs of this disclosure can be used to genetically modify mouse embryonic stem cells using techniques known in the art. Typically, the artificial expression construct is introduced into cultured murine embryonic stem cells. Transformed ES cells are then injected into a blastocyst from a host mother and the host embryo re-implanted into the mother. This results in a chimeric mouse whose tissues are composed of cells derived from both the embryonic stem cells present in the cultured cell line and the embryonic stem cells present in the host embryo. Usually the mice from which the cultured ES cells used for transgenesis are derived are chosen to have a different coat color from the host mouse into whose embryos the transformed cells are to be injected. Chimeric mice will then have a variegated coat color. As long as the germ-line tissue is derived, at least in part, from the genetically modified cells, then the chimeric mice crossed with an appropriate strain can produce offspring that will carry the transgene.

In addition to the methods of delivery described above, the following techniques are also contemplated as alternative methods of delivering artificial expression constructs to target cells or selected tissues and organs of an animal, and in particular, to cells, organs, or tissues of a vertebrate mammal: sonophoresis (e.g., ultrasound, as described in U.S. Pat. No. 5,656,016); intraosseous injection (U.S. Pat. No. 5,779,708); microchip devices (U.S. Pat. No. 5,797, 898); ophthalmic formulations (Bourlais et al., *Prog Retin Eye Res*, 17(1):33-58, 1998); transdermal matrices (U.S. Pat. Nos. 5,770,219 and 5,783,208); feedback-controlled delivery (U.S. Pat. No. 5,697,899), and any other delivery method available and/or described elsewhere in the disclosure.

(v) Methods of Use. In particular embodiments, a composition including a physiologically active component described herein is administered to a subject to result in a physiological effect.

In particular embodiments, the disclosure includes the use of the artificial expression constructs described herein to modulate expression of a heterologous gene which is either partially or wholly encoded in a location downstream to that enhancer in an engineered sequence. Thus, there are provided herein methods of use of the disclosed artificial expression constructs in the research, study, and potential development of medicaments for preventing, treating or ameliorating the symptoms of a disease, dysfunction, or disorder.

Particular embodiments include methods of administering to a subject an artificial expression construct that includes eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, and/or MGT_E83 and/or CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, and/or AiP1273 as described herein to drive selective expression of a gene in a selected cell type. 1, 2, 4, 5, 6, 7, 8, 9, or 10 copy concatemers of disclosed enhancer cores can also be used. The subject can be an isolated cell, a network of cells, a tissue slice, an experimental animal, a veterinary animal, or a human.

As is well known in the medical arts, dosages for any one subject depends upon many factors, including the subject's size, surface area, age, the particular compound to be administered, sex, time and route of administration, general health, and other drugs being administered concurrently. Dosages for the compounds of the disclosure will vary, but, in particular embodiments, a dose could be from $10^5$ to $10^{100}$ copies of an artificial expression construct of the disclosure. In particular embodiments, a patient receiving intravenous, intraparenchymal, intraspinal, retro-orbital, or intrathecal administration can be infused with from $10^6$ to $10^{22}$ copies of the artificial expression construct.

An "effective amount" is the amount of a composition necessary to result in a desired physiological change in the subject. Effective amounts are often administered for research purposes. Effective amounts disclosed herein can cause a statistically-significant effect in an animal model or in vitro assay.

The amount of expression constructs and time of administration of such compositions will be within the purview of the skilled artisan having benefit of the present teachings. It is likely, however, that the administration of effective amounts of the disclosed compositions may be achieved by a single administration, such as for example, a single injection of sufficient numbers of infectious particles to provide an effect in the subject. Alternatively, in some circumstances, it may be desirable to provide multiple, or successive administrations of the artificial expression construct compositions or other genetic constructs, either over a relatively short, or a relatively prolonged period of time, as may be determined by the individual overseeing the administration of such compositions. For example, the number of infectious particles administered to a mammal may be $10^7$, $10^8$, $10^9$, $10^{10}$, $10^{11}$, $10^{12}$, $10^{13}$, or even higher, infectious particles/ml given either as a single dose or divided into two or more administrations as may be required to achieve an intended effect. In fact, in certain embodiments, it may be desirable to administer two or more different expression constructs in combination to achieve a desired effect.

In certain circumstances it will be desirable to deliver the artificial expression construct in suitably formulated compositions disclosed herein either by pipette, retro-orbital injection, subcutaneously, intraocularly, intravitreally, parenterally, subcutaneously, intravenously, intraparenchymally, intracerebro-ventricularly, intramuscularly, intrathecally, intraspinally, intraperitoneally, by oral or nasal inhalation, or by direct application or injection to one or more cells, tissues, or organs. The methods of administration may also include those modalities as described in U.S. Pat. Nos. 5,543,158; 5,641,515 and 5,399,363.

(vi) Kits and Commercial Packages. Kits and commercial packages contain an artificial expression construct described herein. The artificial expression construct can be isolated. In particular embodiments, the components of an expression product can be isolated from each other. In particular embodiments, the expression product can be within a vector, within a viral vector, within a cell, within a tissue slice or sample, and/or within a transgenic animal. Such kits may further include one or more reagents, restriction enzymes, peptides, therapeutics, pharmaceutical compounds, or means for delivery of the compositions such as syringes, injectables, and the like.

Embodiments of a kit or commercial package will also contain instructions regarding use of the included components, for example, in basic research, electrophysiological research, neuroanatomical research, and/or the research and/or treatment of a disorder, disease or condition.

The Exemplary Embodiments and Experimental Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(vii) Exemplary Embodiments

1. A concatenated core including 2, 3, 4, 5, 6, 7, 8, 9, or 10 copies of SEQ ID NOs: 161, 163, or 165.

2. The concatenated enhancer or enhancer core of embodiment 1 wherein the concatenated enhancer or enhancer core includes SEQ ID NO: 162, 164, or 166.

3. An artificial expression construct including (i) an enhancer selected from eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, and MGT_E83; (ii) a promoter; and (iii) a heterologous encoding sequence.

4. The artificial expression construct of embodiment 3, wherein the heterologous encoding sequence encodes an effector element or an expressible element.

5. The artificial expression construct of embodiment 3 or 4, wherein the effector element includes a reporter protein or a functional molecule.

6. The artificial expression construct of embodiment 5, wherein the reporter protein includes a fluorescent protein.

7. The artificial expression construct of embodiment 5 or 6, wherein the functional molecule includes a functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a designer receptor exclusively activated by designer drug (DREADD).

8. The artificial expression construct of any of embodiments 4, wherein the expressible element includes a non-functional molecule.

9. The artificial expression construct of embodiment 8, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or a DREADD.

10. The artificial expression construct of any of embodiments 3-9, wherein the artificial expression construct is associated with a capsid that crosses the blood brain barrier.

11. The artificial expression construct of embodiment 10, wherein the capsid includes PHP.eB, AAV-BR1, AAV-PHP.S, AAV-PHP.B, or AAV-PPS.

12. The artificial expression construct of any of embodiments 3-11, wherein the artificial expression construct includes or encodes a skipping element.

13. The artificial expression construct of embodiment 12, wherein the skipping element includes a 2A peptide and/or an internal ribosome entry site (IRES).

14. The artificial expression construct of embodiment 13, wherein the 2A peptide includes T2A, P2A, E2A, or F2A.

15. The artificial expression construct of any of embodiments 2-14, wherein the artificial expression construct includes or encodes a set of features selected from: eHGT_089h, eHGT_087h, eHGT_154h, eHGT_226h, eHGT_526h, eHGT_512h, eHGT_283h, eHGT_090m, eHGT_076h, eHGT_072h, eHGT_354h, eHGT_354m, eHGT_121h, eHGT_133h, eHGT_219h, eHGT_207h, eHGT_113m, eHGT_111m, eHGT_110h, eHGT_080h, eHGT_060m, eHGT_060h, MGT_E36, MGT_E37, MGT_E41, eHGT_025h, eHGT_096h, eHGT_098h, eHGT_104m, eHGT_107h, eHGT_340m, eHGT_528h, eHGT_515h, 3xCore2_eHGT_226h, 3xCore3_eHGT_226h, eHGT_682h, eHGT_600m, eHGT_759m, eHGT_468m, 3xCore_eHGT_064h, eHGT_170h, eHGT_131hv1, eHGT_519h, eHGT_131hv2, eHGT_130h, eHGT_527h, eHGT_470m, eHGT_174h, eHGT_087m, eHGT_156h, eHGT_338m, eHGT_341m, eHGT_339m, MGT_E81, MGT_E85, MGT_E88, MGT_E83, hsA2, AAV, scAAV, rAAV, minBglobin, CMV, minCMV, minRho, minRho*, fluorescent protein (e.g., EGFP, SYFP, GFP), Cre, iCre, dgCre, FlpO, tTA2, SP10 (e.g., 3xSP10), WPRE, WPRE3, hGHpA, and/or BGHpA.

16. The artificial expression construct of any of embodiments 2-15, wherein the artificial expression construct includes or encodes a set of features selected from:

hsA2-eHGT_089h-minRho-[heterologous encoding sequence]-WPRE3-BGHpA;

hsA2-eHGT_087h-minRho-[heterologous encoding sequence]-WPRE3-BGHpA;

hsA2-eHGT_154h-minRho-[heterologous encoding sequence]-WPRE3-BGHpA;

hsA2-eHGT_226h-minRho-[heterologous encoding sequence]-WPRE3-BGHpA;

eHGT_526h-minBglobin-[heterologous encoding sequence]-WPRE3-BGHpA;

eHGT_512h-minBglobin-[heterologous encoding sequence]-WPRE3-BGHpA;

hsA2-eHGT_283h-minRho-[heterologous encoding sequence]-WPRE3-BGHpA;

hsA2-eHGT_090m-minRho-[heterologous encoding sequence]-WPRE3-BGHpA;

eHGT_076h-minBglobin-[heterologous encoding sequence]-WPRE3-BGHpA;

eHGT_072h-minBglobin-[heterologous encoding sequence]-WPRE3-BGHpA;

3xSP10ins-eHGT_354h-minRho*-[heterologous encoding sequence]-WPRE3-BGHpA;

3xSP10ins-eHGT_354m-minRho*-[heterologous encoding sequence]-WPRE3-BGHpA;

hsA2-eHGT_121h-minRho-[heterologous encoding sequence]-WPRE3-BGHpA;

hsA2-eHGT_133h-minRho-[heterologous encoding sequence]-WPRE3-BGHpA;

hsA2-eHGT_219h-minRho-[heterologous encoding sequence]-WPRE3-BGHpA;

hsA2-eHGT_207h-minRho-[heterologous encoding sequence]-WPRE3-BGHpA;

hsA2-eHGT_113m-minRho-[heterologous encoding sequence]-WPRE3-BGHpA;

hsA2-eHGT_111m-minRho-[heterologous encoding sequence]-WPRE3-BGHpA;

hsA2-eHGT_110h-minRho-[heterologous encoding sequence]-WPRE3-BGHpA;

hsA2-eHGT_080h-minRho-[heterologous encoding sequence]-WPRE3-BGHpA;

eHGT_060m-minBglobin-[heterologous encoding sequence]-WPRE3-BGHpA;

eHGT_060h-minBglobin-[heterologous encoding sequence]-WPRE3-BGHpA;

MGT_E36-minBglobin-[heterologous encoding sequence]-WPRE-hGHpA;

MGT_E37-minBglobin-[heterologous encoding sequence]-WPRE-hGHpA;

MGT_E41-minBglobin-[heterologous encoding sequence]-WPRE-hGHpA;

eHGT_025h-minBGlobin-[heterologous encoding sequence]-WPRE3-BGHpA;

hsA2-eHGT_096h-minRho-[heterologous encoding sequence]-WPRE3-BGHpA;

hsA2-eHGT_098h-minRho-[heterologous encoding sequence]-WPRE3-BGHpA;

hsA2-eHGT_104m-minRho-[heterologous encoding sequence]-WPRE3-BGHpA;

hsA2-eHGT_107h-minRho-[heterologous encoding sequence]-WPRE3-BGHpA;

3xSP10ins-eHGT_340m-minRho*-[heterologous encoding sequence]-WPRE3-BGHpA;

eHGT_528h-minBglobin-[heterologous encoding sequence]-WPRE3-BGHpA;

eHGT_515h-minBglobin-[heterologous encoding sequence]-WPRE3-BGHpA;

3xCore2_eHGT_226h-minBglobin-[heterologous encoding sequence]-WPRE3-BGHpA;

3xCore3_eHGT_226h-minBglobin-[heterologous encoding sequence]-WPRE3-BGHpA;

eHGT_682h-minBglobin-[heterologous encoding sequence]-WPRE3-BGHpA;

eHGT_600m-minBG-[heterologous encoding sequence]-WPRE3-BGHpA;

eHGT_759m-minBglobin-[heterologous encoding sequence]-WPRE3-BGHpA;

eHGT_468m-minBglobin-[heterologous encoding sequence]-WPRE3-BGHpA;

3xCore_eHGT_064h_minBglobin-[heterologous encoding sequence]-WPRE3-BGHpA;

hsA2-eHGT_170h-minRho-[heterologous encoding sequence]-WPRE3-BGHpA;

eHGT_131hv1-minBglobin-[heterologous encoding sequence]-WPRE3-BGHpA;

eHGT_519h-minBglobin-[heterologous encoding sequence]-WPRE3-BGHpA;

hsA2-eHGT_131hv2-minRho-[heterologous encoding sequence]-WPRE3-BGHpA;

eHGT_130h-minBglobin-[heterologous encoding sequence]-WPRE3-BGHpA;

eHGT_527h-minBglobin-[heterologous encoding sequence]-WPRE3-BGHpA;

eHGT_470m-minBglobin-[heterologous encoding sequence]-WPRE3-BGHpA;

hsA2-eHGT_174h-minRho-[heterologous encoding sequence]-WPRE3-BGHpA;

hsA2-eHGT_087m-minRho-[heterologous encoding sequence]-WPRE3-BGHpA;

hsA2-eHGT_156h-minRho-[heterologous encoding sequence]-WPRE3-BGHpA;

pAAV-eHGT_338m-minBGprom-[heterologous encoding sequence]-WPRE-hGHpA;

pAAV-eHGT_341m-monBGprom-[heterologous encoding sequence]-WPRE-hGHpA;

pAAV-eHGT_339m-minBGprom-[heterologous encoding sequence]-WPRE-hGHpA;

pAAV-MGT_E81-minBGprom-[heterologous encoding sequence]-WPRE3-bGHpA;

pAAV-MGT_E85-minBGprom-[heterologous encoding sequence]-WPRE3-bGHpA;

pAAV-MGT_E88-minBGprom-[heterologous encoding sequence]-WPRE3-bGHpA;

pAAV-MGT_E83-minBGprom-[heterologous encoding sequence]-WPRE3-bGHpA; eHGT_089h-promoter-[heterologous encoding sequence]-[post-regulatory element(s)];

eHGT_087h-promoter-[heterologous encoding sequence]-[post-regulatory element(s)];

eHGT_154h-promoter-[heterologous encoding sequence]-[post-regulatory element(s)];

eHGT_226h-promoter-[heterologous encoding sequence]-[post-regulatory element(s)];

eHGT_526h-promoter-[heterologous encoding sequence]-[post-regulatory element(s)];

eHGT_512h-promoter-[heterologous encoding sequence]-[post-regulatory element(s)];

eHGT_283h-promoter-[heterologous encoding sequence]-[post-regulatory element(s)];

eHGT_090m-promoter-[heterologous encoding sequence]-[post-regulatory element(s)];

eHGT_076h-promoter-[heterologous encoding sequence]-[post-regulatory element(s)];

eHGT_072h-promoter-[heterologous encoding sequence]-[post-regulatory element(s)];

3xSP10ins-eHGT_354h-promoter-[heterologous encoding sequence]-[post-regulatory element(s)];

3xSP10ins-eHGT_354m-v-[heterologous encoding sequence]-[post-regulatory element(s)];

eHGT_121h-promoter-[heterologous encoding sequence]-[post-regulatory element(s)];

eHGT_133h-promoter-[heterologous encoding sequence]-[post-regulatory element(s)];

eHGT_219h-v-[heterologous encoding sequence]-[post-regulatory element(s)];

eHGT_207h-promoter-[heterologous encoding sequence]-[post-regulatory element(s)];

eHGT_113m-promoter-[heterologous encoding sequence]-[post-regulatory element(s)];

eHGT_111m-promoter-[heterologous encoding sequence]-[post-regulatory element(s)];

eHGT_110h-promoter-[heterologous encoding sequence]-[post-regulatory element(s)];

eHGT_080h-promoter-[heterologous encoding sequence]-[post-regulatory element(s)];

eHGT_060m-promoter-[heterologous encoding sequence]-[post-regulatory element(s)];

eHGT_060h-promoter-[heterologous encoding sequence]-[post-regulatory element(s)];

MGT_E36-promoter-[heterologous encoding sequence]-[post-regulatory element(s)];

MGT_E37-promoter-[heterologous encoding sequence]-[post-regulatory element(s)];

MGT_E41-promoter-[heterologous encoding sequence]-[post-regulatory element(s)];

eHGT_025h-minBGlobin-[heterologous encoding sequence]-[post-regulatory element(s)];

hsA2-eHGT_096h-minRho-[heterologous encoding sequence]-[post-regulatory element(s)];

hsA2-eHGT_098h-minRho-[heterologous encoding sequence]-[post-regulatory element(s)];

hsA2-eHGT_104m-minRho-[heterologous encoding sequence]-[post-regulatory element(s)];

hsA2-eHGT_107h-minRho-[heterologous encoding sequence]-[post-regulatory element(s)];

3xSP10ins-eHGT_340m-minRho*-[heterologous encoding sequence]-[post-regulatory element(s)];

eHGT_528h-minBglobin-[heterologous encoding sequence]-[post-regulatory element(s)];

eHGT_515h-minBglobin-[heterologous encoding sequence]-[post-regulatory element(s)];

3xCore2_eHGT_226h-minBglobin-[heterologous encoding sequence]-[post-regulatory element(s)];

3xCore3_eHGT_226h-minBglobin-[heterologous encoding sequence]-[post-regulatory element(s)];

eHGT_682h-minBglobin-[heterologous encoding sequence]-[post-regulatory element(s)];

eHGT_600m-minBG-[heterologous encoding sequence]-[post-regulatory element(s)];

eHGT_759m-minBglobin-[heterologous encoding sequence]-[post-regulatory element(s)];

eHGT_468m-minBglobin-[heterologous encoding sequence]-[post-regulatory element(s)];

3xCore_eHGT_064h_minBglobin-[heterologous encoding sequence]-[post-regulatory element(s)];

hsA2-eHGT_170h-minRho-[heterologous encoding sequence]-[post-regulatory element(s)];

eHGT_131hv1-minBglobin-[heterologous encoding sequence]-[post-regulatory element(s)];

eHGT_519h-minBglobin-[heterologous encoding sequence]-[post-regulatory element(s)];

hsA2-eHGT_131hv2-minRho-[heterologous encoding sequence]-[post-regulatory element(s)];

eHGT_130h-minBglobin-[heterologous encoding sequence]-[post-regulatory element(s)];

eHGT_527h-minBglobin-[heterologous encoding sequence]-[post-regulatory element(s)];

eHGT_470m-minBglobin-[heterologous encoding sequence]-[post-regulatory element(s)];

hsA2-eHGT_174h-minRho-[heterologous encoding sequence]-[post-regulatory element(s)];

hsA2-eHGT_087m-minRho-[heterologous encoding sequence]-[post-regulatory element(s)];

hsA2-eHGT_156h-minRho-[heterologous encoding sequence]-[post-regulatory element(s)];

pAAV-eHGT_338m-minBGprom-[heterologous encoding sequence]-[post-regulatory element(s)];

pAAV-eHGT_341m-monBGprom-[heterologous encoding sequence]-[post-regulatory element(s)];

pAAV-eHGT_339m-minBGprom-[heterologous encoding sequence]-[post-regulatory element(s)];

pAAV-MGT_E81-minBGprom-[heterologous encoding sequence]-[post-regulatory element(s)];

pAAV-MGT_E85-minBGprom-[heterologous encoding sequence]-[post-regulatory element(s)];

pAAV-MGT_E88-minBGprom-[heterologous encoding sequence]-[post-regulatory element(s)];

pAAV-MGT_E83-minBGprom-[heterologous encoding sequence]-[post-regulatory element(s)];

hsA2-eHGT_089h-minRho-SYFP2-WPRE3-BGHpA;

hsA2-eHGT_087h-minRho-SYFP2-WPRE3-BGHpA;

hsA2-eHGT_154h-minRho-SYFP2-WPRE3-BGHpA;

hsA2-eHGT_226h-minRho-SYFP2-WPRE3-BGHpA;

eHGT_526h-minBglobin-SYFP2-WPRE3-BGHpA;

eHGT_512h-minBglobin-SYFP2-WPRE3-BGHpA;

hsA2-eHGT_283h-minRho-SYFP2-WPRE3-BGHpA;

hsA2-eHGT_090m-minRho-SYFP2-WPRE3-BGHpA;
eHGT_076h-minBglobin-SYFP2-WPRE3-BGHpA;
eHGT_072h-minBglobin-SYFP2-WPRE3-BGHpA;
3xSP10ins-eHGT_354h-minRho*-SYFP2-WPRE3-
   BGHpA;
3xSP10ins-eHGT_354m-minRho*-SYFP2-WPRE3-
   BGHpA;
hsA2-eHGT_121h-minRho-SYFP2-WPRE3-BGHpA;
hsA2-eHGT_133h-minRho-SYFP2-WPRE3-BGHpA;
hsA2-eHGT_219h-minRho-SYFP2-WPRE3-BGHpA;
hsA2-eHGT_207h-minRho-SYFP2-WPRE3-BGHpA;
hsA2-eHGT_113m-minRho-SYFP2-WPRE3-BGHpA;
hsA2-eHGT_111m-minRho-SYFP2-WPRE3-BGHpA;
hsA2-eHGT_110h-minRho-SYFP2-WPRE3-BGHpA;
hsA2-eHGT_080h-minRho-SYFP2-WPRE3-BGHpA;
eHGT_060m-minBglobin-SYFP2-WPRE3-BGHpA;
eHGT_060h-minBglobin-SYFP2-WPRE3-BGHpA;
MGT_E36-minBglobin-FlpO-WPRE-hGHpA;
MGT_E37-minBglobin-FlpO-WPRE-hGHpA;
MGT_E41-minBglobin-FlpO-WPRE-hGHpA;
eHGT_025h-minBGlobin-SYFP2-WPRE3-BGHpA;
hsA2-eHGT_096h-minRho-SYFP2-WPRE3-BGHpA;
hsA2-eHGT_098h-minRho-SYFP2-WPRE3-BGHpA;
hsA2-eHGT_104m-minRho-SYFP2-WPRE3-BGHpA;
hsA2-eHGT_107h-minRho-SYFP2-WPRE3-BGHpA;
3xSP10ins-eHGT_340m-minRho*-SYFP2-WPRE3-
   BGHpA;
eHGT_528h-minBglobin-SYFP2-WPRE3-BGHpA;
eHGT_515h-minBglobin-SYFP2-WPRE3-BGHpA;
3xCore2_eHGT_226h-minBglobin-SYFP2-WPRE3-
   BGHpA;
3xCore3_eHGT_226h-minBglobin-SYFP2-WPRE3-
   BGHpA;
eHGT_682h-minBglobin-SYFP2-WPRE3-BGHpA;
eHGT_600m-minBG-SYFP2-WPRE3-BGHpA;
eHGT_759m-minBglobin-SYFP2-WPRE3-BGHpA;
eHGT_468m-minBglobin-SYFP2-WPRE3-BGHpA;
3xCore_eHGT_064h_minBglobin-SYFP2-WPRE3-
   BGHpA;
hsA2-eHGT_170h-minRho-SYFP2-WPRE3-BGHpA;
eHGT_131hv1-minBglobin-SYFP2-WPRE3-BGHpA;
eHGT_519h-minBglobin-SYFP2-WPRE3-BGHpA;
hsA2-eHGT_131hv2-minRho-SYFP2-WPRE3-BGHpA;
eHGT_130h-minBglobin-SYFP2-WPRE3-BGHpA;
eHGT_527h-minBglobin-SYFP2-WPRE3-BGHpA;
eHGT_470m-minBglobin-SYFP2-WPRE3-BGHpA;
hsA2-eHGT_174h-minRho-SYFP2-WPRE3-BGHpA;
hsA2-eHGT_087m-minRho-SYFP2-WPRE3-BGHpA;
hsA2-eHGT_156h-minRho-SYFP2-WPRE3-BGHpA;
pAAV-eHGT_338m-minBGprom-FlpO-WPRE-hGHpA;
pAAV-eHGT_341rm-monBGprom-FlpO-WPRE-
   hGHpA;
pAAV-eHGT_339m-minBGprom-FlpO-WPRE-hGHpA;
pAAV-MGT_E81-minBGprom-SYFP2-WPRE3-
   bGHpA;
pAAV-MGT_E85-minBGprom-SYFP2-WPRE3-
   bGHpA;
pAAV-MGT_E88-minBGprom-SYFP2-WPRE3-
   bGHpA; or
pAAV-MGT_E83-minBGprom-SYFP2-WPRE3-
   bGHpA.

17. A vector including an artificial expression construct of
   any of embodiments 2-16.
18. The vector of embodiment 17, wherein the vector
   includes a viral vector.

19. The vector of embodiment 17 or 18, wherein the viral
   vector includes a recombinant adeno-associated viral
   (AAV) vector.
20. An adeno-associated viral (AAV) vector including at
   least one heterologous encoding sequence, wherein the
   heterologous encoding sequence is under control of a
   promoter and an enhancer selected from eHGT_089h,
   eHGT_087h, eHGT_154h, eHGT_226h, eHGT_526h,
   eHGT_512h, eHGT_283h, eHGT_090m, eHGT_076h,
   eHGT_072h, eHGT_354h, eHGT_354m, eHGT_121h,
   eHGT_133h, eHGT_219h, eHGT_207h, eHGT_113m,
   eHGT_111m,      eHGT_110h,      eHGT_080h,
   eHGT_060m, eHGT_060h, MGT_E36, MGT_E37,
   MGT_E41, eHGT_025h, eHGT_096h, eHGT_098h,
   eHGT_104m,      eHGT_107h,      eHGT_340m,
   eHGT_528h,  eHGT_515h,  3xCore2_eHGT_226h,
   3xCore3_eHGT_226h,  eHGT_682h,  eHGT_600m,
   eHGT_759m,  eHGT_468m,  3xCore_eHGT_064h,
   eHGT_170h,      eHGT_131hv1,      eHGT_519h,
   eHGT_131hv2,      eHGT_130h,      eHGT_527h,
   eHGT_470m,      eHGT_174h,      eHGT_087m,
   eHGT_156h,      eHGT_338m,      eHGT_341m,
   eHGT_339m, MGT_E81, MGT_E85, MGT_E88, and
   MGT_E83.
21. A transgenic cell including an expression construct or
   vector of any of the preceding embodiments.
22. The transgenic cell of embodiment 21, wherein the
   transgenic cell is a somatostatin (Sst) GABAergic
   neuron, a parvalbumin (Pvalb) GABAergic neuron, a
   pvalb/Sst GABAergic neuron, a vasointestinal peptide
   (VIP) GABAergic neuron, a Lamp5 GABAergic neu-
   ron, or an astrocyte.
23. The transgenic cell of embodiment 22, wherein the
   transgenic cell is a Lamp5_Lhx6 GABAergic neuron.
24. A non-human transgenic animal including an artificial
   expression construct, vector, or transgenic cell of any of
   the preceding embodiments.
25. The non-human transgenic animal of embodiment 24,
   wherein the non-human transgenic animal is a mouse or
   a non-human primate.
26. An administrable composition including an expression
   construct, vector, or transgenic cell of any of the
   preceding embodiments.
27. A kit including an artificial expression construct,
   vector, transgenic cell, transgenic animal, and/or
   administrable compositions of any of the preceding
   embodiments.
28. A method for selectively expressing a heterologous
   gene within a population of cells in vivo or in vitro, the
   method including providing the administrable compo-
   sition of embodiment 26 in a sufficient dosage and for
   a sufficient time to a sample or subject including the
   population of cells thereby selectively expressing the
   gene within the population of cells.
29. The method of embodiment 28, wherein the heterolo-
   gous gene encodes an effector element or an express-
   ible element.
30. The method of embodiment 29, wherein the effector
   element includes a reporter protein or a functional
   molecule.
31. The method of embodiment 30, wherein the reporter
   protein includes a fluorescent protein.
32. The method of embodiments 30 or 31, wherein the
   functional molecule includes a functional ion trans-
   porter, enzyme, transcription factor, receptor, mem-
   brane protein, cellular trafficking protein, signaling
   molecule, neurotransmitter, calcium reporter, channelrhodopsin, CRISPR/CAS molecule, editase, guide RNA molecule, microRNA, homologous recombination donor cassette, or a DREADD.

33. The method of embodiment 29, wherein the expressible element includes a non-functional molecule.

34. The method of embodiment 33, wherein the non-functional molecule includes a non-functional ion transporter, enzyme, transcription factor, receptor, membrane protein, cellular trafficking protein, signaling molecule, neurotransmitter, calcium reporter, channelrhodopsin, CRISPR/CAS molecule, editase, guide RNA molecule, microRNA, homologous recombination donor cassette, or DREADD.

35. The method of any of embodiments 28-34, wherein the providing includes pipetting.

36. The method of embodiment 35, wherein the pipetting is to a brain slice.

37. The method of embodiment 36, wherein the brain slice includes an Sst GABAergic neuron, a pvalb GABAergic neuron, a pvalb/Sst GABAergic neuron, a VIP GABAergic neuron, a LAMP5 GABAergic neuron, and/or an astrocyte.

38. The method of embodiment 36 of 37, wherein the brain slice includes a Lamp5_Lhx6 GABAergic neuron.

39. The method of any of embodiments 36-38, wherein the brain slice is murine, human, or non-human primate.

40. The method of any of embodiments 28-34, wherein the providing includes administering to a living subject.

41. The method of embodiment 40, wherein the living subject is a human, non-human primate, or a mouse.

42. The method of embodiments 40 or 41, wherein the administering to a living subject is through injection.

43. The method of embodiment 42, wherein the injection includes intravenous injection, intraparenchymal injection into brain tissue, intracerebroventricular (ICV) injection, intra-cisterna magna (ICM) injection, or intrathecal injection.

44. An artificial expression construct including CN1535, CN1533, CN1647, CN1719, CN2365, CN2355, CN1797, CN1584, CN1455, CN1451, CN2039, CN2040, CN1567, CN1626, CN1712, CN1700, CN1607, CN1605, CN1556, CN1526, CN1418, CN1404, AiV1173, AiV1174, AiV1177, CN1261, CN1542, CN1544, CN1598, CN1553, CN1992, CN2367, CN2357, CN2568, CN2569, CN2689, CN2408, CN2596, CN2317, CN2571, CN1663, CN2310, CN2360, CN1624, CN2309, CN2366, CN2257, CN1667, CN1581, CN1649, AiP1099, AiP1102, AiP1100, AiP1270, AiP1271, AiP1272, or AiP1273.

45. Any of embodiments 3-44 utilizing a core or concatenated core of embodiment 1 or 2.

(ix) Closing Paragraphs

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (lie), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (nonpolar): Proline (Pro), Ala, Val, Leu, lie, Phe, Met, and Trp; Group 11 (aliphatic): Gly, Ala, Val, Leu, and lie; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3 M NaCl; 0.2 M $NaH_2PO_4$; 0.02 M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in selective expression in the targeted cell population as determined by scRNA-Seq and the following enhancer/targeted cell population pairings: eHGT_089h, eHGT_087h, eHGT_154h, eHGT_226h, eHGT_526h, eHGT_512h, eHGT_283h, eHGT_090m, eHGT_340m, eHGT_528h, eHGT_515h, eHGT_226h, eHGT_170h, eHGT_519h, eHGT_527h, eHGT_470m, eHGT_174h, eHGT_087m, and eHGT_156h/Sst GABAergic neurons; eHGT_076h, eHGT_759m, and eHGT_064h/Pvalb/Sst GABAergic neurons; eHGT_072h, eHGT_131hv1, eHGT_131hv2, and eHGT_130h/Pvalb GABAergic neurons; eHGT_354h, eHGT_121h, eHGT_133h, eHGT_219h, eHGT_207h, eHGT_113m, eHGT_111m, eHGT_110h, eHGT_080h, eHGT_107h, MGT_E81, MGT_E85, MGT_E88, and MGT_E83/VIP GABAergic neurons; MGT_E36, MGT_E37, and MGT_E41/Lamp5 Lhx6 GABAergic neurons; and eHGT_354m, eHGT_060m, eHGT_060h/VIP GABAergic neurons and astrocytes; eHGT_025h, eHGT_096h, eHGT_098h, and eHGT_104m/Lamp5 GABAergic neurons; eHGT_682h, eHGT_600m, eHGT_468m, eHGT_338m, eHGT_341m, and eHGT_339m/Sst and Chodl GABAergic neurons.

In particular embodiments, artificial means not naturally occurring.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; 16% of the stated value; ±15% of the stated value; 14% of the stated value; ±13% of the stated value; 12% of the stated value; 11% of the stated value; 10% of the stated value; 9% of the stated value; 8% of the stated value; 7% of the stated value; ±6% of the stated value; 5% of the stated value; 4% of the stated value; ±3% of the stated value; 2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An artificial expression construct comprising (i) an enhancer selected from SEQ ID NO: 11, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 162, SEQ ID NO: 164, SEQ ID NO: 140, SEQ ID NO: 141, SEQ ID NO: 142, SEQ ID NO: 143, SEQ ID NO: 166, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 163, and SEQ ID NO: 165 or a sequence having at least 95% sequence identity to the sequence as set forth in any of SEQ ID NOs: 1-25, 132-166; (ii) a promoter; and (iii) a heterologous encoding sequence.

2. The artificial expression construct of claim 1, wherein the heterologous encoding sequence encodes a fluorescent protein.

3. The artificial expression construct of claim 1, wherein the heterologous encoding sequence encodes a neurotransmitter.

4. The artificial expression construct of claim 1, wherein the artificial expression construct is associated with a capsid that crosses the blood brain barrier.

5. The artificial expression construct of claim 4, wherein the capsid comprises PHP.eB, AAV9, AAVrh.10, AAV-BR1, AAV-PHP.S, AAV-PHP.B, or AAV-PPS.

6. The artificial expression construct of claim 1, wherein the artificial expression construct includes or encodes a skipping element.

7. The artificial expression construct of claim 6, wherein the skipping element comprises a T2A peptide, P2A peptide, E2A peptide, F2A peptide, or an internal ribosome entry site (IRES).

8. The artificial expression construct of claim 1, wherein the artificial expression construct is within a viral vector.

9. The artificial expression construct of claim 8, wherein the viral vector comprises a recombinant adeno-associated viral (AAV) vector.

10. A method for selectively expressing a heterologous encoding sequence within a population of cells in vivo or in vitro, the method comprising providing an administrable composition comprising an artificial expression construct, wherein the artificial expression construct comprises (i) and enhancer having a sequence as set forth in SEQ ID NO: 11, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 162, SEQ ID NO: 163, SEQ ID NO: 140, SEQ ID NO: 141, SEQ ID NO: 142, SEQ ID NO: 143, SEQ ID NO: 166, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 163, and SEQ ID NO: 165 or a sequence having at least 95% sequence identity to the sequence as set forth in any of SEQ ID NOs: 1-25, 132-166; (ii) a promoter; and (iii) a heterologous encoding sequence in a sufficient dosage and for a sufficient time to a sample or subject comprising the population of cells thereby selectively expressing the heterologous encoding sequence within the population of cells.

11. The method of claim 10, wherein the heterologous encoding sequence encodes a fluorescent protein or a neurotransmitter.

12. The method of claim 10, wherein the providing comprises pipetting to a brain slice.

13. The method of claim 12, wherein the brain slice comprises an Sst GABAergic neuron, a Pvalb GABAergic neuron, a Pvalb/Sst GABAergic neuron, a Vip GABAergic neuron, a Lamp5 GABAergic neuron, and/or an astrocyte.

14. The method of claim 12, wherein the brain slice comprises a Lamp5_Lhx6 GABAergic neuron.

15. The method of claim 10, wherein the providing comprises administering to a living subject.

16. The method of claim 15, wherein the living subject is a human, non-human primate, or a mouse.

17. The method of claim 15, wherein the administering to a living subject is through injection.

18. The method of claim 17, wherein the injection comprises intravenous injection, intraparenchymal injection into brain tissue, intracerebroventricular (ICV) injection, intra-cisterna magna (ICM) injection, or intrathecal injection.

19. An artificial enhancer comprising 1, 2, 3, 4, 5, 6, 7, 8, 9, or 10 copies of a sequence as set forth in SEQ ID NO: 161, SEQ ID NO: 163, or SEQ ID NO: 165 or a sequence having at least 95% sequence identity to the sequence as set forth in SEQ ID NO: 161, SEQ ID NO: 163, or SEQ ID NO: 165.

20. The artificial enhancer of claim 19, comprising the sequence as set forth in SEQ ID NO: 162, SEQ ID NO: 164, or SEQ ID NO: 166 or a sequence having at least 95% sequence identity to the sequence as set forth in SEQ ID NO: 162, SEQ ID NO: 164, or SEQ ID NO: 166.

* * * * *

SEQUENCE LISTING

```
<160> NUMBER OF SEQ ID NOS: 204

<210> SEQ ID NO 1
<211> LENGTH: 643
<212> TYPE: DNA
<213> ORGANISM: Homo sapiens
```

-continued

<400> SEQUENCE: 1

```
ttccagcttc ttccctaaca attcctaaga aatgttattg ctagttagaa atgctttatc      60
ttttcttcta tcatatccaa tgaaggcctg atcttacaga gtctaaacaa ttgcagtaaa     120
tacattccag atttcagcag cactttacca acacttgtga atcgctgtca ttcttccagg     180
attcagttta agagtggcaa ttacaagtca ctttaatgtc tgaggaaagg atggaaagca     240
agccctgcaa atagaaggcc acatttactc ttttcaaacc acagctcaaa ctatcagagg     300
aaaatacagt ttttatgtaa gcgctcaaac agtttttcccc aaatcttgca gaatccatta     360
cttttaagaa atttccacat gaatagacca aacgaatcag gcatactaat actttgtaca     420
tgcacacaca caagtgccag ttccatatca tactgtcaca aactctagag ctaaacacat     480
tcacacgctt cggattaaat gatcagggta gaaatatgca ttgtgaataa aataacttac     540
ctatcttacc tataaaattc cccatttcag ttgttttctg ccactgccac ttttgaagtt     600
atcctcaact gaactctttg tacacattcc tgcaaaccag ctc                       643
```

<210> SEQ ID NO 2
<211> LENGTH: 530
<212> TYPE: DNA
<213> ORGANISM: Homo sapiens

<400> SEQUENCE: 2

```
aatggggcct cagtttctcc cttgggatta agtgggtacc aggcaggaca aaataagcca      60
cctgtgccat tctacccttt ccatcctgct gtttttccac cctgcagctg ctttctcaaa     120
gaatccctga atctcctctc taaatagtgc aagcttgctg ttgggaacac ccacagatgc     180
actctacaaa tacacaactc actttgagta atcatattga ttcggaatta tcggccattc     240
aaatacctca ttgaagatgc catctgggat gttattgctc ttcagaggta gatcatattc     300
tgagaaaatc tgtcaaaatg tagaaataac tcatcaaaat ggccattgca gaatctagct     360
gcacttctta aggaagcaga ctctgatgct gcgggtttca ttgcccctaa gtgagatgct     420
gaaggaagaa gggctgtttc ttttctgttt tcaagtgtca tgagaaattt aaagttcagg     480
aatgtgcaag ttcagagtgc tcctggactc ctttgctcat tcagagacat                 530
```

<210> SEQ ID NO 3
<211> LENGTH: 433
<212> TYPE: DNA
<213> ORGANISM: Homo sapiens

<400> SEQUENCE: 3

```
ttctttccag ttccacgtag ccttgaaaac cataactttg caaatacagg agttgtgaaa      60
acgagcatcc tagaagtcac tgtaagggca gaatgtgttt ggagaaagtc ccattcccag     120
aaaattgtca ctatttagcc catctgaaag tcgcataaaa agctctactg tcgacatttg     180
tctttatttg agctgattca gagcttgctt tgtgcaacta gcacaaccca tcagaggcaa     240
ttgcttaata ttgcagctgc cttcagtgga gattccagtt gtgactaaca agaagctgtt     300
ttagaaaaat aaaataccct taaaaataaa aactaataca ctcatggaaa cctaaaaaaa     360
ttatgcatat gattagggtt gtgaatacac ttaggaaaga cctaagaggg ccctaatctc     420
tcacagctgg ctg                                                        433
```

<210> SEQ ID NO 4
<211> LENGTH: 733
<212> TYPE: DNA

```
<213> ORGANISM: Homo sapiens

<400> SEQUENCE: 4
cacatttctc atgaagctga ggtagcccag cattctctac tttagaaatc tggatgtatt      60
ttttcctcat gggtctgtaa ttgagtccgt aattgacatt tgtacacttt taagataaat     120
ctagcctgtc ttcaagtata ttttagatct agtgaaatac agagtactat agattagata     180
ttctgaatat catctgtttg ttatttagta atgtgatatg ccttgtgtac ccacttttgt     240
atttaccatt attgcaaaat caatcaaatg tgagcaaaag caaaggcaat ttgaatgact     300
caaaattgaa atttgagctg ccaaatcaag cagtaaaaca attttttacca gctctattga    360 ttgttagaaa gataagttat aaactttatt tcaagtaaat ttctaaaaga tctgggaatg     420
tgattattcc aaggcagatg gcgaagacct ttatttccac tgattattca cagatgcaaa     480
ttattatgca actggaagca tactaagata ttgcaaagat gttctgacat tagtcatctg     540
ctgcctttgt tactttggtg tcaattttct tattctttcc aaaggaagat ccttacagtt     600
tgtattcttt cacagctggg aaatgatcag ttgagaatta ttcaaacaca ccaatctgtt     660
aaccgtactt cttcccagat aatgcaatat tttgcagggt gacaggcaaa aagtggtcat     720
tttttacttc ata                                                        733

<210> SEQ ID NO 5
<211> LENGTH: 846
<212> TYPE: DNA
<213> ORGANISM: Homo sapiens

<400> SEQUENCE: 5
accacctgtg tacattcatt ggcaagtcac catcctatcc tcttgctgca tcttgccttt      60
ccactgcgat tatttttagg ggtgtgtgtg caccgcgctg ggaatatggc aaacgtcccc     120
actccccatc agacgtcatg attcctgcac acactgggct ctcactaacc ccagcttcct     180
ttcccctggt ggttttgaga gcataaattt tatttccagc tgtgggtttg ggtcctatgc     240
agaacacctc cctggagaat tgcaactaag atgtttatgg caatcgccct gcaagtgtct     300
atttaattcc tgaaaatgtc atttactggt gtgtttctgt aaaaatcatt tctgaaaagt     360
tttgtcagct tggcttagca gctgggggaa aaaagcagca aaatgagtcc cctcaatcaa     420
gcctgtgatt tttatttttt tcagactcat gaatcctcct gagaattagg cttatgacaa     480
gcacccaccc cctccaccta ctccctggtt taaaccaggt gcctgctgac acgaaggaag     540
attccggggc attttgatcc tagtcacaca gtgtttctaa gtgggcatta ctcctgtcaa     600
tccacagtct taaagatgtt cctcagacaa aagataatta gtgacaagaa ggcccactag     660
attccatgtc atatcttagt tggcgggcca gagaaggaca gggtctctgg ttggggccgt     720
gtctcccatc gcattctccc tttgcaggtg ctgaagtgag gaaggcccac agctcagcca     780
agcacatggg gtgcctccct cctgggccac tagcccactg gccagtaaga gaaccaggga     840
gccttt                                                                846

<210> SEQ ID NO 6
<211> LENGTH: 524
<212> TYPE: DNA
<213> ORGANISM: Homo sapiens

<400> SEQUENCE: 6
tgtttgatac ttaggggaat agtgggaaaa aataggtgac cctttatgtg gaaaatacat      60
caccttcttt aatcaagata tcatgaaaga aacacagtgg tttccattca gattaattta     120
```

```
ttctccagat gtcctgatag agtgattcag ctgtgataaa acggtggagt caggtttagt      180
tctcctcttc gcgagctagt tctcacacaa tgagttgaat acagttctca gaaatcattc      240
ttactttctt cctcttctcc atcaacttcc tcagtctggg gatgagagat agtataattc      300
tgagtaatca ggctcctctt gaaatcccat ttcagcagaa aactggctgg gttcctagcc      360
aaaaaagaac acctgccaga ctgacttttc cctaggtaat gtaagaagca cagatgtcat      420
cagtcactgt ttacttaaca atatatttcc actggccaca gtctggcctt gtttcttcca      480
tttctgcttc cacctctcat acaactacaa aaacagccct tgac                      524
```

```
<210> SEQ ID NO 7
<211> LENGTH: 623
<212> TYPE: DNA
<213> ORGANISM: Homo sapiens

<400> SEQUENCE: 7
taaatcaaag atatcagctt gtgataaaat aataaataga ttgatctagt atgattggtt       60
ttcttgtcaa gtaatcctta cttacatagt ctgaacacat taaatagccc cagtcactca      120
caaaataata tcattattct ggataaaatg taatgagatt gtgaatgaaa acagtgttga      180
tagtggtaga gagaagtgcc acagtcccta atacacacca gatgttcaaa gaatgattgt      240
ggaatgaata aatgttcata tttaatgaac attcatgtaa ttgaatggta gggcattatg      300
agaagtggga tgaggaaaaa ggatgaatca aagatgattt tcatgtttct atcttggtaa      360
tcactgagat gtgaaattca ggaatatgaa aaagattcta ggaaagagct gataagttta      420 cttttttaaat taatctattt gaaaggtacc tgcatacaca gatgttgcag ataaatgaaa      480
gatgaatgga gctggagcgt aagaaagctc tctgggctgt atatttatgc tctaatatca      540
tctgtttaca tacaaatggt aaaagccaaa gggatgaata aaagtcattt attcattcat      600
aaaatatgta ttaagaccta ggc                                             623
```

```
<210> SEQ ID NO 8
<211> LENGTH: 240
<212> TYPE: DNA
<213> ORGANISM: Mus musculus

<400> SEQUENCE: 8
acttcagcca taccctcccc ttccactcca tcccaaataa aaatgagtta cacagaaccc       60
accagcagta ctttacgagt accagcaatt gcaaccgtgc atccttaata gtggcgtaat      120
caaaagttat gatgcatttt tctgtaatca caagaaatga taccacttag tgctaagtaa      180
agccaattcc ctaccacaca gaaaggcaaa agcgcttcca ttttcacttt gaaatgagtg      240
```

```
<210> SEQ ID NO 9
<211> LENGTH: 369
<212> TYPE: DNA
<213> ORGANISM: Homo sapiens

<400> SEQUENCE: 9
tgaatgaaaa attagactgc ccagatagtc aacaattaaa aaatggttaa gtgaatgata       60
gcaaacgctg tcaatgacag cttcagccgc ttaggaaaat gttgatgatg taacattaag      120
ggaactggtg caagcattgc aattacaatg cttaaaaagt gctctgcgta aacagggcct      180
ggaagaatat agagacaaat gagaacagct gtggtgccgg agacacgaga tcttgcttaa      240
aattttccac tcagtttttgg caaaccgtaa caaccttgtg gctcttcata tccttgaacc      300
```

-continued

```
ttgaaatcaa tctcatttct agagactgct gataagagtc ggaaagacaa agctttaggt      360
agtaatctg                                                              369

<210> SEQ ID NO 10
<211> LENGTH: 677
<212> TYPE: DNA
<213> ORGANISM: Homo sapiens

<400> SEQUENCE: 10
cctgtagaca cggtgccaga acagtgacct cagaccacag cttggacgct gattacaagt       60
aatccagctc cagaggtgat agagtgtcct ttctttaaaa aggagataaa aatagcgaag      120
aaacaacact ttccttagtt ctctgaaagg ttggcattct tccagagtag acttatgtac      180
tttttgtact tggaggaaaa aaagagatgg gatctggtcc aagaatagtc ctgcaaacaa      240
gagaaatatg gagcaggcag ctggagctga gcatccaagt ggtaccacca gctgcaggcc      300
cattaattaa cgatccctgg tatgtagcgg ttcccgtgac cttgattctt gttgaattca      360
cagagataat ttttacagag tctctacttt tctcactgcg gtatatttat ccaaggagta      420
ccttgcatat ttcccccccat ctctccaagc agtaaattta ttctaattgc aaagagatac      480
agtaaaagcc tgattgaata cttggcagtt tatagagatt tatttcggga gcttaagggg      540
gtttttagac tgtatgacta gagcagggtt gaggggagct ggggaaagga gcccaagaga      600
aaatgtagat ttaatggatc tataaaatga ccctgctgta gataaacgtt tgttccaaag      660
aagtttaaac agcctga                                                     677

<210> SEQ ID NO 11
<211> LENGTH: 621
<212> TYPE: DNA
<213> ORGANISM: Homo sapiens

<400> SEQUENCE: 11
aggtacctct acattgatgg acctttctcc agaatgagga gccaaaatca tctgaattaa       60
gtagagatct catttgtccc tgactcatga taatgtctgt gctacagtcc tgcattaatt      120
actttgccca agtagaaata cactacccat ataagaattt cacttctgaa caaaacaaaa      180
taaaaatcca cgagtggtga cctcaaaatg aactggttaa atttaaggac tcattttaa       240 aggtcaatgt cctttgctg caaatacagt tcctatgcag atgagaagtt gaacctgacc      300
tatggagccg agcataatta gccagctgca ccctcataat aaggtgcaga tggttaattg      360
caccagcaaa taactgctta cttgtgggca caaaagcctg tacctaaaat cattgaaagt      420
atacttggga ctatttatgc tcatggcaaa caaaacacat ttccaaggtt tcatctgcga      480
acagatcaca gccagctcca aatccctgct ttgcgggaga gccattcacg ctgctgaggt      540
ctggtccaag agagggacca ctggccacaa agccacatat taactggtga aatatttctt      600
ggggtgctga atcgttgttg a                                                621

<210> SEQ ID NO 12
<211> LENGTH: 552
<212> TYPE: DNA
<213> ORGANISM: Mus musculus

<400> SEQUENCE: 12
agattcctca ccccccaagaa gtatttaagc agttgagatg tggcccccag tccctccctt       60
gaactcgacc tcggcaatgt gaaccacaaa gccctgcagt tggaggctgc cgaggtctat      120
tcacagatga aattttggaa atgtgttttg tttgcctgtg cataaatacg cccaagcata      180
```

-continued

```
ctatcgatac ttttaggtac aggctttttgt gcctactggt aagcagtcat ttgccggggc        240
aattaaccat ctgcacttta ttatcagggt gcagctggct aatgatgctc agtgccacgg        300
ggcaggatca gcttctcatc tgcacaggaa ctgtattcac agcaaaggac attgaccttt        360
aacaatgaat ctttaaattt aaccgggtcc cccagagatc accgcacaca aggtttcatt        420
gtgtttcgat ctgaggtgag attcaaatgt gggccgtggg attcctgttt tgggtagagc        480
ggttaacaca gaacagtagg ataggtcagc aattatcagc caagaacaaa ggagaaccct        540
gatgctcagt ct                                                            552

<210> SEQ ID NO 13
<211> LENGTH: 359
<212> TYPE: DNA
<213> ORGANISM: Homo sapiens

<400> SEQUENCE: 13
gaaaatgact ctatctggtt tataattaga agtgaaatga ttttaaatgg cttccacatg         60
gcttagtttt ccaagcagtt ccagttacat agaacttcat ataaacagat aatgagaggc        120
tagagttgga gagcacagtt cctgcttcca aattggcttg aagtggggac atctgctctg        180
catgaagcct gggtcaggct gcccctctca tctgtgacct cctgtggtcg ggagggactt        240
gctctggatt atataaaggc ttcacaagag tactggaagc ggggacggaa tcaacttgag        300
caaaaaacct aattggcttg aatctttcct tgaccatcag taattatttt gagattgat        359

<210> SEQ ID NO 14
<211> LENGTH: 283
<212> TYPE: DNA
<213> ORGANISM: Homo sapiens

<400> SEQUENCE: 14
aaatttagtt cttatattct caaattaata actcaatgaa ttgctttaag ttttgaaaat         60
ttactttcat aagagtcaga tctgaactgg cttctctatt tcggcagaag caccatcatg        120
aatctcagaa cctttaaaaa gacacccaag agtagcaatt ttctttctga gagtacggat        180
tctatttctg acatgtaatt ttccttatac ccaacaccaa aaatgggggac ttgaatcata        240 aacatattta acactcagag gagacattag taggatcctt tta                         283

<210> SEQ ID NO 15
<211> LENGTH: 227
<212> TYPE: DNA
<213> ORGANISM: Homo sapiens

<400> SEQUENCE: 15
tggtcttgat caattgtccc agcagagttg gtgcatggga aagcctttct tggccttatc         60
agcagctcag cctgggaggt tggcccgggg gctgaccaag cacaaaatag aaaagccact        120
aataagatcc agctggaaca aatagcctct atttatttta ggaaactaat gatatgtcat        180
catgacacat atctaacctt agtatttctg attggacagg ccagtta                     227

<210> SEQ ID NO 16
<211> LENGTH: 229
<212> TYPE: DNA
<213> ORGANISM: Homo sapiens

<400> SEQUENCE: 16
agatgtattt ctttcatggg taccacagct gctaaaccaa gcaggtcttc tcaggacata         60
```

-continued

```
acccacagtg agcatgttag gatgcaggaa catgtgcagg gctctggcaa gaggtactga      120
aacattgaaa acggccttga tagagtatct ctctttgaaa gaggtttaaa aaagatacac      180
taaaagttat tttgcttaac actgtccata taaaccaaag agggcattg                  229

<210> SEQ ID NO 17
<211> LENGTH: 297
<212> TYPE: DNA
<213> ORGANISM: Mus musculus

<400> SEQUENCE: 17
tgcgcatccc acaattcacc gaggtttgtt ttcccctcca actccagatg gcctatctgg       60
ggacagcaga ggcccctagg tgcgggccgt tgcagttttt tgatgagctg cacacatatg      120
gatacccgaa catctggagc ggccatgtgc tgcttggggc aggccagccc tggtgagcca      180
atccaggggc cccggggtgc cgggaggcag cagggcccag ccagtgagcg cggataaatt      240
attcatgaac gagttatttg tggtgcaagg ggttcatcag ctactttgat taaaagt        297

<210> SEQ ID NO 18
<211> LENGTH: 844
<212> TYPE: DNA
<213> ORGANISM: Mus musculus

<400> SEQUENCE: 18
atagttgaga gagatcccta ctctccctgg ccctggcctc caaaccctac cacaccatca       60
gctctggggt caggggatgc cctgtggtgg attctgaatt tctgtgtatg tgcaactgca      120
tggggaacag gcagattatt gggcacatga gactaggctg tctgaatctt ccttgagaga      180
ctcccttacc tccagacacc gacacttgtc tccctaccct acagtcagag gcctgtagga      240
cctcagcact cgagaaagat aaggctgcca aacattgctg tgtccacctc ccagacggga      300
catcctgtgt ggttgctgtc aagtccgggt tctccatcaa agagattctg tctggattgt      360
gtgaacggca tggcatcaat ggggctgctg tggacctctt cctggtgggc ggagacaagg      420
tactgtgcca tgcaggagtg agtgagccac cagtatccta gctctgtctg ctcccttcct      480
cctgccttgt tagtgctcca ctcctgacac caccactacc acccgtgagg cagagcagct      540
gcaggtggag gctcccaggg ggtcggtggg tgcacggcag cacaccccag tgtctagagg      600
gtgtcaggct aattttgccc tggtcttttg ttctcgcagc tgtgtgctgt tacatgtcaa      660
gcccacgtgc tcccacatta actctggtgt ctttgttcct cagcctcttg tgctgcatca      720
ggacagcagc atcctggcca ccagggacct acgcttggaa aagcggactt tgtttcggta      780
agaaaaccgc acacaggttt ctggagattt ccaaagtctc cacagtgtga gcctcaggac      840
ttgt                                                                   844

<210> SEQ ID NO 19
<211> LENGTH: 761
<212> TYPE: DNA
<213> ORGANISM: Homo sapiens

<400> SEQUENCE: 19
ttagttcctt cctctcaaat aatctggttg ggatgagcca gtctggggtc ccagggaaca       60
ttgagagcct accctcccca ccttcactcg ggcccagtgt cctttgcccc gaggagggcc      120
tggctgtcag ccaagccacc cccatcccca gggtcacggt gtgggcagtg cagccacagg      180
aaccagcatg gacccttcat agacctggat gctcccaact tgtcactcgg agcagagcac      240
actgccatct gcagggtcac cgctgggcct cgtcacttat catgattgct aattaaagac      300
```

-continued

```
aaaattaacc gaccctggcc tggtggcacc tctcccaatg cctggctctg gctggctggg        360
cctcagtggg gaaggtctgc ccctgatact tgggatggtg gccagagcga ggggagtgga        420
atcccaccca gaacggagaa ggtgccaagc catctggaaa gctgggggcca gcccgacacc       480 tcaccagcca gctgggagaa atgagatctt gggccaatct gggggtgaca ggaaagggag        540
ggtgagatgt ggacgtctta ttcccaactg tatccccagc cccttagagc agttgttgtt        600
gtcagagaga acagatgtga tgtactgagc atgccaggca cgaaggggggc atttgataaa       660 taataaattg ctgcgtggct tgatggatgg ggctgcaagt gcatagtcag tgctcagcgt        720
tttccgcata cactttcaga ataacaaacc cctctatggt g                            761
```

<210> SEQ ID NO 20
<211> LENGTH: 507
<212> TYPE: DNA
<213> ORGANISM: Homo sapiens

<400> SEQUENCE: 20

```
atgctgaatc acagaaaaaa atccaaagct tgctctgtgt attaaaacat ccatttaaaa        60
atatttagaa agagccacca agcacttgtg agcatatgtg catatgcccg cagttccctt        120
tgctctggaa aatattcaag tggaaagcta ctgctctgtt tcataagtaa cagcaatttg       180
tgacaagcat ggaatatgct gggcatcatc aactgcattg ttatcagctg cagtacaatt       240
taattagcga gcctgagttt gattatctgc cagtgcatgc taccttaact gctctgttcc       300
agtttgagga ctaaattttg tctgatcatg ttaacatatt tgagagcata cctcaacatt       360
ctcaagtgtt ttgttcgtca tattatgctc ccgcatcaac aaaattgtat taaaagcctt       420
gacgtcagct caaaatattc tgaagtgaat caaaagctta ttatttctag acgtaagaat       480
aacttgactt catgttagat atgattt                                            507
```

<210> SEQ ID NO 21
<211> LENGTH: 490
<212> TYPE: DNA
<213> ORGANISM: Mus musculus

<400> SEQUENCE: 21

```
ccagctcctc gttgtagccc cccacacaca agatcaaggg tacagacagc ccctagaagg        60
gcaggaggcc aaggctccat gggcaccta ctctctccat tcccccttgg ctcccaggct        120
tccctccccc tcccagtcct ccttccccgc acgctggtga ctgccgtgac tattaatcac       180
tagccctgtt ctcttcctct ctactaatca ggcacaatta gacaaggcct cttccagctg        240
ggcagtcccc ccctgccctc cccctccctt cacagccctc cctatccgat acccaggaca       300
gctctgaggc aatgaggact tgatgtaagc cctgagctac tctggttgcc ctggtgccca       360
gtttggggct tttcagcaat ctcctctttc catttgtctc ctccttggtc cctggtcttg       420
tctagcgctg tagatcagcc aatattagca ggctcaatct ctaacccact gccactgtca       480
atcaaagggg                                                               490
```

<210> SEQ ID NO 22
<211> LENGTH: 632
<212> TYPE: DNA
<213> ORGANISM: Homo sapiens

<400> SEQUENCE: 22

```
gaggcatggg taggagccag ccccactcct cagggtcctc aagggtccag gcagccccgg        60
```

-continued

```
ggggccagga gcctggggcc ctgtgggcgc ctcactatct ccatcccta tgggctctcc     120 ggtctccctc ccctcccga ccctccttct ccacatgctg gtgactgcca tgactattaa     180
tcactcgccc tgttctcttc ctctctacta atcaggcaca attagacaag gcctcttcca     240
gctgggcagt ccctccctg ccctcctctc tcctctccct gccccaccca gccgccagcc     300
aggacagctc tgaggcacag aaagcatgca agccctctct ctctctggct gtcccaggac     360
ccagtttcgg gctccttagc acccactcct tctgtcccag cgacctcctt agctccttct     420
cttcccagtg tgtggtcagg ccactactga cagtctctgc cctccacccc ctacacttgg     480
ccctgggagg agctactcca cactccatcg agctctaaga aggcggcact gtccctggct     540
cctctgtcct cctgctcagc catcctcagc atgtgcctct catcaccact cttgtcacca     600
cagatcgccg agcagctact ccacactcca tc                                  632
```

```
<210> SEQ ID NO 23
<211> LENGTH: 460
<212> TYPE: DNA
<213> ORGANISM: Mus musculus

<400> SEQUENCE: 23
gagtaatagg cagatctcta taccagccta acttctccct accaccccc tccatcttcc      60 ttcttcttgc agtgcaaacg ccaagtcata tggacttgga ttccgactct cttttctttg     120
ccaagactca tattattgag caagtgagga gagttgagcc aaactgaact aagtgacgcc     180
acagcacact gtgtagtgca gagctagcac tttggatatt gtgtaattaa ggctttaatg     240
aacatcacat agagaattag actgcagatt gtgacacaaa taaatctact ggcttttag      300 aaacattcct taaaaagaaa tattttggta ccagaatgtg ttcaggaggg aaagagcctg     360
tgcccttgac acaggaagta gataacacct gtcagaagaa tcgaaaccac ctgcttgggt     420
gcatctggta ataagtttgc agctggtgct acactctacc                          460
```

```
<210> SEQ ID NO 24
<211> LENGTH: 604
<212> TYPE: DNA
<213> ORGANISM: Mus musculus

<400> SEQUENCE: 24
gacaatcatg agagtacgaa agcatgagag atattatttc aacaacttat tctttatttt      60
agaggaagaa catctgagaa caaaaatatc tataaaggca tgattagcat agaaaacaag     120
ggtattgatc attaatggca cctaatgtca tagataaaaa gagacactca aactttatac     180
atctccaaat agaacacttc acaatctatg aagcaaaaat aaaggaaaaa aaaaacaaca     240
caaatctaat cttacagaac taagtaccaa tttacagcaa gtgtagacaa agtagcacat     300
caaatgacaa taggagatgc catcaagcga aatcaattct gggaaggtct tagagaacaa     360
gcaatagtac ttcttgaaca catccattat aagtgaaaat aaaatgctct agataaaaag     420
agccttagag atgaatgaag gataatgaat ctgctgctta atcacaaaca ttttggtgat     480
gagatgatca agaaaacaaa aagctattac tgaaatagct ggaagtgtaa ttagttactg     540
tggagaagga cagagttgag aagaagtaaa aggattgtgg ttgtgataga tgtatgccaa     600
tgtc                                                                 604
```

```
<210> SEQ ID NO 25
<211> LENGTH: 659
<212> TYPE: DNA
<213> ORGANISM: Mus musculus
```

```
<400> SEQUENCE: 25
cctcatggta ttagtagtaa ccattttgga gagaactata ccactaatcc ttactacccc      60 cccccaatt aatgacaccc cattcgagca tctccaatga aaggcgcatt attaatattc      120
aaggaaaaaa acccttgtaa ccattttagc agatacagct aacaatgaac taaatttgct      180
ttgtgcaaga cagagagtga gcatcccaaa ttagtttatg taaaagctga aatcctcccc      240
tgaaaggtct cagtaccatc ctcaaagaat atcccgatca tcagcagtgc cgtcaagatt      300
cccgccaaca ttatcccctt tgttgtctga aatgtagaat caagcacatc tggcaaatgt      360
cctggagctc acaaatctct caaacggcgt ctaattccca gtggtgaaag agagcgccac      420
tgcctaatcg tgcttctctt caaaacagca ctgactttcc ttcaatcaga aacaatggct      480
ttgctttctt aaaaatatca cacgccagtg attatttgca gagaggccca tttttatgctt      540 gaacctgcgg gtcccagaca gaattcacaa ttaagaccgt gaacctcatt tgaatgtacg      600
cttagttcag tggacagtgg gaagaaagat tgtgacctgt cttctgtggt ttggaggct       659

<210> SEQ ID NO 26
<211> LENGTH: 53
<212> TYPE: DNA
<213> ORGANISM: Artificial Sequence
<220> FEATURE:
<223> OTHER INFORMATION: Beta-Globin Minimal Promoter

<400> SEQUENCE: 26
gggctgggca taaaagtcag ggcagagcca tctattgctt acatttgctt ctg             53

<210> SEQ ID NO 27
<211> LENGTH: 68
<212> TYPE: DNA
<213> ORGANISM: Artificial Sequence
<220> FEATURE:
<223> OTHER INFORMATION: minCMV Promoter

<400> SEQUENCE: 27
gaggtaggcg tgtacggtgg gaggcctata taagcagagc tcgtttagtg aaccgtcaga      60
tcgcctgg                                                               68

<210> SEQ ID NO 28
<211> LENGTH: 68
<212> TYPE: DNA
<213> ORGANISM: Artificial Sequence
<220> FEATURE:
<223> OTHER INFORMATION: Mutated minCMV Promoter (SacI RE site removed)

<400> SEQUENCE: 28
gaggtaggcg tgtacggtgg gaggcctata taagcagagc tggtttagtg aaccgtcaga      60
tcgcctgg                                                               68

<210> SEQ ID NO 29
<211> LENGTH: 120
<212> TYPE: DNA
<213> ORGANISM: Artificial Sequence
<220> FEATURE:
<223> OTHER INFORMATION: minRho Promoter

<400> SEQUENCE: 29
gattcagccg ggagcttagg gaggggaggt cacttcataa gggcctgggg ggggagttgg      60
agccacgagt cgtccagccg gagccccgtg tggctgagct ccggcctcag aagcatcccc      120
```

```
<210> SEQ ID NO 30
<211> LENGTH: 120
<212> TYPE: DNA
<213> ORGANISM: Artificial Sequence
<220> FEATURE:
<223> OTHER INFORMATION: minRho* Promoter

<400> SEQUENCE: 30
gattcagccg ggagcttagg gaggggaggt cacttcataa gggcttgggg ggggagttgg      60
agccacgagt cgtccagccg gagccccgtg tggctgtgct ccggcctcag aagcatcccc     120

<210> SEQ ID NO 31
<211> LENGTH: 867
<212> TYPE: DNA
<213> ORGANISM: Artificial Sequence
<220> FEATURE:
<223> OTHER INFORMATION: Hsp68 minimal Promoter (proHsp68)

<400> SEQUENCE: 31
caggaacatc caaactgagc agccgggggtc cccccaccc cccaccccgc cccacgcggc       60
aactttgagc ctgtgctggg acagagcctc tagttcctaa attagtccat gaggtcagag     120
gcagcactgc cattgtaacg cgattggaga ggatcacgtc accggacacg cccccaggca     180
tctccctggg tctcctaaac ttggcgggga gaagtttttag cccttaagtt ttagccttta    240
acccccatat tcagaactgt gcgagttggc gaaaccccac aaatcacaac aaactgtaca     300
caacaccgag ctagaggtga tctttcttgt ccattccaca caggccttag taatgcgtcg     360
ccatagcaac agtgtcacta gtagcaccag cacttcccca caccctcccc ctcaggaatc     420
cgtactctcc agtgaacccc agaaacctct ggagagttct ggacaagggc ggaacccaca     480
actccgatta tctcaagggag gcggggaagc tccaccagac gcgaaactgc tggaagattc     540
ctggccccaa ggcctcctcc ggctcgctga ttggcccagc ggagagtggg cggggccggt     600
gaagactcct taaaggcgca gggcggcgag caggtcacca gacgctgaca gctactcaga     660
accaaatctg gttccatcca gagacaagcg aagacaagag aagcagagcg agcggcgcgt     720
tcccgatcct cggccaggac cagccttccc cagagcatcc ctgccgcgga gcgcaacctt     780
cccaggagca tccctgccgc ggagcgcaac tttcccccgga gcatccacgc cgcggagcgc     840
agccttccag aagcagagcg cggcgcc                                         867

<210> SEQ ID NO 32
<211> LENGTH: 720
<212> TYPE: DNA
<213> ORGANISM: Artificial Sequence
<220> FEATURE:
<223> OTHER INFORMATION: SYFP2

<400> SEQUENCE: 32
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagct gatctgcacc accggcaagc tgcccgtgcc ctggcccacc     180
ctcgtgacca ccctgggcta cggcgtgcag tgcttcgccc gctacccxga ccacatgaag     240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca ccgccgacaa gcagaagaac     480
```

-continued

```
ggcatcaagg ccaacttcaa gatccgccac aacatcgagg acggcggcgt gcagctcgcc      540
gaccactacc agcagaacac ccccatcggc gacggccccg tgctgctgcc cgacaaccac      600
tacctgagct accagtccaa gctgagcaaa gaccccaacg agaagcgcga tcacatggtc      660
ctgctggagt tcgtgaccgc cgccgggatc actctcggca tggacgagct gtacaagtaa      720
```

```
<210> SEQ ID NO 33
<211> LENGTH: 720
<212> TYPE: DNA
<213> ORGANISM: Artificial Sequence
<220> FEATURE:
<223> OTHER INFORMATION: EGFP

<400> SEQUENCE: 33
```

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgaccta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

```
<210> SEQ ID NO 34
<211> LENGTH: 1299
<212> TYPE: DNA
<213> ORGANISM: Artificial Sequence
<220> FEATURE:
<223> OTHER INFORMATION: Optimized Flp recombinase (FlpO)

<400> SEQUENCE: 34
```

```
atggctccta agaagaagag gaaggtgatg agccagttcg acatcctgtg caagacccccc       60 cccaaggtgc tggtgcggca gttcgtggag agattcgaga ggcccagcgg cgagaagatc      120
gccagctgtg ccgccgagct gacctacctg tgctggatga tcacccacaa cggcaccgcc      180
atcaagaggg ccaccttcat gagctacaac accatcatca gcaacagcct gagcttcgac      240
atcgtgaaca gagagcctgca gttcaagtac aagacccaga aggccaccat cctggaggcc      300
agcctgaaga agctgatccc cgcctgggag ttcaccatca tcccttacaa cggccagaag      360
caccagagcg acatcaccga catcgtgtcc agcctgcagc tgcagttcga gagcagcgag      420
gaggccgaca agggcaacag ccacagcaag aagatgctga aggccctgct gtccgagggc      480
gagagcatct gggagatcac cgagaagatc ctgaacagct tcgagtacac cagcaggttc      540
accaagacca gagaccctgta ccagttcctg ttcctggcca cattcatcaa ctgcggcagg      600
ttcagcgaca tcaagaacgt ggaccccaag agcttcaagc tggtgcagaa caagtacctg      660
ggcgtgatca ttcagtgcct ggtgaccgag accaagacaa gcgtgtccag gcacatctac      720
tttttcagcg ccagaggcag gatcgacccc ctggtgtacc tggacgagtt cctgaggaac      780
```

-continued

```
agcgagcccg tgctgaagag agtgaacagg accggcaaca gcagcagcaa caagcaggag        840
taccagctgc tgaaggacaa cctggtgcgc agctacaaca aggccctgaa gaagaacgcc        900
ccctacccca tcttcgctat caagaacggc cctaagagcc acatcggcag gcacctgatg        960
accagctttc tgagcatgaa gggcctgacc gagctgacaa acgtggtggg caactggagc       1020
gacaagaggg cctccgccgt ggccaggacc acctacaccc accagatcac cgccatcccc       1080
gaccactact cgccctggt gtccaggtac tacgcctacg accccatcag caaggagatg        1140
atcgccctga aggacgagac caaccccatc gaggagtggc agcacatcga gcagctgaag       1200
ggcagcgccg agggcagcat cagataccce gcctggaacg gcatcatcag ccaggaggtg       1260
ctggactacc tgagcagcta catcaacagg cggatctga                             1299
```

<210> SEQ ID NO 35
<211> LENGTH: 1056
<212> TYPE: DNA
<213> ORGANISM: Artificial Sequence
<220> FEATURE:
<223> OTHER INFORMATION: Improved Cre recombinase (iCre)

<400> SEQUENCE: 35

```
atggtgccca agaagaagag gaaagtctcc aacctgctga ctgtgcacca aaacctgcct         60
gccctccctg tggatgccac ctctgatgaa gtcaggaaga acctgatgga catgttcagg        120
gacaggcagg ccttctctga acacacctgg aagatgctcc tgtctgtgtg cagatcctgg        180
gctgcctggt gcaagctgaa caacaggaaa tggttccctg ctgaacctga ggatgtgagg        240
gactacctcc tgtacctgca agccagaggc ctggctgtga agaccatcca acagcacctg        300
ggccagctca acatgctgca caggagatct ggcctgcctc gcccttctga ctccaatgct        360
gtgtccctgg tgatgaggag aatcagaaag gagaatgtgg atgctgggga gagagccaag        420
caggccctgg cctttgaacg cactgacttt gaccaagtca gatccctgat ggagaactct        480
gacagatgcc aggacatcag gaacctggcc ttcctgggca ttgcctacaa caccctgctg        540
cgcattgccg aaattgccag aatcagagtg aaggacatct cccgcaccga tggtgggaga        600
atgctgatcc acattggcag gaccaagacc ctggtgtcca gctggtgtg ggagaaggcc        660 ctgtccctgg gggttaccaa gctggtggag agatggatct ctgtgtctgg tgtggctgat        720
gaccccaaca actacctgtt ctgccgggtc agaaagaatg gtgtggctgc cccttctgcc        780
acctcccaac tgtccacccg ggccctggaa gggatctttg aggccaccca ccgcctgatc        840
tatggtgcca aggatgactc tgggcagaga tacctggcct ggtctggcca ctctgccaga        900
gtgggtgctg ccagggacat ggccagggct ggtgtgtcca tccctgaaat catgcaggct        960
ggtggctgga ccaatgtgaa cattgtgatg aactacatca gaaacctgga ctctgagact       1020
ggggccatgg tgaggctgct cgaggatggg gactaa                                 1056
```

<210> SEQ ID NO 36
<211> LENGTH: 50
<212> TYPE: DNA
<213> ORGANISM: Artificial Sequence
<220> FEATURE:
<223> OTHER INFORMATION: SP10 insulator

<400> SEQUENCE: 36

```
gaagctaccc ctaacacact attctacaca cagaaaatgc tcttcactag                    50
```

<210> SEQ ID NO 37
<211> LENGTH: 150

-continued

```
<212> TYPE: DNA
<213> ORGANISM: Artificial Sequence
<220> FEATURE:
<223> OTHER INFORMATION: 3xSP10ins

<400> SEQUENCE: 37
gaagctaccc ctaacacact attctacaca cagaaaatgc tcttcactag gaagctaccc        60
ctaacacact attctacaca cagaaaatgc tcttcactag gaagctaccc ctaacacact       120
attctacaca cagaaaatgc tcttcactag                                        150

<210> SEQ ID NO 38
<211> LENGTH: 246
<212> TYPE: DNA
<213> ORGANISM: Artificial Sequence
<220> FEATURE:
<223> OTHER INFORMATION: WPRE3

<400> SEQUENCE: 38
ataatcaacc tctggattac aaaatttgtg aaagattgac tggtattctt aactatgttg        60
ctccttttac gctatgtgga tacgctgctt taatgccttt gtatcatgct attgcttccc       120
gtatggcttt cattttctcc tccttgtata atcctggtt agttcttgcc acggcggaac       180
tcatcgccgc ctgccttgcc cgctgctgga caggggctcg gctgttgggc actgacaatt       240
ccgtgg                                                                  246

<210> SEQ ID NO 39
<211> LENGTH: 609
<212> TYPE: DNA
<213> ORGANISM: Artificial Sequence
<220> FEATURE:
<223> OTHER INFORMATION: WPRE

<400> SEQUENCE: 39
gcttatcgat aatcaacctc tggattacaa aatttgtgaa agattgactg gtattcttaa        60
ctatgttgct ccttttacgc tatgtggata cgctgcttta atgcctttgt atcatgctat       120
tgcttcccgt atggctttca ttttctcctc cttgtataaa tcctggttgc tgtctcttta       180
tgaggagttg tggcccgttg tcaggcaacg tggcgtggtg tgcactgtgt ttgctgacgc       240
aacccccact ggttggggca ttgccaccac ctgtcagctc ctttccggga ctttcgcttt       300 cccctccct attgccacgg cggaactcat cgccgcctgc cttgcccgct gctgacagg        360 ggctcggctg ttgggcactg acaattccgt ggtgttgtcg gggaaatcat cgtcctttcc       420
ttggctgctc gcctatgttg ccacctggat tctgcgcggg acgtccttct gctacgtccc       480
ttcggccctc aatccagcgg accttccttc ccgcggcctg ctgccggctc tgcggcctct       540
tccgcgtctt cgccttcgcc ctcagacgag tcggatctcc ctttgggccg cctccccgca       600
tcgataccg                                                               609

<210> SEQ ID NO 40
<211> LENGTH: 204
<212> TYPE: DNA
<213> ORGANISM: Artificial Sequence
<220> FEATURE:
<223> OTHER INFORMATION: BGHpA

<400> SEQUENCE: 40
cgactgtgcc ttctagttgc cagccatctg ttgtttgccc ctcccccgtg ccttccttga        60
ccctggaagg tgccactccc actgtccttt cctaataaaa tgaggaaatt gcatcgcatt       120
```

-continued

```
gtctgagtag gtgtcattct attctggggg gtggggtggg gcaggacagc aagggggagg      180
attgggaaga caatagcagg catg                                            204
```

```
<210> SEQ ID NO 41
<211> LENGTH: 479
<212> TYPE: DNA
<213> ORGANISM: Artificial Sequence
<220> FEATURE:
<223> OTHER INFORMATION: HGHpA

<400> SEQUENCE: 41
acgggtggca tccctgtgac ccctccccag tgcctctcct ggccctggaa gttgccactc       60
cagtgcccac cagccttgtc ctaataaaat taagttgcat cattttgtct gactaggtgt      120
ccttctataa tattatgggg tggagggg99 tggtatggag caagggcaa gttgggaaga       180 caacctgtag ggcctgcggg gtctattggg aaccaagctg gagtgcagtg gcacaatctt      240
ggctcactgc aatctccgcc tcctgggttc aagcgattct cctgcctcag cctcccgagt      300
tgttgggatt ccaggcatgc atgaccaggc tcagctaatt tttgtttttt tggtagagac      360
ggggtttcac catattggcc aggctggtct ccaactccta atctcaggtg atctacccac      420
cttggcctcc caaattgctg ggattacagg cgtgaaccac tgctcccttc cctgtccttt      479
```

```
<210> SEQ ID NO 42
<211> LENGTH: 78
<212> TYPE: DNA
<213> ORGANISM: Artificial Sequence
<220> FEATURE:
<223> OTHER INFORMATION: P2A

<400> SEQUENCE: 42
ggcagcggcg ccaccaactt cagcctgctg aagcaggccg gcgacgtgga ggagaacccc       60
ggccccggag ctagcgga                                                   78
```

```
<210> SEQ ID NO 43
<211> LENGTH: 21
<212> TYPE: PRT
<213> ORGANISM: Artificial Sequence
<220> FEATURE:
<223> OTHER INFORMATION: T2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 43

Gly Ser Gly Glu Gly Arg Gly Ser Leu Leu Thr Cys Gly Asp Val Glu
1               5                   10                  15

Glu Asn Pro Gly Pro
            20
```

```
<210> SEQ ID NO 44
<211> LENGTH: 24
<212> TYPE: PRT
<213> ORGANISM: Artificial Sequence
<220> FEATURE:
<223> OTHER INFORMATION: E2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 44
```

-continued

```
Gly Ser Gly Gln Cys Thr Asn Tyr Ala Leu Leu Lys Leu Ala Gly Asp
1               5                   10                  15

Val Glu Ser Asn Pro Gly Pro Pro
            20

<210> SEQ ID NO 45
<211> LENGTH: 25
<212> TYPE: PRT
<213> ORGANISM: Artificial Sequence
<220> FEATURE:
<223> OTHER INFORMATION: F2A
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 45

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 46
<211> LENGTH: 130
<212> TYPE: DNA
<213> ORGANISM: Artificial Sequence
<220> FEATURE:
<223> OTHER INFORMATION: Exemplary Plasmid Backbone 1 - Left ITR

<400> SEQUENCE: 46
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 47
<211> LENGTH: 141
<212> TYPE: DNA
<213> ORGANISM: Artificial Sequence
<220> FEATURE:
<223> OTHER INFORMATION: Exemplary Plasmid Backbone 1 - Right ITR

<400> SEQUENCE: 47
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc t                                               141

<210> SEQ ID NO 48
<211> LENGTH: 146
<212> TYPE: DNA
<213> ORGANISM: Artificial Sequence
<220> FEATURE:
<223> OTHER INFORMATION: Exemplary Plasmid Backbone 2 - Left ITR

<400> SEQUENCE: 48
catgtcctgc aggcagctgc gcgctcgctc gctcactgag gccgcccggg caaagcccgg      60
gcgtcgggcg acctttggtc gcccggcctc agtgagcgag cgagcgcgca gagagggagt     120
ggccaactcc atcactaggg gttcct                                          146

<210> SEQ ID NO 49
<211> LENGTH: 149
```

```
<212> TYPE: DNA
<213> ORGANISM: Artificial Sequence
<220> FEATURE:
<223> OTHER INFORMATION: Exemplary Plasmid Backbone 2 - Right ITR

<400> SEQUENCE: 49
aggaacccct agtgatggag ttggccactc cctctctgcg cgctcgctcg ctcactgagg        60
ccgggcgacc aaaggtcgcc cgacgcccgg gctttgcccg ggcggcctca gtgagcgagc       120
gagcgcgcag ctgcctgcag gggcgcctg                                          149

<210> SEQ ID NO 50
<211> LENGTH: 743
<212> TYPE: PRT
<213> ORGANISM: Artificial Sequence
<220> FEATURE:
<223> OTHER INFORMATION: PHP.eB capsid

<400> SEQUENCE: 50

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

-continued

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
                580                 585                 590

Pro Phe Lys Ala Gln Ala Gln Thr Gly Trp Val Gln Asn Gln Gly Ile
                595                 600                 605

Leu Pro Gly Met Val Trp Gln Asp Arg Asp Val Tyr Leu Gln Gly Pro
                610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Gln Ile Leu Ile
                645                 650                 655

Lys Asn Thr Pro Val Pro Ala Asp Pro Pro Thr Ala Phe Asn Lys Asp
                660                 665                 670

Lys Leu Asn Ser Phe Ile Thr Gln Tyr Ser Thr Gly Gln Val Ser Val
                675                 680                 685

Glu Ile Glu Trp Glu Leu Gln Lys Glu Asn Ser Lys Arg Trp Asn Pro
                690                 695                 700

Glu Ile Gln Tyr Thr Ser Asn Tyr Tyr Lys Ser Asn Asn Val Glu Phe
705                 710                 715                 720
```

-continued

```
Ala Val Asn Thr Glu Gly Val Tyr Ser Glu Pro Arg Pro Ile Gly Thr
            725                 730                 735

Arg Tyr Leu Thr Arg Asn Leu
            740

<210> SEQ ID NO 51
<211> LENGTH: 736
<212> TYPE: PRT
<213> ORGANISM: Adeno-associated virus

<400> SEQUENCE: 51

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350
```

```
Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 52
<211> LENGTH: 747
<212> TYPE: DNA
<213> ORGANISM: Artificial Sequence
<220> FEATURE:

<223> OTHER INFORMATION: tet-Transactivator version 2

<400> SEQUENCE: 52

```
atgtctagac tggacaagag caaagtcata aactctgctc tggaattact caatgaagtc        60
ggtatcgaag gcctgacgac aaggaaactc gctcaaaagc tgggagttga gcagcctacc       120
ctgtactggc acgtgaagaa caagcgggcc ctgctcgatg ccctggcaat cgagatgctg       180
gacaggcatc atacccactt ctgcccccctg gaaggcgagt catggcaaga ctttctgcgg       240
aacaacgcca agtcattccg ctgtgctctc ctctcacatc gcgacggggc taaagtgcat       300
ctcggcaccc gcccaacaga gaaacagtac gaaaccctgg aaaatcagct cgcgttcctg       360
tgtcagcaag gcttctccct ggagaacgca ctgtacgctc tgtccgccgt gggccacttt       420
acactgggct gcgtattgga ggatcaggag catcaagtag caaaagagga aagagagaca       480
cctaccaccg attctatgcc cccacttctg agacaagcaa ttgagctgtt cgaccatcag       540
ggagccgaac ctgccttcct tttcggcctg gaactaatca tatgtggcct ggagaaacag       600
ctaaagtgcg aaagcggcgg gccggccgac gcccttgacg attttgactt agacatgctc       660
ccagccgatg cccttgacga ctttgacctt gatatgctgc ctgctgacgc tcttgacgat       720
tttgaccttg acatgctccc cgggtaa                                            747
```

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

```
<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
```

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80
<211> LENGTH: 189
<212> TYPE: PRT
<213> ORGANISM: Homo sapiens

<400> SEQUENCE: 80

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr

-continued

```
        50              55              60

Ser Ala Met Arg Asp Gln Tyr Met Arg Thr Gly Glu Gly Phe Leu Cys
65              70              75              80

Val Phe Ala Ile Asn Asn Thr Lys Ser Phe Glu Asp Ile His Gln Tyr
                85              90              95

Arg Glu Gln Ile Lys Arg Val Lys Asp Ser Asp Asp Val Pro Met Val
                100             105             110

Leu Val Gly Asn Lys Cys Asp Leu Ala Ala Arg Thr Val Glu Ser Arg
        115             120             125

Gln Ala Gln Asp Leu Ala Arg Ser Tyr Gly Ile Pro Tyr Ile Glu Thr
        130             135             140

Ser Ala Lys Thr Arg Gln Gly Val Glu Asp Ala Phe Tyr Thr Leu Val
145             150             155             160

Arg Glu Ile Arg Gln His Lys Leu Arg Lys Leu Asn Pro Pro Asp Glu
                165             170             175

Ser Gly Pro Gly Cys Met Ser Cys Lys Cys Val Leu Ser
            180             185
```

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92
<211> LENGTH: 1353
<212> TYPE: DNA
<213> ORGANISM: Artificial Sequence
<220> FEATURE:
<223> OTHER INFORMATION: GCaMP6m

<400> SEQUENCE: 92

```
atgggttctc atcatcatca tcatcatggt atggctagca tgactggtgg acagcaaatg        60
ggtcgggatc tgtacgacga tgacgataag gatctcgcca ccatggtcga ctcatcacgt       120
cgtaagtgga ataagacagg tcacgcagtc agagctatag gtcggctgag ctcactcgag       180
aacgtctata tcaaggccga caagcagaag aacggcatca aggcgaactt caagatccgc       240
cacaacatcg aggacggcgg cgtgcagctc gcctaccact accagcagaa cacccccatc       300
ggcgacggcc ccgtgctgct gcccgacaac cactacctga gcgtgcagtc caaactttcg       360
aaagacccca acgagaagcg cgatcacatg gtcctgctgg agttcgtgac cgccgccggg       420
atcactctcg gcatggacga gctgtacaag ggcggtaccg gagggagcat ggtgagcaag       480
ggcgaggagc tgttcaccgg ggtggtgccc atcctggtcg agctggacgg cgacgtaaac       540
ggccacaagt tcagcgtgtc cggcgagggt gagggcgatg ccacctacgg caagctgacc       600
ctgaagttca tctgcaccac cggcaagctg cccgtgccct ggcccaccct cgtgaccacc       660
ctgacctacg gcgtgcagtg cttcagccgc taccccgacc acatgaagca gcacgacttc       720
ttcaagtccg ccatgcccga aggctacatc caggagcgca ccatcttctt caaggacgac       780
ggcaactaca agacccgcgc cgaggtgaag ttcgagggcg acaccctggt gaaccgcatc       840
gagctgaagg gcatcgactt caaggaggac ggcaacatcc tggggcacaa gctggagtac       900
aacctgccgg accaactgac tgaagagcag atcgcagaat ttaaagaggc tttctcccta       960
tttgacaagg acgggatgg gacaataaca accaaggagc tggggacggt gatgcggtct      1020
ctggggcaga accccacaga agcagagctg caggacatga tcaatgaagt agatgccgac      1080
ggtgacggca caatcgactt ccctgagttc ctgacaatga tggcaagaaa agggagctac      1140
agggacacgg aagaagaaat tagagaagcg ttcggtgtgt ttgataagga tggcaatggc      1200
tacatcagtg cagcagagct tcgccacgtg atgacaaacc ttggagagaa gttaacagat      1260
gaagaggttg atgaaatgat cagggaagca gacatcgatg gggatggtca ggtaaactac      1320
gaagagtttg tacaaatgat gacagcgaag tga                                   1353
```

<210> SEQ ID NO 93
<211> LENGTH: 1353
<212> TYPE: DNA
<213> ORGANISM: Artificial Sequence
<220> FEATURE:
<223> OTHER INFORMATION: GCaMP6s

<400> SEQUENCE: 93

```
atgggttctc atcatcatca tcatcatggt atggctagca tgactggtgg acagcaaatg        60
ggtcgggatc tgtacgacga tgacgataag gatctcgcca ccatggtcga ctcatcacgt       120
cgtaagtgga ataagacagg tcacgcagtc agagctatag gtcggctgag ctcactcgag       180
aacgtctata tcaaggccga caagcagaag aacggcatca aggcgaactt ccacatccgc       240
cacaacatcg aggacggcgg cgtgcagctc gcctaccact accagcagaa cacccccatc       300
ggcgacggcc ccgtgctgct gcccgacaac cactacctga gcgtgcagtc caaactttcg       360
aaagacccca cgagaagcg cgatcacatg gtcctgctgg agttcgtgac cgccgccggg       420
atcactctcg gcatggacga gctgtacaag ggcggtaccg agggagcat ggtgagcaag        480 ggcgaggagc tgttcaccgg ggtggtgccc atcctggtcg agctggacgg cgacgtaaac       540
ggccacaagt tcagcgtgtc cggcgagggt gagggcgatg ccacctacgg caagctgacc       600
ctgaagttca tctgcaccac cggcaagctg cccgtgccct ggcccaccct cgtgaccacc       660
ctgacctacg gcgtgcagtg cttcagccgc taccccgacc acatgaagca gcacgacttc       720
ttcaagtccg ccatgcccga aggctacatc caggagcgca ccatcttctt caaggacgac       780
ggcaactaca gacccgcgc cgaggtgaag ttcgagggcg acaccctggt gaaccgcatc        840
gagctgaagg gcatcgactt caaggaggac ggcaacatcc tggggcacaa gctggagtac       900
aacctgccgg accaactgac tgaagagcag atcgcagaat ttaaagaggc tttctcccta       960
tttgacaagg acgggatgg acaataaca accaaggagc tggggacggt gatgcggtct       1020
ctggggcaga accccacaga agcagagctg caggacatga tcaatgaagt agatgccgac      1080
ggtgacggca caatcgactt ccctgagttc ctgacaatga tggcaagaaa aatgaaatac      1140
agggacacgg aagaagaaat tagagaagcg ttcggtgtgt ttgataagga tggcaatggc      1200
tacatcagtg cagcagagct tcgccacgtg atgacaaacc ttggagagaa gttaacagat      1260
gaagaggttg atgaaatgat cagggaagca gacatcgatg gggatggtca ggtaaactac      1320
gaagagtttg tacaaatgat gacagcgaag tga                                  1353
```

<210> SEQ ID NO 94
<211> LENGTH: 1353
<212> TYPE: DNA
<213> ORGANISM: Artificial Sequence
<220> FEATURE:
<223> OTHER INFORMATION: GCaMP6f

<400> SEQUENCE: 94

```
atgggttctc atcatcatca tcatcatggt atggctagca tgactggtgg acagcaaatg        60
ggtcgggatc tgtacgacga tgacgataag gatctcgcca ccatggtcga ctcatcacgt       120
cgtaagtgga ataagacagg tcacgcagtc agagctatag gtcggctgag ctcactcgag       180
aacgtctata tcaaggccga caagcagaag aacggcatca aggcgaactt caagatccgc       240
cacaacatcg aggacggcgg cgtgcagctc gcctaccact accagcagaa cacccccatc       300
ggcgacggcc ccgtgctgct gcccgacaac cactacctga gcgtgcagtc caaactttcg       360
```

-continued

```
aaagacccca acgagaagcg cgatcacatg gtcctgctgg agttcgtgac cgccgccggg      420
atcactctcg gcatggacga gctgtacaag ggcggtaccg gagggagcat ggtgagcaag      480
ggcgaggagc tgttcaccgg ggtggtgccc atcctggtcg agctggacgg cgacgtaaac      540
ggccacaagt tcagcgtgtc cggcgagggt gagggcgatg ccacctacgg caagctgacc      600
ctgaagttca tctgcaccac cggcaagctg cccgtgccct ggcccaccct cgtgaccacc      660
ctgacctacg gcgtgcagtg cttcagccgc taccccgacc acatgaagca gcacgacttc      720
ttcaagtccg ccatgcccga aggctacatc caggagcgca ccatcttctt caaggacgac      780
ggcaactaca gacccgcgc cgaggtgaag ttcgagggcg acaccctggt gaaccgcatc       840
gagctgaagg gcatcgactt caaggaggac ggcaacatcc tggggcacaa gctggagtac      900
aacctgccgg accaactgac tgaagagcag atcgcagaat ttaaagagga attctcccta      960
tttgacaagg acggggatgg gacaataaca accaaggagc tggggacggt gatgcggtct     1020
ctggggcaga acccccacaga agcagagctg caggacatga tcaatgaagt agatgccgac    1080
ggtgacggca caatcgactt ccctgagttc ctgacaatga tggcaagaaa aatgaaatac     1140
agggacacgg aagaagaaat tagagaagcg ttcggtgtgt ttgataagga tggcaatggc     1200
tacatcagtg cagcagagct tcgccacgtg atgacaaacc ttggagagaa gttaacagat     1260
gaagaggttg atgaaatgat cagggaagca gacatcgatg gggatggtca ggtaaactac     1320
gaagagtttg tacaaatgat gacagcgaag tga                                  1353
```

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

-continued

```
<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107
<211> LENGTH: 2303
<212> TYPE: DNA
<213> ORGANISM: Artificial Sequence
<220> FEATURE:
<223> OTHER INFORMATION: CN1535

<400> SEQUENCE: 107
gcggccgcaa cgcgtttaga acaatggctg gcccatagta aatgccgtgt tagtgtgtta        60
gttgctgttc ttccacgtca gaagaggcac agacaaatta ccaccaggtg gcgctcagag       120
tctgcggagg catcacaaca gccctgaatt tgaatcctgc tctgccactg cctagttgag       180
accttttact acctgactag ctgtttgtgt attttaggtg tttgtttcca cttccagctt       240
cttccctaac aattcctaag aaatgttatt gctagttaga aatgctttat cttttcttct       300
atcatatcca atgaaggcct gatcttacag agtctaaaca attgcagtaa atacattcca       360
gatttcagca gcactttacc aacacttgtg aatcgctgtc attcttccag gattcagttt       420
aagagtggca attacaagtc actttaatgt ctgaggaaag gatggaaagc aagccctgca       480
aatagaaggc cacatttact cttttcaaac cacagctcaa actatcagag gaaaatacag       540
tttttatgta agcgctcaaa cagtttttccc caaatcttgc agaatccatt acttttaaga       600
aatttccaca tgaatagacc aaacgaatca ggcatactaa tactttgtac atgcacacac       660
acaagtgcca gttccatatc atactgtcac aaactctaga gctaaacaca ttcacacgct       720
tcggattaaa tgatcagggt agaaatatgc attgtgaata aaataactta cctatcttac       780
ctataaaatt ccccatttca gttgtttttct gccactgcca cttttgaagt tatcctcaac       840
tgaactcttt gtacacattc ctgcaaacca gctcactgtt ggaatgtctc tgaattcgat       900
```

-continued

```
atcataatca accataggta ccgagctcgg gattcagccg ggagcttagg gaggggaggt      960
cacttcataa gggcctgggg ggggagttgg agccacgagt cgtccagccg gagccccgtg     1020
tggctgagct ccggcctcag aagcatcccc gggttggatc cttcgaagct agcgctaccg     1080
gtcgccacca tggtgagcaa gggcgaggag ctgttcaccg gggtggtgcc catcctggtc     1140
gagctggacg gcgacgtaaa cggccacaag ttcagcgtgt ccggcgaggg cgagggcgat     1200
gccacctacg gcaagctgac cctgaagctg atctgcacca ccggcaagct gcccgtgccc     1260
tggcccaccc tcgtgaccac cctgggctac ggcgtgcagt gcttcgcccg ctaccccgac     1320
cacatgaagc agcacgactt cttcaagtcc gccatgcccg aaggctacgt ccaggagcgc     1380
accatcttct tcaaggacga cggcaactac aagacccgcg ccgaggtgaa gttcgagggc     1440
gacaccctgg tgaaccgcat cgagctgaag ggcatcgact tcaaggagga cggcaacatc     1500
ctggggcaca gctggagta caactacaac agccacaacg tctatatcac cgccgacaag     1560
cagaagaacg gcatcaaggc caacttcaag atccgccaca acatcgagga cggcggcgtg     1620
cagctcgccg accactacca gcagaacacc cccatcggcg acggccccgt gctgctgccc     1680
gacaaccact acctgagcta ccagtccaag ctgagcaaag accccaacga gaagcgcgat     1740
cacatggtcc tgctggagtt cgtgaccgcc gccgggatca ctctcggcat ggacgagctg     1800
tacaagtaag tcgacatcat aatcaacctc tggattacaa aatttgtgaa agattgactg     1860
gtattcttaa ctatgttgct cctttttacgc tatgtggata cgctgcttta atgcctttgt     1920
atcatgctat tgcttcccgt atggctttca ttttctcctc cttgtataaa tcctggttag     1980
ttcttgccac ggcggaactc atcgccgcct gccttgcccg ctgctggaca ggggctcggc     2040
tgttgggcac tgacaattcc gtggctcgag agatcttcga ctgtgccttc tagttgccag     2100
ccatctgttg tttgcccctc ccccgtgcct tccttgaccc tggaaggtgc cactcccact     2160 gtccttttcct aataaaatga ggaaattgca tcgcattgtc tgagtaggtg tcattctatt     2220
ctggggggtg gggtggggca ggacagcaag ggggaggatt gggaagacaa tagcaggcat     2280
gcacgtgcgg accgagcggc cgc                                             2303
```

```
<210> SEQ ID NO 108
<211> LENGTH: 2212
<212> TYPE: DNA
<213> ORGANISM: Artificial Sequence
<220> FEATURE:
<223> OTHER INFORMATION: CN1533

<400> SEQUENCE: 108
```

```
gcggccgcaa cgcgtttaga acaatggctg gcccatagta aatgccgtgt tagtgtgtta       60
gttgctgttc ttccacgtca gaagaggcac agacaaatta ccaccaggtg gcgctcagag      120
tctgcggagg catcacaaca gccctgaatt tgaatcctgc tctgccactg cctagttgag      180 acctttttact acctgactag ctgttttgtgt attttaggtg tttgtttaat ggggcctcag      240 tttctcccctt gggattaagt gggtaccagg caggacaaaa taagccacct gtgccattct      300 acccttttcca tcctgctgtt tttccaccct gcagctgctt tctcaaagaa tccctgaatc      360
tcctctctaa atagtgcaag cttgctgttg ggaacaccca cagatgcact ctacaaatac      420
acaactcact ttgagtaatc atattgattc ggaattatcg gccattcaaa tacctcattg      480
aagatgccat ctgggatgtt attgctcttc agaggtagat catattctga gaaaatctgt      540
caaaatgtag aaataactca tcaaaatggc cattgcagaa tctagctgca cttcttaagg      600
aagcagactc tgatgctgcg ggtttcattg cccctaagtg agatgctgaa ggaagaaggg      660
```

```
ctgtttctt  tctgtttcca agtgtcatga gaaatttaaa gttcaggaat gtgcaagttc    720
agagtgctcc tggactcctt tgctcattca gagacatctc actgaaaaca aacattcctc    780
aaggttatct ctggtcctgg gaattcgata tcataatcaa ccataggtac cgagctcggg    840
attcagccgg gagcttaggg aggggaggtc acttcataag ggcctggggg gggagttgga    900
gccacgagtc gtccagccgg agcccgtgt  ggctgagctc cggcctcaga agcatccccg    960
ggttggatcc ttcgaagcta gcgctaccgg tcgccaccat ggtgagcaag ggcgaggagc   1020
tgttcaccgg ggtggtgccc atcctggtcg agctggacgg cgacgtaaac ggccacaagt   1080
tcagcgtgtc cggcgagggc gagggcgatg ccacctacgg caagctgacc ctgaagctga   1140
tctgcaccac cggcaagctg cccgtgccct ggcccaccct cgtgaccacc ctgggctacg   1200
gcgtgcagtg cttcgcccgc taccccgacc acatgaagca gcacgacttc ttcaagtccg   1260
ccatgcccga aggctacgtc caggagcgca ccatcttctt caaggacgac ggcaactaca   1320
agacccgcgc cgaggtgaag ttcgagggcg acaccctggt gaaccgcatc gagctgaagg   1380
gcatcgactt caaggaggac ggcaacatcc tggggcacaa gctggagtac aactacaaca   1440
gccacaacgt ctatatcacc gccgacaagc agaagaacgg catcaaggcc aacttcaaga   1500
tccgccacaa catcgaggac ggcggcgtgc agctcgccga ccactaccag cagaacaccc   1560
ccatcggcga cggccccgtg ctgctgcccg acaaccacta cctgagctac cagtccaagc   1620
tgagcaaaga ccccaacgag aagcgcgatc acatggtcct gctggagttc gtgaccgccg   1680
ccgggatcac tctcggcatg gacgagctgt acaagtaagt cgacatcata atcaacctct   1740
ggattacaaa atttgtgaaa gattgactgg tattcttaac tatgttgctc cttttacgct   1800
atgtggatac gctgctttaa tgcctttgta tcatgctatt gcttcccgta tggctttcat   1860
tttctcctcc ttgtataaat cctggttagt tcttgccacg gcggaactca tcgccgcctg   1920
ccttgcccgc tgctggacag gggctcggct gttgggcact gacaattccg tggctcgaga   1980
gatcttcgac tgtgccttct agttgccagc catctgttgt ttgcccctcc cccgtgcctt   2040
ccttgaccct ggaaggtgcc actcccactg tcctttccta ataaaatgag gaaattgcat   2100
cgcattgtct gagtaggtgt cattctattc tggggggtgg ggtggggcag gacagcaagg   2160
gggaggattg ggaagacaat agcaggcatg cacgtgcgga ccgagcggcc gc            2212
```

<210> SEQ ID NO 109
<211> LENGTH: 2085
<212> TYPE: DNA
<213> ORGANISM: Artificial Sequence
<220> FEATURE:
<223> OTHER INFORMATION: CN1647

<400> SEQUENCE: 109

```
gcggccgcaa cgcgtttaga acaatggctg gcccatagta aatgccgtgt tagtgtgtta     60
gttgctgttc ttccacgtca gaagaggcac agacaaatta ccaccaggtg gcgctcagag    120
tctgcggagg catcacaaca gccctgaatt tgaatcctgc tctgccactg cctagttgag    180 acctttact  acctgactag ctgtttgtgt attttaggtg tttgtttccc ttctttccag    240
ttccacgtag ccttgaaaac cataactttg caaatacagg agttgtgaaa acgagcatcc    300
tagaagtcac tgtaagggca gaatgtgttt ggagaaagtc ccattcccag aaaattgtca    360
ctatttagcc catctgaaag tcgcataaaa agctctactg tcgacatttg tctttatttg    420
agctgattca gagcttgctt tgtgcaacta gcacaaccca tcagaggcaa ttgcttaata    480
```

-continued

```
ttgcagctgc cttcagtgga gattccagtt gtgactaaca agaagctgtt ttagaaaaat      540 aaaatacccct taaaaataaa aactaataca ctcatggaaa cctaaaaaaa ttatgcatat      600
gattagggtt gtgaatacac ttaggaaaga cctaagaggg ccctaatctc tcacagctgg      660
ctgaggataa ggcgaattcg atatcataat caaccatagg taccgagctc gggattcagc      720
cgggagctta gggaggggag gtcacttcat aagggcctgg ggggggagtt ggagccacga      780
gtcgtccagc cggagccccg tgtggctgag ctccggcctc agaagcatcc ccgggttgga      840
tccttcgaag ctagcgctac cggtcgccac catggtgagc aagggcgagg agctgttcac      900
cggggtggtg cccatcctgg tcgagctgga cggcgacgta aacggccaca agttcagcgt      960
gtccggcgag ggcgagggcg atgccaccta cggcaagctg accctgaagc tgatctgcac     1020
caccggcaag ctgcccgtgc cctggcccac cctcgtgacc accctgggct acggcgtgca     1080
gtgcttcgcc cgctacccccg accacatgaa gcagcacgac ttcttcaagt ccgccatgcc     1140
cgaaggctac gtccaggagc gcaccatctt cttcaaggac gacggcaact acaagacccg     1200
cgccgaggtg aagttcgagg gcgacaccct ggtgaaccgc atcgagctga agggcatcga     1260
cttcaaggag gacggcaaca tcctggggca caagctggag tacaactaca acagccacaa     1320
cgtctatatc accgccgaca gcagaagaa cggcatcaag gccaacttca agatccgcca     1380
caacatcgag gacggcggcg tgcagctcgc cgaccactac cagcagaaca cccccatcgg     1440
cgacggcccc gtgctgctgc ccgacaacca ctacctgagc taccagtcca agctgagcaa     1500
agaccccaac gagaagcgcg atcacatggt cctgctggag ttcgtgaccg ccgccgggat     1560
cactctcggc atggacgagc tgtacaagta agtcgacatc ataatcaacc tctggattac     1620
aaaatttgtg aaagattgac tggtattctt aactatgttg ctccttttac gctatgtgga     1680
tacgctgctt taatgccttt gtatcatgct attgcttccc gtatggcttt cattttctcc     1740
tccttgtata aatcctggtt agttcttgcc acggcggaac tcatcgccgc ctgccttgcc     1800
cgctgctgga caggggctcg gctgttgggc actgacaatt ccgtggctcg agagatcttc     1860
gactgtgcct tctagttgcc agccatctgt tgtttgcccc tcccccgtgc cttccttgac     1920
cctggaaggt gccactccca ctgtcctttc ctaataaaat gaggaaattg catcgcattg     1980
tctgagtagg tgtcattcta ttctgggggg tggggtgggg caggacagca aggggggagga     2040 ttgggaagac aatagcaggc atgcacgtgc ggaccgagcg gccgc             2085
```

<210> SEQ ID NO 110
<211> LENGTH: 2461
<212> TYPE: DNA
<213> ORGANISM: Artificial Sequence
<220> FEATURE:
<223> OTHER INFORMATION: CN1719

<400> SEQUENCE: 110

```
gcggccgcaa cgcgtttaga acaatggctg gcccatagta aatgccgtgt tagtgtgtta       60
gttgctgttc ttccacgtca gaagaggcac agacaaatta ccaccaggtg gcgctcagag      120
tctgcggagg catcacaaca gccctgaatt tgaatcctgc tctgccactg cctagttgag      180
accttttact acctgactag ctgtttgtgt attttaggtg tttgtttact gcacgtacca      240
ctctatgtta ggaaataaac gactcatagt cgtgaaatgc ttcacatttc tcatgaagct      300
gaggtagccc agcattctct actttagaaa tctggatgta tttttcctc atgggtctgt      360 aattgagtcc gtaattgaca tttgtacact tttaagataa atctagcctg tcttcaagta      420
tattttagat ctagtgaaat acagagtact atagattaga tattctgaat atcatctgtt      480
```

```
tgttatttag taatgtgata tgccttgtgt acccacttttt gtatttacca ttattgcaaa    540
atcaatcaaa tgtgagcaaa agcaaaggca atttgaatga ctcaaaattg aaatttgagc    600
tgccaaatca agcagtaaaa caatttttac cagctctatt gattgttaga aagataagtt    660
ataaacttta tttcaagtaa atttctaaaa gatctgggaa tgtgattatt ccaaggcaga    720
tggcgaagac ctttatttcc actgattatt cacagatgca aattattatg caactggaag    780
catactaaga tattgcaaag atgttctgac attagtcatc tgctgccttt gttactttgg    840
tgtcaatttt cttattcttt ccaaaggaag atccttacag tttgtattct ttcacagctg    900
ggaaatgatc agttgagaat tattcaaaca caccaatctg ttaaccgtac ttcttcccag    960
ataatgcaat attttgcagg gtgacaggca aaaagtggtc attttttact tcatatattt   1020
tagggttatt tggttttgat taaatgagtg aattcgatat cataatcaac cataggtacc   1080
gagctcggga ttcagccggg agcttaggga ggggaggtca cttcataagg gcctgggggg   1140
ggagttggag ccacgagtcg tccagccgga gccccgtgtg gctgagctcc ggcctcagaa   1200
gcatccccgg gttggatcct tcgaagctag cgctaccggt cgccaccatg gtgagcaagg   1260
gcgaggagct gttcaccggg gtggtgccca tcctggtcga gctggacggc gacgtaaacg   1320
gccacaagtt cagcgtgtcc ggcgagggcg agggcgatgc cacctacggc aagctgaccc   1380
tgaagctgat ctgcaccacc ggcaagctgc ccgtgccctg gcccaccctc gtgaccaccc   1440
tgggctacgg cgtgcagtgc ttcgcccgct accccgacca catgaagcag cacgacttct   1500
tcaagtccgc catgcccgaa ggctacgtcc aggagcgcac catcttcttc aaggacgacg   1560
gcaactacaa gacccgcgcc gaggtgaagt tcgagggcga caccctggtg aaccgcatcg   1620
agctgaaggg catcgacttc aaggaggacg gcaacatcct ggggcacaag ctggagtaca   1680
actacaacag ccacaacgtc tatatcaccg ccgacaagca gaagaacggc atcaaggcca   1740
acttcaagat ccgccacaac atcgaggacg gcggcgtgca gctcgccgac cactaccagc   1800
agaacacccc catcggcgac ggccccgtgc tgctgcccga caaccactac ctgagctacc   1860
agtccaagct gagcaaagac cccaacgaga agcgcgatca catggtcctg ctggagttcg   1920
tgaccgccgc cgggatcact ctcggcatgg acgagctgta caagtaagtc gacatcataa   1980
tcaacctctg gattacaaaa tttgtgaaag attgactggt attcttaact atgttgctcc   2040
ttttacgcta tgtggatacg ctgctttaat gcctttgtat catgctattg cttcccgtat   2100
ggctttcatt ttctcctcct tgtataaatc ctggttagtt cttgccacgg cggaactcat   2160
cgccgcctgc cttgcccgct gctggacagg ggctcggctg ttgggcactg acaattccgt   2220
ggctcgagag atcttcgact gtgccttcta gttgccagcc atctgttgtt tgcccctccc   2280
ccgtgccttc cttgacccctg gaaggtgcca ctcccactgt cctttcctaa taaaatgagg   2340
aaattgcatc gcattgtctg agtaggtgtc attctattct ggggggtggg gtggggcagg   2400
acagcaaggg ggaggattgg gaagacaata gcaggcatgc acgtgcggac cgagcggccg   2460
c                                                                    2461
```

<210> SEQ ID NO 111
<211> LENGTH: 2204
<212> TYPE: DNA
<213> ORGANISM: Artificial Sequence
<220> FEATURE:
<223> OTHER INFORMATION: CN2365

<400> SEQUENCE: 111

-continued

```
gcggccgcac gcgtaccacc tgtgtacatt cattggcaag tcaccatcct atcctcttgc        60
tgcatcttgc ctttccactg cgattatttt taggggtgtg tgtgcaccgc gctgggaata       120
tggcaaacgt ccccactccc catcagacgt catgattcct gcacacactg ggctctcact       180
aaccccagct tcctttcccc tggtggtttt gagagcataa attttatttc cagctgtggg       240
tttgggtcct atgcagaaca cctccctgga gaattgcaac taagatgttt atggcaatcg       300
ccctgcaagt gtctatttaa ttcctgaaaa tgtcatttac tggtgtgttt ctgtaaaaat       360
catttctgaa aagttttgtc agcttggctt agcagctggg ggaaaaaagc agcaaaatga       420
gtcccctcaa tcaagcctgt gatttttat ttttttcagac tcatgaatcc tcctgagaat       480
taggcttatg acaagcaccc accccctcca cctactccct ggtttaaacc aggtgcctgc       540
tgacacgaag gaagattccg gggcattttg atcctagtca cacagtgttt ctaagtgggc       600
attactcctg tcaatccaca gtcttaaaga tgttcctcag acaaaagata attagtgaca       660
agaaggccca ctagattcca tgtcatatct tagttggcgg gccagagaag gacagggtct       720
ctggttgggg ccgtgtctcc catcgcattc tccctttgca ggtgctgaag tgaggaaggc       780
ccacagctca gccaagcaca tggggtgcct ccctcctggg ccactagccc actggccagt       840
aagagaacca gggagccttt gagctcgggc tgggcataaa agtcagggca gagccatcta       900
ttgcttacat ttgcttctgg gatccagatc tttcgaagct agcgctaccg gtcgccacca       960
tggtgagcaa gggcgaggag ctgttcaccg gggtggtgcc catcctggtc gagctggacg      1020
gcgacgtaaa cggccacaag ttcagcgtgt ccggcgaggg cgagggcgat gccacctacg      1080
gcaagctgac cctgaagctg atctgcacca ccggcaagct gcccgtgccc tggcccaccc      1140
tcgtgaccac cctgggctac ggcgtgcagt gcttcgcccg ctaccccgac cacatgaagc      1200
agcacgactt cttcaagtcc gccatgcccg aaggctacgt ccaggagcgc accatcttct      1260
tcaaggacga cggcaactac aagacccgcg ccgaggtgaa gttcgagggc gacaccctgg      1320
tgaaccgcat cgagctgaag ggcatcgact tcaaggagga cggcaacatc ctggggcaca      1380
agctggagta caactacaac agccacaacg tctatatcac cgccgacaag cagaagaacg      1440
gcatcaaggc caacttcaag atccgccaca acatcgagga cggcggcgtg cagctcgccg      1500
accactacca gcagaacacc cccatcggcg acggccccgt gctgctgccc gacaaccact      1560
acctgagcta ccagtccaag ctgagcaaag accccaacga gaagcgcgat cacatggtcc      1620
tgctggagtt cgtgaccgcc gccgggatca ctctcggcat ggacgagctg tacaagtaag      1680
tcgacggcgc gccgcggccg cgaattcgat atcataatca acctctggat tacaaaattt      1740
gtgaaagatt gactggtatt cttaactatg ttgctccttt tacgctatgt ggatacgctg      1800
ctttaatgcc tttgtatcat gctattgctt cccgtatggc tttcattttc tcctccttgt      1860
ataaatcctg gttagttctt gccacggcgg aactcatcgc cgcctgcctt gcccgctgct      1920
ggacaggggc tcggctgttg ggcactgaca attccgtggc tcgagagatc ttcgactgtg      1980
ccttctagtt gccagccatc tgttgtttgc ccctcccccg tgccttcctt gaccctggaa      2040
ggtgccactc ccactgtcct ttcctaataa aatgaggaaa ttgcatcgca ttgtctgagt      2100
aggtgtcatt ctattctggg gggtggggtg gggcaggaca gcaagggga ggattgggaa       2160 gacaatagca ggcatgagat ctcacgtgcg gaccgagcgg ccgc                      2204
```

<210> SEQ ID NO 112
<211> LENGTH: 1882
<212> TYPE: DNA
<213> ORGANISM: Artificial Sequence

<220> FEATURE:
<223> OTHER INFORMATION: CN2355

<400> SEQUENCE: 112

```
gcggccgcac gcgttgtttg atacttaggg gaatagtggg aaaaaatagg tgacccttta      60
tgtggaaaat acatcacctt ctttaatcaa gatatcatga aagaaacaca gtggtttcca     120
ttcagattaa tttattctcc agatgtcctg atagagtgat tcagctgtga taaaacggtg     180
gagtcaggtt tagttctcct cttcgcgagc tagttctcac acaatgagtt gaatacagtt     240
ctcagaaatc attcttactt tcttcctctt ctccatcaac ttcctcagtc tggggatgag     300
agatagtata attctgagta atcaggctcc tcttgaaatc ccatttcagc agaaaactgg     360
ctgggttcct agccaaaaaa gaacacctgc cagactgact tttccctagg taatgtaaga     420
agcacagatg tcatcagtca ctgtttactt aacaatatat ttccactggc cacagtctgg     480
ccttgtttct tccatttctg cttccacctc tcatacaact acaaaaacag cccttgacga     540
gctcgggctg ggcataaaag tcagggcaga gccatctatt gcttacattt gcttctggga     600
tccagatctt tcgaagctag cgctaccggt cgccaccatg gtgagcaagg gcgaggagct     660
gttcaccggg gtggtgccca tcctggtcga gctggacggc gacgtaaacg ccacaagtt     720 cagcgtgtcc ggcgagggcg agggcgatgc cacctacggc aagctgaccc tgaagctgat     780
ctgcaccacc ggcaagctgc ccgtgccctg gcccaccctc gtgaccaccc tgggctacgg     840
cgtgcagtgc ttcgcccgct accccgacca catgaagcag cacgacttct tcaagtccgc     900
catgcccgaa ggctacgtcc aggagcgcac catcttcttc aaggacgacg gcaactacaa     960
gacccgcgcc gaggtgaagt tcgagggcga caccctggtg aaccgcatcg agctgaaggg    1020
catcgacttc aaggaggacg gcaacatcct ggggcacaag ctggagtaca actacaacag    1080
ccacaacgtc tatatcaccg ccgacaagca gaagaacggc atcaaggcca acttcaagat    1140
ccgccacaac atcgaggacg gcggcgtgca gctcgccgac cactaccagc agaacacccc    1200
catcggcgac ggccccgtgc tgctgcccga caaccactac ctgagctacc agtccaagct    1260
gagcaaagac cccaacgaga agcgcgatca catggtcctg ctggagttcg tgaccgccgc    1320
cgggatcact ctcggcatgg acgagctgta caagtaagtc gacggcgcgc cgcggccgcg    1380
aattcgatat cataatcaac ctctggatta caaaatttgt gaaagattga ctggtattct    1440
taactatgtt gctccttta cgctatgtgg atacgctgct ttaatgcctt tgtatcatgc    1500
tattgcttcc cgtatggctt tcattttctc ctccttgtat aaatcctggt tagttcttgc    1560
cacggcggaa ctcatcgccg cctgccttgc ccgctgctgg acaggggctc ggctgttggg    1620
cactgacaat ccgtggctc gagagatctt cgactgtgcc ttctagttgc cagccatctg    1680
ttgtttgccc ctccccgtg ccttccttga ccctggaagg tgccactccc actgtcctt    1740 cctaataaaa tgaggaaatt gcatcgcatt gtctgagtag gtgtcattct attctggggg    1800
gtggggtggg gcaggacagc aagggggagg attgggaaga caatagcagg catgagatct    1860
cacgtgcgga ccgagcggcc gc                                            1882
```

<210> SEQ ID NO 113
<211> LENGTH: 2370
<212> TYPE: DNA
<213> ORGANISM: Artificial Sequence
<220> FEATURE:
<223> OTHER INFORMATION: CN1797

<400> SEQUENCE: 113

-continued

```
gcggccgcaa cgcgtttaga acaatggctg gcccatagta aatgccgtgt tagtgtgtta        60
gttgctgttc ttccacgtca gaagaggcac agacaaatta ccaccaggtg gcgctcagag       120
tctgcggagg catcacaaca gccctgaatt tgaatcctgc tctgccactg cctagttgag       180
accttttact acctgactag ctgtttgtgt attttaggtg tttgttttgt gtgatatttt       240
ttcccaccac ttattctata tgaatggact aaagttaaat atggttctaa ttataaatca       300
aagatatcag cttgtgataa aataataaat agattgatct agtatgattg gttttcttgt       360
caagtaatcc ttacttacat agtctgaaca cattaaatag ccccagtcac tcacaaaata       420
atatcattat tctggataaa atgtaatgag attgtgaatg aaaacagtgt tgatagtggt       480
agagagaagt gccacagtcc ctaatacaca ccagatgttc aaagaatgat tgtggaatga       540
ataaatgttc atatttaatg aacattcatg taattgaatg gtagggcatt atgagaagtg       600
ggatgaggaa aaaggatgaa tcaaagatga ttttcatgtt tctatcttgg taatcactga       660
gatgtgaaat tcaggaatat gaaaaagatt ctaggaaaga gctgataagt ttactttta        720 aattaatcta tttgaaaggt acctgcatac acagatgttg cagataaatg aaagatgaat       780
ggagctggag cgtaagaaag ctctctgggc tgtatattta tgctctaata tcatctgttt       840
acatacaaat ggtaaaagcc aaagggatga ataaaagtca tttattcatt cataaaatat       900
gtattaagac ctaggccaat ttctggaata agagaaccag atgtcaaaat tcttcgggga       960
attcgatatc ataatcaacc ataggtaccg agctcgggat tcagccggga gcttagggag      1020
gggaggtcac ttcataaggg cctgggggggg gagttggagc cacgagtcgt ccagccggag      1080
ccccgtgtgg ctgagctccg gcctcagaag catccccggg ttggatcctt cgaagctagc      1140
gctaccggtc gccaccatgg tgagcaaggg cgaggagctg ttcaccgggg tggtgcccat      1200
cctggtcgag ctggacggcg acgtaaacgg ccacaagttc agcgtgtccg gcgagggcga      1260
gggcgatgcc acctacggca agctgaccct gaagctgatc tgcaccaccg gcaagctgcc      1320
cgtgccctgg cccaccctcg tgaccaccct gggctacggc gtgcagtgct tcgcccgcta      1380
ccccgaccac atgaagcagc acgacttctt caagtccgcc atgcccgaag gctacgtcca      1440
ggagcgcacc atcttcttca aggacgacgg caactacaag acccgcgccg aggtgaagtt      1500
cgagggcgac accctggtga accgcatcga gctgaagggc atcgacttca aggaggacgg      1560
caacatcctg gggcacaagc tggagtacaa ctacaacagc cacaacgtct atatcaccgc      1620
cgacaagcag aagaacggca tcaaggccaa cttcaagatc cgccacaaca tcgaggacgg      1680
cggcgtgcag ctcgccgacc actaccagca gaacacccccc atcggcgacg gccccgtgct      1740
gctgcccgac aaccactacc tgagctacca gtccaagctg agcaaagacc ccaacgagaa      1800
gcgcgatcac atggtcctgc tggagttcgt gaccgccgcc gggatcactc tcggcatgga      1860
cgagctgtac aagtaagtcg acatcataat caacctctgg attacaaaat ttgtgaaaga      1920
ttgactggta ttcttaacta tgttgctcct tttacgctat gtggatacgc tgctttaatg      1980
cctttgtatc atgctattgc ttcccgtatg gctttcattt tctcctcctt gtataaatcc      2040
tggttagttc ttgccacggc ggaactcatc gccgcctgcc ttgcccgctg ctggacaggg      2100
gctcggctgt tgggcactga caattccgtg gctcgagaga tcttcgactg tgccttctag      2160
ttgccagcca tctgttgttt gcccctcccc cgtgccttcc ttgaccctgg aaggtgccac      2220
tcccactgtc ctttcctaat aaaatgagga aattgcatcg cattgtctga gtaggtgtca      2280
ttctattctg gggggtgggg tggggcagga cagcaagggg gaggattggg aagacaatag      2340
caggcatgca cgtgcggacc gagcggccgc                                      2370
```

```
<210> SEQ ID NO 114
<211> LENGTH: 2006
<212> TYPE: DNA
<213> ORGANISM: Artificial Sequence
<220> FEATURE:
<223> OTHER INFORMATION: CN1584

<400> SEQUENCE: 114
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180 acctttact acctgactag ctgtttgtgt attttaggtg tttgtttcag gcaaggcttc      240
ctcccttgag tccctttctg tctcaggtgg atgatctcat tatacaagtc aagctttgaa     300
ttacttcagc cataccctcc ccttccactc catcccaaat aaaaatgagt tacacagaac     360
ccaccagcag tactttacga gtaccagcaa ttgcaaccgt gcatccttaa tagtggcgta     420
atcaaaagtt atgatgcatt tttctgtaat cacaagaaat gataccactt agtgctaagt     480
aaagccaatt ccctaccaca cagaaaggca aaagcgcttc cattttcact ttgaaatgag     540
tgagtcagaa tcaatttggt aaagcagtta acagcaactg tgtgcccctt cgagaattc      600 gatatcataa tcaaccatag gtaccgagct cgggattcag ccgggagctt agggagggga     660
ggtcacttca taagggcctg ggggggggagt tggagccacg agtcgtccag ccggagcccc     720
gtgtggctga gctccggcct cagaagcatc cccgggttgg atccttcgaa gctagcgcta     780
ccggtcgcca ccatggtgag caagggcgag gagctgttca ccggggtggt gcccatcctg     840
gtcgagctgg acggcgacgt aaacggccac aagttcagcg tgtccggcga gggcgagggc     900
gatgccacct acggcaagct gaccctgaag ctgatctgca ccaccggcaa gctgcccgtg     960
ccctggccca ccctcgtgac caccctgggc tacggcgtgc agtgcttcgc ccgctacccc    1020
gaccacatga gcagcacga cttcttcaag tccgccatgc ccgaaggcta cgtccaggag    1080
cgcaccatct tcttcaagga cgacggcaac tacaagaccc gcgccgaggt gaagttcgag    1140
ggcgacaccc tggtgaaccg catcgagctg aagggcatcg acttcaagga ggacggcaac    1200
atcctggggc acaagctgga gtacaactac aacagccaca cgtctatat caccgccgac    1260 aagcagaaga acggcatcaa ggccaacttc aagatccgcc acaacatcga ggacggcggc    1320
gtgcagctcg ccgaccacta ccagcagaac accccatcg gcgacggccc cgtgctgctg    1380
cccgacaacc actacctgag ctaccagtcc aagctgagca agacccccaa cgagaagcgc    1440
gatcacatgg tcctgctgga gttcgtgacc gccgccggga tcactctcgg catggacgag    1500
ctgtacaagt aagtcgacat cataatcaac ctctggatta caaaatttgt gaaagattga    1560
ctggtattct taactatgtt gctccttta cgctatgtgg atacgctgct ttaatgcctt    1620
tgtatcatgc tattgcttcc cgtatggctt tcattttctc ctccttgtat aaatcctggt    1680
tagttcttgc cacggcggaa ctcatcgccg cctgccttgc ccgctgctgg acaggggctc    1740
ggctgtgggg cactgacaat tccgtggctc gagagatctt cgactgtgcc ttctagttgc    1800
cagccatctg ttgtttgccc ctcccccgtg ccttccttga ccctggaagg tgccactccc    1860
actgtccttt cctaataaaa tgaggaaatt gcatcgcatt gtctgagtag gtgtcattct    1920
attctggggg gtggggtggg gcaggacagc aaggggagg attgggaaga caatagcagg    1980
catgcacgtg cggaccgagc ggccgc                                         2006
```

-continued

<210> SEQ ID NO 115
<211> LENGTH: 1763
<212> TYPE: DNA
<213> ORGANISM: Artificial Sequence
<220> FEATURE:
<223> OTHER INFORMATION: CN1455

<400> SEQUENCE: 115
gcggccgcac gcgtctggaa ctgttgaatg aatgaatgaa tgaatgaatg aatgaatgaa      60
tgaaaaatta gactgcccag atagtcaaca attaaaaaat ggttaagtga atgatagcaa     120
acgctgtcaa tgacagcttc agccgcttag gaaaatgttg atgatgtaac attaagggaa     180
ctggtgcaag cattgcaatt acaatgctta aaaagtgctc tgcgtaaaca gggcctggaa     240
gaatatagag acaaatgaga acagctgtgg tgccggagac acgagatctt gcttaaaatt     300
ttccactcag ttttggcaaa ccgtaacaac cttgtggctc ttcatatcct tgaaccttga     360
aatcaatctc atttctagag actgctgata agagtcggaa agacaaagct ttaggtagta     420
atctggagct cgggctgggc ataaaagtca gggcagagcc atctattgct tacatttgct     480
tctgggatcc agatctttcg aagctagcgc taccggtcgc caccatggtg agcaagggcg     540
aggagctgtt caccgggggtg gtgcccatcc tggtcgagct ggacggcgac gtaaacggcc     600
acaagttcag cgtgtccggc gagggcgagg gcgatgccac ctacggcaag ctgaccctga     660
agctgatctg caccaccggc aagctgcccg tgccctggcc caccctcgtg accaccctgg     720
gctacggcgt gcagtgcttc gcccgctacc ccgaccacat gaagcagcac gacttcttca     780
agtccgccat gcccgaaggc tacgtccagg agcgcaccat cttcttcaag gacgacggca     840
actacaagac ccgcgccgag gtgaagttcg agggcgacac cctggtgaac cgcatcgagc     900
tgaagggcat cgacttcaag gaggacggca acatcctggg gcacaagctg gagtacaact     960
acaacagcca caacgtctat atcaccgccg acaagcagaa gaacggcatc aaggccaact    1020
tcaagatccg ccacaacatc gaggacggcg gcgtgcagct cgccgaccac taccagcaga    1080
acacccccat cggcgacggc cccgtgctgc tgcccgacaa ccactacctg agctaccagt    1140
ccaagctgag caaagacccc aacgagaagc gcgatcacat ggtcctgctg gagttcgtga    1200
ccgccgccgg gatcactctc ggcatggacg agctgtacaa gtaagtcgac ggcgcgccgc    1260
ggccgcgaat tcgatatcat aatcaacctc tggattacaa aatttgtgaa agattgactg    1320
gtattcttaa ctatgttgct ccttttacgc tatgtggata cgctgcttta atgcctttgt    1380
atcatgctat tgcttcccgt atggctttca ttttctcctc cttgtataaa tcctggttag    1440
ttcttgccac ggcggaactc atcgccgcct gccttgcccg ctgctggaca ggggctcggc    1500
tgttgggcac tgacaattcc gtggctcgag agatcttcga ctgtgccttc tagttgccag    1560
ccatctgttg tttgcccctc ccccgtgcct tccttgaccc tggaaggtgc cactcccact    1620
gtcctttcct aataaaatga ggaaattgca tcgcattgtc tgagtaggtg tcattctatt    1680
ctggggggtg gggtggggca ggacagcaag ggggaggatt gggaagacaa tagcaggcat    1740
gcacgtgcgg accgagcggc cgc                                             1763

<210> SEQ ID NO 116
<211> LENGTH: 2050
<212> TYPE: DNA
<213> ORGANISM: Artificial Sequence
<220> FEATURE:
<223> OTHER INFORMATION: CN1451

<400> SEQUENCE: 116

```
gcggccgcac gcgtcaagac atctccctgt agacacggtg ccagaacagt gacctcagac      60
cacagcttgg acgctgatta caagtaatcc agctccagag gtgatagagt gtcctttctt     120
taaaaaggag ataaaaatag cgaagaaaca acactttcct tagttctctg aaaggttggc     180
attcttccag agtagactta tgtacttttt gtacttggag gaaaaaaaga gatgggatct     240
ggtccaagaa tagtcctgca aacaagagaa atatggagca ggcagctgga gctgagcatc     300
caagtggtac caccagctgc aggcccatta attaacgatc cctggtatgt agcggttccc     360
gtgaccttga ttcttgttga attcacagag ataattttta cagagtctct acttttctca     420
ctgcggtata tttatccaag gagtaccttg catatttccc cccatctctc caagcagtaa     480
atttattcta attgcaaaga gatacagtaa aagcctgatt gaatacttgg cagtttatag     540
agatttattt cgggagctta agggggtttt tagactgtat gactagagca gggttgaggg     600
gagctgggga aaggagccca agagaaaatg tagatttaat ggatctataa aatgaccctg     660
ctgtagataa acgtttgttc caaagaagtt taaacagcct gacccaaacc aggagctcgg     720
gctgggcata aaagtcaggg cagagccatc tattgcttac atttgcttct gggatccaga     780
tctttcgaag ctagcgctac cggtcgccac catggtgagc aagggcgagg agctgttcac     840
cggggtggtg cccatcctgg tcgagctgga cggcgacgta aacggccaca gttcagcgt     900 gtccggcgag ggcgagggcg atgccaccta cggcaagctg accctgaagc tgatctgcac     960
caccggcaag ctgcccgtgc cctggcccac cctcgtgacc accctgggct acggcgtgca    1020
gtgcttcgcc cgctacccccg accacatgaa gcagcacgac ttcttcaagt ccgccatgcc    1080
cgaaggctac gtccaggagc gcaccatctt cttcaaggac gacggcaact acaagacccg    1140
cgccgaggtg aagttcgagg gcgacaccct ggtgaaccgc atcgagctga agggcatcga    1200
cttcaaggag gacggcaaca tcctggggca caagctggag tacaactaca acagccacaa    1260
cgtctatatc accgccgaca agcagaagaa cggcatcaag gccaacttca gatccgcca    1320 caacatcgag gacggcggcg tgcagctcgc cgaccactac cagcagaaca cccccatcgg    1380
cgacggcccc gtgctgctgc ccgacaacca ctacctgagc taccagtcca agctgagcaa    1440
agaccccaac gagaagcgcg atcacatggt cctgctggag ttcgtgaccg ccgccgggat    1500
cactctcggc atggacgagc tgtacaagta agtcgacggc gcgccgcggc cgcgaattcg    1560
atatcataat caacctctgg attacaaaat ttgtgaaaga ttgactggta ttcttaacta    1620
tgttgctcct tttacgctat gtggatacgc tgctttaatg cctttgtatc atgctattgc    1680
ttcccgtatg gctttcattt tctcctcctt gtataaatcc tggttagttc ttgccacggc    1740
ggaactcatc gccgcctgcc ttgcccgctg ctggacaggg gctcggctgt tgggcactga    1800
caattccgtg gctcgagaga tcttcgactg tgccttctag ttgccagcca tctgttgttt    1860 gccccctcccc cgtgccttcc ttgaccctgg aaggtgccac tcccactgtc ctttcctaat    1920
aaaatgagga aattgcatcg cattgtctga gtaggtgtca ttctattctg gggggtgggg    1980
tggggcagga cagcaagggg gaggattggg aagacaatag caggcatgca cgtgcggacc    2040
gagcggccgc                                                            2050
```

```
<210> SEQ ID NO 117
<211> LENGTH: 2209
<212> TYPE: DNA
<213> ORGANISM: Artificial Sequence
<220> FEATURE:
<223> OTHER INFORMATION: CN2039
```

<400> SEQUENCE: 117

```
gcggccgcac gcgccggtac cgaagctacc cctaacacac tattctacac acagaaaatg      60
ctcttcacta ggaagctacc cctaacacac tattctacac acagaaaatg ctcttcacta     120
ggaagctacc cctaacacac tattctacac acagaaaatg ctcttcacta gacgcgtagg     180
tacctctaca ttgatggacc tttctccaga atgaggagcc aaaatcatct gaattaagta     240
gagatctcat ttgtccctga ctcatgataa tgtctgtgct acagtcctgc attaattact     300
ttgcccaagt agaaatacac tacccatata agaatttcac ttctgaacaa aacaaaataa     360
aaatccacga gtggtgacct caaaatgaac tggttaaatt taaggactca tttttaaagg     420
tcaatgtcct tttgctgcaa atacagttcc tatgcagatg agaagttgaa cctgacctat     480
ggagccgagc ataattagcc agctgcaccc tcataataag gtgcagatgg ttaattgcac     540
cagcaaataa ctgcttactt gtgggcacaa aagcctgtac ctaaaatcat tgaaagtata     600
cttgggacta tttatgctca tggcaaacaa aacacatttc caaggtttca tctgcgaaca     660
gatcacagcc agctccaaat ccctgctttg cgggagagcc attcacgctg ctgaggtctg     720
gtccaagaga gggaccactg gccacaaagc cacatattaa ctggtgaaat atttcttggg     780
gtgctgaatc gttgttgaga gctcgattca gccgggagct tagggagggg aggtcacttc     840
ataagggctt gggggggggag ttggagccac gagtcgtcca gccggagccc cgtgtggctg     900
tgctccggcc tcagaagcat ccccggatcc agatctttcg aagctagcgc taccggtcgc     960
caccatggtg agcaagggcg aggagctgtt caccggggtg gtgcccatcc tggtcgagct    1020
ggacggcgac gtaaacggcc acaagttcag cgtgtccggc gagggcgagg gcgatgccac    1080
ctacggcaag ctgaccctga agctgatctg caccaccggc aagctgcccg tgccctggcc    1140
caccctcgtg accaccctgg gctacggcgt gcagtgcttc gcccgctacc cgaccacat    1200 gaagcagcac gacttcttca gtccgccat gcccgaaggc tacgtccagg agcgcaccat    1260
cttcttcaag gacgacggca actacaagac ccgcgccgag gtgaagttcg agggcgacac    1320
cctggtgaac cgcatcgagc tgaagggcat cgacttcaag gaggacggca acatcctggg    1380
gcacaagctg gagtacaact acaacagcca caacgtctat atcaccgccg acaagcagaa    1440
gaacggcatc aaggccaact tcaagatccg ccacaacatc gaggacggcg gcgtgcagct    1500
cgccgaccac taccagcaga acacccccat cggcgacggc cccgtgctgc tgcccgacaa    1560
ccactacctg agctaccagt ccaagctgag caaagacccc aacgagaagc gcgatcacat    1620
ggtcctgctg gagttcgtga ccgccgccgg gatcactctc ggcatggacg agctgtacaa    1680
gtaagtcgac ggcgcgccgc ggccgcgaat tcgatatcat aatcaacctc tggattacaa    1740
aatttgtgaa agattgactg gtattcttaa ctatgttgct cctttacgc tatgtggata    1800 cgctgcttta atgcctttgt atcatgctat tgcttcccgt atggctttca ttttctcctc    1860
cttgtataaa tcctggttag ttcttgccac ggcggaactc atcgccgcct gccttgcccg    1920
ctgctggaca ggggctcggc tgttgggcac tgacaattcc gtggctcgag atatcttcga    1980
ctgtgccttc tagttgccag ccatctgttg tttgccccctc ccccgtgcct tccttgaccc    2040
tggaaggtgc cactcccact gtcctttcct aataaaatga ggaaattgca tcgcattgtc    2100
tgagtaggtg tcattctatt ctgggggtg gggtggggca ggacagcaag ggggaggatt    2160
gggaagacaa tagcaggcat gagatctcac gtgcggaccg agcggccgc                2209
```

<210> SEQ ID NO 118
<211> LENGTH: 2140

```
<212> TYPE: DNA
<213> ORGANISM: Artificial Sequence
<220> FEATURE:
<223> OTHER INFORMATION: CN2040

<400> SEQUENCE: 118
gcggccgcac gcgccggtac cgaagctacc cctaacacac tattctacac acagaaaatg      60
ctcttcacta ggaagctacc cctaacacac tattctacac acagaaaatg ctcttcacta     120
ggaagctacc cctaacacac tattctacac acagaaaatg ctcttcacta gacgcgtaga     180
ttcctcaccc ccaagaagta tttaagcagt tgagatgtgg cccccagtcc ctcccttgaa     240
ctcgacctcg gcaatgtgaa ccacaaagcc ctgcagttgg aggctgccga ggtctattca     300
cagatgaaat tttggaaatg tgttttgttt gcctgtgcat aaatacgccc aagcatacta     360
tcgatacttt taggtacagg cttttgtgcc tactggtaag cagtcatttg ccggggcaat     420
taaccatctg cactttatta tcagggtgca gctggctaat gatgctcagt gccacggggc     480
aggatcagct tctcatctgc acaggaactg tattcacagc aaaggacatt gacctttaac     540
aatgaatctt taaatttaac cgggtccccc agagatcacc gcacacaagg tttcattgtg     600
tttcgatctg aggtgagatt caaatgtggg ccgtgggatt cctgtttggg gtagagcggt     660
taacacagaa cagtaggata ggtcagcaat tatcagccaa gaacaaagga gaaccctgat     720
gctcagtctg agctcgattc agccgggagc ttagggaggg gaggtcactt cataagggct     780 tggggggggga gttggagcca cgagtcgtcc agccggagcc ccgtgtggct gtgctccggc     840
ctcagaagca tccccggatc cagatctttc gaagctagcg ctaccggtcg ccaccatggt     900
gagcaagggc gaggagctgt tcaccggggt ggtgcccatc ctggtcgagc tggacggcga     960
cgtaaacggc cacaagttca gcgtgtccgg cgagggcgag ggcgatgcca cctacggcaa    1020
gctgaccctg aagctgatct gcaccaccgg caagctgccc gtgccctggc ccaccctcgt    1080
gaccaccctg ggctacggcg tgcagtgctt cgcccgctac cccgaccaca tgaagcagca    1140
cgacttcttc aagtccgcca tgcccgaagg ctacgtccag gagcgcacca tcttcttcaa    1200
ggacgacggc aactacaaga cccgcgccga ggtgaagttc gagggcgaca ccctggtgaa    1260
ccgcatcgag ctgaagggca tcgacttcaa ggaggacggc aacatcctgg ggcacaagct    1320
ggagtacaac tacaacagcc acaacgtcta tatcaccgcc gacaagcaga gaacggcat     1380 caaggccaac ttcaagatcc gccacaacat cgaggacggc ggcgtgcagc tcgccgacca    1440
ctaccagcag aacacccca tcggcgacgg ccccgtgctg ctgcccgaca accactacct    1500
gagctaccag tccaagctga gcaaagaccc caacgagaag cgcgatcaca tggtcctgct    1560
ggagttcgtg accgccgccg ggatcactct cggcatggac gagctgtaca agtaagtcga    1620
cggcgcgccg cggccgcgaa ttcgatatca taatcaacct ctggattaca aaatttgtga    1680
aagattgact ggtattctta actatgttgc tccttttacg ctatgtggat acgctgcttt    1740
aatgcctttg tatcatgcta ttgcttcccg tatggctttc attttctcct ccttgtataa    1800
atcctggtta gttcttgcca cggcggaact catcgccgcc tgccttgccc gctgctggac    1860
aggggctcgg ctgttgggca ctgacaattc cgtggctcga gagatcttcg actgtgcctt    1920
ctagttgcca gccatctgtt gtttgcccct ccccgtgcc ttccttgacc ctggaaggtg    1980
ccactcccac tgtcctttcc taataaaatg aggaaattgc atcgcattgt ctgagtaggt    2040
gtcattctat tctggggggt ggggtggggc aggacagcaa gggggaggat tgggaagaca    2100
atagcaggca tgagatctca cgtgcggacc gagcggccgc                          2140
```

-continued

```
<210> SEQ ID NO 119
<211> LENGTH: 2051
<212> TYPE: DNA
<213> ORGANISM: Artificial Sequence
<220> FEATURE:
<223> OTHER INFORMATION: CN1567

<400> SEQUENCE: 119
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgttttga agtgttcctg     240
cccttgcatg aaaatgactc tatctggttt ataattagaa gtgaaatgat tttaaatggc     300
ttccacatgg cttagttttc caagcagttc cagttacata gaacttcata taaacagata     360
atgagaggct agagttggag agcacagttc ctgcttccaa attggcttga agtggggaca     420
tctgctctgc atgaagcctg ggtcaggctg cccctctcat ctgtgacctc ctgtggtcgg     480
gagggacttg ctctggatta tataaaggct tcacaagagt actggaagcg gggacggaat     540
caacttgagc aaaaaaccta attggcttga atctttcctt gaccatcagt aattattttg     600
agattgatag cctatcttat aataaaataa ctgtttcctg aattcgatat cataatcaac     660
cataggtacc gagctcggga ttcagccggg agcttaggga ggggaggtca cttcataagg     720
gcctgggggg ggagttggag ccacgagtcg tccagccgga gccccgtgtg gctgagctcc     780
ggcctcagaa gcatccccgg gttggatcct tcgaagctag cgctaccggt cgccaccatg     840
gtgagcaagg gcgaggagct gttcaccggg gtggtgccca tcctggtcga gctggacggc     900
gacgtaaacg gccacaagtt cagcgtgtcc ggcgagggcg agggcgatgc cacctacggc     960
aagctgaccc tgaagctgat ctgcaccacc ggcaagctgc ccgtgccctg ccccaccctc    1020
gtgaccaccc tgggctacgg cgtgcagtgc ttcgcccgct accccgacca catgaagcag    1080
cacgacttct tcaagtccgc catgcccgaa ggctacgtcc aggagcgcac catcttcttc    1140
aaggacgacg gcaactacaa gacccgcgcc gaggtgaagt tcgagggcga caccctggtg    1200
aaccgcatcg agctgaaggg catcgacttc aaggaggacg gcaacatcct ggggcacaag    1260
ctggagtaca actacaacag ccacaacgtc tatatcaccg ccgacaagca gaagaacggc    1320
atcaaggcca acttcaagat ccgccacaac atcgaggacg gcggcgtgca gctcgccgac    1380
cactaccagc agaacacccc catcggcgac ggccccgtgc tgctgcccga caaccactac    1440
ctgagctacc agtccaagct gagcaaagac cccaacgaga agcgcgatca catggtcctg    1500
ctggagttcg tgaccgccgc cgggatcact ctcggcatgg acgagctgta caagtaagtc    1560
gacatcataa tcaacctctg gattacaaaa tttgtgaaag attgactggt attcttaact    1620
atgttgctcc ttttacgcta tgtggatacg ctgctttaat gcctttgtat catgctattg    1680
cttcccgtat ggctttcatt ttctcctcct tgtataaatc ctggttagtt cttgccacgg    1740
cggaactcat cgccgcctgc cttgcccgct gctggacagg ggctcggctg ttgggcactg    1800
acaattccgt ggctcgagag atcttcgact gtgccttcta gttgccagcc atctgttgtt    1860
tgcccctccc ccgtgccttc cttgaccctg gaaggtgcca ctcccactgt cctttcctaa    1920
taaaatgagg aaattgcatc gcattgtctg agtaggtgtc attctattct gggggtggg    1980 gtggggcagg acagcaaggg ggaggattgg gaagacaata gcaggcatgc acgtgcggac    2040
cgagcggccg c                                                       2051
```

```
<210> SEQ ID NO 120
<211> LENGTH: 2058
<212> TYPE: DNA
<213> ORGANISM: Artificial Sequence
<220> FEATURE:
<223> OTHER INFORMATION: CN1626

<400> SEQUENCE: 120
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgtttgct tagaacgtcc     240
accaggattt ttgtggcaga tcgtaatata ggtcaagaag gatttaaatt tagttcttat     300
attctcaaat taataactca atgaattgct ttaagttttg aaaatttact ttcataagag     360
tcagatctga actggcttct ctatttcggc agaagcacca tcatgaatct cagaaccttt     420
aaaaagacac ccaagagtag caattttctt tctgagagta cggattctat ttctgacatg     480
taattttcct tatacccaac accaaaaatg gggacttgaa tcataaacat atttaacact     540
cagaggagac attagtagga tccttttaaa tattgaaaac ataatgaaat caggatccca     600
gtccaaataa tgtgcctttt cttaaaaggc aaaaacagtg tgggaggaat tcgatatcat     660
aatcaaccat aggtaccgag ctcgggattc agccgggagc ttagggaggg gaggtcactt     720
cataagggcc tggggggga gttggagcca cgagtcgtcc agccggagcc ccgtgtggct     780
gagctccggc ctcagaagca tccccgggtt ggatccttcg aagctagcgc taccggtcgc     840
caccatggtg agcaagggcg aggagctgtt caccgggggtg gtgcccatcc tggtcgagct     900
ggacggcgac gtaaacggcc acaagttcag cgtgtccggc gagggcgagg gcgatgccac     960
ctacggcaag ctgaccctga agctgatctg caccaccggc aagctgcccg tgccctggcc    1020
caccctcgtg accaccctgg gctacggcgt gcagtgcttc gcccgctacc ccgaccacat    1080
gaagcagcac gacttcttca gtccgccat gcccgaaggc tacgtccagg agcgcaccat    1140
cttcttcaag gacgacggca actacaagac ccgcgccgag gtgaagttcg agggcgacac    1200
cctggtgaac cgcatcgagc tgaagggcat cgacttcaag gaggacggca acatcctggg    1260
gcacaagctg gagtacaact acaacagcca caacgtctat atcaccgccg acaagcagaa    1320
gaacggcatc aaggccaact tcaagatccg ccacaacatc gaggacggcg cgtgcagct    1380 cgccgaccac taccagcaga acaccccat cggcgacggc cccgtgctgc tgcccgacaa    1440
ccactacctg agctaccagt ccaagctgag caaagacccc aacgagaagc gcgatcacat    1500
ggtcctgctg gagttcgtga ccgccgccgg gatcactctc ggcatggacg agctgtacaa    1560
gtaagtcgac atcataatca acctctggat tacaaaattt gtgaaagatt gactggtatt    1620
cttaactatg ttgctccttt tacgctatgt ggatacgctg ctttaatgcc tttgtatcat    1680
gctattgctt cccgtatggc tttcattttc tcctccttgt ataaatcctg gttagttctt    1740
gccacggcgg aactcatcgc cgcctgcctt gcccgctgct ggacaggggc tcggctgttg    1800
ggcactgaca attccgtggc tcgagagatc ttcgactgtg ccttctagtt gccagccatc    1860
tgttgtttgc ccctcccccg tgccttcctt gaccctggaa ggtgccactc ccactgtcct    1920
ttcctaataa aatgaggaaa ttgcatcgca ttgtctgagt aggtgtcatt ctattctggg    1980
gggtggggtg gggcaggaca gcaagggga ggattgggaa gacaatagca ggcatgcacg    2040
```

-continued tgcggaccga gcggccgc                                                                  2058

<210> SEQ ID NO 121
<211> LENGTH: 1923
<212> TYPE: DNA
<213> ORGANISM: Artificial Sequence
<220> FEATURE:
<223> OTHER INFORMATION: CN1712

<400> SEQUENCE: 121
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180 acctttact acctgactag ctgtttgtgt attttaggtg tttgtttacc aggctgacta     240
gtgctctgtg gtcttgatca attgtcccag cagagttggt gcatgggaaa gcctttcttg     300
gccttatcag cagctcagcc tgggaggttg gcccgggggc tgaccaagca caaaatagaa     360
aagccactaa taagatccag ctggaacaaa tagcctctat ttattttagg aaactaatga     420
tatgtcatca tgacacatat ctaaccttag tatttctgat tggacaggcc agttatgtgg     480
gctatgattc aagccatggt tacggctctg cgaattcgat atcataatca accataggta     540
ccgagctcgg gattcagccg ggagcttagg gaggggaggt cacttcataa gggcctgggg     600
ggggagttgg agccacgagt cgtccagccg gagccccgtg tggctgagct ccggcctcag     660
aagcatcccc gggttggatc cttcgaagct agcgctaccg gtcgccacca tggtgagcaa     720
gggcgaggag ctgttcaccg gggtggtgcc catcctggtc gagctggacg gcgacgtaaa     780
cggccacaag ttcagcgtgt ccggcgaggg cgagggcgat gccacctacg gcaagctgac     840
cctgaagctg atctgcacca ccggcaagct gcccgtgccc tggcccaccc tcgtgaccac     900
cctgggctac ggcgtgcagt gcttcgcccg ctaccccgac cacatgaagc agcacgactt     960
cttcaagtcc gccatgcccg aaggctacgt ccaggagcgc accatcttct tcaaggacga    1020
cggcaactac aagacccgcg ccgaggtgaa gttcgagggc gacaccctgg tgaaccgcat    1080
cgagctgaag ggcatcgact tcaaggagga cggcaacatc ctggggcaca gctggagta    1140 caactacaac agccacaacg tctatatcac cgccgacaag cagaagaacg gcatcaaggc    1200
caacttcaag atccgccaca acatcgagga cggcggcgtg cagctcgccg accactacca    1260
gcagaacacc cccatcggcg acggccccgt gctgctgccc gacaaccact acctgagcta    1320
ccagtccaag ctgagcaaag accccaacga gaagcgcgat cacatggtcc tgctggagtt    1380
cgtgaccgcc gccgggatca ctctcggcat ggacgagctg tacaagtaag tcgacatcat    1440
aatcaacctc tggattacaa aatttgtgaa agattgactg gtattcttaa ctatgttgct    1500
ccttttacgc tatgtggata cgctgcttta atgcctttgt atcatgctat tgcttcccgt    1560
atggctttca ttttctcctc cttgtataaa tcctggttag ttcttgccac ggcggaactc    1620
atcgccgcct gccttgcccg ctgctggaca ggggctcggc tgttgggcac tgacaattcc    1680
gtggctcgag agatcttcga ctgtgccttc tagttgccag ccatctgttg tttgcccctc    1740
ccccgtgcct tccttgaccc tggaaggtgc cactcccact gtcctttcct aataaaatga    1800
ggaaattgca tcgcattgtc tgagtaggtg tcattctatt ctggggggtg gggtggggca    1860
ggacagcaag ggggaggatt gggaagacaa tagcaggcat gcacgtgcgg accgagcggc    1920
cgc                                                                 1923

-continued

```
<210> SEQ ID NO 122
<211> LENGTH: 1969
<212> TYPE: DNA
<213> ORGANISM: Artificial Sequence
<220> FEATURE:
<223> OTHER INFORMATION: CN1700

<400> SEQUENCE: 122
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgttttgg tatagggggt     240
cttacggaaa tgcagggaaa tttgatttca cttaccacag gatcagagat gtatttcttt     300
catgggtacc acagctgcta aaccaagcag gtcttctcag gacataaccc acagtgagca     360
tgttaggatg caggaacatg tgcagggctc tggcaagagg tactgaaaca ttgaaaacgg     420
ccttgataga gtatctctct ttgaaagagg tttaaaaaag atacactaaa agttattttg     480
cttaacactg tccatataaa ccaaagaggg cattgaaatt accaatggcc ctgtatctct     540
tgggcaacag ataaggcgaa ttcgatatca taatcaacca taggtaccga gctcgggatt     600
cagccgggag cttagggagg ggaggtcact tcataagggc ctggggggggg agttggagcc     660 acgagtcgtc cagccggagc cccgtgtggc tgagctccgg cctcagaagc atccccgggt     720
tggatccttc gaagctagcg ctaccggtcg ccaccatggt gagcaagggc gaggagctgt     780
tcaccggggt ggtgcccatc ctggtcgagc tggacggcga cgtaaacggc cacaagttca     840
gcgtgtccgg cgagggcgag ggcgatgcca cctacggcaa gctgaccctg aagctgatct     900
gcaccaccgg caagctgccc gtgccctggc ccaccctcgt gaccaccctg ggctacggcg     960
tgcagtgctt cgcccgctac cccgaccaca tgaagcagca cgacttcttc aagtccgcca    1020
tgcccgaagg ctacgtccag gagcgcacca tcttcttcaa ggacgacggc aactacaaga    1080
cccgcgccga ggtgaagttc gagggcgaca ccctggtgaa ccgcatcgag ctgaagggca    1140
tcgacttcaa ggaggacggc aacatcctgg ggcacaagct ggagtacaac tacaacagcc    1200
acaacgtcta tatcaccgcc gacaagcaga agaacggcat caaggccaac ttcaagatcc    1260
gccacaacat cgaggacggc ggcgtgcagc tcgccgacca ctaccagcag aacacccccca    1320 tcggcgacgg ccccgtgctg ctgcccgaca accactacct gagctaccag tccaagctga    1380
gcaaagaccc caacgagaag cgcgatcaca tggtcctgct ggagttcgtg accgccgccg    1440
ggatcactct cggcatggac gagctgtaca agtaagtcga catcataatc aacctctgga    1500
ttacaaaatt tgtgaaagat tgactggtat tcttaactat gttgctcctt ttacgctatg    1560
tggatacgct gctttaatgc ctttgtatca tgctattgct tcccgtatgg ctttcatttt    1620
ctcctccttg tataaatcct ggttagttct tgccacggcg gaactcatcg ccgcctgcct    1680
tgcccgctgc tggacagggg ctcggctgtt gggcactgac aattccgtgg ctcgagagat    1740
cttcgactgt gccttctagt tgccagccat ctgttgtttg cccctccccc gtgccttcct    1800
tgaccctgga aggtgccact cccactgtcc tttcctaata aaatgaggaa attgcatcgc    1860
attgtctgag taggtgtcat tctattctgg ggggtggggt ggggcaggac agcaaggggg    1920
aggattggga agacaatagc aggcatgcac gtgcggaccg agcggccgc               1969

<210> SEQ ID NO 123
<211> LENGTH: 2032
<212> TYPE: DNA
```

```
<213> ORGANISM: Artificial Sequence
<220> FEATURE:
<223> OTHER INFORMATION: CN1607

<400> SEQUENCE: 123
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180 acctttact acctgactag ctgtttgtgt attttaggtg tttgtttccg gatgccatcg      240
aaggaaactg cgcatcccac aattcaccga ggtttgtttt cccctccaac tccagatggc     300
ctatctgggg acagcagagg cccctaggtg cgggccgttg cagtttttg atgagctgca      360 cacatatgga tacccgaaca tctggagcgg ccatgtgctg cttgggggcag gccagccctg     420 gtgagccaat ccaggggccc cggggtgccg ggaggcagca gggcccagcc agtgagcgcg     480
gataaattat tcatgaacga gttatttgtg gtgcaagggg ttcatcagct actttgatta     540
aaagtccaac gagtaatgaa tatgcaaacg ccagcgactc ctccaagcaa cagatttgtc     600
aaattgtctg tacttcaccg gaattcgata tcataatcaa ccataggtac cgagctcggg     660
attcagccgg gagcttaggg aggggaggtc acttcataag ggcctgggg gggagttgga      720 gccacgagtc gtccagccgg agccccgtgt ggctgagctc cggcctcaga agcatccccg     780
ggttggatcc ttcgaagcta gcgctaccgg tcgccaccat ggtgagcaag ggcgaggagc     840
tgttcaccgg ggtggtgccc atcctggtcg agctggacgg cgacgtaaac ggccacaagt     900
tcagcgtgtc cggcgagggc gagggcgatg ccacctacgg caagctgacc ctgaagctga     960
tctgcaccac cggcaagctg cccgtgccct ggcccaccct cgtgaccacc ctgggctacg    1020
gcgtgcagtg cttcgcccgc taccccgacc acatgaagca gcacgacttc ttcaagtccg    1080
ccatgcccga aggctacgtc caggagcgca ccatcttctt caaggacgac ggcaactaca    1140
agacccgcgc cgaggtgaag ttcgagggcg acaccctggt gaaccgcatc gagctgaagg    1200
gcatcgactt caaggaggac ggcaacatcc tggggcacaa gctggagtac aactacaaca    1260
gccacaacgt ctatatcacc gccgacaagc agaagaacgg catcaaggcc aacttcaaga    1320
tccgccacaa catcgaggac ggcggcgtgc agctcgccga ccactaccag cagaacaccc    1380
ccatcggcga cggccccgtg ctgctgcccg acaaccacta cctgagctac cagtccaagc    1440
tgagcaaaga ccccaacgag aagcgcgatc acatggtcct gctggagttc gtgaccgccg    1500
ccgggatcac tctcggcatg gacgagctgt acaagtaagt cgacatcata atcaacctct    1560
ggattacaaa atttgtgaaa gattgactgg tattcttaac tatgttgctc cttttacgct    1620
atgtggatac gctgctttaa tgcctttgta tcatgctatt gcttcccgta tggctttcat    1680
tttctcctcc ttgtataaat cctggttagt tcttgccacg gcggaactca tcgccgcctg    1740
ccttgcccgc tgctggacag gggctcggct gttgggcact gacaattccg tggctcgaga    1800
gatcttcgac tgtgccttct agttgccagc catctgttgt ttgcccctcc ccgtgccctt    1860
ccttgaccct ggaaggtgcc actcccactg tcctttccta ataaaatgag gaaattgcat    1920
cgcattgtct gagtaggtgt cattctattc tggggggtgg ggtggggcag gacagcaagg    1980
gggaggattg ggaagacaat agcaggcatg cacgtgcgga ccgagcggcc gc           2032

<210> SEQ ID NO 124
<211> LENGTH: 2570
<212> TYPE: DNA
<213> ORGANISM: Artificial Sequence
```

<220> FEATURE:
<223> OTHER INFORMATION: CN1605

<400> SEQUENCE: 124

```
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgtttgca ggacagcagc     240
catgctccag ttgtaagcca tatagttacc atagttgaga gagatcccta ctctccctgg     300
ccctggcctc caaaccctac cacaccatca gctctgggt caggggatgc cctgtggtgg      360
attctgaatt tctgtgtatg tgcaactgca tggggaacag gcagattatt gggcacatga     420
gactaggctg tctgaatctt ccttgagaga ctcccttacc tccagacacc gacacttgtc     480
tccctaccct acagtcagag gcctgtagga cctcagcact cgagaaagat aaggctgcca     540
aacattgctg tgtccacctc ccagacggga catcctgtgt ggttgctgtc aagtccgggt     600
tctccatcaa agagattctg tctggattgt gtgaacggca tggcatcaat ggggctgctg     660
tggacctctt cctggtgggc ggagacaagg tactgtgcca tgcaggagtg agtgagccac     720
cagtatccta gctctgtctg ctcccttcct cctgccttgt tagtgctcca ctcctgacac     780
caccactacc acccgtgagg cagagcagct gcaggtggag gctcccaggg ggtcggtggg     840
tgcacggcag cacaccccag tgtctagagg gtgtcaggct aattttgccc tggtcttttg     900
ttctcgcagc tgtgtgctgt tacatgtcaa gcccacgtgc tcccacatta actctggtgt     960
ctttgttcct cagcctcttg tgctgcatca ggacagcagc atcctggcca ccagggacct    1020
acgcttggaa aagcggactt tgtttcggta agaaaccgc acacaggttt ctggagattt     1080
ccaaagtctc cacagtgtga gcctcaggac ttgtattcct ttctaatgtg agcatgtact    1140
tgtcccatgt caggccatga attcgatatc ataatcaacc ataggtaccg agctcgggat    1200
tcagccggga gcttagggag gggaggtcac ttcataaggg cctggggggg gagttggagc    1260
cacgagtcgt ccagccggag ccccgtgtgg ctgagctccg gcctcagaag catccccggg    1320
ttggatcctt cgaagctagc gctaccggtc gccaccatgg tgagcaaggg cgaggagctg    1380
ttcaccgggg tggtgcccat cctggtcgag ctggacggcg acgtaaacgg ccacaagttc    1440
agcgtgtccg gcgagggcga gggcgatgcc acctacggca agctgaccct gaagctgatc    1500
tgcaccaccg gcaagctgcc cgtgccctgg cccaccctcg tgaccaccct gggctacggc    1560
gtgcagtgct tcgcccgcta ccccgaccac atgaagcagc acgacttctt caagtccgcc    1620
atgcccgaag ctacgtcca ggagcgcacc atcttcttca aggacgacgg caactacaag     1680
acccgcgccg aggtgaagtt cgagggcgac accctggtga accgcatcga gctgaagggc    1740
atcgacttca aggaggacgg caacatcctg gggcacaagc tggagtacaa ctacaacagc    1800
cacaacgtct atatcaccgc cgacaagcag aagaacggca tcaaggccaa cttcaagatc    1860
cgccacaaca tcgaggacgg cggcgtgcag ctcgccgacc actaccagca gaacacccccc   1920 atcggcgacg gccccgtgct gctgcccgac aaccactacc tgagctacca gtccaagctg    1980
agcaaagacc ccaacgagaa gcgcgatcac atggtcctgc tggagttcgt gaccgccgcc    2040
gggatcactc tcggcatgga cgagctgtac aagtaagtcg acatcataat caacctctgg    2100
attacaaaat ttgtgaaaga ttgactggta ttcttaacta tgttgctcct tttacgctat    2160
gtggatacgc tgctttaatg cctttgtatc atgctattgc ttcccgtatg gctttcattt    2220
```

-continued

```
tctcctcctt gtataaatcc tggttagttc ttgccacggc ggaactcatc gccgcctgcc    2280
ttgcccgctg ctggacaggg gctcggctgt tgggcactga caattccgtg gctcgagaga    2340
tcttcgactg tgccttctag ttgccagcca tctgttgttt gcccctcccc cgtgccttcc    2400
ttgaccctgg aaggtgccac tcccactgtc ctttcctaat aaaatgagga aattgcatcg    2460
cattgtctga gtaggtgtca ttctattctg gggggtgggg tggggcagga cagcaagggg    2520
gaggattggg aagacaatag caggcatgca cgtgcggacc gagcggccgc              2570
```

```
<210> SEQ ID NO 125
<211> LENGTH: 2443
<212> TYPE: DNA
<213> ORGANISM: Artificial Sequence
<220> FEATURE:
<223> OTHER INFORMATION: CN1556

<400> SEQUENCE: 125
```

```
gcggccgcaa cgcgtttaga acaatggctg gcccatagta aatgccgtgt tagtgtgtta     60
gttgctgttc ttccacgtca gaagaggcac agacaaatta ccaccaggtg gcgctcagag    120
tctgcggagg catcacaaca gccctgaatt tgaatcctgc tctgccactg cctagttgag    180
accttttact acctgactag ctgtttgtgt attttaggtg tttgtttgtg cttatggtag    240
gggctcaaaa atatttagtt ccttcctctc aaataatctg gttgggatga gccagtctgg    300
ggtcccaggg aacattgaga gcctaccctc cccaccttca ctcgggccca gtgtcctttg    360
ccccgaggag ggcctggctg tcagccaagc cacccccatc cccagggtca cggtgtgggc    420
agtgcagcca caggaaccag catggaccct tcatagacct ggatgctccc aacttgtcac    480
tcggagcaga gcacactgcc atctgcaggg tcaccgctgg gcctcgtcac ttatcatgat    540
tgctaattaa agacaaaatt aaccgaccct ggcctggtgg cacctctccc aatgcctggc    600
tctggctggc tgggcctcag tggggaaggt ctgcccctga tacttgggat ggtggccaga    660
gcgaggggag tggaatccca cccagaacgg agaaggtgcc aagccatctg gaaagctggg    720
gccagcccga cacctcacca gccagctggg agaaatgaga tcttgggcca atctgggggt    780
gacaggaaag ggagggtgag atgtggacgt cttattccca actgtatccc cagcccctta    840
gagcagttgt tgttgtcaga gagaacagat gtgatgtact gagcatgcca ggcacgaagg    900
gggcatttga taaataataa attgctgcgt ggcttgatgg atggggctgc aagtgcatag    960
tcagtgctca gcgttttccg catacacttt cagaataaca aacccctcta tggtgctttt   1020
agtgaggtgt tgaattcgat atcataatca accataggta ccgagctcgg gattcagccg   1080
ggagcttagg gaggggaggt cacttcataa gggcctgggg ggggagttgg agccacgagt   1140
cgtccagccg gagcccgtg tggctgagct ccggcctcag aagcatcccc gggttggatc    1200
cttcgaagct agcgctaccg gtcgccacca tggtgagcaa gggcgaggag ctgttcaccg   1260
gggtggtgcc catcctggtc gagctggacg gcgacgtaaa cggccacaag ttcagcgtgt   1320
ccggcgaggg cgagggcgat gccacctacg gcaagctgac cctgaagctg atctgcacca   1380
ccggcaagct gcccgtgccc tggcccaccc tcgtgaccac cctgggctac ggcgtgcagt   1440
gcttcgcccg ctaccccgac cacatgaagc agcacgactt cttcaagtcc gccatgcccg   1500
aaggctacgt ccaggagcgc accatcttct tcaaggacga cggcaactac aagacccgcg   1560
ccgaggtgaa gttcgagggc gacaccctgg tgaaccgcat cgagctgaag ggcatcgact   1620
tcaaggagga cggcaacatc ctggggcaca agctggagta caactacaac agccacaacg   1680
tctatatcac cgccgacaag cagaagaacg gcatcaaggc caacttcaag atccgccaca   1740
```

-continued

```
acatcgagga cggcggcgtg cagctcgccg accactacca gcagaacacc cccatcggcg    1800
acggccccgt gctgctgccc gacaaccact acctgagcta ccagtccaag ctgagcaaag    1860
accccaacga gaagcgcgat cacatggtcc tgctggagtt cgtgaccgcc gccgggatca    1920
ctctcggcat ggacgagctg tacaagtaag tcgacatcat aatcaacctc tggattacaa    1980
aatttgtgaa agattgactg gtattcttaa ctatgttgct ccttttacgc tatgtggata    2040
cgctgcttta atgcctttgt atcatgctat tgcttcccgt atggctttca ttttctcctc    2100
cttgtataaa tcctggttag ttcttgccac ggcggaactc atcgccgcct gccttgcccg    2160
ctgctggaca ggggctcggc tgttgggcac tgacaattcc gtggctcgag agatcttcga    2220
ctgtgccttc tagttgccag ccatctgttg tttgcccctc ccccgtgcct tccttgaccc    2280
tggaaggtgc cactcccact gtcctttcct aataaaatga ggaaattgca tcgcattgtc    2340
tgagtaggtg tcattctatt ctggggggtg gggtggggca ggacagcaag ggggaggatt    2400
gggaagacaa tagcaggcat gcacgtgcgg accgagcggc cgc    2443
```

```
<210> SEQ ID NO 126
<211> LENGTH: 2262
<212> TYPE: DNA
<213> ORGANISM: Artificial Sequence
<220> FEATURE:
<223> OTHER INFORMATION: CN1526

<400> SEQUENCE: 126
```

```
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgtttgat ggagtacttg     240
acaatgctga atcacagaaa aaaatccaaa gcttgctctg tgtattaaaa catccattta     300 aaaatatttta gaaagagcca ccaagcactt gtgagcatat gtgcatatgc ccgcagttcc     360
ctttgctctg gaaaatattc aagtggaaag ctactgctct gtttcataag taacagcaat     420
ttgtgacaag catggaatat gctgggcatc atcaactgca ttgttatcag ctgcagtaca     480
atttaattag cgagcctgag tttgattatc tgccagtgca tgctaccttaa actgctctgt     540 tccagtttga ggactaaatt ttgtctgatc atgttaacat atttgagagc atacctcaac     600
attctcaagt gttttgttcg tcatattatg ctcccgcatc aacaaaattg tattaaaagc     660
cttgacgtca gctcaaaata ttctgaagtg aatcaaaagc ttattatttc tagacgtaag     720
aataacttga cttcatgtta gatatgattt cctcatttat agtgctgctt aaatcagatg     780
aatgtaaaag gatatactgg tcactataat ttcaagattt ttttagattt aggtgtgttt     840
gtgttcatgt gaattcgata tcataatcaa ccataggtac cgagctcggg attcagccgg     900
gagcttaggg aggggaggtc acttcataag ggcctggggg gggagttgga gccacgagtc     960
gtccagccgg agccccgtgt ggctgagctc cggcctcaga agcatccccg ggttggatcc    1020
ttcgaagcta gcgctaccgg tcgccaccat ggtgagcaag ggcgaggagc tgttcaccgg    1080
ggtggtgccc atcctggtcg agctggacgg cgacgtaaac ggccacaagt tcagcgtgtc    1140
cggcgagggc gagggcgatg ccacctacgg caagctgacc ctgaagctga tctgcaccac    1200
cggcaagctg cccgtgccct ggcccaccct cgtgaccacc ctgggctacg gcgtgcagtg    1260
cttcgcccgc taccccgacc acatgaagca gcacgacttc ttcaagtccg ccatgcccga    1320
```

-continued

```
aggctacgtc caggagcgca ccatcttctt caaggacgac ggcaactaca agacccgcgc      1380
cgaggtgaag ttcgagggcg acaccctggt gaaccgcatc gagctgaagg gcatcgactt      1440
caaggaggac ggcaacatcc tggggcacaa gctggagtac aactacaaca gccacaacgt      1500
ctatatcacc gccgacaagc agaagaacgg catcaaggcc aacttcaaga tccgccacaa      1560
catcgaggac ggcggcgtgc agctcgccga ccactaccag cagaacaccc ccatcggcga      1620
cggccccgtg ctgctgcccg acaaccacta cctgagctac cagtccaagc tgagcaaaga      1680
ccccaacgag aagcgcgatc acatggtcct gctggagttc gtgaccgccg ccgggatcac      1740
tctcggcatg gacgagctgt acaagtaagt cgacatcata atcaacctct ggattacaaa      1800
atttgtgaaa gattgactgg tattcttaac tatgttgctc cttttacgct atgtggatac      1860
gctgctttaa tgcctttgta tcatgctatt gcttcccgta tggctttcat tttctcctcc      1920
ttgtataaat cctggttagt tcttgccacg gcggaactca tcgccgcctg ccttgcccgc      1980
tgctggacag gggctcggct gttgggcact gacaattccg tggctcgaga gatcttcgac      2040
tgtgccttct agttgccagc catctgttgt ttgcccctcc cccgtgcctt ccttgaccct      2100
ggaaggtgcc actcccactg tcctttccta ataaaatgag gaaattgcat cgcattgtct      2160
gagtaggtgt cattctattc tggggggtgg ggtggggcag gacagcaagg gggaggattg      2220
ggaagacaat agcaggcatg cacgtgcgga ccgagcggcc gc                         2262
```

<210> SEQ ID NO 127
<211> LENGTH: 1852
<212> TYPE: DNA
<213> ORGANISM: Artificial Sequence
<220> FEATURE:
<223> OTHER INFORMATION: CN1418

<400> SEQUENCE: 127

```
gcggccgcac gcgtggtccc agctcctcgt tgtagccccc cacacacaag atcaagggta        60
cagacagccc ctagaagggc aggaggccaa ggctccatgg gcaccttact ctctccattc       120 cccctttggct cccaggcttc cctcccccatc ccagtcctcc ttccccgcac gctggtgact      180
gccgtgacta ttaatcacta gccctgttct cttcctctct actaatcagg cacaattaga       240
caaggcctct tccagctggg cagtccccccc ctgccctccc cctcccttca cagccctccc      300
tatccgatac ccaggacagc tctgaggcaa tgaggacttg atgtaagccc tgagctactc       360
tggttgccct ggtgcccagt ttggggcttt tcagcaatct cctcttttcca tttgtctcct      420 ccttggtccc tggtcttgtc tagcgctgta gatcagccaa tattagcagg ctcaatctct       480
aacccactgc cactgtcaat caaagggggcg actcgagctc gggctgggca taaaagtcag      540
ggcagagcca tctattgctt acatttgctt ctgggatcca gatctttcga agctagcgct       600
accggtcgcc accatggtga gcaagggcga ggagctgttc accggggtgg tgcccatcct       660
ggtcgagctg gacggcgacg taaacggcca caagttcagc gtgtccggcg agggcgaggg       720
cgatgccacc tacggcaagc tgaccctgaa gctgatctgc accaccggca agctgcccgt       780 gcccctggcccc accctcgtga ccaccctggg ctacggcgtg cagtgcttcg cccgctaccc      840
cgaccacatg aagcagcacg acttcttcaa gtccgccatg cccgaaggct acgtccagga       900
gcgcaccatc ttcttcaagg acgacggcaa ctacaagacc cgcgccgagg tgaagttcga       960
gggcgacacc ctggtgaacc gcatcgagct gaagggcatc gacttcaagg aggacggcaa      1020
catcctgggg cacaagctgg agtacaacta caacagccac aacgtctata tcaccgccga      1080
caagcagaag aacggcatca aggccaactt caagatccgc cacaacatcg aggacggcgg      1140
```

```
cgtgcagctc gccgaccact accagcagaa cacccccatc ggcgacggcc ccgtgctgct      1200
gcccgacaac cactacctga gctaccagtc caagctgagc aaagacccca acgagaagcg      1260
cgatcacatg gtcctgctgg agttcgtgac cgccgccggg atcactctcg gcatggacga      1320
gctgtacaag taagtcgacg gcgcgccgcg gccgcgaatt cgatatcata atcaacctct      1380
ggattacaaa atttgtgaaa gattgactgg tattcttaac tatgttgctc cttttacgct      1440
atgtggatac gctgctttaa tgcctttgta tcatgctatt gcttcccgta tggctttcat      1500
tttctcctcc ttgtataaat cctggttagt tcttgccacg gcggaactca tcgccgcctg      1560
ccttgcccgc tgctggacag gggctcggct gttgggcact gacaattccg tggctcgaga      1620
gatcttcgac tgtgccttct agttgccagc catctgttgt ttgcccctcc cccgtgcctt      1680
ccttgaccct ggaaggtgcc actcccactg tcctttccta ataaaatgag gaaattgcat      1740
cgcattgtct gagtaggtgt cattctattc tggggggtgg ggtggggcag gacagcaagg      1800
gggaggattg ggaagacaat agcaggcatg cacgtgcgga ccgagcggcc gc            1852
```

```
<210> SEQ ID NO 128
<211> LENGTH: 1984
<212> TYPE: DNA
<213> ORGANISM: Artificial Sequence
<220> FEATURE:
<223> OTHER INFORMATION: CN1404

<400> SEQUENCE: 128
```

```
gcggccgcac gcgtgaggca tgggtaggag ccagccccac tcctcagggt cctcaagggt        60
ccaggcagcc ccggggggcc aggagcctgg ggccctgtgg gcgcctcact atctccatcc       120
cctatgggct ctccggtctc cctccccctc ccgaccctcc ttctccacat gctggtgact       180
gccatgacta ttaatcactc gccctgttct cttcctctct actaatcagg cacaattaga       240
caaggcctct tccagctggg cagtccctcc cctgccctcc tctctcctct ccctgcccca       300
cccagccgcc agccaggaca gctctgaggc acagaaagca tgcaagccct ctctctctct       360
ggctgtccca ggacccagtt tcgggctcct tagcacccac tccttctgtc ccagcgacct       420
ccttagctcc ttctcttccc agtgtgtggt caggccacta ctgacagtct ctgccctcca       480
ccccctacac ttggccctgg gaggagctac tccacactcc atcgagtct aagaaggcgg       540 cactgtccct ggctcctctg tcctcctgct cagccatcct cagcatgtgc ctctcatcac       600
cactcttgtc accacagatc gccgagcagc tactccacac tccatcgagc tcgggctggg      660
cataaaagtc agggcagagc catctattgc ttacatttgc ttctgggatc cagatctttc      720
gaagctagcg ctaccggtcg ccaccatggt gagcaagggc gaggagctgt tcaccggggt      780
ggtgcccatc ctggtcgagc tggacggcga cgtaaacggc cacaagttca gcgtgtccgg      840
cgagggcgag ggcgatgcca cctacggcaa gctgaccctg aagctgatct gcaccaccgg      900
caagctgccc gtgccctggc ccaccctcgt gaccaccctg ggctacggcg tgcagtgctt      960
cgcccgctac cccgaccaca tgaagcagca cgacttcttc aagtccgcca tgcccgaagg     1020
ctacgtccag gagcgcacca tcttcttcaa ggacgacggc aactacaaga cccgcgccga     1080
ggtgaagttc gagggcgaca ccctggtgaa ccgcatcgag ctgaagggca tcgacttcaa     1140
ggaggacggc aacatcctgg ggcacaagct ggagtacaac tacaacagcc acaacgtcta     1200
tatcaccgcc gacaagcaga agaacggcat caaggccaac ttcaagatcc gccacaacat     1260
cgaggacggc ggcgtgcagc tcgccgacca ctaccagcag aacacccca tcggcgacgg     1320
```

-continued

```
ccccgtgctg  ctgcccgaca  accactacct  gagctaccag  tccaagctga  gcaaagaccc     1380
caacgagaag  cgcgatcaca  tggtcctgct  ggagttcgtg  accgccgccg  ggatcactct     1440
cggcatggac  gagctgtaca  agtaagtcga  cggcgcgccg  cggccgcgaa  ttcgatatca     1500
taatcaacct  ctggattaca  aaatttgtga  aagattgact  ggtattctta  actatgttgc     1560
tccttttacg  ctatgtggat  acgctgcttt  aatgcctttg  tatcatgcta  ttgcttcccg     1620
tatggctttc  attttctcct  ccttgtataa  atcctggtta  gttcttgcca  cggcggaact     1680
catcgccgcc  tgccttgccc  gctgctggac  aggggctcgg  ctgttgggca  ctgacaattc     1740
cgtggctcga  gagatcttcg  actgtgcctt  ctagttgcca  gccatctgtt  gtttgcccct     1800
cccccgtgcc  ttccttgacc  ctggaaggtg  ccactcccac  tgtcctttcc  taataaaatg     1860
aggaaattgc  atcgcattgt  ctgagtaggt  gtcattctat  tctggggggt  ggggtggggc     1920
aggacagcaa  gggggaggat  tgggaagaca  atagcaggca  tgcacgtgcg  gaccgagcgg     1980
ccgc                                                                      1984

<210> SEQ ID NO 129
<211> LENGTH: 3009
<212> TYPE: DNA
<213> ORGANISM: Artificial Sequence
<220> FEATURE:
<223> OTHER INFORMATION: AiV1173

<400> SEQUENCE: 129
gcggccgcac  gcgtgagtaa  taggcagatc  tctataccag  cctaacttct  ccctaccacc      60
cccctccatc  ttccttcttc  ttgcagtgca  aacgccaagt  catatggact  tggattccga     120
ctctcttttc  tttgccaaga  ctcatattat  tgagcaagtg  aggagagttg  agccaaactg     180
aactaagtga  cgccacagca  cactgtgtag  tgcagagcta  gcactttgga  tattgtgtaa     240
ttaaggcttt  aatgaacatc  acatagagaa  ttagactgca  gattgtgaca  caaataaatc     300
tacttggctt  ttagaaacat  tccttaaaaa  gaaatatttt  ggtaccagaa  tgtgttcagg     360
agggaaagag  cctgtgccct  tgacacagga  agtagataac  acctgtcaga  agaatcgaaa     420
ccacctgctt  gggtgcatct  ggtaataagt  ttgcagctgg  tgctacactc  tacccttaag     480
gagctcgggc  tgggcataaa  agtcagggca  gagccatcta  ttgcttacat  ttgcttctgg     540
cgtggccacc  atggctccta  agaagaagag  gaaggtgatg  agccagttcg  acatcctgtg     600
caagaccccc  cccaaggtgc  tggtgcggca  gttcgtggag  agattcgaga  ggcccagcgg     660
cgagaagatc  gccagctgtg  ccgccgagct  gacctacctg  tgctggatga  tcacccacaa     720
cggcaccgcc  atcaagaggg  ccaccttcat  gagctacaac  accatcatca  gcaacagcct     780
gagcttcgac  atcgtgaaca  agagcctgca  gttcaagtac  aagacccaga  aggccaccat     840
cctggaggcc  agcctgaaga  agctgatccc  cgcctgggag  ttcaccatca  tcccttacaa     900
cggccagaag  caccagagcg  acatcaccga  catcgtgtcc  agcctgcagc  tgcagttcga     960
gagcagcgag  gaggccgaca  agggcaacag  ccacagcaag  aagatgctga  aggccctgct    1020
gtccgagggc  gagagcatct  gggagatcac  cgagaagatc  ctgaacagct  cgagtacac    1080 cagcaggttc  accaagacca  agaccctgta  ccagttcctg  ttcctggcca  cattcatcaa    1140
ctgcggcagg  ttcagcgaca  tcaagaacgt  ggaccccaag  agcttcaagc  tggtgcagaa    1200
caagtacctg  ggcgtgatca  ttcagtgcct  ggtgaccgag  accaagacaa  gcgtgtccag    1260
gcacatctac  tttttcagcg  ccagaggcag  gatcgacccc  ctggtgtacc  tggacgagtt    1320
cctgaggaac  agcgagcccg  tgctgaagag  agtgaacagg  accggcaaca  gcagcagcaa    1380
```

-continued

```
caagcaggag taccagctgc tgaaggacaa cctggtgcgc agctacaaca aggccctgaa      1440
gaagaacgcc ccctacccca tcttcgctat caagaacggc cctaagagcc acatcggcag      1500
gcacctgatg accagctttc tgagcatgaa gggcctgacc gagctgacaa acgtggtggg      1560
caactggagc gacaagaggg cctccgccgt ggccaggacc acctacaccc accagatcac      1620
cgccatcccc gaccactact tcgccctggt gtccaggtac tacgcctacg accccatcag      1680
caaggagatg atcgccctga aggacgagac caaccccatc gaggagtggc agcacatcga      1740
gcagctgaag ggcagcgccg agggcagcat cagatacccc gcctggaacg gcatcatcag      1800
ccaggaggtg ctggactacc tgagcagcta catcaacagg cggatctgag aattcgatat      1860
caagcttatc gataatcaac ctctggatta caaaatttgt gaaagattga ctggtattct      1920
taactatgtt gctccttta cgctatgtgg atacgctgct ttaatgcctt tgtatcatgc      1980
tattgcttcc cgtatggctt tcattttctc ctccttgtat aaatcctggt tgctgtctct      2040
ttatgaggag ttgtggcccg ttgtcaggca acgtggcgtg gtgtgcactg tgtttgctga      2100
cgcaaccccc actggttggg gcattgccac cacctgtcag ctcctttccg ggactttcgc      2160 tttcccccctc cctattgcca cggcggaact catcgccgcc tgccttgccc gctgctggac      2220
aggggctcgg ctgttgggca ctgacaattc cgtggtgttg tcggggaaat catcgtcctt      2280
tccttggctg ctcgcctatg ttgccacctg gattctgcgc gggacgtcct tctgctacgt      2340
cccttcggcc ctcaatccag cggaccttcc ttcccgcggc ctgctgccgg ctctgcggcc      2400
tcttccgcgt cttcgccttc gccctcagac gagtcggatc tccctttggg ccgcctcccc      2460
gcatcgatac cgagcgctgc tcgagagatc tacgggtggc atccctgtga ccccttcccca     2520 gtgcctctcc tggccctgga agttgccact ccagtgccca ccagccttgt cctaataaaa      2580
ttaagttgca tcattttgtc tgactaggtg tccttctata atattatggg gtggaggggg      2640
gtggtatgga gcaaggggca agttgggaag acaacctgta gggcctgcgg ggtctattgg      2700
gaaccaagct ggagtgcagt ggcacaatct tggctcactg caatctccgc ctcctgggtt      2760
caagcgattc tcctgcctca gcctcccgag ttgttgggat tccaggcatg catgaccagg      2820
ctcagctaat ttttgttttt ttggtagaga cggggtttca ccatattggc caggctggtc      2880
tccaactcct aatctcaggt gatctaccca ccttggcctc ccaaattgct gggattacag      2940
gcgtgaacca ctgctccctt ccctgtcctt ctgattttgt aggtaaccac gtgcggaccg      3000
agcggccgc                                                             3009
```

<210> SEQ ID NO 130
<211> LENGTH: 3153
<212> TYPE: DNA
<213> ORGANISM: Artificial Sequence
<220> FEATURE:
<223> OTHER INFORMATION: AiV1174

<400> SEQUENCE: 130

```
gcggccgcac gcgtgacaat catgagagta cgaaagcatg agagatatta tttcaacaac        60 ttattctta ttttagagga agaacatctg agaacaaaaa tatctataaa ggcatgatta       120
gcatagaaaa caagggtatt gatcattaat ggcacctaat gtcatagata aaaagagaca       180
ctcaaacttt atacatctcc aaatagaaca cttcacaatc tatgaagcaa aaataaagga       240
aaaaaaaaac aacacaaatc taatcttaca gaactaagta ccaatttaca gcaagtgtag       300
acaaagtagc acatcaaatg acaataggag atgccatcaa gcgaaatcaa ttctgggaag       360
```

-continued

```
gtcttagaga acaagcaata gtacttcttg aacacatcca ttataagtga aaataaaatg    420
ctctagataa aaagagcctt agagatgaat gaaggataat gaatctgctg cttaatcaca    480
aacattttgg tgatgagatg atcaagaaaa caaaaagcta ttactgaaat agctggaagt    540
gtaattagtt actgtggaga aggacagagt tgagaagaag taaaaggatt gtggttgtga    600
tagatgtatg ccaatgtcct taaggagctc gggctgggca taaaagtcag ggcagagcca    660
tctattgctt acatttgctt ctggcgtggc caccatggct cctaagaaga agaggaaggt    720
gatgagccag ttcgacatcc tgtgcaagac cccccccaag gtgctggtgc ggcagttcgt    780
ggagagattc gagaggccca gcggcgagaa gatcgccagc tgtgccgccg agctgaccta    840
cctgtgctgg atgatcaccc acaacggcac cgccatcaag agggccacct tcatgagcta    900
caacaccatc atcagcaaca gcctgagctt cgacatcgtg aacaagagcc tgcagttcaa    960
gtacaagacc cagaaggcca ccatcctgga ggccagcctg aagaagctga tccccgcctg    1020
ggagttcacc atcatccctt acaacggcca gaagcaccag agcgacatca ccgacatcgt    1080
gtccagcctg cagctgcagt tcgagagcag cgaggaggcc gacaagggca acagccacag    1140
caagaagatg ctgaaggccc tgctgtccga gggcgagagc atctgggaga tcaccgagaa    1200
gatcctgaac agcttcgagt acaccagcag gttcaccaag accaagaccc tgtaccagtt    1260
cctgttcctg gccacattca tcaactgcgg caggttcagc gacatcaaga acgtggaccc    1320
caagagcttc aagctggtgc agaacaagta cctgggcgtg atcattcagt gcctggtgac    1380
cgagaccaag acaagcgtgt ccaggcacat ctactttttc agcgccagag gcaggatcga    1440 cccccctggtg tacctggacg agttcctgag gaacagcgag cccgtgctga agagagtgaa    1500
caggaccggc aacagcagca gcaacaagca ggagtaccag ctgctgaagg acaacctggt    1560
gcgcagctac aacaaggccc tgaagaagaa cgcccccctac cccatcttcg ctatcaagaa    1620
cggccctaag agccacatcg gcaggcacct gatgaccagc tttctgagca tgaagggcct    1680
gaccgagctg acaaacgtgg tgggcaactg gagcgacaag agggcctccg ccgtggccag    1740
gaccacctac acccaccaga tcaccgccat ccccgaccac tacttcgccc tggtgtccag    1800
gtactacgcc tacgacccca tcagcaagga gatgatcgcc ctgaaggacg agaccaaccc    1860
catcgaggag tggcagcaca tcgagcagct gaagggcagc gccgagggca gcatcagata    1920 cccccgcctgg aacggcatca tcagccagga ggtgctggac tacctgagca gctacatcaa    1980
caggcggatc tgagaattcg atatcaagct tatcgataat caacctctgg attacaaaat    2040
ttgtgaaaga ttgactggta ttcttaacta tgttgctcct tttacgctat gtggatacgc    2100
tgctttaatg cctttgtatc atgctattgc ttcccgtatg gctttcattt tctcctcctt    2160
gtataaatcc tggttgctgt ctctttatga ggagttgtgg cccgttgtca ggcaacgtgg    2220
cgtggtgtgc actgtgtttg ctgacgcaac ccccactggt tggggcattg ccaccacctg    2280
tcagctcctt tccgggactt tcgctttccc cctccctatt gccacggcgg aactcatcgc    2340
cgcctgcctt gcccgctgct ggacaggggc tcggctgttg ggcactgaca attccgtggt    2400
gttgtcgggg aaatcatcgt cctttccttg gctgctcgcc tatgttgcca cctggattct    2460
gcgcgggacg tccttctgct acgtcccttc ggccctcaat ccagcggacc ttccttcccg    2520
cggcctgctg ccggctctgc ggcctcttcc gcgtcttcgc cttcgccctc agacgagtcg    2580
gatctccctt tgggccgcct ccccgcatcg ataccgagcg ctgctcgaga gatctacggg    2640
tggcatccct gtgacccctc cccagtgcct ctcctggccc tggaagttgc cactccagtg    2700
cccaccagcc ttgtcctaat aaaattaagt tgcatcattt tgtctgacta ggtgtccttc    2760
```

-continued

```
tataatatta tggggtggag gggggtggta tggagcaagg ggcaagttgg gaagacaacc      2820
tgtagggcct gcggggtcta ttgggaacca agctggagtg cagtggcaca atcttggctc      2880
actgcaatct ccgcctcctg ggttcaagcg attctcctgc ctcagcctcc cgagttgttg      2940
ggattccagg catgcatgac caggctcagc taatttttgt tttttttggta gagacggggg      3000 ttcaccatat tggccaggct ggtctccaac tcctaatctc aggtgatcta cccaccttgg      3060
cctcccaaat tgctgggatt acaggcgtga accactgctc ccttccctgt ccttctgatt      3120
ttgtaggtaa ccacgtgcgg accgagcggc cgc                                   3153
```

<210> SEQ ID NO 131
<211> LENGTH: 3208
<212> TYPE: DNA
<213> ORGANISM: Artificial Sequence
<220> FEATURE:
<223> OTHER INFORMATION: AiV1177

<400> SEQUENCE: 131

```
gcggccgcac gcgtcctcat ggtattagta gtaaccattt tggagagaac tataccacta        60
atccttacta cccccccccc aattaatgac accccattcg agcatctcca atgaaaggcg       120
cattattaat attcaaggaa aaaaaccctt gtaaccattt tagcagatac agctaacaat       180
gaactaaatt tgctttgtgc aagacagaga gtgagcatcc caaattagtt tatgtaaaag       240
ctgaaatcct cccctgaaag gtctcagtac catcctcaaa gaatatcccg atcatcagca       300
gtgccgtcaa gattcccgcc aacattatcc cctttgttgt ctgaaatgta gaatcaagca       360
catctggcaa atgtcctgga gctcacaaat ctctcaaacg gcgtctaatt cccagtggtg       420
aaagagagcg ccactgccta atcgtgcttc tcttcaaaac agcactgact ttccttcaat       480
cagaaacaat ggctttgctt tcttaaaaat atcacacgcc agtgattatt tgcagagagg       540 cccatttat gcttgaacct gcgggtccca gacagaattc acaattaaga ccgtgaacct        600
catttgaatg tacgcttagt tcagtggaca gtgggaagaa agattgtgac ctgtcttctg       660
tggtttggag gctcttaagg agctcgggct gggcataaaa gtcagggcag agccatctat       720
tgcttacatt tgcttctggc gtggccacca tggctcctaa gaagaagagg aaggtgatga       780
gccagttcga catcctgtgc aagaccccc ccaaggtgct ggtgcggcag ttcgtggaga        840
gattcgagag gcccagcggc gagaagatcg ccagctgtgc cgccgagctg acctacctgt       900
gctggatgat cacccacaac ggcaccgcca tcaagagggc caccttcatg agctacaaca       960
ccatcatcag caacagcctg agcttcgaca tcgtgaacaa gagcctgcag ttcaagtaca      1020
agacccagaa ggccaccatc ctggaggcca gcctgaagaa gctgatcccc gcctgggagt      1080
tcaccatcat cccttacaac ggccagaagc accagagcga catcaccgac atcgtgtcca      1140
gcctgcagct gcagttcgag agcagcgagg aggccgacaa gggcaacagc cacagcaaga      1200
agatgctgaa ggccctgctg tccgaggcg agagcatctg ggagatcacc gagaagatcc       1260
tgaacagctt cgagtacacc agcaggttca ccaagaccaa gaccctgtac cagttcctgt      1320
tcctggccac attcatcaac tgcggcaggt tcagcgacat caagaacgtg accccaaga       1380 gcttcaagct ggtgcagaac aagtacctgg gcgtgatcat tcagtgcctg gtgaccgaga      1440
ccaagacaag cgtgtccagg cacatctact ttttcagcgc cagaggcagg atcgaccccc      1500
tggtgtacct ggacgagttc ctgaggaaca cgcagcccgt gctgaagaga gtgaacagga      1560
ccggcaacag cagcagcaac aagcaggagt accagctgct gaaggacaac ctggtgcgca      1620
```

-continued

```
gctacaacaa ggccctgaag aagaacgccc cctaccccat cttcgctatc aagaacggcc     1680
ctaagagcca catcggcagg cacctgatga ccagctttct gagcatgaag ggcctgaccg     1740
agctgacaaa cgtggtgggc aactggagcg acaagagggc ctccgccgtg gccaggacca     1800
cctacaccca ccagatcacc gccatccccg accactactt cgccctggtg tccaggtact     1860
acgcctacga ccccatcagc aaggagatga tcgccctgaa ggacgagacc aaccccatcg     1920
aggagtggca gcacatcgag cagctgaagg gcagcgccga gggcagcatc agataccccg     1980
cctggaacgg catcatcagc caggaggtgc tggactacct gagcagctac atcaacaggc     2040
ggatctgaga attcgatatc aagcttatcg ataatcaacc tctggattac aaaatttgtg     2100
aaagattgac tggtattctt aactatgttg ctccttttac gctatgtgga tacgctgctt     2160
taatgccttt gtatcatgct attgcttccc gtatggcttt cattttctcc tccttgtata     2220
aatcctggtt gctgtctctt tatgaggagt tgtggcccgt tgtcaggcaa cgtggcgtgg     2280
tgtgcactgt gtttgctgac gcaacccccca ctggttgggg cattgccacc acctgtcagc     2340
tcctttccgg actttcgct ttcccctcc ctattgccac ggcggaactc atcgccgcct     2400
gccttgcccg ctgctggaca ggggctcggc tgttgggcac tgacaattcc gtggtgttgt     2460
cggggaaatc atcgtcctt ccttggctgc tcgcctatgt tgccacctgg attctgcgcg     2520
ggacgtcctt ctgctacgtc ccttcggccc tcaatccagc ggaccttcct tcccgcggcc     2580
tgctgccggc tctgcggcct cttccgcgtc ttcgccttcg ccctcagacg agtcggatct     2640
ccctttgggc cgcctccccg catcgatacc gagcgctgct cgagagatct acgggtggca     2700
tccctgtgac ccctccccag tgcctctcct ggccctggaa gttgccactc cagtgcccac     2760
cagccttgtc ctaataaaat taagttgcat cattttgtct gactaggtgt ccttctataa     2820
tattatgggg tggaggggg tggtatggag caaggggcaa gttgggaaga caacctgtag     2880
ggcctgcggg gtctattggg aaccaagctg gagtgcagtg gcacaatctt ggctcactgc     2940
aatctccgcc tcctgggttc aagcgattct cctgcctcag cctcccgagt tgttgggatt     3000
ccaggcatgc atgaccaggc tcagctaatt tttgttttt tggtagagac ggggtttcac     3060
catattggcc aggctggtct ccaactccta atctcaggtg atctacccac cttggcctcc     3120
caaattgctg ggattacagg cgtgaaccac tgctccttc cctgtccttc tgattttgta     3180
ggtaaccacg tgcggaccga gcggccgc                                       3208
```

<210> SEQ ID NO 132
<211> LENGTH: 475
<212> TYPE: DNA
<213> ORGANISM: Homo sapiens

<400> SEQUENCE: 132

```
cccaaactct catctgctcc aagctgtata gaagtttctt tcagagttat ttcagttcat       60
ttcaatgaaa aaattatcaa atataataaa acatttttgg aaagacagga gggatttggg      120
acattacaat tggtattaaa agaactaatg agctttgcta ctgataaagt atttcttgca      180
ttcttttttg gttcaaagag tgatacccaa ttattaattc ttaagcacat aaatcttttc      240
catttttgtt tttcctgctc ggtgcctgaa ttttcttggc tactactgaa atgtgttgaa      300
taggctgatt ctactttta tctgcatatt ctatggatct agtggctctg aatccaagcc      360
actataataa tgatggaaac aaaatatttc tgatgaacat ataaccagat attgctgaca      420
aatagaaaaa agaacaggct gatggggggcc agactgtgca tatgatctgt attcc          475
```

<210> SEQ ID NO 133
<211> LENGTH: 371
<212> TYPE: DNA
<213> ORGANISM: Homo sapiens

<400> SEQUENCE: 133
cagagaccca gtgactgatg ttgtcccaga aagtagaatt cttgtgatgc ataaatgata        60
gctgatccag ccaacacaac tgttggagga attatagctt atagagttgc ttggcagatg       120
aaatcacttg actaattaga aaataatgca ttatgctgtg ctagaaaaat cacagagcag       180
cagaagcgga actgtgttct gggttgctgt gggctgccag tcacaatttt gagcctgtgc       240
cttgcattct ttaccttttt ttttcccact atccctacag cccagaaatt gaaacagacc       300
ctggagcctt gtgatactga atatccagca ttcgtctctg agcgcaccat caaggagact       360
acagggaata t                                                            371

<210> SEQ ID NO 134
<211> LENGTH: 869
<212> TYPE: DNA
<213> ORGANISM: Homo sapiens

<400> SEQUENCE: 134
tccctgaaaa ctagcatcgg ggaatgacat acagtttgat aacataagat gcttaggttt        60
tttggctcaa gtgagatgtt cagagctaat agccctgcga gctgagtttt agctgtgatc       120
tgcaccttga gatatccgtt atgtctggat caggaaaaag ggaaaagaat gagagcttat       180
ttctagaaag gtttccgatg agcagcattt gtcattgaag gggaagatgg gtataattag       240
cttgtcagtc tagtttgggc tgagcaggct gtctctgcta agaaagatgg actaactgcc       300
agggccactg acaggcagtc gatagcgcag caattaatgt cataaataat tccagaacca       360
attacatcaa aatggactca gagctttaaa aaggtacaga attctcttat tcttcctgct       420
aacagcaaga aacagctttc attttttctct gtaattactt ttcattgtat atagcaatac       480
agctgagctt ttctgtccat atttaagcct tgtctttctc caagcctctt ccccaccac       540 cagcctccct ccttcacccc acaggataag gctgttaaag ttgttcttcc ctgccagagc       600
agtggggtga atgtataatc ttttaacttg gctgttgcag gagaactcca gctacaccta       660
aatgattaag agccaagttt ttgaaaatgt catggacaat gacagcacag tgccccaaac       720
aatggcattt ggaaatgaag acatttgtga aataaatgga tttgtcttat tattttaaag       780
gttgctgtga ctttgcttac actgaattta ttgattttttc ccccttctcc ttctccttcc       840
tcttcttgtt ctcctcctcc ttctgtaca                                         869

<210> SEQ ID NO 135
<211> LENGTH: 269
<212> TYPE: DNA
<213> ORGANISM: Mus musculus

<400> SEQUENCE: 135
agtggcctgg tattgggtgg acccgtcacc tgagacaagg actcctgaca acccaagtcc        60
ccagaggcct ccctgccctt ccctcattcc gttgttccac ttttagagaa ccccgggact       120
cctcagcagg cagcagccta ttttgccagg atccacatag agcagtgcct ggcacagtag       180
cggtgaagcg ggaagtgggt ctctgttggc gggcaccgtg gtgcccggaa ctcgctattc       240
ctccccagtg ttaattatca aaattaacc                                         269

<210> SEQ ID NO 136

```
<211> LENGTH: 1084
<212> TYPE: DNA
<213> ORGANISM: Homo sapiens

<400> SEQUENCE: 136
acaagttttc ctgtggcaga aagatgtttc cattgttttg ttttgtttgt tttgtttcgt      60 tttgtttttaa atgcatctct gccttacctt acttgcgggc cagtgagcta gcctaaaatc     120
gaagctctgt gaagcccgct cttgccattt tattttttgaa ggctgtccct tggccacatc     180
tgacccacca gctcctgtca ttagcatctg agtgttaagc cagaggaact caatctggga      240
acaccaccaa cgtggccagt aagctgcaat ttagttaatg tgcactcctt gtaggccctg      300
gttttggccc gagtgtattt gggtagagtg tgtggtggtg atggtaggga gctagagagg      360
aaggggaggg tgatggactc atttgcaaga actgcccagc tgagataaca tttaaaatga      420
acaggagaag gtccaatgct ttgtaatcct ccagcagctg ctcattttgg gttgggatca      480
ggaaggagca ctttgccatt agtccccgag ccaaaagtgg ccggtggtgg tttctggtct      540
ccctaagcca cctccaaagg ggtcactcag ctgtgtccta gggaagcgaa acaagagaaa      600
aagaacaaga tggcttgtac gctccatcca tgtgtgtggc cccagggatg cccctgcaga      660
tgggcctggt tggagatggt gatatcttgg atgggttcac tgcagctccg tgcccgaaaa      720
gggcagctgg tgggcttgtt ccgctgttct tcagcctgtc actgcaccac tcttaacaag      780
ttatccacat cccagagatg cagattatgc ctcagcttag agggccaagc ttccctccaa      840
gagactgagc ctgcaaaaag ctgccagagt ccctgtagcc tgcccagatc ctgcctgaac      900
ccagcccaaa gagatggttg tcattccagg caagggctca cccgggccag atgccttcct      960
tccccaggcc tgtggtttct cccacttgag gaagaattgc tatttcttttt gctgtatcat    1020 tacaaataaa acaaaactga ctttgaacat attaatgata acagatggct tcataaaatg    1080
taaa                                                                  1084

<210> SEQ ID NO 137
<211> LENGTH: 807
<212> TYPE: DNA
<213> ORGANISM: Mus musculus

<400> SEQUENCE: 137
tacctgccat tccaactctg gcctctgtga gcatatacac acacatgcgc acattaacat       60
cccccccccc ccacacacac ctcaggcata gacatacact tttaaaaagg cagccacaat      120
atcaatttaa ttcagataaa atcacaacac aaccttcttt agtactgagt cttacaaagt      180
tgtatgcttg aggtgtcctg agaaccccac taaggtaatg gctgtaacat tcctcagagg      240
tgaactcatt tccatgactc attctgaaaa gcacaggctc cttgtccttt cacacgcatc      300
acaatgcaac ctaaaataga tcctcatcag cgcctctttc agggttatga atagcactac      360
cttgaaaagg gccaagaggg atgcatgcat gggattcaga aaggaggcat tcaagaaaac      420
caagcaggag gcaggctgcc taagtacttt gagcatggag catgacggga cccctctgg      480 ctcccacgca ggcaaccagg tgccacactc aatggagatg gagtgggtgg gagctctgag      540
aaggagctgc atctactggg caaagtggtt gaaaaacccg aagaggacct aagtaagcat      600
cggcttagac tgctgacccc gttctccacc tctttatcca ccccccttttc tgggtggctg      660 gaaaaatcaa atggtatttc tctaccttcc tgattgtcac attcaatgta cccaacggaa      720
ggaattcaca gtgggccacc tcctgctcaa gaagccaagg cactttgcat tctgcctctt      780
gtctttgctg ggagaatggc atgacaa                                          807
```

```
<210> SEQ ID NO 138
<211> LENGTH: 680
<212> TYPE: DNA
<213> ORGANISM: Homo sapiens

<400> SEQUENCE: 138
acaagcatga ctataaaacc caagcaatgt ttttgcacca gatcccagaa gtaaagttta       60
ttagtcagtg gaattcttgt attagatttc agaaagcacc caactaccaa acgagaatga      120
ggttcctcca ccattccagc agagggcaca cttttagcag cttttgtagc tggttgcttc      180
ctggatgttt gaataccaat tgatttgtca gcaatgagcc attgcagcaa tgctgtcaaa      240
gtctggatcc ctgactggtg gctgcaaact gtttattaac agcttgatgc tcattaagga      300
cattgagcca gaatataagt caactgtgtc actaagtgtg ctatttagca tagctggcat      360
tatgtgtgtt gtgggagagg caagactctc aatgaaagag gcaatacatt gattttcatt      420
ctgatgtaag ccattccact tttgattggg acttcacaga attcttttca tagctggcct      480
ctctcctcat tctgatggaa atctgcaagc taaaggcagt cctgatgata ggaagcaaaa      540
cagcaacctc agaaggattt caaaatgatt cattttcttt acaaaaatat atatcattag      600
cctaacataa gtaagtgttg aatattatga tcttgagaat gaaaaagata tacctttagt      660
gttgctgtga ctgaagatga                                                  680

<210> SEQ ID NO 139
<211> LENGTH: 596
<212> TYPE: DNA
<213> ORGANISM: Homo sapiens

<400> SEQUENCE: 139
tccaccattc cagcagaggg cacacttttta gcagcttttg tagctggttg cttcctggat       60
gtttgaatac caattgattt gtcagcaatg agccattgca gcaatgctgt caaagtctgg      120
atccctgact ggtggctgca aactgtttat taacagcttg atgctcatta aggacattga      180
gccagaatat aagtcaactg tgtcactaag tgtgctattt agcatagctg gcattatgtg      240
tgttgtggga gaggcaagac tctcaatgaa agaggcaata cattgatttt cattctgatg      300
taagccattt cacttttgat tgggacttca cagaattctt ttcatagctg gcctctctcc      360
tcattctgat ggaaatctgc aagctaaagg cagtcctgat gataggaagc aaaacagcaa      420
cctcagaagg atttcaaaat gattcatttt ctttacaaaa atatatatca ttagcctaac      480
ataagtaagc gttgaatatt atgatcttga gaatgaaaaa gatataacctt tagtgttgct      540 gtgactgaag atgatatttg acccttttaaa atgcattaag tttctttcta ttggcc        596

<210> SEQ ID NO 140
<211> LENGTH: 749
<212> TYPE: DNA
<213> ORGANISM: Homo sapiens

<400> SEQUENCE: 140
aagacggtct gattgcaacc ctccaggagg aaaacaaatt cacaaagcag tcccaggttg       60
ccagttctca aagtcagcaa accaaatcct aacgtgcaat cttcccaggt ttttcaaaag      120
ccatgggatt gatagtcagt ggggaaagga agaggtgtcg aatccaggcc tgatggatgg      180
gtgcagaggc aatcagacgt gttttcagag ccactgtgct ctgacacctg cccccatttt      240
ccacagagtt tggctctgaa tgcgtccctg gaccacgccc tccgtctcct ttacctggcg      300
```

-continued

```
ttcctattct tgtagaaagg aacacagcct aatgatggat ttgttcaatg tgatcattct      360
cgcttatgta caaaacaaag gcaggattga tgaactccta aagaagcaca ttcacaggcc      420
tgatctatgc ctcttacctt ggagcaggca gcaagtacag cctccaaggg aatgtcaaca      480
tctttgcact ttgtcaatag gaccttgatt ctctaaaggc tgaaaggtgt tttcatgggt      540
gaatgcttag agccagctca tggtttttcca aaccccactc aaagcttcca gatgactctt      600
tttgcatctg tgagcttctt tcatccctag atatcaccct ggggagaggg caggcaaaag      660
atgttctctg tacttgcaag gaagaaatgg taaaggcatg ggggtcgagt gggggctggg      720
gactcctatg ttccggaaag agcgaggtt                                         749

<210> SEQ ID NO 141
<211> LENGTH: 893
<212> TYPE: DNA
<213> ORGANISM: Mus musculus

<400> SEQUENCE: 141
aacaggactt cagggaaggc cacggagctt aagcaagaac ttgcccaaag tttagaaaga       60
aagctccaag ttacagaacc aagtgcccga ccccagagtc tttctttgtc tgacctgagg      120
gctttctgtt aaaatcctta tacagcagat aagtaagtca gcagtcttag aggtgtgggaag      180 aggtctgtct gccagtcatc tggctccctg caaacacagg catccccacc cctgaacaat      240
tttcttcata ggaaagttgt gagggaagtc acaggtgcag acaccgcccc ggggggggag      300
ggggggctca gagttgttcc ttcattcagt caccaattca gtcttccaga atcaaggccc      360
tattgacaga gggctaagcc accggggcgc tgccttcaag gtaagaggca tagatcagtc      420
tcctgaatgt agagggatga attccctcct tcacataagt gaaagcgatc atagggaacg      480
gaggcatcat tagggcgccc tccttctgac agggatgcag acaggcaggt gagggtggag      540
gggtgtggcc cagggcacat tcagagccaa actctgttga gaacaaggca ggtgtttctg      600
aaaacctctc tgattgcacc cgtaccctcc catcaggccc gaatcgcaca cctctctgcc      660
tctcctcaga cgccggccca catggctttt gaaaacctgg ggagattata ccttccagct      720
tgctttgctg agtctgagga acctggctgc cttttctctt ctgttaactg caatcaaact      780
ggttttgagc accagcccca agatgtcttt gccagtccac atccatcttc catgatgagc      840
taaggttccc tatttgtacc cttactttct gggctgagtc atgacatctg gga              893

<210> SEQ ID NO 142
<211> LENGTH: 770
<212> TYPE: DNA
<213> ORGANISM: Mus musculus

<400> SEQUENCE: 142
ttctgccata gaaaagcatc agtgtctata gagagaaatg ataacaaatg aaggaaattg       60 tctaatttttc taactcactt acataatgga cagatgcggt aagtaaacag cacacactag      120
tgcatcttag atgggcactg tactaagatg tgataatgat gtttcagcca gacttactta      180
ttttatcccg taatcacagg aagctctaat cagaggaagc atgaggaaga gacagaatgt      240
gctaaggatg tgtcacactc tgatgggtca ctggaagtga ggaaacaagg gtgtgcagct      300
gtgtatcagg tccaggcaga gagcagatgt tctattcacg agtatgctta cttacatctg      360
tcgccctcca acacaccatt ccaaactgaa aactgagtgt gcttcatcaa gccagaaact      420
taggaaaatg ttgtaaggga caatgtttgc atgtcacagt gaagtaaacg caggagagtg      480
atggcatcta gctgctgtga gaagtggctg gaaaaatgca gctaacacga ctaactcaaa      540
```

```
acgctgggac acaagagaag gaagacaggc acctcacgct tgctgggatc tacaagttta      600
gccagaccag ttcttaagat aaactgcaat gggtatgcct gaaaggccat tcttgtttgt      660
ttctttatct gtttcagtgt tggttataac ttaccctatc ttgccacagg aagggcactt      720
ccttagacag gaagatagct gattttaaaa agccctgttt caacctacag                 770
```

<210> SEQ ID NO 143
<211> LENGTH: 791
<212> TYPE: DNA
<213> ORGANISM: Mus musculus
<220> FEATURE:
<221> NAME/KEY: misc_feature
<222> LOCATION: (107)..(107)
<223> OTHER INFORMATION: n is a, c, g, or t

<400> SEQUENCE: 143

```
agaatgctca gggcctcagc atcagctaag aggctttctg gttgcttgat tctccccaat       60
aaacaccctg aagtctcatc aaactgctca tttattttcc tgtaaangct tctattgcta      120
accaggcctt ggccattttt cccatgggaa atggagttgt tggcttcccc tggttcctgt      180
tcaccatcca ggaagtcgaa taaataatga ccgtagccca tactggtggg atggatacag      240
gaggaggact gaaagcagga gaatatcaaa cccatcaaaa atcaccgaga tcagtgcaaa      300
gactgaagca gaaagacaca gcctctaaat aggagcggcc ttaatgaaag tgcatcacct      360
cagagccaac atgaagtctg cagatgggat gcacctgcct cctgagaacc tcacagaggg      420
aaatcaagca tcagaaccca gaatggaagc agaaaacccc caatcagact cctcggagac      480
acttcagaaa aggaactctc agcttgcaaa acaacaggtg catctctaaa gagatgtggc      540
tcctgccccc accccatacc accgcaccct gagattgcag cactgctctg aactctccaa      600
tcaagcctct ttctttggtc actcttaaag tggttggttt ccagcactaa ccctcactcc      660
tccaccgaaa tgaaatctgc tagctttggc tgatgtttaa acagcttcaa tctctggggt      720
cttttgtgag agaggataat tttaacactg gtgataaacc caccagaatt ccaggtgag      780 aggagaagcc t                                                           791
```

<210> SEQ ID NO 144
<211> LENGTH: 641
<212> TYPE: DNA
<213> ORGANISM: Homo sapiens

<400> SEQUENCE: 144

```
ccactgaaca tactccccct tatttattcc atatacacat aaatagcacc accatgcacc       60
tgtggccaaa agccagaaaa tggagtgcca tcctccacaa caccttactc acactacctt      120
gatgcctaga tggtcttaaa gtcttaaaga ttctgcttcc ttattacttc taaaatctgt      180
tcccaccacc ctacttctac tgtcttttag ctaatctcac aatattcaat atttcttgcc      240
aggattattg caattccctc ctgttaagtc tccccactta aactccagct gcaccaatct      300
acactttaca attctgcaga gatgtctttt taacatgcaa atatgcttat attatttctt      360
tgcttacaca ttccaataac tcctctaaat aaaactctta agttgcttag actgacacaa      420
ggctctcatg aatgtgtccc tgcctgccct tctgcttcta ccttctagca ttccctttg      480 taaatcctat gcacttctct gagcacatca ttttctgtct tttctttttt tcttttttctt      540 tgagatgaag tctttcaaca ttgcccaggc tggtctcaaa ctcctgggct caagcgatcc      600
tctcgcctca acctcctgag tagctgggac tacagccacg c                          641
```

-continued

```
<210> SEQ ID NO 145
<211> LENGTH: 526
<212> TYPE: DNA
<213> ORGANISM: Homo sapiens

<400> SEQUENCE: 145
tattttggga tgtataaatc agacgaaaag tcacaaaatc gtgtgccatt caaaggtggt        60
ggaagttgaa gaggaagcgt atctaaatga cagataatga gtctttatga agttacgaaa       120
aagaggtcag cacctgagaa acagactaaa ctagaatagt catatgacat ctgatgttca       180
ctgtaaaatg agatgagtgc tgttggtgta atgaggttcc ttagtatgct actaagttta       240
actgcataaa ttataccaat tagctccaaa atgaatgtaa atcctcaact ataaaatgtt       300
tcaatgtgta cttagtgcta ataggaaatg tttgtggctg tgagccatcc tgaaacttct       360
gacttaaagc tctgaaagaa atgccactat atatattttt ctagcccata gaaggataaa       420 cttttttgccc tctgattgca gtggggatga ggagtccaag taacatgata ttcatattgt      480
taaaactgat ccctcgcatt gcctctttag ggtcagtgac tgctag                      526

<210> SEQ ID NO 146
<211> LENGTH: 385
<212> TYPE: DNA
<213> ORGANISM: Homo sapiens

<400> SEQUENCE: 146
agctccttgt ttgcacgtgt gttctcacag ttctctttgt ccagaccagg tacactgcag        60
ccaaagacag cgtggttcag ttcttctttt accagcccat cagtcatcag tggagacaaa       120
ctgacttctt tccctgcact gtgacgtgtg gaggaggtga ggcccaggct ttgttcatga       180
atatttagag ctcagagtta gataaattac acatttacat ttttgaagct gattttaaaa       240
ttggtgtggt gattagagat gtctcatcac acagcacctt actcagcagc ctgaatgcaa       300
tcgtgttaat gaagaagatg catttgcctt tattcttgaa gacaggtgca aaactggatt       360
tggaaaatac cttttacttt tagcc                                             385

<210> SEQ ID NO 147
<211> LENGTH: 601
<212> TYPE: DNA
<213> ORGANISM: Homo sapiens

<400> SEQUENCE: 147
agcagcctct ccagtggagt atgattcctt ttaattttgg agttaaagtt ttggatgtta        60
ttttgggatg tataaatcag acgaaaagtc acaaaatcgt gtgccattca aaggtggtgg       120
aagttgaaga ggaagcgtat ctaaatgaca gataatgagt ctttatgaag ttacgaaaaa       180
gaggtcagca cctgagaaac agactaaact agaatagtca tatgacatct gatgttcact       240
gtaaaatgag atgagtgctg ttggtgtaat gaggttcctt agtatgctac taagtttaac       300
tgcataaatt ataccaatta gctccaaaat gaatgtaaat cctcaactat aaaatgtttc       360
aatgtgtact tagtgctaat aggaaatgtt tgtggctgtg agccatcctg aaacttctga       420
cttaaagctc tgaaagaaat gccactatat atttttct agcccataga aggataaact          480
ttttgccctc tgattgcagt ggggatgagg agtccaagta acatgatatt catattgtta       540
aaactgatcc ctcgcattgc ctctttaggg tcagtgactg ctagcatggc tgctcagtga       600
t                                                                       601
```

```
<210> SEQ ID NO 148
<211> LENGTH: 512
<212> TYPE: DNA
<213> ORGANISM: Homo sapiens

<400> SEQUENCE: 148
gggaagggca gctacagcta gaggtcagaa ggctggtggg gtgagggctg cagagcgttg      60
ccttcaaggg ttcactggag atctgaccag tgcatgcaca tgagaaagct tccccaaagt     120
attagaggaa caattctcag ataccacaca gggctgagga tgctgcttct tcctgtcatc     180
cggaatgcaa agccttacgc tatataggac attgagcaga gcaatcagaa gggtttaact     240
ttagcaatgg gccaatttta gccatagtct aacagctgct ctggtttcag caaacaaagt     300
ttagaagcaa gactctaaaa gaacaagcca tttctaagta acttaaacac atcctggaat     360
gaaattcaaa aacagttata aaaataaaaa agaatcccat acccagaaca ctgaaattca     420
caacatctgg cagccaatca acaactaaca ggcaaggaaa gaagcagaaa atgggagctg     480
ccaaaatatt tgaataaata atggctgaag ca                                   512

<210> SEQ ID NO 149
<211> LENGTH: 324
<212> TYPE: DNA
<213> ORGANISM: Homo sapiens

<400> SEQUENCE: 149
ttcggcctct gtcttctgcc atcttcataa attattcaca ctacccagcg cttatgcctt      60
cccgcttcag accctctcca taactgttct ctgctctttc atttacagct gtggaacaac     120
tattttcatc tggcagtggc ttttatcacc caggattctc tgcagctgga gcagttctca     180
cacgccaaat acaacaaaat cctgaataag taggttgcat ttttggattt cctgaagagg     240
gggaggtcca tgagatcctc tgagatggtg cctgaagcag aggttttttgt tcctcctagg     300 tatggggaca tgagacggct aatt                                            324

<210> SEQ ID NO 150
<211> LENGTH: 611
<212> TYPE: DNA
<213> ORGANISM: Mus musculus

<400> SEQUENCE: 150
ggaggggcat agtgtccaca cttcagtctt cattcttctt gagtttcatg tgtttagcaa      60
atgaaaactt ttatatttct gtctttgata ggcttaccaa atccaaagtg ctcccctcc     120 cccaactatt tcaggttgaa tatctgttct ctgaaatgtt tggtctgaaa agcatatcca     180
aatttggaag atctgcatat atgtaatgag acctcttggg atgcatctca agtccaaaca     240
caaaagtcat ttatgtttca tgcacacttg acacacctag cctgaagcta atttgatacc     300
atgtctttag tgcacctgtg ttctgactgc aaaccactat aaggagtcag gtgtggaatt     360
ttccatttac agcatcgagt cactgttcca aaatgttcag cttttagagt gctctgtgat     420 ttgtatttt ggatcaggaa tgctcaacct gtattttaat gctttggcct gaaaccttcc     480
cctcagaagg aaatgtttga ttgcagactg gcatttttgc ctcctgggat agtgagttgt     540
gttttgactt ttttcattta tttatttatt ttatattcat gcctgattga gggaggcttt     600
tagaccatgg t                                                          611

<210> SEQ ID NO 151
<211> LENGTH: 1035
<212> TYPE: DNA
```

-continued

<213> ORGANISM: Homo sapiens

<400> SEQUENCE: 151

```
tgctacccta aatattccct gtgctccatc tattcatttc tcctcccttc catcttgaaa          60
ccactgatct ttctgcttcc tctataattt tgccttttcc ttttccagaa tgttataagg         120
gtggaatcat atagtgtgca gccttgaaag agtggcttct tccaccaaat aatgtgcatt         180
taaggttcct tcatgtcttt acatggcttg atagctcact ttttatccct gaataataac         240
tcattataca gatgtatcac catttgttta cccattcatc tgttgaaggg catgttgatt         300
gcttccagct tttgtcaatt atggataggc tgctataaac attcatgtgt aggctttttac        360 caacacattt ggacaaactc caaggagcac aattgctgga ttatgtaagt agactatgtt         420
tcattacgta agaagctttc aacctgtctt gtaaagtggt tctatcattt tgcattccca         480
ctagcaataa aggagagttg ttctacattt ttggaacatt tggtgttgtc atattgggca         540
aggggtattt tagctattct aaaagggatc tcataagttt aatttgcaat atcctaataa        600
aatatgatgt tgaacatctt ttcatacgat tatttgctat ttgtatattg tctttgatga        660
cgtgcctact cagacatttt ccccactgtt taaatggatt ttttgttttc caatttgttt        720
catgtggaca aaattataat ttatgttata ttgccttgta gaatgctgtg tagataatgt        780
aacaggctaa ggaatagaaa taatttgatg gaaaaacaaa tctacttttt gttttacaaa       840
gaaatgttat gaaagccctt tctgaggaga aagcctttta cttgaaaatt ttttaataga        900
ggcagggtct tgttctgttc cccaggttgg agtgcagtga cacaaccata gctcattgca        960
gccttgaact cctgagctca agcgatcctc cagagtagct agcactttag gccagagcca       1020 ctataacca gccag                                                          1035
```

<210> SEQ ID NO 152
<211> LENGTH: 584
<212> TYPE: DNA
<213> ORGANISM: Mus musculus

<400> SEQUENCE: 152

```
ggccaagaaa aggaagcagt gaatgaatgg atgatgattc tgacttctgc tttggggatg          60
aagtgggtac cacgcactga gagagaactc acgttcatcc ttctaagctt tccccattct         120
gttccctgtt cttccccccc tgcagctgtt ttcctaaaga atctctgaat ctctcccttt         180
tttttgaatc acaagcactg gctgttggga acacccacag atgcactcta caaacacaca         240
acttactctg agtaatcaca ttgatttgga attaacggcc attcagatac ctcattgaag         300
ataccatctg ggatgttgcc gctcttctga ggtatatcat attctgagaa aatccgtccg         360
attgtacaaa taactcatca gaatggctct ggctgcatct tgatgtgctg gctaggcgca         420
cgagagtcgg aggcttcagc ttcccccttcc ccctctcgag acactgaagg aagtagagcc        480
atttcttctt ctcaagagaa aaagcaacag agagtttggc aacatccaaa aagttggtcc        540
tggtgccacc aggcatccaa aaacatctcc ttgaaaattg cctt                        584
```

<210> SEQ ID NO 153
<211> LENGTH: 429
<212> TYPE: DNA
<213> ORGANISM: Homo sapiens

<400> SEQUENCE: 153

```
gagcacctgt tcctcccaat aggacctgcc caatttcagt tccttgagct ttcctggttg          60
ggctgatctg catttccaca aagtgttttt ctgagacatg ggcctcagct catgcgaagg         120
```

-continued

```
gttttcagca taaagaatac tggtcgggtc catctggtag cattgcatat tcaaggttct      180
gcatgatttg aatgaaacat gaaacaataa attcatccac tgcctagaaa catctggtct      240
cttttaataa actcctacca cttggctgtc tgaaacaaga ctatttgtat ccaacatgta      300
tgctgagagt tctttattt ttttccctct ctccagctgc aaagccacat gagaagtaaa        360
catgctcttt catgttattc tccattgaat atgatctgaa agtacttccc aacttcctga      420
atagactca                                                                429
```

```
<210> SEQ ID NO 154
<211> LENGTH: 972
<212> TYPE: DNA
<213> ORGANISM: Mus musculus

<400> SEQUENCE: 154
ttccctttag ctccttggtt actttctcta gctcctccct tgggagccct gcgatttatc        60
catgtaatgt tttggaattt ttaccaagtc tgatacatat aaagataaaa caaaacaaaa      120
tattttctta tgactagtcc aagcatgaag aaggacaagg ctaagcagaa gtttatcaaa      180
gcagcattca aattagaagg tagtcaaaac aaaaatacaa tgaatcagaa cagaaaaaga      240
acctgaatct caaaggttta gggaattctg ctgagatggt aaaagtgtaa tgggttgtta      300
ggaacatatg gttcaaagtc tcttgctctc tctttcatt tctgttagtt ttacttaaga        360
gataggtcca acaaaatcaa gttataagta taattgtctc agtaagaaga tgactaaatt      420
gataaggatc cgaagagtga ataaagatgc tgacgacatg gccaaagtaa aatggattag      480
gctgtcttca tgctaggact ttaaattgat gtgtacaaaa ttaagaagtg ctgttgcaac      540
agtgtttcaa acatcctagc caggtgatgt ttattctggg gttaaacaca agaagggtaa      600
atgtaggcag atggattctg aagaaatcaa aagcttgttt aaatgcaaat ttttctacag      660
agaagaagca ttcagagaag aaatgatatc taaataaatt ttctttcagc agaatgcttt      720
ctttttcagg tttgaaagag gcaaactcag gtgtctaatg gagatttact aaagaactaa      780
aactgggtac ctttgcaaac ggaatttcag tgcctctaaa agcctactct ctgaagcact      840
ttacttagct gtggagctga acctgcaatc aaattacaat cttctttgaa ttttgcatac      900
caatcttgac ttcaagatga gttgatactt caagacataa atgtacaatt tggtctctct      960
cttatgatcc ac                                                            972
```

```
<210> SEQ ID NO 155
<211> LENGTH: 422
<212> TYPE: DNA
<213> ORGANISM: Mus musculus

<400> SEQUENCE: 155
cctgtagtga cagggacaga taggggcacg tttagaatcc aaactctcag agcacccta        60 cacttcatgt taagggaatc tgcatattca ctgtttaagc agcccagccc acacaccagt      120
gcttagcctt tctgagttaa gctttgagat gctaaaaggc cacctggaag gatgtggggc      180
tcagccacct cggtgcattg agtaactccc actatgtgga gctaggagaa gatgcaagga      240
gaaaaacacc cacatcttca gtgttacaga caaggttgag cacctggctg gaggggcgag      300
attaagcttt ggagggaggg cagcctctga gtccactccc ttgtgtctgg ctgagacgga      360
gtggaagaca gctatctagg atttccatcc aatgcctttt caggttacct gttctctggg      420
ta                                                                        422
```

```
<210> SEQ ID NO 156
<211> LENGTH: 386
<212> TYPE: DNA
<213> ORGANISM: Mus musculus

<400> SEQUENCE: 156
acacaaggac aagctggtga gcgctgttaa atctctacta caagctgaca ctgtcacacc      60
cacagataca ccggagtgtc agatggcccc atctcatggt acatgaaatg cagtaatcct     120
gcggtgcaat tttctgagct attttccaga gctttctctt gaaaagcagg tgacttcttg     180
ggtagcagca atttaccttt cacaccgggt aatcatcaag gtgcctgatt gccctgaata     240
cctttcccgg ctgtcagaat acttcaaggc tgagaattag catttcaaaa cctttcaaa     300 tgagggtagg ggggctcatt cccttggttg aaggttcccc aggctgcaaa gaagcaagtg     360
ttaagtgcac acctggggaa gccata                                         386

<210> SEQ ID NO 157
<211> LENGTH: 621
<212> TYPE: DNA
<213> ORGANISM: Mus musculus

<400> SEQUENCE: 157
atactgtaaa aagcaagaag aaccaatcac ttaatctaaa atttagaact ctgaagtgat      60
tcattccact gaccattctc tttttcccagt tctcttatct tgtcagatac acaggaagct     120
caggacagtt ttgctcatcc ctttgtttct agcagttctg agtaatgaat tcaaatagca     180
gttattatct caatgccatg acaattggct aagctaacta cccagttcac ttatcgaggg     240
agcaaaacac tagatggcca ataagaatga cagacagaat gtatgattga tgtgaaacac     300
ccagagaatc aagtgctttc aaagagttaa atgtgttctc cattatggct gacagctgga     360
gaaactatca ttggaaactg agatgaattg tttgctctgt gcaggtggga gaagagaatt     420
aaatgacaga cacatgaaac tgtgctttgc atcttcttgt cagcactact ctgttggcca     480
agagtgaaat gcaatttcag ttggcttgaa cgccacagga ttttacatct gaatcaacta     540
agttctaatt atgggcagat ttatctacta ataccatcac cataacaacc aaaaccatgc     600
cccatgcctt tcatgtcttc a                                               621

<210> SEQ ID NO 158
<211> LENGTH: 818
<212> TYPE: DNA
<213> ORGANISM: Mus musculus

<400> SEQUENCE: 158
agctgtaaag tctggaggtg tgcttttcag gagctgggga ggttagaggg aagacctcga      60
acaggacaca ctatcactgt ctttcttgtg ccaatgcaat tggaagaaac aaacacagcc     120
atcatttagc ccacatgaat taggtcctgt aaagagtgaa ggggaaaagg ttgttggaaa     180
tctaattagt aggctttgca agtgtggagt ttatggctac atattcagtt aaattcagtt     240 ctgtttttgta gctatcagcc agggaagagt caagtgccat gtggattggg aacataaata     300
gcccattctt catgtccatt gctctatcat taaccttccc actcagtcct ggaaatgaaa     360
aacccagcgt ccttccatct gctccacgtt atttatgatg atgcctctaa ttatgttcaa     420
ttgagttgct gtcgatgatt aaaggtaata ggtaataata acttggcctc atcattacca     480
ccattattat tagctcattg attgcaataa tttctaaaat taccccttgg aataaaatat     540
gttaagcacc tggtttatcc ttttttttt ttttttaaaaa aggaacatct gctctaaatg     600
```

```
tgtgatagca gaggaccaaa cgtgtcttga tctgaagggg aagcaaaaac gatgctgaca       660
ctggggagcc ttgtctgggc tggaatggat gtattgtggg atgctgagag gaagagtagt       720
cacgatcaag ttcaatgcta ggattacagg gctgctgaga gacggagaca cgtgggaagc       780
tgagctattc catggctact gcaggctta cttcttct                                818

<210> SEQ ID NO 159
<211> LENGTH: 757
<212> TYPE: DNA
<213> ORGANISM: Mus musculus

<400> SEQUENCE: 159
attttagtag gaaagtggga tactatcttc taaagagact gtgcatctta tactcctatc        60
taccacatca tatttactgt ctattcttag ttgggtctaa atttctaagt aattttaagt       120
attcatattc taggctactg ggtcctatag attaatataa atatttgatt gtaagttatg       180
caataaaaat gaagagattt gtttatatgc atctaaataa gaacatgcag aatgtgttcg       240
gaacttgaat atccttatct ccatgaaaat gggaaaaata aaaataattt aaacaaagtg       300
ttgagtggaa catgtgtagc tgaaacactt gattttccct aaaatatctg agtaattact       360
tgaatttcct actttatcat ttgtccatgg acagctggta tcaggctata aaaacaacaa       420
taattagagg cccaaatagt tcttttaatt accctaaaag tctgaaattc acgtttttgt       480
tgtctagaag tattctaatc atgtttaaca gctgattagc aattggtcca tttttatgtt       540
gtagaaaagt gaaatgtgaa tggaaaattg aagaataatt ccaaaccaag gtaaattatt       600 actgctttc cctgcaattg ttagttgaaa ggtgtgattt gagataagat catttacact        660
taaaagtgaa tagaagaaat ataataagag ggaataggcc tgtgaagttg tcaagaataa       720
attttaaaat aaatgcagca tttttgcat ttatgtc                                757

<210> SEQ ID NO 160
<211> LENGTH: 1044
<212> TYPE: DNA
<213> ORGANISM: Mus musculus

<400> SEQUENCE: 160
ctggctgtcc tggaactcac tctgtagacc aggctggcct caaactcaga aatctgcctg        60
cctctgcctc ccaagtgctg ggattaaagg catgtgccac cacacctggc ctagaaataa       120 tgactttaa aattatctaa aggttaccag atgaaattat caacctcagc tctgtggtat        180
aatttaaatc tagttctgat tcagtaagag tgttattttc agtaccctca gtagcagaat       240
cctattgcct cttatatcta agcaggagag gcaattcaga aacaaagacc caaggacagg       300
agccctattg catctactct caataattaa ggcctttgat gactaaaata atttagataa       360
taagattggt ttgggtaaat aaatatcaaa ttagggttta tggcagtcac aggtgtttgg       420
caggtctggc ctataatcac agagaaaatg aatgcatttt atttagcata attgggaaaa       480
ggaatgaagc ttatatgcaa attgtgtacc acttttgtta aagatagctg gtcagactca       540
tgatgataat ccaaaccttt atcccagtga aaattttcaa catatctatt ttctgtggaa       600
ttttaccaca tctgactgca ttctcccagt cttctgagat ggatttcagt gtccttggtc       660
accatctagc ctttctattt tgttgacagg atgcctgagt ttagctgttt ctgtttattt       720
gtttgttttt aagcttgatt tctcctactc gtgtctatag ctggaatcgg aggttacatg       780
agatttctca gcatcagcat ccagcactgc cacaaagggg atgtgggaga tgagaaggga       840
```

-continued

```
aaacaagaca gtgaagagaa taaaaatgaa atcctggagg caagataatt aagagaccag      900
aaaatagagt tgaatttcca ttaggaacat ttacaagaat gtgttcacag gcacacacac      960
aggaatcccc aactgctagc tttggaatgc ccatagatgc cactgctact ggactctgtg     1020
atcagcgctc ttgactagga ctac                                           1044
```

```
<210> SEQ ID NO 161
<211> LENGTH: 279
<212> TYPE: DNA
<213> ORGANISM: Homo sapiens

<400> SEQUENCE: 161
ccacttttgt atttaccatt attgcaaaat caatcaaatg tgagcaaaag caaaggcaat       60
ttgaatgact caaaattgaa atttgagctg ccaaatcaag cagtaaaaca atttttacca      120
gctctattga ttgttagaaa gataagttat aaactttatt tcaagtaaat ttctaaaaga      180
tctgggaatg tgattattcc aaggcagatg gcgaagacct ttatttccac tgattattca      240
cagatgcaaa ttattatgca actggaagca tactaagat                             279
```

```
<210> SEQ ID NO 162
<211> LENGTH: 837
<212> TYPE: DNA
<213> ORGANISM: Artificial Sequence
<220> FEATURE:
<223> OTHER INFORMATION: 3xCore2_eHGT_226h

<400> SEQUENCE: 162
ccacttttgt atttaccatt attgcaaaat caatcaaatg tgagcaaaag caaaggcaat       60
ttgaatgact caaaattgaa atttgagctg ccaaatcaag cagtaaaaca atttttacca      120
gctctattga ttgttagaaa gataagttat aaactttatt tcaagtaaat ttctaaaaga      180
tctgggaatg tgattattcc aaggcagatg gcgaagacct ttatttccac tgattattca      240
cagatgcaaa ttattatgca actggaagca tactaagatc cacttttgta tttaccatta      300
ttgcaaaatc aatcaaatgt gagcaaaagc aaaggcaatt gaatgactc aaaattgaaa       360 tttgagctgc caaatcaagc agtaaaacaa tttttaccag ctctattgat tgttagaaag      420
ataagttata aactttattt caagtaaatt tctaaaagat ctgggaatgt gattattcca      480
aggcagatgg cgaagacctt tatttccact gattattcac agatgcaaat tattatgcaa      540
ctggaagcat actaagatcc acttttgtat ttaccattat tgcaaaatca atcaaatgtg      600
agcaaaagca aaggcaattt gaatgactca aaattgaaa ttgagctgcc aaatcaagca       660
gtaaaacaat ttttaccagc tctattgatt gttagaaaga taagttataa actttatttc      720
aagtaaattt ctaaaagatc tgggaatgtg attattccaa ggcagatggc gaagaccttt      780
atttccactg attattcaca gatgcaaatt attatgcaac tggaagcata ctaagat         837
```

```
<210> SEQ ID NO 163
<211> LENGTH: 280
<212> TYPE: DNA
<213> ORGANISM: Homo sapiens

<400> SEQUENCE: 163
tttccactga ttattcacag atgcaaatta ttatgcaact ggaagcatac taagatattg       60
caaagatgtt ctgacattag tcatctgctg cctttgttac tttggtgtca attttcttat      120
tctttccaaa ggaagatcct tacagtttgt attcttcac agctgggaaa tgatcagttg       180
agaattattc aaacacacca atctgttaac cgtacttctt cccagataat gcaatatttt      240
```

-continued

```
gcagggtgac aggcaaaaag tggtcatttt ttacttcata                           280

<210> SEQ ID NO 164
<211> LENGTH: 840
<212> TYPE: DNA
<213> ORGANISM: Artificial Sequence
<220> FEATURE:
<223> OTHER INFORMATION: 3xCore3_eHGT_226h

<400> SEQUENCE: 164
tttccactga ttattcacag atgcaaatta ttatgcaact ggaagcatac taagatattg    60
caaagatgtt ctgacattag tcatctgctg cctttgttac tttggtgtca attttcttat    120
tctttccaaa ggaagatcct tacagtttgt attctttcac agctgggaaa tgatcagttg    180
agaattattc aaacacacca atctgttaac cgtacttctt cccagataat gcaatatttt    240
gcagggtgac aggcaaaaag tggtcatttt ttacttcata tttccactga ttattcacag    300
atgcaaatta ttatgcaact ggaagcatac taagatattg caaagatgtt ctgacattag    360
tcatctgctg cctttgttac tttggtgtca attttcttat tctttccaaa ggaagatcct    420
tacagtttgt attctttcac agctgggaaa tgatcagttg agaattattc aaacacacca    480
atctgttaac cgtacttctt cccagataat gcaatatttt gcagggtgac aggcaaaaag    540
tggtcatttt ttacttcata tttccactga ttattcacag atgcaaatta ttatgcaact    600
ggaagcatac taagatattg caaagatgtt ctgacattag tcatctgctg cctttgttac    660
tttggtgtca attttcttat tctttccaaa ggaagatcct tacagtttgt attctttcac    720
agctgggaaa tgatcagttg agaattattc aaacacacca atctgttaac cgtacttctt    780
cccagataat gcaatatttt gcagggtgac aggcaaaaag tggtcatttt ttacttcata    840

<210> SEQ ID NO 165
<211> LENGTH: 242
<212> TYPE: DNA
<213> ORGANISM: Homo sapiens

<400> SEQUENCE: 165
ttcaattggt aaagttgtgg tatataatta caattgaact ctcttgtact tgcctctttt    60
acaaaaattc tctcctagca gaacgtagtg tgagtcatct acacagctgt ttttctgatt    120
attggaattt tcttttgaca tgaaggaagt atctcattga cagaactgcg ttgtgaagga    180
gtgctaactg tagcataaaa tacaaaattg gattttttaga ttgcaaaata cagtaaagct    240
tt                                                                    242

<210> SEQ ID NO 166
<211> LENGTH: 726
<212> TYPE: DNA
<213> ORGANISM: Artificial Sequence
<220> FEATURE:
<223> OTHER INFORMATION: 3xCore_eHGT_064h

<400> SEQUENCE: 166
ttcaattggt aaagttgtgg tatataatta caattgaact ctcttgtact tgcctctttt    60
acaaaaattc tctcctagca gaacgtagtg tgagtcatct acacagctgt ttttctgatt    120
attggaattt tcttttgaca tgaaggaagt atctcattga cagaactgcg ttgtgaagga    180
gtgctaactg tagcataaaa tacaaaattg gattttttaga ttgcaaaata cagtaaagct    240
ttttcaattg gtaaagttgt ggtatataat tacaattgaa ctctcttgta cttgcctctt    300
```

-continued

```
ttacaaaaat tctctcctag cagaacgtag tgtgagtcat ctacacagct gtttttctga      360
ttattggaat tttctttttga catgaaggaa gtatctcatt gacagaactg cgttgtgaag      420
gagtgctaac tgtagcataa aatacaaaat tggatttta gattgcaaaa tacagtaaag       480 cttttcaat tggtaaagtt gtggtatata attacaattg aactctcttg tacttgcctc        540
ttttacaaaa attctctcct agcagaacgt agtgtgagtc atctacacag ctgttttct         600 gattattgga attttctttt gacatgaagg aagtatctca ttgacagaac tgcgttgtga       660
aggagtgcta actgtagcat aaaatacaaa attggattt tagattgcaa aatacagtaa        720
agcttt                                                                   726

<210> SEQ ID NO 167
<211> LENGTH: 1802
<212> TYPE: DNA
<213> ORGANISM: Artificial Sequence
<220> FEATURE:
<223> OTHER INFORMATION: CN1261

<400> SEQUENCE: 167
cctaggacgc gtcccaaact ctcatctgct ccaagctgta tagaagtttc tttcagagtt        60
atttcagttc atttcaatga aaaaattatc aaatataata aaacattttt ggaaagacag       120
gagggatttg ggacattaca attggtatta aaagaactaa tgagctttgc tactgataaa      180
gtatttcttg cattctttt tggttcaaag agtgataccc aattattaat tcttaagcac         240
ataaatcttt tccattttg tttttcctgc tcggtgcctg aattttcttg gctactactg         300 aaatgtgtt aataggctga ttctactttt tatctgcata ttctatggat ctagtggctc        360
tgaatccaag ccactataat aatgatggaa acaaaatatt tctgatgaac atataaccag       420
atattgctga caaatagaaa aaagaacagg ctgatggggg ccagactgtg catatgatct      480
gtattccgag ctcgggctgg gcataaaagt cagggcagag ccatctattg cttacatttg       540
cttctgggat ccagatcttt cgaagctagc gctaccggtc gccaccatgg tgagcaaggg      600
cgaggagctg ttcaccgggg tggtgcccat cctggtcgag ctggacggcg acgtaaacgg      660
ccacaagttc agcgtgtccg gcgagggcga gggcgatgcc acctacggca agctgaccct      720
gaagctgatc tgcaccaccg gcaagctgcc cgtgccctgg cccaccctcg tgaccaccct      780
gggctacggc gtgcagtgct tcgcccgcta ccccgaccac atgaagcagc acgacttctt      840
caagtccgcc atgcccgaag gctacgtcca ggagcgcacc atcttcttca aggacgacgg      900
caactacaag acccgcgccg aggtgaagtt cgagggcgac accctggtga accgcatcga      960
gctgaagggc atcgacttca aggaggacgg caacatcctg gggcacaagc tggagtacaa     1020
ctacaacagc cacaacgtct atatcaccgc cgacaagcag aagaacggca tcaaggccaa     1080
cttcaagatc cgccacaaca tcgaggacgg cggcgtgcag ctcgccgacc actaccagca     1140
gaacaccccc atcggcgacg gccccgtgct gctgcccgac aaccactacc tgagctacca     1200
gtccaagctg agcaaagacc ccaacgagaa gcgcgatcac atggtcctgc tggagttcgt     1260
gaccgccgcc gggatcactc tcggcatgga cgagctgtac aagtaagtcg acggcgcgcc     1320
gcggccgcga attcgatatc ataatcaacc tctggattac aaaatttgtg aaagattgac     1380
tggtattctt aactatgttg ctcctttac gctatgtgga tacgctgctt taatgccttt     1440
gtatcatgct attgcttccc gtatggcttt cattttctcc tccttgtata aatcctggtt     1500
agttcttgcc acgcggaac tcatcgccgc ctgccttgcc cgctgctgga caggggctcg     1560
gctgttgggc actgacaatt ccgtggctcg agcgactgtg ccttctagtt gccagccatc     1620
```

```
tgttgtttgc ccctcccccg tgccttcctt gaccctggaa ggtgccactc ccactgtcct    1680
ttcctaataa aatgaggaaa ttgcatcgca ttgtctgagt aggtgtcatt ctattctggg    1740
gggtggggtg gggcaggaca gcaagggggga ggattgggaa gacaatagca ggcatgacta    1800
gt                                                                    1802

<210> SEQ ID NO 168
<211> LENGTH: 2031
<212> TYPE: DNA
<213> ORGANISM: Artificial Sequence
<220> FEATURE:
<223> OTHER INFORMATION: CN1542

<400> SEQUENCE: 168
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgttttca gagacccagt     240
gactgatgtt gtcccagaaa gtagaattct tgtgatgcat aaatgatagc tgatccagcc     300
aacacaactg ttggaggaat tatagcttat agagttgctt ggcagatgaa atcacttgac     360
taattagaaa ataatgcatt atgctgtgct agaaaaatca cagagcagca gaagcggaac     420
tgtgttctgg gttgctgtgg gctgccagtc acaattttga gcctgtgcct tgcattcttt     480
accttttttt ttcccactat ccctacagcc cagaaattga aacagaccct ggagccttgt     540
gatactgaat atccagcatt cgtctctgag cgcaccatca aggagactac agggaatatt     600
gcttgtgaag actgctccag aattcgatat cataatcaac cataggtacc gagctcggga     660
ttcagccggg agcttaggga ggggaggtca cttcataagg gcctgggggg ggagttggag     720
ccacgagtcg tccagccgga gccccgtgtg gctgagctcc ggcctcagaa gcatccccgg     780
gttggatcct tcgaagctag cgctaccggt cgccaccatg gtgagcaagg gcgaggagct     840
gttcaccggg gtggtgccca tcctggtcga gctggacggc gacgtaaacg gccacaagtt     900
cagcgtgtcc ggcgagggcg agggcgatgc cacctacggc aagctgaccc tgaagctgat     960
ctgcaccacc ggcaagctgc ccgtgccctg gcccaccctc gtgaccaccc tgggctacgg    1020
cgtgcagtgc ttcgcccgct accccgacca catgaagcag cacgacttct tcaagtccgc    1080
catgcccgaa ggctacgtcc aggagcgcac catcttcttc aaggacgacg gcaactacaa    1140
gacccgcgcc gaggtgaagt tcgagggcga caccctggtg aaccgcatcg agctgaaggg    1200
catcgacttc aaggaggacg gcaacatcct ggggcacaag ctggagtaca actacaacag    1260
ccacaacgtc tatatcaccg ccgacaagca gaagaacggc atcaaggcca cttcaagat    1320 ccgccacaac atcgaggacg gcggcgtgca gctcgccgac cactaccagc agaacacccc    1380
catcggcgac ggccccgtgc tgctgcccga caaccactac ctgagctacc agtccaagct    1440
gagcaaagac cccaacgaga agcgcgatca catggtcctg ctggagttcg tgaccgccgc    1500
cgggatcact ctcggcatgg acgagctgta caagtaagtc gacatcataa tcaacctctg    1560
gattacaaaa tttgtgaaag attgactggt attcttaact atgttgctcc ttttacgcta    1620
tgtggatacg ctgctttaat gcctttgtat catgctattg cttcccgtat ggctttcatt    1680
ttctcctcct tgtataaatc ctggttagtt cttgccacgg cggaactcat cgccgcctgc    1740
cttgcccgct gctggacagg ggctcggctg ttgggcactg acaattccgt ggctcgagag    1800
```

-continued

```
atcttcgact gtgccttcta gttgccagcc atctgttgtt tgcccctccc ccgtgccttc    1860
cttgaccctg gaaggtgcca ctcccactgt cctttcctaa taaaatgagg aaattgcatc    1920
gcattgtctg agtaggtgtc attctattct ggggggtggg gtggggcagg acagcaaggg    1980
ggaggattgg gaagacaata gcaggcatgc acgtgcggac cgagcggccg c             2031

<210> SEQ ID NO 169
<211> LENGTH: 2557
<212> TYPE: DNA
<213> ORGANISM: Artificial Sequence
<220> FEATURE:
<223> OTHER INFORMATION: CN1544

<400> SEQUENCE: 169
gcggccgcaa cgcgtttaga acaatggctg gcccatagta aatgccgtgt tagtgtgtta      60
gttgctgttc ttccacgtca gaagaggcac agacaaatta ccaccaggtg gcgctcagag     120
tctgcggagg catcacaaca gccctgaatt tgaatcctgc tctgccactg cctagttgag     180
accttttact acctgactag ctgtttgtgt attttaggtg tttgtttttga ctgacaggcc     240 gggcccctgc tcatccctga aaactagcat cggggaatga catacagttt gataacataa     300
gatgcttagg tttttttggct caagtgagat gttcagagct aatagccctg cgagctgagt     360
tttagctgtg atctgcacct tgagatatcc gttatgtctg gatcaggaaa aagggaaaag     420
aatgagagct tatttctaga aaggtttccg atgagcagca tttgtcattg aaggggaaga     480
tgggtataat tagcttgtca gtctagtttg ggctgagcag gctgtctctg ctaagaaaga     540
tggactaact gccagggcca ctgacaggca gtcgatagcg cagcaattaa tgtcataaat     600
aattccagaa ccaattacat caaaatggac tcagagcttt aaaaaggtac agaattctct     660
tattcttcct gctaacagca agaaacagct ttcatttttc tctgtaatta cttttcattg     720
tatatagcaa tacagctgag cttttctgtc catatttaag ccttgtcttt ctccaagcct     780
cttcccccac caccagcctc cctccttcac cccacaggat aaggctgtta aagttgttct     840
tccctgccag agcagtgggg tgaatgtata atcttttaac ttggctgttg caggagaact     900
ccagctacac ctaaatgatt aagagccaag ttttttgaaaa tgtcatggac aatgacagca     960
cagtgcccca aacaatggca tttggaaatg aagacatttg tgaaataaat ggatttgtct    1020
tattatttta aaggttgctg tgactttgct tacactgaat ttattgattt ttccccttc    1080 tccttctcct tcctcttctt gttctcctcc tccttctgta cagttgcagg catagaagct    1140
gggccgaatt cgatatcata atcaaccata ggtaccgagc tcgggattca gccgggagct    1200
tagggagggg aggtcacttc ataagggcct gggggggggag ttggagccac gagtcgtcca    1260 gccgagccc cgtgtggctg agctccggcc tcagaagcat ccccgggttg gatccttcga    1320
agctagcgct accggtcgcc accatggtga gcaagggcga ggagctgttc accggggtgg    1380
tgcccatcct ggtcgagctg gacggcgacg taaacggcca caagttcagc gtgtccggcg    1440
agggcgaggg cgatgccacc tacggcaagc tgaccctgaa gctgatctgc accaccggca    1500
agctgcccgt gccctggccc accctcgtga ccaccctggg ctacggcgtg cagtgcttcg    1560
cccgctaccc cgaccacatg aagcagcacg acttcttcaa gtccgccatg cccgaaggct    1620
acgtccagga gcgcaccatc ttcttcaagg acgacggcaa ctacaagacc cgcgccgagg    1680
tgaagttcga gggcgacacc ctggtgaacc gcatcgagct gaagggcatc gacttcaagg    1740
aggacggcaa catcctgggg cacaagctgg agtacaacta caacagccac aacgtctata    1800
tcaccgccga caagcagaag aacggcatca aggccaactt caagatccgc cacaacatcg    1860
```

-continued

```
aggacggcgg cgtgcagctc gccgaccact accagcagaa cacccccatc ggcgacggcc      1920
ccgtgctgct gcccgacaac cactacctga gctaccagtc caagctgagc aaagacccca      1980
acgagaagcg cgatcacatg gtcctgctgg agttcgtgac cgccgccggg atcactctcg      2040
gcatggacga gctgtacaag taagtcgaca tcataatcaa cctctggatt acaaaatttg      2100
tgaaagattg actggtattc ttaactatgt tgctcctttt acgctatgtg gatacgctgc      2160
tttaatgcct ttgtatcatg ctattgcttc ccgtatggct ttcattttct cctccttgta      2220
taaatcctgg ttagttcttg ccacggcgga actcatcgcc gcctgccttg cccgctgctg      2280 gacagggggct cggctgttgg gcactgacaa ttccgtggct cgagagatct tcgactgtgc      2340
cttctagttg ccagccatct gttgtttgcc cctcccccgt gccttccttg accctggaag      2400
gtgccactcc cactgtcctt tcctaataaa atgaggaaat tgcatcgcat tgtctgagta      2460
ggtgtcattc tattctgggg ggtggggtgg ggcaggacag caaggggggag gattgggaag      2520 acaatagcag gcatgcacgt gcggaccgag cggccgc                               2557
```

<210> SEQ ID NO 170
<211> LENGTH: 1988
<212> TYPE: DNA
<213> ORGANISM: Artificial Sequence
<220> FEATURE:
<223> OTHER INFORMATION: CN1598

<400> SEQUENCE: 170

```
gcggccgcaa cgcgtttaga acaatggctg gcccatagta aatgccgtgt tagtgtgtta        60
gttgctgttc ttccacgtca gaagaggcac agacaaatta ccaccaggtg gcgctcagag       120
tctgcggagg catcacaaca gccctgaatt tgaatcctgc tctgccactg cctagttgag       180
accttttact acctgactag ctgtttgtgt attttaggtg tttgttttgt ttggatctgg       240
ggcgaagctt ccctagccct gtccctgcag tggcctggta ttgggtggac ccgtcacctg       300
agacaaggac tcctgacaac ccaagtcccc agaggcctcc ctgcccttcc ctcattccgt       360
tgttccactt ttagagaacc ccgggactcc tcagcaggca gcagcctatt ttgccaggat       420
ccacatagag cagtgcctgg cacagtagcg gtgaagcggg aagtgggtct ctgttggcgg       480
gcaccgtggt gcccggaact cgctattcct ccccagtgtt aattatcaaa attaaccgaa       540
cactataaat aacccaactc agagactcga agtgccgaat tcgatatcat aatcaaccat       600
aggtaccgag ctcgggattc agccgggagc ttagggaggg gaggtcactt cataagggcc       660
tgggggggga gttggagcca cgagtcgtcc agccggagcc ccgtgtggct gagctccggc       720
ctcagaagca tccccgggtt ggatccttcg aagctagcgc taccggtcgc caccatggtg       780
agcaagggcg aggagctgtt caccggggtg gtgcccatcc tggtcgagct ggacggcgac       840
gtaaacggcc acaagttcag cgtgtccggc gagggcgagg gcgatgccac ctacggcaag       900
ctgaccctga agctgatctg caccaccggc aagctgcccg tgccctggcc caccctcgtg       960
accaccctgg gctacggcgt gcagtgcttc gcccgctacc ccgaccacat gaagcagcac      1020
gacttcttca gtccgccat gcccgaaggc tacgtccagg agcgcaccat cttcttcaag      1080
gacgacggca actacaagac ccgcgccgag gtgaagttcg agggcgacac cctggtgaac      1140
cgcatcgagc tgaagggcat cgacttcaag gaggacggca acatcctggg gcacaagctg      1200
gagtacaact acaacagcca caacgtctat atcaccgccg acaagcagaa gaacggcatc      1260
aaggccaact tcaagatccg ccacaacatc gaggacggcg gcgtgcagct cgccgaccac      1320
```

-continued

```
taccagcaga acacccccat cggcgacggc cccgtgctgc tgcccgacaa ccactacctg      1380
agctaccagt ccaagctgag caaagacccc aacgagaagc gcgatcacat ggtcctgctg      1440
gagttcgtga ccgccgccgg gatcactctc ggcatggacg agctgtacaa gtaagtcgac      1500
atcataatca acctctggat tacaaaattt gtgaaagatt gactggtatt cttaactatg      1560
ttgctccttt tacgctatgt ggatacgctg ctttaatgcc tttgtatcat gctattgctt      1620
cccgtatggc tttcattttc tcctccttgt ataaatcctg gttagttctt gccacggcgg      1680
aactcatcgc cgcctgcctt gcccgctgct ggacaggggc tcggctgttg ggcactgaca      1740
attccgtggc tcgagagatc ttcgactgtg ccttctagtt gccagccatc tgttgtttgc      1800
ccctcccccg tgccttcctt gaccctggaa ggtgccactc ccactgtcct ttcctaataa      1860
aatgaggaaa ttgcatcgca ttgtctgagt aggtgtcatt ctattctggg gggtggggtg      1920
gggcaggaca gcaagggggga ggattgggaa gacaatagca ggcatgcacg tgcggaccga      1980
gcggccgc                                                               1988
```

<210> SEQ ID NO 171
<211> LENGTH: 2768
<212> TYPE: DNA
<213> ORGANISM: Artificial Sequence
<220> FEATURE:
<223> OTHER INFORMATION: CN1553

<400> SEQUENCE: 171

```
gcggccgcaa cgcgtttaga acaatggctg gcccatagta aatgccgtgt tagtgtgtta       60
gttgctgttc ttccacgtca gaagaggcac agacaaatta ccaccaggtg gcgctcagag      120
tctgcggagg catcacaaca gccctgaatt tgaatcctgc tctgccactg cctagttgag      180
accttttact acctgactag ctgtttgtgt attttaggtg tttgtttcag ttatgaagta      240
caagttttcc tgtggcagaa agatgtttcc attgtttgt tttgtttgtt ttgtttcgtt       300
ttgttttaaa tgcatctctg ccttacctta cttgcgggcc agtgagctag cctaaaatcg      360
aagctctgtg aagcccgctc ttgccatttt attttttgaag gctgtccctt ggccacatct      420
gacccaccag ctcctgtcat tagcatctga gtgttaagcc agaggaactc aatctgggaa      480
caccaccaac gtggccagta agctgcaatt tagttaatgt gcactccttg taggccctgg      540
ttttggcccg agtgtatttg ggtagagtgt gtggtggtga tggtagggag ctagagagga      600
aggggagggt gatggactca tttgcaagaa ctgcccagct gagataacat ttaaaatgaa      660
caggagaagg tccaatgctt tgtaatcctc cagcagctgc tcattttggg ttgggatcag      720
gaaggagcac tttgccatta gtccccgagc caaaagtggc cggtggtggt ttctggtctc      780
cctaagccac ctccaaaggg gtcactcagc tgtgtcctag ggaagcgaaa caagagaaaa      840
agaacaagat ggcttgtacg ctccatccat gtgtgtggcc ccagggatgc ccctgcagat      900
gggcctggtt ggagatggtg atatcttgga tgggttcact gcagctccgt gcccgaaaag      960
ggcagctggt gggcttgttc cgctgttctt cagcctgtca ctgcaccact cttaacaagt     1020
tatccacatc ccagagatgc agattatgcc tcagcttaga gggccaagct tccctccaag     1080
agactgagct gcaaaaagc tgccagagtc cctgtagcct gcccagatcc tgcctgaacc      1140
cagcccaaag agatggttgt cattccaggc aagggctcac ccgggccaga tgccttcctt     1200
ccccaggcct gtggtttctc ccacttgagg aagaattgct atttctttg ctgtatcatt      1260 acaaataaaa caaaactgac tttgaacata ttaatgataa cagatggctt cataaaatgt     1320
aaacagagca atgaaagtac aaatgggggt cctaccgaat tcgatatcat aatcaaccat     1380
```

-continued

```
aggtaccgag ctcgggattc agccgggagc ttagggaggg gaggtcactt cataagggcc      1440
tgggggggga gttggagcca cgagtcgtcc agccggagcc ccgtgtggct gagctccggc      1500
ctcagaagca tccccgggtt ggatccttcg aagctagcgc taccggtcgc caccatggtg      1560
agcaagggcg aggagctgtt caccggggtg gtgcccatcc tggtcgagct ggacggcgac      1620
gtaaacggcc acaagttcag cgtgtccggc gagggcgagg gcgatgccac ctacggcaag      1680
ctgaccctga agctgatctg caccaccggc aagctgcccg tgccctggcc cacccptcgtg      1740 accaccctgg gctacggcgt gcagtgcttc gcccgctacc ccgaccacat gaagcagcac      1800
gacttcttca gtccgccat gcccgaaggc tacgtccagg agcgcaccat cttcttcaag      1860
gacgacggca actacaagac ccgcgccgag gtgaagttcg agggcgacac cctggtgaac      1920
cgcatcgagc tgaagggcat cgacttcaag gaggacggca acatcctggg gcacaagctg      1980
gagtacaact acaacagcca caacgtctat atcaccgccg acaagcagaa gaacggcatc      2040
aaggccaact tcaagatccg ccacaacatc gaggacggcg gcgtgcagct cgccgaccac      2100
taccagcaga acacccccat cggcgacggc cccgtgctgc tgcccgacaa ccactacctg      2160
agctaccagt ccaagctgag caaagacccc aacgagaagc gcgatcacat ggtcctgctg      2220
gagttcgtga ccgccgccgg gatcactctc ggcatggacg agctgtacaa gtaagtcgac      2280
atcataatca acctctggat tacaaaattt gtgaaagatt gactggtatt cttaactatg      2340
ttgctccttt tacgctatgt ggatacgctg ctttaatgcc tttgtatcat gctattgctt      2400
cccgtatggc tttcattttc tcctccttgt ataaatcctg gttagttctt gccacggcgg      2460
aactcatcgc cgcctgcctt gcccgctgct ggacaggggc tcggctgttg ggcactgaca      2520
attccgtggc tcgagagatc ttcgactgtg ccttctagtt gccagccatc tgttgtttgc      2580 ccctccccg tgccttcctt gaccctggaa ggtgccactc ccactgtcct ttcctaataa      2640
aatgaggaaa ttgcatcgca ttgtctgagt aggtgtcatt ctattctggg gggtggggtg      2700
gggcaggaca gcaaggggga ggattgggaa gacaatagca ggcatgcacg tgcggaccga      2760
gcggccgc                                                            2768
```

<210> SEQ ID NO 172
<211> LENGTH: 2401
<212> TYPE: DNA
<213> ORGANISM: Artificial Sequence
<220> FEATURE:
<223> OTHER INFORMATION: CN1992

<400> SEQUENCE: 172

```
gcggccgcac gcgccggtac cgaagctacc cctaacacac tattctacac acagaaaatg       60
ctcttcacta ggaagctacc cctaacacac tattctacac acagaaaatg ctcttcacta      120
ggaagctacc cctaacacac tattctacac acagaaaatg ctcttcacta gacgcgttac      180
ctgccattcc aactctggcc tctgtgagca tatacacaca catgcgcaca ttaacatccc      240 cccccccca cacacacctc aggcatagac atacactttt aaaaaggcag ccacaatatc      300
aatttaattc agataaaatc acaacacaac cttctttagt actgagtctt acaaagttgt      360
atgcttgagg tgtcctgaga accccactaa ggtaatggct gtaacattcc tcagaggtga      420
actcatttcc atgactcatt ctgaaaagca caggctcctt gtcctttcac acgcatcaca      480
atgcaaccta aaatagatcc tcatcagcgc ctctttcagg gttatgaata gcactacctt      540
gaaaagggcc aagagggatg catgcatggg attcagaaag gaggcattca agaaaaccaa      600
```

-continued

```
gcaggaggca ggctgcctaa gtactttgag catggagcat gacgggaccc cctctggctc      660
ccacgcaggc aaccaggtgc cacactcaat ggagatggag tgggtgggag ctctgagaag      720
gagctgcatc tactgggcaa agtggttgaa aaacccgaag aggacctaag taagcatcgg      780
cttagactgc tgaccccgtt ctccacctct ttatccaccc cccttcttgg gtggctggaa      840
aaatcaaatg gtatttctct accttcctga ttgtcacatt caatgtaccc aacggaagga      900
attcacagtg ggccacctcc tgctcaagaa gccaaggcac tttgcattct gcctcttgtc      960
tttgctggga gaatggcatg acaacttaag gagctcgatt cagccgggag cttagggagg     1020
ggaggtcact tcataagggc ttggggggg agttggagcc acgagtcgtc cagccggagc       1080
cccgtgtggc tgtgctccgg cctcagaagc atccccggat ccagatcttt cgaagctagc     1140
gctaccggtc gccaccatgg tgagcaaggg cgaggagctg ttcaccgggg tggtgcccat     1200
cctggtcgag ctggacggcg acgtaaacgg ccacaagttc agcgtgtccg gcgagggcga     1260
gggcgatgcc acctacggca agctgaccct gaagctgatc tgcaccaccg gcaagctgcc     1320
cgtgccctgg cccaccctcg tgaccaccct gggctacggc gtgcagtgct tcgcccgcta     1380
ccccgaccac atgaagcagc acgacttctt caagtccgcc atgcccgaag gctacgtcca     1440
ggagcgcacc atcttcttca aggacgacgg caactacaag acccgcgccg aggtgaagtt     1500
cgagggcgac accctggtga accgcatcga gctgaagggc atcgacttca aggaggacgg     1560
caacatcctg gggcacaagc tggagtacaa ctacaacagc cacaacgtct atatcaccgc     1620
cgacaagcag aagaacggca tcaaggccaa cttcaagatc cgccacaaca tcgaggacgg     1680
cggcgtgcag ctcgccgacc actaccagca gaacaccccc atcggcgacg ccccgtgct      1740 gctgcccgac aaccactacc tgagctacca gtccaagctg agcaaagacc ccaacgagaa     1800
gcgcgatcac atggtcctgc tggagttcgt gaccgccgcc gggatcactc tcggcatgga     1860
cgagctgtac aagtaagtcg acggcgcgcc gcggccgcga attcgatatc ataatcaacc     1920
tctggattac aaaatttgtg aaagattgac tggtattctt aactatgttg ctccttttac     1980
gctatgtgga tacgctgctt taatgccttt gtatcatgct attgcttccc gtatggcttt     2040
cattttctcc tccttgtata aatcctggtt agttcttgcc acggcggaac tcatcgccgc     2100
ctgccttgcc cgctgctgga caggggctcg gctgttgggc actgacaatt ccgtggctcg     2160
agagatcttc gactgtgcct tctagttgcc agccatctgt tgtttgcccc tccccgtgc      2220 cttccttgac cctggaaggt gccactccca ctgtcctttc ctaataaaat gaggaaattg     2280
catcgcattg tctgagtagg tgtcattcta ttctgggggg tggggtgggg caggacagca     2340 aggggggagga ttgggaagac aatagcaggc atgagatctc acgtgcggac cgagcggccg     2400
c                                                                      2401
```

```
<210> SEQ ID NO 173
<211> LENGTH: 2038
<212> TYPE: DNA
<213> ORGANISM: Artificial Sequence
<220> FEATURE:
<223> OTHER INFORMATION: CN2367

<400> SEQUENCE: 173
```

```
gcggccgcac gcgtacaagc atgactataa aacccaagca atgttttgtgc accagatccc       60 agaagtaaag tttattagtc agtggaattc ttgtattaga tttcagaaag cacccaacta      120
ccaaacgaga atgaggttcc tccaccattc agcagagggg cacacttttta gcagcttttg      180 tagctggttg cttcctggat gtttgaatac caattgattt gtcagcaatg agccattgca      240
```

```
gcaatgctgt caaagtctgg atccctgact ggtggctgca aactgtttat taacagcttg      300
atgctcatta aggacattga gccagaatat aagtcaactg tgtcactaag tgtgctattt      360
agcatagctg gcattatgtg tgttgtggga gaggcaagac tctcaatgaa agaggcaata      420
cattgatttt cattctgatg taagccattt cacttttgat tgggacttca cagaattctt      480
ttcatagctg gcctctctcc tcattctgat ggaaatctgc aagctaaagg cagtcctgat      540
gataggaagc aaaacagcaa cctcagaagg atttcaaaat gattcatttt ctttacaaaa      600
atatatatca ttagcctaac ataagtaagt gttgaatatt atgatcttga gaatgaaaaa      660
gatatacctt tagtgttgct gtgactgaag atgagagctc gggctgggca taaaagtcag      720
ggcagagcca tctattgctt acatttgctt ctgggatcca gatctttcga agctagcgct      780
accggtcgcc accatggtga gcaagggcga ggagctgttc accggggtgg tgcccatcct      840
ggtcgagctg gacggcgacg taaacggcca caagttcagc gtgtccggcg agggcgaggg      900
cgatgccacc tacggcaagc tgaccctgaa gctgatctgc accaccggca agctgcccgt      960
gccctggccc accctcgtga ccaccctggg ctacggcgtg cagtgcttcg cccgctaccc     1020
cgaccacatg aagcagcacg acttcttcaa gtccgccatg cccgaaggct acgtccagga     1080
gcgcaccatc ttcttcaagg acgacggcaa ctacaagacc cgcgccgagg tgaagttcga     1140
gggcgacacc ctggtgaacc gcatcgagct gaagggcatc gacttcaagg aggacggcaa     1200
catcctgggg cacaagctgg agtacaacta caacagccac aacgtctata tcaccgccga     1260
caagcagaag aacggcatca aggccaactt caagatccgc cacaacatcg aggacggcgg     1320
cgtgcagctc gccgaccact accagcagaa cacccccatc ggcgacggcc ccgtgctgct     1380
gcccgacaac cactacctga gctaccagtc caagctgagc aaagacccca acgagaagcg     1440
cgatcacatg gtcctgctgg agttcgtgac cgccgccggg atcactctcg gcatggacga     1500
gctgtacaag taagtcgacg gcgcgccgcg gccgcgaatt cgatatcata atcaacctct     1560
ggattacaaa atttgtgaaa gattgactgg tattcttaac tatgttgctc cttttacgct     1620
atgtggatac gctgctttaa tgcctttgta tcatgctatt gcttcccgta tggctttcat     1680
tttctcctcc ttgtataaat cctggttagt tcttgccacg gcggaactca tcgccgcctg     1740
ccttgcccgc tgctggacag gggctcggct gttgggcact gacaattccg tggctcgaga     1800
gatcttcgac tgtgccttct agttgccagc catctgttgt ttgcccctcc ccgtgccttt     1860
ccttgaccct ggaaggtgcc actcccactg tcctttccta ataaaatgag gaaattgcat     1920
cgcattgtct gagtaggtgt cattctattc tggggggtgg ggtggggcag gacagcaagg     1980
gggaggattg ggaagacaat agcaggcatg agatctcacg tgcggaccga gcggccgc      2038
```

<210> SEQ ID NO 174
<211> LENGTH: 1954
<212> TYPE: DNA
<213> ORGANISM: Artificial Sequence
<220> FEATURE:
<223> OTHER INFORMATION: CN12357

<400> SEQUENCE: 174

```
gcggccgcac gcgttccacc attccagcag agggcacact tttagcagct tttgtagctg       60
gttgcttcct ggatgtttga ataccaattg atttgtcagc aatgagccat tgcagcaatg      120
ctgtcaaagt ctggatccct gactggtggc tgcaaactgt ttattaacag cttgatgctc      180
attaaggaca ttgagccaga atataagtca actgtgtcac taagtgtgct atttagcata      240
```

-continued

```
gctggcatta tgtgtgttgt gggagaggca agactctcaa tgaaagaggc aatacattga      300
ttttcattct gatgtaagcc atttcacttt tgattgggac ttcacagaat tcttttcata      360
gctggcctct ctcctcattc tgatggaaat ctgcaagcta aaggcagtcc tgatgatagg      420
aagcaaaaca gcaacctcag aaggatttca aaatgattca ttttctttac aaaaatatat      480
atcattagcc taacataagt aagcgttgaa tattatgatc ttgagaatga aaaagatata      540
cctttagtgt tgctgtgact gaagatgata tttgaccctt taaaatgcat taagtttctt      600
tctattggcc gagctcgggc tgggcataaa agtcagggca gagccatcta ttgcttacat      660
ttgcttctgg gatccagatc tttcgaagct agcgctaccg gtcgccacca tggtgagcaa      720
gggcgaggag ctgttcaccg gggtggtgcc catcctggtc gagctggacg gcgacgtaaa      780
cggccacaag ttcagcgtgt ccggcgaggg cgagggcgat gccacctacg gcaagctgac      840
cctgaagctg atctgcacca ccggcaagct gcccgtgccc tggcccaccc tcgtgaccac      900
cctgggctac ggcgtgcagt gcttcgcccg ctaccccgac cacatgaagc agcacgactt      960
cttcaagtcc gccatgcccg aaggctacgt ccaggagcgc accatcttct tcaaggacga     1020
cggcaactac aagacccgcg ccgaggtgaa gttcgagggc gacaccctgg tgaaccgcat     1080
cgagctgaag ggcatcgact tcaaggagga cggcaacatc ctggggcaca gctggagta     1140 caactacaac agccacaacg tctatatcac cgccgacaag cagaagaacg gcatcaaggc     1200
caacttcaag atccgccaca acatcgagga cggcggcgtg cagctcgccg accactacca     1260
gcagaacacc cccatcggcg acggccccgt gctgctgccc gacaaccact acctgagcta     1320
ccagtccaag ctgagcaaag accccaacga gaagcgcgat cacatggtcc tgctggagtt     1380
cgtgaccgcc gccgggatca ctctcggcat ggacgagctg tacaagtaag tcgacggcgc     1440
gccgcggccg cgaattcgat atcataatca acctctggat tacaaaattt gtgaaagatt     1500
gactggtatt cttaactatg ttgctccttt tacgctatgt ggatacgctg ctttaatgcc     1560
tttgtatcat gctattgctt cccgtatggc tttcattttc tcctccttgt ataaatcctg     1620
gttagttctt gccacggcgg aactcatcgc cgcctgcctt gcccgctgct ggacaggggc     1680
tcggctgttg ggcactgaca attccgtggc tcgagagatc ttcgactgtg ccttctagtt     1740
gccagccatc tgttgtttgc ccctcccccg tgccttcctt gaccctggaa ggtgccactc     1800
ccactgtcct ttcctaataa aatgaggaaa ttgcatcgca ttgtctgagt aggtgtcatt     1860
ctattctggg gggtggggtg gggcaggaca gcaaggggga ggattgggaa gacaatagca     1920
ggcatgagat ctcacgtgcg gaccgagcgg ccgc                                 1954
```

<210> SEQ ID NO 175
<211> LENGTH: 2189
<212> TYPE: DNA
<213> ORGANISM: Artificial Sequence
<220> FEATURE:
<223> OTHER INFORMATION: CN2568

<400> SEQUENCE: 175

```
gcggccgcac gcgtccactt ttgtatttac cattattgca aaatcaatca aatgtgagca       60
aaagcaaagg caatttgaat gactcaaaat tgaaatttga gctgccaaat caagcagtaa      120
aacaattttt accagctcta ttgattgtta gaaagataag ttataaactt tatttcaagt      180
aaatttctaa aagatctggg aatgtgatta ttccaaggca gatggcgaag acctttattt      240
ccactgatta ttcacagatg caaattatta tgcaactgga agcatactaa gatccacttt      300
tgtatttacc attattgcaa aatcaatcaa atgtgagcaa aagcaaaggc aatttgaatg      360
```

-continued

```
actcaaaatt gaaatttgag ctgccaaatc aagcagtaaa acaatttttta ccagctctat      420 tgattgttag aaagataagt tataaacttt atttcaagta aatttctaaa agatctggga      480
atgtgattat tccaaggcag atggcgaaga cctttatttc cactgattat tcacagatgc      540
aaattattat gcaactggaa gcatactaag atccactttt gtatttacca ttattgcaaa      600
atcaatcaaa tgtgagcaaa agcaaaggca atttgaatga ctcaaaattg aaatttgagc      660
tgccaaatca agcagtaaaa caattttttac cagctctatt gattgttaga aagataagtt      720
ataaacttta tttcaagtaa atttctaaaa gatctgggaa tgtgattatt ccaaggcaga      780
tggcgaagac ctttatttcc actgattatt cacagatgca aattattatg caactggaag      840
catactaaga tgagctcggg ctgggcataa aagtcagggc agagccatct attgcttaca      900
tttgcttctg ggatccagat ctttcgaagc tagcgctacc ggtcgccacc atggtgagca      960
agggcgagga gctgttcacc ggggtggtgc ccatcctggt cgagctggac ggcgacgtaa     1020
acggccacaa gttcagcgtg tccggcgagg gcgaggcgga tgccacctac ggcaagctga     1080
ccctgaagct gatctgcacc accggcaagc tgcccgtgcc ctggcccacc ctcgtgacca     1140
ccctgggcta cggcgtgcag tgcttcgccc gctaccccga ccacatgaag cagcacgact     1200
tcttcaagtc cgccatgccc gaaggctacg tccaggagcg caccatcttc ttcaaggacg     1260
acggcaacta caagacccgc gccgaggtga agttcgaggg cgacaccctg gtgaaccgca     1320
tcgagctgaa gggcatcgac ttcaaggagg acggcaacat cctggggcac aagctggagt     1380
acaactacaa cagccacaac gtctatatca ccgccgacaa gcagaagaac ggcatcaagg     1440
ccaacttcaa gatccgccac aacatcgagg acggcggcgt gcagctcgcc gaccactacc     1500
agcagaacac ccccatcggc gacggccccg tgctgctgcc cgacaaccac tacctgagct     1560
accagtccaa gctgagcaaa gaccccaacg agaagcgcga tcacatggtc ctgctggagt     1620
tcgtgaccgc cgccgggatc actctcggca tggacgagct gtacaagtaa gtcgacggcg     1680
cgccgcggcc gcgaattcga tatcataatc aacctctgga ttacaaaatt tgtgaaagat     1740
tgactggtat tcttaactat gttgctcctt ttacgctatg tggatacgct gctttaatgc     1800
ctttgtatca tgctattgct tcccgtatgg ctttcatttt ctcctccttg tataaatcct     1860
ggttagttct tgccacggcg gaactcatcg ccgcctgcct tgcccgctgc tggacagggg     1920
ctcggctgtt gggcactgac aattccgtgg ctcgagagat cttcgactgt gccttctagt     1980
tgccagccat ctgttgtttg cccctccccc gtgccttcct tgaccctgga aggtgccact     2040
cccactgtcc tttcctaata aaatgaggaa attgcatcgc attgtctgag taggtgtcat     2100
tctattctgg ggggtggggt ggggcaggac agcaaggggg aggattggga agacaatagc     2160
aggcatgcac gtgcggaccg agcggccgc                                      2189
```

```
<210> SEQ ID NO 176
<211> LENGTH: 2192
<212> TYPE: DNA
<213> ORGANISM: Artificial Sequence
<220> FEATURE:
<223> OTHER INFORMATION: CN2569

<400> SEQUENCE: 176
gcggccgcac gcgtttttcca ctgattattc acagatgcaa attattatgc aactggaagc      60
atactaagat attgcaaaga tgttctgaca ttagtcatct gctgcctttg ttactttggt     120 gtcaatttttc ttattctttc caaaggaaga tccttacagt ttgtattctt tcacagctgg     180
```

-continued

```
gaaatgatca gttgagaatt attcaaacac accaatctgt taaccgtact tcttcccaga      240
taatgcaata ttttgcaggg tgacaggcaa aaagtggtca tttttttactt catatttcca      300 ctgattattc acagatgcaa attattatgc aactggaagc atactaagat attgcaaaga      360
tgttctgaca ttagtcatct gctgcctttg ttactttggt gtcaatttttc ttattctttc      420 caaaggaaga tccttacagt ttgtattctt tcacagctgg gaaatgatca gttgagaatt      480
attcaaacac accaatctgt taaccgtact tcttcccaga taatgcaata ttttgcaggg      540
tgacaggcaa aaagtggtca tttttttactt catatttcca ctgattattc acagatgcaa      600
attattatgc aactggaagc atactaagat attgcaaaga tgttctgaca ttagtcatct      660
gctgcctttg ttactttggt gtcaatttttc ttattctttc caaaggaaga tccttacagt      720
ttgtattctt tcacagctgg gaaatgatca gttgagaatt attcaaacac accaatctgt      780
taaccgtact tcttcccaga taatgcaata ttttgcaggg tgacaggcaa aaagtggtca      840 tttttttactt catagagctc gggctgggca taaaagtcag ggcagagcca tctattgctt      900
acatttgctt ctgggatcca gatctttcga agctagcgct accggtcgcc accatggtga      960
gcaagggcga ggagctgttc accggggtgg tgcccatcct ggtcgagctg gacggcgacg     1020
taaacggcca caagttcagc gtgtccggcg agggcgaggg cgatgccacc tacggcaagc     1080
tgaccctgaa gctgatctgc accaccggca agctgcccgt gccctggccc accctcgtga     1140
ccaccctggg ctacggcgtg cagtgcttcg cccgctaccc cgaccacatg aagcagcacg     1200
acttcttcaa gtccgccatg cccgaaggct acgtccagga gcgcaccatc ttcttcaagg     1260
acgacggcaa ctacaagacc cgcgccgagg tgaagttcga gggcgacacc ctggtgaacc     1320
gcatcgagct gaagggcatc gacttcaagg aggacggcaa catcctgggg cacaagctgg     1380
agtacaacta caacagccac aacgtctata tcaccgccga caagcagaag aacggcatca     1440
aggccaactt caagatccgc cacaacatcg aggacggcgg cgtgcagctc gccgaccact     1500
accagcagaa cacccccatc ggcgacggcc ccgtgctgct gcccgacaac cactacctga     1560
gctaccagtc caagctgagc aaagacccca acgagaagcg cgatcacatg gtcctgctgg     1620
agttcgtgac cgccgccggg atcactctcg gcatggacga gctgtacaag taagtcgacg     1680
gcgcgccgcg gccgcgaatt cgatatcata atcaacctct ggattacaaa atttgtgaaa     1740
gattgactgg tattcttaac tatgttgctc cttttacgct atgtggatac gctgctttaa     1800
tgcctttgta tcatgctatt gcttcccgta tggctttcat tttctcctcc ttgtataaat     1860
cctggttagt tcttgccacg gcggaactca tcgccgcctg ccttgcccgc tgctggacag     1920
gggctcggct gttgggcact gacaattccg tggctcgaga gatcttcgac tgtgccttct     1980
agttgccagc catctgttgt ttgcccctcc ccgtgccttt ccttgaccct ggaaggtgcc     2040
actcccactg tcctttccta ataaaatgag gaaattgcat cgcattgtct gagtaggtgt     2100
cattctattc tggggggtgg ggtggggcag gacagcaagg gggaggattg ggaagacaat     2160
agcaggcatg cacgtgcgga ccgagcggcc gc                                   2192
```

<210> SEQ ID NO 177
<211> LENGTH: 2107
<212> TYPE: DNA
<213> ORGANISM: Artificial Sequence
<220> FEATURE:
<223> OTHER INFORMATION: CN2689

<400> SEQUENCE: 177

```
gcggccgcac gcgtaagacg gtctgattgc aaccctccag gaggaaaaca aattcacaaa       60
```

-continued

```
gcagtcccag gttgccagtt ctcaaagtca gcaaaccaaa tcctaacgtg caatcttccc     120
aggtttttca aaagccatgg gattgatagt cagtggggaa aggaagaggt gtcgaatcca     180
ggcctgatgg atgggtgcag aggcaatcag acgtgttttc agagccactg tgctctgaca     240 cctgcccca ttttccacag agtttggctc tgaatgcgtc cctggaccac gccctccgtc      300
tcctttacct ggcgttccta ttcttgtaga aaggaacaca gcctaatgat ggatttgttc     360
aatgtgatca ttctcgctta tgtacaaaac aaaggcagga ttgatgaact cctaaagaag     420
cacattcaca ggcctgatct atgcctctta ccttggagca ggcagcaagt acagcctcca     480
agggaatgtc aacatctttg cactttgtca ataggacctt gattctctaa aggctgaaag     540
gtgttttcat gggtgaatgc ttagagccag ctcatggttt tccaaacccc actcaaagct     600
tccagatgac tcttttgca tctgtgagct tctttcatcc ctagatatca ccctgggggag     660 agggcaggca aaagatgttc tctgtacttg caaggaagaa atggtaaagg catgggggtc     720 gagtggggg tggggactcc tatgttccgg aaagagcgag gttgagctcg ggctgggcat      780
aaaagtcagg gcagagccat ctattgctta catttgcttc tgggatccag atctttcgaa     840
gctagcgcta ccggtcgcca ccatggtgag caagggcgag gagctgttca ccggggtggt     900
gcccatcctg gtcgagctgg acggcgacgt aaacggccac aagttcagcg tgtccggcga     960
gggcgagggc gatgccacct acggcaagct gaccctgaag ctgatctgca ccaccggcaa     1020
gctgcccgtg ccctggccca ccctcgtgac caccctgggc tacggcgtgc agtgcttcgc     1080
ccgctacccc gaccacatga gcagcacga cttcttcaag tccgccatgc ccgaaggcta       1140
cgtccaggag cgcaccatct tcttcaagga cgacggcaac tacaagaccc gcgccgaggt      1200
gaagttcgag ggcgacaccc tggtgaaccg catcgagctg aagggcatcg acttcaagga     1260
ggacggcaac atcctggggc acaagctgga gtacaactac aacagccaca cgtctatat      1320 caccgccgac aagcagaaga acggcatcaa ggccaacttc aagatccgcc acaacatcga     1380
ggacggcggc gtgcagctcg ccgaccacta ccagcagaac acccccatcg gcgacggccc     1440
cgtgctgctg cccgacaacc actacctgag ctaccagtcc aagctgagca agacccccaa     1500
cgagaagcgc gatcacatgg tcctgctgga gttcgtgacc gccgccggga tcactctcgg     1560
catggacgag ctgtacaagt aagtcgacgg cgcgccgcgg ccgcgaattc gatatcataa     1620
tcaacctctg gattacaaaa tttgtgaaag attgactggt attcttaact atgttgctcc     1680
ttttacgcta tgtggatacg ctgctttaat gcctttgtat catgctattg cttcccgtat     1740
ggctttcatt ttctcctcct tgtataaatc ctggttagtt cttgccacgg cggaactcat     1800
cgccgcctgc cttgcccgct gctggacagg ggctcggctg ttgggcactg acaattccgt     1860
ggctcgagag atcttcgact gtgccttcta gttgccagcc atctgttgtt tgcccctccc     1920
ccgtgccttc cttgaccctg gaaggtgcca ctcccactgt cctttcctaa taaaatgagg     1980
aaattgcatc gcattgtctg agtaggtgtc attctattct ggggggtggg gtggggcagg     2040
acagcaaggg ggaggattgg gaagacaata gcaggcatga gatctcacgt gcggaccgag     2100
cggccgc                                                                2107
```

```
<210> SEQ ID NO 178
<211> LENGTH: 2251
<212> TYPE: DNA
<213> ORGANISM: Artificial Sequence
<220> FEATURE:
<223> OTHER INFORMATION: CN2408
```

-continued

```
<400> SEQUENCE: 178
gcggccgcac gcgtaacagg acttcaggga aggccacgga gcttaagcaa gaacttgccc        60
aaagtttaga aagaaagctc caagttacag aaccaagtgc ccgaccccag agtctttctt       120
tgtctgacct gagggctttc tgttaaaatc cttatacagc agataagtaa gtcagcagtc       180
ttagaggtgg gaagaggtct gtctgccagt catctggctc cctgcaaaca caggcatccc       240
cacccctgaa caattttctt cataggaaag ttgtgaggga agtcacaggt gcagacaccg       300
ccccgggggg ggagggggggg ctcagagttg ttccttcatt cagtcaccaa ttcagtcttc       360
cagaatcaag gccctattga cagagggcta agccaccggg gcgctgcctt caaggtaaga       420
ggcatagatc agtctcctga atgtagaggg atgaattccc tccttcacat aagtgaaagc       480
gatcataggg aacggaggca tcattagggc gccctccttc tgacagggat gcagacaggc       540
aggtgagggt ggaggggtgt ggcccagggc acattcagag ccaaactctg ttgagaacaa       600
ggcaggtgtt tctgaaaacc tctctgattg cacccgtacc ctcccatcag gcccgaatcg       660
cacacctctc tgcctctcct cagacgccgg cccacatggc ttttgaaaac ctggggagat       720
tataccttcc agcttgcttt gctgagtctg aggaacctgg ctgccttttc tcttctgtta       780
actgcaatca aactggtttt gagcaccagc cccaagatgt ctttgccagt ccacatccat       840
cttccatgat gagctaaggt tccctatttg tacccttact ttctgggctg agtcatgaca       900
tctgggagag ctcgggctgg gcataaaagt cagggcagga ccatctattg cttacatttg       960
cttctgggat ccagatcttt cgaagctagc gctaccggtc gccaccatgg tgagcaaggg      1020
cgaggagctg ttcaccgggg tggtgcccat cctggtcgag ctggacggcg acgtaaacgg      1080
ccacaagttc agcgtgtccg gcgagggcga gggcgatgcc acctacggca agctgaccct      1140
gaagctgatc tgcaccaccg gcaagctgcc cgtgccctgg cccaccctcg tgaccaccct      1200
gggctacggc gtgcagtgct tcgcccgcta ccccgaccac atgaagcagc acgacttctt      1260
caagtccgcc atgcccgaag gctacgtcca ggagcgcacc atcttcttca aggacgacgg      1320
caactacaag acccgcgccg aggtgaagtt cgagggcgac accctggtga accgcatcga      1380
gctgaagggc atcgacttca aggaggacgg caacatcctg gggcacaagc tggagtacaa      1440
ctacaacagc cacaacgtct atatcaccgc cgacaagcag aagaacggca tcaaggccaa      1500
cttcaagatc cgccacaaca tcgaggacgg cggcgtgcag ctcgccgacc actaccagca      1560 gaacacccc atcggcgacg gccccgtgct gctgcccgac aaccactacc tgagctacca      1620
gtccaagctg agcaaagacc ccaacgagaa gcgcgatcac atggtcctgc tggagttcgt      1680
gaccgccgcc gggatcactc tcggcatgga cgagctgtac aagtaagtcg acggcgcgcc      1740
gcggccgcga attcgatatc ataatcaacc tctggattac aaaatttgtg aaagattgac      1800
tggtattctt aactatgttg ctcctttttac gctatgtgga tacgctgctt taatgccttt      1860
gtatcatgct attgcttccc gtatggcttt cattttctcc tccttgtata aatcctggtt      1920
agttcttgcc acggcggaac tcatcgccgc ctgccttgcc cgctgctgga caggggctcg      1980
gctgttgggc actgacaatt ccgtggctcg agagatcttc gactgtgcct ctagttgcc       2040 agccatctgt tgtttgcccc tccccgtgc cttccttgac cctggaaggt gccactccca       2100
ctgtcctttc ctaataaaat gaggaaattg catcgcattg tctgagtagg tgtcattcta       2160
ttctgggggg tggggtgggg caggacagca aggggggagga ttgggaagac aatagcaggc      2220
atgagatctc acgtgcggac cgagcggccg c                                     2251
```

-continued

```
<210> SEQ ID NO 179
<211> LENGTH: 2128
<212> TYPE: DNA
<213> ORGANISM: Artificial Sequence
<220> FEATURE:
<223> OTHER INFORMATION: CN2596

<400> SEQUENCE: 179
gcggccgcac gcgtttctgc catagaaaag catcagtgtc tatagagaga aatgataaca      60
aatgaaggaa attgtctaat tttctaactc acttacataa tggacagatg cggtaagtaa     120
acagcacaca ctagtgcatc ttagatgggc actgtactaa gatgtgataa tgatgtttca     180
gccagactta cttattttat cccgtaatca caggaagctc taatcagagg aagcatgagg     240
aagagacaga atgtgctaag gatgtgtcac actctgatgg gtcactggaa gtgaggaaac     300
aagggtgtgc agctgtgtat caggtccagg cagagagcag atgttctatt cacgagtatg     360
cttacttaca tctgtcgccc tccaacacac cattccaaac tgaaaactga gtgtgcttca     420
tcaagccaga aacttaggaa aatgttgtaa gggacaatgt ttgcatgtca cagtgaagta     480
aacgcaggag agtgatggca tctagctgct gtgagaagtg gctggaaaaa tgcagctaac     540
acgactaact caaaacgctg ggacacaaga gaaggaagac aggcacctca cgcttgctgg     600
gatctacaag tttagccaga ccagttctta agataaactg caatgggtat gcctgaaagg     660
ccattcttgt ttgtttcttt atctgtttca gtgttggtta taacttaccc tatcttgcca     720
caggaagggc acttccttag acaggaagat agctgatttt aaaaagccct gtttcaacct     780
acaggagctc gggctgggca taaaagtcag ggcagagcca tctattgctt acatttgctt     840
ctgggatcca gatctttcga agctagcgct accggtcgcc accatggtga gcaagggcga     900
ggagctgttc accggggtgg tgcccatcct ggtcgagctg gacggcgacg taaacggcca     960
caagttcagc gtgtccggcg agggcgaggg cgatgccacc tacggcaagc tgaccctgaa    1020
gctgatctgc accaccggca agctgcccgt gccctggccc accctcgtga ccaccctggg    1080
ctacggcgtg cagtgcttcg cccgctaccc cgaccacatg aagcagcacg acttcttcaa    1140
gtccgccatg cccgaaggct acgtccagga gcgcaccatc ttcttcaagg acgacggcaa    1200
ctacaagacc cgcgccgagg tgaagttcga gggcgacacc ctggtgaacc gcatcgagct    1260
gaagggcatc gacttcaagg aggacggcaa catcctgggg cacaagctgg agtacaacta    1320
caacagccac aacgtctata tcaccgccga caagcagaag aacggcatca aggccaactt    1380
caagatccgc cacaacatcg aggacggcgg cgtgcagctc gccgaccact accagcagaa    1440
cacccccatc ggcgacggcc ccgtgctgct gcccgacaac cactacctga gctaccagtc    1500
caagctgagc aaagacccca acgagaagcg cgatcacatg gtcctgctgg agttcgtgac    1560
cgccgccggg atcactctcg gcatggacga gctgtacaa taagtcgacg gcgcgccgcg    1620
gccgcgaatt cgatatcata atcaacctct ggattacaaa atttgtgaaa gattgactgg    1680
tattcttaac tatgttgctc cttttacgct atgtggatac gctgctttaa tgcctttgta    1740
tcatgctatt gcttcccgta tggctttcat tttctcctcc ttgtataaat cctggttagt    1800
tcttgccacg gcggaactca tcgccgcctg ccttgcccgc tgctggacag gggctcggct    1860
gttgggcact gacaattccg tggctcgaga gatcttcgac tgtgccttct agttgccagc    1920
catctgttgt ttgcccctcc cccgtgcctt ccttgaccct ggaaggtgcc actcccactg    1980
tcctttccta ataaaatgag gaaattgcat cgcattgtct gagtaggtgt cattctattc    2040
tggggggtgg ggtggggcag gacagcaagg gggaggattg ggaagacaat agcaggcatg    2100
```

-continued

```
agatctcacg tgcggaccga gcggccgc                                        2128

<210> SEQ ID NO 180
<211> LENGTH: 2149
<212> TYPE: DNA
<213> ORGANISM: Artificial Sequence
<220> FEATURE:
<223> OTHER INFORMATION: CN2317
<220> FEATURE:
<221> NAME/KEY: misc_feature
<222> LOCATION: (121)..(121)
<223> OTHER INFORMATION: n is a, c, g, or t

<400> SEQUENCE: 180
gcggccgcac gcgtagaatg ctcagggcct cagcatcagc taagaggctt tctggttgct      60
tgattctccc caataaacac cctgaagtct catcaaactg ctcatttatt ttcctgtaaa     120
ngcttctatt gctaaccagg ccttggccat ttttcccatg ggaaatggag ttgttggctt     180
cccctggttc ctgttcacca tccaggaagt cgaataaata atgaccgtag cccatactgg     240
tgggatggat acaggaggag gactgaaagc aggagaatat caaacccatc aaaaatcacc     300
gagatcagtg caaagactga agcagaaaga cacagcctct aaataggagc ggccttaatg     360
aaagtgcatc acctcagagc caacatgaag tctgcagatg ggatgcacct gcctcctgag     420
aacctcacag agggaaatca agcatcagaa cccagaatgg aagcagaaaa cccccaatca     480
gactcctcgg agacacttca gaaaaggaac tctcagcttg caaacaaca ggtgcatctc      540 taaagagatg tggctcctgc ccccacccca taccaccgca ccctgagatt gcagcactgc     600
tctgaactct ccaatcaagc ctctttcttt ggtcactctt aaagtggttg gtttccagca     660
ctaaccctca ctcctccacc gaaatgaaat ctgctagctt tggctgatgt ttaaacagct     720
tcaatctctg gggtcttttg tgagagagga taattttaac actggtgata aacccaccag     780
aatttccagg tgagaggaga agcctgagct cgggctgggc ataaaagtca gggcagagcc     840
atctattgct tacatttgct tctgggatcc agatctttcg aagctagcgc taccggtcgc     900
caccatggtg agcaagggcg aggagctgtt caccggggtg gtgcccatcc tggtcgagct     960
ggacggcgac gtaaacggcc acaagttcag cgtgtccggc gagggcgagg gcgatgccac    1020
ctacggcaag ctgaccctga agctgatctg caccaccggc aagctgcccg tgccctggcc    1080
caccctcgtg accaccctgg gctacggcgt gcagtgcttc gcccgctacc cgaccacat    1140 gaagcagcac gacttcttca gtccgccat gcccgaaggc tacgtccagg agcgcaccat    1200
cttcttcaag gacgacggca actacaagac ccgcgccgag gtgaagttcg agggcgacac    1260
cctggtgaac cgcatcgagc tgaagggcat cgacttcaag gaggacggca acatcctggg    1320
gcacaagctg gagtacaact acaacagcca acgtctat atcaccgccg acaagcagaa     1380
gaacggcatc aaggccaact tcaagatccg ccacaacatc gaggacggcg gcgtgcagct    1440
cgccgaccac taccagcaga acacccccat cggcgacggc cccgtgctgc tgcccgacaa    1500
ccactacctg agctaccagt ccaagctgag caaagacccc aacgagaagc gcgatcacat    1560
ggtcctgctg gagttcgtga ccgccgccgg gatcactctc ggcatggacg agctgtacaa    1620
gtaagtcgac ggcgcgccgc ggccgcgaat tcgatatcat aatcaacctc tggattacaa    1680
aatttgtgaa agattgactg gtattcttaa ctatgttgct cctttacgc tatgtggata     1740 cgctgcttta atgcctttgt atcatgctat tgcttcccgt atggctttca ttttctcctc    1800
cttgtataaa tcctggttag ttcttgccac ggcggaactc atcgccgcct gccttgcccg    1860
ctgctggaca ggggctcggc tgttgggcac tgacaattcc gtggctcgag agatcttcga    1920
```

-continued

```
ctgtgccttc tagttgccag ccatctgttg tttgccccctc cccgtgcct tccttgaccc    1980 tggaaggtgc cactcccact gtcctttcct aataaaatga ggaaattgca tcgcattgtc    2040
tgagtaggtg tcattctatt ctggggggtg gggtggggca ggacagcaag ggggaggatt    2100
gggaagacaa tagcaggcat gagatctcac gtgcggaccg agcggccgc               2149

<210> SEQ ID NO 181
<211> LENGTH: 2078
<212> TYPE: DNA
<213> ORGANISM: Artificial Sequence
<220> FEATURE:
<223> OTHER INFORMATION: CN2571

<400> SEQUENCE: 181
gcggccgcac gcgtttcaat tggtaaagtt gtggtatata attacaattg aactctcttg      60
tacttgcctc ttttacaaaa attctctcct agcagaacgt agtgtgagtc atctacacag     120
ctgtttttct gattattgga attttctttt gacatgaagg aagtatctca ttgacagaac     180
tgcgttgtga aggagtgcta actgtagcat aaaatacaaa attggatttt tagattgcaa     240
aatacagtaa agcttttca attggtaaag ttgtggtata taattacaat tgaactctct     300
tgtacttgcc tcttttacaa aaattctctc ctagcagaac gtagtgtgag tcatctacac     360
agctgttttt ctgattattg aattttctt ttgacatgaa ggaagtatct cattgacaga     420
actgcgttgt gaaggagtgc taactgtagc ataaaataca aaattggatt tttagattgc     480
aaaatacagt aaagcttttt caattggtaa agttgtggta tataattaca attgaactct     540
cttgtacttg cctcttttac aaaaattctc tcctagcaga acgtagtgtg agtcatctac     600
acagctgttt ttctgattat tggaattttc ttttgacatg aaggaagtat ctcattgaca     660
gaactgcgtt gtgaaggagt gctaactgta gcataaaata caaaattgga ttttttagatt     720 gcaaaataca gtaaagcttt gagctcgggc tgggcataaa agtcagggca gagccatcta     780
ttgcttacat ttgcttctgg gatccagatc tttcgaagct agcgctaccg gtcgccacca     840
tggtgagcaa gggcgaggag ctgttcaccg gggtggtgcc catcctggtc gagctggacg     900
gcgacgtaaa cggccacaag ttcagcgtgt ccggcgaggg cgagggcgat gccacctacg     960
gcaagctgac cctgaagctg atctgcacca ccggcaagct gcccgtgccc tggcccaccc    1020
tcgtgaccac cctgggctac ggcgtgcagt gcttcgcccg ctaccccgac cacatgaagc    1080
agcacgactt cttcaagtcc gccatgcccg aaggctacgt ccaggagcgc accatcttct    1140
tcaaggacga cggcaactac aagacccgcg ccgaggtgaa gttcgagggc gacaccctgg    1200
tgaaccgcat cgagctgaag ggcatcgact tcaaggagga cggcaacatc ctggggcaca    1260
agctggagta caactacaac agccacaacg tctatatcac cgccgacaag cagaagaacg    1320
gcatcaaggc caacttcaag atccgccaca acatcgagga cggcggcgtg cagctcgccg    1380
accactacca gcagaacacc cccatcggcg acggccccgt gctgctgccc gacaaccact    1440
acctgagcta ccagtccaag ctgagcaaag accccaacga gaagcgcgat cacatggtcc    1500
tgctggagtt cgtgaccgcc gccgggatca ctctcggcat ggacgagctg tacaagtaag    1560
tcgacggcgc gccgcggccg cgaattcgat atcataatca acctctggat tacaaaattt    1620
gtgaaagatt gactggtatt cttaactatg ttgctccttt tacgctatgt ggatacgctg    1680
ctttaatgcc tttgtatcat gctattgctt cccgtatggc tttcattttc tcctccttgt    1740
ataaatcctg gttagttctt gccacggcgg aactcatcgc cgcctgcctt gcccgctgct    1800
```

```
ggacaggggc tcggctgttg ggcactgaca attccgtggc tcgagagatc ttcgactgtg      1860
ccttctagtt gccagccatc tgttgtttgc ccctcccccg tgccttcctt gaccctggaa      1920
ggtgccactc ccactgtcct ttcctaataa aatgaggaaa ttgcatcgca ttgtctgagt      1980
aggtgtcatt ctattctggg gggtggggtg gggcaggaca gcaaggggga ggattgggaa      2040
gacaatagca ggcatgcacg tgcggaccga gcggccgc                              2078

<210> SEQ ID NO 182
<211> LENGTH: 2280
<212> TYPE: DNA
<213> ORGANISM: Artificial Sequence
<220> FEATURE:
<223> OTHER INFORMATION: CN1663

<400> SEQUENCE: 182
gcggccgcaa cgcgtttaga acaatggctg gcccatagta aatgccgtgt tagtgtgtta        60
gttgctgttc ttccacgtca gaagaggcac agacaaatta ccaccaggtg gcgctcagag       120
tctgcggagg catcacaaca gccctgaatt tgaatcctgc tctgccactg cctagttgag       180 acctttact acctgactag ctgtttgtgt attttaggtg tttgtttcca ctgaacatac        240
tcccccttat ttattccata tacacataaa tagcaccacc atgcacctgt ggccaaaagc       300
cagaaaatgg agtgccatcc tccacaacac cttactcaca ctaccttgat gcctagatgg       360
tcttaaagtc ttaaagattc tgcttcctta ttacttctaa aatctgttcc caccacccta       420
cttctactgt cttttagcta atctcacaat attcaatatt tcttgccagg attattgcaa       480
ttccctcctg ttaagtctcc ccacttaaac tccagctgca ccaatctaca ctttacaatt      540
ctgcagagat gtcttttttaa catgcaaata tgcttatatt atttctttgc ttacacattc     600
caataactcc tctaaataaa actcttaagt tgcttagact gacacaaggc tctcatgaat      660
gtgtccctgc ctgcccttct gcttctacct tctagcattc ccctttgtaa atcctatgca      720
cttctctgag cacatcattt tctgtctttt cttttttttct ttttctttga gatgaagtct     780
ttcaacattg cccaggctgg tctcaaactc ctgggctcaa gcgatcctct cgcctcaacc     840
tcctgagtag ctgggactac agccacgcga attcgatatc ataatcaacc ataggtaccg     900
agctcgggat tcagccggga gcttagggag gggaggtcac ttcataaggg cctgggggggg   960 gagttggagc cacgagtcgt ccagccggag ccccgtgtgg ctgagctccg gcctcagaag    1020
catccccggg ttggatcctt cgaagctagc gctaccggtc gccaccatgg tgagcaaggg    1080
cgaggagctg ttcaccgggg tggtgcccat cctggtcgag ctggacggcg acgtaaacgg    1140
ccacaagttc agcgtgtccg gcgagggcga gggcgatgcc acctacggca agctgaccct    1200
gaagctgatc tgcaccaccg gcaagctgcc cgtgccctgg cccaccctcg tgaccaccct    1260
gggctacggc gtgcagtgct tcgcccgcta ccccgaccac atgaagcagc acgacttctt    1320
caagtccgcc atgcccgaag ctacgtccga ggagcgcacc atcttcttca aggacgacgg    1380
caactacaag acccgcgccg aggtgaagtt cgagggcgac accctggtga accgcatcga    1440
gctgaagggc atcgacttca aggaggacgg caacatcctg gggcacaagc tggagtacaa    1500
ctacaacagc cacaacgtct atatcaccgc cgacaagcag aagaacggca tcaaggccaa    1560
cttcaagatc cgccacaaca tcgaggacgg cggcgtgcag ctcgccgacc actaccagca    1620 gaacacccc atcggcgacg gccccgtgct gctgcccgac aaccactacc tgagctacca    1680
gtccaagctg agcaaagacc ccaacgagaa gcgcgatcac atggtcctgc tggagttcgt    1740
gaccgccgcc gggatcactc tcggcatgga cgagctgtac aagtaagtcg acatcataat    1800
```

-continued

```
caacctctgg attacaaaat ttgtgaaaga ttgactggta ttcttaacta tgttgctcct    1860
tttacgctat gtggatacgc tgctttaatg cctttgtatc atgctattgc ttcccgtatg    1920
gctttcattt tctcctcctt gtataaatcc tggttagttc ttgccacggc ggaactcatc    1980
gccgcctgcc ttgcccgctg ctggacaggg gctcggctgt tgggcactga caattccgtg    2040
gctcgagaga tcttcgactg tgccttctag ttgccagcca tctgttgttt gcccctcccc    2100
cgtgccttcc ttgaccctgg aaggtgccac tcccactgtc ctttcctaat aaaatgagga    2160
aattgcatcg cattgtctga gtaggtgtca ttctattctg gggggtgggg tggggcagga    2220
cagcaagggg gaggattggg aagacaatag caggcatgca cgtgcggacc gagcggccgc    2280
```

```
<210> SEQ ID NO 183
<211> LENGTH: 1884
<212> TYPE: DNA
<213> ORGANISM: Artificial Sequence
<220> FEATURE:
<223> OTHER INFORMATION: CN2310

<400> SEQUENCE: 183
gcggccgcac gcgttatttt gggatgtata aatcagacga aaagtcacaa aatcgtgtgc      60
cattcaaagg tggtggaagt tgaagaggaa gcgtatctaa atgacagata atgagtcttt     120
atgaagttac gaaaagagg tcagcacctg agaaacagac taaactagaa tagtcatatg      180
acatctgatg ttcactgtaa aatgagatga gtgctgttgg tgtaatgagg ttccttagta     240
tgctactaag tttaactgca taaattatac caattagctc caaatgaat gtaaatcctc       300 aactataaaa tgtttcaatg tgtacttagt gctaatagga aatgtttgtg ctgtgagcc      360 atcctgaaac ttctgactta aagctctgaa agaaatgcca ctatatatat ttttctagcc     420
catagaagga taaacttttt gccctctgat tgcagtgggg atgaggagtc caagtaacat     480
gatattcata ttgttaaaac tgatccctcg cattgcctct ttagggtcag tgactgctag     540
gagctcgggc tgggcataaa agtcagggca gagccatcta ttgcttacat ttgcttctgg     600
gatccagatc tttcgaagct agcgctaccg gtcgccacca tggtgagcaa gggcgaggag     660
ctgttcaccg gggtggtgcc catcctggtc gagctggacg gcgacgtaaa cggccacaag     720
ttcagcgtgt ccggcgaggg cgagggcgat gccacctacg gcaagctgac cctgaagctg     780
atctgcacca ccggcaagct gcccgtgccc tggcccaccc tcgtgaccac cctgggctac     840
ggcgtgcagt gcttcgcccg ctaccccgac cacatgaagc agcacgactt cttcaagtcc     900
gccatgcccg aaggctacgt ccaggagcgc accatcttct tcaaggacga cggcaactac     960
aagacccgcg ccgaggtgaa gttcgagggc gacaccctgg tgaaccgcat cgagctgaag    1020
ggcatcgact tcaaggagga cggcaacatc ctggggcaca gctggagta caactacaac     1080 agccacaacg tctatatcac cgccgacaag cagaagaacg gcatcaaggc caacttcaag    1140
atccgccaca acatcgagga cggcggcgtg cagctcgccg accactacca gcagaacacc    1200
cccatcggcg acggccccgt gctgctgccc gacaaccact acctgagcta ccagtccaag    1260
ctgagcaaag accccaacga gaagcgcgat cacatggtcc tgctggagtt cgtgaccgcc    1320
gccgggatca ctctcggcat ggacgagctg tacaagtaag tcgacggcgc gccgcggccg    1380
cgaattcgat atcataatca acctctggat tacaaaattt gtgaaagatt gactggtatt    1440
cttaactatg ttgctccttt tacgctatgt ggatacgctg ctttaatgcc tttgtatcat    1500
gctattgctt cccgtatggc tttcattttc tcctccttgt ataaatcctg gttagttctt    1560
```

-continued

---

```
gccacggcgg aactcatcgc cgcctgcctt gcccgctgct ggacaggggc tcggctgttg      1620
ggcactgaca attccgtggc tcgagagatc ttcgactgtg ccttctagtt gccagccatc      1680
tgttgtttgc ccctcccccg tgccttcctt gaccctggaa ggtgccactc ccactgtcct      1740
ttcctaataa aatgaggaaa ttgcatcgca ttgtctgagt aggtgtcatt ctattctggg      1800
gggtggggtg gggcaggaca gcaaggggga ggattgggaa gacaatagca ggcatgagat      1860
ctcacgtgcg gaccgagcgg ccgc                                             1884

<210> SEQ ID NO 184
<211> LENGTH: 1743
<212> TYPE: DNA
<213> ORGANISM: Artificial Sequence
<220> FEATURE:
<223> OTHER INFORMATION: CN2360

<400> SEQUENCE: 184
gcggccgcac gcgtagctcc ttgtttgcac gtgtgttctc acagttctct ttgtccagac        60
caggtacact gcagccaaag acagcgtggt tcagttcttc ttttaccagc ccatcagtca       120
tcagtggaga caaactgact tctttccctg cactgtgacg tgtggaggag gtgaggccca       180
ggctttgttc atgaatattt agagctcaga gttagataaa ttacacattt acatttttga       240
agctgatttt aaaattggtg tggtgattag agatgtctca tcacacagca ccttactcag       300
cagcctgaat gcaatcgtgt taatgaagaa gatgcatttg cctttattct tgaagacagg       360
tgcaaaactg gatttggaaa ataccttta cttttagccg agctcgggct gggcataaaa       420
gtcagggcag agccatctat tgcttacatt tgcttctggg atccagatct ttcgaagcta       480
gcgctaccgg tcgccaccat ggtgagcaag ggcgaggagc tgttcaccgg ggtggtgccc       540
atcctggtcg agctggacgg cgacgtaaac ggccacaagt tcagcgtgtc cggcgagggc       600
gagggcgatg ccacctacgg caagctgacc ctgaagctga tctgcaccac cggcaagctg       660
cccgtgccct ggcccaccct cgtgaccacc ctgggctacg gcgtgcagtg cttcgcccgc       720
taccccgacc acatgaagca gcacgacttc ttcaagtccg ccatgcccga aggctacgtc       780
caggagcgca ccatcttctt caaggacgac ggcaactaca agacccgcgc cgaggtgaag       840
ttcgagggcg acaccctggt gaaccgcatc gagctgaagg gcatcgactt caaggaggac       900
ggcaacatcc tggggcacaa gctggagtac aactacaaca gccacaacgt ctatatcacc       960
gccgacaagc agaagaacgg catcaaggcc aacttcaaga tccgccacaa catcgaggac      1020
ggcggcgtgc agctcgccga ccactaccag cagaacaccc ccatcggcga cggccccgtg      1080
ctgctgcccg acaaccacta cctgagctac cagtccaagc tgagcaaaga ccccaacgag      1140
aagcgcgatc acatggtcct gctggagttc gtgaccgccg ccgggatcac tctcggcatg      1200
gacgagctgt acaagtaagt cgacggcgcg ccgcggccgc gaattcgata tcataatcaa      1260
cctctggatt acaaaatttg tgaaagattg actggtattc ttaactatgt tgctcctttt      1320
acgctatgtg gatacgctgc tttaatgcct ttgtatcatg ctattgcttc ccgtatggct      1380
ttcattttct cctccttgta taaatcctgg ttagttcttg ccacggcgga actcatcgcc      1440
gcctgccttg cccgctgctg gacaggggct cggctgttgg gcactgacaa ttccgtggct      1500
cgagagatct tcgactgtgc cttctagttg ccagccatct gttgtttgcc cctcccccgt      1560
gccttccttg accctggaag gtgccactcc cactgtcctt tcctaataaa atgaggaaat      1620
tgcatcgcat tgtctgagta ggtgtcattc tattctgggg ggtggggtgg ggcaggacag      1680
caagggggag gattgggaag acaatagcag gcatgagatc tcacgtgcgg accgagcggc      1740
```

-continued

```
cgc                                                                  1743

<210> SEQ ID NO 185
<211> LENGTH: 2240
<212> TYPE: DNA
<213> ORGANISM: Artificial Sequence
<220> FEATURE:
<223> OTHER INFORMATION: CN1624

<400> SEQUENCE: 185
gcggccgcaa cgcgtttaga acaatggctg gcccatagta aatgccgtgt tagtgtgtta    60
gttgctgttc ttccacgtca gaagaggcac agacaaatta ccaccaggtg gcgctcagag   120
tctgcggagg catcacaaca gccctgaatt tgaatcctgc tctgccactg cctagttgag   180
accttttact acctgactag ctgtttgtgt attttaggtg tttgtttagc agcctctcca   240
gtggagtatg attccttta attttggagt taaagttttg gatgttattt tgggatgtat   300
aaatcagacg aaaagtcaca aaatcgtgtg ccattcaaag gtggtggaag ttgaagagga   360
agcgtatcta aatgacagat aatgagtctt tatgaagtta cgaaaaagag gtcagcacct   420
gagaaacaga ctaaactaga atagtcatat gacatctgat gttcactgta aaatgagatg   480
agtgctgttg gtgtaatgag gttccttagt atgctactaa gtttaactgc ataaattata   540
ccaattagct ccaaaatgaa tgtaaatcct caactataaa atgtttcaat gtgtacttag   600
tgctaatagg aaatgtttgt ggctgtgagc catcctgaaa cttctgactt aaagctctga   660
aagaaatgcc actatatata tttttctagc ccatagaagg ataaacttttt tgccctctga   720 ttgcagtggg gatgaggagt ccaagtaaca tgatattcat attgttaaaa ctgatccctc   780
gcattgcctc tttagggtca gtgactgcta gcatggctgc tcagtgatga attcgatatc   840
ataatcaacc ataggtaccg agctcgggat tcagccggga gcttagggag gggaggtcac   900
ttcataaggg cctggggggg gagttggagc cacgagtcgt ccagccggag ccccgtgtgg   960
ctgagctccg gcctcagaag catccccggg ttggatcctt cgaagctagc gctaccggtc  1020
gccaccatgg tgagcaaggg cgaggagctg ttcaccgggg tggtgcccat cctggtcgag  1080
ctggacggcg acgtaaacgg ccacaagttc agcgtgtccg gcgagggcga gggcgatgcc  1140
acctacggca agctgaccct gaagctgatc tgcaccaccg gcaagctgcc cgtgccctgg  1200
cccaccctcg tgaccaccct gggctacggc gtgcagtgct tcgcccgcta ccccgaccac  1260
atgaagcagc acgacttctt caagtccgcc atgcccgaag gctacgtcca ggagcgcacc  1320
atcttcttca aggacgacgg caactacaag acccgcgccg aggtgaagtt cgagggcgac  1380
accctggtga accgcatcga gctgaagggc atcgacttca aggaggacgg caacatcctg  1440
gggcacaagc tggagtacaa ctacaacagc cacaacgtct atatcaccgc cgacaagcag  1500
aagaacggca tcaaggccaa cttcaagatc cgccacaaca tcgaggacgg cggcgtgcag  1560
ctcgccgacc actaccagca gaacaccccc atcggcgacg gccccgtgct gctgcccgac  1620
aaccactacc tgagctacca gtccaagctg agcaaagacc ccaacgagaa gcgcgatcac  1680
atggtcctgc tggagttcgt gaccgccgcc gggatcactc tcggcatgga cgagctgtac  1740
aagtaagtcg acatcataat caacctctgg attacaaaat ttgtgaaaga ttgactggta  1800
ttcttaacta tgttgctcct tttacgctat gtggatacgc tgctttaatg cctttgtatc  1860
atgctattgc ttcccgtatg gctttcattt tctcctcctt gtataaatcc tggttagttc  1920
ttgccacggc ggaactcatc gccgcctgcc ttgcccgctg ctggacaggg gctcggctgt  1980
```

-continued

```
tgggcactga caattccgtg gctcgagaga tcttcgactg tgccttctag ttgccagcca      2040
tctgttgttt gcccctcccc cgtgccttcc ttgaccctgg aaggtgccac tcccactgtc      2100
ctttcctaat aaaatgagga aattgcatcg cattgtctga gtaggtgtca ttctattctg      2160
gggggtgggg tggggcagga cagcaagggg gaggattggg aagacaatag caggcatgca      2220
cgtgcggacc gagcggccgc                                                  2240

<210> SEQ ID NO 186
<211> LENGTH: 1870
<212> TYPE: DNA
<213> ORGANISM: Artificial Sequence
<220> FEATURE:
<223> OTHER INFORMATION: CN2309

<400> SEQUENCE: 186
gcggccgcac gcgtgggaag ggcagctaca gctagaggtc agaaggctgg tggggtgagg        60
gctgcagagc gttgccttca agggttcact ggagatctga ccagtgcatg cacatgagaa       120
agcttcccca aagtattaga ggaacaattc tcagatacca cacagggctg aggatgctgc       180
ttcttcctgt catccggaat gcaaagcctt acgctatata ggacattgag cagagcaatc       240
agaagggttt aactttagca atgggccaat tttagccata gtctaacagc tgctctggtt       300
tcagcaaaca aagtttagaa gcaagactct aaaagaacaa gccatttcta agtaacttaa       360
acacatcctg gaatgaaatt caaaaacagt tataaaaata aaaagaatc ccatacccag        420 aacactgaaa ttcacaacat ctggcagcca atcaacaact aacaggcaag gaaagaagca       480
gaaaatggga gctgccaaaa tatttgaata ataatggct gaagcagagc tcgggctggg        540
cataaaagtc agggcagagc catctattgc ttacatttgc ttctgggatc cagatctttc       600
gaagctagcg ctaccggtcg ccaccatggt gagcaagggc gaggagctgt tcaccggggt       660
ggtgcccatc ctggtcgagc tggacggcga cgtaaacggc cacaagttca gcgtgtccgg       720
cgagggcgag ggcgatgcca cctacggcaa gctgaccctg aagctgatct gcaccaccgg       780
caagctgccc gtgccctggc ccaccctcgt gaccaccctg ggctacggcg tgcagtgctt       840
cgcccgctac cccgaccaca tgaagcagca cgacttcttc aagtccgcca tgcccgaagg       900
ctacgtccag gagcgcacca tcttcttcaa ggacgacggc aactacaaga cccgcgccga       960
ggtgaagttc gagggcgaca ccctggtgaa ccgcatcgag ctgaagggca tcgacttcaa      1020
ggaggacggc aacatcctgg ggcacaagct ggagtacaac tacaacagcc acaacgtcta      1080
tatcaccgcc gacaagcaga agaacggcat caaggccaac ttcaagatcc gccacaacat      1140
cgaggacggc ggcgtgcagc tcgccgacca ctaccagcag aacacccca tcggcgacgg      1200 ccccgtgctg ctgcccgaca accactacct gagctaccag tccaagctga gcaaagaccc      1260
caacgagaag cgcgatcaca tggtcctgct ggagttcgtg accgccgccg ggatcactct      1320
cggcatggac gagctgtaca gtaagtcga cggcgcgccg cggccgcgaa ttcgatatca      1380
taatcaacct ctggattaca aaatttgtga aagattgact ggtattctta actatgttgc      1440
tccttttacg ctatgtggat acgctgcttt aatgcctttg tatcatgcta ttgcttcccg      1500
tatggctttc attttctcct ccttgtataa atcctggtta gttcttgcca cggcggaact      1560
catcgccgcc tgccttgccc gctgctggac aggggctcgg ctgttgggca ctgacaattc      1620
cgtggctcga gagatcttcg actgtgcctt ctagttgcca gccatctgtt gtttgcccct      1680
cccccgtgcc ttccttgacc ctggaaggtg ccactcccac tgtcctttcc taataaaatg      1740
aggaaattgc atcgcattgt ctgagtaggt gtcattctat tctggggggt ggggtggggc      1800
```

-continued

```
aggacagcaa gggggaggat tgggaagaca atagcaggca tgagatctca cgtgcggacc    1860
gagcggccgc                                                          1870

<210> SEQ ID NO 187
<211> LENGTH: 1682
<212> TYPE: DNA
<213> ORGANISM: Artificial Sequence
<220> FEATURE:
<223> OTHER INFORMATION: CN2366

<400> SEQUENCE: 187
gcggccgcac gcgtttcggc ctctgtcttc tgccatcttc ataaattatt cacactaccc      60
agcgcttatg ccttcccgct tcagaccctc tccataactg ttctctgctc tttcatttac     120
agctgtggaa caactatttt catctggcag tggcttttat cacccaggat tctctgcagc     180
tggagcagtt ctcacacgcc aaatacaaca aaatcctgaa taagtaggtt gcattttttgg    240 atttcctgaa gagggggagg tccatgagat cctctgagat ggtgcctgaa gcagaggttt     300
ttgttcctcc taggtatggg gacatgagac ggctaattga gctcgggctg ggcataaaag     360
tcagggcaga gccatctatt gcttacattt gcttctggga tccagatctt tcgaagctag     420
cgctaccggt cgccaccatg gtgagcaagg gcgaggagct gttcaccggg gtggtgccca     480
tcctggtcga gctggacggc gacgtaaacg gccacaagtt cagcgtgtcc ggcgagggcg     540
agggcgatgc cacctacggc aagctgaccc tgaagctgat ctgcaccacc ggcaagctgc     600
ccgtgccctg gcccaccctc gtgaccaccc tgggctacgg cgtgcagtgc ttcgcccgct     660
accccgacca catgaagcag cacgacttct tcaagtccgc catgcccgaa ggctacgtcc     720
aggagcgcac catcttcttc aaggacgacg gcaactacaa gacccgcgcc gaggtgaagt     780
tcgagggcga caccctggtg aaccgcatcg agctgaaggg catcgacttc aaggaggacg     840
gcaacatcct ggggcacaag ctggagtaca actacaacag ccacaacgtc tatatcaccg     900
ccgacaagca gaagaacggc atcaaggcca acttcaagat ccgccacaac atcgaggacg     960
gcggcgtgca gctcgccgac cactaccagc agaacacccc catcggcgac ggccccgtgc    1020
tgctgcccga caaccactac ctgagctacc agtccaagct gagcaaagac cccaacgaga    1080
agcgcgatca catggtcctg ctggagttcg tgaccgccgc cgggatcact ctcggcatgg    1140
acgagctgta caagtaagtc gacggcgcgc cgcggccgcg aattcgatat cataatcaac    1200
ctctggatta caaaatttgt gaaagattga ctggtattct taactatgtt gctcctttta    1260
cgctatgtgg atacgctgct ttaatgcctt tgtatcatgc tattgcttcc cgtatggctt    1320
tcattttctc ctccttgtat aaatcctggt tagttcttgc cacggcggaa ctcatcgccg    1380
cctgccttgc ccgctgctgg acaggggctc ggctgttggg cactgacaat tccgtggctc    1440
gagagatctt cgactgtgcc ttctagttgc cagccatctg ttgtttgccc ctcccccgtg    1500
ccttccttga ccctggaagg tgccactccc actgtccttt cctaataaaa tgaggaaatt    1560
gcatcgcatt gtctgagtag gtgtcattct attctggggg gtggggtggg gcaggacagc    1620 aaggggagg attgggaaga caatagcagg catgagatct cacgtgcgga ccgagcggcc    1680
gc                                                                  1682

<210> SEQ ID NO 188
<211> LENGTH: 1969
<212> TYPE: DNA
<213> ORGANISM: Artificial Sequence
<220> FEATURE:
```

<223> OTHER INFORMATION: CN2257

<400> SEQUENCE: 188
gcggccgcac gcgtggaggg gcatagtgtc cacacttcag tcttcattct tcttgagttt       60
catgtgttta gcaaatgaaa acttttatat ttctgtcttt gataggctta ccaaatccaa      120
agtgctcccc ctcccccaac tatttcaggt tgaatatctg ttctctgaaa tgtttggtct      180
gaaaagcata tccaaatttg gaagatctgc atatatgtaa tgagacctct tgggatgcat      240
ctcaagtcca aacacaaaag tcatttatgt ttcatgcaca cttgacacac ctagcctgaa      300
gctaatttga taccatgtct ttagtgcacc tgtgttctga ctgcaaacca ctataaggag      360
tcaggtgtgg aattttccat ttacagcatc gagtcactgt tccaaaatgt tcagctttta      420
gagtgctctg tgatttgtat ttttggatca ggaatgctca acctgtattt taatgctttg      480
gcctgaaacc ttcccctcag aaggaaatgt ttgattgcag actggcattt ttgcctcctg      540
ggatagtgag ttgtgttttg acttttttca tttatttatt tattttatat tcatgcctga      600
ttgagggagg cttttagacc atggtgagct cgggctgggc ataaaagtca gggcagagcc      660
atctattgct tacatttgct tctgggatcc agatctttcg aagctagcgc taccggtcgc      720
caccatggtg agcaagggcg aggagctgtt caccgggtg gtgcccatcc tggtcgagct      780
ggacggcgac gtaaacggcc acaagttcag cgtgtccggc gagggcgagg gcgatgccac      840
ctacggcaag ctgaccctga agctgatctg caccaccggc aagctgcccg tgccctggcc      900 cacccctcgtg accaccctgg ctacggcgt gcagtgcttc gcccgctacc ccgaccacat      960
gaagcagcac gacttcttca gtccgccat gcccgaaggc tacgtccagg agcgcaccat     1020
cttcttcaag gacgacggca actacaagac ccgcgccgag gtgaagttcg agggcgacac     1080
cctggtgaac cgcatcgagc tgaagggcat cgacttcaag gaggacggca acatcctggg     1140
gcacaagctg gagtacaact acaacagcca caacgtctat atcaccgccg acaagcagaa     1200
gaacggcatc aaggccaact tcaagatccg ccacaacatc gaggacggcg cgtgcagct     1260 cgccgaccac taccagcaga acacccccat cggcgacggc cccgtgctgc tgcccgacaa     1320
ccactacctg agctaccagt ccaagctgag caaagacccc aacgagaagc gcgatcacat     1380
ggtcctgctg gagttcgtga ccgccgccgg gatcactctc ggcatggacg agctgtacaa     1440
gtaagtcgac ggcgcgccgc ggccgcgaat tcgatatcat aatcaacctc tggattacaa     1500
aatttgtgaa agattgactg gtattcttaa ctatgttgct cctttttacgc tatgtggata     1560 cgctgctttta atgcctttgt atcatgctat tgcttcccgt atggctttca ttttctcctc     1620
cttgtataaa tcctggttag ttcttgccac ggcggaactc atcgccgcct gccttgcccg     1680
ctgctggaca ggggctcggc tgttgggcac tgacaattcc gtggctcgag agatcttcga     1740
ctgtgccttc tagttgccag ccatctgttg tttgccccctc ccccgtgcct tccttgaccc     1800
tggaaggtgc cactcccact gtcctttcct aataaaatga ggaaattgca tcgcattgtc     1860
tgagtaggtg tcattctatt ctggggggtg gggtggggca ggacagcaag ggggaggatt     1920
gggaagacaa tagcaggcat gagatctcac gtgcggaccg agcggccgc              1969

<210> SEQ ID NO 189
<211> LENGTH: 2674
<212> TYPE: DNA
<213> ORGANISM: Artificial Sequence
<220> FEATURE:
<223> OTHER INFORMATION: CN1667

<400> SEQUENCE: 189

-continued

```
gcggccgcaa cgcgtttaga acaatggctg gcccatagta aatgccgtgt tagtgtgtta     60
gttgctgttc ttccacgtca gaagaggcac agacaaatta ccaccaggtg gcgctcagag    120
tctgcggagg catcacaaca gccctgaatt tgaatcctgc tctgccactg cctagttgag    180
accttttact acctgactag ctgtttgtgt attttaggtg tttgttttgc taccctaaat    240
attccctgtg ctccatctat tcatttctcc tcccttccat cttgaaacca ctgatctttc    300
tgcttcctct ataattttgc cttttccttt tccagaatgt tataagggtg gaatcatata    360
gtgtgcagcc ttgaaagagt ggcttcttcc accaaataat gtgcatttaa ggttccttca    420
tgtctttaca tggcttgata gctcactttt tatccctgaa taataactca ttatacagat    480
gtatcaccat ttgtttaccc attcatctgt tgaagggcat gttgattgct tccagctttt    540
gtcaattatg dataggctgc tataaacatt catgtgtagg cttttaccaa cacatttgga    600
caaactccaa ggagcacaat tgctggatta tgtaagtaga ctatgtttca ttacgtaaga    660
agctttcaac ctgtcttgta aagtggttct atcattttgc attcccacta gcaataaagg    720
agagttgttc tacatttttg gaacatttgg tgttgtcata ttgggcaagg ggtattttag    780
ctattctaaa agggatctca taagtttaat ttgcaatatc ctaataaaat atgatgttga    840
acatcttttc atacgattat ttgctatttg tatattgtct ttgatgacgt gcctactcag    900
acattttccc cactgtttaa atggatttt tgttttccaa tttgtttcat gtggacaaaa    960
ttataattta tgttatattg ccttgtagaa tgctgtgtag ataatgtaac aggctaagga   1020
atagaaataa tttgatggaa aaacaaatct actttttgtt ttacaaagaa atgttatgaa   1080
agccctttct gaggagaaag ccttttactt gaaaattttt taatagaggc agggtcttgt   1140
tctgttcccc aggttggagt gcagtgacac aaccatagct cattgcagcc ttgaactcct   1200
gagctcaagc gatcctccag agtagctagc actttaggcc agagccacta taacccagcc   1260
aggaattcga tatcataatc aaccataggt accgagctcg ggattcagcc gggagcttag   1320
ggaggggagg tcacttcata agggcctggg gggggagttg gagccacgag tcgtccagcc   1380
ggagccccgt gtggctgagc tccggcctca gaagcatccc cgggttggat ccttcgaagc   1440
tagcgctacc ggtcgccacc atggtgagca agggcgagga gctgttcacc ggggtggtgc   1500
ccatcctggt cgagctggac ggcgacgtaa acggccacaa gttcagcgtg tccggcgagg   1560
gcgagggcga tgccacctac ggcaagctga ccctgaagct gatctgcacc accggcaagc   1620
tgcccgtgcc ctggcccacc ctcgtgacca ccctgggcta cggcgtgcag tgcttcgccc   1680
gctaccccga ccacatgaag cagcacgact tcttcaagtc cgccatgccc gaaggctacg   1740
tccaggagcg caccatcttc ttcaaggacg acggcaacta caagacccgc gccgaggtga   1800
agttcgaggg cgacaccctg gtgaaccgca tcgagctgaa gggcatcgac ttcaaggagg   1860
acggcaacat cctggggcac aagctggagt acaactacaa cagccacaac gtctatatca   1920
ccgccgacaa gcagaagaac ggcatcaagg ccaacttcaa gatccgccac aacatcgagg   1980
acggcggcgt gcagctcgcc gaccactacc agcagaacac ccccatcggc gacggccccg   2040
tgctgctgcc cgacaaccac tacctgagct accagtccaa gctgagcaaa gaccccaacg   2100
agaagcgcga tcacatggtc ctgctggagt tcgtgaccgc cgccgggatc actctcggca   2160
tggacgagct gtacaagtaa gtcgacatca taatcaacct ctggattaca aaatttgtga   2220
aagattgact ggtattctta actatgttgc tccttttacg ctatgtggat acgctgcttt   2280
aatgcctttg tatcatgcta ttgcttcccg tatggctttc attttctcct ccttgtataa   2340
```

-continued

```
atcctggtta gttcttgcca cggcggaact catcgccgcc tgccttgccc gctgctggac      2400
aggggctcgg ctgttgggca ctgacaattc cgtggctcga gagatcttcg actgtgcctt      2460
ctagttgcca gccatctgtt gtttgcccct ccccgtgcc ttccttgacc ctggaaggtg       2520
ccactcccac tgtcctttcc taataaaatg aggaaattgc atcgcattgt ctgagtaggt      2580
gtcattctat tctggggggt ggggtggggc aggacagcaa gggggaggat tgggaagaca      2640
atagcaggca tgcacgtgcg gaccgagcgg ccgc                                  2674

<210> SEQ ID NO 190
<211> LENGTH: 2223
<212> TYPE: DNA
<213> ORGANISM: Artificial Sequence
<220> FEATURE:
<223> OTHER INFORMATION: CN1581

<400> SEQUENCE: 190
gcggccgcaa cgcgtttaga acaatggctg gcccatagta aatgccgtgt tagtgtgtta       60
gttgctgttc ttccacgtca gaagaggcac agacaaatta ccaccaggtg gcgctcagag      120
tctgcggagg catcacaaca gccctgaatt tgaatcctgc tctgccactg cctagttgag      180
accttttact acctgactag ctgtttgtgt attttaggtg tttgtttggc caagaaaagg      240
aagcagtgaa tgaatggatg atgattctga cttctgcttt ggggatgaag tgggtaccac      300
gcactgagag agaactcacg ttcatccttc taagctttcc ccattctgtt ccctgttctt      360 cccccctgc agctgttttc ctaaagaatc tctgaatctc tccttttttt ttgaatcaca       420
agcactggct gttgggaaca cccacagatg cactctacaa acacacaact tactctgagt      480
aatcacattg atttggaatt aacggccatt cagatacctc attgaagata ccatctggga      540
tgttgccgct cttctgaggt atatcatatt ctgagaaaat ccgtccgatt gtacaaataa      600
ctcatcagaa tggctctggc tgcatcttga tgtgctggct aggcgcacga gagtcggagg      660
cttcagcttc cccttccccc tctcgagaca ctgaaggaag tagagccatt tcttcttctc      720
aagagaaaaa gcaacagaga gtttggcaac atccaaaaag ttggtcctgg tgccaccagg      780
catccaaaaa catctccttg aaaattgcct tgaattcgat atcataatca accataggta      840
ccgagctcgg gattcagccg ggagcttagg gaggggaggt cacttcataa gggcctgggg      900
ggggagttgg agccacgagt cgtccagccg gagccccgtg tggctgagct ccggcctcag      960
aagcatcccc gggttggatc cttcgaagct agcgctaccg gtcgccacca tggtgagcaa     1020
gggcgaggag ctgttcaccg gggtggtgcc catcctggtc gagctggacg gcgacgtaaa     1080
cggccacaag ttcagcgtgt ccggcgaggg cgagggcgat gccacctacg gcaagctgac     1140
cctgaagctg atctgcacca ccggcaagct gcccgtgccc tggcccaccc tcgtgaccac     1200
cctgggctac ggcgtgcagt gcttcgcccg ctaccccgac cacatgaagc agcacgactt     1260
cttcaagtcc gccatgcccg aaggctacgt ccaggagcgc accatcttct tcaaggacga     1320
cggcaactac aagacccgcg ccgaggtgaa gttcgagggc gacaccctgg tgaaccgcat     1380
cgagctgaag ggcatcgact tcaaggagga cggcaacatc ctggggcaca agctggagta     1440
caactacaac agccacaacg tctatatcac cgccgacaag cagaagaacg gcatcaaggc     1500
caacttcaag atccgccaca acatcgagga cggcggcgtg cagctcgccg accactacca     1560
gcagaacacc cccatcggcg acggccccgt gctgctgccc gacaaccact acctgagcta     1620
ccagtccaag ctgagcaaag accccaacga gaagcgcgat cacatggtcc tgctggagtt     1680
cgtgaccgcc gccgggatca ctctcggcat ggacgagctg tacaagtaag tcgacatcat     1740
```

-continued

```
aatcaacctc tggattacaa aatttgtgaa agattgactg gtattcttaa ctatgttgct     1800
ccttttacgc tatgtggata cgctgcttta atgcctttgt atcatgctat tgcttcccgt     1860
atggctttca ttttctcctc cttgtataaa tcctggttag ttcttgccac ggcggaactc     1920
atcgccgcct gccttgcccg ctgctggaca ggggctcggc tgttgggcac tgacaattcc     1980
gtggctcgag agatcttcga ctgtgccttc tagttgccag ccatctgttg tttgcccctc     2040
ccccgtgcct tccttgaccc tggaaggtgc cactcccact gtcctttcct aataaaatga     2100
ggaaattgca tcgcattgtc tgagtaggtg tcattctatt ctggggggtg gggtggggca     2160
ggacagcaag ggggaggatt gggaagacaa tagcaggcat gcacgtgcgg accgagcggc     2220
cgc                                                                   2223
```

<210> SEQ ID NO 191
<211> LENGTH: 2068
<212> TYPE: DNA
<213> ORGANISM: Artificial Sequence
<220> FEATURE:
<223> OTHER INFORMATION: CN1649

<400> SEQUENCE: 191

```
gcggccgcaa cgcgtttaga acaatggctg gcccatagta aatgccgtgt tagtgtgtta       60
gttgctgttc ttccacgtca gaagaggcac agacaaatta ccaccaggtg gcgctcagag      120
tctgcggagg catcacaaca gccctgaatt tgaatcctgc tctgccactg cctagttgag      180 acctttact acctgactag ctgtttgtgt attttaggtg tttgtttgag cacctgttcc      240
tcccaatagg acctgcccaa tttcagttcc ttgagctttc ctggttgggc tgatctgcat      300
ttccacaaag tgtttttctg agacatgggc ctcagctcat gcgaagggtt ttcagcataa      360
agaatactgg tcgggtccat ctggtagcat tgcatattca aggttctgca tgatttgaat      420
gaaacatgaa acaataaatt catccactgc ctagaaacat ctggtctctt ttaataaact      480
cctaccactt ggctgtctga aacaagacta tttgtatcca acatgtatgc tgagagttct      540 tttattttt tccctctctc cagctgcaaa gccacatgag aagtaaacat gctctttcat      600
gttattctcc attgaatatg atctgaaagt acttcccaac ttcctgaata gactcagaat      660
tcgatatcat aatcaaccat aggtaccgag ctcgggattc agccgggagc ttagggaggg      720
gaggtcactt cataagggcc tggggggggga gttggagcca cgagtcgtcc agccggagcc      780
ccgtgtggct gagctccggc ctcagaagca tccccgggtt ggatccttcg aagctagcgc      840
taccggtcgc caccatggtg agcaagggcg aggagctgtt caccggggtg gtgcccatcc      900
tggtcgagct ggacggcgac gtaaacggcc acaagttcag cgtgtccggc gagggcgagg      960
gcgatgccac ctacggcaag ctgaccctga agctgatctg caccaccggc aagctgcccg     1020
tgccctggcc caccctcgtg accaccctgg gctacggcgt gcagtgcttc gcccgctacc     1080
ccgaccacat gaagcagcac gacttcttca gtccgccat gcccgaaggc tacgtccagg      1140
agcgcaccat cttcttcaag gacgacggca actacaagac ccgcgccgag gtgaagttcg      1200
agggcgacac cctggtgaac cgcatcgagc tgaagggcat cgacttcaag gaggacggca      1260
acatcctggg gcacaagctg gagtacaact acaacagcca caacgtctat atcaccgccg      1320
acaagcagaa gaacggcatc aaggccaact tcaagatccg ccacaacatc gaggacggcg      1380
gcgtgcagct cgccgaccac taccagcaga acacccccat cggcgacggc cccgtgctgc     1440
tgcccgacaa ccactacctg agctaccagt ccaagctgag caaagacccc aacgagaagc     1500
```

-continued

```
gcgatcacat ggtcctgctg gagttcgtga ccgccgccgg gatcactctc ggcatggacg   1560
agctgtacaa gtaagtcgac atcataatca acctctggat tacaaaattt gtgaaagatt   1620
gactggtatt cttaactatg ttgctccttt tacgctatgt ggatacgctg ctttaatgcc   1680
tttgtatcat gctattgctt cccgtatggc tttcattttc tcctccttgt ataaatcctg   1740
gttagttctt gccacggcgg aactcatcgc cgcctgcctt gcccgctgct ggacaggggc   1800
tcggctgttg ggcactgaca attccgtggc tcgagagatc ttcgactgtg ccttctagtt   1860
gccagccatc tgttgtttgc ccctcccccg tgccttcctt gaccctggaa ggtgccactc   1920
ccactgtcct ttcctaataa aatgaggaaa ttgcatcgca ttgtctgagt aggtgtcatt   1980
ctattctggg gggtggggtg gggcaggaca gcaaggggga ggattgggaa gacaatagca   2040
ggcatgcacg tgcggaccga gcggccgc                                      2068
```

```
<210> SEQ ID NO 192
<211> LENGTH: 3515
<212> TYPE: DNA
<213> ORGANISM: Artificial Sequence
<220> FEATURE:
<223> OTHER INFORMATION: AiP1099

<400> SEQUENCE: 192
gcggccgcac gcgtttccct ttagctcctt ggttactttc tctagctcct cccttgggag    60
ccctgcgatt tatccatgta atgtttugga atttttacca agtctgatac atataaagat   120
aaaacaaaac aaaatatttt cttatgacta gtccaagcat gaagaaggac aaggctaagc   180
agaagtttat caaagcagca ttcaaattag aaggtagtca aaacaaaaat acaatgaatc   240
agaacagaaa aagaacctga atctcaaagg tttagggaat tctgctgaga tggtaaaagt   300
gtaatgggtt gttaggaaca tatggttcaa agtctcttgc tctctctttt catttctgtt   360
agttttactt aagagatagg tccaacaaaa tcaagttata agtataattg tctcagtaag   420
aagatgacta aattgataag gatccgaaga gtgaataaag atgctgacga catggccaaa   480
gtaaaatgga ttaggctgtc ttcatgctag gactttaaat tgatgtgtac aaaattaaga   540
agtgctgttg caacagtgtt tcaaacatcc tagccaggtg atgtttattc tggggttaaa   600
cacaagaagg gtaaatgtag gcagatggat tctgaagaaa tcaaaagctt gtttaaatgc   660 aaattttct acagaagaaga agcattcaga gaagaaatga tatctaaaata aattttcttt   720 cagcagaatg ctttctttt caggtttgaa agaggcaaac tcaggtgtct aatggagatt   780
tactaaagaa ctaaaactgg gtaccttgc aaacggaatt tcagtgcctc taaaagccta   840
ctctctgaag cactttactt agctgtggag ctgaacctgc aatcaaatta caatcttctt   900
tgaattttgc ataccaatct tgacttcaag atgagttgat acttcaagac ataaatgtac   960
aatttggtct ctctcttatg atccacgagc tcgggctggg cataaaagtc agggcagagc   1020
catctattgc ttacatttgc ttctggcgtg gccaccatgg ctcctaagaa gaagaggaag   1080
gtgatgagcc agttcgacat cctgtgcaag acccccccca aggtgctggt gcggcagttc   1140
gtggagagat tcgagaggcc cagcggcgag aagatcgcca gctgtgccgc cgagctgacc   1200
tacctgtgct ggatgatcac ccacaacggc accgccatca gagaggccac cttcatgagc   1260
tacaacacca tcatcagcaa cagcctgagc ttcgacatcg tgaacaagag cctgcagttc   1320
aagtacaaga cccagaaggc caccatcctg gaggccagcc tgaagaagct gatccccgcc   1380
tgggagttca ccatcatccc ttacaacggc cagaagcacc agagcgacat caccgacatc   1440
gtgtccagcc tgcagctgca gttcgagagc agcgaggagg ccgacaaggg caacagccac   1500
```

-continued

```
agcaagaaga tgctgaaggc cctgctgtcc gagggcgaga gcatctggga gatcaccgag    1560
aagatcctga acagcttcga gtacaccagc aggttcacca agaccaagac cctgtaccag    1620
ttcctgttcc tggccacatt catcaactgc ggcaggttca gcgacatcaa gaacgtggac    1680
cccaagagct tcaagctggt gcagaacaag tacctgggcg tgatcattca gtgcctggtg    1740
accgagacca agacaagcgt gtccaggcac atctactttt tcagcgccag aggcaggatc    1800
gaccccctgg tgtacctgga cgagttcctg aggaacagcg agcccgtgct gaagagagtg    1860
aacaggaccg gcaacagcag cagcaacaag caggagtacc agctgctgaa ggacaacctg    1920
gtgcgcagct acaacaaggc cctgaagaag aacgccccct accccatctt cgctatcaag    1980
aacggcccta agagccacat cggcaggcac ctgatgacca gctttctgag catgaagggc    2040
ctgaccgagc tgacaaacgt ggtgggcaac tggagcgaca agagggcctc cgccgtggcc    2100
aggaccacct acacccacca gatcaccgcc atccccgacc actacttcgc cctggtgtcc    2160
aggtactacg cctacgaccc catcagcaag gagatgatcg ccctgaagga cgagaccaac    2220
cccatcgagg agtggcagca catcgagcag ctgaagggca gcgccgaggg cagcatcaga    2280
taccccgcct ggaacggcat catcagccag gaggtgctgg actacctgag cagctacatc    2340
aacaggcgga tctgagaatt cgatatcaag cttatcgata tcaacctct ggattacaaa    2400 atttgtgaaa gattgactgg tattcttaac tatgttgctc cttttacgct atgtggatac    2460
gctgctttaa tgcctttgta tcatgctatt gcttcccgta tggctttcat tttctcctcc    2520
ttgtataaat cctggttgct gtctctttat gaggagttgt ggcccgttgt caggcaacgt    2580
ggcgtggtgt gcactgtgtt tgctgacgca accccccactg gttggggcat tgccaccacc    2640
tgtcagctcc tttccgggac tttcgctttc cccctcccta ttgccacggc ggaactcatc    2700
gccgcctgcc ttgcccgctg ctggacaggg gctcggctgt tgggcactga caattccgtg    2760
gtgttgtcgg ggaaatcatc gtcctttcct tggctgctcg cctatgttgc cacctggatt    2820
ctgcgcggga cgtccttctg ctacgtccct tcggccctca atccagcgga ccttccttcc    2880
cgcggcctgc tgccggctct gcggcctctt ccgcgtcttc gccttcgccc tcagacgagt    2940
cggatctccc tttgggccgc ctccccgcat cgataccgag cgctgctcga gagatctacg    3000
ggtggcatcc ctgtgacccc tccccagtgc ctctcctggc cctggaagtt gccactccag    3060
tgcccaccag ccttgtccta ataaaattaa gttgcatcat tttgtctgac taggtgtcct    3120
tctataatat tatgggtgg aggggggtgg tatggagcaa ggggcaagtt gggaagacaa    3180
cctgtagggc ctgcggggtc tattgggaac caagctggag tgcagtggca caatcttggc    3240
tcactgcaat ctccgcctcc tgggttcaag cgattctcct gcctcagcct cccgagttgt    3300
tgggattcca ggcatgcatg accaggctca gctaattttt gtttttttgg tagagacggg    3360
gtttcaccat attggccagg ctggtctcca actcctaatc tcaggtgatc tacccacctt    3420
ggcctcccaa attgctggga ttacaggcgt gaaccactgc tcccttccct gtccttctga    3480
ttttgtaggt aaccacgtgc ggaccgagcg gccgc                               3515
```

<210> SEQ ID NO 193
<211> LENGTH: 2965
<212> TYPE: DNA
<213> ORGANISM: Artificial Sequence
<220> FEATURE:
<223> OTHER INFORMATION: AiP1102

<400> SEQUENCE: 193

```
gcggccgcac gcgtcctgta gtgacaggga cagataggg cacgtttaga atccaaactc      60
tcagagcacc cctacacttc atgttaaggg aatctgcata ttcactgttt aagcagccca     120
gcccacacac cagtgcttag cctttctgag ttaagctttg agatgctaaa aggccacctg     180
gaaggatgtg gggctcagcc acctcggtgc attgagtaac tcccactatg tggagctagg     240
agaagatgca aggagaaaaa cacccacatc ttcagtgtta cagacaaggt tgagcacctg     300
gctggagggg cgagattaag ctttggaggg agggcagcct ctgagtccac tcccttgtgt     360
ctggctgaga cggagtggaa gacagctatc taggatttcc atccaatgcc tttttcaggtt    420 acctgttctc tgggtagagc tcgggctggg cataaaagtc agggcagagc catctattgc     480
ttacatttgc ttctggcgtg gccaccatgg ctcctaagaa gaagaggaag gtgatgagcc     540
agttcgacat cctgtgcaag acccccccca aggtgctggt gcggcagttc gtggagagat     600
tcgagaggcc cagcggcgag aagatcgcca gctgtgccgc cgagctgacc tacctgtgct     660
ggatgatcac ccacaacggc accgccatca agagggccac cttcatgagc tacaacacca     720
tcatcagcaa cagcctgagc ttcgacatcg tgaacaagag cctgcagttc aagtacaaga     780
cccagaaggc caccatcctg gaggccagcc tgaagaagct gatccccgcc tgggagttca     840
ccatcatccc ttacaacggc cagaagcacc agagcgacat caccgacatc gtgtccagcc     900
tgcagctgca gttcgagagc agcgaggagg ccgacaaggg caacagccac agcaagaaga     960
tgctgaaggc cctgctgtcc gagggcgaga gcatctggga gatcaccgag aagatcctga    1020
acagcttcga gtacaccagc aggttcacca agaccaagac cctgtaccag ttcctgttcc    1080
tggccacatt catcaactgc ggcaggttca gcgacatcaa gaacgtggac cccaagagct    1140
tcaagctggt gcagaacaag tacctgggcg tgatcattca gtgcctggtg accgagacca    1200
agacaagcgt gtccaggcac atctactttt tcagcgccag aggcaggatc gaccccctgg    1260
tgtacctgga cgagttcctg aggaacagcg agcccgtgct gaagagagtg aacaggaccg    1320
gcaacagcag cagcaacaag caggagtacc agctgctgaa ggacaacctg gtgcgcagct    1380
acaacaaggc cctgaagaag aacgccccct accccatctt cgctatcaag aacggcccta    1440
agagccacat cggcaggcac ctgatgacca gctttctgag catgaagggc ctgaccgagc    1500
tgacaaacgt ggtgggcaac tggagcgaca agagggcctc cgccgtggcc aggaccacct    1560
acacccacca gatcaccgcc atccccgacc actacttcgc cctggtgtcc aggtactacg    1620
cctacgaccc catcagcaag gagatgatcg ccctgaagga cgagaccaac cccatcgagg    1680
agtggcagca catcgagcag ctgaagggca gcgccgaggg cagcatcaga taccccgcct    1740
ggaacggcat catcagccag gaggtgctgg actacctgag cagctacatc aacaggcgga    1800
tctgagaatt cgatatcaag cttatcgata atcaacctct ggattacaaa atttgtgaaa    1860
gattgactgg tattcttaac tatgttgctc cttttacgct atgtggatac gctgctttaa    1920
tgcctttgta tcatgctatt gcttcccgta tggctttcat tttctcctcc ttgtataaat    1980
cctggttgct gtctctttat gaggagttgt ggcccgttgt caggcaacgt ggcgtggtgt    2040
gcactgtgtt tgctgacgca acccccactg gttggggcat tgccaccacc tgtcagctcc    2100
tttccgggac tttcgctttc ccctccccta ttgccacggc ggaactcatc gccgcctgcc    2160
ttgcccgctg ctggacaggg gctcggctgt tgggcactga caattccgtg gtgttgtcgg    2220
ggaaatcatc gtcctttcct tggctgctcg cctatgttgc cacctggatt ctgcgcggga    2280
cgtccttctg ctacgtccct tcggccctca atccagcgga ccttccttcc cgcggcctgc    2340
tgccggctct gcggcctctt ccgcgtcttc gccttcgccc tcagacgagt cggatctccc    2400
```

-continued

```
tttgggccgc ctccccgcat cgataccgag cgctgctcga gagatctacg ggtggcatcc      2460
ctgtgacccc tccccagtgc ctctcctggc cctggaagtt gccactccag tgcccaccag      2520
ccttgtccta ataaaattaa gttgcatcat tttgtctgac taggtgtcct tctataatat      2580
tatggggtgg aggggggtgg tatggagcaa ggggcaagtt gggaagacaa cctgtagggc      2640
ctgcggggtc tattgggaac caagctggag tgcagtggca caatcttggc tcactgcaat      2700
ctccgcctcc tgggttcaag cgattctcct gcctcagcct cccgagttgt tgggattcca      2760
ggcatgcatg accaggctca gctaattttt gtttttttgg tagagacggg gtttcaccat      2820
attggccagg ctggtctcca actcctaatc tcaggtgatc tacccacctt ggcctcccaa      2880
attgctggga ttacaggcgt gaaccactgc tcccttccct gtccttctga ttttgtaggt      2940
aaccacgtgc ggaccgagcg gccgc                                           2965

<210> SEQ ID NO 194
<211> LENGTH: 2929
<212> TYPE: DNA
<213> ORGANISM: Artificial Sequence
<220> FEATURE:
<223> OTHER INFORMATION: AiP1100

<400> SEQUENCE: 194
gcggccgcac gcgtacacaa ggacaagctg gtgagcgctg ttaaatctct actacaagct        60
gacactgtca cacccacaga tacaccggag tgtcagatgg ccccatctca tggtacatga       120
aatgcagtaa tcctgcggtg caattttctg agctattttc cagagctttc tcttgaaaag       180
caggtgactt cttgggtagc agcaatttac ctttcacacc gggtaatcat caaggtgcct       240
gattgccctg aatacctttc ccggctgtca gaatacttca aggctgagaa ttagcatttc       300
aaaacctttt caaatgaggg tagggggggct cattccttg gttgaaggtt ccccaggctg       360
caaagaagca agtgttaagt gcacacctgg ggaagccata gagctcgggc tgggcataaa       420
agtcagggca gagccatcta ttgcttacat ttgcttctgg cgtggccacc atggctccta       480
agaagaagag gaaggtgatg agccagttcg acatcctgtg caagacccc cccaaggtgc        540 tggtgcggca gttcgtggag agattcgaga ggcccagcgg cgagaagatc gccagctgtg       600
ccgccgagct gacctacctg tgctggatga tcacccacaa cggcaccgcc atcaagaggg       660
ccaccttcat gagctacaac accatcatca gcaacagcct gagcttcgac atcgtgaaca       720
agagcctgca gttcaagtac aagacccaga aggccaccat cctggaggcc agcctgaaga       780
agctgatccc cgcctgggag ttcaccatca tcccttacaa cggccagaag caccagagcg       840
acatcaccga catcgtgtcc agcctgcagc tgcagttcga gagcagcgag gaggccgaca       900
agggcaacag ccacagcaag aagatgctga aggccctgct gtccgagggc gagagcatct       960
gggagatcac cgagaagatc ctgaacagct cgagtacac cagcaggttc accaagacca      1020
agaccctgta ccagttcctg ttcctggcca cattcatcaa ctgcggcagg ttcagcgaca      1080
tcaagaacgt ggaccccaag agcttcaagc tggtgcagaa caagtacctg ggcgtgatca      1140
ttcagtgcct ggtgaccgag accaagacaa gcgtgtccag gcacatctac tttttcagcg      1200
ccagaggcag gatcgacccc ctggtgtacc tggacgagtt cctgaggaac agcgagcccg      1260
tgctgaagag agtgaacagg accggcaaca gcagcagcaa caagcaggag taccagctgc      1320
tgaaggacaa cctggtgcgc agctacaaca aggccctgaa gaagaacgcc ccctaccca       1380 tcttcgctat caagaacggc cctaagagcc acatcggcag gcacctgatg accagctttc      1440
```

```
tgagcatgaa gggcctgacc gagctgacaa acgtggtggg caactggagc gacaagaggg   1500
cctccgccgt ggccaggacc acctacaccc accagatcac cgccatcccc gaccactact   1560
tcgccctggt gtccaggtac tacgcctacg accccatcag caaggagatg atcgccctga   1620
aggacgagac caaccccatc gaggagtggc agcacatcga gcagctgaag ggcagcgccg   1680
agggcagcat cagataccccc gcctggaacg gcatcatcag ccaggaggtg ctggactacc   1740
tgagcagcta catcaacagg cggatctgag aattcgatat caagcttatc gataatcaac   1800
ctctggatta caaaatttgt gaaagattga ctggtattct taactatgtt gctccttttta   1860 cgctatgtgg atacgctgct ttaatgcctt tgtatcatgc tattgcttcc cgtatggctt   1920
tcattttctc ctccttgtat aaatcctggt tgctgtctct ttatgaggag ttgtggcccg   1980
ttgtcaggca acgtggcgtg gtgtgcactg tgtttgctga cgcaacccccc actggttggg   2040 gcattgccac cacctgtcag ctcctttccg ggactttcgc tttccccctc cctattgcca   2100
cggcggaact catcgccgcc tgccttgccc gctgctggac aggggctcgg ctgttgggca   2160
ctgacaattc cgtggtgttg tcggggaaat catcgtcctt ccttggctg ctcgcctatg   2220 ttgccacctg gattctgcgc gggacgtcct tctgctacgt cccttcggcc ctcaatccag   2280
cggaccttcc ttcccgcggc ctgctgccgg ctctgcggcc tcttccgcgt cttcgccttc   2340
gccctcagac gagtcggatc tcccctttggg ccgcctcccc gcatcgatac cgagcgctgc   2400
tcgagagatc tacgggtggc atccctgtga ccccctcccca gtgcctctcc tggccctgga   2460
agttgccact ccagtgccca ccagccttgt cctaataaaa ttaagttgca tcattttgtc   2520
tgactaggtg tccttctata atattatggg gtggaggggg gtggtatgga caagggggca   2580
agttgggaag acaacctgta gggcctgcgg ggtctattgg gaaccaagct ggagtgcagt   2640
ggcacaatct tggctcactg caatctccgc ctcctgggtt caagcgattc tcctgcctca   2700
gcctcccgag ttgttgggat tccaggcatg catgaccagg ctcagctaat ttttgttttt   2760
ttggtagaga cggggtttca ccatattggc caggctggtc tccaactcct aatctcaggt   2820
gatctaccca ccttggcctc ccaaattgct gggattacag gcgtgaacca ctgctccctt   2880
ccctgtcctt ctgattttgt aggtaaccac gtgcggaccg agcggccgc        2929
```

```
<210> SEQ ID NO 195
<211> LENGTH: 1995
<212> TYPE: DNA
<213> ORGANISM: Artificial Sequence
<220> FEATURE:
<223> OTHER INFORMATION: AiP1270

<400> SEQUENCE: 195
gcggccgcac gcgtatactg taaaaagcaa gaagaaccaa tcacttaatc taaaatttag     60
aactctgaag tgattcattc cactgaccat tctcttttcc cagttctctt atcttgtcag    120
atacacagga agctcaggac agttttgctc atcccctttgt ttctagcagt tctgagtaat    180
gaattcaaat agcagttatt atctcaatgc catgacaatt ggctaagcta actacccagt    240
tcacttatcg agggagcaaa acactagatg gccaataaga atgacagaca gaatgtatga    300
ttgatgtgaa acaccagag aatcaagtgc tttcaaagag ttaaatgtgt ctccattat    360 ggctgacagc tggagaaact atcattggaa actgagatga attgtttgct ctgtgcaggt    420
gggagaagag aattaaatga cagacacatg aaactgtgct ttgcatcttc ttgtcagcac    480
tactctgttg gccaagagtg aaatgcaatt tcagttggct tgaacgccac aggattttac    540
atctgaatca actaagttct aattatgggc agatttatct actaatacca tcaccataac    600
```

-continued

```
aaccaaaacc atgccccatg cctttcatgt cttcactatt tcactgagtt tgagctcggg      660
ctgggcataa aagtcagggc agagccatct attgcttaca tttgcttctg ggatccagat      720 cttcgaagc tagcgctacc ggtcgccacc atggtgagca agggcgagga gctgttcacc       780
ggggtggtgc ccatcctggt cgagctggac ggcgacgtaa acggccacaa gttcagcgtg      840
tccggcgagg gcgagggcga tgccacctac ggcaagctga ccctgaagct gatctgcacc      900
accggcaagc tgcccgtgcc ctggcccacc ctcgtgacca ccctgggcta cggcgtgcag      960
tgcttcgccc gctaccccga ccacatgaag cagcacgact tcttcaagtc cgccatgccc     1020
gaaggctacg tccaggagcg caccatcttc ttcaaggacg acggcaacta caagacccgc     1080
gccgaggtga agttcgaggg cgacaccctg gtgaaccgca tcgagctgaa gggcatcgac     1140
ttcaaggagg acggcaacat cctggggcac aagctggagt acaactacaa cagccacaac     1200
gtctatatca ccgccgacaa gcagaagaac ggcatcaagg ccaacttcaa gatccgccac     1260
aacatcgagg acggcggcgt gcagctcgcc gaccactacc agcagaacac ccccatcggc     1320
gacggccccg tgctgctgcc cgacaaccac tacctgagct accagtccaa gctgagcaaa     1380 gacccccaacg agaagcgcga tcacatggtc ctgctggagt tcgtgaccgc cgccgggatc    1440
actctcggca tggacgagct gtacaagtaa gtcgacggcg cgccgcggcc gcgaattcga     1500
tatcataatc aacctctgga ttacaaaatt tgtgaaagat tgactggtat tcttaactat     1560
gttgctcctt ttacgctatg tggatacgct gctttaatgc ctttgtatca tgctattgct     1620
tcccgtatgg ctttcatttt ctcctccttg tataaatcct ggttagttct tgccacggcg     1680
gaactcatcg ccgcctgcct tgcccgctgc tggacagggg ctcggctgtt gggcactgac     1740
aattccgtgg ctcgagagat cttcgactgt gccttctagt tgccagccat ctgttgtttg     1800
cccctccccc gtgccttcct tgaccctgga aggtgccact cccactgtcc tttcctaata     1860
aaatgaggaa attgcatcgc attgtctgag taggtgtcat tctattctgg ggggtggggt     1920
ggggcaggac agcaaggggg aggattggga agacaatagc aggcatgaga tctcacgtgc     1980
ggaccgagcg gccgc                                                       1995
```

<210> SEQ ID NO 196
<211> LENGTH: 2209
<212> TYPE: DNA
<213> ORGANISM: Artificial Sequence
<220> FEATURE:
<223> OTHER INFORMATION: AiP1271

<400> SEQUENCE: 196

```
gcggccgcac gcgttgactc actaaagtat ttgcatgttt tcaaagctgt aaagtctgga       60
ggtgtgcttt tcaggagctg gggaggttag agggaagacc tcgaacagga cacactatca      120
ctgtctttct tgtgccaatg caattggaag aaacaaacac agccatcatt tagcccacat       180
gaattaggtc ctgtaaagag tgaaggggaa aaggttgttg gaaatctaat tagtaggctt       240
tgcaagtgtg gagtttatgg ctacatattc agttaaattc agttctgttt tgtagctatc       300
agccagggaa gagtcaagtg ccatgtggat tgggaacata aatagcccat tcttcatgtc       360
cattgctcta tcattaacct tcccactcag tcctggaaat gaaaaaccca gcgtccttcc        420
atctgctcca cgttatttat gatgatgcct ctaattatgt tcaattgagt tgctgtcgat       480
gattaaaggt aataggtaat aataacttgg cctcatcatt accaccatta ttattagctc       540
attgattgca ataatttcta aaattacccc ttggaataaa atatgttaag cacctggttt       600
```

-continued

```
atcctttttt tttttttta aaaaaggaac atctgctcta aatgtgtgat agcagaggac       660
caaacgtgtc ttgatctgaa ggggaagcaa aaacgatgct gacactgggg agccttgtct       720
gggctggaat ggatgtattg tgggatgctg agaggaagag tagtcacgat caagttcaat       780
gctaggatta cagggctgct gagagacgga gacacgtggg aagctgagct attccatggc       840
tactgcaggc tttacttctt cttctgagct cgggctgggc ataaaagtca gggcagagcc       900
atctattgct tacatttgct tctgggatcc agatctttcg aagctagcgc taccggtcgc       960
caccatggtg agcaagggcg aggagctgtt caccggggtg gtgcccatcc tggtcgagct      1020
ggacggcgac gtaaacggcc acaagttcag cgtgtccggc gagggcgagg gcgatgccac      1080
ctacggcaag ctgaccctga agctgatctg caccaccggc aagctgcccg tgccctggcc      1140
caccctcgtg accaccctgg gctacggcgt gcagtgcttc gcccgctacc ccgaccacat      1200
gaagcagcac gacttcttca gtccgccat gcccgaaggc tacgtccagg agcgcaccat      1260
cttcttcaag gacgacggca actacaagac ccgcgccgag gtgaagttcg agggcgacac      1320
cctggtgaac cgcatcgagc tgaagggcat cgacttcaag gaggacggca acatcctggg      1380
gcacaagctg gagtacaact acaacagcca caacgtctat atcaccgccg acaagcagaa      1440
gaacggcatc aaggccaact tcaagatccg ccacaacatc gaggacggcg gcgtgcagct      1500
cgccgaccac taccagcaga acacccccat cggcgacggc cccgtgctgc tgcccgacaa      1560
ccactacctg agctaccagt ccaagctgag caaagacccc aacgagaagc gcgatcacat      1620
ggtcctgctg gagttcgtga ccgccgccgg gatcactctc ggcatggacg agctgtacaa      1680
gtaagtcgac ggcgcgccgc ggccgcgaat tcgatatcat aatcaacctc tggattacaa      1740
aatttgtgaa agattgactg gtattcttaa ctatgttgct ccttttacgc tatgtggata      1800
cgctgcttta atgcctttgt atcatgctat tgcttcccgt atggctttca ttttctcctc      1860
cttgtataaa tcctggttag ttcttgccac ggcggaactc atcgccgcct gccttgcccg      1920
ctgctggaca ggggctcggc tgttgggcac tgacaattcc gtggctcgag agatcttcga      1980
ctgtgccttc tagttgccag ccatctgttg tttgcccctc ccccgtgcct tccttgaccc      2040
tggaaggtgc cactcccact gtcctttcct aataaaatga ggaaattgca tcgcattgtc      2100
tgagtaggtg tcattctatt ctggggggtg gggtggggca ggacagcaag ggggaggatt      2160
gggaagacaa tagcaggcat gagatctcac gtgcggaccg agcggccgc                 2209
```

<210> SEQ ID NO 197
<211> LENGTH: 2133
<212> TYPE: DNA
<213> ORGANISM: Artificial Sequence
<220> FEATURE:
<223> OTHER INFORMATION: AiP1272

<400> SEQUENCE: 197

```
gcggccgcac gcgttcattt tagtaggaaa gtgggatact atcttctaaa gagactgtgc        60
atcttatact cctatctacc acatcatatt tactgtctat tcttagttgg gtctaaattt       120
ctaagtaatt ttaagtattc atattctagg ctactgggtc ctatagatta atataaatat       180
ttgattgtaa gttatgcaat aaaaatgaag agatttgttt atatgcatct aaataagaac       240
atgcagaatg tgttcggaac ttgaatatcc ttatctccat gaaaatggga aaaataaaaa       300
taatttaaac aaagtgttga gtggaacatg tgtagctgaa acacttgatt ttccctaaaa       360
tatctgagta attacttgaa tttcctactt tatcatttgt ccatggacag ctggtatcag       420
gctataaaaa caacaataat tagaggccca aatagttctt ttaattaccc taaaagtctg       480
```

-continued

```
aaattcacgt ttttgttgtc tagaagtatt ctaatcatgt ttaacagctg attagcaatt      540
ggtccatttt tatgttgtag aaaagtgaaa tgtgaatgga aaattgaaga ataattccaa      600
accaaggtaa attattactg cttttccctg caattgttag ttgaaaggtg tgatttgaga      660
taagatcatt tacacttaaa agtgaataga agaaatataa taagagggaa taggcctgtg      720
aagttgtcaa gaataaattt taaaataaat gcagcatttt ttgcatttat gtcatagtct      780
gtttaagcag agctcgggct gggcataaaa gtcaggcag agccatctat tgcttacatt      840
tgcttctggg atccagatct ttcgaagcta gcgctaccgg tcgccaccat ggtgagcaag      900
ggcgaggagc tgttcaccgg ggtggtgccc atcctggtcg agctggacgg cgacgtaaac      960
ggccacaagt tcagcgtgtc cggcgagggc gagggcgatg ccacctacgg caagctgacc      1020
ctgaagctga tctgcaccac cggcaagctg cccgtgccct ggcccaccct cgtgaccacc      1080
ctgggctacg gcgtgcagtg cttcgcccgc taccccgacc acatgaagca gcacgacttc      1140
ttcaagtccg ccatgcccga aggctacgtc caggagcgca ccatcttctt caaggacgac      1200
ggcaactaca agacccgcgc cgaggtgaag ttcgagggcg acaccctggt gaaccgcatc      1260
gagctgaagg gcatcgactt caaggaggac ggcaacatcc tggggcacaa gctggagtac      1320
aactacaaca gccacaacgt ctatatcacc gccgacaagc agaagaacgg catcaaggcc      1380
aacttcaaga tccgccacaa catcgaggac ggcggcgtgc agctcgccga ccactaccag      1440
cagaacaccc ccatcggcga cggccccgtg ctgctgcccg acaaccacta cctgagctac      1500
cagtccaagc tgagcaaaga ccccaacgag aagcgcgatc acatggtcct gctggagttc      1560
gtgaccgccg ccgggatcac tctcggcatg gacgagctgt acaagtaagt cgacggcgcg      1620
ccgcggccgc gaattcgata tcataatcaa cctctggatt acaaaatttg tgaaagattg      1680
actggtattc ttaactatgt tgctcctttt acgctatgtg gatacgctgc tttaatgcct      1740
ttgtatcatg ctattgcttc ccgtatggct ttcattttct cctccttgta taaatcctgg      1800
ttagttcttg ccacggcgga actcatcgcc gcctgccttg cccgctgctg gacaggggct      1860
cggctgttgg gcactgacaa ttccgtggct cgagagatct tcgactgtgc cttctagttg      1920
ccagccatct gttgtttgcc cctcccccgt gccttccttg accctggaag gtgccactcc      1980
cactgtcctt tcctaataaa atgaggaaat tgcatcgcat tgtctgagta ggtgtcattc      2040
tattctgggg ggtggggtgg ggcaggacag caagggggag gattgggaag acaatagcag      2100
gcatgagatc tcacgtgcgg accgagcggc cgc                                  2133
```

<210> SEQ ID NO 198
<211> LENGTH: 2402
<212> TYPE: DNA
<213> ORGANISM: Artificial Sequence
<220> FEATURE:
<223> OTHER INFORMATION: AiP1273

<400> SEQUENCE: 198

```
gcggccgcac gcgtctggct gtcctggaac tcactctgta gaccaggctg gcctcaaact      60
cagaaatctg cctgcctctg cctcccaagt gctgggatta aaggcatgtg ccaccacacc      120
tggcctagaa ataatgactt ttaaaattat ctaaaggtta ccagatgaaa ttatcaacct      180
cagctctgtg gtataattta aatctagttc tgattcagta agagtgttat tttcagtacc      240
ctcagtagca gaatcctatt gcctcttata tctaagcagg agaggcaatt cagaaacaaa      300
gacccaagga caggagccct attgcatcta ctctcaataa ttaaggcctt tgatgactaa      360
```

-continued

```
aataatttag ataataagat tggtttgggt aaataaatat caaattaggg tttatggcag    420
tcacaggtgt ttggcaggtc tggcctataa tcacagagaa aatgaatgca ttttatttag    480
cataattggg aaaaggaatg aagcttatat gcaaattgtg taccactttt gttaaagata    540
gctggtcaga ctcatgatga taatccaaac ctttatccca gtgaaaattt tcaacatatc    600
tattttctgt ggaattttac cacatctgac tgcattctcc cagtcttctg agatggattt    660
cagtgtcctt ggtcaccatc tagcctttct attttgttga caggatgcct gagtttagct    720
gtttctgttt atttgtttgt ttttaagctt gatttctcct actcgtgtct atagctggaa    780
tcggaggtta catgagattt ctcagcatca gcatccagca ctgccacaaa ggggatgtgg    840
gagatgagaa gggaaaacaa gacagtgaag agaataaaaa tgaaatcctg gaggcaagat    900
aattaagaga ccagaaaata gagttgaatt tccattagga acatttacaa gaatgtgttc    960
acaggcacac acacaggaat ccccaactgc tagctttgga atgcccatag atgccactgc   1020
tactggactc tgtgatcagc gctcttgact aggactacga gctcgggctg ggcataaaag   1080
tcagggcaga gccatctatt gcttacattt gcttctggga tccagatctt tcgaagctag   1140
cgctaccggt cgccaccatg gtgagcaagg gcgaggagct gttcaccggg gtggtgccca   1200
tcctggtcga gctggacggc gacgtaaacg gccacaagtt cagcgtgtcc ggcgagggcg   1260
agggcgatgc cacctacggc aagctgaccc tgaagctgat ctgcaccacc ggcaagctgc   1320
ccgtgccctg gcccaccctc gtgaccaccc tgggctacgg cgtgcagtgc ttcgcccgct   1380
accccgacca catgaagcag cacgacttct tcaagtccgc catgcccgaa ggctacgtcc   1440
aggagcgcac catcttcttc aaggacgacg gcaactacaa gacccgcgcc gaggtgaagt   1500
tcgagggcga caccctggtg aaccgcatcg agctgaaggg catcgacttc aaggaggacg   1560
gcaacatcct ggggcacaag ctggagtaca actacaacag ccacaacgtc tatatcaccg   1620
ccgacaagca gaagaacggc atcaaggcca acttcaagat ccgccacaac atcgaggacg   1680
gcggcgtgca gctcgccgac cactaccagc agaacacccc catcggcgac ggccccgtgc   1740
tgctgcccga caaccactac ctgagctacc agtccaagct gagcaaagac cccaacgaga   1800
agcgcgatca catggtcctg ctggagttcg tgaccgccgc cgggatcact ctcggcatgg   1860
acgagctgta caagtaagtc gacggcgcgc cgcggccgcg aattcgatat cataatcaac   1920
ctctggatta caaaatttgt gaaagattga ctggtattct taactatgtt gctccttttta   1980 cgctatgtgg atacgctgct ttaatgcctt tgtatcatgc tattgcttcc cgtatggctt   2040
tcattttctc ctccttgtat aaatcctggt tagttcttgc cacggcggaa ctcatcgccg   2100
cctgccttgc ccgctgctgg acaggggctc ggctgttggg cactgacaat tccgtggctc   2160
gagagatctt cgactgtgcc ttctagttgc cagccatctg ttgtttgccc ctcccccgtg   2220
ccttccttga ccctggaagg tgccactccc actgtccttt cctaataaaa tgaggaaatt   2280
gcatcgcatt gtctgagtag gtgtcattct attctggggg gtggggtggg caggacagc   2340 aaggggagg attgggaaga caatagcagg catgagatct cacgtgcgga ccgagcggcc   2400
gc                                                                   2402
```

<210> SEQ ID NO 199
<211> LENGTH: 4
<212> TYPE: PRT
<213> ORGANISM: Artificial Sequence
<220> FEATURE:
<223> OTHER INFORMATION: AAAV9 amino acids starting at residues 586

<400> SEQUENCE: 199

-continued

```
Ser Ala Gln Ala
1

<210> SEQ ID NO 200
<211> LENGTH: 11
<212> TYPE: PRT
<213> ORGANISM: Artificial Sequence
<220> FEATURE:
<223> OTHER INFORMATION: PHP.eB capid amino acids starting at residue
      586

<400> SEQUENCE: 200

Ser Asp Gly Thr Leu Ala Val Pro Phe Lys Ala
1               5                   10

<210> SEQ ID NO 201
<211> LENGTH: 7
<212> TYPE: PRT
<213> ORGANISM: Artificial Sequence
<220> FEATURE:
<223> OTHER INFORMATION: AAV-BR1

<400> SEQUENCE: 201

Asn Arg Gly Thr Glu Trp Asp
1               5

<210> SEQ ID NO 202
<211> LENGTH: 7
<212> TYPE: PRT
<213> ORGANISM: Artificial Sequence
<220> FEATURE:
<223> OTHER INFORMATION: AAV-PHP.S

<400> SEQUENCE: 202

Gln Ala Val Arg Thr Ser Leu
1               5

<210> SEQ ID NO 203
<211> LENGTH: 7
<212> TYPE: PRT
<213> ORGANISM: Artificial Sequence
<220> FEATURE:
<223> OTHER INFORMATION: AAV-PHP.B

<400> SEQUENCE: 203

Thr Leu Ala Val Pro Phe Lys
1               5

<210> SEQ ID NO 204
<211> LENGTH: 7
<212> TYPE: PRT
<213> ORGANISM: Artificial Sequence
<220> FEATURE:
<223> OTHER INFORMATION: AAV-PPS

<400> SEQUENCE: 204

Asp Ser Pro Ala His Pro Ser
1               5
```